(12) United States Patent
Ibrahim et al.

(10) Patent No.: US 7,498,342 B2
(45) Date of Patent: Mar. 3, 2009

(54) COMPOUNDS MODULATING C-KIT ACTIVITY

(75) Inventors: Prabha N. Ibrahim, Mountain View, CA (US); Clarence R. Hurt, San Ramon, CA (US); Chao Zhang, Moraga, CA (US); Jiazhong Zhang, Oakland, CA (US)

(73) Assignee: Plexxikon, Inc., Berkeley, CA (US)

( * ) Notice: Subject to any disclaimer, the term of this patent is extended or adjusted under 35 U.S.C. 154(b) by 482 days.

(21) Appl. No.: 11/154,988

(22) Filed: Jun. 16, 2005

(65) Prior Publication Data

US 2006/0058340 A1 Mar. 16, 2006

Related U.S. Application Data

(60) Provisional application No. 60/682,076, filed on May 17, 2005, provisional application No. 60/580,898, filed on Jun. 17, 2004.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ........................... 514/300; 546/113
(58) Field of Classification Search ................. 546/113; 514/300
See application file for complete search history.

(56) References Cited

U.S. PATENT DOCUMENTS

| | | | |
|---|---|---|---|
| 2,234,705 A | 3/1941 | Normington et al. |
| 4,150,949 A | 4/1979 | Smith |
| 4,568,649 A | 2/1986 | Bertoglio-Matte |
| 4,626,513 A | 12/1986 | Burton et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pederson et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,178,384 B1 | 1/2001 | Kolossváry |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |

(Continued)

FOREIGN PATENT DOCUMENTS

| | | |
|---|---|---|
| DE | 2413258 | 10/1975 |
| EP | 0154734 | 9/1985 |
| EP | 870768 | 5/2002 |
| GB | 2299581 | 10/1996 |
| JP | 6135946 | 5/1994 |
| WO | WO93/13099 | 7/1993 |
| WO | WO 94/14808 | 7/1994 |

(Continued)

OTHER PUBLICATIONS

Minakata et al., "Functionalization of 1*H*-Pyrrolo[2,3-*b*]pyridine." Bulletin of the Chemical Society of Japan (1992), 65(11): 2992-2997.
Sawada et al., "4-(Benzoylindolizinyl)butyric acids; Novel nonsteroidal inhibitors of steroid 5α-reductase. III." Chemical and Pharmaceutical Bulletin (2001), 49(7): 799-813.
Song et al., "Isomerism of Bis(7-azaindolyl)methane." Organic Letters (2002), 4:23, 4049-4052, "Table of content" p. 1-16 and "Supporting information" p. 1-15.

(Continued)

*Primary Examiner*—D. Margaret Seaman
*Assistant Examiner*—Niloofar Rahmani
(74) *Attorney, Agent, or Firm*—Foley & Lardner LLP

(57) ABSTRACT

Compounds with 7-azaindole core structure with activity toward the receptor protein tyrosine kinase c-kit, compositions useful for treatment c-kit-mediate diseases or conditions, and methods of use thereof, are provided. Further provided are methods of c-kit ligand identification and design.

11 Claims, No Drawings

U.S. PATENT DOCUMENTS

| | | |
|---|---|---|
| 6,288,234 B1 | 9/2001 | Griffin |
| 6,294,330 B1 | 9/2001 | Michnick et al. |
| 6,545,014 B2 | 4/2003 | Verner |
| 6,858,860 B2 | 2/2005 | Hosono et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2004/0002534 A1 | 1/2004 | Lipson et al. |
| 2004/0167030 A1 | 8/2004 | Bernotas et al. |
| 2005/0085463 A1 | 4/2005 | Weiner et al. |
| 2005/0154014 A1 | 7/2005 | Bloxham et al. |
| 2005/0256151 A1 | 11/2005 | Salom et al. |
| 2006/0058339 A1* | 3/2006 | Ibrahim et al. ............... 514/300 |
| 2007/0032519 A1* | 2/2007 | Zhang et al. ................. 514/300 |
| 2007/0049615 A1 | 3/2007 | Ibrahim et al. |

FOREIGN PATENT DOCUMENTS

| | | |
|---|---|---|
| WO | WO94/20459 | 9/1994 |
| WO | WO95/04742 | 2/1995 |
| WO | WO96/11929 | 2/1996 |
| WO | WO96/05200 | 4/1996 |
| WO | WO 96/17958 | 6/1996 |
| WO | WO 97/46313 | 12/1997 |
| WO | WO97/49703 | 12/1997 |
| WO | WO98/22457 | 5/1998 |
| WO | WO98/47899 | 10/1998 |
| WO | WO 99/09217 | 5/1999 |
| WO | WO99/51231 | 10/1999 |
| WO | WO 99/51773 | 10/1999 |
| WO | WO00/12074 | 3/2000 |
| WO | WO00/12514 | 3/2000 |
| WO | WO00/53582 | 9/2000 |
| WO | WO00/71537 | 11/2000 |
| WO | WO00/75139 | 12/2000 |
| WO | WO01/09121 | 2/2001 |
| WO | WO01/62255 | 8/2001 |
| WO | WO01/98299 | 12/2001 |
| WO | WO02/00657 | 1/2002 |
| WO | WO02/18346 | 3/2002 |
| WO | WO02/083175 | 10/2002 |
| WO | WO02/085896 | 10/2002 |
| WO | WO02/102783 | 12/2002 |
| WO | WO03/000258 | 1/2003 |
| WO | WO03/006459 | 1/2003 |
| WO | WO03/008422 | 1/2003 |
| WO | WO 2003/003004 | 1/2003 |
| WO | WO03/011868 | 2/2003 |
| WO | WO03/028724 | 4/2003 |
| WO | WO03/037862 | 5/2003 |
| WO | WO03/051838 | 6/2003 |
| WO | WO03/068221 | 8/2003 |
| WO | WO03/082289 | 10/2003 |
| WO | WO03/082868 | 10/2003 |
| WO | WO03/082869 | 10/2003 |
| WO | WO03/087087 | 10/2003 |
| WO | WO03/101990 | 12/2003 |
| WO | WO2004/009600 | 1/2004 |
| WO | WO 2004/016609 | 2/2004 |
| WO | WO 2004/016610 | 2/2004 |
| WO | WO2004/065393 | 8/2004 |
| WO | WO2004/065394 | 8/2004 |
| WO | WO2004/074286 | 9/2004 |
| WO | WO2004/078756 | 9/2004 |
| WO | WO2004/101565 | 11/2004 |
| WO | WO2005/028475 | 3/2005 |
| WO | WO2005/044181 | 5/2005 |
| WO | WO2005/058891 | 6/2005 |
| WO | WO2005/062795 | 7/2005 |
| WO | WO2005/063746 | 7/2005 |
| WO | WO2005/063747 | 7/2005 |
| WO | WO2005/082367 | 9/2005 |
| WO | WO2005/085244 | 9/2005 |
| WO | WO2005/095400 | 10/2005 |
| WO | WO2005/103050 | 11/2005 |
| WO | WO2005/115363 | 12/2005 |
| WO | WO2006/004984 | 1/2006 |
| WO | WO 2006/009755 | 1/2006 |
| WO | WO 2006/009797 | 1/2006 |
| WO | WO2006/015123 | 2/2006 |
| WO | WO2006/127587 | 11/2006 |
| WO | WO 2007/013896 | 2/2007 |
| WO | WO 2007/106236 | 9/2007 |

OTHER PUBLICATIONS

Yakhontov et al., Derivatives of 7-azaindole. XV. Electrophilic substitution of 4-methyl-7-azaindole and its derivatives. Zhurnal Obshchei Khimii (1965), 1(11): 2032-2040. (English abstract only).

Yeung et al., "Friedel-Crafts acylation of indoles in acidic imidazolium chloroaluminate ionic liquid at room temperature." Tetrahedron Letters (2002), 43(33), 5793-5795.

Zhang et al., "An effective procedure for the acylation of azaindoles at C-3." Journal of Organic Chemistry (2002), 67(17): 6226-6227 and p. S1-S30.

Alfthan, K., "Surface Plasmon Resonance Biosensors as a Tool in Antibody Engineering" *Biosensors & Bioelectronics* 13:653-663 (1998).

al-Obeidi, et al., "Peptide and Peptidomimetic Libraries" *Mol Biotechnol* 9:205-223 (1998).

Amersdorfer and Marks "Phage Libraries for Generation of Anti-Botulinum scFv Antibodies" *Methods in Molecular Biology* 145:219-240 (2000).

Bancalari, et al., "Blood Markers of Early and Late Airway Responses to Allergen in Asthmatic Subjects. Relationship with Functional Findings" *Allergy* 52:32-40 (1997).

Bartlett, et al., "CAVEAT: A Program to Facilitate the Structure-Derived Design of Biologically Active Molecules" *Royal Society of Chemistry* 78:I80-I96 (1989).

Bagshaw and Harris "Measurement of Ligand Binding to Proteins" *Spectrophotometry and Spectrofluorimetry* 4:91-113 (1987).

Bedi, et al., "BCR-ABL-Mediated Inhibition of Apoptosis With Delay of G2/M Transition After DNA Damage: A Mechanism of Resistance to Multiple Anticancer Agents" *Blood* 86:1148-1158 (1995).

Bell, J., "Fluorescence: Solution Studies" *Spectroscopy In Biochemistry* I:155-194 (1981).

Bellone, et al., "Growth Stimulation of Colorectal Carcinoma Cells Via the c-Kit Receptor is Inhibited by TGF-β1" *J. Cell Physiol.* 172:1-11 (1997).

Berdel, et al., "Recombinant Human Stem Cell Factor Stimulates Growth of a Human Glioblastoma Cell Line Expressing c-*kit* Protooncogene" *Canc. Res.* 52:3498-3502 (1992).

Blundell et al., "Knowledge-Based Protein Modelling and Design" *Eur. J. Biochem.* 172:513-520 (1988).

Böhm, H. "On the Use of LUDI to Search the Fine Chemicals Directory for Ligands of Proteins of Known Three-Dimensional Structure" *J. Comp. Aided Molec. Design* 8:623-632 (1994).

Bolger and Sherman "Computer Modeling of Combining Site Structure of Anti-Hapten Monoclonal Antibodies" *Methods Enz.* 203:21-45 (1991).

Bokenmeyer, et al., "Expression of Stem-Cell Factor and Its Receptor c-*kit* Protein in Normal Testicular Tissue and Malignant Germ-Cell Tumours" *J. Cancer Res. Clin. Oncol.* 122:301-306 (1996).

Bothwell, M., "Keeping Track of Neurotrophin Receptors" *Cell* 65:915-918 (1991).

Bowtell, D. "Options Available—From Start to Finish—For Obtaining Expression Data by Microarray" *Nature Genetics Supp.* 21:25-32 (1999).

Brenner et al., "Encoded Combinatorial Chemistry" *Proc. Natl. Acad. Sci.* USA 89:5381-5383 (1992).

Broudy, V., "Stem Cell Factor and Hematopoiesis" *Blood* 90:1345-1364 (1997).

Brünger, A., "Free $R$ Value: a Novel Statistical Quantity for Assessing the Accuracy of Crystal Structures" *Nature* 355:472-475 (1992).

Buchschacher and Panganiban "Human Immunodeficiency Virus Vectors for Inducible Expression of Foreign Genes" *J. Virol.* 66:2731-2739 (1992).

Capon, et al., "Designing CD4 Immunoadhesins for AIDS Therapy" *Nature* 337:525-531 (1989).

Carell et al., "New Promise in Combinatorial Chemistry: Synthesis, Characterization, and Screening of Small-Molecule Libraries in Solution" *Chem. Biol.* 2:171-183 (1995).

Carpino, et al., "p62$^{dok}$: A Constitutively Tyrosine-Phosphorylated, GAP-Associated Protein in Chronic Myelogenous Leukemia Progenitor Cells" *Cell* 88:197-204 (1997).

Castells, et al., "The Presence of Membrane-Bound Stem Cell Factor on Highly Immature Nonmetachromatic Mast Cells in the Peripheral Blood of a Patient with Aggressive Systemic Mastocytosis" *J. Aller. Clin. Immunol.* 98:831-840 (1996).

Chabala, J. "Solid-Phase Combinatorial Chemistry and Novel Tagging Methods for Identifying Leads" *Curr Opin Biotechnol* 6:632-639 (1995).

Checovich, et al., "Fluorescence Polarization—A New Tool For Cell and Molecular Biology" *Nature* 375:254-256 (1995).

Clark, et al., "Pro_Ligand: An Approach to De Novo Molecular Design. 1. Application to the Design of Organic Molecules" *J. Comp. Aided Molec. Design* 9:13-32 (1995).

Coe, et al., "Solution-Phase Combinatorial Chemistry" *Mol Divers.* 4:31-38 (1999).

Cohen, et al., "Expression of Stem Cell Factor and c-*kit* in Human Neuroblastoma" *Blood* 84:3465-3472 (1994).

Collioud, et al., "Oriented and Covalent Immobilization of Target Molecules to Solid Supports: Synthesis and Application of a Light-Activatable and Thiol-Reactive Cross-Linking Reagent" *Bioconjugate Chem.* 4:528-536 (1993).

Columbo, et al., "The Human Recombinant c-*kit* Receptor Ligand, rhSCF, Induces Mediator Release From Human Cutaneous Mast Cells and Enhances IgE-Dependent Mediator Release From Both Skin Mast Cells and Peripheral Blood Basophils" *J. Immunol* 149:599-608 (1992).

Costa, et al., "The Cells of the Allergic Response" *JAMA* 278:1815-1822 (1997).

Creighton, T., "An Empirical Approach to Protein Conformation Stability and Flexibility" *Biopolymers* 22(1):49-58 (1983).

Cwirla et al., "Peptides on Phage: A Vast Library of Peptides for Identifying Ligands" *Biochemistry* 87:6378-6382 (1990).

Dandliker, et al., "Equilibrium and Kinetic Inhibition Assays Based Upon Fluorescence Polarization" *Methods in Enzymology* 74:3-28 (1981).

Dastych, et al., "Stem Cell Factor Induces Mast Cell Adhesion to Fibronection" *J. Immunol.* 152:213-219 (1994).

Döbeli, et al., "Recombinant Fusion Proteins for the Industrial Production of Disulfide Bridge Containing Peptides: Purification, Oxidation Without Concatamer Formation, and Selective Cleavage" *Protein Expr. Purif.* 12:404-414 (1998).

Dolle et al., "Comprehensive Survey of Combinatorial Library Synthesis: 1998" *J Comb Chem* 1:235-282 (1999).

Dyson, et al., "The Human Papilloma Virus—16 E7 Oncoprotein is Able to Bind to the Retinoblastoma Gene Product" *Science* 243:934-937 (1989).

Eliseev and Lehn, "Dynamic Combinatorial Chemistry: Evolutionary Formation and Screening of Molecular Libraries" *Current Topics in Microbiology & Immunology* 243:159-172 (1999).

Enjalbal, et al., "Mass Spectrometry in Combinatorial Chemistry" *Mass Spectrometry Reviews.* 19:139-161 (2000).

Escribano, et al., "Expression of the c-kit (CD117) Molecule in Normal and Malignant Hematopoiesis" *Leuk. Lymph.* 30:459-466 (1998).

Feng, et al., "Stable in Vivo Gene Transduction Via a Novel Adenoviral/Retroviral Chimeric Vector" *Nature Biotechnology* 15:866-870 (1997).

Finotto, et al., "Glucocorticoids Decrease Tissue Mast Cell Number by Reducing the Production of the c-kit Ligand, Stem Cell Factor, by Resident Cells" *J. Clin. Invest.* 99:1721-1728 (1997).

Fivash et al., "BIAcore for Macromolecular Interaction" *Current Opinion in Biotechnology.* 9:97-101 (1998).

Furitsu, et al., "Identification of Mutations in the Coding Sequence of the Proto-Oncogene c-*kit* in a Human Mast Cell Leukemia Cell Line Causing Ligand-Independent Activation of c-*kit* Product" *J. Clin. Invest.* 92:1736-1744 (1993).

Furuta, et al., "Stem Cell Factor Influences Mast Cell Mediator Release in Response to Eosinophil-Derived Granule Major Basic Protein" *Blood* 92:1055-1061 (1998).

Gallop et al., "Applications of Combinatorial Technologies to Drug Discovery. 1. Background and Peptide Combinatorial Libraries" *J. Med. Chem.* 37:1233-1251 (1994).

Golkar, et al., "Mastocytosis" *Lancet* 349:1379-1385 (1997).

Goodford, P.J., "A Computational Procedure for Determining Energetically Favorable Binding Sites on Biologically Important Macromolecules" *J. Med. Chem.* 28:849-857 (1985).

Goodsell and Olson, "Automated Docking of Substrates to Proteins by Simulated Annealing" *Proteins: Structure, Function, and Genetics* 8:195-202 (1990).

Gordon et al., "Applications of Combinatorial Technologies to Drug Discovery. 2. Combinatorial Organic Synthesis, Library Screening Strategies, and Future Directions" *J. Med. Chem.* 37:1384-1401 (1994).

Gram H., "Phage Display in Proteolysis and Signal Transduction" *Combinatorial Chemistry & High Throughput Screening* 2:19-28 (1999).

Gravert and Janda, "Synthesis on Soluble Polymers: New Reactions and the Construction of Small Molecules" *Curr Opin Chem Biol* 1:107-113 (1997).

Greer, J. "Model Structure for the Inflammatory Protein C5a" *Science* 228:1055-1060 (1985).

Hafner et al., "Isothermal Amplification and Multimerization of DNA by *Bst* DNA Polymerase" *Biotechniques* 30:852-867 (2001).

Hallek, et al., "Interaction of the Receptor Tyrosine Kinase p145$^{c-kit}$ with the p210$^{bcr/abl}$ Kinase in Myeloid Cells" *Brit. J Haem.* 94:5-16 (1996).

Hamel, et al., "The Road Travelled: c-kit and Stem Cell Factor" *J. Neuro-Onc.* 35:327-333 (1997).

Hanselman, et al., "A cDNA-Dependent Scintillation Proximity Assay for Quantifying Apolipoprotein A-1" *J. Lipid Res.* 38:2365-2373 (1997).

Hassan and Zander, "Stem Cell Factor as a Survival and Growth Factor in Human Normal and Malignant Hematopoiesis" *Acta. Hem.* 95:257-262 (1996).

Hassan, et al., "Expression of Protooncogene c-*kit* and Its Ligand Stem Cell Factor (SCF) in Gastric Carcinoma Cell Lines" *Digest. Dis. & Sciences* 43:8-14 (1998).

Heim, et al., "Engineering Green Fluorescent Protein for Improved Brightness, Longer Wavelengths and Fluorescence Resonance Energy Transfer" *Curr. Biol.* 6:178-182 (1996).

Hibi, et al., "Coexpression of the Stem Cell Factor and the c-*kit* Genes in Small-Cell Lung Cancer" *Oncogene* 6:2291-2296 (1991).

Hirota, et al., "Gain-of-Function Mutations of c-*kit* in Human Gastrointestinal Stromal Tumors" *Science* 279:577-580 (1998).

Hogaboam, et al., "Novel Role of Transmembrane SCF for Mast Cell Activation and Eotaxin Production in Mast Cell-Fibroblast Interactions" *J. Immunol.* 160:6166-6171 (1998).

Houghten, et al., "Generation and Use of Synthetic Peptide Combinatorial Libraries for Basic Research and Drug Discovery" *Nature* 354:84-86 (1991).

Houghton, R., "Peptide Libraries: Criteria and Trends" *Trends Genet.* 9:235-239 (1993).

Houghton, R., "Parallel Array and Mixture-Based Synthetic Combinatorial Chemistry: Tools for the Next Millennium" *Annu Rev Pharmacol Toxicol* 40:273-282 (2000).

Hughes-Jones, et al., "Synthesis of Rh Fv Phage-Antibodies Using VH and VL Germline Genes" *British Journal of Haematology* 105:811-816 (1999).

Inoue, et al., "Coexpression of the c-*kit* Receptor and the Stem Cell Factor in Gynecological Tumors" *Cancer Res.* 54:3049-3053 (1994).

Isozaki, et al., "Deficiency of *c-kit*+ Cells in Patients with a Myopathic Form of Chronic Idiopathic Intestinal Pseudo-Obstruction" *Amer. J. of Gast.* 92:332-334 (1997).

Iwane, et al., "Myosin Subfragment-1 is Fully Equipped with Factors Essential for Motor Function" *Biophys. Biochem. Res. Comm.* 230:76-80 (1997).

Izquierdo, et al., "Differential Expression of the *c-kit* Proto-Oncogene in Germ Cell Tumours" *J. Pathol.* 177:253-258 (1995).

Johann, et al., "GLVR1, a Receptor for Gibbon Ape Leukemia Virus, Is Homologous to a Phosphate Permease of *Neurospora crassa* and Is Expressed at High Levels in the Brain and Thymus" *J. Virol.* 66:1635-1640 (1992).

Johnston, M., "Gene Chips: Array of Hope for Understanding Gene Regulation" *Curr. Biol.* 8:R171-R174 (1998).

Jones, T., "Interactive Computer Graphics: FRODO" *Methods in Enzymology* 115:157-171 (1985).

Jones, R., "Biology and Treatment of Chronic Myeloid Leukemia" *Curr. Opin. Onc.* 9:3-7 (1997).

Joseph-McCarthy, D., "Computational Approaches to Structure-Based Ligand Design" *Pharmacology & Therapeutics* 84:179-191 (1999).

Kahl, et al., "A Multiple-Approach Scintillation Proximity Assay to Measure the Association Between Ras and Raf" *Anal. Biochem.* 243:282-283 (1996).

Kay, et al., "Eosinophils and Eosinophil-Associated Cytokines in Allergic Inflammation" *Int. Arch. Aller. Immunol.* 113:196-199 (1997).

Kern and Hampton, "Direct Hybridization of Large-Insert Genomic Clones on High-Density Gridded cDNA Filter Arrays" *Biotechniques* 23:120-124 (1997).

Kim and Kahn, "A Merger of Rational Drug Design and Combinatorial Chemistry: Development and Application of Peptide Secondary Structure Mimetics" *Combinatorial Chemistry & High Throughput Screening* 3:167-183 (2000).

Kinashi, et al., "Steel Factor and *c-kit* Regulate Cell-Matrix Adhesion" *Blood* 83:1033-1038 (1994).

Kirkpatrick, et al., "Structure-Based Drug Design: Combinatorial Chemistry and Molecular Modeling" *Combinatorial Chemistry & High Throughput Screening* 2:211-221 (1999).

Kitamura, et al., "Synthesis of Quinolines and 2*H*-Dihydropyrroles by Nucleophillic Substitution at the Nitrogen Atom of Oxime Derivatives" *Synthesis* 15:2415-2416 (2003).

Kline et al., "Studies by $^1$H Nuclear Magnetic Resonance and Distance Geometry of the Solution Conformation of the x-Amylase Inhibitor Tendamistat" *J. Mol. Biol.* 189:377-382 (1986).

Knighton, et al. "Structural Basis of the Intrasteric Regulation of Myosin Light Chain Kinases" *Science* 258:130-135 (1992).

Kolaskar and Tongaonkar, "A Semi-Empirical Method for Prediction of Antigenic Determinants on Protein Antigens" *FEBS Lett.* 276:172-174 (1990).

Kondoh, et al., "Very High Incidence of Germ Cell Tumorigenesis (Seminomagenesis in Human Papillomavirus Type 16 Transgenic Mice" *J. Virol.* 65:3335-3339 (1991).

Kondoh, et al., "Establishment and Further Characterization of a Line of Transgenic Mice Showing Testicular Tumorigenesis at 100% Incidence" *J. Urol.* 152:2151-2154 (1994).

Kondoh, et al., "An in vivo Model for Receptor Tyrosine Kinase Autocrine/Paracrine Activation: Auto-Stimulated KIT Receptor Acts as a Tumor Promoting Factor in Papillomavirus-Induced Tumorigenesis" *Oncogene* 10:341-347 (1995).

Kroll, et al., "A Multifunctional Prokaryotic Protein Expression System: Overproduction, Affinity Purification, and Selective Detection" *DNA Cell. Biol.* 12:441-453 (1993).

Kundu, et al., "Combinatorial Chemistry: Polymer Supported Synthesis of Peptide and Non-Peptide Libraries" *Progress in Drug Research* 53:89-156 (1999).

Kunisada, et al., "Murine Cutaneous Mastocytosis and Epidermal Melanocytosis Induced by Keratinocyte Expression of Transgenic Stem Cell Factor" *J. Exp. Med.* 187:1565-1573 (1998).

Kunkel, T., "Rapid and Efficient Site-Specific Mutagenesis Without Phenotypic Selection" *Proc. Natl. Acad. Sci. USA* 82:488-492 (1985).

Kuntz, et al., "A Geometric Approach to Macromolecule-Ligand Interactions" *J. Mol. Biol.* 161:269-288 (1982).

Kuntz, et al., "Structure-Based Molecular Design" *Acc. Chem. Res.* 27:117-123 (1994).

Lahm, et al., "Interleukin 4 Down-Regulates Expression of *c-kit* and Autocrine Stem Cell Factor in Human Colorectal Carcinoma Cells" *Cell Growth & Differ.* 6:1111-1118 (1995).

Lam, et al., "A New Type of Synthetic Peptide Library for Identifying Ligand-Binding Activity" *Nature* 354:82-84 (1991).

Lebl, et al., "One-Bead-One-Structure Combinatorial Libraries" *Biopolymers* 37:177-198 (1995).

Lee, et al., "Mast Cells: A Cellular Link Between Autoantibodies and Inflammatory Arthritis" *Science* 297:1689-1692 (2002).

Lee, et al., "HLA-DR-Triggered Inhibition of Hemopoiesis Involves Fas/Fas Ligand Interactions and is Prevented by *c-kit* Ligand" *J. Immunol.* 159:3211-3219 (1997).

Lemura, et al., "The *c-kit* Ligand, Stem Cell Factor, Promotes Mast Cell Survival by Suppressing Apoptosis" *Amer. J. Pathol* 144:321-328 (1994).

Levin, et al., "Neoplasms of the Central Nervous System" *Cancer Principles & Practice of Oncology* 2:2022-2082 (1997).

Li, et al., "Abrogation of *c-kit/Steel Factor*-Dependent Tumorigenesis by Kinase Defective Mutants of the *c-kit* Receptor: *c-kit* Kinase Defective Mutants as Candidate Tools for Cancer Gene Therapy" *Canc. Res.* 56:4343-4346 (1996).

Liparoto, et al., "Biosensor Analysis of the Interleukin-2 Receptor Complex" *Journal of Molecular Recognition* 12:316-321 (1999).

Lipinski, et al., "Experimental and Computational Approaches to Estimate Solubility and Permeability in Drug Discovery and Development Settings" *Advanced Drug Delivery Reviews* 23:3-25 (1997).

Lipschultz, et al., "Experimental Design for Analysis of Complex Kinetics Using Surface Plasmon Resonance" *Methods* 20:310-318 (2000).

London, et al., "Expression of Stem Cell Factor Receptor (c-*kit*) by the Malignant Mast Cells from Spontaneous Canine Mast Cell Tumours" *J. Compar. Pathol.* 115:399-414 (1996).

Longley, et al., "Altered Metabolism of Mast-Cell Growth Factor (*c-kit* Ligand) in Cutaneous Mastocytosis" *New Engl. J. Med.* 328:1302-1307 (1993).

Longley, et al., "Somatic *c-KIT* Activating Mutation in Urticaria Pigmentosa and Aggressive Mastocytosis: Establishment of Clonality in a Human Mast Cell Neoplasm" *Nat. Gen.* 12:312-314 (1996).

Longley, et al., "Chymase Cleavage of Stem Cell Factor Yields a Bioactive Soluble Product" *Proc. Natl. Acad. Sci.* USA 94:9017-9021 (1997).

Loveland and Schlatt, "Stem Cell Factor and c-*kit* in the Mamalian Testis: Lessons Originating from Mother Nature's Gene Knockouts" *J. Endocrinol* 153:337-344 (1997).

Lu, et al., "Oriented Immobilization of Fab' Fragments on Silica Surface" *Anal. Chem.* 67:83-87 (1995).

Lukacs, et al., "Stem Cell Factor (*c-kit* Ligand) Influences Eosinophil Recruitment and Histamine Levels in Allergic Airway Inflammation" *J. Immunol.* 156:3945-3951 (1996).

Lyman, et al., "c-kit Ligand and Flt3 Ligand: Stem/Progenitor Cell Factors With Overlapping Yet Distinct Activities" *Blood* 91:1101-1134 (1998).

Ma, et al., "Indolinone Derivatives Inhibit Constitutively Activated KIT Mutants and Kill Neoplastic Mast Cells" *J Invest Dermatol.* 114:392-394 (2000).

Ma, et al., "The *c-KIT* Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations" *Blood* 99:1741-1744 (2002).

McCall, et al., "Characterization of Anti-Mouse FcγRII Single-Chain Fv Fragments Derived from Human Phage Display Libraries" *Immunotechnology* 4:71-87 (1998).

Madden, et al., "Synthetic Combinatorial Libraries: Views on Techniques and Their Application" *Perspectives in Drug Discovery and Design* 2:269-285 (1994).

Malmborg, et al., "BIAcore as a Tool in Antibody Engineering" *Journal of Immunological Methods* 183:7-13 (1995).

Malmqvist, et al., "Biomolecular Interaction Analysis: Affinity Biosensor Technologies for Functional Analysis of Proteins" *Current Opinion in Chemical Biology* 1:378-383 (1997).

Malmqvist., M., "BIACORE: an Affinity Biosensor System for Characterization of Biomolecular Interactions" *Biochemical Society Transactions* 27:335-340 (1999).

Markiewicz, et al., "Synthetic Oligonucleotide Combinatorial Libraries and Their Applications" *Il Farmaco* 55:174-177 (2000).

Martin, Y., "Computer-Assisted Rational Drug Design" *Methods Enz.* 203:587-613 (1991).

McPherson, A., "Current Approaches to Macromolecule Crystallization" *Eur. J. Biochem.* 189:1-23 (1990).

Mekori, et al., "Transforming Growth Factor-β Prevents Stem Cell Factor-Mediated Rescue of Mast Cells from Apoptosis After IL-3 Deprivation" *J. Immunol.* 153:2194-2203 (1994).

Mekori, et al., "The Role of c-Kit and Its Ligand, Stem Cell Factor, in Mast Cell Apoptosis" *Int. Arch. Allergy Immunol.* 107:136-138 (1995).

Meng, et al., "Automated Docking with Grid-Based Energy Evaluation" *J. Compt. Chem.* 13:505-524 (1992).

Merritt, A., "Solution Phase Combinatorial Chemistry" *Comb Chem High Throughput Screen* 1:57-72 (1998).

Metcalf, D., "Lineage Commitment in the Progeny of Murine Hematopoietic Preprogenitor Cells: Influence of Thrombopoietin and Interleukin 5" *Proc. Natl. Acad. Sci. USA* 95:6408-6412 (1998).

Metcalfe, et al., "Mast Cells" *Physiol Rev* 77:1033-1079 (1997).

Miller, et al., "FLOG: A System to Select 'Quasi-Flexible' Ligands Complementary to a Receptor of Known Three-Dimensional Structure" *J. Comp. Aided Molec. Design* 8:153-174 (1994).

Miranker and Karplus, "Functionality Maps of Binding Sites: A Multiple Copy Simultaneous Search Method" *Proteins: Structure, Function, and Genetics* 11:29-34 (1991).

Mitra, et al., "Fluorescence Resonance Energy Transfer Between Blue-Emitting and Red-Shifted Excitation Derivatives of the Green Fluorescent Protein" *Gene* 173:13-17 (1996).

Mol, et al. "Structural Basis for the Autoinhibition and STI-571 Inhibition of c-Kit Tyrosine Kinase" *J. Biol. Chem.* 279:31655-31663 (2004).

Mol, et al., "Structure of a c-Kit Product Complex Reveals the Basis for Kinase Transactivation" *J. Biol. Chem.* 278:31461-31464 (2003).

Murty, et al., "A Genetic Perspective of Male Germ Cell Tumors" *Sem. Oncol.* 25:133-144 (1998).

Naclerio, et al., "Rhinitis and Inhalant Allergens" *JAMA* 278:1842-1848 (1997).

Nagata, et al., "Elevated Expression of the Proto-Oncogene *c-kit* in Patients with Mastocytosis" *Leukemia* 12:175-181 (1998).

Navaza, J., "AMoRe: an Automated Package for Molecular Replacement" *Acta Cryst.* A50:157-163 (1994).

Neidle, et al., "Molecular Modeling to Study DNA Intercalation by Anti-Tumor Drugs" *Methods Enz.* 203:433-458 (1991).

Ng, et al., "Engineering Protein-Lipid Interactions: Targeting of Histidine-Tagged Proteins to Metal-Chelating Lipid Monolayers" *Langmuir* 11:4048-4055 (1995).

Nicholls, et al., "Protein Folding and Association: Insights From the Interfacial and Thermodynamic Properties of Hydrocarbons" *Proteins* 11:281-296 (1991).

Nichols, et al., "Development of a Scintillation Proximity Assay for Peroxisome Proliferator-Activated Receptor γ Ligand Binding Domain" *Anal. Biochem.* 257:112-119 (1998).

O'Shannessy and Winzor, "Interpretation of Deviations from Pseudo-First-Order Kinetic Behavior in the Characterization of Ligand Binding by Biosensor Technology" *Analytical Biochemistry* 236:275-283 (1996).

O'Shannessy, D., "Determination of Kinetic Rate and Equilibrium Binding Constants for Macromolecular Interactions: a Critique of the Surface Plasmon Resonance Literature" *Current Opinions in Biotechnology* 5:65-72 (1994).

Okada, et al., "Gene Therapy Against an Experimental Glioma Using Adeno-Associated Virus Vectors" *Gene Ther.* 3:957-964 (1996).

Okayama, et al., "Activation of Eosinophils with Cytokines Produced by Lung Mast Cells" *Int. Arch. Aller. Immunol.* 114(suppl. 1):75-77 (1997).

Okayama, et al., "Human Lung Mast Cells are Enriched in the Capacity to Produce Granulocyte-Macrophage Colony-Stimulating Factor in Response to IgE-Dependent Stimulation" *Eur. J. Immunol.* 28:708-715 (1998).

Otwinowski, Z., "Masimum Likelihood Refinement of Heavy Atom Parameters" *Dept. of Molecular Biophysics and Biochemistry* pp. 80-86 (1991).

Parker, et al., "Development of High Throughput Screening Assays Using Fluorescence Polarization: Nuclear Receptor-Ligand-Binding and Kinase/Phosphatase Assays" *J Biomol Screen* 5:77-88 (2000).

Perrin, D., "Nucleic Acids for Recognition and Catalysis: Landmarks, Limitations, and Looking to the Future" *Combinatorial Chemistry & High Throughput Screening* 3:243-269 (2000).

Pflugrath, et al., "Crystal Structure Determination, Refinement and the Molecular Model of the x-Amylase Inhibitor Hoe-467A" *J. Mol. Biol.* 189:383-386 (1986).

Pignon, J., "C-Kit Mutations and Mast Cell Disorders A Model of Activating Mutations of Growth Factor Receptors" *Hermatol Cell Ther* 39:114-116 (1997).

Plunkett, and Ellman, "A Silicon-Based Linker for Traceless Solid-Phase Synthesis" *J. Org. Chem.* 60:6006-6007 (1995).

Poul, et al., "Selection of Tumor-Specific Internalizing Human Antibodies from Phage Libraries" *J. Mol. Biol.* 301:1149-1161 (2000).

Price, et al., "Summary Report on the ISOBM TD-4 Workshop: Analysis of 56 Monoclonal Antibodies Against the MUC1 Mucin" *Tumour Biology* 19(Suppl 1):1-20 (1998).

Rajpert-de Meyts, et al., "Expression of the *c-kit* Protein Product in Carcinoma-in-situ and Invasive Testicular Germ Cell Tumours" *Int. J. Androl.* 17:85-92 (1994).

Ricotti, et al., "*c-kit* is Expressed in Soft Tissue Sarcoma of Neuroectodermic Origin and its Ligand Prevents Apoptosis of Neoplastic Cells" *Blood* 91:2397-2405 (1998).

Roberts, et al., "Generation of an Antibody with Enhanced Affinity and Specificity for its Antigen by Protein Engineering" *Nature* 328:731-734 (1987).

Robison and Robison, "7-Azaindole. I. Synthesis and Conversion to 7-Azatryptophan and Other Derivatives" *J. Am. Chem. Soc.* 77:457-460 (1955).

Rosenfeld, M., "Human Artificial Chromsomes Get Real" *Nat. Genet.* 15:333-335 (1997).

Ryan, et al., "Role for the Stem Cell Factor/KIT Complex in Schwann Cell Neoplasia and Mast Cell Proliferation Associated with Neurofibromatosis" *J. Neuro. Res.* 37:415-432 (1994).

Saiki, R., "Amplification of Genomic DNA" *PCR Protocols* 2:13-20 (1990).

Sambrook, et al., "Introduction of Recombinant Vectors into Mammalian Cells" *Molecular Cloning: A Laboratory Manual* 2:16.30-16.37 (1989).

Sandlow, et al., "Expression of *c-KIT* and Its Ligand, Stem Cell Factor, in Normal and Subfetile Human Testicular Tissue" *J. Androl.* 17:403-408 (1996).

Sawada, et al., "Role of Cytokines in Leukemic Type Growth of Myelodysplastic CD34+ Cells" *Blood* 88:319-327 (1996).

Sawai, et al., "Aberrant Growth of Granulocyte-Macrophage Progenitors in Juvenile Chronic Myelogenous Leukemia in Serum-Free Culture" *Exp. Hem.* 2:116-122 (1996).

Scheffner, et al., "The E6 Oncoprotein Encoded by Human Papillomavirus Types 16 and 18 Promotes the Degredation of p53" *Cell* 63:1129-1136 (1990).

Schneider, et al., "Functional Purification of a Bacterial ATP-Binding Cassette Transporter Protein (MalK) from the Cytoplasmic Fraction of an Overproducing Strain" *Protein Expr. Purif.* 6:10-14 (1995).

Schuhmann, et al., "Immobilization of Enzymes on Langmuir-Blodgett Films Via a Membrane-Bound Receptor. Possible Applications for Amperometric Biosensors" *Adv. Mater.* 3:388-391 (1991).

Schummer, et al., "Inexpensive Handheld Device for the Construction of High-Density Nucleic Acid Arrays" *Biotechniques* 23:1087-1092 (1997).

Schweizer, et al., "Combinatorial Synthesis of Carbohydrates" *Curr Opin. Chem. Biol.* 3:291-298 (1999).

Secor, et al., "Mast Cells are Essential for Early Onset and Severe Disease in a Murine Model of Multiple Sclerosis" *J Exp Med* 191:813-821 (2000).

Selvin, P., "Fluorescence Resonance Energy Transfer" *Meth. Enzymol.* 246:300-345 (1995).

Sheets, et al., "Efficient Construction of a Large Nonimmune Phage Antibody Library: The Production of High-Affinity Human Single-Chain Antibodies to Protein Antigens" *Proc Natl Acad Sci* USA 95:6157-6162 (1998).

Siegel, et al., "Mass Spectral Analysis of a Protein Complex Using Single-Chain Antibodies Selected on a Peptide Target: Applications to Functional Genomics" *Journal of Molecular Biology* 302:285-293 (2000).

Sigal, et al., "A Self-Assembled Monolayer for the Binding and Study of Histidine-Tagged Proteins by Surface Plasmon Resonance" *Anal. Chem.* 68:490-497 (1996).

Solinas-Toldo, et al., "Matrix-Based Comparative Genomic Hybridization: Biochips to Screen for Genomic Imbalances" *Genes, Chromosomes & Cancer* 20:399-407 (1997).

Sperling, et al., "Expression of the Stem Cell Factor Receptor c-Kit (CD117) in Acute Leukemias" *Haemat* 82:617-621 (1997).

Stanulla, et al., "Coexpression of Stem Cell Factor and Its Receptor c-Kit in Human Malignant Glioma Cell Lines" *Act Neuropath* 89:158-165 (1995).

Steinman, L., "Multiple Sclerosis: A Coordinated Immunological Attack Against Myelin in the Central Nervous System" *Cell* 85:299-302 (1996).

Strohmeyer, et al., "Expression of the *hst*-1 and *c-kit* Protooncogenes in Human Testicular Germ Cell Tumors" *Canc. Res.* 51:1811-1816 (1991).

Strohmeyer, et al., "Expression of the C-Kit Proto-Oncogene and Its Ligand Stem Cell Factor (SCF) in Normal and Malignant Human Testicular Tissue" *J. Urol.* 153:511-515 (1995).

Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases" *J. Med. Chem.* 42:5120-5130 (1999).

Tada, et al., "Analysis of Cytokine Receptor Messenger RNA Expression in Human Glioblastoma Cells and Normal Astrocytes by Reverse-Transcription Polymerase Chain Reaction" *J. Neuro* 80:1063-1073 (1994).

Takahashi & Cooper, "*ret* Transforming Gene Encodes a Fusion Protein Homologous to Tyrosine Kinases" *Mol Cell Biol.* 7:1378-1385 (1987).

Taylor, et al., "The Rapid Generation of Oligonucleotide-Directed Mutations at High Frequency Using Phosphorothioate-Modified DNA" *Nucl. Acids Res.* 13:8765-8785 (1985).

Thomas and Warner, "The Eosinophil and Its Role in Asthma" *Gen. Pharmac.* 27:593-597 (1996).

Toyota, et al., "Expression of *c-kit* and *kit* Ligand in Human Colon Carcinoma Cells" *Tum Biol* 14:295-302 (1993).

Tsujimura, T., "Role of *c-kit* Receptor Tyrosine Kinase in the Development, Survival and Neoplastic Transformation of Mast Cells" *Pathol Int* 46:933-938 (1996).

Tsujimura, et al., "Ligand-Independent Activation of *c-kit* Receptor Tyrosine Kinase in a Murine Mastocytoma Cell Line P-815 Generated by a Point Mutation" *Blood* 9:2619-2626 (1994).

Tsujimura, et al., "Substitution of an Aspartic Acid Results in Constitutive Activation of *c-kit* Receptor Tyrosine Kinase in a Rat Tumor Mast Cell Line RBL-2H3" *Int. Arch. Aller. Immunol* 106:377-385 (1995).

Turner, et al., "Nonhematopoietic Tumor Cell Lines Express Stem Cell Factor and Display *c-kit* Receptors" *Blood* 80:374-381 (1992).

Udenfriend, et al., "Scintillation Proximity Assay: A Sensitive and Continuous Isotopic Method for Monitoring Ligand/Receptor and Antigen/Antibody Interactions" *Anal. Biochem.* 161:494-500 (1987).

Valent, P., "Biology, Classification and Treatment of Human Mastocytosis" *Wein/Klin Wochenschr* 108:385-397 (1996).

Van Regenmortel, M., "Use of Biosensors to Characterize Recombinant Proteins" *Developments in Biological Standardization* 83:143-151 (1994).

Vely, et al., "BIAcore® Analysis to Test Phosphopeptide-SH2 Domain Interactions" *Methods in Molecular Biology* 121:313-321 (2000).

Verfaillie, CM, "Chronic Myelogenous Leukemia: Too Much or Too Little Growth, or Both" *Leuk.* 12:136-138 (1998).

Viskochil, "It Takes Two to Tango: Mast Cell and Schwann Cell Interactions in Neurofibromas" *J Clin Invest.* 112:1791-1793 (2003).

Vliagoftis, et al., "The Protooncogene *c-kit* and *c-kit* Ligand in Human Disease" *Clin Immunol* 100:435-440 (1997).

Weber, P., "Physical Principles of Protein Crystallization" *Adv. Protein Chem.* 41:1-36 (1991).

Werness, et al., "Association of Human Papillomavirus Types 16 and 18 E6 Proteins with p53" *Science* 248:76-79 (1990).

Wessjohann, L., "Synthesis of Natural-Product-Based Compound Libraries" *Curr Opin Chem Biol* 4:303-309 (2000).

Wharam, et al., "Specific Detection of DNA and RNA Targets Using a Novel Isothermal Nucleic Acid Amplification Assay Based on the Formation of a Three-Way Junction Structure" *Nucleic Acids Res.* 29:1-8 (2001).

Williams, et al., "Dissection of the Extracellular Human Interferon γ Receptor a-Chain into Two Immunoglobulin-Like Domains. Production in an *Escherichia coli* Thioredoxin Gene Fusion Expression System and Recognition by Neutralizing Antibodies" *Biochemistry* 34:1787-1797 (1995).

Woon, et al., "Construction and Characterization of a 10-Fold Genome Equivalent Rat P1-Derived Artificial Chromosome Library" *Genomics* 50:306-316 (1998).

Wuthrich, K., "Chapter 10—Three-Dimensional Protein Structures by NMR" *NMR of Proteins and Nucleic Acids* 10:176-199 (1986).

Yang, et al., "Neurofibromin-Deficient Schwann Cells Secrete a Potent Migratory Stimulus for $NF1^{+/-}$ Mast Cells" *J Clin Invest.* 112:1851-1861 (2003).

Yee, et al., "Role of *kit*-Ligand in Proliferation and Suppression of Apoptosis in Mast Cells: Basis for Radiosensitivity of White Spotting and Steel Mutant Mice" *J. Exp. Med.* 179:1777-1787 (1994).

Yuan, et al., "Human Peripheral Blood Eosinophils Express a Functional *c-kit* Receptor for Stem Cell Factor that Stimulates Very Late Antigen 4 (VLA-4)-Mediated Cell Adhesion to Fibronectin and Vascular Cell Adhesion Molecule 1 (VCAM-1)" *J. Exp. Med.* 186:313-323 (1997).

Baston et al., "the Chemistry of Pentavalent Organobismuth Regents-past-X-".

PCT International Search Report for International Application No. PCT/US2007/085299 dated Jul. 28, 2008.

PCT International Search Report for International Application No. PCT/US2007/085289 dated Jun. 5, 2008.

\* cited by examiner

COMPOUNDS MODULATING C-KIT ACTIVITY

CROSS REFERENCE TO RELATED PATENT APPLICATIONS

This application claims the benefit of Ibrahim et al. U.S. Prov. App. No. 60/580,898, filed Jun. 17, 2004, and Ibrahim et al. U.S. Prov. App. No. 60/682,076, filed May 17, 2005, each of which are incorporated herein by reference in their entireties including all specifications, figures, and tables, and for all purposes.

FIELD OF THE INVENTION

This invention relates to the development of ligands for c-kit and uses of such ligands.

BACKGROUND OF THE INVENTION

The information provided is intended solely to assist the understanding of the reader. None of the information provided nor references cited is admitted to be prior art to the present invention. Each of the references cited is incorporated herein in its entirety.

Receptor protein tyrosine kinases (RPTKs) regulate key signal transduction cascades that control cellular growth and proliferation. The Stem Cell Factor (SCF) receptor c-kit is a type III transmembrane RPTK that includes five extracellular immunoglobulin (IG) domains, a single transmembrane domain, and a split cytoplasmic kinase domain separated by a kinase insert segment. C-kit plays an important role in the development of melanocytes, mast, germ, and hematopoietic cells.

Stem Cell Factor (SCF) is a protein encoded by the SI locus, and has also been called kit ligand (KL) and mast cell growth factor (MGF), based on the biological properties used to identify it (reviewed in Tsujimura, *Pathol Int* 1996, 46:933-938; Loveland, et al., *J. Endocrinol* 1997, 153:337-344; Vliagoftis, et al., *Clin Immunol* 1997, 100:435-440; Broudy, *Blood* 1997, 90:1345-1364; Pignon, *Hermatol Cell Ther* 1997, 39:114-116; and Lyman, et al., *Blood* 1998, 91:1101-1134.). Herein we use the abbreviation SCF to refer to the ligand for the c-Kit RTK.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate c-Kit. For example, in the skin, SCF is predominantly expressed by fibroblasts, keratinocytes, and endothelial cells, which modulate the activity of melanocytes and mast cells expressing c-Kit. In bone, marrow stromal cells express SCF and regulate hematopoiesis of c-Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with c-Kit on germ cells.

Additional RPTK proteins, for example Ret, and NTRK1, have been described (Takahashi & Cooper, Mol Cell Biol. 1987, 7:1378-85; Bothwell, Cell. 1991, 65:915-8.). Ret and NTRK1 play a role in the development and maturation of specific components of the nervous system. Alterations in Ret and NTRK1 have been associated with several human diseases, including some forms of cancer and developmental abnormalities. The correlation between genetic alteration and the appearance of various diseases has contributed to the concept that one gene can be responsible for more than one disease. Moreover, genetic alterations in both Ret and NTRK1 have been observed that belong to either "gain of function" or "loss of function" class of mutations. In fact, receptor rearrangements or point mutations convert Ret and NTRK1 into dominantly acting transforming genes leading to thyroid tumors, whereas inactivating mutations, associated with Hirschsprung's disease (HSCR) and congenital insensitivity to pain with anhidrosis (CIPA), impair Ret and NTRK1 functions, respectively.

A co-crystal structure of c-kit kinase domain with the compound STI-571 (Gleevec, Imatinib) is reported by Mol et al. (*J. Biol. Chem.* 2003, 278:31461-4). A structure of auto-inhibited c-kit, along with a structure of c-kit in complex with STI-571 is described by Mol et al., (*J. Biol. Chem.* 2004, 279:31655-63). Cloning, crystallization conditions and structure determination are also described.

Modulation of c-Kit using indolinone compounds is described in Lipson et al., U.S. 20040002534 (U.S. application Ser. No. 10/600,868, filed Jun. 23, 2003).

Aberrant expression and/or activation of c-Kit has been implicated in a variety of pathologic states. For example, evidence for a contribution of c-Kit to neoplastic pathology includes its association with leukemias and mast cell tumors, small cell lung cancer, testicular cancer, and some cancers of the gastrointestinal tract and central nervous system. In addition, c-Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., *J Clin Invest.* 2003, 112:1851-1861; Viskochil, *J Clin Invest.* 2003, 112:1791-1793). Accordingly, there is a need in the art for modulators of c-kit activity.

SUMMARY OF THE INVENTION

The present invention relates to compounds with activity toward c-Kit, and to methods of designing such compounds. In particular, the invention provides compounds of Formula I as described below. Thus, the invention provides compounds that can be used for therapeutic and/or prophylactic methods involving modulation of c-Kit.

The compounds of Formula I have the following structure:

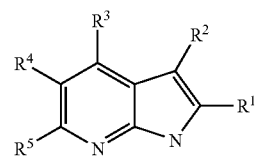

Formula I wherein:
R$^1$ and R$^5$ are independently hydrogen, halo, hydroxy, substituted oxy, thiol, substituted thiol, optionally substituted lower alkyl, optionally substituted lower alkenyl, optionally substituted lower alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —C(X)NR$^{16}$R$^{17}$, —C(X)R$^{20}$, or —NR$^{22}$R$^{23}$;

R³ and R⁴ are independently hydrogen, halo, hydroxy, substituted oxy, thiol, substituted thiol, optionally substituted lower alkyl, optionally substituted lower alkenyl, optionally substituted lower alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, —C(X)R²⁰, —C(X)NR¹⁶R¹⁷, —S(O)₂NR¹⁶R¹⁷, —NR²²R²³, or —S(O)ₙR²¹;

R² is hydrogen, halo, hydroxy, substituted oxy, thiol, substituted thiol, optionally substituted lower alkyl, optionally substituted lower alkenyl, optionally substituted lower alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, —C(X)R²⁰, —C(X)NR¹⁶R¹⁷, —S(O)₂NR R¹⁷, —NR²²R²³, —S(O)ₙR²¹, or —X¹—X²—X³—X⁴ wherein:
X¹ is selected from the group consisting of lower alkylene, substituted lower alkylene, —C(O)—, —CH₂C(O)—, —C(O)CH₂—, —C(S)—, —CH₂C(S)—, —C(S)CH₂—, —O—, —S—, —S(O₂)—, and —NRᵃ—, wherein:
Rᵃ is selected from the group consisting of hydrogen, lower alkyl and lower alkyl substituted with fluoro, hydroxyl, alkoxy, thiol, thioalkoxy, or amino, provided, however, that hydroxyl, alkoxy, thiol, thioalkyoxy or amino are not substituted at the carbon bound to the nitrogen of —NRᵃ—;

X² is selected from the group consisting of arylene and heteroarylene;

X³ is selected from the group consisting of

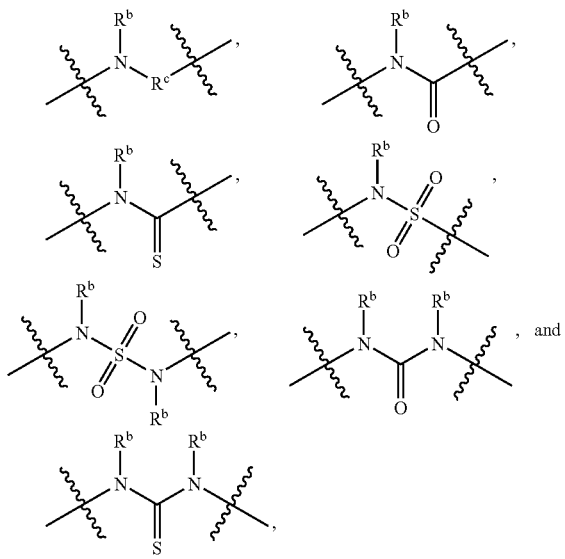

wherein:
Rᵇ at each occurrence is independently selected from the group consisting of hydrogen, lower alkyl and lower alkyl substituted with fluoro, hydroxyl, alkoxy, thiol, thioalkoxy, or amino, provided, however, that hydroxyl, alkoxy, thiol, thioalkyoxy or amino are not substituted at the carbon bound to the nitrogen of NRᵇ; and Rᶜ is selected from the group consisting of alkylene and substituted alkylene; and X⁴ is selected from the group consisting of alkyl, substituted alkyl, and

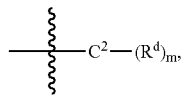

wherein
C² is selected from the group consisting of aryl and heteroaryl;
Rᵈ is selected from the group consisting of halogen, lower alkyl, substituted lower alkyl, optionally substituted lower alkoxy, optionally substituted alkylthio, optionally substituted alkenyl, optionally substituted alkynyl, optionally substituted amine, optionally substituted amido, carboxyl, hydroxyl, optionally substituted aryl, aryloxy, optionally substituted heterocycle, optionally substituted heteroaryl, nitro, cyano, thiol, and sulfonylamino; and
m is in the range 0-2;

R¹⁶ and R¹⁷ are independently hydrogen, optionally substituted lower alkyl, optionally substituted lower alkenyl, provided, however, that nitrogen is not attached to the alpha carbon of the alkene bond; optionally substituted lower alkynyl, provided, however, that nitrogen is not attached to the alpha carbon of the alkyne bond; optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl; or R¹⁶ and R¹⁷ together with the nitrogen form an optionally substituted 5-7 membered heterocyclic or heteroaryl ring;

R²⁰ is hydroxyl, substituted oxy, optionally substituted amine, optionally substituted lower alkyl, optionally substituted lower alkenyl, provided, however, that —C(X)— is not attached to the alpha carbon of the alkene bond, optionally substituted lower alkynyl, provided, however, that —C(X)— is not attached to the alpha carbon of the alkyne bond, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl;

R²¹ is hydrogen provided n=0, optionally substituted lower alkyl, optionally substituted amine, optionally substituted lower alkenyl, provided, however, that —S(O)ₙ— is not attached to the alpha carbon of the alkene bond, optionally substituted lower alkynyl, provided, however, that —S(O)ₙ— is not attached to the alpha carbon of the alkyne bond, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl;

$R^{22}$ and $R^{23}$ are independently hydrogen, optionally substituted lower alkyl, optionally substituted lower alkenyl, provided, however, that nitrogen is not attached to the alpha carbon of the alkene bond, optionally substituted lower alkynyl, provided, however, that nitrogen is not attached to the alpha carbon of the alkyne bond, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —C(X)$R^{20}$, —C(X)N$R^{16}R^{17}$, and —S(O)$_2$$R^{21}$; or $R^{22}$ and $R^{23}$ together with the nitrogen form an optionally substituted 5-7 membered heterocyclic or heteroaryl ring;

X is O or S; and n is 0, 1, or 2.

For the compounds described herein, the following definitions apply:

"Halo" and "halogen" refer to all halogens including chloro (Cl), fluoro (F), bromo (Br), or iodo (I).

"Hydroxyl" and "hydroxy" refer to the group —OH.

"Substituted oxy" refers to the group —O$R^f$, where $R^f$ is alkyl, substituted alkyl, acyl, substituted acyl, aryl, substituted aryl, heteroaryl, substituted heteroaryl, aralkyl, substituted aralkyl, heterocyclylalkyl, substituted heterocyclylalkyl, heteroarylalkyl, substituted heteroarylalkyl, cycloalkyl, substituted cycloalkyl, heterocyclyl, or substituted heterocyclyl.

"Thiol" and "mercapto" refer to the group —SH.

"Substituted thiol" refers to the group —SR, where R is alkyl, substituted alkyl, acyl, substituted acyl, aryl, substituted aryl, heteroaryl, substituted heteroaryl, aralkyl, substituted aralkyl, heterocyclylalkyl, substituted heterocyclylalkyl, heteroarylalkyl, substituted heteroarylalkyl, cycloalkyl, substituted cycloalkyl, heterocyclyl, or substituted heterocyclyl.

"Alkyl" refers to an alkane-derived radical containing from 1 to 20, preferably 1 to 15, carbon atoms. Alkyl includes straight chain alkyl, branched alkyl and cycloalkyl. Straight chain or branched alkyl groups contain from 1-15, preferably 1 to 8, more preferably 1-6, yet more preferably 1-4 and most preferably 1-2, carbon atoms, such as methyl, ethyl, propyl, isopropyl, butyl, t-butyl, and the like. Alkyl also includes straight chain or branched alkyl groups that contain or are interrupted by one or more cycloalkyl portions. Examples of this include, but are not limited to, 4-(isopropyl)-cyclohexylethyl or 2-methyl-cyclopropylpentyl. The alkyl group is attached at any available point to produce a stable compound.

A "substituted alkyl" is an alkyl group independently substituted with 1 or more, e.g., 1, 2, or 3, groups or substituents such as halo, hydroxy, optionally substituted alkoxy, optionally substituted alkylthio, alkylsulfinyl, alkylsulfonyl, acyloxy, optionally substituted aryl, optionally substituted aryloxy, optionally substituted heteroaryloxy, optionally substituted amino, optionally substituted amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, heterocycle, substituted heterocycle, heteroaryl, substituted heteroaryl, nitrogen, cyano, thiol, sulfonylamino, or the like attached at any available point to produce a stable compound.

"Lower alkyl" refers to an alkyl group having 1-6 carbon atoms.

A "substituted lower alkyl" is a lower alkyl which is substituted with 1 or more, e.g., 1, 2, or 3, groups or substitutents as defined in [0020] attached at any available point to produce a stable compound.

"Cycloalkyl" refers to saturated or unsaturated, non-aromatic monocyclic, bicyclic or tricyclic carbon ring system of 3-8, more preferably 3-6, ring members per ring, such as cyclopropyl, cyclopentyl, cyclohexyl, adamantyl, and the like.

A "substituted cycloalkyl" is a cycloalkyl which is indepentently substituted with 1 or more, e.g., 1, 2, or 3, groups or substitutents as defined in [0020], optionally substituted alkyl, optionally substituted alkenyl, or optionally substituted alkynyl, attached at any available point to produce a stable compound.

"Alkylene" refers to a divalent alkane-derived radical containing 1-20, preferably 1-15, carbon atoms, straight chain or branched, from which two hydrogen atoms are taken from the same carbon atom or from different carbon atoms. Examples of alkylene include, but are not limited to, methylene —CH$_2$—, ethylene —CH$_2$CH$_2$—, and the like.

A "substituted alkylene" is an alkylene which is independently substituted with 1 or more, e.g., 1, 2, or 3, groups or substitutents as defined in [0020] attached at any available point to produce a stable compound.

A "lower alkylene" is an alkylene containing 1-6 carbon atoms.

A "substituted lower alkylene" is a lower alkylene which is independently substituted with 1 or more, e.g., 1, 2, or 3, groups or substitutents as defined in [0020] attached at any available point to produce a stable compound.

"Alkenyl" refers to a straight chain, branched, or cyclic hydrocarbon containing 2-20, preferably 2-17, more preferably 2-10, even more preferably 2-8, most preferably 2-4, carbon atoms, and which contains at least one, preferably 1-3, more preferably 1-2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include, but are not limited to, ethenyl, propenyl, isopropenyl, butenyl, cyclohexenyl, cyclohexenylalkyl, and the like.

A "substituted alkenyl" is an alkenyl which is independently substituted with 1 or more, e.g., 1, 2, or 3, groups or substituents as defined in [0020], attached at any available point to produce a stable compound.

"Lower alkenyl" refers to an alkenyl group having 1-6 carbon atoms.

A "substituted lower alkenyl" is a lower alkenyl which is substituted with 1 or more, e.g., 1, 2, or 3, groups or substitutents as defined in [0020] attached at any available point to produce a stable compound.

"Alkynyl" refers to a straight chain or branched hydrocarbon containing 2-20, preferably 2-17, more preferably 2-10, even more preferably 2-8, most preferably 2-4, carbon atoms, and which contains at least one, preferably one, carbon to carbon triple bond. Examples of alkynyl groups include, but are not limited to, ethynyl, propynyl, butynyl, and the like.

A "substituted alkynyl" is an alkynyl which is independently substituted with 1 or more, e.g., 1, 2, or 3, groups or substituents as defined in [0020], attached at any available point to produce a stable compound.

"Lower alkynyl" refers to an alkynyl group having 1-6 carbon atoms.

A "substituted lower alkynyl" is a lower alkynyl which is substituted with 1 or more, e.g., 1, 2, or 3, groups or substitutents as defined in [0020] attached at any available point to produce a stable compound.

"Alkoxy" denotes the group —$OR^f$, where $R^f$ is lower alkyl.

"Substituted alkoxy" denotes the group —$OR^f$, where $R^f$ is substituted lower alkyl.

"Alkylthio" or "thioalkoxy" refers to the group —S—R, where R is lower alkyl.

"Substituted alkylthio" or "substituted thioalkoxy" refers to the group —S—R, where R is substituted lower alkyl.

"Sulfinyl" denotes the group —S(O)—.

"Substituted sulfinyl" denotes the group —S(O)—R, where R is lower alkyl, substituted lower alkyl, aryl, substituted aryl, heteroaryl, substituted heteroaryl, heteroaralkyl, substituted heteroaralkyl, aralkyl or substituted aralkyl.

"Sulfonyl" denotes the group —$S(O)_2$—.

"Substituted sulfonyl" denotes the group —$S(O)_2$—R, where R is lower alkyl, substituted lower alkyl, aryl, substituted aryl, heteroaryl, substituted heteroaryl, heteroaralkyl, substituted heteroaralkyl, aralkyl or substituted aralkyl.

"Sulfonylamino" denotes the group —$NRS(O)_2$—, where R is hydrogen or lower alkyl.

"Substituted sulfonylamino" denotes the group —$NR^aS(O)_2$—$R^b$, where $R^a$ is hydrogen or lower alkyl and $R^b$ is lower alkyl, substituted lower alkyl, cycloalkyl, substituted cycloalkyl, heterocyclyl, substituted heterocyclyl, aryl, substituted aryl, heteroaryl, substituted heteroaryl, heteroarallkyl, substituted heteroaralkyl, aralkyl or substituted aralkyl.

"Acyl" denotes the group —$C(O)R^h$, where $R^h$ is hydrogen, lower alkyl, aryl, heteroaryl and the like.

"Substituted acyl" denotes the group —$C(O)R^{h'}$, where $R^{h'}$ is substituted lower alkyl, substituted aryl, substituted heteroaryl and the like.

"Acyloxy" denotes the group —$OC(O)R^h$, where $R^h$ is hydrogen, lower alkyl, substituted lower alkyl, aryl, substituted aryl, heteroaryl, substituted heteroaryl and the like.

"Aryloxy" denotes the group —OAr, where Ar is an aryl or substituted aryl group.

"Heteroaryloxy" denotes groups —OHet, wherein Het is an optionally substituted heteroaryl group.

"Amino" or "amine" denotes the group —$NH_2$.

"Substituted amino" or "substituted amine" denotes the group —$NR^iR^j$, wherein $R^i$ and $R^j$ are independently hydrogen, lower alkyl, substituted lower alkyl, aryl, substituted aryl, heteroaryl, substituted heteroaryl, acyl, substituted acyl, sulfonyl or substituted sulfonyl, provided, however, that at least one of $R^i$ and $R^j$ is not hydrogen. $R^iR^j$ in combination with the nitrogen may form an optionally substituted heterocyclic or heteroaryl ring.

"Amido" denotes the group —$C(O)NH_2$

"Substituted amido" denotes the group —$C(O)NR^kR^l$, wherein $R^k$ and $R^l$ are independently hydrogen, lower alkyl, substituted lower alkyl, aryl, substituted aryl, heteroaryl, or substituted heteroaryl, provided, however, that at least one of $R^k$ and $R^l$ is not hydrogen. $R^kR^l$ in combination with the nitrogen may form an optionally substituted heterocyclic or heteroaryl ring.

"Amidino" denotes the group —$C(=NR^m)NR^nR^o$, wherein $R^m$, $R^n$, and $R^o$ are independently hydrogen or optionally substituted lower alkyl.

"Alkylsulfinyl" denotes the group —$S(O)R^p$, wherein $R^p$ is optionally substituted alkyl.

"Alkylsulfonyl" denotes the group —$S(O)_2R^p$, wherein $R^p$ is optionally substituted alkyl.

"Alkylsulfonylamino" denotes the group —$NR^qS(O)_2R^p$, wherein $R^p$ is optionally substituted alkyl, and $R^q$ is hydrogen or lower alkyl.

"Arylsulfonylamino" denotes the group —$NR^qS(O)_2R^s$, wherein $R^s$ is optionally substituted aryl, and $R^q$ is hydrogen or lower alkyl.

"Heteroarylsulfonylamino" denotes the group —$NR^qS(O)_2R^t$, wherein $R^t$ is optionally substituted heteroaryl, and $R^q$ is hydrogen or lower alkyl.

"Carbonylamino" denotes the group —$NR^qC(O)H$, wherein $R^q$ is hydrogen or lower alkyl.

"Substituted carbonylamino" denotes the group —$NR^qC(O)R^p$, wherein $R^q$ is hydrogen or lower alkyl and $R^p$ is optionally substituted alkyl, optionally substituted cycloalkyl, optionally substituted heterocyclyl, optionally substituted aryl, or optionally substituted heteroaryl.

"Alkylcarbonylamino" denotes the group —$NR^qC(O)R^p$, wherein $R^p$ is optionally substituted alkyl, and $R^q$ is hydrogen or lower alkyl.

"Arylcarbonylamino" denotes the group —$NR^qC(O)R^s$, wherein $R^s$ is optionally substituted aryl, and $R^q$ is hydrogen or lower alkyl.

"Heteroarylcarbonylamino" denotes the group —$NR^qC(O)R^t$, wherein $R^t$ is optionally substituted aryl, and $R^q$ is hydrogen or lower alkyl.

"Carboxyl" denotes the group —$C(O)OR^r$, wherein $R^r$ is hydrogen, lower alkyl, substituted lower alkyl, aryl, substituted aryl, heteroaryl, or substituted heteroaryl.

"Aryl" means phenyl or naphthyl optionally fused with a cycloalkyl of preferably 5-7, more preferably 5-6, ring members.

"Arylene" means a divalent aryl

A "substituted aryl" is an aryl group which is independently substituted with 1 or more, e.g., 1, 2, or 3, groups or substituents as defined in [0020], optionally substituted alkyl, optionally substituted alkenyl, or optionally substituted alkynyl, attached at any available point to produce a stable compound.

"Heterocycle" or "heterocyclyl" means a saturated or unsaturated, non-aromatic carbocyclic group having a single ring or multiple condensed rings, e.g. a cycloalkyl group having from 5 to 10 atoms in which from 1 to 3 carbon atoms in a ring are replaced by heteroatoms, such as O, S, N, and are optionally fused with benzo or heteroaryl of 5-6 ring members and/or are optionally substituted. Heterocyclyl is intended to include oxidized S or N, such as sulfinyl, sulfonyl and N-oxide of a tertiary ring nitrogen. The point of attachment is at a carbon or nitrogen atom. Examples of heterocycle or heterocyclyl groups are morpholino, tetrahydrofuranyl, dihydropyridinyl, piperidinyl, pyrrolidinyl, piperazinyl, dihydrobenzofuryl, dihydroindolyl, and the like.

A "substituted heterocycle" or "substituted heterocyclyl" is a heterocycle substituted with 1 or more, e.g., 1, 2, or 3, substituents as defined in 100201, optionally substituted alkyl, optionally substituted alkenyl, optionally substituted alkynyl, or oxo group, attached at any available point to produce a stable compound.

"Oxo" refers to an oxygen substituent double bonded to the attached carbon.

"Heteroaryl" means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are naphthpyridyl, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like.

"Heteroarylene" means a divalent heteroaryl.

A "substituted heteroaryl" is a heteroaryl which is independently substituted with 1 or more, e.g., 1, 2, or 3, groups or substituents as defined in [0020], optionally substituted alkyl, optionally substituted alkenyl, or optionally substituted alkynyl, attached at any available point to produce a stable compound.

"Aralkyl" refers to the group —R—Ar where Ar is an aryl group and R is lower alkylene.

"Substituted aralkyl" refers to the aralkyl group which is independently substituted with 1 or more, e.g., 1, 2, or 3, groups or substituents as defined in [0020], optionally substituted alkyl, optionally substituted alkenyl, or optionally substituted alkynyl, attached at any available point to produce a stable compound.

"Hetercyclylalkyl" refers to the group —R-Het where Het is a heterocycle group and R is a lower alkylene group.

"Substituted heterocyclylalkyl" refers to a heterocyclylalkyl group which is independently substituted with 1 or more, e.g., 1, 2, or 3, groups or substituents as defined in [0020], optionally substituted alkyl, optionally substituted alkenyl, optionally substituted alkynyl, or oxo group attached at any available point to produce a stable compound.

"Cycloalkylalkyl" refers to the group —R-Cyc where Cyc is a cycloalkyl group and R is a lower alkylene group.

"Substituted cycloalkylalkyl" refers to a cycloalkylalkyl group which is independently substituted with 1 or more, e.g., 1, 2, or 3, groups or substituents as defined in [0020], optionally substituted alkyl, optionally substituted alkenyl, or optionally substituted alkynyl, attached at any available point to produce a stable compound.

"Heteroarylalkyl" and "heteroaralkyl" refer to the group —R-HetAr where HetAr is an heteroaryl group and R lower alkylene.

"Substituted heteroarylalkyl" and "substituted heteroaralkyl" refer to the heteroarylalkyl group which is independently substituted with 1 or more, e.g., 1, 2, or 3, groups or substituents as defined in [00201, optionally substituted alkyl, optionally substituted alkenyl, or optionally substituted alkynyl, attached at any available point to produce a stable compound.

In reference to Formula I, the core structure shown above without the substituents is referred to as the "azaindole core." For that azaindole core, reference to ring atoms or ring positions is as shown in the following structure:

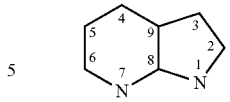

In particular embodiments involving compounds of Formula I, $R^1$ and $R^5$ are hydrogen. In particular embodiments, compounds of Formula I have other than hydrogen at $R^2$; other than hydrogen at $R^3$, other than hydrogen at $R^4$, other than hydrogen at $R^2$ and $R^3$; and other than hydrogen at $R^2$ and $R^4$. In certain embodiments, the substitutions as listed are the only substitutions; the substitutions as listed are combined with $R^1$ and $R^5$ as H; the substitutions as listed are combined with substitution at one other of the substitution positions shown in Formula I.

In one embodiment, the invention provides a method for treating a subject suffering from or at risk of a c-Kit mediated disease or condition, comprising administering to the subject an effective amount of a compound of Formula I as given above.

In a further embodiment, the c-Kit mediated disease or condition which is the object of treatment is associated with improperly regulated kinase signal transduction.

In a further embodiment of the invention relating to the treatment of a c-Kit mediated disease or condition, the improperly regulated kinase signal transduction is of mast cells.

In a further embodiment of the invention relating to the treatment of a c-Kit mediated disease or condition, the c-Kit mediated disease or condition is mastocytosis, asthma, rheumatoid arthritis or chronic rhinitis.

In a further embodiment of the invention relating to the treatment of a c-Kit mediated disease or condition, the c-Kit mediated disease or condition is a cell proliferative disorder, a fibrotic disorder, or a metabolic disorder.

In a further embodiment, the cell proliferative disorder is cancer.

In a further embodiment, the cancer is leukemia, mast cell tumor, small cell lung cancer, testicular cancer, cancer of the gastrointestinal tract, cancer of the central nervous system, cancer of the female genital tract, sarcoma of neuroectodermal origin, or Schwann cell neoplasia associated with neurofibromatosis.

In a further embodiment of the invention relating to the treatment of a c-Kit mediated disease or condition, the c-Kit mediated disease or condition is multiple sclerosis.

In particular embodiments, the compound of Formula I has a structure according to the following sub-generic structure, Formula Ia, where $R^2$ is as defined for Formula I. In another embodiment of Formula Ia, $R^2$ is —$X^1$—$X^2$—$X^3$—$X^4$ where $X^1$, $X^2$, $X^3$ and $X^4$ are defined as in Formula I, Formula Ia

In another embodiment of the invention, with reference to Formula Ia, when —X¹—X²—X³—X⁴ is

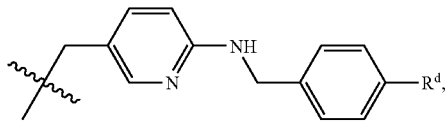

then $R^d$ is not F, Cl, CH$_3$ or CF$_3$.

In a further embodiment, $X^1$ is selected from the group consisting of methylene and substituted methylene.

In a further embodiment, $X^1$ is difluoromethylene or —C(O)—, further wherein $X^2$ is phenylene.

In a further embodiment, $X^2$ contains one or two nitrogen atoms.

In further embodiments, $X^2$ is pyridinediyl, pyrimidinediyl, pyrazinediyl, or pyridazinediyl.

In yet a further embodiment, $X^2$ is

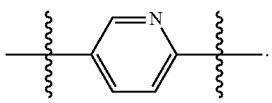

In a further embodiment, $X^4$ is

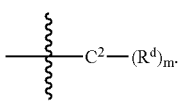

In further embodiments, $X^3$ is

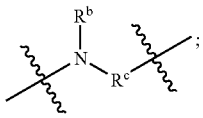

wherein:
$R^b$ is hydrogen or lower alkyl; and
$R^c$ is methylene or substituted methylene.

In further embodiments, X is —NHCH$_2$—, or —NHC(O)—, further wherein $x^2$ is heteroaryl.

In a further embodiment, $X^3$ is

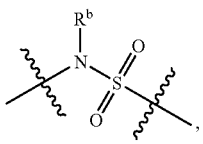

and $R^b$ is hydrogen or lower alkyl.

In a further embodiment, $X^4$ is

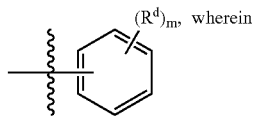

wherein $R^d$ at each occurrence is independently halogen, lower alkyl, substituted lower alkyl, optionally substituted lower alkoxy, optionally substituted alkylthio, optionally substituted alkenyl, optionally substituted alkyknyl, optionally substituted amine, optionally substituted amido, carboxyl, hydroxyl, optionally substituted aryl, aryloxy, optionally substituted heterocycle, heteroaryl, substituted heteroaryl, nitro, cyano, thiol, or sulfonylamino; and m is in the range 0-2.

In a further embodiment, $X^4$ is

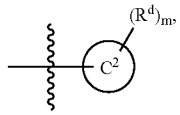

and $C^2$ is thienyl, substituted thienyl, pyridinyl, pyrimidinyl, pyrazinyl, pyridazinyl, pyrrolyl, imidazolyl, or furanyl.

In a further embodiment, $X^4$ is alkyl or substituted alkyl.

In a further embodiment, the invention provides a composition comprising a pharmaceutically acceptable carrier and one or more compounds having the structure of Formula Ia

Formula Ia wherein:
$R^2$ is $X^1$—$X^2$—$X^3$—$X^4$;
$X^1$ is selected from the group consisting of lower alkylene, substituted lower alkylene, —O—, —S—, and $NR^a$,
wherein $R^a$ is selected from the group consisting of hydrogen, lower alkyl and lower alkyl substituted with fluoro, hydroxyl, alkoxy, thiol, thioalkoxy, or amino, provided hydroxyl, alkoxy, thiol, thioalkyoxy or amino are not substituted at the carbon bound to the nitrogen of —$NR^a$—;
$X^2$ is selected from the group consisting of arylene and heteroarylene;
$X^3$ is selected from the group consisting of

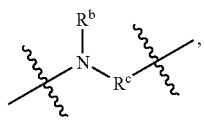 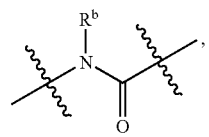

-continued

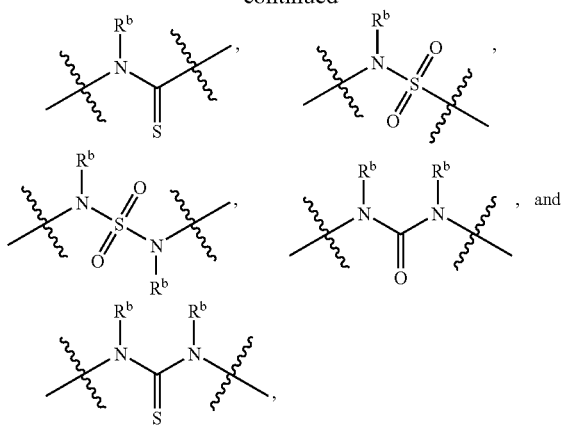

wherein
$R^b$ at each occurrence is independently selected from the group consisting of hydrogen, lower alkyl, and lower alkyl substituted with fluoro, hydroxyl, alkoxy, thiol, thioalkoxy, or amino, provided hydroxyl, alkoxy, thiol, thioalkyoxy or amino are not substituted at the carbon bound to the nitrogen of $NR^b$; and
$R^c$ is selected from the group consisting of alkylene and substituted alkylene; and
$X^4$ is selected from the group consisting of alkyl, substituted alkyl, and

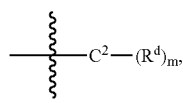

wherein
$C^2$ is selected from the group consisting of aryl and heteroaryl;
$R^d$ is selected from the group consisting of halogen, lower alkyl, substituted lower alkyl, optionally substituted lower alkoxy, optionally substituted alkylthio, optionally substituted alkenyl, optionally substituted alkyknyl, optionally substituted amine, optionally substituted amido, carboxyl, hydroxyl, optionally substituted aryl, aryloxy, optionally substituted heterocycle, optionally substituted heteroaryl, nitro, cyano, thiol, and sulfonylamino; and
m is in the range 0-2;
provided, however, that the compound is not

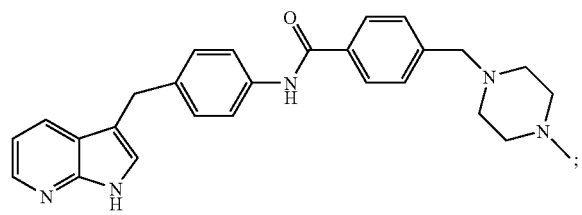

provided, however, that the compound is not

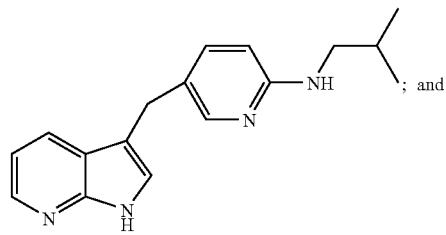

pharmaceutically acceptable salts, prodrugs, and isomers thereof.

In a further embodiment, the invention provides a composition as given above, provided, however, that when $X^1$—$X^2$—$X^3$—$X^4$ is

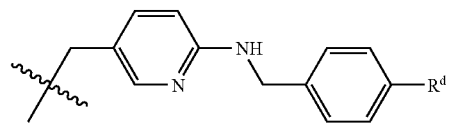

then $R^d$ is not selected from the group consisting of F, Cl, $CH_3$, and $CF_3$.

In a further embodiment, the invention provides a method for treating a subject suffering from or at risk of a c-Kit mediated disease or condition, wherein the method comprises administering to the subject an effective amount of a composition of Formula I.

In a further aspect of the composition above, the c-Kit mediated disease or condition is associated with improperly regulated kinase signal transduction.

In a further aspect of the composition above, the improperly regulated kinase signal transduction is of mast cells.

In a further aspect of the composition above, the c-Kit mediated disease or condition is mastocytosis, asthma, or chronic rhinitis.

In a further aspect of the composition above, the c-Kit mediated disease or condition is a cell proliferative disorder, a fibrotic disorder, or a metabolic disorder.

In a further aspect of the composition above, the cell proliferative disorder is cancer.

In a further aspect of the composition above, the cancer is leukemia, mast cell tumor, small cell lung cancer, testicular cancer, cancer of the gastrointestinal tract, cancer of the central nervous system, cancer of the female genital tract, sarcoma of neuroectodermal origin, or Schwann cell neoplasia associated with neurofibromatosis.

In a further aspect of the composition above, the c-Kit mediated disease or condition is multiple sclerosis.

Further to any of the above embodiments, when $R^1$, $R^3$, $R^4$ and $R^5$ are hydrogen,

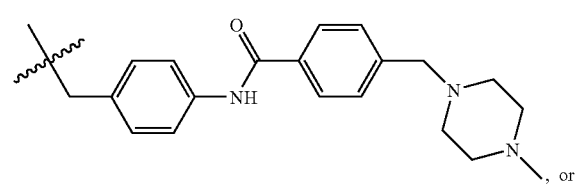

-continued

R² is not

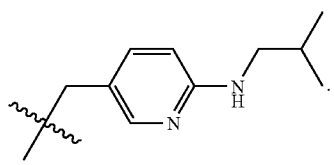

In reference to c-kit modulator compounds herein, specification of a compound or group of compounds includes pharmaceutically acceptable salts of such compound(s) unless clearly indicated to the contrary, prodrugs, and all isomers.

Thus, in one aspect, the invention provides methods for treating a c-Kit-mediated disease or condition in an animal subject, e.g., a mammal such as a human, e.g., a disease or condition characterized by abnormal c-Kit activity (e.g., kinase activity), where the method involves administering to the subject a compound of Formula I.

As used herein, the term c-kit-mediated disease or condition refers to a disease or condition in which the biological function of c-Kit affects the development and/or course of the disease or condition, and/or in which modulation of c-Kit alters the development, course, and/or symptoms.

Specific diseases or disorders which can be treated or prevented include those described in the Detailed Description herein, and in the references cited therein. Exemplary diseases and conditions include but are not limited to cancer, asthma, arthritis, chronic rhinitis, multiple sclerosis, GIST, and mastocytosis disorders.

In a related aspect, compounds of Formula I can be used in the preparation of a medicament for the treatment of a c-Kit-mediated disease or condition, such as a cancer, asthma, arthritis, chronic rhinitis, multiple sclerosis, or other disease indicated herein.

In another aspect, the invention provides compounds of Formula I as described herein (e.g., compounds that have advantageous levels of activity and/or selectivity on c-Kit). In certain embodiments, the compounds are substituted at the 3-position of the core bicyclic ring structure (azaindole core) with a substituent group that in order includes a first linker bound to a first aryl or heteroaryl group, which is bound to a linker of 1 to 3 atoms bound to a second aryl or heteroaryl group. In certain embodiments including the just-described 3-position substituent group, the first linker is methylene, ethylene, —C(O)—, —CH$_2$—C(O)—, —C(O)CH$_2$—, —C(S)—, —CH$_2$—C(S)—, —C(S)CH$_2$—, —O—, —S—, or —S(O$_2$)—; the first aryl or heteroaryl group is pyridinyl, pyrimidinyl, pyrazinyl, pyridazinyl, pyrrolyl, imidazolyl, triazolyl, thiazolyl, furanyl, or oxazolyl; the second linker is methyl amino —(NH—CH$_2$)—, ethyl amino —(NH—CH$_2$—CH$_2$)—, amide (—NH—C(O)—), sulfonamide (—NH—(SO$_2$)—) urea (—NH—C(O)—NH—), thiourea (—NH—C(S)—NH—), or sulfonyl urea (—NH—S(O)$_2$—NH—); the second aryl or heteroaryl group is phenyl, pyridinyl, pyrimidinyl, pyrazinyl, pyridazinyl, pyrrolyl, imidazolyl, triazolyl, thiazolyl, furanyl, or oxazolyl; the second aryl or heteroaryl group is substituted with a lower alkyl group, a methyl group, an ethyl group, a propyl group, a butyl group, a lower alkoxy group, a methoxy group, an ethoxy group, a propoxy group, a butoxy group, a halo subsitituted lower alkyl, —CH$_2$F, —CHF$_2$, —CF$_3$, halo, F, Cl. In further particular embodiments, the substituent group at the 3-position is each specific combination of the first linker, first aryl or heteroaryl group, second linker, second aryl or heteroaryl group, and with each of the specified substitutions on the second aryl or heteroaryl group. In particular embodiments, the second aryl or heteroaryl group is a 6-membered ring; the 6-membered ring is substituted at the para position; the 6-membered ring is substituted at the meta position; the 6-membered ring is substituted at the ortho position; the 6-membered ring is substituted at the meta and para positions. In particular embodiments, the second aryl or heteroaryl group is a 5-membered ring; the 5-membered ring is substituted at position adjacent to the atom bound to the second linker; the 5-membered ring is substituted at a position not adjacent to the atom bound to the second linker. In particular embodiments, the 3-position substituent group is the only non-hydrogen substituent on the azaindole core.

In particular embodiments, the compound has an IC$_{50}$ of less than 100 nM, less than 50 nM, less than 20 nM, less than 10 nM, less than 5 nM as determined in a generally accepted kinase activity assay. In certain embodiments, the selectivity of the compound is such that the compound is at least 2-fold, 5-fold, 10-fold, or 100-fold more active with respect to c-Kit than with respect to Ret. In certain embodiments, the compound has in combination each pairing of activity (e.g., IC$_{50}$) and selectivity as specified in this paragraph An additional aspect of this invention relates to compositions, that include a therapeutically effective amount of a compound of Formula I (or a compound within a sub-group of compounds within any of the generic formulae) and at least one pharmaceutically acceptable carrier, excipient, and/or diluent. The composition can include a plurality of different pharmacologically active compounds, which can include a plurality of compounds of Formula I.

As used herein, the term "pharmaceutical composition" refers to a formulation suitable for administration to an intended animal subject for therapeutic purposes that contains at least one active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the terms "therapeutically effective" and "effective amount" indicates that the materials and amount of material is effective to prevent, alleviate, or ameliorate one or more symptoms of a disease or medical condition, and/or to prolong the survival of the subject being treated.

In a related aspect, the invention provides kits that include a pharmaceutical composition as described herein. In particular embodiments, the pharmaceutical composition is packaged, e.g., in a vial, bottle, flask, which may be further packaged, e.g., within a box, envelope, or bag; the pharmaceutical composition is approved by the U.S. Food and Drug Administration or similar regulatory agency for administration to a mammal, e.g., a human; the pharmaceutical composition is approved for administration to a mammal, e.g., a human for a c-Kit mediated disease or condition; the kit includes written instructions of use and/or other indication that the composition is suitable or approved for administration to a mammal, e.g., a human, for a c-Kit mediated disease or condition; the pharmaceutical composition is packaged in unit does or single dose form, e.g., single dose pills, capsules, or the like.

In aspects of the present invention involving treatment or prophylaxis of a disease or conditions, the disease or condition is cancer, asthma, arthritis, chronic rhinitis, multiple sclerosis, a mastocytosis disorder, or other disease.

The identification of compounds of Formula I with activity toward c-kit also provides a method for identifying or developing additional compounds active on c-kit, e.g., improved modulators, by determining whether any of a plurality of test compounds of Formula I with activity toward c-kit provides an improvement in one or more desired pharmacologic properties relative to a reference compound with activity toward c-kit, and selecting a compound if any, that has an improvement in the desired pharmacologic property, thereby providing an improved modulator.

In particular embodiments of modulator development, the desired pharmacologic property is serum half-life longer than 2 hr or longer than 4 hr or longer than 8 hr, aqeous solubility, oral bioavailability more than 10%, oral bioavailability more than 20%.

Also in particular embodiments of modulator development, the process can be repeated multiple times, i.e., multiple rounds of preparation of derivatives and/or selection of additional related compounds and evaluation of such further derivatives of related compounds, e.g., 1, 2, 3, 4, 5, 6, 7, 8, 9, 10 or more additional rounds.

In additional aspects, structural information about c-Kit is utilized, e.g., in conjunction with compounds of Formula I or a molecular scaffold or scaffold core of Formula I.

The invention also provides a method for developing ligands binding to c-Kit, where the method includes identifying as molecular scaffolds one or more compounds of Formula I that bind to a binding site of the kinase; determining the orientation of at least one such molecular scaffold in co-crystals with the kinase; identifying chemical structures of one or more of the molecular scaffolds, that, when modified, alter the binding affinity or binding specificity or both between the molecular scaffold and the kinase; and synthesizing a ligand in which one or more of the chemical structures of the molecular scaffold is modified to provide a ligand that binds to the kinase with altered binding affinity or binding specificity or both.

Reference to particular amino acid residues in human c-Kit polypeptide residue number is defined by the numbering corresponding to the Kit sequence in GenBank NP_000213 (SEQ ID NO:1). Reference to particular nucleotide positions in a nucleotide sequence encoding all or a portion of c-Kit is defined by the numbering corresponding to the sequence provided in GenBank NM_000222 (SEQ ID NO:2).

The terms "Kit", "c-Kit", and "c-kit" mean an enzymatically active kinase that contains a portion with greater than 90% amino acid sequence identity to amino acid residues including the ATP binding site of full-length c-Kit (e.g., human c-Kit, e.g., the sequence NP_000213), for a maximal alignment over an equal length segment; or that contains a portion with greater than 90% amino acid sequence identity to at least 200 contiguous amino acids of native c-Kit and retains kinase activity. Preferably the sequence identity is at least 95, 97, 98, 99, or even 100%. Preferably the specified level of sequence identity is over a sequence at least 300 contiguous amino acid residues in length. Unless indicated to the contrary, the term includes reference wild-type c-Kit, allelic variants, and mutated forms (e.g., having activating mutations).

The term "c-Kit kinase domain" refers to a reduced length c-Kit (i.e., shorter than a fill-length c-Kit by at least 50, at least 100, at least 150, or at least 200, amino acids that includes the kinase catalytic region in c-Kit. Highly preferably for use in this invention, the kinase domain retains kinase activity, preferably at least 60, 70, 80, 90, or 100% of the native c-Kit kinase activity.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule" refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined for a particular biological system or therapeutic use. In terms of the development of ligands from scaffolds, a ligand is a derivative of a scaffold.

In the context of binding compounds, molecular scaffolds, and ligands, the term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound for another compound, having structural features retained in the derivative compound. Often but not always, a parent compound has a simpler chemical structure than the derivative.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($k_d$) of 1 mM or less. A binding compound can bind with "low affinity", "very low affinity", "extremely low affinity", "moderate affinity", "moderately high affinity", or "high affinity" as described herein.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of c-Kit, other tyrosine kinases or even other type of enzymes. In particular embodiments, the greater specificity is at least 2, 3, 4, 5, 8, 10, 50, 100, 200, 400, 500, or 1000-fold greater specificity.

As used in connection with binding of a compound with a target, the term "interact" indicates that the distance from a bound compound to a particular amino acid residue will be 5.0 angstroms or less. In particular embodiments, the distance from the compound to the particular amino acid residue is 4.5 angstroms or less, 4.0 angstroms or less, or 3.5 angstroms or less. Such distances can be determined, for example, using co-crystallography, or estimated using computer fitting of a compound in an active site.

In a related aspect, the invention provides a method for developing ligands specific for c-Kit, where the method involves determining whether a derivative of a compound of Formula I that binds to a plurality of kinases has greater specificity for that particular kinase than the parent compound with respect to other kinases.

As used herein in connection with binding compounds or ligands, the term "specific for c-Kit kinase", "specific for c-Kit" and terms of like import mean that a particular compound binds to c-Kit to a statistically greater extent than to other kinases that may be present in a particular organism. Also, where biological activity other than binding is indicated, the term "specific for c-Kit" indicates that a particular compound has greater biological effect associated with binding c-Kit than to other tyrosine kinases, e.g., kinase activity inhibition. Preferably, the specificity is also with respect to other biomolecules (not limited to tyrosine kinases) that may be present within an organism.

In another aspect, the invention provides a method for obtaining improved ligands binding to c-Kit, where the method involves identifying a compound of Formula I that binds to that particular kinase, determining whether that compound interacts with one or more conserved active site residues, and determining whether a derivative of that compound binds to that kinase with greater affinity or greater specificity or both than the parent binding compound. Binding with greater affinity or greater specificity or both than the parent compound indicates that the derivative is an improved ligand. This process can also be carried out in successive rounds of selection and derivatization and/or with multiple parent compounds to provide a compound or compounds with improved ligand characteristics. Likewise, the derivative compounds can be tested and selected to give high selectivity for that kinase, or to give cross-reactivity to a particular set of targets, for example to a subset of kinases that includes c-Kit. In particular embodiments, known c-Kit inhibitors can be used, and derivatives with greater affinity and/or greater specificity can be developed, preferably using c-Kit structure information; greater specificity for c-Kit relative to other tyrosine kinases is developed.

By "molecular scaffold" or "scaffold" is meant a simple target binding molecule to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group including, but not limited to, those recited in this application. Molecular scaffolds bind to at least one target molecule, preferably to a plurality of molecules in a protein family, and the target molecule can preferably be a enzyme, receptor, or other protein. Preferred characteristics of a scaffold can include binding at a target molecule binding site such that one or more substituents on the scaffold are situated in binding pockets in the target molecule binding site; having chemically tractable structures that can be chemically modified, particularly by synthetic reactions, so that a combinatorial library can be easily constructed; having chemical positions where moieties can be attached that do not interfere with binding of the scaffold to a protein binding site, such that the scaffold or library members can be modified to form ligands, to achieve additional desirable characteristics, e.g., enabling the ligand to be actively transported into cells and/or to specific organs, or enabling the ligand to be attached to a chromatography column for additional analysis. Thus, a molecular scaffold is an identified target binding molecule prior to modification to improve binding affinity and/or specificity, or other pharmacological properties.

The term "scaffold core" refers to the core structure of a molecular scaffold onto which various substituents can be attached. Thus, for a number of scaffold molecules of a particular chemical class, the scaffold core is common to all the scaffold molecules. In many cases, the scaffold core will consist of or include one or more ring structures.

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket can often be a particular shape, indentation, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation", in reference to a binding compound bound to a target molecule is meant the spatial relationship of the binding compound (which can be defined by reference to at least some of its consitituent atoms) to the binding pocket and/or atoms of the target molecule at least partially defining the binding pocket.

In the context of target molecules in this invention, the term "crystal" refers to a regular assemblage of a target molecule of a type suitable for X-ray crystallography. That is, the assemblage produces an X-ray diffraction pattern when illuminated with a beam of X-rays. Thus, a crystal is distinguished from an agglomerationor other complex of target molecule that does not give a diffraction pattern.

By "co-crystal" is meant a complex of the compound, molecular scaffold, or ligand bound non-covalently to the target molecule and present in a crystal form appropriate for analysis by X-ray or protein crystallography. In preferred embodiments the target molecule-ligand complex can be a protein-ligand complex.

The phrase "alter the binding affinity or binding specificity" refers to changing the binding constant of a first compound for another, or changing the level of binding of a first compound for a second compound as compared to the level of binding of the first compound for third compounds, respectively. For example, the binding specificity of a compound for a particular protein is increased if the relative level of binding to that particular protein is increased as compared to binding of the compound to unrelated proteins.

As used herein in connection with test compounds, binding compounds, and modulators (ligands), the term "synthesizing" and like terms means chemical synthesis from one or more precursor materials.

The phrase "chemical structure of the molecular scaffold is modified" means that a derivative molecule has a chemical structure that differs from that of the molecular scaffold but still contains common core chemical structural features. The phrase does not necessarily mean that the molecular scaffold is used as a precursor in the synthesis of the derivative.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

By a "set" of compounds is meant a collection of compounds. The compounds may or may not be structurally related.

As used herein, the term "azaindole scaffold" or azaindole scaffold structure" refers to the structure shown in Formula I. Similarly, the term "azaindole core" refers to the structure shown above as Formula I excluding the R groups.

The invention further relates to co-crystals of c-Kit, which may be a reduced length polypeptide, e.g., a kinase domain, and a c-Kit binding compound of Formula I or including the core structure of Formula I. Advantageously, such co-crystals are of sufficient size and quality to allow structural determination of the c-Kit to at least 3 Angstroms, 2.5 Angstroms, 2.0 Angstroms, 1.8 Angstroms, 1.7 Angstroms, 1.5 Angstroms, 1.4 Angstroms, 1.3 Angstroms, or 1.2 Angstroms. The co-crystals can, for example, be in a crystallography plate, be mounted for X-ray crystallography and/or in an X-ray beam. Such co-crystals are beneficial, for example, for obtaining structural information concerning interaction between c-Kit and binding compounds.

Crystallization conditions can be initially identified using a screening kit, such as a Hampton Research (Riverside, Calif.) screening kit 1. Conditions resulting in crystals can be selected and crystallization conditions optimized based on the demonstrated crystallization conditions. To assist in subsequent crystallography, the protein can be seleno-methionine labeled. Also, as indicated above, the protein may be any of various forms, e.g., truncated to provide a catalytic domain, which can be selected to be of various lengths.

In another aspect, provision of compounds of Formula I with activity toward c-kit (such as compounds developed using methods described herein) also provides a method for modulating the c-Kit activity by contacting c-Kit with a compound of Formula I. The compound is preferably provided at a level sufficient to modulate the activity of the c-Kit by at least 10%, more preferably at least 20%, 30%, 40%, or 50%. In many embodiments, the compound will be at a concentration of about 1 μM, 100 μM, or 1 mM, or in a range of 1-100 nM, 100-500 nM, 500-1000 nM, 1-100 μM, 100-500 μM, or 500-1000 μM. In particular embodiments, the contacting is carried out in vitro.

As used herein, the term "modulating" or "modulate" refers to an effect of altering a biological activity, especially a biological activity associated with a particular biomolecule such as c-Kit. For example, an agonist or antagonist of a particular biomolecule modulates the activity of that biomolecule, e.g., an enzyme.

The term "c-Kit activity" refers to a biological activity of c-Kit, particularly including kinase activity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As co-crystals of c-Kit have been developed and analyzed, another aspect relates to an electronic representation of c-Kit (which may be a reduced length c-Kit, usually a kinase domain), for example, an electronic representation containing atomic coordinate representations for c-Kit corresponding to the coordinates listed for c-Kit in Protein Data Bank (PDB) as 1PDG or Molecular Modeling DataBase (MMDB) as 23938, modified by the replacement of STI-571 (Gleevec) with a compound of Formula I, or a schematic representation such as one showing secondary structure and/or chain folding, and may also show conserved active site residues.

The electronic representation can also be modified by replacing electronic representations of particular residues with electronic representations of other residues. Thus, for example, an electronic representation containing atomic coordinate representations corresponding to the coordinates for c-Kit listed in a database as indicated above can be modified by the replacement of coordinates for a particular conserved residue in a binding site by a different amino acid. Following a modification or modifications, the representation of the overall structure can be adjusted to allow for the known interactions that would be affected by the modification or modifications. In most cases, a modification involving more than one residue will be performed in an iterative manner.

A binding site or catalytic domain can be represented in various ways, e.g., as representations of atomic coordinates of residues around the binding site and/or as a binding site surface contour, and can include representations of the binding character of particular residues at the binding site, e.g., conserved residues.

In another aspect, the c-Kit structural information provides a method for developing useful biological agents based on c-Kit, by analyzing a c-Kit structure to identify at least one sub-structure for forming the biological agent. Such sub-structures can include epitopes for antibody formation, and the method includes developing antibodies against the epitopes, e.g., by injecting an epitope presenting composition in a mammal such as a rabbit, guinea pig, pig, goat, or horse. The sub-structure can also include a mutation site at which mutation is expected to or is known to alter the activity of c-Kit, and the method includes creating a mutation at that site. Still further, the sub-structure can include an attachment point for attaching a separate moiety, for example, a peptide, a polypeptide, a solid phase material (e.g., beads, gels, chromatographic media, slides, chips, plates, and well surfaces), a linker, and a label (e.g., a direct label such as a fluorophore or an indirect label, such as biotin or other member of a specific binding pair). The method can include attaching the separate moiety.

In another aspect, the invention provides a method for identifying potential c-Kit binding compounds by fitting at least one electronic representation of a compound in an electronic representation of the c-Kit binding site. The representation of the binding site may be part of an electronic representation of a larger portion(s) or all of a c-Kit molecule or may be a representation of only the catalytic domain or of the binding site or active site. The electronic representation may be as described above or otherwise described herein.

In particular embodiments, the method involves fitting a computer representation of a compound from a computer database with a computer representation of the active site of the kinase, and involves removing a computer representation of a compound complexed with the kinase molecule and identifying compounds that best fit the active site based on favorable geometric fit and energetically favorable complementary interactions as potential binding compounds. In particular embodiments, the compound is a known c-Kit inhibitor, e.g., as described in a reference cited herein, or a derivative thereof.

In other embodiments, the method involves modifying a computer representation of a compound complexed with the kinase molecule, by the deletion or addition or both of one or more chemical groups; fitting a computer representation of a compound from a computer database with a computer representation of the active site of the kinase molecule; and identifying compounds that best fit the active site based on favorable geometric fit and energetically favorable complementary interactions as potential binding compounds.

In still other embodiments, the method involves removing a computer representation of a compound complexed with the kinase, and searching a database for compounds having structural similarity to the complexed compound using a compound searching computer program or replacing portions of the complexed compound with similar chemical structures using a compound construction computer program.

Fitting a compound can include determining whether a compound will interact with one or more conserved active site residues for the kinase. Compounds selected for fitting or that are complexed with the kinase can, for example, be a known c-Kit inhibitor compound, or a compound including the core structure of such compound.

In another aspect, the invention provides a method for attaching a c-Kit binding compound to an attachment component, as well as a method for indentifying attachment sites on a c-Kit binding compound. The method involves identifying energetically allowed sites for attachment of an attachment component for the binding compound bound to a binding site of c-Kit; and attaching the compound or a derivative thereof to the attachment component at the energetically allowed site.

Attachment components can include, for example, linkers (including traceless linkers) for attachment to a solid phase or to another molecule or other moiety. Such attachment can be formed by synthesizing the compound or derivative on the linker attached to a solid phase medium e.g., in a combinatorial synthesis in a plurality of compound. Likewise, the attachment to a solid phase medium can provide an affinity medium (e.g., for affinity chromatography).

The attachment component can also include a label, which can be a directly detectable label such as a fluorophore, or an indirectly detectable such as a member of a specific binding pair, e.g., biotin.

The ability to identify energetically allowed sites on a c-Kit binding compound, also, in a related aspect, provides modified binding compounds that have linkers attached, preferably at an energetically allowed site for binding of the modified compound to c-Kit. The linker can be attached to an attachment component as described above.

Another aspect of the present invention relates to a modified c-Kit polypeptide that includes a modification that makes the modified c-Kit more similar than native c-Kit to another tyrosine kinase, and can also include other mutations or other modifications. In various embodiments, the polypeptide includes a full-length c-Kit polypeptide, includes a modified c-Kit binding site, includes at least 20, 30, 40, 50, 60, 70, or 80 contiguous amino acid residues derived from c-Kit including a conserved site.

The invention also provides compounds that bind to and/or modulate (e.g., inhibit) c-Kit activity e.g., compounds identified by the methods described herein. Accordingly, in aspects and embodiments involving c-Kit binding compounds, molecular scaffolds, and ligands or modulators, the compound is a weak binding compound; a moderate binding compound; a strong binding compound; the compound interacts with one or more conserved active site residues in the kinase; the compound is a small molecule; the compound binds to a plurality of different kinases (e.g., at least 2, 3, 4, 5, 7, 10, or more different kinases). In particular, the invention relates to compounds identified or selected using the methods described herein, or compounds of Formula I.

In the various aspects described above that involve atomic coordinates for c-Kit binding site in connection with binding compounds, the coordinates provided in the listed databases can be used. Those coordinates can then be adjusted using conventional modeling methods to fit compounds having structures different from the compounds identified herein, and can thus be used for development of c-Kit modulators different from currently described c-Kit modulators.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the particular molecule constitutes a significantly greater proportion of the biomolecules in a composition than in a prior composition, e.g., in a cell culture. The greater proportion can be 2-fold, 5-fold, 10-fold or more greater.

Additional aspects and embodiments will be apparent from the following Detailed Description and from the claims.

DETAILED DESCRIPTION OF THE PREFERRED EMBODIMENTS

I. General

The present invention provides compounds of Formula I that are inhibitors of c-Kit, and the use of models of the binding site of c-Kit, structural information, and related compositions for developing improved compounds with those structures that modulate c-Kit activity.

Table 1 provides the structures and names of a set of exemplary compounds of Formula I with activity toward c-kit.

Table 2 provides descriptions of additional exemplary compounds of Formula I.

Exemplary compounds of Formula I active against c-kit are shown in Table 1.

TABLE 1

| Table Cmpd | Cmpd # | Structure | Name | MW |
|---|---|---|---|---|
| 1-1 | 9 | 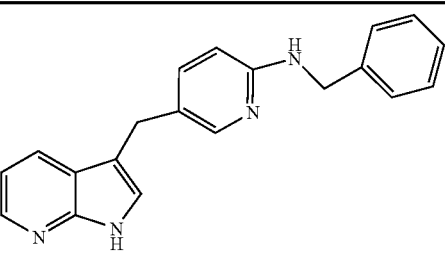 | benzyl-[5-(1H-pyrrolo[2,3-b]pyridin-3-ylmethyl)-pyridin-2-yl]-amine | 315 |

TABLE 1-continued

| Table Cmpd | Cmpd # | Structure | Name | MW |
|---|---|---|---|---|
| 1-2 | 11 | 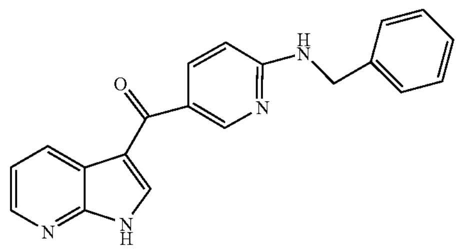 | (6-Benzylamino-pyridin-3-yl)-(1H-pyrrolo[2,3-b]pyridin-3-yl)-methanone | 329 |
| 1-3 | 12 | 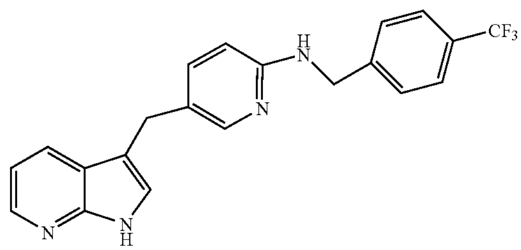 | [5-(1H-Pyrrolo[2,3-b]pyridin-3-ylmethyl)-pyridin-2-yl]-(4-trifluoromethyl-benzyl)-amine | 383 |
| 1-4 | 15 | 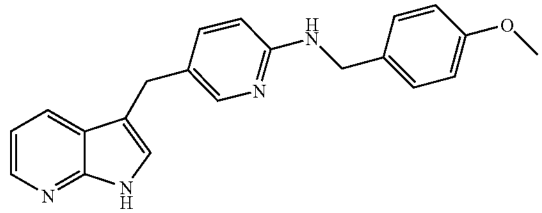 | (4-methoxy-benzyl)-[5-(1H-pyrrolo[2,3-b]pyridin-3-ylmethyl)-pyridin-2-yl]-amine | 344.4 |
| 1-5 | 16 | 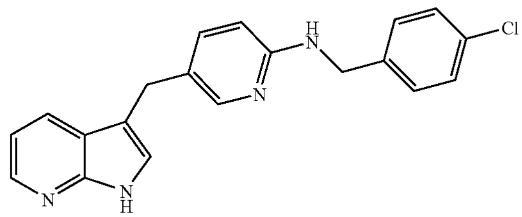 | (4-chloro-benzyl)-[5-(1H-pyrrolo[2,3-b]pyridin-3-ylmethyl)-pyridin-2-yl]-amine | 348.8 |
| 1-6 | 17 | 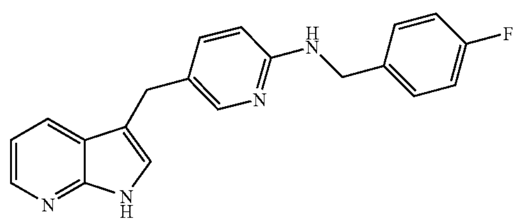 | (4-fluoro-benzyl)-[5-(1H-pyrrolo[2,3-b]pyridin-3-ylmethyl)-pyridin-2-yl]-amine | 332.4 |
| 1-7 | 18 | 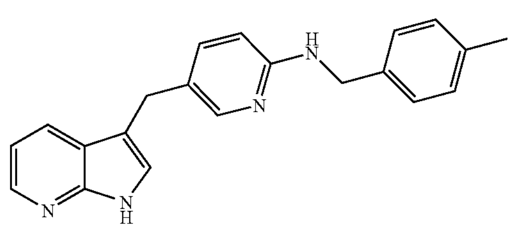 | (4-methyl-benzyl)-[5-(1H-pyrrolo[2,3-b]pyridin-3-ylmethyl)-pyridin-2-yl]-amine | 328.4 |

TABLE 1-continued

| Table Cmpd | Cmpd # | Structure | Name | MW |
|---|---|---|---|---|
| 1-8 | 19 | 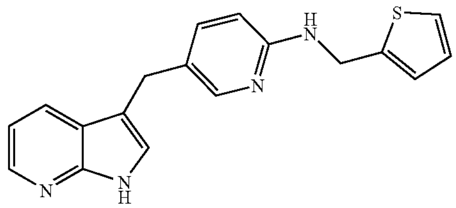 | [5-(1H-pyrrolo[2,3-b]pyridin-3-ylmethyl)-pyridin-2-yl]-thiophen-2-ylmethyl-amine | 330.4 |

Additional exemplary compounds of Formula I are described in Table 2 by describing the moieties present in the following sub-generic structure of Formula I. In this sub-generic structure, $L^1$ is a non-cyclic linker with 1-3 linked atoms connecting $C^1$ with the bi-cyclic core (not counting any side groups or atoms); $C^1$ is cyclic group, preferably an aryl or heteroaryl group, $L^2$ is a non-cyclic linker with 1-4 linked atoms connecting $C^1$ and $C^2$ (not counting any side groups or atoms); $Z_p$ represents p non-hydrogen substituents on $C^2$, where p is 0-4 and each Z may be the same or different.

TABLE 2

$L^1$—$C^1$—$L^2$—$C^2$—$Z_p$

| $L^1$ | $C^1$ | $L^2$ | $C^2$ | Z |
|---|---|---|---|---|
| CH$_2$ | pyridinyl | NH—CH$_2$ | Phenyl | None |
| CH$_2$ | pyridinyl | NH—CH$_2$ | Phenyl | $Z_1$: F (para) |
| CH$_2$ | pyridinyl | NH—CH$_2$ | Phenyl | $Z_1$: F (meta) |
| CH$_2$ | pyridinyl | NH—CH$_2$ | Phenyl | $Z_1$: F (ortho) |
| CH$_2$ | pyridinyl | NH—CH$_2$ | Phenyl | $Z_1$: F (para) $Z_2$: F (meta) |
| CH$_2$ | Pyridinyl | NH—CH$_2$ | Phenyl | $Z_1$: Cl (meta) |
| CH$_2$ | Pyridinyl | NH—CH$_2$ | Phenyl | $Z_1$: Cl (para) |
| CH$_2$ | Pyridinyl | NH—CH$_2$ | Phenyl | $Z_1$: Cl (para) $Z_2$: Cl (meta) |
| CH$_2$ | Pyridinyl | NH—CH$_2$ | Phenyl | $Z_1$: F (para) $Z_2$: Cl (meta) |
| CH$_2$ | Pyridinyl | NH—CH$_2$ | Phenyl | $Z_1$: Cl (para) $Z_2$: F (meta) |
| CH$_2$ | Pyridinyl | NH—CH$_2$ | Phenyl | $Z_1$: CH$_3$ (para) |
| CH$_2$ | Pyridinyl | NH—CH$_2$ | Phenyl | $Z_1$: CH$_3$ (meta) |
| CH$_2$ | Pyridinyl | NH—CH$_2$ | Phenyl | $Z_1$: CH$_3$ (ortho) |
| CH$_2$ | Pyridinyl | NH—CH$_2$ | Phenyl | $Z_1$: CH$_2$—CH$_3$ (para) |
| CH$_2$ | Pyridinyl | NH—CH$_2$ | Phenyl | $Z_1$: CH$_2$—CH$_3$ (meta) |
| CH$_2$ | Pyridinyl | NH—CH$_2$ | Phenyl | $Z_1$: CH$_2$—CH$_3$ (ortho) |
| CH$_2$ | Pyridinyl | NH—CH$_2$ | Phenyl | $Z_1$: CH$_2$—CH$_2$—CH$_3$ or iPr (para) |
| CH$_2$ | Pyridinyl | NH—CH$_2$ | Phenyl | $Z_1$: CH$_2$—CH$_2$—CH$_3$ or iPr (meta) |
| CH$_2$ | Pyridinyl | NH—CH$_2$ | Phenyl | $Z_1$: CH$_2$—CH$_2$—CH$_3$ or iPr (ortho) |
| CH$_2$ | Pyridinyl | NH—CH$_2$ | Phenyl | $Z_1$: CH$_2$F (para) |
| CH$_2$ | Pyridinyl | NH—CH$_2$ | Phenyl | $Z_1$: CH$_2$F (meta) |
| CH$_2$ | Pyridinyl | NH—CH$_2$ | Phenyl | $Z_1$: CH$_2$F (ortho) |
| CH$_2$ | Pyridinyl | NH—CH$_2$ | Phenyl | $Z_1$: CHF$_2$ (para) |
| CH$_2$ | Pyridinyl | NH—CH$_2$ | Phenyl | $Z_1$: CHF$_2$ (meta) |
| CH$_2$ | Pyridinyl | NH—CH$_2$ | Phenyl | $Z_1$: CHF$_2$ (ortho) |
| CH$_2$ | Pyridinyl | NH—CH$_2$ | Phenyl | $Z_1$: CF$_3$ (para) |
| CH$_2$ | Pyridinyl | NH—CH$_2$ | Phenyl | $Z_1$: CF$_3$ (meta) |
| CH$_2$ | Pyridinyl | NH—CH$_2$ | Phenyl | $Z_1$: CF$_3$ (ortho) |
| CH$_2$ | Pyridinyl | NH—CH$_2$ | Phenyl | $Z_1$: CH$_2$—CH$_2$F (para) |
| CH$_2$ | Pyridinyl | NH—CH$_2$ | Phenyl | $Z_1$: CH$_2$—CH$_2$F (meta) |
| CH$_2$ | Pyridinyl | NH—CH$_2$ | Phenyl | $Z_1$: CH$_2$—CH$_2$F (ortho) |
| CH$_2$ | Pyridinyl | NH—CH$_2$ | Phenyl | $Z_1$: CH$_2$—CHF$_2$ (para) |
| CH$_2$ | Pyridinyl | NH—CH$_2$ | Phenyl | $Z_1$: CH$_2$—CHF$_2$ (meta) |
| CH$_2$ | Pyridinyl | NH—CH$_2$ | Phenyl | $Z_1$: CH$_2$—CHF$_2$ (ortho) |
| CH$_2$ | Pyridinyl | NH—CH$_2$ | Phenyl | $Z_1$: CH$_2$—CF$_3$ (para) |
| CH$_2$ | Pyridinyl | NH—CH$_2$ | Phenyl | $Z_1$: CH$_2$—CF$_3$ (meta) |

TABLE 2-continued $$L^1-C^1-L^2-C^2-Z_p$$

(7-azaindole structure)

| L¹ | C¹ | L² | C² | Z |
|---|---|---|---|---|
| CH₂ | Pyridinyl | NH—CH₂ | Phenyl | Z₁: CH₂—CF₃ (ortho) |
| CH₂ | pyridinyl | NH—CH₂ | Pyridinyl | None |
| CH₂ | pyridinyl | NH—CH₂ | Pyridinyl | Z₁: F (para) |
| CH₂ | pyridinyl | NH—CH₂ | Pyridinyl | Z₁: F (meta) |
| CH₂ | pyridinyl | NH—CH₂ | Pyridinyl | Z₁: F (ortho) |
| CH₂ | pyridinyl | NH—CH₂ | Pyridinyl | Z₁: F (para) Z₂: F (meta) |
| CH₂ | Pyridinyl | NH—CH₂ | Pyridinyl | Z₁: Cl (meta) |
| CH₂ | Pyridinyl | NH—CH₂ | Pyridinyl | Z₁: Cl (para) |
| CH₂ | Pyridinyl | NH—CH₂ | Pyridinyl | Z₁: Cl (para) Z₂: Cl (meta) |
| CH₂ | Pyridinyl | NH—CH₂ | Pyridinyl | Z₁: F (para) Z₂: Cl (meta) |
| CH₂ | Pyridinyl | NH—CH₂ | Pyridinyl | Z₁: Cl (para) Z₂: F (meta) |
| CH₂ | Pyridinyl | NH—CH₂ | Pyridinyl | Z₁: CH₃ (para) |
| CH₂ | Pyridinyl | NH—CH₂ | Pyridinyl | Z₁: CH₃ meta) |
| CH₂ | Pyridinyl | NH—CH₂ | Pyridinyl | Z₁: CH₃ (ortho) |
| CH₂ | Pyridinyl | NH—CH₂ | Pyridinyl | Z₁: CH₂—CH₃ (para) |
| CH₂ | Pyridinyl | NH—CH₂ | Pyridinyl | Z₁: CH₂—CH₃ (meta) |
| CH₂ | Pyridinyl | NH—CH₂ | Pyridinyl | Z₁: CH₂—CH₃ ortho |
| CH₂ | Pyridinyl | NH—CH₂ | Pyridinyl | Z₁: CH₂—CH₂—CH₃ or iPr (para) |
| CH₂ | Pyridinyl | NH—CH₂ | Pyridinyl | Z₁: CH₂—CH₂—CH₃ or iPr (meta) |
| CH₂ | Pyridinyl | NH—CH₂ | Pyridinyl | Z₁: CH₂—CH₂—CH₃ or iPr (ortho) |
| CH₂ | Pyridinyl | NH—CH₂ | Pyridinyl | Z₁: CH₂F (para) |
| CH₂ | Pyridinyl | NH—CH₂ | Pyridinyl | Z₁: CH₂F (meta) |
| CH₂ | Pyridinyl | NH—CH₂ | Pyridinyl | Z₁: CH₂F (ortho) |
| CH₂ | Pyridinyl | NH—CH₂ | Pyridinyl | Z₁: CHF₂ (para) |
| CH₂ | Pyridinyl | NH—CH₂ | Pyridinyl | Z₁: CHF₂ (meta) |
| CH₂ | Pyridinyl | NH—CH₂ | Pyridinyl | Z₁: CHF₂ (ortho) |
| CH₂ | Pyridinyl | NH—CH₂ | Pyridinyl | Z₁: CF₃ (para) |
| CH₂ | Pyridinyl | NH—CH₂ | Pyridinyl | Z₁: CF₃ (meta) |
| CH₂ | Pyridinyl | NH—CH₂ | Pyridinyl | Z₁: CF₃ (ortho) |
| CH₂ | Pyridinyl | NH—CH₂ | Pyridinyl | Z₁: CH₂—CH₂F (para) |
| CH₂ | Pyridinyl | NH—CH₂ | Pyridinyl | Z₁: CH₂—CH₂F (meta) |
| CH₂ | Pyridinyl | NH—CH₂ | Pyridinyl | Z₁: CH₂—CH₂F (ortho) |
| CH₂ | Pyridinyl | NH—CH₂ | Pyridinyl | Z₁: CH₂—CHF₂ (para) |
| CH₂ | Pyridinyl | NH—CH₂ | Pyridinyl | Z₁: CH₂—CHF₂ (meta) |
| CH₂ | Pyridinyl | NH—CH₂ | Pyridinyl | Z₁: CH₂—CHF₂ (ortho) |
| CH₂ | Pyridinyl | NH—CH₂ | Pyridinyl | Z₁: CH₂—CF₃ (para) |
| CH₂ | Pyridinyl | NH—CH₂ | Pyridinyl | Z₁: CH₂—CF₃ (meta) |
| CH₂ | Pyridinyl | NH—CH₂ | Pyridinyl | Z₁: CH₂—CF₃ (ortho) |
| CH₂ | pyridinyl | NH—CH₂ | Pyrimidinyl | None |
| CH₂ | pyridinyl | NH—CH₂ | Pyrimidinyl | Z₁: F (para) |
| CH₂ | pyridinyl | NH—CH₂ | Pyrimidinyl | Z₁: F (meta) |
| CH₂ | pyridinyl | NH—CH₂ | Pyrimidinyl | Z₁: F (ortho) |
| CH₂ | pyridinyl | NH—CH₂ | Pyrimidinyl | Z₁: F (para) Z₂: F (meta) |
| CH₂ | Pyridinyl | NH—CH₂ | Pyrimidinyl | Z₁: Cl (meta) |
| CH₂ | Pyridinyl | NH—CH₂ | Pyrimidinyl | Z₁: Cl (para) |
| CH₂ | Pyridinyl | NH—CH₂ | Pyrimidinyl | Z₁: Cl (para) Z₂: Cl (meta) |
| CH₂ | Pyridinyl | NH—CH₂ | Pyrimidinyl | Z₁: F (para) Z₂: Cl (meta) |
| CH₂ | Pyridinyl | NH—CH₂ | Pynmidinyl | Z₁: Cl (para) Z₂: F (meta) |
| CH₂ | Pyridinyl | NH—CH₂ | Pyrimidinyl | Z₁: CH₃ (para) |
| CH₂ | Pyridinyl | NH—CH₂ | Pyrimidinyl | Z₁: CH₃ (meta) |
| CH₂ | Pyridinyl | NH—CH₂ | Pyrimidinyl | Z₁: CH₃ (ortho) |
| CH₂ | Pyridinyl | NH—CH₂ | Pyrimidinyl | Z₁: CH₂—CH₃ (para) |
| CH₂ | Pyridinyl | NH—CH₂ | Pyrimidinyl | Z₁: CH₂—CH₃ (meta) |
| CH₂ | Pyridinyl | NH—CH₂ | Pyrimidinyl | Z₁: CH₂—CH₃ (ortho) |
| CH₂ | Pyridinyl | NH—CH₂ | Pyrimidinyl | Z₁: CH₂—CH₂—CH₃ or iPr (para) |
| CH₂ | Pyridinyl | NH—CH₂ | Pyrimidinyl | Z₁: CH₂—CH₂—CH₃ or iPr (meta) |

TABLE 2-continued

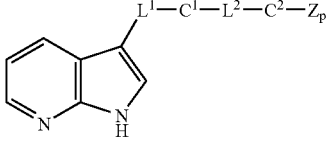

| L¹ | C¹ | L² | C² | Z |
|---|---|---|---|---|
| CH₂ | Pyridinyl | NH—CH₂ | Pyrimidinyl | $Z_1$: CH₂—CH₂—CH₃ or iPr (ortho) |
| CH₂ | Pyridinyl | NH—CH₂ | Pyrimidinyl | $Z_1$: CH₂F (para) |
| CH₂ | Pyridinyl | NH—CH₂ | Pyrimidinyl | $Z_1$: CH₂F (meta) |
| CH₂ | Pyridinyl | NH—CH₂ | Pyrimidinyl | $Z_1$: CH₂F (ortho) |
| CH₂ | Pyridinyl | NH—CH₂ | Pyrimidinyl | $Z_1$: CHF₂ (para) |
| CH₂ | Pyridinyl | NH—CH₂ | Pyrimidinyl | $Z_1$: CHF₂ (meta) |
| CH₂ | Pyridinyl | NH—CH₂ | Pyrimidinyl | $Z_1$: CHF₂ (ortho) |
| CH₂ | Pyridinyl | NH—CH₂ | Pyrimidinyl | $Z_1$: CF₃ (para) |
| CH₂ | Pyridinyl | NH—CH₂ | Pyrimidinyl | $Z_1$: CF₃ (meta) |
| CH₂ | Pyridinyl | NH—CH₂ | Pyrimidinyl | $Z_1$: CF₃ (ortho) |
| CH₂ | Pyridinyl | NH—CH₂ | Pyrimidinyl | $Z_1$: CH₂—CH₂F (para) |
| CH₂ | Pyridinyl | NH—CH₂ | Pyrimidinyl | $Z_1$: CH₂—CH₂F (meta) |
| CH₂ | Pyridinyl | NH—CH₂ | Pyrimidinyl | $Z_1$: CH₂—CH₂F (ortho) |
| CH₂ | Pyridinyl | NH—CH₂ | Pyrimidinyl | $Z_1$: CH₂—CHF₂ (para) |
| CH₂ | Pyridinyl | NH—CH₂ | Pyrimidinyl | $Z_1$: CH₂—CHF₂ (meta) |
| CH₂ | Pyridinyl | NH—CH₂ | Pyrimidinyl | $Z_1$: CH₂—CHF₂ (ortho) |
| CH₂ | Pyridinyl | NH—CH₂ | Pyrimidinyl | $Z_1$: CH₂—CF₃ (para) |
| CH₂ | Pyridinyl | NH—CH₂ | Pyrimidinyl | $Z_1$: CH₂—CF₃ (meta) |
| CH₂ | Pyridinyl | NH—CH₂ | Pyrimidinyl | $Z_1$: CH₂—CF₃ (ortho) |
| CH₂ | pyridinyl | NH—CH₂ | Pyrazinyl | None |
| CH₂ | pyridinyl | NH—CH₂ | Pyrazinyl | $Z_1$: F (para) |
| CH₂ | pyridinyl | NH—CH₂ | Pyrazinyl | $Z_1$: F (meta) |
| CH₂ | pyridinyl | NH—CH₂ | Pyrazinyl | $Z_1$: F (ortho) |
| CH₂ | pyridinyl | NH—CH₂ | Pyrazinyl | $Z_1$: F (para) $Z_2$: F (meta) |
| CH₂ | Pyridinyl | NH—CH₂ | Pyrazinyl | $Z_1$: Cl (meta) |
| CH₂ | Pyridinyl | NH—CH₂ | Pyrazinyl | $Z_1$: Cl (para) |
| CH₂ | Pyridinyl | NH—CH₂ | Pyrazinyl | $Z_1$: Cl (para) $Z_2$: Cl (meta) |
| CH₂ | Pyridinyl | NH—CH₂ | Pyrazinyl | $Z_1$: F (para) $Z_2$: Cl (meta) |
| CH₂ | Pyridinyl | NH—CH₂ | Pyrazinyl | $Z_1$: Cl (para) $Z_2$: F (meta) |
| CH₂ | Pyridinyl | NH—CH₂ | Pyrazinyl | $Z_1$: CH₃ (para) |
| CH₂ | Pyridinyl | NH—CH₂ | Pyrazinyl | $Z_1$: CH₃ (meta) |
| CH₂ | Pyridinyl | NH—CH₂ | Pyrazinyl | $Z_1$: CH₃ (ortho) |
| CH₂ | Pyridinyl | NH—CH₂ | Pyrazinyl | $Z_1$: CH₂—CH₃ (para) |
| CH₂ | Pyridinyl | NH—CH₂ | Pyrazinyl | $Z_1$: CH₂—CH₃ (meta) |
| CH₂ | Pyridinyl | NH—CH₂ | Pyrazinyl | $Z_1$: CH₂—CH₃ (ortho) |
| CH₂ | Pyridinyl | NH—CH₂ | Pyrazinyl | $Z_1$: CH₂—CH₂—CH₃ or iPr (para) |
| CH₂ | Pyridinyl | NH—CH₂ | Pyrazinyl | $Z_1$: CH₂—CH₂—CH₃ or iPr (meta) |
| CH₂ | Pyridinyl | NH—CH₂ | Pyrazinyl | $Z_1$: CH₂—CH₂—CH₃ or iPr (ortho) |
| CH₂ | Pyridinyl | NH—CH₂ | Pyrazinyl | $Z_1$: CH₂F (para) |
| CH₂ | Pyridinyl | NH—CH₂ | Pyrazinyl | $Z_1$: CH₂F (meta) |
| CH₂ | Pyridinyl | NH—CH₂ | Pyrazinyl | $Z_1$: CH₂F (ortho) |
| CH₂ | Pyridinyl | NH—CH₂ | Pyrazinyl | $Z_1$: CHF₂ (para) |
| CH₂ | Pyridinyl | NH—CH₂ | Pyrazinyl | $Z_1$: CHF₂ (meta) |
| CH₂ | Pyridinyl | NH—CH₂ | Pyrazinyl | $Z_1$: CHF₂ (ortho) |
| CH₂ | Pyridinyl | NH—CH₂ | Pyrazinyl | $Z_1$: CF₃ (para) |
| CH₂ | Pyridinyl | NH—CH₂ | Pyrazinyl | $Z_1$: CF₃ (meta) |
| CH₂ | Pyridinyl | NH—CH₂ | Pyrazinyl | $Z_1$: CF₃ (ortho) |
| CH₂ | Pyridinyl | NH—CH₂ | Pyrazinyl | $Z_1$: CH₂—CH₂F (para) |
| CH₂ | Pyridinyl | NH—CH₂ | Pyrazinyl | $Z_1$: CH₂—CH₂F (meta) |
| CH₂ | Pyridinyl | NH—CH₂ | Pyrazinyl | $Z_1$: CH₂—CH₂F (ortho) |
| CH₂ | Pyridinyl | NH—CH₂ | Pyrazinyl | $Z_1$: CH₂—CHF₂ (para) |
| CH₂ | Pyridinyl | NH—CH₂ | Pyrazinyl | $Z_1$: CH₂—CHF₂ (meta) |
| CH₂ | Pyridinyl | NH—CH₂ | Pyrazinyl | $Z_1$: CH₂—CHF₂ (ortho) |
| CH₂ | Pyridinyl | NH—CH₂ | Pyrazinyl | $Z_1$: CH₂—CF₃ (para) |
| CH₂ | Pyridinyl | NH—CH₂ | Pyrazinyl | $Z_1$: CH₂—CF₃ (meta) |
| CH₂ | Pyridinyl | NH—CH₂ | Pyrazinyl | $Z_1$: CH₂—CF₃ (ortho) |
| CH₂ | pyridinyl | NH—CH₂ | Pyrrolyl | None |
| CH₂ | pyridinyl | NH—CH₂ | Pyrrolyl | $Z_1$: F (2) |
| CH₂ | pyridinyl | NH—CH₂ | Pyrrolyl | $Z_1$: F (3) |
| CH₂ | pyridinyl | NH—CH₂ | Pyrrolyl | $Z_1$: F (2) $Z_2$: F (3) |

TABLE 2-continued $$L^1-C^1-L^2-C^2-Z_p$$

[Structure: 7-azaindole (1H-pyrrolo[2,3-b]pyridine) with substitution at 3-position]

| L¹ | C¹ | L² | C² | Z |
|---|---|---|---|---|
| CH₂ | Pyridinyl | NH—CH₂ | Pyrrolyl | $Z_1$: Cl (2) |
| CH₂ | Pyridinyl | NH—CH₂ | Pyrrolyl | $Z_1$: Cl (3) |
| CH₂ | Pyridinyl | NH—CH₂ | Pyrrolyl | $Z_1$: Cl (2) $Z_2$: Cl (3) |
| CH₂ | Pyridinyl | NH—CH₂ | Pyrrolyl | $Z_1$: F (2) $Z_2$: Cl (3) |
| CH₂ | Pyridinyl | NH—CH₂ | Pyrrolyl | $Z_1$: Cl (2) $Z_2$: F (3) |
| CH₂ | Pyridinyl | NH—CH₂ | Pyrrolyl | $Z_1$: CH₃ (2) |
| CH₂ | Pyridinyl | NH—CH₂ | Pyrrolyl | $Z_1$: CH₃ (3) |
| CH₂ | Pyridinyl | NH—CH₂ | Pyrrolyl | $Z_1$: CH₂—CH₃ (2) |
| CH₂ | Pyridinyl | NH—CH₂ | Pyrrolyl | $Z_1$: CH₂—CH₃ (3) |
| CH₂ | Pyridinyl | NH—CH₂ | Pyrrolyl | $Z_1$: CH₂—CH₂—CH₃ or iPr (2) |
| CH₂ | Pyridinyl | NH—CH₂ | Pyrrolyl | $Z_1$: CH₂—CH₂—CH₃ or iPr (3) |
| CH₂ | Pyridinyl | NH—CH₂ | Pyrrolyl | $Z_1$: CH₂F (2) |
| CH₂ | Pyridinyl | NH—CH₂ | Pyrrolyl | $Z_1$: CH₂F (3) |
| CH₂ | Pyridinyl | NH—CH₂ | Pyrrolyl | $Z_1$: CHF₂ (2) |
| CH₂ | Pyridinyl | NH—CH₂ | Pyrrolyl | $Z_1$: CHF₂ (3) |
| CH₂ | Pyridinyl | NH—CH₂ | Pyrrolyl | $Z_1$: CF₃ (2) |
| CH₂ | Pyridinyl | NH—CH₂ | Pyrrolyl | $Z_1$: CF₃ (3) |
| CH₂ | Pyridinyl | NH—CH₂ | Pyrrolyl | $Z_1$: CH₂—CH₂F (2) |
| CH₂ | Pyridinyl | NH—CH₂ | Pyrrolyl | $Z_1$: CH₂—CH₂F (3) |
| CH₂ | Pyridinyl | NH—CH₂ | Pyrrolyl | $Z_1$: CH₂—CHF₂ (2) |
| CH₂ | Pyridinyl | NH—CH₂ | Pyrrolyl | $Z_1$: CH₂—CHF₂ (3) |
| CH₂ | Pyridinyl | NH—CH₂ | Pyrrolyl | $Z_1$: CH₂—CF₃ (2) |
| CH₂ | Pyridinyl | NH—CH₂ | Pyrrolyl | $Z_1$: CH₂—CF₃ (3) |
| CH₂ | pyridinyl | NH—CH₂ | Imidazolyl | None |
| CH₂ | pyridinyl | NH—CH₂ | Imidazolyl | $Z_1$: F (2) |
| CH₂ | pyridinyl | NH—CH₂ | Imidazolyl | $Z_1$: F (3) |
| CH₂ | pyridinyl | NH—CH₂ | Imidazolyl | $Z_1$: F (2) $Z_2$: F (3) |
| CH₂ | Pyridinyl | NH—CH₂ | Imidazolyl | $Z_1$: Cl (2) |
| CH₂ | Pyridinyl | NH—CH₂ | Imidazolyl | $Z_1$: Cl (3) |
| CH₂ | Pyridinyl | NH—CH₂ | Imidazolyl | $Z_1$: Cl (2) $Z_2$: Cl (3) |
| CH₂ | Pyridinyl | NH—CH₂ | Imidazolyl | $Z_1$: F (2) $Z_2$: Cl (3) |
| CH₂ | Pyridinyl | NH—CH₂ | Imidazolyl | $Z_1$: Cl (2) $Z_2$: F (3) |
| CH₂ | Pyridinyl | NH—CH₂ | Imidazolyl | $Z_1$: CH₃ (2) |
| CH₂ | Pyridinyl | NH—CH₂ | Imidazolyl | $Z_1$: CH₃ (3) |
| CH₂ | Pyridinyl | NH—CH₂ | Imidazolyl | $Z_1$: CH₂—CH₃ (2) |
| CH₂ | Pyridinyl | NH—CH₂ | Imidazolyl | $Z_1$: CH₂—CH₃ (3) |
| CH₂ | Pyridinyl | NH—CH₂ | Imidazolyl | $Z_1$: CH₂—CH₂—CH₃ or iPr (2) |
| CH₂ | Pyridinyl | NH—CH₂ | Imidazolyl | $Z_1$: CH₂—CH₂—CH₃ or iPr (3) |
| CH₂ | Pyridinyl | NH—CH₂ | Imidazolyl | $Z_1$: CH₂F (2) |
| CH₂ | Pyridinyl | NH—CH₂ | Imidazolyl | $Z_1$: CH₂F (3) |
| CH₂ | Pyridinyl | NH—CH₂ | Imidazolyl | $Z_1$: CHF₂ (2) |
| CH₂ | Pyridinyl | NH—CH₂ | Imidazolyl | $Z_1$: CHF₂ (3) |
| CH₂ | Pyridinyl | NH—CH₂ | Imidazolyl | $Z_1$: CF₃ (2) |
| CH₂ | Pyridinyl | NH—CH₂ | Imidazolyl | $Z_1$: CF₃ (3) |
| CH₂ | Pyridinyl | NH—CH₂ | Imidazolyl | $Z_1$: CH₂—CH₂F (2) |
| CH₂ | Pyridinyl | NH—CH₂ | Imidazolyl | $Z_1$: CH₂—CH₂F (3) |
| CH₂ | Pyridinyl | NH—CH₂ | Imidazolyl | $Z_1$: CH₂—CHF₂ (2) |
| CH₂ | Pyridinyl | NH—CH₂ | Imidazolyl | $Z_1$: CH₂—CHF₂ (3) |
| CH₂ | Pyridinyl | NH—CH₂ | Imidazolyl | $Z_1$: CH₂—CF₃ (2) |
| CH₂ | Pyridinyl | NH—CH₂ | Imidazolyl | $Z_1$: CH₂—CF₃ (3) |
| CH₂ | pyridinyl | NH—CH₂ | Furanyl | None |
| CH₂ | pyridinyl | NH—CH₂ | Furanyl | $Z_1$: F (2) |
| CH₂ | pyridinyl | NH—CH₂ | Furanyl | $Z_1$: F (3) |
| CH₂ | pyridinyl | NH—CH₂ | Furanyl | $Z_1$: F (2) $Z_2$: F (3) |
| CH₂ | Pyridinyl | NH—CH₂ | Furanyl | $Z_1$: Cl (2) |
| CH₂ | Pyridinyl | NH—CH₂ | Furanyl | $Z_1$: Cl (3) |
| CH₂ | Pyridinyl | NH—CH₂ | Furanyl | $Z_1$: Cl (2) $Z_2$: Cl (3) |
| CH₂ | Pyridinyl | NH—CH₂ | Furanyl | $Z_1$: F (2) $Z_2$: Cl (3) |

TABLE 2-continued

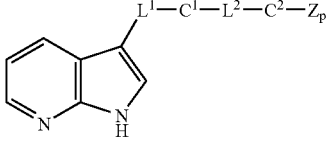

| L$^1$ | C$^1$ | L$^2$ | C$^2$ | Z |
|---|---|---|---|---|
| CH$_2$ | Pyridinyl | NH—CH$_2$ | Furanyl | Z$_1$: Cl (2) |
|  |  |  |  | Z$_2$: F (3) |
| CH$_2$ | Pyridinyl | NH—CH$_2$ | Furanyl | Z$_1$: CH$_3$ (2) |
| CH$_2$ | Pyridinyl | NH—CH$_2$ | Furanyl | Z$_1$: CH$_3$ (3) |
| CH$_2$ | Pyridinyl | NH—CH$_2$ | Furanyl | Z$_1$: CH$_2$—CH$_3$ (2) |
| CH$_2$ | Pyridinyl | NH—CH$_2$ | Furanyl | Z$_1$: CH$_2$—CH$_3$ (3) |
| CH$_2$ | Pyridinyl | NH—CH$_2$ | Furanyl | Z$_1$: CH$_2$—CH$_2$—CH$_3$ or iPr (2) |
| CH$_2$ | Pyridinyl | NH—CH$_2$ | Furanyl | Z$_1$: CH$_2$—CH$_2$—CH$_3$ or iPr (3) |
| CH$_2$ | Pyridinyl | NH—CH$_2$ | Furanyl | Z$_1$: CH$_2$F (2) |
| CH$_2$ | Pyridinyl | NH—CH$_2$ | Furanyl | Z$_1$: CH$_2$F (3) |
| CH$_2$ | Pyridinyl | NH—CH$_2$ | Furanyl | Z$_1$: CHF$_2$ (2) |
| CH$_2$ | Pyridinyl | NH—CH$_2$ | Furanyl | Z$_1$: CHF$_2$ (3) |
| CH$_2$ | Pyridinyl | NH—CH$_2$ | Furanyl | Z$_1$: CF$_3$ (2) |
| CH$_2$ | Pyridinyl | NH—CH$_2$ | Furanyl | Z$_1$: CF$_3$ (3) |
| CH$_2$ | Pyridinyl | NH—CH$_2$ | Furanyl | Z$_1$: CH$_2$—CH$_2$F 2 |
| CH$_2$ | Pyridinyl | NH—CH$_2$ | Furanyl | Z$_1$: CH$_2$—CH$_2$F (3) |
| CH$_2$ | Pyridinyl | NH—CH$_2$ | Furanyl | Z$_1$: CH$_2$—CHF$_2$ (2) |
| CH$_2$ | Pyridinyl | NH—CH$_2$ | Furanyl | Z$_1$: CH$_2$—CHF$_2$ (3) |
| CH$_2$ | Pyridinyl | NH—CH$_2$ | Furanyl | Z$_1$: CH$_2$—CF$_3$ (2) |
| CH$_2$ | Pyridinyl | NH—CH$_2$ | Furanyl | Z$_1$: CH$_2$—CF$_3$ (3) |
| CH$_2$ | pyridinyl | NH—CH$_2$ | Oxazolyl | None |
| CH$_2$ | pyridinyl | NH—CH$_2$ | Oxazolyl | Z$_1$: F (2) |
| CH$_2$ | pyridinyl | NH—CH$_2$ | Oxazolyl | Z$_1$: F (3) |
| CH$_2$ | pyridinyl | NH—CH$_2$ | Oxazolyl | Z$_1$: F (2) |
|  |  |  |  | Z$_2$: F (3) |
| CH$_2$ | Pyridinyl | NH—CH$_2$ | Oxazolyl | Z$_1$: Cl (2) |
| CH$_2$ | Pyridinyl | NH—CH$_2$ | Oxazolyl | Z$_1$: Cl (3) |
| CH$_2$ | Pyridinyl | NH—CH$_2$ | Oxazolyl | Z$_1$: Cl (2) |
|  |  |  |  | Z$_2$: Cl (3) |
| CH$_2$ | Pyridinyl | NH—CH$_2$ | Oxazolyl | Z$_1$: F (2) |
|  |  |  |  | Z$_2$: Cl (3) |
| CH$_2$ | Pyridinyl | NH—CH$_2$ | Oxazolyl | Z$_1$: Cl (2) |
|  |  |  |  | Z$_2$: F (3) |
| CH$_2$ | Pyridinyl | NH—CH$_2$ | Oxazolyl | Z$_1$: CH$_3$ (2) |
| CH$_2$ | Pyridinyl | NH—CH$_2$ | Oxazolyl | Z$_1$: CH$_3$ (3) |
| CH$_2$ | Pyridinyl | NH—CH$_2$ | Oxazolyl | Z$_1$: CH$_2$—CH$_3$ (2) |
| CH$_2$ | Pyridinyl | NH—CH$_2$ | Oxazolyl | Z$_1$: CH$_2$—CH$_3$ (3) |
| CH$_2$ | Pyridinyl | NH—CH$_2$ | Oxazolyl | Z$_1$: CH$_2$—CH$_2$—CH$_3$ or iPr (2) |
| CH$_2$ | Pyridinyl | NH—CH$_2$ | Oxazolyl | Z$_1$: CH$_2$—CH$_2$—CH$_3$ or iPr (3) |
| CH$_2$ | Pyridinyl | NH—CH$_2$ | Oxazolyl | Z$_1$: CH$_2$F (2) |
| CH$_2$ | Pyridinyl | NH—CH$_2$ | Oxazolyl | Z$_1$: CH$_2$F (3) |
| CH$_2$ | Pyridinyl | NH—CH$_2$ | Oxazolyl | Z$_1$: CHF$_2$ (2) |
| CH$_2$ | Pyridinyl | NH—CH$_2$ | Oxazolyl | Z$_1$: CHF$_2$ (3) |
| CH$_2$ | Pyridinyl | NH—CH$_2$ | Oxazolyl | Z$_1$: CF$_3$ (2) |
| CH$_2$ | Pyridinyl | NH—CH$_2$ | Oxazolyl | Z$_1$: CF$_3$ (3) |
| CH$_2$ | Pyridinyl | NH—CH$_2$ | Oxazolyl | Z$_1$: CH$_2$—CH$_2$F (2) |
| CH$_2$ | Pyridinyl | NH—CH$_2$ | Oxazolyl | Z$_1$: CH$_2$—CH$_2$F (3) |
| CH$_2$ | Pyridinyl | NH—CH$_2$ | Oxazolyl | Z$_1$: CH$_2$—CHF$_2$ (2) |
| CH$_2$ | Pyridinyl | NH—CH$_2$ | Oxazolyl | Z$_1$: CH$_2$—CHF$_2$ (3) |
| CH$_2$ | Pyridinyl | NH—CH$_2$ | Oxazolyl | Z$_1$: CH$_2$—CF$_3$ (2) |
| CH$_2$ | Pyridinyl | NH—CH$_2$ | Oxazolyl | Z$_1$: CH$_2$—CF$_3$ (3) |
| CH$_2$ | pyridinyl | NH—CH$_2$ | Thiophenyl | None |
| CH$_2$ | pyridinyl | NH—CH$_2$ | Thiophenyl | Z$_1$: F (2) |
| CH$_2$ | pyridinyl | NH—CH$_2$ | Thiophenyl | Z$_1$: F (3) |
| CH$_2$ | pyridinyl | NH—CH$_2$ | Thiophenyl | Z$_1$: F (2) |
|  |  |  |  | Z$_2$: F (3) |
| CH$_2$ | Pyridinyl | NH—CH$_2$ | Thiophenyl | Z$_1$: Cl (2) |
| CH$_2$ | Pyridinyl | NH—CH$_2$ | Thiophenyl | Z$_1$: Cl (3) |
| CH$_2$ | Pyridinyl | NH—CH$_2$ | Thiophenyl | Z$_1$: Cl (2) |
|  |  |  |  | Z$_2$: Cl (3) |
| CH$_2$ | Pyridinyl | NH—CH$_2$ | Thiophenyl | Z$_1$: F (2) |
|  |  |  |  | Z$_2$: Cl (3) |
| CH$_2$ | Pyridinyl | NH—CH$_2$ | Thiophenyl | Z$_1$: Cl (2) |
|  |  |  |  | Z$_2$: F (3) |
| CH$_2$ | Pyridinyl | NH—CH$_2$ | Thiophenyl | Z$_1$: CH$_3$ (2) |
| CH$_2$ | Pyridinyl | NH—CH$_2$ | Thiophenyl | Z$_1$: CH$_3$ (3) |
| CH$_2$ | Pyridinyl | NH—CH$_2$ | Thiophenyl | Z$_1$: CH$_2$—CH$_3$ (2) |
| CH$_2$ | Pyridinyl | NH—CH$_2$ | Thiophenyl | Z$_1$: CH$_2$—CH$_3$ (3) |
| CH$_2$ | Pyridinyl | NH—CH$_2$ | Thiophenyl | Z$_1$: CH$_2$—CH$_2$—CH$_3$ or iPr (2) |

TABLE 2-continued

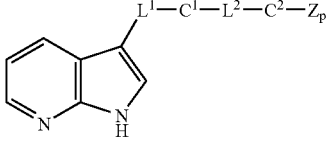

| L¹ | C¹ | L² | C² | Z |
|---|---|---|---|---|
| CH₂ | Pyridinyl | NH—CH₂ | Thiophenyl | $Z_1$: CH₂—CH₂—CH₃ or iPr (3) |
| CH₂ | Pyridinyl | NH—CH₂ | Thiophenyl | $Z_1$: CH₂F (2) |
| CH₂ | Pyridinyl | NH—CH₂ | Thiophenyl | $Z_1$: CH₂F (3) |
| CH₂ | Pyridinyl | NH—CH₂ | Thiophenyl | $Z_1$: CHF₂ (2) |
| CH₂ | Pyridinyl | NH—CH₂ | Thiophenyl | $Z_1$: CHF₂ (3) |
| CH₂ | Pyridinyl | NH—CH₂ | Thiophenyl | $Z_1$: CF₃ (2) |
| CH₂ | Pyridinyl | NH—CH₂ | Thiophenyl | $Z_1$: CF₃ (3) |
| CH₂ | Pyridinyl | NH—CH₂ | Thiophenyl | $Z_1$: CH₂—CH₂F (2) |
| CH₂ | Pyridinyl | NH—CH₂ | Thiophenyl | $Z_1$: CH₂—CH₂F (3) |
| CH₂ | Pyridinyl | NH—CH₂ | Thiophenyl | $Z_1$: CH₂—CHF₂ (2) |
| CH₂ | Pyridinyl | NH—CH₂ | Thiophenyl | $Z_1$: CH₂—CHF₂ (3) |
| CH₂ | Pyridinyl | NH—CH₂ | Thiophenyl | $Z_1$: CH₂—CF₃ (2) |
| CH₂ | Pyridinyl | NH—CH₂ | Thiophenyl | $Z_1$: CH₂—CF₃ (3) |
| CH₂ | pyridinyl | NH—CH₂ | Thiazolyl | None |
| CH₂ | pyridinyl | NH—CH₂ | Thiazolyl | $Z_1$: F (2) |
| CH₂ | pyridinyl | NH—CH₂ | Thiazolyl | $Z_1$: F (3) |
| CH₂ | pyridinyl | NH—CH₂ | Thiazolyl | $Z_1$: F (2)<br>$Z_2$: F (3) |
| CH₂ | Pyridinyl | NH—CH₂ | Thiazolyl | $Z_1$: Cl (2) |
| CH₂ | Pyridinyl | NH—CH₂ | Thiazolyl | $Z_1$: Cl (3) |
| CH₂ | Pyridinyl | NH—CH₂ | Thiazolyl | $Z_1$: Cl (2)<br>$Z_2$: Cl (3) |
| CH₂ | Pyridinyl | NH—CH₂ | Thiazolyl | $Z_1$: F (2)<br>$Z_2$: Cl (3) |
| CH₂ | Pyridinyl | NH—CH₂ | Thiazolyl | $Z_1$: Cl (2)<br>$Z_2$: F (3) |
| CH₂ | Pyridinyl | NH—CH₂ | Thiazolyl | $Z_1$: CH₃ (2) |
| CH₂ | Pyridinyl | NH—CH₂ | Thiazolyl | $Z_1$: CH₃ (3) |
| CH₂ | Pyridinyl | NH—CH₂ | Thiazolyl | $Z_1$: CH₂—CH₃ (2) |
| CH₂ | Pyridinyl | NH—CH₂ | Thiazolyl | $Z_1$: CH₂—CH₃ (3) |
| CH₂ | Pyridinyl | NH—CH₂ | Thiazolyl | $Z_1$: CH₂—CH₂—CH₃ or iPr (2) |
| CH₂ | Pyridinyl | NH—CH₂ | Thiazolyl | $Z_1$: CH₂—CH₂—CH₃ or iPr (3) |
| CH₂ | Pyridinyl | NH—CH₂ | Thiazolyl | $Z_1$: CH₂F (2) |
| CH₂ | Pyridinyl | NH—CH₂ | Thiazolyl | $Z_1$: CH₂F (3) |
| CH₂ | Pyridinyl | NH—CH₂ | Thiazolyl | $Z_1$: CHF₂ (2) |
| CH₂ | Pyridinyl | NH—CH₂ | Thiazolyl | $Z_1$: CHF₂ (3) |
| CH₂ | Pyridinyl | NH—CH₂ | Thiazolyl | $Z_1$: CF₃ (2) |
| CH₂ | Pyridinyl | NH—CH₂ | Thiazolyl | $Z_1$: CF₃ (3) |
| CH₂ | Pyridinyl | NH—CH₂ | Thiazolyl | $Z_1$: CH₂—CH₂F (2) |
| CH₂ | Pyridinyl | NH—CH₂ | Thiazolyl | $Z_1$: CH₂—CH₂F (3) |
| CH₂ | Pyridinyl | NH—CH₂ | Thiazolyl | $Z_1$: CH₂—CHF₂ (2) |
| CH₂ | Pyridinyl | NH—CH₂ | Thiazolyl | $Z_1$: CH₂—CHF₂ (3) |
| CH₂ | Pyridinyl | NH—CH₂ | Thiazolyl | $Z_1$: CH₂—CF₃ (2) |
| CH₂ | Pyridinyl | NH—CH₂ | Thiazolyl | $Z_1$: CH₂—CF₃ (3) |
| CH₂ | pyridinyl | NH—C(O) | Phenyl | None |
| CH₂ | pyridinyl | NH—C(O) | Phenyl | $Z_1$: F (para) |
| CH₂ | pyridinyl | NH—C(O) | phenyl | $Z_1$: F (meta) |
| CH₂ | pyridinyl | NH—C(O) | phenyl | $Z_1$: F (ortho) |
| CH₂ | pyridinyl | NH—C(O) | phenyl | $Z_1$: F (para)<br>$Z_2$: F (meta) |
| CH₂ | Pyridinyl | NH—C(O) | Phenyl | $Z_1$: Cl (meta) |
| CH₂ | Pyridinyl | NH—C(O) | Phenyl | $Z_1$: Cl (para) |
| CH₂ | Pyridinyl | NH—C(O) | Phenyl | $Z_1$: Cl (para)<br>$Z_2$: Cl (meta) |
| CH₂ | Pyridinyl | NH—C(O) | Phenyl | $Z_1$: F (para)<br>$Z_2$: Cl (meta) |
| CH₂ | Pyridinyl | NH—C(O) | Phenyl | $Z_1$: Cl (para)<br>$Z_2$: F (meta) |
| CH₂ | Pyridinyl | NH—C(O) | Phenyl | $Z_1$: CH₃ (para) |
| CH₂ | Pyridinyl | NH—C(O) | Phenyl | $Z_1$: CH₃ (meta) |
| CH₂ | Pyridinyl | NH—C(O) | Phenyl | $Z_1$: CH₃ (ortho) |
| CH₂ | Pyridinyl | NH—C(O) | Phenyl | $Z_1$: CH₂—CH₃ (para) |
| CH₂ | Pyridinyl | NH—C(O) | Phenyl | $Z_1$: CH₂—CH₃ (meta) |
| CH₂ | Pyridinyl | NH—C(O) | Phenyl | $Z_1$: CH₂—CH₃ (ortho) |
| CH₂ | Pyridinyl | NH—C(O) | Phenyl | $Z_1$: CH₂—CH₂—CH₃ or iPr (para) |
| CH₂ | Pyridinyl | NH—C(O) | Phenyl | $Z_1$: CH₂—CH₂—CH₃ or iPr (meta) |

TABLE 2-continued

L¹—C¹—L²—C²—Z$_p$ 7-azaindole (1H-pyrrolo[2,3-b]pyridine) with substituent at 3-position

| L¹ | C¹ | L² | C² | Z |
|---|---|---|---|---|
| CH$_2$ | Pyridinyl | NH—C(O) | Phenyl | Z$_1$: CH$_2$—CH$_2$—CH$_3$ or iPr (ortho) |
| CH$_2$ | Pyridinyl | NH—C(O) | Phenyl | Z$_1$: CH$_2$F (para) |
| CH$_2$ | Pyridinyl | NH—C(O) | Phenyl | Z$_1$: CH$_2$F (meta) |
| CH$_2$ | Pyridinyl | NH—C(O) | Phenyl | Z$_1$: CH$_2$F (ortho) |
| CH$_2$ | Pyridinyl | NH—C(O) | Phenyl | Z$_1$: CHF$_2$ (para) |
| CH$_2$ | Pyridinyl | NH—C(O) | Phenyl | Z$_1$: CHF$_2$ (meta) |
| CH$_2$ | Pyridinyl | NH—C(O) | Phenyl | Z$_1$: CHF$_2$ (ortho) |
| CH$_2$ | Pyridinyl | NH—C(O) | Phenyl | Z$_1$: CF$_3$ (para) |
| CH$_2$ | Pyridinyl | NH—C(O) | Phenyl | Z$_1$: CF$_3$ (meta) |
| CH$_2$ | Pyridinyl | NH—C(O) | Phenyl | Z$_1$: CF$_3$ (ortho) |
| CH$_2$ | Pyridinyl | NH—C(O) | Phenyl | Z$_1$: CH$_2$—CH$_2$F (para) |
| CH$_2$ | Pyridinyl | NH—C(O) | Phenyl | Z$_1$: CH$_2$—CH$_2$F meta |
| CH$_2$ | Pyridinyl | NH—C(O) | Phenyl | Z$_1$: CH$_2$—CH$_2$F (ortho) |
| CH$_2$ | Pyridinyl | NH—C(O) | Phenyl | Z$_1$: CH$_2$—CHF$_2$ (para) |
| CH$_2$ | Pyridinyl | NH—C(O) | Phenyl | Z$_1$: CH$_2$—CHF$_2$ (meta) |
| CH$_2$ | Pyridinyl | NH—C(O) | Phenyl | Z$_1$: CH$_2$—CHF$_2$ (ortho) |
| CH$_2$ | Pyridinyl | NH—C(O) | Phenyl | Z$_1$: CH$_2$—CF$_3$ (para) |
| CH$_2$ | Pyridinyl | NH—C(O) | Phenyl | Z$_1$: CH$_2$—CF$_3$ (meta) |
| CH$_2$ | Pyridinyl | NH—C(O) | Phenyl | Z$_1$: CH$_2$—CF$_3$ (ortho) |
| CH$_2$ | pyridinyl | NH—C(O) | Pyridinyl | None |
| CH$_2$ | pyridinyl | NH—C(O) | Pyridinyl | Z$_1$: F (para) |
| CH$_2$ | pyridinyl | NH—C(O) | Pyridinyl | Z$_1$: F (meta) |
| CH$_2$ | pyridinyl | NH—C(O) | Pyridinyl | Z$_1$: F (ortho) |
| CH$_2$ | pyridinyl | NH—C(O) | Pyridinyl | Z$_1$: F (para) Z$_2$: F (meta) |
| CH$_2$ | Pyridinyl | NH—C(O) | Pyridinyl | Z$_1$: Cl (meta) |
| CH$_2$ | Pyridinyl | NH—C(O) | Pyridinyl | Z$_1$: Cl (para) |
| CH$_2$ | Pyridinyl | NH—C(O) | Pyridinyl | Z$_1$: Cl (para) Z$_2$: Cl (meta) |
| CH$_2$ | Pyridinyl | NH—C(O) | Pyridinyl | Z$_1$: F (para) Z$_2$: Cl (meta) |
| CH$_2$ | Pyridinyl | NH—C(O) | Pyridinyl | Z$_1$: Cl (para) Z$_2$: F (meta) |
| CH$_2$ | Pyridinyl | NH—C(O) | Pyridinyl | Z$_1$: CH$_3$ (para) |
| CH$_2$ | Pyridinyl | NH—C(O) | Pyridinyl | Z$_1$: CH$_3$ (meta) |
| CH$_2$ | Pyridinyl | NH—C(O) | Pyridinyl | Z$_1$: CH$_3$ (ortho) |
| CH$_2$ | Pyridinyl | NH—C(O) | Pyridinyl | Z$_1$: CH$_2$—CH$_3$ (para) |
| CH$_2$ | Pyridinyl | NH—C(O) | Pyridinyl | Z$_1$: CH$_2$—CH$_3$ (meta) |
| CH$_2$ | Pyridinyl | NH—C(O) | Pyridinyl | Z$_1$: CH$_2$—CH$_3$ (ortho) |
| CH$_2$ | Pyridinyl | NH—C(O) | Pyridinyl | Z$_1$: CH$_2$—CH$_2$—CH$_3$ or iPr (para) |
| CH$_2$ | Pyridinyl | NH—C(O) | Pyridinyl | Z$_1$: CH$_2$—CH$_2$—CH$_3$ or iPr (meta) |
| CH$_2$ | Pyridinyl | NH—C(O) | Pyridinyl | Z$_1$: CH$_2$—CH$_2$—CH$_3$ or iPr (ortho) |
| CH$_2$ | Pyridinyl | NH—C(O) | Pyridinyl | Z$_1$: CH$_2$F (para) |
| CH$_2$ | Pyridinyl | NH—C(O) | Pyridinyl | Z$_1$: CH$_2$F (meta) |
| CH$_2$ | Pyridinyl | NH—C(O) | Pyridinyl | Z$_1$: CH$_2$F (ortho) |
| CH$_2$ | Pyridinyl | NH—C(O) | Pyridinyl | Z$_1$: CHF$_2$ (para) |
| CH$_2$ | Pyridinyl | NH—C(O) | Pyridinyl | Z$_1$: CHF$_2$ (meta) |
| CH$_2$ | Pyridinyl | NH—C(O) | Pyridinyl | Z$_1$: CHF$_2$ (ortho) |
| CH$_2$ | Pyridinyl | NH—C(O) | Pyridinyl | Z$_1$: CF$_3$ (para) |
| CH$_2$ | Pyridinyl | NH—C(O) | Pyridinyl | Z$_1$: CF$_3$ (meta) |
| CH$_2$ | Pyridinyl | NH—C(O) | Pyridinyl | Z$_1$: CF$_3$ (ortho) |
| CH$_2$ | Pyridinyl | NH—C(O) | Pyridinyl | Z$_1$: CH$_2$—CH$_2$F (para) |
| CH$_2$ | Pyridinyl | NH—C(O) | Pyridinyl | Z$_1$: CH$_2$—CH$_2$F (meta) |
| CH$_2$ | Pyridinyl | NH—C(O) | Pyridinyl | Z$_1$: CH$_2$—CH$_2$F (ortho) |
| CH$_2$ | Pyridinyl | NH—C(O) | Pyridinyl | Z$_1$: CH$_2$—CHF$_2$ (para) |
| CH$_2$ | Pyridinyl | NH—C(O) | Pyridinyl | Z$_1$: CH$_2$—CHF$_2$ (meta) |
| CH$_2$ | Pyridinyl | NH—C(O) | Pyridinyl | Z$_1$: CH$_2$—CHF$_2$ (ortho) |
| CH$_2$ | Pyridinyl | NH—C(O) | Pyridinyl | Z$_1$: CH$_2$—CF$_3$ (para) |
| CH$_2$ | Pyridinyl | NH—C(O) | Pyridinyl | Z$_1$: CH$_2$—CF$_3$ (meta) |
| CH$_2$ | Pyridinyl | NH—C(O) | Pyridinyl | Z$_1$: CH$_2$—CF$_3$ (ortho) |
| CH$_2$ | pyridinyl | NH—C(O) | Pyrimidinyl | None |
| CH$_2$ | pyridinyl | NH—C(O) | Pyrimidinyl | Z$_1$: F (para) |
| CH$_2$ | pyridinyl | NH—C(O) | Pyrimidinyl | Z$_1$: F (meta) |
| CH$_2$ | pyridinyl | NH—C(O) | Pyrimidinyl | Z$_1$: F (ortho) |

TABLE 2-continued

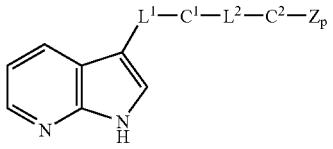

| L¹ | C¹ | L² | C² | Z |
|---|---|---|---|---|
| CH₂ | pyridinyl | NH—C(O) | Pyrimidinyl | $Z_1$: F (para)<br>$Z_2$: F (meta) |
| CH₂ | Pyridinyl | NH—C(O) | Pyrimidinyl | $Z_1$: Cl (meta) |
| CH₂ | Pyridinyl | NH—C(O) | Pyrimidinyl | $Z_1$: Cl (para) |
| CH₂ | Pyridinyl | NH—C(O) | Pyrimidinyl | $Z_1$: Cl (para)<br>$Z_2$: Cl (meta) |
| CH₂ | Pyridinyl | NH—C(O) | Pyrimidinyl | $Z_1$: F (para)<br>$Z_2$: Cl (meta) |
| CH₂ | Pyridinyl | NH—C(O) | Pyrimidinyl | $Z_1$: Cl (para)<br>$Z_2$: F (meta) |
| CH₂ | Pyridinyl | NH—C(O) | Pyrimidinyl | $Z_1$: CH₃ (para) |
| CH₂ | Pyridinyl | NH—C(O) | Pyrimidinyl | $Z_1$: CH₃ (meta) |
| CH₂ | Pyridinyl | NH—C(O) | Pyrimidinyl | $Z_1$: CH₃ (ortho) |
| CH₂ | Pyridinyl | NH—C(O) | Pyrimidinyl | $Z_1$: CH₂—CH₃ (para) |
| CH₂ | Pyridinyl | NH—C(O) | Pyrimidinyl | $Z_1$: CH₂—CH₃ (meta) |
| CH₂ | Pyridinyl | NH—C(O) | Pyrimidinyl | $Z_1$: CH₂—CH₃ (ortho) |
| CH₂ | Pyridinyl | NH—C(O) | Pyrimidinyl | $Z_1$: CH₂—CH₂—CH₃ or iPr (para) |
| CH₂ | Pyridinyl | NH—C(O) | Pyrimidinyl | $Z_1$: CH₂—CH₂—CH₃ or iPr (meta) |
| CH₂ | Pyridinyl | NH—C(O) | Pyrimidinyl | $Z_1$: CH₂—CH₂—CH₃ or iPr (ortho) |
| CH₂ | Pyridinyl | NH—C(O) | Pyrimidinyl | $Z_1$: CH₂F (para) |
| CH₂ | Pyridinyl | NH—C(O) | Pyrimidinyl | $Z_1$: CH₂F (meta) |
| CH₂ | Pyridinyl | NH—C(O) | Pyrimidinyl | $Z_1$: CH₂F (ortho) |
| CH₂ | Pyridinyl | NH—C(O) | Pyrimidinyl | $Z_1$: CHF₂ (para) |
| CH₂ | Pyridinyl | NH—C(O) | Pyrimidinyl | $Z_1$: CHF₂ (meta) |
| CH₂ | Pyridinyl | NH—C(O) | Pyrimidinyl | $Z_1$: CHF₂ (ortho) |
| CH₂ | Pyridinyl | NH—C(O) | Pyrimidinyl | $Z_1$: CF₃ (para) |
| CH₂ | Pyridinyl | NH—C(O) | Pyrimidinyl | $Z_1$: CF₃ (meta) |
| CH₂ | Pyridinyl | NH—C(O) | Pyrimidinyl | $Z_1$: CF₃ (ortho) |
| CH₂ | Pyridinyl | NH—C(O) | Pyrimidinyl | $Z_1$: CH₂—CH₂F (para) |
| CH₂ | Pyridinyl | NH—C(O) | Pyrimidinyl | $Z_1$: CH₂—CH₂F (meta) |
| CH₂ | Pyridinyl | NH—C(O) | Pyrimidinyl | $Z_1$: CH₂—CH₂F (ortho) |
| CH₂ | Pyridinyl | NH—C(O) | Pyrimidinyl | $Z_1$: CH₂—CHF₂ (para) |
| CH₂ | Pyridinyl | NH—C(O) | Pyrimidinyl | $Z_1$: CH₂—CHF₂ (meta) |
| CH₂ | Pyridinyl | NH—C(O) | Pyrimidinyl | $Z_1$: CH₂—CHF₂ (ortho) |
| CH₂ | Pyridinyl | NH—C(O) | Pyrimidinyl | $Z_1$: CH₂—CF₃ (para) |
| CH₂ | Pyridinyl | NH—C(O) | Pyrimidinyl | $Z_1$: CH₂—CF₃ (meta) |
| CH₂ | Pyridinyl | NH—C(O) | Pyrimidinyl | $Z_1$: CH₂—CF₃ (ortho) |
| CH₂ | pyridinyl | NH—C(O) | Pyrazinyl | None |
| CH₂ | pyridinyl | NH—C(O) | Pyrazinyl | $Z_1$: F (para) |
| CH₂ | pyridinyl | NH—C(O) | Pyrazinyl | $Z_1$: F (meta) |
| CH₂ | pyridinyl | NH—C(O) | Pyrazinyl | $Z_1$: F (ortho) |
| CH₂ | pyridinyl | NH—C(O) | Pyrazinyl | $Z_1$: F (para)<br>$Z_2$: F (meta) |
| CH₂ | Pyridinyl | NH—C(O) | Pyrazinyl | $Z_1$: Cl (meta) |
| CH₂ | Pyridinyl | NH—C(O) | Pyrazinyl | $Z_1$: Cl (para)<br>$Z_2$: Cl (meta) |
| CH₂ | Pyridinyl | NH—C(O) | Pyrazinyl | $Z_1$: F (para)<br>$Z_2$: Cl (meta) |
| CH₂ | Pyridinyl | NH—C(O) | Pyrazinyl | $Z_1$: Cl (para)<br>$Z_2$: F (meta) |
| CH₂ | Pyridinyl | NH—C(O) | Pyrazinyl | $Z_1$: CH₃ (para) |
| CH₂ | Pyridinyl | NH—C(O) | Pyrazinyl | $Z_1$: CH₃ (meta) |
| CH₂ | Pyridinyl | NH—C(O) | Pyrazinyl | $Z_1$: CH₃ (ortho) |
| CH₂ | Pyridinyl | NH—C(O) | Pyrazinyl | $Z_1$: CH₂—CH₃ (para) |
| CH₂ | Pyridinyl | NH—C(O) | Pyrazinyl | $Z_1$: CH₂—CH₃ (meta) |
| CH₂ | Pyridinyl | NH—C(O) | Pyrazinyl | $Z_1$: CH₂—CH₃ (ortho) |
| CH₂ | Pyridinyl | NH—C(O) | Pyrazinyl | $Z_1$: CH₂—CH₂—CH₃ or iPr (para) |
| CH₂ | Pyridinyl | NH—C(O) | Pyrazinyl | $Z_1$: CH₂—CH₂—CH₃ or iPr (meta) |
| CH₂ | Pyridinyl | NH—C(O) | Pyrazinyl | $Z_1$: CH₂—CH₂—CH₃ or iPr (ortho) |
| CH₂ | Pyridinyl | NH—C(O) | Pyrazinyl | $Z_1$: CH₂F (para) |
| CH₂ | Pyridinyl | NH—C(O) | Pyrazinyl | $Z_1$: CH₂F (meta) |
| CH₂ | Pyridinyl | NH—C(O) | Pyrazinyl | $Z_1$: CH₂F (ortho) |

TABLE 2-continued

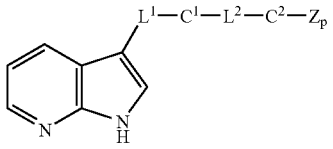

| L$^1$ | C$^1$ | L$^2$ | C$^2$ | Z |
|---|---|---|---|---|
| CH$_2$ | Pyridinyl | NH—C(O) | Pyrazinyl | Z$_1$: CHF$_2$ (para) |
| CH$_2$ | Pyridinyl | NH—C(O) | Pyrazinyl | Z$_1$: CHF$_2$ (meta) |
| CH$_2$ | Pyridinyl | NH—C(O) | Pyrazinyl | Z$_1$: CHF$_2$ (ortho) |
| CH$_2$ | Pyridinyl | NH—C(O) | Pyrazinyl | Z$_1$: CF$_3$ (para) |
| CH$_2$ | Pyridinyl | NH—C(O) | Pyrazinyl | Z$_1$: CF$_3$ (meta) |
| CH$_2$ | Pyridinyl | NH—C(O) | Pyrazinyl | Z$_1$: CF$_3$ (ortho) |
| CH$_2$ | Pyridinyl | NH—C(O) | Pyrazinyl | Z$_1$: CH$_2$—CH$_2$F (para) |
| CH$_2$ | Pyridinyl | NH—C(O) | Pyrazinyl | Z$_1$: CH$_2$—CH$_2$F (meta) |
| CH$_2$ | Pyridinyl | NH—C(O) | Pyrazinyl | Z$_1$: CH$_2$—CH$_2$F (ortho) |
| CH$_2$ | Pyridinyl | NH—C(O) | Pyrazinyl | Z$_1$: CH$_2$—CHF$_2$ (para) |
| CH$_2$ | Pyridinyl | NH—C(O) | Pyrazinyl | Z$_1$: CH$_2$—CHF$_2$ (meta) |
| CH$_2$ | Pyridinyl | NH—C(O) | Pyrazinyl | Z$_1$: CH$_2$—CHF$_2$ (ortho) |
| CH$_2$ | Pyridinyl | NH—C(O) | Pyrazinyl | Z$_1$: CH$_2$—CF$_3$ (para) |
| CH$_2$ | Pyridinyl | NH—C(O) | Pyrazinyl | Z$_1$: CH$_2$—CF$_3$ (meta) |
| CH$_2$ | Pyridinyl | NH—C(O) | Pyrazinyl | Z$_1$: CH$_2$—CF$_3$ (ortho) |
| CH$_2$ | pyridinyl | NH—C(O) | Pyrrolyl | None |
| CH$_2$ | pyridinyl | NH—C(O) | Pyrrolyl | Z$_1$: F (2) |
| CH$_2$ | pyridinyl | NH—C(O) | Pyrrolyl | Z$_1$: F (3) |
| CH$_2$ | pyridinyl | NH—C(O) | Pyrrolyl | Z$_1$: F (2) Z$_2$: F (3) |
| CH$_2$ | Pyridinyl | NH—C(O) | Pyrrolyl | Z$_1$: Cl (2) |
| CH$_2$ | Pyridinyl | NH—C(O) | Pyrrolyl | Z$_1$: Cl (3) |
| CH$_2$ | Pyridrnyl | NH—C(O) | Pyrrolyl | Z$_1$: Cl (2) Z$_2$: Cl (3) |
| CH$_2$ | Pyridinyl | NH—C(O) | Pyrrolyl | Z$_1$: F (2) Z$_2$: Cl (3) |
| CH$_2$ | Pyridinyl | NH—C(O) | Pyrrolyl | Z$_1$: Cl (2) Z$_2$: F (3) |
| CH$_2$ | Pyridinyl | NH—C(O) | Pyrrolyl | Z$_1$: CH$_3$ (2) |
| CH$_2$ | Pyridinyl | NH—C(O) | Pyrrolyl | Z$_1$: CH$_3$ (3) |
| CH$_2$ | Pyridinyl | NH—C(O) | Pyrrolyl | Z$_1$: CH$_2$—CH$_3$ (2) |
| CH$_2$ | Pyridinyl | NH—C(O) | Pyrrolyl | Z$_1$: CH$_2$—CH$_3$ (3) |
| CH$_2$ | Pyridinyl | NH—C(O) | Pyrrolyl | Z$_1$: CH$_2$—CH$_2$—CH$_3$ or iPr (2) |
| CH$_2$ | Pyridinyl | NH—C(O) | Pyrrolyl | Z$_1$: CH$_2$—CH$_2$—CH$_3$ or iPr (3) |
| CH$_2$ | Pyridinyl | NH—C(O) | Pyrrolyl | Z$_1$: CH$_2$F (2) |
| CH$_2$ | Pyridinyl | NH—C(O) | Pyrrolyl | Z$_1$: CH$_2$F (3) |
| CH$_2$ | Pyridinyl | NH—C(O) | Pyrrolyl | Z$_1$: CHF$_2$ (2) |
| CH$_2$ | Pyridinyl | NH—C(O) | Pyrrolyl | Z$_1$: CHF$_2$ (3) |
| CH$_2$ | Pyridinyl | NH—C(O) | Pyrrolyl | Z$_1$: CF$_3$ (2) |
| CH$_2$ | Pyridinyl | NH—C(O) | Pyrrolyl | Z$_1$: CF$_3$ (3) |
| CH$_2$ | Pyridinyl | NH—C(O) | Pyrrolyl | Z$_1$: CH$_2$—CH$_2$F (2) |
| CH$_2$ | Pyridinyl | NH—C(O) | Pyrrolyl | Z$_1$: CH$_2$—CH$_2$F (3) |
| CH$_2$ | Pyridinyl | NH—C(O) | Pyrrolyl | Z$_1$: CH$_2$—CHF$_2$ (2) |
| CH$_2$ | Pyridinyl | NH—C(O) | Pyrrolyl | Z$_1$: CH$_2$—CHF$_2$ (3) |
| CH$_2$ | Pyridinyl | NH—C(O) | Pyrrolyl | Z$_1$: CH$_2$—CF$_3$ (2) |
| CH$_2$ | Pyridinyl | NH—C(O) | Pyrrolyl | Z$_1$: CH$_2$—CF$_3$ (3) |
| CH$_2$ | pyridinyl | NH—C(O) | Imidazolyl | None |
| CH$_2$ | pyridinyl | NH—C(O) | Imidazolyl | Z$_1$: F (2) |
| CH$_2$ | pyridinyl | NH—C(O) | Imidazolyl | Z$_1$: F (3) |
| CH$_2$ | pyridinyl | NH—C(O) | Imidazolyl | Z$_1$: F (2) Z$_2$: F (3) |
| CH$_2$ | Pyridinyl | NH—C(O) | Imidazolyl | Z$_1$: Cl (2) |
| CH$_2$ | Pyridinyl | NH—C(O) | Imidazolyl | Z$_1$: Cl (3) |
| CH$_2$ | Pyridinyl | NH—C(O) | Imidazolyl | Z$_1$: Cl (2) Z$_2$: Cl (3) |
| CH$_2$ | Pyridinyl | NH—C(O) | Imidazolyl | Z$_1$: F (2) Z$_2$: Cl (3) |
| CH$_2$ | Pyridinyl | NH—C(O) | Imidazolyl | Z$_1$: Cl (2) Z$_2$: F (3) |
| CH$_2$ | Pyridinyl | NH—C(O) | Imidazolyl | Z$_1$: CH$_3$ (2) |
| CH$_2$ | Pyridinyl | NH—C(O) | Imidazolyl | Z$_1$: CH$_3$ (3) |
| CH$_2$ | Pyridinyl | NH—C(O) | Imidazolyl | Z$_1$: CH$_2$—CH$_3$ (2) |
| CH$_2$ | Pyridinyl | NH—C(O) | Imidazolyl | Z$_1$: CH$_2$—CH$_3$ (3) |
| CH$_2$ | Pyridinyl | NH—C(O) | Imidazolyl | Z$_1$: CH$_2$—CH$_2$—CH$_3$ or iPr (2) |
| CH$_2$ | Pyridinyl | NH—C(O) | Imidazolyl | Z$_1$: CH$_2$—CH$_2$—CH$_3$ or iPr (3) |
| CH$_2$ | Pyridinyl | NH—C(O) | Imidazolyl | Z$_1$: CH$_2$F (2) |
| CH$_2$ | Pyridinyl | NH—C(O) | Imidazolyl | Z$_1$: CH$_2$F (3) |
| CH$_2$ | Pyridinyl | NH—C(O) | Imidazolyl | Z$_1$: CHF$_2$ (2) |
| CH$_2$ | Pyridinyl | NH—C(O) | Imidazolyl | Z$_1$: CHF$_2$ (3) |

TABLE 2-continued

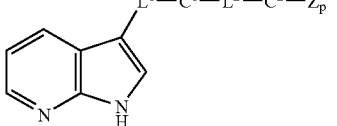

| L¹ | C¹ | L² | C² | Z |
|---|---|---|---|---|
| CH₂ | Pyridinyl | NH—C(O) | Imidazolyl | $Z_1$: $CF_3$ (2) |
| CH₂ | Pyridinyl | NH—C(O) | Imidazolyl | $Z_1$: $CF_3$ (3) |
| CH₂ | Pyridinyl | NH—C(O) | Imidazolyl | $Z_1$: $CH_2$—$CH_2F$ (2) |
| CH₂ | Pyridinyl | NH—C(O) | Imidazolyl | $Z_1$: $CH_2$—$CH_2F$ (3) |
| CH₂ | Pyridinyl | NH—C(O) | Imidazolyl | $Z_1$: $CH_2$—$CHF_2$ (2) |
| CH₂ | Pyridinyl | NH—C(O) | Imidazolyl | $Z_1$: $CH_2$—$CHF_2$ (3) |
| CH₂ | Pyridinyl | NH—C(O) | Imidazolyl | $Z_1$: $CH_2$—$CF_3$ (2) |
| CH₂ | Pyridinyl | NH—C(O) | Imidazolyl | $Z_1$: $CH_2$—$CF_3$ (3) |
| CH₂ | pyridinyl | NH—C(O) | Furanyl | None |
| CH₂ | pyridinyl | NH—C(O) | Furanyl | $Z_1$: F (2) |
| CH₂ | pyridinyl | NH—C(O) | Furanyl | $Z_1$: F (3) |
| CH₂ | pyridinyl | NH—C(O) | Furanyl | $Z_1$: F (2) $Z_2$: F (3) |
| CH₂ | Pyridinyl | NH—C(O) | Furanyl | $Z_1$: Cl (2) |
| CH₂ | Pyridinyl | NH—C(O) | Furanyl | $Z_1$: Cl (3) |
| CH₂ | Pyridinyl | NH—C(O) | Furanyl | $Z_1$: Cl (2) $Z_2$: Cl (3) |
| CH₂ | Pyridinyl | NH—C(O) | Furanyl | $Z_1$: F (2) $Z_2$: Cl (3) |
| CH₂ | Pyridinyl | NH—C(O) | Furanyl | $Z_1$: Cl (2) $Z_2$: F (3) |
| CH₂ | Pyridinyl | NH—C(O) | Furanyl | $Z_1$: $CH_3$ (2) |
| CH₂ | Pyridinyl | NH—C(O) | Furanyl | $Z_1$: $CH_3$ (3) |
| CH₂ | Pyridinyl | NH—C(O) | Furanyl | $Z_1$: $CH_2$—$CH_3$ (2) |
| CH₂ | Pyridinyl | NH—C(O) | Furanyl | $Z_1$: $CH_2$—$CH_3$ (3) |
| CH₂ | Pyridinyl | NH—C(O) | Furanyl | $Z_1$: $CH_2$—$CH_2$—$CH_3$ or iPr (2) |
| CH₂ | Pyridinyl | NH—C(O) | Furanyl | $Z_1$: $CH_2$—$CH_2$—$CH_3$ or iPr (3) |
| CH₂ | Pyridinyl | NH—C(O) | Furanyl | $Z_1$: $CH_2F$ (2) |
| CH₂ | Pyridinyl | NH—C(O) | Furanyl | $Z_1$: $CH_2F$ (3) |
| CH₂ | Pyridinyl | NH—C(O) | Furanyl | $Z_1$: $CHF_2$ (2) |
| CH₂ | Pyridinyl | NH—C(O) | Furanyl | $Z_1$: $CHF_2$ (3) |
| CH₂ | Pyridinyl | NH—C(O) | Furanyl | $Z_1$: $CF_3$ (2) |
| CH₂ | Pyridinyl | NH—C(O) | Furanyl | $Z_1$: $CF_3$ (3) |
| CH₂ | Pyridinyl | NH—C(O) | Furanyl | $Z_1$: $CH_2$—$CH_2F$ (2) |
| CH₂ | Pyridinyl | NH—C(O) | Furanyl | $Z_1$: $CH_2$—$CH_2F$ (3) |
| CH₂ | Pyridinyl | NH—C(O) | Furanyl | $Z_1$: $CH_2$—$CHF_2$ (2) |
| CH₂ | Pyridinyl | NH—C(O) | Furanyl | $Z_1$: $CH_2$—$CHF_2$ (3) |
| CH₂ | Pyridinyl | NH—C(O) | Furanyl | $Z_1$: $CH_2$—$CF_3$ (2) |
| CH₂ | Pyridinyl | NH—C(O) | Furanyl | $Z_1$: $CH_2$—$CF_3$ (3) |
| CH₂ | pyridinyl | NH—C(O) | Oxazolyl | None |
| CH₂ | pyridinyl | NH—C(O) | Oxazolyl | $Z_1$: F (2) |
| CH₂ | pyridinyl | NH—C(O) | Oxazolyl | $Z_1$: F (3) |
| CH₂ | pyridinyl | NH—C(O) | Oxazolyl | $Z_1$: F (2) $Z_2$: F (3) |
| CH₂ | Pyridinyl | NH—C(O) | Oxazolyl | $Z_1$: Cl (2) |
| CH₂ | Pyridinyl | NH—C(O) | Oxazolyl | $Z_1$: Cl (3) |
| CH₂ | Pyridinyl | NH—C(O) | Oxazolyl | $Z_1$: Cl (2) $Z_2$: Cl (3) |
| CH₂ | Pyridinyl | NH—C(O) | Oxazolyl | $Z_1$: F (2) $Z_2$: Cl (3) |
| CH₂ | Pyridinyl | NH—C(O) | Oxazolyl | $Z_1$: Cl (2) $Z_2$: F (3) |
| CH₂ | Pyridinyl | NH—C(O) | Oxazolyl | $Z_1$: $CH_3$ (2) |
| CH₂ | Pyridinyl | NH—C(O) | Oxazolyl | $Z_1$: $CH_3$ (3) |
| CH₂ | Pyridinyl | NH—C(O) | Oxazolyl | $Z_1$: $CH_2$—$CH_3$ (2) |
| CH₂ | Pyridinyl | NH—C(O) | Oxazolyl | $Z_1$: $CH_2$—$CH_3$ (3) |
| CH₂ | Pyridinyl | NH—C(O) | Oxazolyl | $Z_1$: $CH_2$—$CH_2$—$CH_3$ or iPr (2) |
| CH₂ | Pyridinyl | NH—C(O) | Oxazolyl | $Z_1$: $CH_2$—$CH_2$—$CH_3$ or iPr (3) |
| CH₂ | Pyridinyl | NH—C(O) | Oxazolyl | $Z_1$: $CH_2F$ (2) |
| CH₂ | Pyridinyl | NH—C(O) | Oxazolyl | $Z_1$: $CH_2F$ (3) |
| CH₂ | Pyridinyl | NH—C(O) | Oxazolyl | $Z_1$: $CHF_2$ (2) |
| CH₂ | Pyridinyl | NH—C(O) | Oxazolyl | $Z_1$: $CHF_2$ (3) |
| CH₂ | Pyridinyl | NH—C(O) | Oxazolyl | $Z_1$: $CF_3$ (2) |
| CH₂ | Pyridinyl | NH—C(O) | Oxazolyl | $Z_1$: $CF_3$ (3) |
| CH₂ | Pyridinyl | NH—C(O) | Oxazolyl | $Z_1$: $CH_2$—$CH_2F$ (2) |
| CH₂ | Pyridinyl | NH—C(O) | Oxazolyl | $Z_1$: $CH_2$—$CH_2F$ (3) |
| CH₂ | Pyridinyl | NH—C(O) | Oxazolyl | $Z_1$: $CH_2$—$CHF_2$ (2) |
| CH₂ | Pyridinyl | NH—C(O) | Oxazolyl | $Z_1$: $CH_2$—$CHF_2$ (3) |
| CH₂ | Pyridinyl | NH—C(O) | Oxazolyl | $Z_1$: $CH_2$—$CF_3$ (2) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| CH₂ | Pyridinyl | NH—C(O) | Oxazolyl | Z₁: CH₂—CF₃ (3) |
| CH₂ | pyridinyl | NH—C(O) | Thiophenyl | None |
| CH₂ | pyridinyl | NH—C(O) | Thiophenyl | Z₁: F (2) |
| CH₂ | pyridinyl | NH—C(O) | Thiophenyl | Z₁: F (3) |
| CH₂ | pyridinyl | NH—C(O) | Thiophenyl | Z₁: F (2) <br> Z₂: F (3) |
| CH₂ | Pyridinyl | NH—C(O) | Thiophenyl | Z₁: Cl (2) |
| CH₂ | Pyridinyl | NH—C(O) | Thiophenyl | Z₁: Cl (3) |
| CH₂ | Pyridinyl | NH—C(O) | Thiophenyl | Z₁: Cl (2) <br> Z₂: Cl (3) |
| CH₂ | Pyridinyl | NH—C(O) | Thiophenyl | Z₁: F (2) <br> Z₂: Cl (3) |
| CH₂ | Pyridinyl | NH—C(O) | Thiophenyl | Z₁: Cl (2) <br> Z₂: F (3) |
| CH₂ | Pyridinyl | NH—C(O) | Thiophenyl | Z₁: CH₃ (2) |
| CH₂ | Pyridinyl | NH—C(O) | Thiophenyl | Z₁: CH₃ (3) |
| CH₂ | Pyridinyl | NH—C(O) | Thiophenyl | Z₁: CH₂—CH₃ (2) |
| CH₂ | Pyridinyl | NH—C(O) | Thiophenyl | Z₁: CH₂—CH₃ (3) |
| CH₂ | Pyridinyl | NH—C(O) | Thiophenyl | Z₁: CH₂—CH₂CH₃ or iPr (2) |
| CH₂ | Pyridinyl | NH—C(O) | Thiophenyl | Z₁: CH₂—CH₂—CH₃ or iPr (3) |
| CH₂ | Pyridinyl | NH—C(O) | Thiophenyl | Z₁: CH₂F (2) |
| CH₂ | Pyridinyl | NH—C(O) | Thiophenyl | Z₁: CH₂F (3) |
| CH₂ | Pyridinyl | NH—C(O) | Thiophenyl | Z₁: CHF₂ (2) |
| CH₂ | Pyridinyl | NH—C(O) | Thiophenyl | Z₁: CHF₂ (3) |
| CH₂ | Pyridinyl | NH—C(O) | Thiophenyl | Z₁: CF₃ (2) |
| CH₂ | Pyridinyl | NH—C(O) | Thiophenyl | Z₁: CF₃ (3) |
| CH₂ | Pyridinyl | NH—C(O) | Thiophenyl | Z₁: CH₂—CH₂F (2) |
| CH₂ | Pyridinyl | NH—C(O) | Thiophenyl | Z₁: CH₂—CH₂F (3) |
| CH₂ | Pyridinyl | NH—C(O) | Thiophenyl | Z₁: CH₂—CHF₂ (2) |
| CH₂ | Pyridinyl | NH—C(O) | Thiophenyl | Z₁: CH₂—CHF₂ (3) |
| CH₂ | Pyridinyl | NH—C(O) | Thiophenyl | Z₁: CH₂—CF₃ (2) |
| CH₂ | Pyridinyl | NH—C(O) | Thiophenyl | Z₁: CH₂—CF₃ (3) |
| CH₂ | pyridinyl | NH—C(O) | Thiazolyl | None |
| CH₂ | pyridinyl | NH—C(O) | Thiazolyl | Z₁: F (2) |
| CH₂ | pyridinyl | NH—C(O) | Thiazolyl | Z₁: F (3) |
| CH₂ | pyridinyl | NH—C(O) | Thiazolyl | Z₁: F (2) <br> Z₂: F (3) |
| CH₂ | Pyridinyl | NH—C(O) | Thiazolyl | Z₁: Cl (2) |
| CH₂ | Pyridinyl | NH—C(O) | Thiazolyl | Z₁: Cl (3) |
| CH₂ | Pyridinyl | NH—C(O) | Thiazolyl | Z₁: Cl (2) <br> Z₂: Cl (3) |
| CH₂ | Pyridinyl | NH—C(O) | Thiazolyl | Z₁: F (2) <br> Z₂: Cl (3) |
| CH₂ | Pyridinyl | NH—C(O) | Thiazolyl | Z₁: Cl (2) <br> Z₂: F (3) |
| CH₂ | Pyridinyl | NH—C(O) | Thiazolyl | Z₁: CH₃ (2) |
| CH₂ | Pyridinyl | NH—C(O) | Thiazolyl | Z₁: CH₃ (3) |
| CH₂ | Pyridinyl | NH—C(O) | Thiazolyl | Z₁: CH₂—CH₃ (2) |
| CH₂ | Pyridinyl | NH—C(O) | Thiazolyl | Z₁: CH₂—CH₃ (3) |
| CH₂ | Pyridinyl | NH—C(O) | Thiazolyl | Z₁: CH₂—CH₂—CH₃ or iPr (2) |
| CH₂ | Pyridinyl | NH—C(O) | Thiazolyl | Z₁: CH₂—CH₂—CH₃ or iPr (3) |
| CH₂ | Pyridinyl | NH—C(O) | Thiazolyl | Z₁: CH₂F (2) |
| CH₂ | Pyridinyl | NH—C(O) | Thiazolyl | Z₁: CH₂F (3) |
| CH₂ | Pyridinyl | NH—C(O) | Thiazolyl | Z₁: CHF₂ (2) |
| CH₂ | Pyridinyl | NH—C(O) | Thiazolyl | Z₁: CHF₂ (3) |
| CH₂ | Pyridinyl | NH—C(O) | Thiazolyl | Z₁: CF₃ (2) |
| CH₂ | Pyridinyl | NH—C(O) | Thiazolyl | Z₁: CF₃ (3) |
| CH₂ | Pyridinyl | NH—C(O) | Thiazolyl | Z₁: CH₂—CH₂F (2) |
| CH₂ | Pyridinyl | NH—C(O) | Thiazolyl | Z₁: CH₂—CH₂F (3) |
| CH₂ | Pyridinyl | NH—C(O) | Thiazolyl | Z₁: CH₂—CHF₂ (2) |
| CH₂ | Pyridinyl | NH—C(O) | Thiazolyl | Z₁: CH₂—CHF₂ (3) |
| CH₂ | Pyridinyl | NH—C(O) | Thiazolyl | Z₁: CH₂—CF₃ (2) |
| CH₂ | Pyridinyl | NH—C(O) | Thiazolyl | Z₁: CH₂—CF₃ (3) |
| CH₂ | pyridinyl | NH—SO₂ | Phenyl | None |
| CH₂ | pyridinyl | NH—SO₂ | Phenyl | Z₁: F (para) |
| CH₂ | pyridinyl | NH—SO₂ | phenyl | Z₁: F (meta) |
| CH₂ | pyridinyl | NH—SO₂ | phenyl | Z₁: F (ortho) |
| CH₂ | pyridinyl | NH—SO₂ | phenyl | Z₁: F (para) <br> Z₂: F (meta) |

TABLE 2-continued

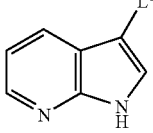

| $L^1$ | $C^1$ | $L^2$ | $C^2$ | Z |
|---|---|---|---|---|
| $CH_2$ | Pyridinyl | $NH-SO_2$ | Phenyl | $Z_1$: Cl (meta) |
| $CH_2$ | Pyridinyl | $NH-SO_2$ | Phenyl | $Z_1$: Cl (para) |
| $CH_2$ | Pyridinyl | $NH-SO_2$ | Phenyl | $Z_1$: Cl (para)<br>$Z_2$: Cl (meta) |
| $CH_2$ | Pyridinyl | $NH-SO_2$ | Phenyl | $Z_1$: F (para)<br>$Z_2$: Cl (meta) |
| $CH_2$ | Pyridinyl | $NH-SO_2$ | Phenyl | $Z_1$: Cl (para)<br>$Z_2$: F (meta) |
| $CH_2$ | Pyridinyl | $NH-SO_2$ | Phenyl | $Z_1$: $CH_3$ (para) |
| $CH_2$ | Pyridinyl | $NH-SO_2$ | Phenyl | $Z_1$: $CH_3$ (meta) |
| $CH_2$ | Pyridinyl | $NH-SO_2$ | Phenyl | $Z_1$: $CH_3$ (ortho) |
| $CH_2$ | Pyridinyl | $NH-SO_2$ | Phenyl | $Z_1$: $CH_2-CH_3$ (para) |
| $CH_2$ | Pyridinyl | $NH-SO_2$ | Phenyl | $Z_1$: $CH_2-CH_3$ (meta) |
| $CH_2$ | Pyridinyl | $NH-SO_2$ | Phenyl | $Z_1$: $CH_2-CH_3$ (ortho) |
| $CH_2$ | Pyridinyl | $NH-SO_2$ | Phenyl | $Z_1$: $CH_2-CH_2-CH_3$ or iPr (para) |
| $CH_2$ | Pyridinyl | $NH-SO_2$ | Phenyl | $Z_1$: $CH_2-CH_2-CH_3$ or iPr (meta) |
| $CH_2$ | Pyridinyl | $NH-SO_2$ | Phenyl | $Z_1$: $CH_2-CH_2-CH_3$ or iPr (ortho) |
| $CH_2$ | Pyridinyl | $NH-SO_2$ | Phenyl | $Z_1$: $CH_2F$ (para) |
| $CH_2$ | Pyridinyl | $NH-SO_2$ | Phenyl | $Z_1$: $CH_2F$ (meta) |
| $CH_2$ | Pyridinyl | $NH-SO_2$ | Phenyl | $Z_1$: $CH_2F$ (ortho) |
| $CH_2$ | Pyridinyl | $NH-SO_2$ | Phenyl | $Z_1$: $CHF_2$ (para) |
| $CH_2$ | Pyridinyl | $NH-SO_2$ | Phenyl | $Z_1$: $CHF_2$ (meta) |
| $CH_2$ | Pyridinyl | $NH-SO_2$ | Phenyl | $Z_1$: $CHF_2$ (ortho) |
| $CH_2$ | Pyridinyl | $NH-SO_2$ | Phenyl | $Z_1$: $CF_3$ (para) |
| $CH_2$ | Pyridinyl | $NH-SO_2$ | Phenyl | $Z_1$: $CF_3$ (meta) |
| $CH_2$ | Pyridinyl | $NH-SO_2$ | Phenyl | $Z_1$: $CF_3$ (ortho) |
| $CH_2$ | Pyridinyl | $NH-SO_2$ | Phenyl | $Z_1$: $CH_2-CH_2F$ (para) |
| $CH_2$ | Pyridinyl | $NH-SO_2$ | Phenyl | $Z_1$: $CH_2-CH_2F$ (meta) |
| $CH_2$ | Pyridinyl | $NH-SO_2$ | Phenyl | $Z_1$: $CH_2-CH_2F$ (ortho) |
| $CH_2$ | Pyridinyl | $NH-SO_2$ | Phenyl | $Z_1$: $CH_2-CHF_2$ (para) |
| $CH_2$ | Pyridinyl | $NH-SO_2$ | Phenyl | $Z_1$: $CH_2-CHF_2$ (meta) |
| $CH_2$ | Pyridinyl | $NH-SO_2$ | Phenyl | $Z_1$: $CH_2-CHF_2$ (ortho) |
| $CH_2$ | Pyridinyl | $NH-SO_2$ | Phenyl | $Z_1$: $CH_2-CF_3$ (para) |
| $CH_2$ | Pyridinyl | $NH-SO_2$ | Phenyl | $Z_1$: $CH_2-CF_3$ (meta) |
| $CH_2$ | Pyridinyl | $NH-SO_2$ | Phenyl | $Z_1$: $CH_2-CF_3$ (ortho) |
| $CH_2$ | pyridinyl | $NH-SO_2$ | Pyridinyl | None |
| $CH_2$ | pyridinyl | $NH-SO_2$ | Pyridinyl | $Z_1$: F (para) |
| $CH_2$ | pyridinyl | $NH-SO_2$ | Pyridinyl | $Z_1$: F (meta) |
| $CH_2$ | pyridinyl | $NH-SO_2$ | Pyridinyl | $Z_1$: F (ortho) |
| $CH_2$ | pyridinyl | $NH-SO_2$ | Pyridinyl | $Z_1$: F (para)<br>$Z_2$: F (meta) |
| $CH_2$ | Pyridinyl | $NH-SO_2$ | Pyridinyl | $Z_1$: Cl (meta) |
| $CH_2$ | Pyridinyl | $NH-SO_2$ | Pyridinyl | $Z_1$: Cl (para) |
| $CH_2$ | Pyridinyl | $NH-SO_2$ | Pyridinyl | $Z_1$: Cl (para)<br>$Z_2$: Cl (meta) |
| $CH_2$ | Pyridinyl | $NH-SO_2$ | Pyridinyl | $Z_1$: F (para)<br>$Z_2$: Cl (meta) |
| $CH_2$ | Pyridinyl | $NH-SO_2$ | Pyridinyl | $Z_1$: Cl (para)<br>$Z_2$: F (meta) |
| $CH_2$ | Pyridinyl | $NH-SO_2$ | Pyridinyl | $Z_1$: $CH_3$ (para) |
| $CH_2$ | Pyridinyl | $NH-SO_2$ | Pyridinyl | $Z_1$: $CH_3$ (meta) |
| $CH_2$ | Pyridinyl | $NH-SO_2$ | Pyridinyl | $Z_1$: $CH_3$ (ortho) |
| $CH_2$ | Pyridinyl | $NH-SO_2$ | Pyridinyl | $Z_1$: $CH_2-CH_3$ (para) |
| $CH_2$ | Pyridinyl | $NH-SO_2$ | Pyridinyl | $Z_1$: $CH_2-CH_3$ (meta) |
| $CH_2$ | Pyridinyl | $NH-SO_2$ | Pyridinyl | $Z_1$: $CH_2-CH_3$ (ortho) |
| $CH_2$ | Pyridinyl | $NH-SO_2$ | Pyridinyl | $Z_1$: $CH_2-CH_2-CH_3$ or iPr (para) |
| $CH_2$ | Pyridinyl | $NH-SO_2$ | Pyridinyl | $Z_1$: $CH_2-CH_2-CH_3$ or iPr (meta) |
| $CH_2$ | Pyridinyl | $NH-SO_2$ | Pyridinyl | $Z_1$: $CH_2-CH_2-CH_3$ or iPr (ortho) |
| $CH_2$ | Pyridinyl | $NH-SO_2$ | Pyridinyl | $Z_1$: $CH_2F$ (para) |
| $CH_2$ | Pyridinyl | $NH-SO_2$ | Pyridinyl | $Z_1$: $CH_2F$ (meta) |
| $CH_2$ | Pyridinyl | $NH-SO_2$ | Pyridinyl | $Z_1$: $CH_2F$ (ortho) |
| $CH_2$ | Pyridinyl | $NH-SO_2$ | Pyridinyl | $Z_1$: $CHF_2$ (para) |
| $CH_2$ | Pyridinyl | $NH-SO_2$ | Pyridinyl | $Z_1$: $CHF_2$ (meta) |

TABLE 2-continued

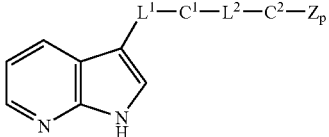

| L$^1$ | C$^1$ | L$^2$ | C$^2$ | Z |
|---|---|---|---|---|
| CH$_2$ | Pyridinyl | NH—SO$_2$ | Pyridinyl | Z$_1$: CHF$_2$ (ortho) |
| CH$_2$ | Pyridinyl | NH—SO$_2$ | Pyridinyl | Z$_1$: CF$_3$ (para) |
| CH$_2$ | Pyridinyl | NH—SO$_2$ | Pyridinyl | Z$_1$: CF$_3$ (meta) |
| CH$_2$ | Pyridinyl | NH—SO$_2$ | Pyridinyl | Z$_1$: CF$_3$ (ortho) |
| CH$_2$ | Pyridinyl | NH—SO$_2$ | Pyridinyl | Z$_1$: CH$_2$—CH$_2$F (para) |
| CH$_2$ | Pyridinyl | NH—SO$_2$ | Pyridinyl | Z$_1$: CH$_2$—CH$_2$F (meta) |
| CH$_2$ | Pyridinyl | NH—SO$_2$ | Pyridinyl | Z$_1$: CH$_2$—CH$_2$F (ortho) |
| CH$_2$ | Pyridinyl | NH—SO$_2$ | Pyridinyl | Z$_1$: CH$_2$—CHF$_2$ (para) |
| CH$_2$ | Pyridinyl | NH—SO$_2$ | Pyridinyl | Z$_1$: CH$_2$—CHF$_2$ (meta) |
| CH$_2$ | Pyridinyl | NH—SO$_2$ | Pyridinyl | Z$_1$: CH$_2$—CHF$_2$ (ortho) |
| CH$_2$ | Pyridinyl | NH—SO$_2$ | Pyridinyl | Z$_1$: CH$_2$—CF$_3$ (para) |
| CH$_2$ | Pyridinyl | NH—SO$_2$ | Pyridinyl | Z$_1$: CH$_2$—CF$_3$ (meta) |
| CH$_2$ | Pyridinyl | NH—SO$_2$ | Pyridinyl | Z$_1$: CH$_2$—CF3 ortho) |
| CH$_2$ | pyridinyl | NH—SO$_2$ | Pyrimidinyl | None |
| CH$_2$ | pyridinyl | NH—SO$_2$ | Pyrimidinyl | Z$_1$: F (para) |
| CH$_2$ | pyridinyl | NH—SO$_2$ | Pyrimidinyl | Z$_1$: F (meta) |
| CH$_2$ | pyridinyl | NH—SO$_2$ | Pyrimidinyl | Z$_1$: F (ortho) |
| CH$_2$ | pyridinyl | NH—SO$_2$ | Pyrimidinyl | Z$_1$: F (para) Z$_2$: F (meta) |
| CH$_2$ | Pyridinyl | NH—SO$_2$ | Pyrimidinyl | Z$_1$: Cl (meta) |
| CH$_2$ | Pyridinyl | NH—SO$_2$ | Pyrimidinyl | Z$_1$: Cl (para) |
| CH$_2$ | Pyridinyl | NH—SO$_2$ | Pyrimidinyl | Z$_1$: Cl (para) Z$_2$: Cl (meta) |
| CH$_2$ | Pyridinyl | NH—SO$_2$ | Pyrimidinyl | Z$_1$: F (para) Z$_2$: Cl (meta) |
| CH$_2$ | Pyridinyl | NH—SO$_2$ | Pyrimidinyl | Z$_1$: Cl (para) Z$_2$: F (meta) |
| CH$_2$ | Pyridinyl | NH—SO$_2$ | Pyrimidinyl | Z$_1$: CH$_3$ (para) |
| CH$_2$ | Pyridinyl | NH—SO$_2$ | Pyrimidinyl | Z$_1$: CH$_3$ (meta) |
| CH$_2$ | Pyridinyl | NH—SO$_2$ | Pyrimidinyl | Z$_1$: CH$_3$ (ortho) |
| CH$_2$ | Pyridinyl | NH—SO$_2$ | Pyrimidinyl | Z$_1$: CH$_2$—CH$_3$ (para) |
| CH$_2$ | Pyridinyl | NH—SO$_2$ | Pyrimidinyl | Z$_1$: CH$_2$—CH$_3$ (meta) |
| CH$_2$ | Pyridinyl | NH—SO$_2$ | Pyrimidinyl | Z$_1$: CH$_2$—CH$_3$ (ortho) |
| CH$_2$ | Pyridinyl | NH—SO$_2$ | Pyrimidinyl | Z$_1$: CH$_2$—CH$_2$—CH$_3$ or iPr (para) |
| CH$_2$ | Pyridinyl | NH—SO$_2$ | Pyrimidinyl | Z$_1$: CH$_2$—CH$_2$—CH$_3$ or iPr (meta) |
| CH$_2$ | Pyridinyl | NH—SO$_2$ | Pyrimidinyl | Z$_1$: CH$_2$—CH$_2$—CH$_3$ or iPr (ortho) |
| CH$_2$ | Pyridinyl | NH—SO$_2$ | Pyrimidinyl | Z$_1$: CH$_2$F (para) |
| CH$_2$ | Pyridinyl | NH—SO$_2$ | Pyrimidinyl | Z$_1$: CH$_2$F (meta) |
| CH$_2$ | Pyridinyl | NH—SO$_2$ | Pyrimidinyl | Z$_1$: CH$_2$F (ortho) |
| CH$_2$ | Pyridinyl | NH—SO$_2$ | Pyrimidinyl | Z$_1$: CHF$_2$ (para) |
| CH$_2$ | Pyridinyl | NH—SO$_2$ | Pyrimidinyl | Z$_1$: CHF$_2$ (meta) |
| CH$_2$ | Pyridinyl | NH—SO$_2$ | Pyrimidinyl | Z$_1$: CHF$_2$ (ortho) |
| CH$_2$ | Pyridinyl | NH—SO$_2$ | Pyrimidinyl | Z$_1$: CF$_3$ (para) |
| CH$_2$ | Pyridinyl | NH—SO$_2$ | Pyrimidinyl | Z$_1$: CF$_3$ (meta) |
| CH$_2$ | Pyridinyl | NH—SO$_2$ | Pyrimidinyl | Z$_1$: CF$_3$ (ortho) |
| CH$_2$ | Pyridinyl | NH—SO$_2$ | Pyrimidinyl | Z$_1$: CH$_2$—CH$_2$F (para) |
| CH$_2$ | Pyridinyl | NH—SO$_2$ | Pyrimidinyl | Z$_1$: CH$_2$—CH$_2$F (meta) |
| CH$_2$ | Pyridinyl | NH—SO$_2$ | Pyriiidinyl | Z$_1$: CH$_2$—CH$_2$F (ortho) |
| CH$_2$ | Pyridinyl | NH—SO$_2$ | Pyrimidinyl | Z$_1$: CH$_2$—CHF$_2$ (para) |
| CH$_2$ | Pyridinyl | NH—SO$_2$ | Pyrimidinyl | Z$_1$: CH$_2$—CHF$_2$ (meta) |
| CH$_2$ | Pyridinyl | NH—SO$_2$ | Pyrimidinyl | Z$_1$: CH$_2$—CHF$_2$ (ortho) |
| CH$_2$ | Pyridinyl | NH—SO$_2$ | Pyrimidinyl | Z$_1$: CH$_2$—CF$_3$ (para) |
| CH$_2$ | Pyridinyl | NH—SO$_2$ | Pyrimidinyl | Z$_1$: CH$_2$—CF$_3$ (meta) |
| CH$_2$ | Pyridinyl | NH—SO$_2$ | Pyrimidinyl | Z$_1$: CH$_2$—CF$_3$ (ortho) |
| CH$_2$ | pyridinyl | NH—SO$_2$ | Pyrazinyl | None |
| CH$_2$ | pyridinyl | NH—SO$_2$ | Pyrazinyl | Z$_1$: F (para) |
| CH$_2$ | pyridinyl | NH—SO$_2$ | Pyrazinyl | Z$_1$: F (meta) |
| CH$_2$ | pyridinyl | NH—SO$_2$ | Pyrazinyl | Z$_1$: F (ortho) |
| CH$_2$ | pyridinyl | NH—SO$_2$ | Pyrazinyl | Z$_1$: F (para) Z$_2$: F (meta) |
| CH$_2$ | Pyridinyl | NH—SO$_2$ | Pyrazinyl | Z$_1$: Cl (meta) |
| CH$_2$ | Pyridinyl | NH—SO$_2$ | Pyrazinyl | Z$_1$: Cl (para) |
| CH$_2$ | Pyridinyl | NH—SO$_2$ | Pyrazinyl | Z$_1$: Cl (para) Z$_2$: Cl (meta) |
| CH$_2$ | Pyridinyl | NH—SO$_2$ | Pyrazinyl | Z$_1$: F (para) Z$_2$: Cl (meta) |

TABLE 2-continued

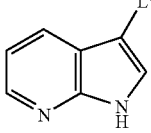

| $L^1$ | $C^1$ | $L^2$ | $C^2$ | Z |
|---|---|---|---|---|
| $CH_2$ | Pyridinyl | $NH-SO_2$ | Pyrazinyl | $Z_1$: Cl (para) |
| | | | | $Z_2$: F (meta) |
| $CH_2$ | Pyridinyl | $NH-SO_2$ | Pyrazinyl | $Z_1$: $CH_3$ (para) |
| $CH_2$ | Pyridinyl | $NH-SO_2$ | Pyrazinyl | $Z_1$: $CH_3$ (meta) |
| $CH_2$ | Pyridinyl | $NH-SO_2$ | Pyrazinyl | $Z_1$: $CH_3$ (ortho) |
| $CH_2$ | Pyridinyl | $NH-SO_2$ | Pyrazinyl | $Z_1$: $CH_2-CH_3$ (para) |
| $CH_2$ | Pyridinyl | $NH-SO_2$ | Pyrazinyl | $Z_1$: $CH_2-CH_3$ (meta) |
| $CH_2$ | Pyridinyl | $NH-SO_2$ | Pyrazinyl | $Z_1$: $CH_2-CH_3$ (ortho) |
| $CH_2$ | Pyridinyl | $NH-SO_2$ | Pyrazinyl | $Z_1$: $CH_2-CH_2-CH_3$ or iPr (para) |
| $CH_2$ | Pyridinyl | $NH-SO_2$ | Pyrazinyl | $Z_1$: $CH_2-CH_2-CH_3$ or iPr (meta) |
| $CH_2$ | Pyridinyl | $NH-SO_2$ | Pyrazinyl | $Z_1$: $CH_2-CH_2-CH_3$ or iPr (ortho) |
| $CH_2$ | Pyridinyl | $NH-SO_2$ | Pyrazinyl | $Z_1$: $CH_2F$ (para) |
| $CH_2$ | Pyridinyl | $NH-SO_2$ | Pyrazinyl | $Z_1$: $CH_2F$ (meta) |
| $CH_2$ | Pyridinyl | $NH-SO_2$ | Pyrazinyl | $Z_1$: $CH_2F$ (ortho) |
| $CH_2$ | Pyridinyl | $NH-SO_2$ | Pyrazinyl | $Z_1$: $CHF_2$ (para) |
| $CH_2$ | Pyridinyl | $NH-SO_2$ | Pyrazinyl | $Z_1$: $CHF_2$ (meta) |
| $CH_2$ | Pyridinyl | $NH-SO_2$ | Pyrazinyl | $Z_1$: $CHF_2$ (ortho) |
| $CH_2$ | Pyridinyl | $NH-SO_2$ | Pyrazinyl | $Z_1$: $CF_3$ (para) |
| $CH_2$ | Pyridinyl | $NH-SO_2$ | Pyrazinyl | $Z_1$: $CF_3$ (meta) |
| $CH_2$ | Pyridinyl | $NH-SO_2$ | Pyrazinyl | $Z_1$: $CF_3$ (ortho) |
| $CH_2$ | Pyridinyl | $NH-SO_2$ | Pyrazinyl | $Z_1$: $CH_2-CH_2F$ (para) |
| $CH_2$ | Pyridinyl | $NH-SO_2$ | Pyrazinyl | $Z_1$: $CH_2-CH_2F$ (meta) |
| $CH_2$ | Pyridinyl | $NH-SO_2$ | Pyrazinyl | $Z_1$: $CH_2-CH_2F$ (ortho) |
| $CH_2$ | Pyridinyl | $NH-SO_2$ | Pyrazinyl | $Z_1$: $CH_2-CHF_2$ (para) |
| $CH_2$ | Pyridinyl | $NH-SO_2$ | Pyrazinyl | $Z_1$: $CH_2-CHF_2$ (meta) |
| $CH_2$ | Pyridinyl | $NH-SO_2$ | Pyrazinyl | $Z_1$: $CH_2-CHF_2$ (ortho) |
| $CH_2$ | Pyridinyl | $NH-SO_2$ | Pyrazinyl | $Z_1$: $CH_2-CF_3$ (para) |
| $CH_2$ | Pyridinyl | $NH-SO_2$ | Pyrazinyl | $Z_1$: $CH_2-CF_3$ (meta) |
| $CH_2$ | Pyridinyl | $NH-SO_2$ | Pyrazinyl | $Z_1$: $CH_2-CF_3$ (ortho) |
| $CH_2$ | pyridinyl | $NH-SO_2$ | Pyrrolyl | None |
| $CH_2$ | pyridinyl | $NH-SO_2$ | Pyrrolyl | $Z_1$: F (2) |
| $CH_2$ | pyridinyl | $NH-SO_2$ | Pyrrolyl | $Z_1$: F (3) |
| $CH_2$ | pyridinyl | $NH-SO_2$ | Pyrrolyl | $Z_1$: F (2) |
| | | | | $Z_2$: F (3) |
| $CH_2$ | Pyridinyl | $NH-SO_2$ | Pyrrolyl | $Z_1$: Cl (2) |
| $CH_2$ | Pyridinyl | $NH-SO_2$ | Pyrrolyl | $Z_1$: Cl (3) |
| $CH_2$ | Pyridinyl | $NH-SO_2$ | Pyrrolyl | $Z_1$: Cl (2) |
| | | | | $Z_2$: Cl (3) |
| $CH_2$ | Pyridinyl | $NH-SO_2$ | Pyrrolyl | $Z_1$: F (2) |
| | | | | $Z_2$: Cl (3) |
| $CH_2$ | Pyridinyl | $NH-SO_2$ | Pyrrolyl | $Z_1$: Cl (2) |
| | | | | $Z_2$: F (3) |
| $CH_2$ | Pyridinyl | $NH-SO_2$ | Pyrrolyl | $Z_1$: $CH_3$ (2) |
| $CH_2$ | Pyridinyl | $NH-SO_2$ | Pyrrolyl | $Z_1$: $CH_3$ (3) |
| $CH_2$ | Pyridinyl | $NH-SO_2$ | Pyrrolyl | $Z_1$: $CH_2-CH_3$ (2) |
| $CH_2$ | Pyridinyl | $NH-SO_2$ | Pyrrolyl | $Z_1$: $CH_2-CH_3$ (3) |
| $CH_2$ | Pyridinyl | $NH-SO_2$ | Pyrrolyl | $Z_1$: $CH_2-CH_2-CH_3$ or iPr (2) |
| $CH_2$ | Pyridinyl | $NH-SO_2$ | Pyrrolyl | $Z_1$: $CH_2-CH_2-CH_3$ or iPr (3) |
| $CH_2$ | Pyridinyl | $NH-SO_2$ | Pyrrolyl | $Z_1$: $CH_2F$ (2) |
| $CH_2$ | Pyridinyl | $NH-SO_2$ | Pyrrolyl | $Z_1$: $CH_2F$ (3) |
| $CH_2$ | Pyridinyl | $NH-SO_2$ | Pyrrolyl | $Z_1$: $CHF_2$ (2) |
| $CH_2$ | Pyridinyl | $NH-SO_2$ | Pyrrolyl | $Z_1$: $CHF_2$ (3) |
| $CH_2$ | Pyridinyl | $NH-SO_2$ | Pyrrolyl | $Z_1$: $CF_3$ (2) |
| $CH_2$ | Pyridinyl | $NH-SO_2$ | Pyrrolyl | $Z_1$: $CF_3$ (3) |
| $CH_2$ | Pyridinyl | $NH-SO_2$ | Pyrrolyl | $Z_1$: $CH_2-CH_2F$ (2) |
| $CH_2$ | Pyridinyl | $NH-SO_2$ | Pyrrolyl | $Z_1$: $CH_2-CH_2F$ (3) |
| $CH_2$ | Pyridinyl | $NH-SO_2$ | Pyrrolyl | $Z_1$: $CH_2-CHF_2$ (2) |
| $CH_2$ | Pyridinyl | $NH-SO_2$ | Pyrrolyl | $Z_1$: $CH_2-CHF_2$ (3) |
| $CH_2$ | Pyridinyl | $NH-SO_2$ | Pyrrolyl | $Z_1$: $CH_2-CF_3$ (2) |
| $CH_2$ | Pyridinyl | $NH-SO_2$ | Pyrrolyl | $Z_1$: $CH_2-CF_3$ (3) |
| $CH_2$ | pyridinyl | $NH-SO_2$ | Imidazolyl | None |
| $CH_2$ | pyridinyl | $NH-SO_2$ | Imidazolyl | $Z_1$: F (2) |
| $CH_2$ | pyridinyl | $NH-SO_2$ | Imidazolyl | $Z_1$: F (3) |
| $CH_2$ | pyridinyl | $NH-SO_2$ | Imidazolyl | $Z_1$: F (2) |
| | | | | $Z_2$: F (3) |
| $CH_2$ | Pyridinyl | $NH-SO_2$ | Imidazolyl | $Z_1$: Cl (2) |

TABLE 2-continued

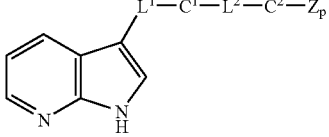

| L$^1$ | C$^1$ | L$^2$ | C$^2$ | Z |
|---|---|---|---|---|
| CH$_2$ | Pyridinyl | NH—SO$_2$ | Imidazolyl | Z$_1$: Cl (3) |
| CH$_2$ | Pyridinyl | NH—SO$_2$ | Imidazolyl | Z$_1$: Cl (2) |
|  |  |  |  | Z$_2$: Cl (3) |
| CH$_2$ | Pyridinyl | NH—SO$_2$ | Imidazolyl | Z$_1$: F (2) |
|  |  |  |  | Z$_2$: Cl (3) |
| CH$_2$ | Pyridinyl | NH—SO$_2$ | Imidazolyl | Z$_1$: Cl (2) |
|  |  |  |  | Z$_2$: F (3) |
| CH$_2$ | Pyridinyl | NH—SO$_2$ | Imidazolyl | Z$_1$: CH$_3$ (2) |
| CH$_2$ | Pyridinyl | NH—SO$_2$ | Imidazolyl | Z$_1$: CH$_3$ (3) |
| CH$_2$ | Pyridinyl | NH—SO$_2$ | Imidazolyl | Z$_1$: CH$_2$—CH$_3$ (2) |
| CH$_2$ | Pyridinyl | NH—SO$_2$ | Imidazolyl | Z$_1$: CH$_2$—CH$_3$ (3) |
| CH$_2$ | Pyridinyl | NH—SO$_2$ | Imidazolyl | Z$_1$: CH$_2$—CH$_2$—CH$_3$ or iPr (2) |
| CH$_2$ | Pyridinyl | NH—SO$_2$ | Imidazolyl | Z$_1$: CH$_2$—CH$_2$—CH$_3$ or iPr (3) |
| CH$_2$ | Pyridinyl | NH—SO$_2$ | Imidazolyl | Z$_1$: CH$_2$F (2) |
| CH$_2$ | Pyridinyl | NH—SO$_2$ | Imidazolyl | Z$_1$: CH$_2$F (3) |
| CH$_2$ | Pyridinyl | NH—SO$_2$ | Imidazolyl | Z$_1$: CHF$_2$ (2) |
| CH$_2$ | Pyridinyl | NH—SO$_2$ | Imidazolyl | Z$_1$: CHF$_2$ (3) |
| CH$_2$ | Pyridinyl | NH—SO$_2$ | Imidazolyl | Z$_1$: CF$_3$ (2) |
| CH$_2$ | Pyridinyl | NH—SO$_2$ | Imidazolyl | Z$_1$: CF$_3$ (3) |
| CH$_2$ | Pyridinyl | NH—SO$_2$ | Imidazolyl | Z$_1$: CH$_2$—CH$_2$F (2) |
| CH$_2$ | Pyridinyl | NH—SO$_2$ | Imidazolyl | Z$_1$: CH$_2$—CH$_2$F (3) |
| CH$_2$ | Pyridinyl | NH—SO$_2$ | Imidazolyl | Z$_1$: CH$_2$—CHF$_2$ (2) |
| CH$_2$ | Pyridinyl | NH—SO$_2$ | Imidazolyl | Z$_1$: CH$_2$—CHF$_2$ (3) |
| CH$_2$ | Pyridinyl | NH—SO$_2$ | Imidazolyl | Z$_1$: CH$_2$—CF$_3$ (2) |
| CH$_2$ | Pyridinyl | NH—SO$_2$ | Imidazolyl | Z$_1$: CH$_2$—CF$_3$ (3) |
| CH$_2$ | pyridinyl | NH—SO$_2$ | Furanyl | None |
| CH$_2$ | pyridinyl | NH—SO$_2$ | Furanyl | Z$_1$: F (2) |
| CH$_2$ | pyridinyl | NH—SO$_2$ | Furanyl | Z$_1$: F (3) |
| CH$_2$ | pyridinyl | NH—SO$_2$ | Furanyl | Z$_1$: F (2) |
|  |  |  |  | Z$_2$: F (3) |
| CH$_2$ | Pyridinyl | NH—SO$_2$ | Furanyl | Z$_1$: Cl (2) |
| CH$_2$ | Pyridinyl | NH—SO$_2$ | Furanyl | Z$_1$: Cl (3) |
| CH$_2$ | Pyridinyl | NH—SO$_2$ | Furanyl | Z$_1$: Cl (2) |
|  |  |  |  | Z$_2$: Cl (3) |
| CH$_2$ | Pyridinyl | NH—SO$_2$ | Furanyl | Z$_1$: F (2) |
|  |  |  |  | Z$_2$: Cl (3) |
| CH$_2$ | Pyridinyl | NH—SO$_2$ | Furanyl | Z$_1$: Cl (2) |
|  |  |  |  | Z$_2$: F (3) |
| CH$_2$ | Pyridinyl | NH—SO$_2$ | Furanyl | Z$_1$: CH$_3$ (2) |
| CH$_2$ | Pyridinyl | NH—SO$_2$ | Furanyl | Z$_1$: CH$_3$ (3) |
| CH$_2$ | Pyridinyl | NH—SO$_2$ | Furanyl | Z$_1$: CH$_2$—CH$_3$ (2) |
| CH$_2$ | Pyridinyl | NH—SO$_2$ | Furanyl | Z$_1$: CH$_2$—CH$_3$ (3) |
| CH$_2$ | Pyridinyl | NH—SO$_2$ | Furanyl | Z$_1$: CH$_2$—CH$_2$—CH3 or iPr (2) |
| CH$_2$ | Pyridinyl | NH—SO$_2$ | Furanyl | Z$_1$: CH$_2$—CH$_2$—CH3 or iPr (3) |
| CH$_2$ | Pyridinyl | NH—SO$_2$ | Furanyl | Z$_1$: CH$_2$F (2) |
| CH$_2$ | Pyridinyl | NH—SO$_2$ | Furanyl | Z$_1$: CH$_2$F (3) |
| CH$_2$ | Pyridinyl | NH—SO$_2$ | Furanyl | Z$_1$: CHF$_2$ (2) |
| CH$_2$ | Pyridinyl | NH—SO$_2$ | Furanyl | Z$_1$: CHF$_2$ (3) |
| CH$_2$ | Pyridinyl | NH—SO$_2$ | Furanyl | Z$_1$: CF$_3$ (2) |
| CH$_2$ | Pyridinyl | NH—SO$_2$ | Furanyl | Z$_1$: CF$_3$ (3) |
| CH$_2$ | Pyridinyl | NH—SO$_2$ | Furanyl | Z$_1$: CH$_2$—CH$_2$F (2) |
| CH$_2$ | Pyridinyl | NH—SO$_2$ | Furanyl | Z$_1$: CH$_2$—CH$_2$F (3) |
| CH$_2$ | Pyridinyl | NH—SO$_2$ | Furanyl | Z$_1$: CH$_2$—CHF$_2$ (2) |
| CH$_2$ | Pyridinyl | NH—SO$_2$ | Furanyl | Z$_1$: CH$_2$—CHF$_2$ (3) |
| CH$_2$ | Pyridinyl | NH—SO$_2$ | Furanyl | Z$_1$: CH$_2$—CF$_3$ (2) |
| CH$_2$ | Pyridinyl | NH—SO$_2$ | Furanyl | Z$_1$: CH$_2$—CF$_3$ (3) |
| CH$_2$ | pyridinyl | NH—SO$_2$ | Oxazolyl | None |
| CH$_2$ | pyridinyl | NH—SO$_2$ | Oxazolyl | Z$_1$: F (2) |
| CH$_2$ | pyridinyl | NH—SO$_2$ | Oxazolyl | Z$_1$: F (3) |
| CH$_2$ | pyridinyl | NH—SO$_2$ | Oxazolyl | Z$_1$: F (2) |
|  |  |  |  | Z$_2$: F (3) |
| CH$_2$ | Pyridinyl | NH—SO$_2$ | Oxazolyl | Z$_1$: Cl (2) |
| CH$_2$ | Pyridinyl | NH—SO$_2$ | Oxazolyl | Z$_1$: Cl (3) |
| CH$_2$ | Pyridinyl | NH—SO$_2$ | Oxazolyl | Z$_1$: Cl (2) |
|  |  |  |  | Z$_2$: Cl (3) |
| CH$_2$ | Pyridinyl | NH—SO$_2$ | Oxazolyl | Z$_1$: F (2) |
|  |  |  |  | Z$_2$: Cl (3) |
| CH$_2$ | Pyridinyl | NH—SO$_2$ | Oxazolyl | Z$_1$: Cl (2) |
|  |  |  |  | Z$_2$: F (3) |

TABLE 2-continued

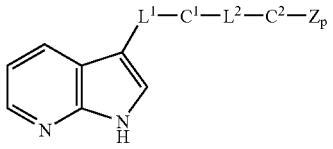

| L¹ | C¹ | L² | C² | Z |
|---|---|---|---|---|
| CH$_2$ | Pyridinyl | NH—SO$_2$ | Oxazolyl | Z$_1$: CH$_3$ (2) |
| CH$_2$ | Pyridinyl | NH—SO$_2$ | Oxazolyl | Z$_1$: CH$_3$ (3) |
| CH$_2$ | Pyridinyl | NH—SO$_2$ | Oxazolyl | Z$_1$: CH$_2$—CH$_3$ (2) |
| CH$_2$ | Pyridinyl | NH—SO$_2$ | Oxazolyl | Z$_1$: CH$_2$—CH$_3$ (3) |
| CH$_2$ | Pyridinyl | NH—SO$_2$ | Oxazolyl | Z$_1$: CH$_2$—CH$_2$—CH$_3$ or iPr (2) |
| CH$_2$ | Pyridinyl | NH—SO$_2$ | Oxazolyl | Z$_1$: CH$_2$—CH$_2$—CH$_3$ or iPr (3) |
| CH$_2$ | Pyridinyl | NH—SO$_2$ | Oxazolyl | Z$_1$: CH$_2$F (2) |
| CH$_2$ | Pyridinyl | NH—SO$_2$ | Oxazolyl | Z$_1$: CH$_2$F (3) |
| CH$_2$ | Pyridinyl | NH—SO$_2$ | Oxazolyl | Z$_1$: CHF$_2$ (2) |
| CH$_2$ | Pyridinyl | NH—SO$_2$ | Oxazolyl | Z$_1$: CHF$_2$ (3) |
| CH$_2$ | Pyridinyl | NH—SO$_2$ | Oxazolyl | Z$_1$: CF$_3$ (2) |
| CH$_2$ | Pyridinyl | NH—SO$_2$ | Oxazolyl | Z$_1$: CF$_3$ (3) |
| CH$_2$ | Pyridinyl | NH—SO$_2$ | Oxazolyl | Z$_1$: CH$_2$—CH$_2$F (2) |
| CH$_2$ | Pyridinyl | NH—SO$_2$ | Oxazolyl | Z$_1$: CH$_2$—CH$_2$F (3) |
| CH$_2$ | Pyridinyl | NH—SO$_2$ | Oxazolyl | Z$_1$: CH$_2$—CHF$_2$ (2) |
| CH$_2$ | Pyridinyl | NH—SO$_2$ | Oxazolyl | Z$_1$: CH$_2$—CHF$_2$ (3) |
| CH$_2$ | Pyridinyl | NH—SO$_2$ | Oxazolyl | Z$_1$: CH$_2$—CF$_3$ (2) |
| CH$_2$ | Pyridinyl | NH—SO$_2$ | Oxazolyl | Z$_1$: CH$_2$—CF$_3$ (3) |
| CH$_2$ | pyridinyl | NH—SO$_2$ | Thiophenyl | None |
| CH$_2$ | pyridinyl | NH—SO$_2$ | Thiophenyl | Z$_1$: F (2) |
| CH$_2$ | pyridinyl | NH—SO$_2$ | Thiophenyl | Z$_1$: F (3) |
| CH$_2$ | pyridinyl | NH—SO$_2$ | Thiophenyl | Z$_1$: F (2) Z$_2$: F (3) |
| CH$_2$ | Pyridinyl | NH—SO$_2$ | Thiophenyl | Z$_1$: Cl (2) |
| CH$_2$ | Pyridinyl | NH—SO$_2$ | Thiophenyl | Z$_1$: Cl (3) |
| CH$_2$ | Pyridinyl | NH—SO$_2$ | Thiophenyl | Z$_1$: Cl (2) Z$_2$: Cl (3) |
| CH$_2$ | Pyridinyl | NH—SO$_2$ | Thiophenyl | Z$_1$: F (2) Z$_2$: Cl (3) |
| CH$_2$ | Pyridinyl | NH—SO$_2$ | Thiophenyl | Z$_1$: Cl (2) Z$_2$: F (3) |
| CH$_2$ | Pyridinyl | NH—SO$_2$ | Thiophenyl | Z$_1$: CH$_3$ (2) |
| CH$_2$ | Pyridinyl | NH—SO$_2$ | Thiophenyl | Z$_1$: CH$_3$ (3) |
| CH$_2$ | Pyridinyl | NH—SO$_2$ | Thiophenyl | Z$_1$: CH$_2$—CH$_3$ (2) |
| CH$_2$ | Pyridinyl | NH—SO$_2$ | Thiophenyl | Z$_1$: CH$_2$—CH$_3$ (3) |
| CH$_2$ | Pyridinyl | NH—SO$_2$ | Thiophenyl | Z$_1$: CH$_2$—CH$_2$—CH$_3$ or iPr (2) |
| CH$_2$ | Pyridinyl | NH—SO$_2$ | Thiophenyl | Z$_1$: CH$_2$—CH$_2$—CH$_3$ or iPr (3) |
| CH$_2$ | Pyridinyl | NH—SO$_2$ | Thiophenyl | Z$_1$: CH$_2$F (2) |
| CH$_2$ | Pyridinyl | NH—SO$_2$ | Thiophenyl | Z$_1$: CH$_2$F (3) |
| CH$_2$ | Pyridinyl | NH—SO$_2$ | Thiophenyl | Z$_1$: CHF$_2$ (2) |
| CH$_2$ | Pyridinyl | NH—SO$_2$ | Thiophenyl | Z$_1$: CHF$_2$ (3) |
| CH$_2$ | Pyridinyl | NH—SO$_2$ | Thiophenyl | Z$_1$: CF$_3$ (2) |
| CH$_2$ | Pyridinyl | NH—SO$_2$ | Thiophenyl | Z$_1$: CF$_3$ (3) |
| CH$_2$ | Pyridinyl | NH—SO$_2$ | Thiophenyl | Z$_1$: CH$_2$—CH$_2$F (2) |
| CH$_2$ | Pyridinyl | NH—SO$_2$ | Thiophenyl | Z$_1$: CH$_2$—CH$_2$F (3) |
| CH$_2$ | Pyridinyl | NH—SO$_2$ | Thiophenyl | Z$_1$: CH$_2$—CHF$_2$ (2) |
| CH$_2$ | Pyridinyl | NH—SO$_2$ | Thiophenyl | Z$_1$: CH$_2$—CHF$_2$ (3) |
| CH$_2$ | Pyridinyl | NH—SO$_2$ | Thiophenyl | Z$_1$: CH$_2$—CF$_3$ (2) |
| CH$_2$ | Pyridinyl | NH—SO$_2$ | Thiophenyl | Z$_1$: CH$_2$—CF$_3$ (3) |
| CH$_2$ | pyridinyl | NH—SO$_2$ | Thiazolyl | None |
| CH$_2$ | pyridinyl | NH—SO$_2$ | Thiazolyl | Z$_1$: F (2) |
| CH$_2$ | pyridinyl | NH—SO$_2$ | Thiazolyl | Z$_1$: F (3) |
| CH$_2$ | pyridinyl | NH—SO$_2$ | Thiazolyl | Z$_1$: F (2) Z$_2$: F (3) |
| CH$_2$ | Pyridinyl | NH—SO$_2$ | Thiazolyl | Z$_1$: Cl (2) |
| CH$_2$ | Pyridinyl | NH—SO$_2$ | Thiazolyl | Z$_1$: Cl (3) |
| CH$_2$ | Pyridinyl | NH—SO$_2$ | Thiazolyl | Z$_1$: Cl (2) Z$_2$: Cl (3) |
| CH$_2$ | Pyridinyl | NH—SO$_2$ | Thiazolyl | Z$_1$: F (2) Z$_2$: Cl (3) |
| CH$_2$ | Pyridinyl | NH—SO$_2$ | Thiazolyl | Z$_1$: Cl (2) Z$_2$: F (3) |
| CH$_2$ | Pyridinyl | NH—SO$_2$ | Thiazolyl | Z$_1$: CH$_3$ (2) |
| CH$_2$ | Pyridinyl | NH—SO$_2$ | Thiazolyl | Z$_1$: CH$_3$ (3) |
| CH$_2$ | Pyridinyl | NH—SO$_2$ | Thiazolyl | Z$_1$: CH$_2$—CH$_3$ (2) |
| CH$_2$ | Pyridinyl | NH—SO$_2$ | Thiazolyl | Z$_1$: CH$_2$—CH$_3$ (3) |
| CH$_2$ | Pyridinyl | NH—SO$_2$ | Thiazolyl | Z$_1$: CH$_2$—CH$_2$—CH$_3$ or iPr (2) |
| CH$_2$ | Pyridinyl | NH—SO$_2$ | Thiazolyl | Z$_1$: CH$_2$—CH$_2$—CH$_3$ or iPr (3) |
| CH$_2$ | Pyridinyl | NH—SO$_2$ | Thiazolyl | Z$_1$: CH$_2$F (2) |

TABLE 2-continued $$L^1-C^1-L^2-C^2-Z_p$$

[7-azaindole structure with L¹—C¹—L²—C²—Z_p substituent at 3-position]

| L¹ | C¹ | L² | C² | Z |
|---|---|---|---|---|
| CH₂ | Pyridinyl | NH—SO₂ | Thiazolyl | Z₁: CH₂F (3) |
| CH₂ | Pyridinyl | NH—SO₂ | Thiazolyl | Z₁: CHF₂ (2) |
| CH₂ | Pyridinyl | NH—SO₂ | Thiazolyl | Z₁: CHF₂ (3) |
| CH₂ | Pyridinyl | NH—SO₂ | Thiazolyl | Z₁: CF₃ (2) |
| CH₂ | Pyridinyl | NH—SO₂ | Thiazolyl | Z₁: CF₃ (3) |
| CH₂ | Pyridinyl | NH—SO₂ | Thiazolyl | Z₁: CH₂—CH₂F (2) |
| CH₂ | Pyridinyl | NH—SO₂ | Thiazolyl | Z₁: CH₂—CH₂F (3) |
| CH₂ | Pyridinyl | NH—SO₂ | Thiazolyl | Z₁: CH₂—CHF₂ (2) |
| CH₂ | Pyridinyl | NH—SO₂ | Thiazolyl | Z₁: CH₂—CHF₂ (3) |
| CH₂ | Pyridinyl | NH—SO₂ | Thiazolyl | Z₁: CH₂—CF₃ (2) |
| CH₂ | Pyridinyl | NH—SO₂ | Thiazolyl | Z₁: CH₂—CF₃ (3) |
| CH₂ | Pyrimidinyl | NH—CH₂ | Phenyl | None |
| CH₂ | Pyrimidinyl | NH—CH₂ | Phenyl | Z₁: F (para) |
| CH₂ | Pyrimidinyl | NH—CH₂ | Phenyl | Z₁: F (meta) |
| CH₂ | Pyrimidinyl | NH—CH₂ | phenyl | Z₁: F (ortho) |
| CH₂ | Pyrimidinyl | NH—CH₂ | phenyl | Z₁: F (para)<br>Z₂: F (meta) |
| CH₂ | Pyrimidinyl | NH—CH₂ | Phenyl | Z₁: Cl (meta) |
| CH₂ | Pyrimidinyl | NH—CH₂ | Phenyl | Z₁: Cl (para) |
| CH₂ | Pyrimidinyl | NH—CH₂ | Phenyl | Z₁: Cl (para)<br>Z₂: Cl (meta) |
| CH₂ | Pyrimidinyl | NH—CH₂ | Phenyl | Z₁: F (para)<br>Z₂: Cl (meta) |
| CH₂ | Pyrimidinyl | NH—CH₂ | Phenyl | Z₁: Cl (para)<br>Z₂: F (meta) |
| CH₂ | Pyrimidinyl | NH—CH₂ | Phenyl | Z₁: CH₃ (para) |
| CH₂ | Pyrimidinyl | NH—CH₂ | Phenyl | Z₁: CH₃ (meta) |
| CH₂ | Pyrimidinyl | NH—CH₂ | Phenyl | Z₁: CH₃ (ortho) |
| CH₂ | Pyrimidinyl | NH—CH₂ | Phenyl | Z₁: CH₂—CH₃ (para) |
| CH₂ | Pyrnnidinyl | NH—CH₂ | Phenyl | Z₁: CH₂—CH₃ (meta) |
| CH₂ | Pyrimidinyl | NH—CH₂ | Phenyl | Z₁: CH₂—CH₃ (ortho) |
| CH₂ | Pyrimidinyl | NH—CH₂ | Phenyl | Z₁: CH₂—CH₂—CH₃ or iPr (para) |
| CH₂ | Pyrimidinyl | NH—CH₂ | Phenyl | Z₁: CH₂—CH₂—CH₃ or iPr (meta) |
| CH₂ | Pyrimidinyl | NH—CH₂ | Phenyl | Z₁: CH₂—CH₂—CH₃ or iPr (ortho) |
| CH₂ | Pyrimidinyl | NH—CH₂ | Phenyl | Z₁: CH₂F (para) |
| CH₂ | Pyrimidinyl | NH—CH₂ | Phenyl | Z₁: CH₂F (meta) |
| CH₂ | Pyrimidinyl | NH—CH₂ | Phenyl | Z₁: CH₂F (ortho) |
| CH₂ | Pyrimidinyl | NH—CH₂ | Phenyl | Z₁: CHF₂ (para) |
| CH₂ | Pyrimidinyl | NH—CH₂ | Phenyl | Z₁: CHF₂ (meta) |
| CH₂ | Pyrimidinyl | NH—CH₂ | Phenyl | Z₁: CHF₂ (ortho) |
| CH₂ | Pyrimidinyl | NH—CH₂ | Phenyl | Z₁: CF₃ (para) |
| CH₂ | Pyrimidinyl | NH—CH₂ | Phenyl | Z₁: CF₃ (meta) |
| CH₂ | Pyrimidinyl | NH—CH₂ | Phenyl | Z₁: CF₃ (ortho) |
| CH₂ | Pyrimidinyl | NH—CH₂ | Phenyl | Z₁: CH₂—CH₂F (para) |
| CH₂ | Pyrimidinyl | NH—CH₂ | Phenyl | Z₁: CH₂—CH₂F (meta) |
| CH₂ | Pyrimidinyl | NH—CH₂ | Phenyl | Z₁: CH₂—CH₂F (ortho) |
| CH₂ | Pyrimidinyl | NH—CH₂ | Phenyl | Z₁: CH₂—CHF₂ (para) |
| CH₂ | Pyrimidinyl | NH—CH₂ | Phenyl | Z₁: CH₂—CHF₂ (meta) |
| CH₂ | Pyrimidinyl | NH—CH₂ | Phenyl | Z₁: CH₂—CHF₂ (ortho) |
| CH₂ | Pyrimidinyl | NH—CH₂ | Phenyl | Z₁: CH₂—CF₃ (para) |
| CH₂ | Pyrimidinyl | NH—CH₂ | Phenyl | Z₁: CH₂—CF₃ (meta) |
| CH₂ | Pynrmdinyl | NH—CH₂ | Phenyl | Z₁: CH₂—CF₃ (ortho) |
| CH₂ | Pyrimidinyl | NH—CH₂ | Pyridinyl | None |
| CH₂ | Pyrimidinyl | NH—CH₂ | Pyridinyl | Z₁: F (para) |
| CH₂ | Pyrimidinyl | NH—CH₂ | Pyridinyl | Z₁: F (meta) |
| CH₂ | Pyrimidinyl | NH—CH₂ | Pyridinyl | Z₁: F (ortho) |
| CH₂ | Pyrimidinyl | NH—CH₂ | Pyridinyl | Z₁: F (para)<br>Z₂: F (meta) |
| CH₂ | Pyrimidinyl | NH—CH₂ | Pyridinyl | Z₁: Cl (meta) |
| CH₂ | Pyrimidinyl | NH—CH₂ | Pyridinyl | Z₁: Cl (para) |
| CH₂ | Pyrimidinyl | NH—CH₂ | Pyridinyl | Z₁: Cl (para)<br>Z₂: Cl (meta) |
| CH₂ | Pyrimidinyl | NH—CH₂ | Pyridinyl | Z₁: F (para)<br>Z₂: Cl (meta) |
| CH₂ | Pyrimidinyl | NH—CH₂ | Pyridinyl | Z₁: Cl (para)<br>Z₂: F (meta) |

TABLE 2-continued

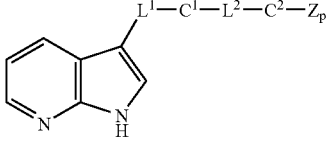

| L¹ | C¹ | L² | C² | Z |
|---|---|---|---|---|
| CH₂ | Pyrimidinyl | NH—CH₂ | Pyridinyl | Z₁: CH₃ (para) |
| CH₂ | Pyrimidinyl | NH—CH₂ | Pyridinyl | Z₁: CH₃ (meta) |
| CH₂ | Pyrimidinyl | NH—CH₂ | Pyridinyl | Z₁: CH₃ (ortho) |
| CH₂ | Pyrimidinyl | NH—CH₂ | Pyridinyl | Z₁: CH₂—CH₃ (para) |
| CH₂ | Pyrimidinyl | NH—CH₂ | Pyridinyl | Z₁: CH₂—CH₃ (meta) |
| CH₂ | Pyrimidinyl | NH—CH₂ | Pyridinyl | Z₁: CH₂—CH₃ (ortho) |
| CH₂ | Pyrimidinyl | NH—CH₂ | Pyridinyl | Z₁: CH₂—CH₂—CH₃ or iPr (para) |
| CH₂ | Pyrimidinyl | NH—CH₂ | Pyridinyl | Z₁: CH₂—CH₂—CH₃ or iPr (meta) |
| CH₂ | Pyrimidinyl | NH—CH₂ | Pyridinyl | Z₁: CH₂—CH₂—CH₃ or iPr (ortho) |
| CH₂ | Pyrimidinyl | NH—CH₂ | Pyridinyl | Z₁: CH₂F (para) |
| CH₂ | Pyrimidinyl | NH—CH₂ | Pyridinyl | Z₁: CH₂F (meta) |
| CH₂ | Pyrimidinyl | NH—CH₂ | Pyridinyl | Z₁: CH₂F (ortho) |
| CH₂ | Pyrimidinyl | NH—CH₂ | Pyridinyl | Z₁: CHF₂ (para) |
| CH₂ | Pyrimidinyl | NH—CH₂ | Pyridinyl | Z₁: CHF₂ (meta) |
| CH₂ | Pyrimidinyl | NH—CH₂ | Pyridinyl | Z₁: CHF₂ (ortho) |
| CH₂ | Pyrimidinyl | NH—CH₂ | Pyridinyl | Z₁: CF₃ (para) |
| CH₂ | Pyrimidinyl | NH—CH₂ | Pyridinyl | Z₁: CF₃ (meta) |
| CH₂ | Pyrimidinyl | NH—CH₂ | Pyridinyl | Z₁: CF₃ (ortho) |
| CH₂ | Pyrimidinyl | NH—CH₂ | Pyridinyl | Z₁: CH₂—CH₂F (para) |
| CH₂ | Pyrimidinyl | NH—CH₂ | Pyridinyl | Z₁: CH₂—CH₂F (meta) |
| CH₂ | Pyrimidinyl | NH—CH₂ | Pyridinyl | Z₁: CH₂—CH₂F (ortho) |
| CH₂ | Pyrimidinyl | NH—CH₂ | Pyridinyl | Z₁: CH₂—CHF₂ (para) |
| CH₂ | Pyrimidinyl | NH—CH₂ | Pyridinyl | Z₁: CH₂—CHF₂ (meta) |
| CH₂ | Pyrimidinyl | NH—CH₂ | Pyridinyl | Z₁: CH₂—CHF₂ (ortho) |
| CH₂ | Pyrimidinyl | NH—CH₂ | Pyridinyl | Z₁: CH₂—CF₃ (para) |
| CH₂ | Pyrimidinyl | NH—CH₂ | Pyridinyl | Z₁: CH₂—CF₃ (meta) |
| CH₂ | Pyrimidinyl | NH—CH₂ | Pyridinyl | Z₁: CH₂—CF₃ (ortho) |
| CH₂ | Pyrimidinyl | NH—CH₂ | Pyrimidinyl | None |
| CH₂ | Pyrimidinyl | NH—CH₂ | Pyrimidinyl | Z₁: F (para) |
| CH₂ | Pyrimidinyl | NH—CH₂ | Pyrimidinyl | Z₁: F (meta) |
| CH₂ | Pyrimidinyl | NH—CH₂ | Pyrimidinyl | Z₁: F (ortho) |
| CH₂ | Pyrimidinyl | NH—CH₂ | Pyrimidinyl | Z₁: F (para) Z₂: F (meta) |
| CH₂ | Pyrimidinyl | NH—CH₂ | Pyrimidinyl | Z₁: Cl (meta) |
| CH₂ | Pyrimidinyl | NH—CH₂ | Pyrimidinyl | Z₁: Cl (para) |
| CH₂ | Pyrimidinyl | NH—CH₂ | Pyrimidinyl | Z₁: Cl (para) Z₂: Cl (meta) |
| CH₂ | Pyrimidinyl | NH—CH₂ | Pyrimidinyl | Z₁: F (para) Z₂: Cl (meta) |
| CH₂ | Pyrimidinyl | NH—CH₂ | Pyrimidinyl | Z₁: Cl (para) Z₂: F (meta) |
| CH₂ | Pyrimidinyl | NH—CH₂ | Pyrimidinyl | Z₁: CH₃ (para) |
| CH₂ | Pyrimidinyl | NH—CH₂ | Pyrimidinyl | Z₁: CH₃ (meta) |
| CH₂ | Pyrimidinyl | NH—CH₂ | Pyrimidinyl | Z₁: CH₃ (ortho) |
| CH₂ | Pyrimidinyl | NH—CH₂ | Pyrimidinyl | Z₁: CH₂—CH₃ (para) |
| CH₂ | Pyrimidinyl | NH—CH₂ | Pyrimidinyl | Z₁: CH₂—CH₃ (meta) |
| CH₂ | Pyrimidinyl | NH—CH₂ | Pyrimidinyl | Z₁: CH₂—CH₃ (ortho) |
| CH₂ | Pyrimidinyl | NH—CH₂ | Pyrimidinyl | Z₁: CH₂—CH₂—CH₃ or iPr (para) |
| CH₂ | Pyrimidinyl | NH—CH₂ | Pyrimidinyl | Z₁: CH₂—CH₂—CH₃ or iPr (meta) |
| CH₂ | Pyrimidinyl | NH—CH₂ | Pyrimidinyl | Z₁: CH₂—CH₂—CH₃ or iPr (ortho) |
| CH₂ | Pyrimidinyl | NH—CH₂ | Pyrimidinyl | Z₁: CH₂F (para) |
| CH₂ | Pyrimidinyl | NH—CH₂ | Pyrimidinyl | Z₁: CH₂F (meta) |
| CH₂ | Pyrimidinyl | NH—CH₂ | Pyrimidinyl | Z₁: CH₂F (ortho) |
| CH₂ | Pyrimidinyl | NH—CH₂ | Pyrimidinyl | Z₁: CHF₂ (para) |
| CH₂ | Pyrimidinyl | NH—CH₂ | Pyrimidinyl | Z₁: CHF₂ (meta) |
| CH₂ | Pyrimidinyl | NH—CH₂ | Pyrimidinyl | Z₁: CHF₂ (ortho) |
| CH₂ | Pyrimidinyl | NH—CH₂ | Pyrimidinyl | Z₁: CF₃ (para) |
| CH₂ | Pyrimidinyl | NH—CH₂ | Pyrimidinyl | Z₁: CF₃ (meta) |
| CH₂ | Pyrimidinyl | NH—CH₂ | Pyrimidinyl | Z₁: CF₃ (ortho) |
| CH₂ | Pyrimidinyl | NH—CH₂ | Pyrimidinyl | Z₁: CH₂—CH₂F (para) |
| CH₂ | Pyrunidinyl | NH—CH₂ | Pyrimidinyl | Z₁: CH₂—CH₂F (meta) |
| CH₂ | Pyrimidinyl | NH—CH₂ | Pyrimidinyl | Z₁: CH₂—CH₂F (ortho) |
| CH₂ | Pyrimidinyl | NH—CH₂ | Pyrimidinyl | Z₁: CH₂—CHF₂ (para) |

TABLE 2-continued

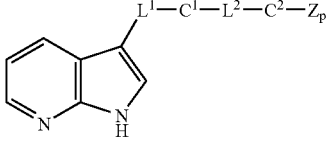

| L¹ | C¹ | L² | C² | Z |
|---|---|---|---|---|
| $CH_2$ | Pyrimidinyl | $NH-CH_2$ | Pyrimidinyl | $Z_1$: $CH_2-CHF_2$ (meta) |
| $CH_2$ | Pyrimidinyl | $NH-CH_2$ | Pyrimidinyl | $Z_1$: $CH_2-CHF_2$ (ortho) |
| $CH_2$ | Pyrimidinyl | $NH-CH_2$ | Pyrimidinyl | $Z_1$: $CH_2-CF_3$ (para) |
| $CH_2$ | Pyrimidinyl | $NH-CH_2$ | Pyrimidinyl | $Z_1$: $CH_2-CF_3$ (meta) |
| $CH_2$ | Pyrimidinyl | $NH-CH_2$ | Pyrimidinyl | $Z_1$: $CH_2-CF_3$ (ortho) |
| $CH_2$ | Pyrimidinyl | $NH-CH_2$ | Pyrazinyl | None |
| $CH_2$ | Pyrimidinyl | $NH-CH_2$ | Pyrazinyl | $Z_1$: F (para) |
| $CH_2$ | Pyrimidinyl | $NH-CH_2$ | Pyrazinyl | $Z_1$: F (meta) |
| $CH_2$ | Pyrimidinyl | $NH-CH_2$ | Pyrazinyl | $Z_1$: F (ortho) |
| $CH_2$ | Pyrimidinyl | $NH-CH_2$ | Pyrazinyl | $Z_1$: F (para) $Z_2$: F (meta) |
| $CH_2$ | Pyrimidinyl | $NH-CH_2$ | Pyrazinyl | $Z_1$: Cl (meta) |
| $CH_2$ | Pyrimidinyl | $NH-CH_2$ | Pyrazinyl | $Z_1$: Cl (para) |
| $CH_2$ | Pyrimidinyl | $NH-CH_2$ | Pyrazinyl | $Z_1$: Cl (para) $Z_2$: Cl (meta) |
| $CH_2$ | Pyrimidinyl | $NH-CH_2$ | Pyrazinyl | $Z_1$: F (para) $Z_2$: Cl (meta) |
| $CH_2$ | Pyrimidinyl | $NH-CH_2$ | Pyrazinyl | $Z_1$: Cl (para) $Z_2$: F (meta) |
| $CH_2$ | Pyrimidinyl | $NH-CH_2$ | Pyrazinyl | $Z_1$: $CH_3$ (para) |
| $CH_2$ | Pyrimidinyl | $NH-CH_2$ | Pyrazinyl | $Z_1$: $CH_3$ (meta) |
| $CH_2$ | Pyrimidinyl | $NH-CH_2$ | Pyrazinyl | $Z_1$: $CH_3$ (ortho) |
| $CH_2$ | Pyrimidinyl | $NH-CH_2$ | Pyrazinyl | $Z_1$: $CH_2-CH_3$ (para) |
| $CH_2$ | Pyrimidinyl | $NH-CH_2$ | Pyrazinyl | $Z_1$: $CH_2-CH_3$ (meta) |
| $CH_2$ | Pyrimidinyl | $NH-CH_2$ | Pyrazinyl | $Z_1$: $CH_2-CH_3$ (ortho) |
| $CH_2$ | Pyrimidinyl | $NH-CH_2$ | Pyrazinyl | $Z_1$: $CH_2-CH_2-CH_3$ or iPr (para) |
| $CH_2$ | Pyrimidinyl | $NH-CH_2$ | Pyrazinyl | $Z_1$: $CH_2-CH_2-CH_3$ or iPr (meta) |
| $CH_2$ | Pyrimidinyl | $NH-CH_2$ | Pyrazinyl | $Z_1$: $CH_2-CH_2-CH_3$ or iPr (ortho) |
| $CH_2$ | Pyrimidinyl | $NH-CH_2$ | Pyrazinyl | $Z_1$: $CH_2F$ (para) |
| $CH_2$ | Pyrimidinyl | $NH-CH_2$ | Pyrazinyl | $Z_1$: $CH_2F$ (meta) |
| $CH_2$ | Pyrimidinyl | $NH-CH_2$ | Pyrazinyl | $Z_1$: $CH_2F$ (ortho) |
| $CH_2$ | Pyrimidinyl | $NH-CH_2$ | Pyrazinyl | $Z_1$: $CHF_2$ (para) |
| $CH_2$ | Pyrimidinyl | $NH-CH_2$ | Pyrazinyl | $Z_1$: $CHF_2$ (meta) |
| $CH_2$ | Pyrimidinyl | $NH-CH_2$ | Pyrazinyl | $Z_1$: $CHF_2$ (ortho) |
| $CH_2$ | Pyrimidinyl | $NH-CH_2$ | Pyrazinyl | $Z_1$: $CF_3$ (para) |
| $CH_2$ | Pyrimidinyl | $NH-CH_2$ | Pyrazinyl | $Z_1$: $CF_3$ (meta) |
| $CH_2$ | Pyrimidinyl | $NH-CH_2$ | Pyrazinyl | $Z_1$: $CF_3$ (ortho) |
| $CH_2$ | Pyrimidinyl | $NH-CH_2$ | Pyrazinyl | $Z_1$: $CH_2-CH_2F$ (para) |
| $CH_2$ | Pyrimidinyl | $NH-CH_2$ | Pyrazinyl | $Z_1$: $CH_2-CH_2F$ (meta) |
| $CH_2$ | Pyrimidinyl | $NH-CH_2$ | Pyrazinyl | $Z_1$: $CH_2-CH_2F$ (ortho) |
| $CH_2$ | Pyrimidinyl | $NH-CH_2$ | Pyrazinyl | $Z_1$: $CH_2-CHF_2$ (para) |
| $CH_2$ | Pyrimidinyl | $NH-CH_2$ | Pyrazinyl | $Z_1$: $CH_2-CHF_2$ (meta) |
| $CH_2$ | Pyrimidinyl | $NH-CH_2$ | Pyrazinyl | $Z_1$: $CH_2-CHF_2$ (ortho) |
| $CH_2$ | Pyrimidinyl | $NH-CH_2$ | Pyrazinyl | $Z_1$: $CH_2-CF_3$ (para) |
| $CH_2$ | Pyrimidinyl | $NH-CH_2$ | Pyrazinyl | $Z_1$: $CH_2-CF_3$ (meta) |
| $CH_2$ | Pyrimidinyl | $NH-CH_2$ | Pyrazinyl | $Z_1$: $CH_2-CF_3$ (ortho) |
| $CH_2$ | Pyrimidinyl | $NH-CH_2$ | Pyrrolyl | None |
| $CH_2$ | Pyrimidinyl | $NH-CH_2$ | Pyrrolyl | $Z_1$: F (2) |
| $CH_2$ | Pyrimidinyl | $NH-CH_2$ | Pyrrolyl | $Z_1$: F (3) |
| $CH_2$ | Pyrimidinyl | $NH-CH_2$ | Pyrrolyl | $Z_1$: F (2) $Z_2$: F (3) |
| $CH_2$ | Pyrimidinyl | $NH-CH_2$ | Pyrrolyl | $Z_1$: Cl (2) |
| $CH_2$ | Pyrimidinyl | $NH-CH_2$ | Pyrrolyl | $Z_1$: Cl (3) |
| $CH_2$ | Pyrimidinyl | $NH-CH_2$ | Pyrrolyl | $Z_1$: Cl (2) $Z_2$: Cl (3) |
| $CH_2$ | Pyrimidinyl | $NH-CH_2$ | Pyrrolyl | $Z_1$: F (2) $Z_2$: Cl (3) |
| $CH_2$ | Pyrimidinyl | $NH-CH_2$ | Pyrrolyl | $Z_1$: Cl (2) $Z_2$: F (3) |
| $CH_2$ | Pyrimidinyl | $NH-CH_2$ | Pyrrolyl | $Z_1$: $CH_3$ (2) |
| $CH_2$ | Pyrimidinyl | $NH-CH_2$ | Pyrrolyl | $Z_1$: $CH_3$ (3) |
| $CH_2$ | Pyrimidinyl | $NH-CH_2$ | Pyrrolyl | $Z_1$: $CH_2-CH_3$ (2) |
| $CH_2$ | Pyrimidinyl | $NH-CH_2$ | Pyrrolyl | $Z_1$: $CH_2-CH_3$ (3) |
| $CH_2$ | Pyrimidinyl | $NH-CH_2$ | Pyrrolyl | $Z_1$: $CH_2-CH_2-CH_3$ or iPr (2) |
| $CH_2$ | Pyrimidinyl | $NH-CH_2$ | Pyrrolyl | $Z_1$: $CH_2-CH_2-CH_3$ or iPr (3) |
| $CH_2$ | Pyrimidinyl | $NH-CH_2$ | Pyrrolyl | $Z_1$: $CH_2F$ (2) |

TABLE 2-continued

L¹—C¹—L²—C²—Z_p (7-azaindole structure with L¹—C¹—L²—C²—Z_p substituent at the 3-position)

| L¹ | C¹ | L² | C² | Z |
|---|---|---|---|---|
| CH₂ | Pyrimidinyl | NH—CH₂ | Pyrrolyl | Z₁: CH₂F (3) |
| CH₂ | Pyrimidinyl | NH—CH₂ | Pyrrolyl | Z₁: CHF₂ (2) |
| CH₂ | Pyrimidinyl | NH—CH₂ | Pyrrolyl | Z₁: CHF₂ (3) |
| CH₂ | Pyrimidinyl | NH—CH₂ | Pyrrolyl | Z₁: CF₃ (2) |
| CH₂ | Pyrimidinyl | NH—CH₂ | Pyrrolyl | Z₁: CF₃ (3) |
| CH₂ | Pyrimidinyl | NH—CH₂ | Pyrrolyl | Z₁: CH₂—CH₂F (2) |
| CH₂ | Pyrimidinyl | NH—CH₂ | Pyrrolyl | Z₁: CH₂—CH₂F (3) |
| CH₂ | Pyrimidinyl | NH—CH₂ | Pyrrolyl | Z₁: CH₂—CHF₂ (2) |
| CH₂ | Pyrimidinyl | NH—CH₂ | Pyrrolyl | Z₁: CH₂—CHF₂ (3) |
| CH₂ | Pyrimidinyl | NH—CH₂ | Pyrrolyl | Z₁: CH₂—CF₃ (2) |
| CH₂ | Pyrimidinyl | NH—CH₂ | Pyrrolyl | Z₁: CH₂—CF₃ (3) |
| CH₂ | Pyrimidinyl | NH—CH₂ | Imidazolyl | None |
| CH₂ | Pyrimidinyl | NH—CH₂ | Imidazolyl | Z₁: F (2) |
| CH₂ | Pyrimidinyl | NH—CH₂ | Imidazolyl | Z₁: F (3) |
| CH₂ | Pyrimidinyl | NH—CH₂ | Imidazolyl | Z₁: F (2) <br> Z₂: F (3) |
| CH₂ | Pyrimidinyl | NH—CH₂ | Imidazolyl | Z₁: Cl (2) |
| CH₂ | Pyrimidinyl | NH—CH₂ | Imidazolyl | Z₁: Cl (3) |
| CH₂ | Pyrimidinyl | NH—CH₂ | Imidazolyl | Z₁: Cl (2) <br> Z₂: Cl (3) |
| CH₂ | Pyrimidinyl | NH—CH₂ | Imidazolyl | Z₁: F (2) <br> Z₂: Cl (3) |
| CH₂ | Pyrimidinyl | NH—CH₂ | Imidazolyl | Z₁: Cl (2) <br> Z₂: F (3) |
| CH₂ | Pyrimidinyl | NH—CH₂ | Imidazolyl | Z₁: CH₃ (2) |
| CH₂ | Pyrimidinyl | NH—CH₂ | Imidazolyl | Z₁: CH₃ (3) |
| CH₂ | Pyrimidinyl | NH—CH₂ | Imidazolyl | Z₁: CH₂—CH₃ (2) |
| CH₂ | Pyrimidinyl | NH—CH₂ | Imidazolyl | Z₁: CH₂—CH₃ (3) |
| CH₂ | Pyrimidinyl | NH—CH₂ | Imidazolyl | Z₁: CH₂—CH₂—CH₃ or iPr (2) |
| CH₂ | Pyrimidinyl | NH—CH₂ | Imidazolyl | Z₁: CH₂—CH₂—CH₃ or iPr (3) |
| CH₂ | Pyrimidinyl | NH—CH₂ | Imidazolyl | Z₁: CH₂F (2) |
| CH₂ | Pyrimidinyl | NH—CH₂ | Imidazolyl | Z₁: CH₂F (3) |
| CH₂ | Pyrimidinyl | NH—CH₂ | Imidazolyl | Z₁: CHF₂ (2) |
| CH₂ | Pyrimidinyl | NH—CH₂ | Imidazolyl | Z₁: CHF₂ (3) |
| CH₂ | Pyrimidinyl | NH—CH₂ | Imidazolyl | Z₁: CF₃ (2) |
| CH₂ | Pyrimidinyl | NH—CH₂ | Imidazolyl | Z₁: CF₃ (3) |
| CH₂ | Pyrimidinyl | NH—CH₂ | Imidazolyl | Z₁: CH₂—CH₂F (2) |
| CH₂ | Pyrimidinyl | NH—CH₂ | Imidazolyl | Z₁: CH₂—CH₂F (3) |
| CH₂ | Pyrimidinyl | NH—CH₂ | Imidazolyl | Z₁: CH₂—CHF₂ (2) |
| CH₂ | Pyrimidinyl | NH—CH₂ | Imidazolyl | Z₁: CH₂—CHF₂ (3) |
| CH₂ | Pyrimidinyl | NH—CH₂ | Imidazolyl | Z₁: CH₂—CF₃ (2) |
| CH₂ | Pyrimidinyl | NH—CH₂ | Imidazolyl | Z₁: CH₂—CF₃ (3) |
| CH₂ | Pyrimidinyl | NH—CH₂ | Furanyl | None |
| CH₂ | Pyrimidinyl | NH—CH₂ | Furanyl | Z₁: F (2) |
| CH₂ | Pyrimidinyl | NH—CH₂ | Furanyl | Z₁: F (3) |
| CH₂ | Pyrimidinyl | NH—CH₂ | Furanyl | Z₁: F (2) <br> Z₂: F (3) |
| CH₂ | Pyrimidinyl | NH—CH₂ | Furanyl | Z₁: Cl (2) |
| CH₂ | Pyrimidinyl | NH—CH₂ | Furanyl | Z₁: Cl (3) |
| CH₂ | Pyrimidinyl | NH—CH₂ | Furanyl | Z₁: Cl (2) <br> Z₂: Cl (3) |
| CH₂ | Pyrimidinyl | NH—CH₂ | Furanyl | Z₁: F (2) <br> Z₂: Cl (3) |
| CH₂ | Pyrimidinyl | NH—CH₂ | Furanyl | Z₁: Cl (2) <br> Z₂: F (3) |
| CH₂ | Pyrimidinyl | NH—CH₂ | Furanyl | Z₁: CH₃ (2) |
| CH₂ | Pyrimidinyl | NH—CH₂ | Furanyl | Z₁: CH₃ (3) |
| CH₂ | Pyrimidinyl | NH—CH₂ | Furanyl | Z₁: CH₂—CH₃ (2) |
| CH₂ | Pyrimidinyl | NH—CH₂ | Furanyl | Z₁: CH₂—CH₃ (3) |
| CH₂ | Pyrimidinyl | NH—CH₂ | Furanyl | Z₁: CH₂—CH₂—CH₃ or iPr (2) |
| CH₂ | Pyrimidinyl | NH—CH₂ | Furanyl | Z₁: CH₂—CH₂—CH₃ or iPr (3) |
| CH₂ | Pyrimidinyl | NH—CH₂ | Furanyl | Z₁: CH₂F (2) |
| CH₂ | Pyrimidinyl | NH—CH₂ | Furanyl | Z₁: CH₂F (3) |
| CH₂ | Pyrimidinyl | NH—CH₂ | Furanyl | Z₁: CHF₂ (2) |
| CH₂ | Pyrimidinyl | NH—CH₂ | Furanyl | Z₁: CHF₂ (3) |
| CH₂ | Pyrimidinyl | NH—CH₂ | Furanyl | Z₁: CF₃ (2) |
| CH₂ | Pyrimidinyl | NH—CH₂ | Furanyl | Z₁: CF₃ (3) |
| CH₂ | Pyrimidinyl | NH—CH₂ | Furanyl | Z₁: CH₂—CH₂F (2) |
| CH₂ | Pyrimidinyl | NH—CH₂ | Furanyl | Z₁: CH₂—CH₂F (3) |

TABLE 2-continued

L¹—C¹—L²—C²—Z$_p$ (attached to 1H-pyrrolo[2,3-b]pyridine at 3-position)

| L¹ | C¹ | L² | C² | Z |
|---|---|---|---|---|
| CH₂ | Pyrimidinyl | NH—CH₂ | Furanyl | Z₁: CH₂—CHF₂ (2) |
| CH₂ | Pyrimidinyl | NH—CH₂ | Furanyl | Z₁: CH₂—CHF₂ (3) |
| CH₂ | Pyrimidinyl | NH—CH₂ | Furanyl | Z₁: CH₂—CF₃ (2) |
| CH₂ | Pyrimidinyl | NH—CH₂ | Furanyl | Z₁: CH₂—CF₃ (3) |
| CH₂ | Pyrimidinyl | NH—CH₂ | Oxazolyl | None |
| CH₂ | Pyrimidinyl | NH—CH₂ | Oxazolyl | Z₁: F (2) |
| CH₂ | Pyrimidinyl | NH—CH₂ | Oxazolyl | Z₁: F (3) |
| CH₂ | Pyrimidinyl | NH—CH₂ | Oxazolyl | Z₁: F (2) Z₂: F (3) |
| CH₂ | Pyrimidinyl | NH—CH₂ | Oxazolyl | Z₁: Cl (2) |
| CH₂ | Pyrimidinyl | NH—CH₂ | Oxazolyl | Z₁: Cl (3) |
| CH₂ | Pyrimidinyl | NH—CH₂ | Oxazolyl | Z₁: Cl (2) Z₂: Cl (3) |
| CH₂ | Pyrimidinyl | NH—CH₂ | Oxazolyl | Z₁: F (2) Z₂: Cl (3) |
| CH₂ | Pyrimidinyl | NH—CH₂ | Oxazolyl | Z₁: Cl (2) Z₂: F (3) |
| CH₂ | Pyrimidinyl | NH—CH₂ | Oxazolyl | Z₁: CH₃ (2) |
| CH₂ | Pyrimidinyl | NH—CH₂ | Oxazolyl | Z₁: CH₃ (3) |
| CH₂ | Pyrimidinyl | NH—CH₂ | Oxazolyl | Z₁: CH₂—CH₃ (2) |
| CH₂ | Pyrimidinyl | NH—CH₂ | Oxazolyl | Z₁: CH₂—CH₃ (3) |
| CH₂ | Pyrimidinyl | NH—CH₂ | Oxazolyl | Z₁: CH₂—CH₂—CH₃ or iPr (2) |
| CH₂ | Pyrimidinyl | NH—CH₂ | Oxazolyl | Z₁: CH₂—CH₂—CH₃ or iPr (3) |
| CH₂ | Pyrimidinyl | NH—CH₂ | Oxazolyl | Z₁: CH₂F (2) |
| CH₂ | Pyrimidinyl | NH—CH₂ | Oxazolyl | Z₁: CH₂F (3) |
| CH₂ | Pyrimidinyl | NH—CH₂ | Oxazolyl | Z₁: CHF₂ (2) |
| CH₂ | Pyrimidinyl | NH—CH₂ | Oxazolyl | Z₁: CHF₂ (3) |
| CH₂ | Pyrimidinyl | NH—CH₂ | Oxazolyl | Z₁: CF₃ (2) |
| CH₂ | Pyrimidinyl | NH—CH₂ | Oxazolyl | Z₁: CF₃ (3) |
| CH₂ | Pyrimidinyl | NH—CH₂ | Oxazolyl | Z₁: CH₂—CH₂F (2) |
| CH₂ | Pyrimidinyl | NH—CH₂ | Oxazolyl | Z₁: CH₂—CH₂F (3) |
| CH₂ | Pyrimidinyl | NH—CH₂ | Oxazolyl | Z₁: CH₂—CHF₂ (2) |
| CH₂ | Pyrimidinyl | NH—CH₂ | Oxazolyl | Z₁: CH₂—CHF₂ (3) |
| CH₂ | Pyrimidinyl | NH—CH₂ | Oxazolyl | Z₁: CH₂—CF₃ (2) |
| CH₂ | Pyrimidinyl | NH—CH₂ | Oxazolyl | Z₁: CH₂—CF₃ (3) |
| CH₂ | Pyrimidinyl | NH—CH₂ | Thiophenyl | None |
| CH₂ | Pyrimidinyl | NH—CH₂ | Thiophenyl | Z₁: F (2) |
| CH₂ | Pyrimidinyl | NH—CH₂ | Thiophenyl | Z₁: F (3) |
| CH₂ | Pyrimidinyl | NH—CH₂ | Thiophenyl | Z₁: F (2) Z₂: F (3) |
| CH₂ | Pyrimidinyl | NH—CH₂ | Thiophenyl | Z₁: Cl (2) |
| CH₂ | Pyrimidinyl | NH—CH₂ | Thiophenyl | Z₁: Cl (3) |
| CH₂ | Pyrimidinyl | NH—CH₂ | Thiophenyl | Z₁: Cl (2) Z₂: Cl (3) |
| CH₂ | Pyrimidinyl | NH—CH₂ | Thiophenyl | Z₁: F (2) Z₂: Cl (3) |
| CH₂ | Pyrimidinyl | NH—CH₂ | Thiophenyl | Z₁: Cl (2) Z₂: F (3) |
| CH₂ | Pyrimidinyl | NH—CH₂ | Thiophenyl | Z₁: CH₃ (2) |
| CH₂ | Pyrimidinyl | NH—CH₂ | Thiophenyl | Z₁: CH₃ (3) |
| CH₂ | Pyrimidinyl | NH—CH₂ | Thiophenyl | Z₁: CH₂—CH₃ (2) |
| CH₂ | Pyrimidinyl | NH—CH₂ | Thiophenyl | Z₁: CH₂—CH₃ (3) |
| CH₂ | Pyrimidinyl | NH—CH₂ | Thiophenyl | Z₁: CH₂—CH₂—CH₃ or iPr (2) |
| CH₂ | Pyrimidinyl | NH—CH₂ | Thiophenyl | Z₁: CH₂—CH₂—CH₃ or iPr (3) |
| CH₂ | Pyrimidinyl | NH—CH₂ | Thiophenyl | Z₁: CH₂F (2) |
| CH₂ | Pyrimidinyl | NH—CH₂ | Thiophenyl | Z₁: CH₂F (3) |
| CH₂ | Pyrimidinyl | NH—CH₂ | Thiophenyl | Z₁: CHF₂ (2) |
| CH₂ | Pyrimidinyl | NH—CH₂ | Thiophenyl | Z₁: CHF₂ (3) |
| CH₂ | Pyrimidinyl | NH—CH₂ | Thiophenyl | Z₁: CF₃ (2) |
| CH₂ | Pyrimidinyl | NH—CH₂ | Thiophenyl | Z₁: CF₃ (3) |
| CH₂ | Pyrimidinyl | NH—CH₂ | Thiophenyl | Z₁: CH₂—CH₂F (2) |
| CH₂ | Pyrimidinyl | NH—CH₂ | Thiophenyl | Z₁: CH₂—CH₂F (3) |
| CH₂ | Pyrimidinyl | NH—CH₂ | Thiophenyl | Z₁: CH₂—CHF₂ (2) |
| CH₂ | Pyrimidinyl | NH—CH₂ | Thiophenyl | Z₁: CH₂—CHF₂ (3) |
| CH₂ | Pyrimidinyl | NH—CH₂ | Thiophenyl | Z₁: CH₂—CF₃ (2) |
| CH₂ | Pyrimidinyl | NH—CH₂ | Thiophenyl | Z₁: CH₂—CF₃ (3) |
| CH₂ | Pyrimidinyl | NH—CH₂ | Thiazolyl | None |
| CH₂ | Pyrimidinyl | NH—CH₂ | Thiazolyl | Z₁: F (2) |
| CH₂ | Pyrimidinyl | NH—CH₂ | Thiazolyl | Z₁: F (3) |

TABLE 2-continued $$L^1-C^1-L^2-C^2-Z_p$$

[7-azaindole core structure with substituent at position 3]

| L¹ | C¹ | L² | C² | Z |
|---|---|---|---|---|
| CH₂ | Pyrimidinyl | NH—CH₂ | Thiazolyl | Z₁: F (2)<br>Z₂: F (3) |
| CH₂ | Pyrimidinyl | NH—CH₂ | Thiazolyl | Z₁: Cl (2) |
| CH₂ | Pyrimidinyl | NH—CH₂ | Thiazolyl | Z₁: Cl (3) |
| CH₂ | Pyrimidinyl | NH—CH₂ | Thiazolyl | Z₁: Cl (2)<br>Z₂: Cl (3) |
| CH₂ | Pyrimidinyl | NH—CH₂ | Thiazolyl | Z₁: F (2)<br>Z₂: Cl (3) |
| CH₂ | Pyrimiinyl | NH—CH₂ | Thiazolyl | Z₁: Cl (2)<br>Z₂: F (3) |
| CH₂ | Pyrimidinyl | NH—CH₂ | Thiazolyl | Z₁: CH₃ (2) |
| CH₂ | Pyrimidinyl | NH—CH₂ | Thiazolyl | Z₁: CH₃ (3) |
| CH₂ | Pyrimidinyl | NH—CH₂ | Thiazolyl | Z₁: CH₂—CH₃ (2) |
| CH₂ | Pyrimidinyl | NH—CH₂ | Thiazolyl | Z₁: CH₂—CH₃ (3) |
| CH₂ | Pyrimidinyl | NH—CH₂ | Thiazolyl | Z₁: CH₂—CH₂—CH₃ or iPr (2) |
| CH₂ | Pyrimidinyl | NH—CH₂ | Thiazolyl | Z₁: CH₂—CH₂—CH₃ or iPr (3) |
| CH₂ | Pyrimidinyl | NH—CH₂ | Thiazolyl | Z₁: CH₂F (2) |
| CH₂ | Pyrimidinyl | NH—CH₂ | Thiazolyl | Z₁: CH₂F (3) |
| CH₂ | Pyrimidinyl | NH—CH₂ | Thiazolyl | Z₁: CHF₂ (2) |
| CH₂ | Pyrimidinyl | NH—CH₂ | Thiazolyl | Z₁: CHF₂ (3) |
| CH₂ | Pyrimidinyl | NH—CH₂ | Thiazolyl | Z₁: CF₃ (2) |
| CH₂ | Pyrimidinyl | NH—CH₂ | Thiazolyl | Z₁: CF₃ (3) |
| CH₂ | Pyrimidinyl | NH—CH₂ | Thiazolyl | Z₁: CH₂—CH₂F (2) |
| CH₂ | Pyrimidinyl | NH—CH₂ | Thiazolyl | Z₁: CH₂—CH₂F (3) |
| CH₂ | Pyrimidinyl | NH—CH₂ | Thiazolyl | Z₁: CH₂—CHF₂ (2) |
| CH₂ | Pyrimidinyl | NH—CH₂ | Thiazolyl | Z₁: CH₂—CHF₂ (3) |
| CH₂ | Pyrimidinyl | NH—CH₂ | Thiazolyl | Z₁: CH₂—CF₃ (2) |
| CH₂ | Pyrimidinyl | NH—CH₂ | Thiazolyl | Z₁: CH₂—CF₃ (3) |
| CH₂ | Pyrimidinyl | NH—C(O) | Phenyl | None |
| CH₂ | Pyrimidinyl | NH—C(O) | Phenyl | Z₁: F (para) |
| CH₂ | Pyrimidinyl | NH—C(O) | phenyl | Z₁: F (meta) |
| CH₂ | Pyrimidinyl | NH—C(O) | phenyl | Z₁: F (ortho) |
| CH₂ | Pyrimidinyl | NH—C(O) | phenyl | Z₁: F (para)<br>Z₂: F (meta) |
| CH₂ | Pyrimidinyl | NH—C(O) | Phenyl | Z₁: Cl (meta) |
| CH₂ | Pyrimidinyl | NH—C(O) | Phenyl | Z₁: Cl (para) |
| CH₂ | Pyrimidinyl | NH—C(O) | Phenyl | Z₁: Cl (para)<br>Z₂: Cl (meta) |
| CH₂ | Pyrimidinyl | NH—C(O) | Phenyl | Z₁: F (para)<br>Z₂: Cl (meta) |
| CH₂ | Pyrimidinyl | NH—C(O) | Phenyl | Z₁: Cl (para)<br>Z₂: F (meta) |
| CH₂ | Pyrimidinyl | NH—C(O) | Phenyl | Z₁: CH₃ (para) |
| CH₂ | Pyrimidinyl | NH—C(O) | Phenyl | Z₁: CH₃ (meta) |
| CH₂ | Pyrimidinyl | NH—C(O) | Phenyl | Z₁: CH₃ (ortho) |
| CH₂ | Pyrimidinyl | NH—C(O) | Phenyl | Z₁: CH₂—CH₃ (para) |
| CH₂ | Pyrimidinyl | NH—C(O) | Phenyl | Z₁: CH₂—CH₃ (meta) |
| CH₂ | Pyrimidinyl | NH—C(O) | Phenyl | Z₁: CH₂—CH₃ (ortho) |
| CH₂ | Pyrimidinyl | NH—C(O) | Phenyl | Z₁: CH₂—CH₂—CH₃ or iPr (para) |
| CH₂ | Pyrimidinyl | NH—C(O) | Phenyl | Z₁: CH₂—CH₂—CH₃ or iPr (meta) |
| CH₂ | Pyrimidinyl | NH—C(O) | Phenyl | Z₁: CH₂—CH₂—CH₃ or iPr (ortho) |
| CH₂ | Pyrimidinyl | NH—C(O) | Phenyl | Z₁: CH₂F (para) |
| CH₂ | Pyrimidinyl | NH—C(O) | Phenyl | Z₁: CH₂F (meta) |
| CH₂ | Pyrimidinyl | NH—C(O) | Phenyl | Z₁: CH₂F (ortho) |
| CH₂ | Pyrimidinyl | NH—C(O) | Phenyl | Z₁: CHF₂ (para) |
| CH₂ | Pyrimidinyl | NH—C(O) | Phenyl | Z₁: CHF₂ (meta) |
| CH₂ | Pyrimidinyl | NH—C(O) | Phenyl | Z₁: CHF₂ (ortho) |
| CH₂ | Pyrimidinyl | NH—C(O) | Phenyl | Z₁: CF₃ (para) |
| CH₂ | Pyrimidinyl | NH—C(O) | Phenyl | Z₁: CF₃ (meta) |
| CH₂ | Pyrimiidinyl | NH—C(O) | Phenyl | Z₁: CF₃ (ortho) |
| CH₂ | Pyrimidinyl | NH—C(O) | Phenyl | Z₁: CH₂—CH₂F (para) |
| CH₂ | Pyrimidinyl | NH—C(O) | Phenyl | Z₁: CH₂—CH₂F (meta) |
| CH₂ | Pyrimidinyl | NH—C(O) | Phenyl | Z₁: CH₂—CH₂F (ortho) |
| CH₂ | Pyrimidinyl | NH—C(O) | Phenyl | Z₁: CH₂—CHF₂ (para) |
| CH₂ | Pyrimidinyl | NH—C(O) | Phenyl | Z₁: CH₂—CHF₂ (meta) |
| CH₂ | Pynrmidinyl | NH—C(O) | Phenyl | Z₁: CH₂—CHF₂ (ortho) |

TABLE 2-continued

L¹—C¹—L²—C²—Zp (7-azaindole structure)

| L¹ | C¹ | L² | C² | Z |
|---|---|---|---|---|
| CH₂ | Pyrimidinyl | NH—C(O) | Phenyl | Z₁: CH₂—CF₃ (para) |
| CH₂ | Pyrimidinyl | NH—C(O) | Phenyl | Z₁: CH₂—CF₃ (meta) |
| CH₂ | Pyrimidinyl | NH—C(O) | Phenyl | Z₁: CH₂—CF₃ (ortho) |
| CH₂ | Pyrimidinyl | NH—C(O) | Pyridinyl | None |
| CH₂ | Pyrimidinyl | NH—C(O) | Pyridinyl | Z₁: F (para) |
| CH₂ | Pyrimidinyl | NH—C(O) | Pyridinyl | Z₁: F (meta) |
| CH₂ | Pyrimidinyl | NH—C(O) | Pyridinyl | Z₁: F (ortho) |
| CH₂ | Pyrimidinyl | NH—C(O) | Pyridinyl | Z₁: F (para) Z₂: F (meta) |
| CH₂ | Pyrimidinyl | NH—C(O) | Pyridinyl | Z₁: Cl (meta) |
| CH₂ | Pyrimidinyl | NH—C(O) | Pyridinyl | Z₁: Cl (para) |
| CH₂ | Pyrimidinyl | NH—C(O) | Pyridinyl | Z₁: Cl (para) Z₂: Cl (meta) |
| CH₂ | Pyrimidinyl | NH—C(O) | Pyridinyl | Z₁: F (para) Z₂: Cl (meta) |
| CH₂ | Pyrimidinyl | NH—C(O) | Pyridinyl | Z₁: Cl (para) Z₂: F (meta) |
| CH₂ | Pyrimidinyl | NH—C(O) | Pyridinyl | Z₁: CH₃ (para) |
| CH₂ | Pyrimidinyl | NH—C(O) | Pyridinyl | Z₁: CH₃ (meta) |
| CH₂ | Pyrimidinyl | NH—C(O) | Pyridinyl | Z₁: CH₃ (ortho) |
| CH₂ | Pyrimidinyl | NH—C(O) | Pyridinyl | Z₁: CH₂—CH₃ (para) |
| CH₂ | Pyrimidinyl | NH—C(O) | Pyridinyl | Z₁: CH₂—CH₃ (meta) |
| CH₂ | Pyrimidinyl | NH—C(O) | Pyridinyl | Z₁: CH₂—CH₃ (ortho) |
| CH₂ | Pyrimidinyl | NH—C(O) | Pyridinyl | Z₁: CH₂—CH₂—CH₃ or iPr (para) |
| CH₂ | Pyrimidinyl | NH—C(O) | Pyridinyl | Z₁: CH₂—CH₂—CH₃ or iPr (meta) |
| CH₂ | Pyrimidinyl | NH—C(O) | Pyridinyl | Z₁: CH₂—CH₂—CH₃ or iPr (ortho) |
| CH₂ | Pyrimidinyl | NH—C(O) | Pyridinyl | Z₁: CH₂F (para) |
| CH₂ | Pyrimidinyl | NH—C(O) | Pyridinyl | Z₁: CH₂F (meta) |
| CH₂ | Pyrimidinyl | NH—C(O) | Pyridinyl | Z₁: CH₂F (ortho) |
| CH₂ | Pyrimidinyl | NH—C(O) | Pyridinyl | Z₁: CHF₂ (para) |
| CH₂ | Pyrimidinyl | NH—C(O) | Pyridinyl | Z₁: CHF₂ (meta) |
| CH₂ | Pyrimidinyl | NH—C(O) | Pyridinyl | Z₁: CHF₂ (ortho) |
| CH₂ | Pyrimidinyl | NH—C(O) | Pyridinyl | Z₁: CF₃ (para) |
| CH₂ | Pyrimidinyl | NH—C(O) | Pyridinyl | Z₁: CF₃ (meta) |
| CH₂ | Pyrimidinyl | NH—C(O) | Pyridinyl | Z₁: CF₃ (ortho) |
| CH₂ | Pyrimidinyl | NH—C(O) | Pyridinyl | Z₁: CH₂—CH₂F (para) |
| CH₂ | Pyrimidinyl | NH—C(O) | Pyridinyl | Z₁: CH₂—CH₂F (meta) |
| CH₂ | Pyrimidinyl | NH—C(O) | Pyridinyl | Z₁: CH₂—CH₂F (ortho) |
| CH₂ | Pyrimidinyl | NH—C(O) | Pyridinyl | Z₁: CH₂—CHF₂ (para) |
| CH₂ | Pyrimidinyl | NH—C(O) | Pyridinyl | Z₁: CH₂—CHF₂ (meta) |
| CH₂ | Pyrimidinyl | NH—C(O) | Pyridinyl | Z₁: CH₂—CHF₂ (ortho) |
| CH₂ | Pyrimidinyl | NH—C(O) | Pyridinyl | Z₁: CH₂—CF₃ (para) |
| CH₂ | Pyrimidinyl | NH—C(O) | Pyridinyl | Z₁: CH₂—CF₃ (meta) |
| CH₂ | Pyrimidinyl | NH—C(O) | Pyridinyl | Z₁: CH₂—CF₃ (ortho) |
| CH₂ | Pyrimidinyl | NH—C(O) | Pyrimidinyl | None |
| CH₂ | Pyrimidinyl | NH—C(O) | Pyrimidinyl | Z₁: F (para) |
| CH₂ | Pyrimidinyl | NH—C(O) | Pyrimidinyl | Z₁: F (meta) |
| CH₂ | Pyrimidinyl | NH—C(O) | Pyrimidinyl | Z₁: F (ortho) |
| CH₂ | Pyrimidinyl | NH—C(O) | Pyrimidinyl | Z₁: F (para) Z₂: F (meta) |
| CH₂ | Pyrimidinyl | NH—C(O) | Pyrimidinyl | Z₁: Cl (meta) |
| CH₂ | Pyrimidinyl | NH—C(O) | Pyrimidinyl | Z₁: Cl (para) |
| CH₂ | Pyrimidinyl | NH—C(O) | Pyrimidinyl | Z₁: Cl (para) Z₂: Cl (meta) |
| CH₂ | Pyrimidinyl | NH—C(O) | Pyrimidinyl | Z₁: F (para) Z₂: Cl (meta) |
| CH₂ | Pyrimidinyl | NH—C(O) | Pyrimidinyl | Z₁: Cl (para) Z₂: F (meta) |
| CH₂ | Pyrimidinyl | NH—C(O) | Pyrimidinyl | Z₁: CH₃ (para) |
| CH₂ | Pyrimidinyl | NH—C(O) | Pyrimidinyl | Z₁: CH₃ (meta) |
| CH₂ | Pyrimidinyl | NH—C(O) | Pyrimidinyl | Z₁: CH₃ (ortho) |
| CH₂ | Pyrimidinyl | NH—C(O) | Pyrimidinyl | Z₁: CH₂—CH₃ (para) |
| CH₂ | Pyrimidinyl | NH—C(O) | Pyrimidinyl | Z₁: CH₂—CH₃ (meta) |
| CH₂ | Pyrimidinyl | NH—C(O) | Pyrimidinyl | Z₁: CH₂—CH₃ (ortho) |
| CH₂ | Pyrimidinyl | NH—C(O) | Pyrimidinyl | Z₁: CH₂—CH₂—CH₃ or iPr (para) |

TABLE 2-continued

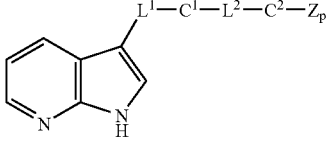

| L$^1$ | C$^1$ | L$^2$ | C$^2$ | Z |
|---|---|---|---|---|
| CH$_2$ | Pyrimidinyl | NH—C(O) | Pyrimidinyl | Z$_1$: CH$_2$—CH$_2$—CH$_3$ or iPr (meta) |
| CH$_2$ | Pyrimidinyl | NH—C(O) | Pyrimidinyl | Z$_1$: CH$_2$—CH$_2$—CH$_3$ or iPr (ortho) |
| CH$_2$ | Pyrimidinyl | NH—C(O) | Pyrimidinyl | Z$_1$: CH$_2$F (para) |
| CH$_2$ | Pyrimidinyl | NH—C(O) | Pyrimidinyl | Z$_1$: CH$_2$F (meta) |
| CH$_2$ | Pyrimidinyl | NH—C(O) | Pyrimidinyl | Z$_1$: CH$_2$F (ortho) |
| CH$_2$ | Pyrimidinyl | NH—C(O) | Pyrimidinyl | Z$_1$: CHF$_2$ (para) |
| CH$_2$ | Pyrimidinyl | NH—C(O) | Pyrimidinyl | Z$_1$: CHF$_2$ (meta) |
| CH$_2$ | Pyrimidinyl | NH—C(O) | Pyrimidinyl | Z$_1$: CHF$_2$ (ortho) |
| CH$_2$ | Pyrimidinyl | NH—C(O) | Pyrimidinyl | Z$_1$: CF$_3$ (para) |
| CH$_2$ | Pyrimidinyl | NH—C(O) | Pyrimidinyl | Z$_1$: CF$_3$ (meta) |
| CH$_2$ | Pyrimidinyl | NH—C(O) | Pyrimidinyl | Z$_1$: CF$_3$ (ortho) |
| CH$_2$ | Pyrimidinyl | NH—C(O) | Pyrimidinyl | Z$_1$: CH$_2$—CH$_2$F (para) |
| CH$_2$ | Pyrimidinyl | NH—C(O) | Pyrimidinyl | Z$_1$: CH$_2$—CH$_2$F (meta) |
| CH$_2$ | Pyrimidinyl | NH—C(O) | Pyrimidinyl | Z$_1$: CH$_2$—CH$_2$F (ortho) |
| CH$_2$ | Pyrimidinyl | NH—C(O) | Pyrimidinyl | Z$_1$: CH$_2$—CHF$_2$ (para) |
| CH$_2$ | Pyrimidinyl | NH—C(O) | Pyrimidinyl | Z$_1$: CH$_2$—CHF$_2$ (meta) |
| CH$_2$ | Pyrimidinyl | NH—C(O) | Pyrimidinyl | Z$_1$: CH$_2$—CHF$_2$ (ortho) |
| CH$_2$ | Pyrimidinyl | NH—C(O) | Pyrimidinyl | Z$_1$: CH$_2$—CF$_3$ (para) |
| CH$_2$ | Pyrimidinyl | NH—C(O) | Pyrimidinyl | Z$_1$: CH$_2$—CF$_3$ (meta) |
| CH$_2$ | Pyrimidinyl | NH—C(O) | Pyrimidinyl | Z$_1$: CH$_2$—CF$_3$ (ortho) |
| CH$_2$ | Pyrimidinyl | NH—C(O) | Pyrazinyl | None |
| CH$_2$ | Pyrimidinyl | NH—C(O) | Pyrazinyl | Z$_1$: F (para) |
| CH$_2$ | Pyrimidinyl | NH—C(O) | Pyrazinyl | Z$_1$: F (meta) |
| CH$_2$ | Pyrimidinyl | NH—C(O) | Pyrazinyl | Z$_1$: F (ortho) |
| CH$_2$ | Pyrimidinyl | NH—C(O) | Pyrazinyl | Z$_1$: F (para) Z$_2$: F (meta) |
| CH$_2$ | Pyrimidinyl | NH—C(O) | Pyrazinyl | Z$_1$: Cl (meta) |
| CH$_2$ | Pyrimidinyl | NH—C(O) | Pyrazinyl | Z$_1$: Cl (para) |
| CH$_2$ | Pyrimidinyl | NH—C(O) | Pyrazinyl | Z$_1$: Cl (para) Z$_2$: Cl (meta) |
| CH$_2$ | Pyrimidinyl | NH—C(O) | Pyrazinyl | Z$_1$: F (para) Z$_2$: Cl (meta) |
| CH$_2$ | Pyrimidinyl | NH—C(O) | Pyrazinyl | Z$_1$: Cl (para) Z$_2$: F (meta) |
| CH$_2$ | Pyrimidinyl | NH—C(O) | Pyrazinyl | Z$_1$: CH$_3$ (para) |
| CH$_2$ | Pyrimidinyl | NH—C(O) | Pyrazinyl | Z$_1$: CH$_3$ (meta) |
| CH$_2$ | Pyrimidinyl | NH—C(O) | Pyrazinyl | Z$_1$: CH$_3$ (ortho) |
| CH$_2$ | Pyrimidinyl | NH—C(O) | Pyrazinyl | Z$_1$: CH$_2$—CH$_3$ (para) |
| CH$_2$ | Pyrimidinyl | NH—C(O) | Pyrazinyl | Z$_1$: CH$_2$—CH$_3$ (meta) |
| CH$_2$ | Pyrimidinyl | NH—C(O) | Pyrazinyl | Z$_1$: CH$_2$—CH$_3$ (ortho) |
| CH$_2$ | Pyrimidinyl | NH—C(O) | Pyrazinyl | Z$_1$: CH$_2$—CH$_2$—CH$_3$ or iPr (para) |
| CH$_2$ | Pyrimidinyl | NH—C(O) | Pyrazinyl | Z$_1$: CH$_2$—CH$_2$—CH$_3$ or iPr (meta) |
| CH$_2$ | Pyrimidinyl | NH—C(O) | Pyrazinyl | Z$_1$: CH$_2$—CH$_2$—CH$_3$ or iPr (ortho) |
| CH$_2$ | Pyrimidinyl | NH—C(O) | Pyrazinyl | Z$_1$: CH$_2$F (para) |
| CH$_2$ | Pyrimidinyl | NH—C(O) | Pyrazinyl | Z$_1$: CH$_2$F (meta) |
| CH$_2$ | Pyrimidinyl | NH—C(O) | Pyrazinyl | Z$_1$: CH$_2$F (ortho) |
| CH$_2$ | Pyrimidinyl | NH—C(O) | Pyrazinyl | Z$_1$: CHF$_2$ (para) |
| CH$_2$ | Pyrimidinyl | NH—C(O) | Pyrazinyl | Z$_1$: CHF$_2$ (meta) |
| CH$_2$ | Pyrimidinyl | NH—C(O) | Pyrazinyl | Z$_1$: CHF$_2$ (ortho) |
| CH$_2$ | Pyrimidinyl | NH—C(O) | Pyrazinyl | Z$_1$: CF$_3$ (para) |
| CH$_2$ | Pyrimidinyl | NH—C(O) | Pyrazinyl | Z$_1$: CF$_3$ (meta) |
| CH$_2$ | Pyrimidinyl | NH—C(O) | Pyrazinyl | Z$_1$: CF$_3$ (ortho) |
| CH$_2$ | Pyrimidinyl | NH—C(O) | Pyrazinyl | Z$_1$: CH$_2$—CH$_2$F (para) |
| CH$_2$ | Pyrimidinyl | NH—C(O) | Pyrazinyl | Z$_1$: CH$_2$—CH$_2$F (meta) |
| CH$_2$ | Pyrimidinyl | NH—C(O) | Pyrazinyl | Z$_1$: CH$_2$—CH$_2$F (ortho) |
| CH$_2$ | Pyrimidinyl | NH—C(O) | Pyrazinyl | Z$_1$: CH$_2$—CHF$_2$ (para) |
| CH$_2$ | Pyrimidinyl | NH—C(O) | Pyrazinyl | Z$_1$: CH$_2$—CHF$_2$ (meta) |
| CH$_2$ | Pyrimidinyl | NH—C(O) | Pyrazinyl | Z$_1$: CH$_2$—CHF$_2$ (ortho) |
| CH$_2$ | Pyrimidinyl | NH—C(O) | Pyrazinyl | Z$_1$: CH$_2$—CF$_3$ (para) |
| CH$_2$ | Pyrimidinyl | NH—C(O) | Pyrazinyl | Z$_1$: CH$_2$—CF$_3$ (meta) |
| CH$_2$ | Pyrimidinyl | NH—C(O) | Pyrazinyl | Z$_1$: CH$_2$—CF$_3$ (ortho) |
| CH$_2$ | Pyrimidinyl | NH—C(O) | Pyrrolyl | None |
| CH$_2$ | Pyrimidinyl | NH—C(O) | Pyrrolyl | Z$_1$: F (2) |
| CH$_2$ | Pyrimidinyl | NH—C(O) | Pyrrolyl | Z$_1$: F (3) |

TABLE 2-continued

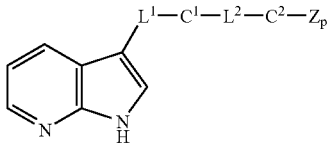

| L¹ | C¹ | L² | C² | Z |
|---|---|---|---|---|
| CH₂ | Pyrimidinyl | NH—C(O) | Pyrrolyl | Z₁: F (2)<br>Z₂: F (3) |
| CH₂ | Pyrimidinyl | NH—C(O) | Pyrrolyl | Z₁: Cl (2) |
| CH₂ | Pyrimidinyl | NH—C(O) | Pyrrolyl | Z₁: Cl (3) |
| CH₂ | Pyrimidinyl | NH—C(O) | Pyrrolyl | Z₁: Cl (2)<br>Z₂: Cl (3) |
| CH₂ | Pyrimidinyl | NH—C(O) | Pyrrolyl | Z₁: F (2)<br>Z₂: Cl (3) |
| CH₂ | Pyrimidinyl | NH—C(O) | Pyrrolyl | Z₁: Cl (2)<br>Z₂: F (3) |
| CH₂ | Pyrimidinyl | NH—C(O) | Pyrrolyl | Z₁: CH₃ (2) |
| CH₂ | Pyrimidinyl | NH—C(O) | Pyrrolyl | Z₁: CH₃ (3) |
| CH₂ | Pyrimidinyl | NH—C(O) | Pyrrolyl | Z₁: CH₂—CH₃ (2) |
| CH₂ | Pyrimidinyl | NH—C(O) | Pyrrolyl | Z₁: CH₂—CH₃ (3) |
| CH₂ | Pyrimidinyl | NH—C(O) | Pyrrolyl | Z₁: CH₂—CH₂—CH₃ or iPr (2) |
| CH₂ | Pyrimidinyl | NH—C(O) | Pyrrolyl | Z₁: CH₂—CH₂—CH₃ or iPr (3) |
| CH₂ | Pyrimidinyl | NH—C(O) | Pyrrolyl | Z₁: CH₂F (2) |
| CH₂ | Pyrimidinyl | NH—C(O) | Pyrrolyl | Z₁: CH₂F (3) |
| CH₂ | Pyrimidinyl | NH—C(O) | Pyrrolyl | Z₁: CHF₂ (2) |
| CH₂ | Pyrimidinyl | NH—C(O) | Pyrrolyl | Z₁: CHF₂ (3) |
| CH₂ | Pyrimidinyl | NH—C(O) | Pyrrolyl | Z₁: CF₃ (2) |
| CH₂ | Pyrimidinyl | NH—C(O) | Pyrrolyl | Z₁: CF₃ (3) |
| CH₂ | Pyrimidinyl | NH—C(O) | Pyrrolyl | Z₁: CH₂—CH₂F (2) |
| CH₂ | Pyrimidinyl | NH—C(O) | Pyrrolyl | Z₁: CH₂—CH₂F (3) |
| CH₂ | Pyrimidinyl | NH—C(O) | Pyrrolyl | Z₁: CH₂—CHF₂ (2) |
| CH₂ | Pyrimidinyl | NH—C(O) | Pyrrolyl | Z₁: CH₂—CHF₂ (3) |
| CH₂ | Pyrimidinyl | NH—C(O) | Pyrrolyl | Z₁: CH₂—CF₃ (2) |
| CH₂ | Pyrimidinyl | NH—C(O) | Pyrrolyl | Z₁: CH₂—CF₃ (3) |
| CH₂ | Pyrimidinyl | NH—C(O) | Imidazolyl | None |
| CH₂ | Pyrimidinyl | NH—C(O) | Imidazolyl | Z₁: F (2) |
| CH₂ | Pyrimidinyl | NH—C(O) | Imidazolyl | Z₁: F (3) |
| CH₂ | Pyrimidinyl | NH—C(O) | Imidazolyl | Z₁: F(2)<br>Z₂: F (3) |
| CH₂ | Pyrimidinyl | NH—C(O) | Imidazolyl | Z₁: Cl (2) |
| CH₂ | Pyrimidinyl | NH—C(O) | Imidazolyl | Z₁: Cl (3) |
| CH₂ | Pyrimidinyl | NH—C(O) | Imidazolyl | Z₁: Cl (2)<br>Z₂: Cl (3) |
| CH₂ | Pyrimidinyl | NH—C(O) | Imidazolyl | Z₁: F (2)<br>Z₂: Cl (3) |
| CH₂ | Pyrimidinyl | NH—C(O) | Imidazolyl | Z₁: Cl (2)<br>Z₂: F (3) |
| CH₂ | Pyrimidinyl | NH—C(O) | Imidazolyl | Z₁: CH₃ (2) |
| CH₂ | Pyrimidinyl | NH—C(O) | Imidazolyl | Z₁: CH₃ (3) |
| CH₂ | Pyrimidinyl | NH—C(O) | Imidazolyl | Z₁: CH₂—CH₃ (2) |
| CH₂ | Pyrimidinyl | NH—C(O) | Imidazolyl | Z₁: CH₂—CH₃ (3) |
| CH₂ | Pyrimidinyl | NH—C(O) | Imidazolyl | Z₁: CH₂—CH₂—CH₃ or iPr (2) |
| CH₂ | Pyrimidinyl | NH—C(O) | Imidazolyl | Z₁: CH₂—CH₂—CH₃ or iPr (3) |
| CH₂ | Pyrimidinyl | NH—C(O) | Imidazolyl | Z₁: CH₂F (2) |
| CH₂ | Pyrimidinyl | NH—C(O) | Imidazolyl | Z₁: CH₂F (3) |
| CH₂ | Pyrimidinyl | NH—C(O) | Imidazolyl | Z₁: CHF₂ (2) |
| CH₂ | Pyrimidinyl | NH—C(O) | Imidazolyl | Z₁: CHF₂ (3) |
| CH₂ | Pyrimidinyl | NH—C(O) | Imidazolyl | Z₁: CF₃ (2) |
| CH₂ | Pyrimidinyl | NH—C(O) | Imidazolyl | Z₁: CF₃ (3) |
| CH₂ | Pyrimidinyl | NH—C(O) | Imidazolyl | Z₁: CH₂—CH₂F (2) |
| CH₂ | Pyrimidinyl | NH—C(O) | Imidazolyl | Z₁: CH₂—CH₂F (3) |
| CH₂ | Pyrimidinyl | NH—C(O) | Imidazolyl | Z₁: CH₂—CHF₂ (2) |
| CH₂ | Pyrimidinyl | NH—C(O) | Imidazolyl | Z₁: CH₂—CHF₂ (3) |
| CH₂ | Pyrimidinyl | NH—C(O) | Imidazolyl | Z₁: CH₂—CF₃ (2) |
| CH₂ | Pyrimidinyl | NH—C(O) | Imidazolyl | Z₁: CH₂—CF₃ (3) |
| CH₂ | Pyrimidinyl | NH—C(O) | Furanyl | None |
| CH₂ | Pyrimidinyl | NH—C(O) | Furanyl | Z₁: F (2) |
| CH₂ | Pyrimidinyl | NH—C(O) | Furanyl | Z₁: F (3) |
| CH₂ | Pyrimidinyl | NH—C(O) | Furanyl | Z₁: F (2)<br>Z₂: F (3) |
| CH₂ | Pyrimidinyl | NH—C(O) | Furanyl | Z₁: Cl (2) |
| CH₂ | Pyrimidinyl | NH—C(O) | Furanyl | Z₁: Cl (3) |
| CH₂ | Pyrimidinyl | NH—C(O) | Furanyl | Z₁: Cl (2)<br>Z₂: Cl (3) |

TABLE 2-continued

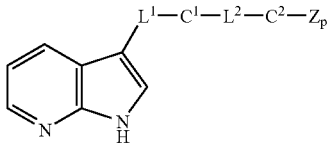

| L¹ | C¹ | L² | C² | Z |
|---|---|---|---|---|
| CH₂ | Pyrimidinyl | NH—C(O) | Furanyl | Z₁: F (2)<br>Z₂: Cl (3) |
| CH₂ | Pyrimidinyl | NH—C(O) | Furanyl | Z₁: Cl (2)<br>Z₂: F (3) |
| CH₂ | Pyrimidinyl | NH—C(O) | Furanyl | Z₁: CH₃ (2) |
| CH₂ | Pyrimidinyl | NH—C(O) | Furanyl | Z₁: CH₃ (3) |
| CH₂ | Pyrimidinyl | NH—C(O) | Furanyl | Z₁: CH₂—CH₃ (2) |
| CH₂ | Pyrimidinyl | NH—C(O) | Furanyl | Z₁: CH₂—CH₃ (3) |
| CH₂ | Pyrimidinyl | NH—C(O) | Furanyl | Z₁: CH₂—CH₂—CH₃ or iPr (2) |
| CH₂ | Pyrimidinyl | NH—C(O) | Furanyl | Z₁: CH₂—CH₂—CH₃ or iPr (3) |
| CH₂ | Pyrimidinyl | NH—C(O) | Furanyl | Z₁: CH₂F (2) |
| CH₂ | Pyrimidinyl | NH—C(O) | Furanyl | Z₁: CH₂F (3) |
| CH₂ | Pyrimidinyl | NH—C(O) | Furanyl | Z₁: CHF₂ (2) |
| CH₂ | Pyrimidinyl | NH—C(O) | Furanyl | Z₁: CHF₂ (3) |
| CH₂ | Pyrimidinyl | NH—C(O) | Furanyl | Z₁: CF₃ (2) |
| CH₂ | Pyrimidinyl | NH—C(O) | Furanyl | Z₁: CF₃ (3) |
| CH₂ | Pyrimidinyl | NH—C(O) | Furanyl | Z₁: CH₂—CH₂F (2) |
| CH₂ | Pyrimidinyl | NH—C(O) | Furanyl | Z₁: CH₂—CH₂F (3) |
| CH₂ | Pyrimidinyl | NH—C(O) | Furanyl | Z₁: CH₂—CHF₂ (2) |
| CH₂ | Pyrimidinyl | NH—C(O) | Furanyl | Z₁: CH₂—CHF₂ (3) |
| CH₂ | Pyrimidinyl | NH—C(O) | Furanyl | Z₁: CH₂—CF₃ (2) |
| CH₂ | Pyrimidinyl | NH—C(O) | Furanyl | Z₁: CH₂—CF₃ (3) |
| CH₂ | Pyrimidinyl | NH—C(O) | Oxazolyl | None |
| CH₂ | Pyrimidinyl | NH—C(O) | Oxazolyl | Z₁: F (2) |
| CH₂ | Pyrimidinyl | NH—C(O) | Oxazolyl | Z₁: F (3) |
| CH₂ | Pyrimidinyl | NH—C(O) | Oxazolyl | Z₁: F (2)<br>Z₂: F (3) |
| CH₂ | Pyrimidinyl | NH—C(O) | Oxazolyl | Z₁: Cl (2) |
| CH₂ | Pyrimidinyl | NH—C(O) | Oxazolyl | Z₁: Cl (3) |
| CH₂ | Pyrimidinyl | NH—C(O) | Oxazolyl | Z₁: Cl (2)<br>Z₂: Cl (3) |
| CH₂ | Pyrimidinyl | NH—C(O) | Oxazolyl | Z₁: F (2)<br>Z₂: Cl (3) |
| CH₂ | Pyrimidinyl | NH—C(O) | Oxazolyl | Z₁: Cl (2)<br>Z₂: F (3) |
| CH₂ | Pyrimidinyl | NH—C(O) | Oxazolyl | Z₁: CH₃ (2) |
| CH₂ | Pyrimidinyl | NH—C(O) | Oxazolyl | Z₁: CH₃ (3) |
| CH₂ | Pyrimidinyl | NH—C(O) | Oxazolyl | Z₁: CH₂—CH₃ (2) |
| CH₂ | Pyrimidinyl | NH—C(O) | Oxazolyl | Z₁: CH₂—CH₃ (3) |
| CH₂ | Pyrimidinyl | NH—C(O) | Oxazolyl | Z₁: CH₂—CH₂—CH₃ or iPr (2) |
| CH₂ | Pyrimidinyl | NH—C(O) | Oxazolyl | Z₁: CH₂—CH₂—CH₃ or iPr (3) |
| CH₂ | Pyrimidinyl | NH—C(O) | Oxazolyl | Z₁: CH₂F (2) |
| CH₂ | Pyrimidinyl | NH—C(O) | Oxazolyl | Z₁: CH₂F (3) |
| CH₂ | Pyrimidinyl | NH—C(O) | Oxazolyl | Z₁: CH₂ (2) |
| CH₂ | Pyrimidinyl | NH—C(O) | Oxazolyl | Z₁: CHF₂ (3) |
| CH₂ | Pyrimidinyl | NH—C(O) | Oxazolyl | Z₁: CF₃ (2) |
| CH₂ | Pyrimidinyl | NH—C(O) | Oxazolyl | Z₁: CF₃ (3) |
| CH₂ | Pyrimidinyl | NH—C(O) | Oxazolyl | Z₁: CH₂—CH₂F (2) |
| CH₂ | Pyrimidinyl | NH—C(O) | Oxazolyl | Z₁: CH₂—CH₂F (3) |
| CH₂ | Pyrimidinyl | NH—C(O) | Oxazolyl | Z₁: CH₂—CHF₂ (2) |
| CH₂ | Pyrimidinyl | NH—C(O) | Oxazolyl | Z₁: CH₂—CHF₂ (3) |
| CH₂ | Pyrimidinyl | NH—C(O) | Oxazolyl | Z₁: CH₂—CF₃ (2) |
| CH₂ | Pyrimidinyl | NH—C(O) | Oxazolyl | Z₁: CH₂—CF₃ (3) |
| CH₂ | Pyrimidinyl | NH—C(O) | Thiophenyl | None |
| CH₂ | Pyrimidinyl | NH—C(O) | Thiophenyl | Z₁: F (2) |
| CH₂ | Pyrimidinyl | NH—C(O) | Thiophenyl | Z₁: F (3) |
| CH₂ | Pyrimidinyl | NH—C(O) | Thiophenyl | Z₁: F (2)<br>Z₂: F (3) |
| CH₂ | Pyrimidinyl | NH—C(O) | Thiophenyl | Z₁: Cl (2) |
| CH₂ | Pyrimidinyl | NH—C(O) | Thiophenyl | Z₁: Cl (3) |
| CH₂ | Pyrimidinyl | NH—C(O) | Thiophenyl | Z₁: Cl (2)<br>Z₂: Cl (3) |
| CH₂ | Pyrimidinyl | NH—C(O) | Thiophenyl | Z₁: F (2)<br>Z₂: Cl (3) |
| CH₂ | Pyrimidinyl | NH—C(O) | Thiophenyl | Z₁: Cl (2)<br>Z₂: F (3) |
| CH₂ | Pyrimidinyl | NH—C(O) | Thiophenyl | Z₁: CH₃ (2) |
| CH₂ | Pyrimidinyl | NH—C(O) | Thiophenyl | Z₁: CH₃ (3) |
| CH₂ | Pyrimidinyl | NH—C(O) | Thiophenyl | Z₁: CH₂—CH₃ (2) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| CH₂ | Pyrimidinyl | NH—C(O) | Thiophenyl | Z₁: CH₂—CH₃ (3) |
| CH₂ | Pyrimidinyl | NH—C(O) | Thiophenyl | Z₁: CH₂—CH₂—CH₃ or iPr (2) |
| CH₂ | Pyrimidinyl | NH—C(O) | Thiophenyl | Z₁: CH₂—CH₂—CH₃ or iPr (3) |
| CH₂ | Pyrimidinyl | NH—C(O) | Thiophenyl | Z₁: CH₂F (2) |
| CH₂ | Pyrimidinyl | NH—C(O) | Thiophenyl | Z₁: CH₂F (3) |
| CH₂ | Pyrimidinyl | NH—C(O) | Thiophenyl | Z₁: CHF₂ (2) |
| CH₂ | Pyrimidinyl | NH—C(O) | Thiophenyl | Z₁: CHF₂ (3) |
| CH₂ | Pyrimidinyl | NH—C(O) | Thiophenyl | Z₁: CF₃ (2) |
| CH₂ | Pyrimidinyl | NH—C(O) | Thiophenyl | Z₁: CF₃ (3) |
| CH₂ | Pyrimidinyl | NH—C(O) | Thiophenyl | Z₁: CH₂—CH₂F (2) |
| CH₂ | Pyrimidinyl | NH—C(O) | Thiophenyl | Z₁: CH₂—CH₂F (3) |
| CH₂ | Pyrimidinyl | NH—C(O) | Thiophenyl | Z₁: CH₂—CHF₂ (2) |
| CH₂ | Pyrimidinyl | NH—C(O) | Thiophenyl | Z₁: CH₂—CHF₂ (3) |
| CH₂ | Pyrimidinyl | NH—C(O) | Thiophenyl | Z₁: CH₂—CF₃ (2) |
| CH₂ | Pyrimidinyl | NH—C(O) | Thiophenyl | Z₁: CH₂—CF₃ (3) |
| CH₂ | Pyrimidinyl | NH—C(O) | Thiazolyl | None |
| CH₂ | Pyrimidinyl | NH—C(O) | Thiazolyl | Z₁: F (2) |
| CH₂ | Pyrimidinyl | NH—C(O) | Thiazolyl | Z₁: F (3) |
| CH₂ | Pyrimidinyl | NH—C(O) | Thiazolyl | Z₁: F (2)<br>Z₂: F (3) |
| CH₂ | Pyrimidinyl | NH—C(O) | Thiazolyl | Z₁: Cl (2) |
| CH₂ | Pyrimidinyl | NH—C(O) | Thiazolyl | Z₁: Cl (3) |
| CH₂ | Pyrimidinyl | NH—C(O) | Thiazolyl | Z₁: Cl (2)<br>Z₂: Cl (3) |
| CH₂ | Pyrimidinyl | NH—C(O) | Thiazolyl | Z₁: F (2)<br>Z₂: Cl (3) |
| CH₂ | Pyrimidinyl | NH—C(O) | Thiazolyl | Z₁: Cl (2)<br>Z₂: F (3) |
| CH₂ | Pyrimidinyl | NH—C(O) | Thiazolyl | Z₁: CH₃ (2) |
| CH₂ | Pyrimidinyl | NH—C(O) | Thiazolyl | Z₁: CH₃ (3) |
| CH₂ | Pyrimidinyl | NH—C(O) | Thiazolyl | Z₁: CH₂—CH₃ (2) |
| CH₂ | Pyrimidinyl | NH—C(O) | Thiazolyl | Z₁: CH₂—CH₃ (3) |
| CH₂ | Pyrimidinyl | NH—C(O) | Thiazolyl | Z₁: CH₂—CH₂—CH₃ or iPr (2) |
| CH₂ | Pyrimidinyl | NH—C(O) | Thiazolyl | Z₁: CH₂—CH₂—CH₃ or iPr (3) |
| CH₂ | Pyrimidinyl | NH—C(O) | Thiazolyl | Z₁: CH₂F (2) |
| CH₂ | Pyrimidinyl | NH—C(O) | Thiazolyl | Z₁: CH₂F (3) |
| CH₂ | Pyrimidinyl | NH—C(O) | Thiazolyl | Z₁: CHF₂ (2) |
| CH₂ | Pyrimidinyl | NH—C(O) | Thiazolyl | Z₁: CHF₂ (3) |
| CH₂ | Pyrimidinyl | NH—C(O) | Thiazolyl | Z₁: CF₃ (2) |
| CH₂ | Pyrimidinyl | NH—C(O) | Thiazolyl | Z₁: CF₃ (3) |
| CH₂ | Pyrimidinyl | NH—C(O) | Thiazolyl | Z₁: CH₂—CH₂F (2) |
| CH₂ | Pyrimidinyl | NH—C(O) | Thiazolyl | Z₁: CH₂—CH₂F (3) |
| CH₂ | Pyrimidinyl | NH—C(O) | Thiazolyl | Z₁: CH₂—CHF₂ (2) |
| CH₂ | Pyrimidinyl | NH—C(O) | Thiazolyl | Z₁: CH₂—CHF₂ (3) |
| CH₂ | Pyrimidinyl | NH—C(O) | Thiazolyl | Z₁: CH₂—CF₃ (2) |
| CH₂ | Pyrimidinyl | NH—C(O) | Thiazolyl | Z₁: CH₂—CF₃ (3) |
| CH₂ | Pyrimidinyl | NH—SO₂ | Phenyl | None |
| CH₂ | Pyrimidinyl | NH—SO₂ | Phenyl | Z₁: F (para) |
| CH₂ | Pyrimidinyl | NH—SO₂ | phenyl | Z₁: F (meta) |
| CH₂ | Pyrimidinyl | NH—SO₂ | phenyl | Z₁: F (ortho) |
| CH₂ | Pyrimidinyl | NH—SO₂ | phenyl | Z₁: F (para)<br>Z₂: F (meta) |
| CH₂ | Pyrimidinyl | NH—SO₂ | Phenyl | Z₁: Cl (meta) |
| CH₂ | Pyrimidinyl | NH—SO₂ | Phenyl | Z₁: Cl (para) |
| CH₂ | Pyrimidinyl | NH—SO₂ | Phenyl | Z₁: Cl (para)<br>Z₂: Cl (meta) |
| CH₂ | Pyrimidinyl | NH—SO₂ | Phenyl | Z₁: F (para)<br>Z₂: Cl (meta) |
| CH₂ | Pyrimidinyl | NH—SO₂ | Phenyl | Z₁: Cl (para)<br>Z₂: F (meta) |
| CH₂ | Pyrimidinyl | NH—SO₂ | Phenyl | Z₁: CH₃ (para) |
| CH₂ | Pyrimidinyl | NH—SO₂ | Phenyl | Z₁: CH₃ (meta) |
| CH₂ | Pyrimidinyl | NH—SO₂ | Phenyl | Z₁: CH₃ (ortho) |
| CH₂ | Pyrimidinyl | NH—SO₂ | Phenyl | Z₁: CH₂—CH₃ (para) |
| CH₂ | Pyrimidinyl | NH—SO₂ | Phenyl | Z₁: CH₂—CH₃ (meta) |
| CH₂ | Pyrimidinyl | NH—SO₂ | Phenyl | Z₁: CH₂—CH₃ (ortho) |
| CH₂ | Pyrimidinyl | NH—SO₂ | Phenyl | Z₁: CH₂—CH₂—CH₃ or iPr (para) |

TABLE 2-continued

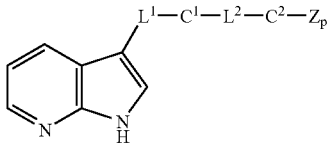

| L¹ | C¹ | L² | C² | Z |
|---|---|---|---|---|
| CH$_2$ | Pyrimidinyl | NH—SO$_2$ | Phenyl | Z$_1$: CH$_2$—CH$_2$—CH$_3$ or iPr (meta) |
| CH$_2$ | Pyrimidinyl | NH—SO$_2$ | Phenyl | Z$_1$: CH$_2$—CH$_2$—CH$_3$ or iPr (ortho) |
| CH$_2$ | Pyrimidinyl | NH—SO$_2$ | Phenyl | Z$_1$: CH$_2$F (para) |
| CH$_2$ | Pyrimidinyl | NH—SO$_2$ | Phenyl | Z$_1$: CH$_2$F (meta) |
| CH$_2$ | Pyrimidinyl | NH—SO$_2$ | Phenyl | Z$_1$: CH$_2$F (ortho) |
| CH$_2$ | Pyrimidinyl | NH—SO$_2$ | Phenyl | Z$_1$: CHF$_2$ (para) |
| CH$_2$ | Pyrimidinyl | NH—SO$_2$ | Phenyl | Z$_1$: CHF$_2$ (meta) |
| CH$_2$ | Pyrimidinyl | NH—SO$_2$ | Phenyl | Z$_1$: CHF$_2$ (ortho) |
| CH$_2$ | Pyrimidinyl | NH—SO$_2$ | Phenyl | Z$_1$: CF$_3$ (para) |
| CH$_2$ | Pyrimidinyl | NH—SO$_2$ | Phenyl | Z$_1$: CF$_3$ (meta) |
| CH$_2$ | Pyrimidinyl | NH—SO$_2$ | Phenyl | Z$_1$: CF$_3$ (ortho) |
| CH$_2$ | Pyrimidinyl | NH—SO$_2$ | Phenyl | Z$_1$: CH$_2$—CH$_2$F (para) |
| CH$_2$ | Pyrimidinyl | NH—SO$_2$ | Phenyl | Z$_1$: CH$_2$—CH$_2$F (meta) |
| CH$_2$ | Pyrimidinyl | NH—SO$_2$ | Phenyl | Z$_1$: CH$_2$—CH$_2$F (ortho) |
| CH$_2$ | Pyrimidinyl | NH—SO$_2$ | Phenyl | Z$_1$: CH$_2$—CHF$_2$ (para) |
| CH$_2$ | Pyrimidinyl | NH—SO$_2$ | Phenyl | Z$_1$: CH$_2$—CHF$_2$ (meta) |
| CH$_2$ | Pyrimidinyl | NH—SO$_2$ | Phenyl | Z$_1$: CH$_2$—CHF$_2$ (ortho) |
| CH$_2$ | Pyrimidinyl | NH—SO$_2$ | Phenyl | Z$_1$: CH$_2$—CF$_3$ (para) |
| CH$_2$ | Pyrimidinyl | NH—SO$_2$ | Phenyl | Z$_1$: CH$_2$—CF$_3$ (meta) |
| CH$_2$ | Pyrimidinyl | NH—SO$_2$ | Phenyl | Z$_1$: CH$_2$—CF$_3$ (ortho) |
| CH$_2$ | Pyrimidinyl | NH—SO$_2$ | Pyridinyl | None |
| CH$_2$ | Pyrimidinyl | NH—SO$_2$ | Pyridinyl | Z$_1$: F (para) |
| CH$_2$ | Pyrimidinyl | NH—SO$_2$ | Pyridinyl | Z$_1$: F (meta) |
| CH$_2$ | Pyrimidinyl | NH—SO$_2$ | Pyridinyl | Z$_1$: F (ortho) |
| CH$_2$ | Pyrimidinyl | NH—SO$_2$ | Pyridinyl | Z$_1$: F (para) Z$_2$: F (meta) |
| CH$_2$ | Pyrimidinyl | NH—SO$_2$ | Pyridinyl | Z$_1$: Cl (meta) |
| CH$_2$ | Pyrimidinyl | NH—SO$_2$ | Pyridinyl | Z$_1$: Cl (para) |
| CH$_2$ | Pyrimidinyl | NH—SO$_2$ | Pyridinyl | Z$_1$: Cl (para) Z$_2$: Cl (meta) |
| CH$_2$ | Pyrimidinyl | NH—SO$_2$ | Pyridinyl | Z$_1$: F (para) Z$_2$: Cl (meta) |
| CH$_2$ | Pyrimidinyl | NH—SO$_2$ | Pyridinyl | Z$_1$: Cl (para) Z$_2$: F (meta) |
| CH$_2$ | Pyrimidinyl | NH—SO$_2$ | Pyridinyl | Z$_1$: CH$_3$ (para) |
| CH$_2$ | Pyrimidinyl | NH—SO$_2$ | Pyridinyl | Z$_1$: CH$_3$ (meta) |
| CH$_2$ | Pyrimidinyl | NH—SO$_2$ | Pyridinyl | Z$_1$: CH$_3$ (ortho) |
| CH$_2$ | Pyrimidinyl | NH—SO$_2$ | Pyridinyl | Z$_1$: CH$_2$—CH$_3$ (para) |
| CH$_2$ | Pyrimidinyl | NH—SO$_2$ | Pyridinyl | Z$_1$: CH$_2$—CH$_3$ (meta) |
| CH$_2$ | Pyrimidinyl | NH—SO$_2$ | Pyridinyl | Z$_1$: CH$_2$—CH$_3$ (ortho) |
| CH$_2$ | Pyrimidinyl | NH—SO$_2$ | Pyridinyl | Z$_1$: CH$_2$—CH$_2$—CH$_3$ or iPr (para) |
| CH$_2$ | Pyrimidinyl | NH—SO$_2$ | Pyridinyl | Z$_1$: CH$_2$—CH$_2$—CH$_3$ or iPr (meta) |
| CH$_2$ | Pyrimidinyl | NH—SO$_2$ | Pyridinyl | Z$_1$: CH$_2$—CH$_2$—CH$_3$ or iPr (ortho) |
| CH$_2$ | Pyrimidinyl | NH—SO$_2$ | Pyridinyl | Z$_1$: CH$_2$F (para) |
| CH$_2$ | Pyrimidinyl | NH—SO$_2$ | Pyridinyl | Z$_1$: CH$_2$F (meta) |
| CH$_2$ | Pyrimidinyl | NH—SO$_2$ | Pyridinyl | Z$_1$: CH$_2$F (ortho) |
| CH$_2$ | Pyrimidinyl | NH—SO$_2$ | Pyridinyl | Z$_1$: CHF$_2$ (para) |
| CH$_2$ | Pyrimidinyl | NH—SO$_2$ | Pyridinyl | Z$_1$: CHF$_2$ (meta) |
| CH$_2$ | Pyrimidinyl | NH—SO$_2$ | Pyridinyl | Z$_1$: CHF$_2$ (ortho) |
| CH$_2$ | Pyrimidinyl | NH—SO$_2$ | Pyridinyl | Z$_1$: CF$_3$ (para) |
| CH$_2$ | Pyrimidinyl | NH—SO$_2$ | Pyridinyl | Z$_1$: CF$_3$ (meta) |
| CH$_2$ | Pyrimidinyl | NH—SO$_2$ | Pyridinyl | Z$_1$: CF$_3$ (ortho) |
| CH$_2$ | Pyrimidinyl | NH—SO$_2$ | Pyridinyl | Z$_1$: CH$_2$—CH$_2$F (para) |
| CH$_2$ | Pyrimidinyl | NH—SO$_2$ | Pyridinyl | Z$_1$: CH$_2$—CH$_2$F (meta) |
| CH$_2$ | Pyrimidinyl | NH—SO$_2$ | Pyridinyl | Z$_1$: CH$_2$—CH$_2$F (ortho) |
| CH$_2$ | Pyrimidinyl | NH—SO$_2$ | Pyridinyl | Z$_1$: CH$_2$—CHF$_2$ (para) |
| CH$_2$ | Pyrimidinyl | NH—SO$_2$ | Pyridinyl | Z$_1$: CH$_2$—CHF$_2$ (meta) |
| CH$_2$ | Pyrimidinyl | NH—SO$_2$ | Pyridinyl | Z$_1$: CH$_2$—CHF$_2$ (ortho) |
| CH$_2$ | Pyrimidinyl | NH—SO$_2$ | Pyridinyl | Z$_1$: CH$_2$—CF$_3$ (para) |
| CH$_2$ | Pyrimidinyl | NH—SO$_2$ | Pyridinyl | Z$_1$: CH$_2$—CF$_3$ (meta) |
| CH$_2$ | Pyrimidinyl | NH—SO$_2$ | Pyridinyl | Z$_1$: CH$_2$—CF$_3$ (ortho) |
| CH$_2$ | Pyrimidinyl | NH—SO$_2$ | Pyrimidinyl | None |
| CH$_2$ | Pyrimidinyl | NH—SO$_2$ | Pyrimidinyl | Z$_1$: F (para) |
| CH$_2$ | Pyrimidinyl | NH—SO$_2$ | Pyrimidinyl | Z$_1$: F (meta) |

TABLE 2-continued

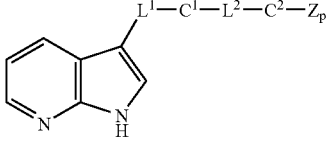

| L$^1$ | C$^1$ | L$^2$ | C$^2$ | Z |
|---|---|---|---|---|
| CH$_2$ | Pyrimidinyl | NH—SO$_2$ | Pyrimidinyl | Z$_1$: F (ortho) |
| CH$_2$ | Pyrimidinyl | NH—SO$_2$ | Pyrimidinyl | Z$_1$: F (para) |
| | | | | Z$_2$: F (meta) |
| CH$_2$ | Pyrimidinyl | NH—SO$_2$ | Pyrimidinyl | Z$_1$: Cl (meta) |
| CH$_2$ | Pyrimidinyl | NH—SO$_2$ | Pyrimidinyl | Z$_1$: Cl (para) |
| CH$_2$ | Pyrimidinyl | NH—SO$_2$ | Pyrimidinyl | Z$_1$: Cl (para) |
| | | | | Z$_2$: Cl (meta) |
| CH$_2$ | Pyrimidinyl | NH—SO$_2$ | Pyrimidinyl | Z$_1$: F (para) |
| | | | | Z$_2$: Cl (meta) |
| CH$_2$ | Pyrimidinyl | NH—SO$_2$ | Pyrimidinyl | Z$_1$: Cl (para) |
| | | | | Z$_2$: F (meta) |
| CH$_2$ | Pyrimidinyl | NH—SO$_2$ | Pyrimidinyl | Z$_1$: CH$_3$ (para) |
| CH$_2$ | Pyrimidinyl | NH—SO$_2$ | Pyrimidinyl | Z$_1$: CH$_3$ (meta) |
| CH$_2$ | Pyrimidinyl | NH—SO$_2$ | Pyrimidinyl | Z$_1$: CH$_3$ (ortho) |
| CH$_2$ | Pyrimidinyl | NH—SO$_2$ | Pyrimidinyl | Z$_1$: CH$_2$—CH$_3$ ara) |
| CH$_2$ | Pyrimidinyl | NH—SO$_2$ | Pyrimidinyl | Z$_1$: CH$_2$—CH$_3$ (meta) |
| CH$_2$ | Pyrimidinyl | NH—SO$_2$ | Pyrimidinyl | Z$_1$: CH$_2$—CH$_3$ (ortho) |
| CH$_2$ | Pyrimidinyl | NH—SO$_2$ | Pyrimidinyl | Z$_1$: CH$_2$—CH$_2$—CH$_3$ or iPr (para) |
| CH$_2$ | Pyrimidinyl | NH—SO$_2$ | Pyrimidinyl | Z$_1$: CH$_2$—CH$_2$—CH$_3$ or iPr (meta) |
| CH$_2$ | Pyrimidinyl | NH—SO$_2$ | Pyrimidinyl | Z$_1$: CH$_2$—CH$_2$—CH$_3$ or iPr (ortho) |
| CH$_2$ | Pyrimidinyl | NH—SO$_2$ | Pyrimidinyl | Z$_1$: CH$_2$F (para) |
| CH$_2$ | Pyrimidinyl | NH—SO$_2$ | Pyrimidinyl | Z$_1$: CH$_2$F (meta) |
| CH$_2$ | Pyrimidinyl | NH—SO$_2$ | Pyrimidinyl | Z$_1$: CH$_2$F (ortho) |
| CH$_2$ | Pyrimidinyl | NH—SO$_2$ | Pyrimidinyl | Z$_1$: CHF$_2$ (para) |
| CH$_2$ | Pyrimidinyl | NH—SO$_2$ | Pyrimidinyl | Z$_1$: CHF$_2$ (meta) |
| CH$_2$ | Pyrimidinyl | NH—SO$_2$ | Pyrimidinyl | Z$_1$: CHF$_2$ (ortho) |
| CH$_2$ | Pyrimidinyl | NH—SO$_2$ | Pyrimidinyl | Z$_1$: CF$_3$ (para) |
| CH$_2$ | Pyrimidinyl | NH—SO$_2$ | Pyrimidinyl | Z$_1$: CF$_3$ (meta) |
| CH$_2$ | Pyrimidinyl | NH—SO$_2$ | Pyrimidinyl | Z$_1$: CF$_3$ (ortho) |
| CH$_2$ | Pyrimidinyl | NH—SO$_2$ | Pyrimidinyl | Z$_1$: CH$_2$—CH$_2$F (para) |
| CH$_2$ | Pyrimidinyl | NH—SO$_2$ | Pyrimidinyl | Z$_1$: CH$_2$—CH$_2$F (meta) |
| CH$_2$ | Pyrimidinyl | NH—SO$_2$ | Pyrimidinyl | Z$_1$: CH$_2$—CH$_2$F (ortho) |
| CH$_2$ | Pyrimidinyl | NH—SO$_2$ | Pyrimidinyl | Z$_1$: CH$_2$—CHF$_2$ (para) |
| CH$_2$ | Pyrimidinyl | NH—SO$_2$ | Pyrimidinyl | Z$_1$: CH$_2$—CHF$_2$ (meta) |
| CH$_2$ | Pyrimidinyl | NH—SO$_2$ | Pyrimidinyl | Z$_1$: CH$_2$—CHF$_2$ (ortho) |
| CH$_2$ | Pyrimidinyl | NH—SO$_2$ | Pyrimidinyl | Z$_1$: CH$_2$—CF$_3$ (para) |
| CH$_2$ | Pyrimidinyl | NH—SO$_2$ | Pyrimidinyl | Z$_1$: CH$_2$—CF$_3$ (meta) |
| CH$_2$ | Pyrimidinyl | NH—SO$_2$ | Pyrimidinyl | Z$_1$: CH$_2$—CF$_3$ (ortho) |
| CH$_2$ | Pyrimidinyl | NH—SO$_2$ | Pyrazinyl | None |
| CH$_2$ | Pyrimidinyl | NH—SO$_2$ | Pyrazinyl | Z$_1$: F (para) |
| CH$_2$ | Pyrimidinyl | NH—SO$_2$ | Pyrazinyl | Z$_1$: F (meta) |
| CH$_2$ | Pyrimidinyl | NH—SO$_2$ | Pyrazinyl | Z$_1$: F ortho) |
| CH$_2$ | Pyrimidinyl | NH—SO$_2$ | Pyrazinyl | Z$_1$: F (para) |
| | | | | Z$_2$: F (meta) |
| CH$_2$ | Pyrimidinyl | NH—SO$_2$ | Pyrazinyl | Z$_1$: Cl (meta) |
| CH$_2$ | Pyrimidinyl | NH—SO$_2$ | Pyrazinyl | Z$_1$: Cl (para) |
| CH$_2$ | Pyrimidinyl | NH—SO$_2$ | Pyrazinyl | Z$_1$: Cl (para) |
| | | | | Z$_2$: Cl (meta) |
| CH$_2$ | Pyrimidinyl | NH—SO$_2$ | Pyrazinyl | Z$_1$: F (para) |
| | | | | Z$_2$: Cl (meta) |
| CH$_2$ | Pyrimidinyl | NH—SO$_2$ | Pyrazinyl | Z$_1$: Cl (para) |
| | | | | Z$_2$: F (meta) |
| CH$_2$ | Pyrimidinyl | NH—SO$_2$ | Pyrazinyl | Z$_1$: CH$_3$ (para) |
| CH$_2$ | Pyrimidinyl | NH—SO$_2$ | Pyrazinyl | Z$_1$: CH$_3$ (meta) |
| CH$_2$ | Pyrimidinyl | NH—SO$_2$ | Pyrazinyl | Z$_1$: CH$_3$ (ortho) |
| CH$_2$ | Pyrimidinyl | NH—SO$_2$ | Pyrazinyl | Z$_1$: CH$_2$—CH$_3$ (para) |
| CH$_2$ | Pyrimidinyl | NH—SO$_2$ | Pyrazinyl | Z$_1$: CH$_2$—CH$_3$ (meta) |
| CH$_2$ | Pyrimidinyl | NH—SO$_2$ | Pyrazinyl | Z$_1$: CH$_2$—CH$_3$ (ortho) |
| CH$_2$ | Pyrimidinyl | NH—SO$_2$ | Pyrazinyl | Z$_1$: CH$_2$—CH$_2$—CH$_3$ or iPr (para) |
| CH$_2$ | Pyrimidinyl | NH—SO$_2$ | Pyrazinyl | Z$_1$: CH$_2$—CH$_2$—CH$_3$ or iPr (meta) |
| CH$_2$ | Pyrimidinyl | NH—SO$_2$ | Pyrazinyl | Z$_1$: CH$_2$—CH$_2$—CH$_3$ or iPr (ortho) |
| CH$_2$ | Pyrimidinyl | NH—SO$_2$ | Pyrazinyl | Z$_1$: CH$_2$F (para) |
| CH$_2$ | Pyrimidinyl | NH—SO$_2$ | Pyrazinyl | Z$_1$: CH$_2$F (meta) |

TABLE 2-continued $$L^1\text{—}C^1\text{—}L^2\text{—}C^2\text{—}Z_p$$

(7-azaindole structure)

| L¹ | C¹ | L² | C² | Z |
|---|---|---|---|---|
| CH₂ | Pyrimidinyl | NH—SO₂ | Pyrazinyl | Z₁: CH₂F (ortho) |
| CH₂ | Pyrimidinyl | NH—SO₂ | Pyrazinyl | Z₁: CHF₂ (para) |
| CH₂ | Pyrimidinyl | NH—SO₂ | Pyrazinyl | Z₁: CHF₂ (meta) |
| CH₂ | Pyrimidinyl | NH—SO₂ | Pyrazinyl | Z₁: CHF₂ (ortho) |
| CH₂ | Pyrimidinyl | NH—SO₂ | Pyrazinyl | Z₁: CF₃ (para) |
| CH₂ | Pyrimidinyl | NH—SO₂ | Pyrazinyl | Z₁: CF₃ (meta) |
| CH₂ | Pyrimidinyl | NH—SO₂ | Pyrazinyl | Z₁: CF₃ (ortho) |
| CH₂ | Pyrimidinyl | NH—SO₂ | Pyrazinyl | Z₁: CH₂—CH₂F (para) |
| CH₂ | Pyrimidinyl | NH—SO₂ | Pyrazinyl | Z₁: CH₂—CH₂F (meta) |
| CH₂ | Pyrimidinyl | NH—SO₂ | Pyrazinyl | Z₁: CH₂—CH₂F (ortho) |
| CH₂ | Pyrimidinyl | NH—SO₂ | Pyrazinyl | Z₁: CH₂—CHF₂ (para) |
| CH₂ | Pyrimidinyl | NH—SO₂ | Pyrazinyl | Z₁: CH₂—CHF₂ (meta) |
| CH₂ | Pyrimidinyl | NH—SO₂ | Pyrazinyl | Z₁: CH₂—CHF₂ (ortho) |
| CH₂ | Pyrimidinyl | NH—SO₂ | Pyrazinyl | Z₁: CH₂—CF₃ (para) |
| CH₂ | Pyrimidinyl | NH—SO₂ | Pyrazinyl | Z₁: CH₂—CF₃ (meta) |
| CH₂ | Pyrimidinyl | NH—SO₂ | Pyrazinyl | Z₁: CH₂—CF₃ (ortho) |
| CH₂ | Pyrimidinyl | NH—SO₂ | Pyrrolyl | None |
| CH₂ | Pyrimidinyl | NH—SO₂ | Pyrrolyl | Z₁: F (2) |
| CH₂ | Pyrimidinyl | NH—SO₂ | Pyrrolyl | Z₁: F (3) |
| CH₂ | Pyrimidinyl | NH—SO₂ | Pyrrolyl | Z₁: F (2)<br>Z₂: F (3) |
| CH₂ | Pyrimidinyl | NH—SO₂ | Pyrrolyl | Z₁: Cl (2) |
| CH₂ | Pyrimidinyl | NH—SO₂ | Pyrrolyl | Z₁: Cl (3) |
| CH₂ | Pyrimidinyl | NH—SO₂ | Pyrrolyl | Z₁: Cl (2)<br>Z₂: Cl (3) |
| CH₂ | Pyrimidinyl | NH—SO₂ | Pyrrolyl | Z₁: F (2)<br>Z₂: Cl (3) |
| CH₂ | Pyrimidinyl | NH—SO₂ | Pyrrolyl | Z₁: Cl (2)<br>Z₂: F (3) |
| CH₂ | Pyrimidinyl | NH—SO₂ | Pyrrolyl | Z₁: CH₃ (2) |
| CH₂ | Pyrimidinyl | NH—SO₂ | Pyrrolyl | Z₁: CH₃ (3) |
| CH₂ | Pyrimidinyl | NH—SO₂ | Pyrrolyl | Z₁: CH₂—CH₃ (2) |
| CH₂ | Pyrimidinyl | NH—SO₂ | Pyrrolyl | Z₁: CH₂—CH₃ (3) |
| CH₂ | Pyrimidinyl | NH—SO₂ | Pyrrolyl | Z₁: CH₂—CH₂—CH₃ or iPr (2) |
| CH₂ | Pyrimidinyl | NH—SO₂ | Pyrrolyl | Z₁: CH₂—CH₂—CH₃ or iPr (3) |
| CH₂ | Pyrimidinyl | NH—SO₂ | Pyrrolyl | Z₁: CH₂F (2) |
| CH₂ | Pyrimidinyl | NH—SO₂ | Pyrrolyl | Z₁: CH₂F (3) |
| CH₂ | Pyrimidinyl | NH—SO₂ | Pyrrolyl | Z₁: CHF₂ (2) |
| CH₂ | Pyrimidinyl | NH—SO₂ | Pyrrolyl | Z₁: CHF₂ (3) |
| CH₂ | Pyrimidinyl | NH—SO₂ | Pyrrolyl | Z₁: CF₃ (2) |
| CH₂ | Pyrimidinyl | NH—SO₂ | Pyrrolyl | Z₁: CF₃ (3) |
| CH₂ | Pyrimidinyl | NH—SO₂ | Pyrrolyl | Z₁: CH₂—CH₂F (2) |
| CH₂ | Pyrimidinyl | NH—SO₂ | Pyrrolyl | Z₁: CH₂—CH₂F (3) |
| CH₂ | Pyrimidinyl | NH—SO₂ | Pyrrolyl | Z₁: CH₂—CHF₂ (2) |
| CH₂ | Pyrimidinyl | NH—SO₂ | Pyrrolyl | Z₁: CH₂—CHF₂ (3) |
| CH₂ | Pyrimidinyl | NH—SO₂ | Pyrrolyl | Z₁: CH₂—CF₃ (2) |
| CH₂ | Pyrimidinyl | NH—SO₂ | Pyrrolyl | Z₁: CH₂—CF₃ (3) |
| CH₂ | Pyrimidinyl | NH—SO₂ | Imidazolyl | None |
| CH₂ | Pyrimidinyl | NH—SO₂ | Imidazolyl | Z₁: F (2) |
| CH₂ | Pyrimidinyl | NH—SO₂ | Imidazolyl | Z₁: F (3) |
| CH₂ | Pyrimidinyl | NH—SO₂ | Imidazolyl | Z₁: F (2)<br>Z₂: F (3) |
| CH₂ | Pyrimidinyl | NH—SO₂ | Imidazolyl | Z₁: Cl (2) |
| CH₂ | Pyrimidinyl | NH—SO₂ | Imidazolyl | Z₁: Cl (3) |
| CH₂ | Pyrimidinyl | NH—SO₂ | Imidazolyl | Z₁: Cl (2)<br>Z₂: Cl (3) |
| CH₂ | Pyrimidinyl | NH—SO₂ | Imidazolyl | Z₁: F (2)<br>Z₂: Cl (3) |
| CH₂ | Pyrimidinyl | NH—SO₂ | Imidazolyl | Z₁: Cl (2)<br>Z₂: F (3) |
| CH₂ | Pyrimidinyl | NH—SO₂ | Imidazolyl | Z₁: CH₃ (2) |
| CH₂ | Pyrimidinyl | NH—SO₂ | Imidazolyl | Z₁: CH₃ (3) |
| CH₂ | Pyrimidinyl | NH—SO₂ | Imidazolyl | Z₁: CH₂—CH₃ (2) |
| CH₂ | Pyrimidinyl | NH—SO₂ | Imidazolyl | Z₁: CH₂—CH₃ (3) |
| CH₂ | Pyrimidinyl | NH—SO₂ | Imidazolyl | Z₁: CH₂—CH₂—CH₃ or iPr (2) |
| CH₂ | Pyrimidinyl | NH—SO₂ | Imidazolyl | Z₁: CH₂—CH₂—CH₃ or iPr (3) |
| CH₂ | Pyrimidinyl | NH—SO₂ | Imidazolyl | Z₁: CH₂F (2) |
| CH₂ | Pyrimidinyl | NH—SO₂ | Imidazolyl | Z₁: CH₂F (3) |
| CH₂ | Pyrimidinyl | NH—SO₂ | Imidazolyl | Z₁: CHF₂ (2) |

TABLE 2-continued $$L^1-C^1-L^2-C^2-Z_p$$

[Structure: 7-azaindole (1H-pyrrolo[2,3-b]pyridine) with substituent $L^1-C^1-L^2-C^2-Z_p$ at the 3-position]

| L¹ | C¹ | L² | C² | Z |
|---|---|---|---|---|
| CH₂ | Pyrimidinyl | NH—SO₂ | Imidazolyl | Z₁: CHF₂ (3) |
| CH₂ | Pyrimidinyl | NH—SO₂ | Imidazolyl | Z₁: CF₃ (2) |
| CH₂ | Pyrimidinyl | NH—SO₂ | Imidazolyl | Z₁: CF₃ (3) |
| CH₂ | Pyrimidinyl | NH—SO₂ | Imidazolyl | Z₁: CH₂—CH₂F (2) |
| CH₂ | Pyrimidinyl | NH—SO₂ | Imidazolyl | Z₁: CH₂—CH₂F (3) |
| CH₂ | Pyrimidinyl | NH—SO₂ | Imidazolyl | Z₁: CH₂—CHF₂ (2) |
| CH₂ | Pyrimidinyl | NH—SO₂ | Imidazolyl | Z₁: CH₂—CHF₂ (3) |
| CH₂ | Pyrimidinyl | NH—SO₂ | Imidazolyl | Z₁: CH₂—CF₃ (2) |
| CH₂ | Pyrimidinyl | NH—SO₂ | Imidazolyl | Z₁: CH₂—CF₃ (3) |
| CH₂ | Pyrimidinyl | NH—SO₂ | Furanyl | None |
| CH₂ | Pyrimidinyl | NH—SO₂ | Furanyl | Z₁: F (2) |
| CH₂ | Pyrimidinyl | NH—SO₂ | Furanyl | Z₁: F (3) |
| CH₂ | Pyrimidinyl | NH—SO₂ | Furanyl | Z₁: F (2) Z₂: F (3) |
| CH₂ | Pyrimidinyl | NH—SO₂ | Furanyl | Z₁: Cl (2) |
| CH₂ | Pyrimidinyl | NH—SO₂ | Furanyl | Z₁: Cl (3) |
| CH₂ | Pyrimidinyl | NH—SO₂ | Furanyl | Z₁: Cl (2) Z₂: Cl (3) |
| CH₂ | Pyrimidinyl | NH—SO₂ | Furanyl | Z₁: F (2) Z₂: Cl (3) |
| CH₂ | Pyrimidinyl | NH—SO₂ | Furanyl | Z₁: Cl (2) Z₂: F (3) |
| CH₂ | Pyrimidinyl | NH—SO₂ | Furanyl | Z₁: CH₃ (2) |
| CH₂ | Pyrimidinyl | NH—SO₂ | Furanyl | Z₁: CH₃ (3) |
| CH₂ | Pyrimidinyl | NH—SO₂ | Furanyl | Z₁: CH₂—CH₃ (2) |
| CH₂ | Pyrimidinyl | NH—SO₂ | Furanyl | Z₁: CH₂—CH₃ (3) |
| CH₂ | Pyrimidinyl | NH—SO₂ | Furanyl | Z₁: CH₂—CH₂—CH₃ or iPr (2) |
| CH₂ | Pyrimidinyl | NH—SO₂ | Furanyl | Z₁: CH₂—CH₂—CH₃ or iPr (3) |
| CH₂ | Pyrimidinyl | NH—SO₂ | Furanyl | Z₁: CH₂F (2) |
| CH₂ | Pyrimidinyl | NH—SO₂ | Furanyl | Z₁: CH₂F (3) |
| CH₂ | Pyrimidinyl | NH—SO₂ | Furanyl | Z₁: CHF₂ (2) |
| CH₂ | Pyrimidinyl | NH—SO₂ | Furanyl | Z₁: CHF₂ (3) |
| CH₂ | Pyrimidinyl | NH—SO₂ | Furanyl | Z₁: CF₃ (2) |
| CH₂ | Pyrimidinyl | NH—SO₂ | Furanyl | Z₁: CF₃ (3) |
| CH₂ | Pyrimidinyl | NH—SO₂ | Furanyl | Z₁: CH₂—CH₂F (2) |
| CH₂ | Pyrimidinyl | NH—SO₂ | Furanyl | Z₁: CH₂—CH₂F (3) |
| CH₂ | Pyrimidinyl | NH—SO₂ | Furanyl | Z₁: CH₂—CHF₂ (2) |
| CH₂ | Pyrimidinyl | NH—SO₂ | Furanyl | Z₁: CH₂—CHF₂ (3) |
| CH₂ | Pyrimidinyl | NH—SO₂ | Furanyl | Z₁: CH₂—CF₃ (2) |
| CH₂ | Pyrimidinyl | NH—SO₂ | Furanyl | Z₁: CH₂—CF₃ (3) |
| CH₂ | Pyrimidinyl | NH—SO₂ | Oxazolyl | None |
| CH₂ | Pyrimidinyl | NH—SO₂ | Oxazolyl | Z₁: F (2) |
| CH₂ | Pyrimidinyl | NH—SO₂ | Oxazolyl | Z₁: F (3) |
| CH₂ | Pyrimidinyl | NH—SO₂ | Oxazolyl | Z₁: F (2) Z₂: F (3) |
| CH₂ | Pyrimidinyl | NH—SO₂ | Oxazolyl | Z₁: Cl (2) |
| CH₂ | Pyrimidinyl | NH—SO₂ | Oxazolyl | Z₁: Cl (3) |
| CH₂ | Pyrimidinyl | NH—SO₂ | Oxazolyl | Z₁: Cl (2) Z₂: Cl (3) |
| CH₂ | Pyrimidinyl | NH—SO₂ | Oxazolyl | Z₁: F (2) Z₂: Cl (3) |
| CH₂ | Pyrimidinyl | NH—SO₂ | Oxazolyl | Z₁: Cl (2) Z₂: F (3) |
| CH₂ | Pyrimidinyl | NH—SO₂ | Oxazolyl | Z₁: CH₃ (2) |
| CH₂ | Pyrimidinyl | NH—SO₂ | Oxazolyl | Z₁: CH₃ (3) |
| CH₂ | Pyrimidinyl | NH—SO₂ | Oxazolyl | Z₁: CH₂—CH₃ (2) |
| CH₂ | Pyrimidinyl | NH—SO₂ | Oxazolyl | Z₁: CH₂—CH₃ (3) |
| CH₂ | Pyrimidinyl | NH—SO₂ | Oxazolyl | Z₁: CH₂—CH₂—CH₃ or iPr (2) |
| CH₂ | Pyrimidinyl | NH—SO₂ | Oxazolyl | Z₁: CH₂—CH₂—CH₃ or iPr (3) |
| CH₂ | Pyrimidinyl | NH—SO₂ | Oxazolyl | Z₁: CH₂F (2) |
| CH₂ | Pyrimidinyl | NH—SO₂ | Oxazolyl | Z₁: CH₂F (3) |
| CH₂ | Pyrimidinyl | NH—SO₂ | Oxazolyl | Z₁: CHF₂ (2) |
| CH₂ | Pyrimidinyl | NH—SO₂ | Oxazolyl | Z₁: CHF₂ (3) |
| CH₂ | Pyrimidinyl | NH—SO₂ | Oxazolyl | Z₁: CF₃ (2) |
| CH₂ | Pyrimidinyl | NH—SO₂ | Oxazolyl | Z₁: CF₃ (3) |
| CH₂ | Pyrimidinyl | NH—SO₂ | Oxazolyl | Z₁: CH₂—CH₂F (2) |
| CH₂ | Pyrimidinyl | NH—SO₂ | Oxazolyl | Z₁: CH₂—CH₂F (3) |
| CH₂ | Pyrimidinyl | NH—SO₂ | Oxazolyl | Z₁: CH₂—CHF₂ (2) |
| CH₂ | Pyrimidinyl | NH—SO₂ | Oxazolyl | Z₁: CH₂—CHF₂ (3) |

TABLE 2-continued $$L^1-C^1-L^2-C^2-Z_p$$

(7-azaindole structure with L¹—C¹—L²—C²—Zp substituent at 3-position)

| L¹ | C¹ | L² | C² | Z |
|---|---|---|---|---|
| CH₂ | Pyrimidinyl | NH—SO₂ | Oxazolyl | $Z_1$: CH₂—CF₃ (2) |
| CH₂ | Pyrimidinyl | NH—SO₂ | Oxazolyl | $Z_1$: CH₂—CF₃ (3) |
| CH₂ | Pyrimidinyl | NH—SO₂ | Thiophenyl | None |
| CH₂ | Pyrimidinyl | NH—SO₂ | Thiophenyl | $Z_1$: F (2) |
| CH₂ | Pyrimidinyl | NH—SO₂ | Thiophenyl | $Z_1$: F (3) |
| CH₂ | Pyrimidinyl | NH—SO₂ | Thiophenyl | $Z_1$: F (2)<br>$Z_2$: F (3) |
| CH₂ | Pyrimidinyl | NH—SO₂ | Thiophenyl | $Z_1$: Cl (2) |
| CH₂ | Pyrimidinyl | NH—SO₂ | Thiophenyl | $Z_1$: Cl (3) |
| CH₂ | Pyrimidinyl | NH—SO₂ | Thiophenyl | $Z_1$: Cl (2)<br>$Z_2$: Cl (3) |
| CH₂ | Pyrimidinyl | NH—SO₂ | Thiophenyl | $Z_1$: F (2)<br>$Z_2$: Cl (3) |
| CH₂ | Pyrimidinyl | NH—SO₂ | Thiophenyl | $Z_1$: Cl (2)<br>$Z_2$: F (3) |
| CH₂ | Pyrimidinyl | NH—SO₂ | Thiophenyl | $Z_1$: CH₃ (2) |
| CH₂ | Pyrimidinyl | NH—SO₂ | Thiophenyl | $Z_1$: CH₃ (3) |
| CH₂ | Pyrimidinyl | NH—SO₂ | Thiophenyl | $Z_1$: CH₂—CH₃ (2) |
| CH₂ | Pyrimidinyl | NH—SO₂ | Thiophenyl | $Z_1$: CH₂—CH₃ (3) |
| CH₂ | Pyrimidinyl | NH—SO₂ | Thiophenyl | $Z_1$: CH₂—CH₂—CH₃ or iPr (2) |
| CH₂ | Pyrimidinyl | NH—SO₂ | Thiophenyl | $Z_1$: CH₂—CH₂—CH₃ or iPr (3) |
| CH₂ | Pyrimidinyl | NH—SO₂ | Thiophenyl | $Z_1$: CH₂F (2) |
| CH₂ | Pyrimidinyl | NH—SO₂ | Thiophenyl | $Z_1$: CH₂F (3) |
| CH₂ | Pyrimidinyl | NH—SO₂ | Thiophenyl | $Z_1$: CHF₂ (2) |
| CH₂ | Pyrimidinyl | NH—SO₂ | Thiophenyl | $Z_1$: CHF₂ (3) |
| CH₂ | Pyrimidinyl | NH—SO₂ | Thiophenyl | $Z_1$: CF₃ (2) |
| CH₂ | Pyrimidinyl | NH—SO₂ | Thiophenyl | $Z_1$: CF₃ (3) |
| CH₂ | Pyrimidinyl | NH—SO₂ | Thiophenyl | $Z_1$: CH₂—CH₂F (2) |
| CH₂ | Pyrimidinyl | NH—SO₂ | Thiophenyl | $Z_1$: CH₂—CH₂F (3) |
| CH₂ | Pyrimidinyl | NH—SO₂ | Thiophenyl | $Z_1$: CH₂—CHF₂ (2) |
| CH₂ | Pyrimidinyl | NH—SO₂ | Thiophenyl | $Z_1$: CH₂—CHF₂ (3) |
| CH₂ | Pyrimidinyl | NH—SO₂ | Thiophenyl | $Z_1$: CH₂—CF₃ (2) |
| CH₂ | Pyrimidinyl | NH—SO₂ | Thiophenyl | $Z_1$: CH₂—CF₃ (3) |
| CH₂ | Pyrimidinyl | NH—SO₂ | Thiazolyl | None |
| CH₂ | Pyrimidinyl | NH—SO₂ | Thiazolyl | $Z_1$: F (2) |
| CH₂ | Pyrimidinyl | NH—SO₂ | Thiazolyl | $Z_1$: F (3) |
| CH₂ | Pyrimidinyl | NH—SO₂ | Thiazolyl | $Z_1$: F (2)<br>$Z_2$: F (3) |
| CH₂ | Pyrimidinyl | NH—SO₂ | Thiazolyl | $Z_1$: Cl (2) |
| CH₂ | Pyrimidinyl | NH—SO₂ | Thiazolyl | $Z_1$: Cl (3) |
| CH₂ | Pyrimidinyl | NH—SO₂ | Thiazolyl | $Z_1$: Cl (2)<br>$Z_2$: Cl (3) |
| CH₂ | Pyrimidinyl | NH—SO₂ | Thiazolyl | $Z_1$: F (2)<br>$Z_2$: Cl (3) |
| CH₂ | Pyrimidinyl | NH—SO₂ | Thiazolyl | $Z_1$: Cl (2)<br>$Z_2$: F (3) |
| CH₂ | Pyrimidinyl | NH—SO₂ | Thiazolyl | $Z_1$: CH₃ (2) |
| CH₂ | Pyrimidinyl | NH—SO₂ | Thiazolyl | $Z_1$: CH₃ (3) |
| CH₂ | Pyrimidinyl | NH—SO₂ | Thiazolyl | $Z_1$: CH₂—CH₃ (2) |
| CH₂ | Pyrimidinyl | NH—SO₂ | Thiazolyl | $Z_1$: CH₂—CH₃ (3) |
| CH₂ | Pyrimidinyl | NH—SO₂ | Thiazolyl | $Z_1$: CH₂—CH₂—CH₃ or iPr (2) |
| CH₂ | Pyrimidinyl | NH—SO₂ | Thiazolyl | $Z_1$: CH₂—CH₂—CH₃ or iPr (3) |
| CH₂ | Pyrimidinyl | NH—SO₂ | Thiazolyl | $Z_1$: CH₂F (2) |
| CH₂ | Pyrimidinyl | NH—SO₂ | Thiazolyl | $Z_1$: CH₂F (3) |
| CH₂ | Pyrimidinyl | NH—SO₂ | Thiazolyl | $Z_1$: CHF₂ (2) |
| CH₂ | Pyrimidinyl | NH—SO₂ | Thiazolyl | $Z_1$: CHF₂ (3) |
| CH₂ | Pyrimidinyl | NH—SO₂ | Thiazolyl | $Z_1$: CF₃ (2) |
| CH₂ | Pyrimidinyl | NH—SO₂ | Thiazolyl | $Z_1$: CF₃ (3) |
| CH₂ | Pyrimidinyl | NH—SO₂ | Thiazolyl | $Z_1$: CH₂—CH₂F (2) |
| CH₂ | Pyrimidinyl | NH—SO₂ | Thiazolyl | $Z_1$: CH₂—CH₂F (3) |
| CH₂ | Pyrimidinyl | NH—SO₂ | Thiazolyl | $Z_1$: CH₂—CHF₂ (2) |
| CH₂ | Pyrimidinyl | NH—SO₂ | Thiazolyl | $Z_1$: CH₂—CHF₂ (3) |
| CH₂ | Pyrimidinyl | NH—SO₂ | Thiazolyl | $Z_1$: CH₂—CF₃ (2) |
| CH₂ | Pyrimidinyl | NH—SO₂ | Thiazolyl | $Z_1$: CH₂—CF₃ (3) |
| CH₂ | Pyrazinyl | NH—CH₂ | Phenyl | None |
| CH₂ | Pyrazinyl | NH—CH₂ | Phenyl | $Z_1$: F (para) |
| CH₂ | Pyrazinyl | NH—CH₂ | phenyl | $Z_1$: F (meta) |
| CH₂ | Pyrazinyl | NH—CH₂ | phenyl | $Z_1$: F (ortho) |

TABLE 2-continued

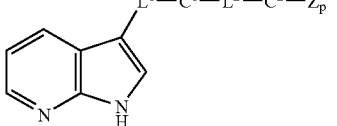

| L¹ | C¹ | L² | C² | Z |
|---|---|---|---|---|
| CH₂ | Pyrazinyl | NH—CH₂ | phenyl | $Z_1$: F (para) |
|  |  |  |  | $Z_2$: F (meta) |
| CH₂ | Pyrazinyl | NH—CH₂ | Phenyl | $Z_1$: Cl (meta) |
| CH₂ | Pyrazinyl | NH—CH₂ | Phenyl | $Z_1$: Cl (para) |
| CH₂ | Pyrazinyl | NH—CH₂ | Phenyl | $Z_1$: Cl (para) |
|  |  |  |  | $Z_2$: Cl (meta) |
| CH₂ | Pyrazinyl | NH—CH₂ | Phenyl | $Z_1$: F (para) |
|  |  |  |  | $Z_2$: Cl (meta) |
| CH₂ | Pyrazinyl | NH—CH₂ | Phenyl | $Z_1$: Cl (para) |
|  |  |  |  | $Z_2$: F (meta) |
| CH₂ | Pyrazinyl | NH—CH₂ | Phenyl | $Z_1$: CH₃ (para) |
| CH₂ | Pyrazinyl | NH—CH₂ | Phenyl | $Z_1$: CH₃ (meta) |
| CH₂ | Pyrazinyl | NH—CH₂ | Phenyl | $Z_1$: CH₃ (ortho) |
| CH₂ | Pyrazinyl | NH—CH₂ | Phenyl | $Z_1$: CH₂—CH₃ (para) |
| CH₂ | Pyrazinyl | NH—CH₂ | Phenyl | $Z_1$: CH₂—CH₃ (meta) |
| CH₂ | Pyrazinyl | NH—CH₂ | Phenyl | $Z_1$: CH₂—CH₃ (ortho) |
| CH₂ | Pyrazinyl | NH—CH₂ | Phenyl | $Z_1$: CH₂—CH₂—CH₃ or iPr (para) |
| CH₂ | Pyrazinyl | NH—CH₂ | Phenyl | $Z_1$: CH₂—CH₂—CH₃ or iPr (meta) |
| CH₂ | Pyrazinyl | NH—CH₂ | Phenyl | $Z_1$: CH₂—CH₂—CH₃ or iPr (ortho) |
| CH₂ | Pyrazinyl | NH—CH₂ | Phenyl | $Z_1$: CH₂F (para) |
| CH₂ | Pyrazinyl | NH—CH₂ | Phenyl | $Z_1$: CH₂F (meta) |
| CH₂ | Pyrazinyl | NH—CH₂ | Phenyl | $Z_1$: CH₂F (ortho) |
| CH₂ | Pyrazinyl | NH—CH₂ | Phenyl | $Z_1$: CHF₂ (para) |
| CH₂ | Pyrazinyl | NH—CH₂ | Phenyl | $Z_1$: CHF₂ (meta) |
| CH₂ | Pyrazinyl | NH—CH₂ | Phenyl | $Z_1$: CHF₂ (ortho) |
| CH₂ | Pyrazinyl | NH—CH₂ | Phenyl | $Z_1$: CF₃ (para) |
| CH₂ | Pyrazinyl | NH—CH₂ | Phenyl | $Z_1$: CF₃ (meta) |
| CH₂ | Pyrazinyl | NH—CH₂ | Phenyl | $Z_1$: CF₃ (ortho) |
| CH₂ | Pyrazinyl | NH—CH₂ | Phenyl | $Z_1$: CH₂—CH₂F (para) |
| CH₂ | Pyrazinyl | NH—CH₂ | Phenyl | $Z_1$: CH₂—CH₂F (meta) |
| CH₂ | Pyrazinyl | NH—CH₂ | Phenyl | $Z_1$: CH₂—CH₂F (ortho) |
| CH₂ | Pyrazinyl | NH—CH₂ | Phenyl | $Z_1$: CH₂—CHF₂ (para) |
| CH₂ | Pyrazinyl | NH—CH₂ | Phenyl | $Z_1$: CH₂—CHF₂ (meta) |
| CH₂ | Pyrazinyl | NH—CH₂ | Phenyl | $Z_1$: CH₂—CHF₂ (ortho) |
| CH₂ | Pyrazinyl | NH—CH₂ | Phenyl | $Z_1$: CH₂—CF₃ (para) |
| CH₂ | Pyrazinyl | NH—CH₂ | Phenyl | $Z_1$: CH₂—CF₃ (meta) |
| CH₂ | Pyrazinyl | NH—CH₂ | Phenyl | $Z_1$: CH₂—CF₃ (ortho) |
| CH₂ | Pyrazinyl | NH—CH₂ | Pyridinyl | None |
| CH₂ | Pyrazinyl | NH—CH₂ | Pyridinyl | $Z_1$: F (para) |
| CH₂ | Pyrazinyl | NH—CH₂ | Pyridinyl | $Z_1$: F (meta) |
| CH₂ | Pyrazinyl | NH—CH₂ | Pyridinyl | $Z_1$: F (ortho) |
| CH₂ | Pyrazinyl | NH—CH₂ | Pyridinyl | $Z_1$: F (para) |
|  |  |  |  | $Z_2$: F (meta) |
| CH₂ | Pyrazinyl | NH—CH₂ | Pyridinyl | $Z_1$: Cl (meta) |
| CH₂ | Pyrazinyl | NH—CH₂ | Pyridinyl | $Z_1$: Cl (para) |
| CH₂ | Pyrazinyl | NH—CH₂ | Pyridinyl | $Z_1$: Cl (para) |
|  |  |  |  | $Z_2$: Cl (meta) |
| CH₂ | Pyrazinyl | NH—CH₂ | Pyridinyl | $Z_1$: F (para) |
|  |  |  |  | $Z_2$: Cl (meta) |
| CH₂ | Pyrazinyl | NH—CH₂ | Pyridinyl | $Z_1$: Cl (para) |
|  |  |  |  | $Z_2$: F (meta) |
| CH₂ | Pyrazinyl | NH—CH₂ | Pyridinyl | $Z_1$: CH₃ (para) |
| CH₂ | Pyrazinyl | NH—CH₂ | Pyridinyl | $Z_1$: CH₃ (meta) |
| CH₂ | Pyrazinyl | NH—CH₂ | Pyridinyl | $Z_1$: CH₃ (ortho) |
| CH₂ | Pyrazinyl | NH—CH₂ | Pyridinyl | $Z_1$: CH₂—CH₃ (para) |
| CH₂ | Pyrazinyl | NH—CH₂ | Pyridinyl | $Z_1$: CH₂—CH₃ (meta) |
| CH₂ | Pyrazinyl | NH—CH₂ | Pyridinyl | $Z_1$: CH₂—CH₃ (ortho) |
| CH₂ | Pyrazinyl | NH—CH₂ | Pyridinyl | $Z_1$: CH₂—CH₂—CH₃ or iPr (para) |
| CH₂ | Pyrazinyl | NH—CH₂ | Pyridinyl | $Z_1$: CH₂—CH₂—CH₃ or iPr (meta) |
| CH₂ | Pyrazinyl | NH—CH₂ | Pyridinyl | $Z_1$: CH₂—CH₂—CH₃ or iPr (ortho) |
| CH₂ | Pyrazinyl | NH—CH₂ | Pyridinyl | $Z_1$: CH₂F (para) |
| CH₂ | Pyrazinyl | NH—CH₂ | Pyridinyl | $Z_1$: CH₂F (meta) |
| CH₂ | Pyrazinyl | NH—CH₂ | Pyridinyl | $Z_1$: CH₂F (ortho) |

TABLE 2-continued

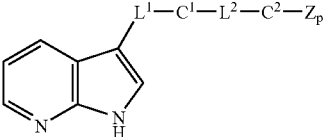

| $L^1$ | $C^1$ | $L^2$ | $C^2$ | Z |
|---|---|---|---|---|
| $CH_2$ | Pyrazinyl | $NH-CH_2$ | Pyridinyl | $Z_1$: $CHF_2$ (para) |
| $CH_2$ | Pyrazinyl | $NH-CH_2$ | Pyridinyl | $Z_1$: $CHF_2$ (meta) |
| $CH_2$ | Pyrazinyl | $NH-CH_2$ | Pyridinyl | $Z_1$: $CHF_2$ (ortho) |
| $CH_2$ | Pyrazinyl | $NH-CH_2$ | Pyridinyl | $Z_1$: $CF_3$ (para) |
| $CH_2$ | Pyrazinyl | $NH-CH_2$ | Pyridinyl | $Z_1$: $CF_3$ (meta) |
| $CH_2$ | Pyrazinyl | $NH-CH_2$ | Pyridinyl | $Z_1$: $CF_3$ (ortho) |
| $CH_2$ | Pyrazinyl | $NH-CH_2$ | Pyridinyl | $Z_1$: $CH_2-CH_2F$ (para) |
| $CH_2$ | Pyrazinyl | $NH-CH_2$ | Pyridinyl | $Z_1$: $CH_2-CH_2F$ (meta) |
| $CH_2$ | Pyrazinyl | $NH-CH_2$ | Pyridinyl | $Z_1$: $CH_2-CH_2F$ (ortho) |
| $CH_2$ | Pyrazinyl | $NH-CH_2$ | Pyridinyl | $Z_1$: $CH_2-CHF_2$ (para) |
| $CH_2$ | Pyrazinyl | $NH-CH_2$ | Pyridinyl | $Z_1$: $CH_2-CHF_2$ (meta) |
| $CH_2$ | Pyrazinyl | $NH-CH_2$ | Pyridinyl | $Z_1$: $CH_2-CHF_2$ (ortho) |
| $CH_2$ | Pyrazinyl | $NH-CH_2$ | Pyridinyl | $Z_1$: $CH_2-CF_3$ (para) |
| $CH_2$ | Pyrazinyl | $NH-CH_2$ | Pyridinyl | $Z_1$: $CH_2-CF_3$ (meta) |
| $CH_2$ | Pyrazinyl | $NH-CH_2$ | Pyridinyl | $Z_1$: $CH_2-CF_3$ (ortho) |
| $CH_2$ | Pyrazinyl | $NH-CH_2$ | Pyrimidinyl | None |
| $CH_2$ | Pyrazinyl | $NH-CH_2$ | Pyrimidinyl | $Z_1$: F (para) |
| $CH_2$ | Pyrazinyl | $NH-CH_2$ | Pyrimidinyl | $Z_1$: F (meta) |
| $CH_2$ | Pyrazinyl | $NH-CH_2$ | Pyrimidinyl | $Z_1$: F (ortho) |
| $CH_2$ | Pyrazinyl | $NH-CH_2$ | Pyrimidinyl | $Z_1$: F (para) $Z_2$: F (meta) |
| $CH_2$ | Pyrazinyl | $NH-CH_2$ | Pyrimidinyl | $Z_1$: Cl (meta) |
| $CH_2$ | Pyrazinyl | $NH-CH_2$ | Pyrimidinyl | $Z_1$: Cl (para) |
| $CH_2$ | Pyrazinyl | $NH-CH_2$ | Pyrimidinyl | $Z_1$: Cl (para) $Z_2$: Cl (meta) |
| $CH_2$ | Pyrazinyl | $NH-CH_2$ | Pyrimidinyl | $Z_1$: F (para) $Z_2$: Cl (meta) |
| $CH_2$ | Pyrazinyl | $NH-CH_2$ | Pyrimidinyl | $Z_1$: Cl (para) $Z_2$: F (meta) |
| $CH_2$ | Pyrazinyl | $NH-CH_2$ | Pyrimidinyl | $Z_1$: $CH_3$ (para) |
| $CH_2$ | Pyrazinyl | $NH-CH_2$ | Pyrimidinyl | $Z_1$: $CH_3$ (meta) |
| $CH_2$ | Pyrazinyl | $NH-CH_2$ | Pyrimidinyl | $Z_1$: $CH_3$ (ortho) |
| $CH_2$ | Pyrazinyl | $NH-CH_2$ | Pyrimidinyl | $Z_1$: $CH_2-CH_3$ (para) |
| $CH_2$ | Pyrazinyl | $NH-CH_2$ | Pyrimidinyl | $Z_1$: $CH_2-CH_3$ (meta) |
| $CH_2$ | Pyrazinyl | $NH-CH_2$ | Pyrimidinyl | $Z_1$: $CH_2-CH_3$ (ortho) |
| $CH_2$ | Pyrazinyl | $NH-CH_2$ | Pyrimidinyl | $Z_1$: $CH_2-CH_2-CH_3$ or iPr (para) |
| $CH_2$ | Pyrazinyl | $NH-CH_2$ | Pyrimidinyl | $Z_1$: $CH_2-CH_2-CH_3$ or iPr (meta) |
| $CH_2$ | Pyrazinyl | $NH-CH_2$ | Pyrimidinyl | $Z_1$: $CH_2-CH_2-CH_3$ or iPr (ortho) |
| $CH_2$ | Pyrazinyl | $NH-CH_2$ | Pyrimidinyl | $Z_1$: $CH_2F$ (para) |
| $CH_2$ | Pyrazinyl | $NH-CH_2$ | Pyrimidinyl | $Z_1$: $CH_2F$ (meta) |
| $CH_2$ | Pyrazinyl | $NH-CH_2$ | Pyrimidinyl | $Z_1$: $CH_2F$ (ortho) |
| $CH_2$ | Pyrazinyl | $NH-CH_2$ | Pyrimidinyl | $Z_1$: $CHF_2$ (para) |
| $CH_2$ | Pyrazinyl | $NH-CH_2$ | Pyrimidinyl | $Z_1$: $CHF_2$ (meta) |
| $CH_2$ | Pyrazinyl | $NH-CH_2$ | Pyrimidinyl | $Z_1$: $CHF_2$ (ortho) |
| $CH_2$ | Pyrazinyl | $NH-CH_2$ | Pyrimidinyl | $Z_1$: $CF_3$ (para) |
| $CH_2$ | Pyrazinyl | $NH-CH_2$ | Pyrimidinyl | $Z_1$: $CF_3$ (meta) |
| $CH_2$ | Pyrazinyl | $NH-CH_2$ | Pyrimidinyl | $Z_1$: $CF_3$ (ortho) |
| $CH_2$ | Pyrazinyl | $NH-CH_2$ | Pyrimidinyl | $Z_1$: $CH_2-CH_2F$ (para) |
| $CH_2$ | Pyrazinyl | $NH-CH_2$ | Pyrimidinyl | $Z_1$: $CH_2-CH_2F$ (meta) |
| $CH_2$ | Pyrazinyl | $NH-CH_2$ | Pyrimidinyl | $Z_1$: $CH_2-CH_2F$ (ortho) |
| $CH_2$ | Pyrazinyl | $NH-CH_2$ | Pyrimidinyl | $Z_1$: $CH_2-CHF_2$ (para) |
| $CH_2$ | Pyrazinyl | $NH-CH_2$ | Pyrimidinyl | $Z_1$: $CH_2-CHF_2$ (meta) |
| $CH_2$ | Pyrazinyl | $NH-CH_2$ | Pyrimidinyl | $Z_1$: $CH_2-CHF_2$ (ortho) |
| $CH_2$ | Pyrazinyl | $NH-CH_2$ | Pyrimidinyl | $Z_1$: $CH_2-CF_3$ (para) |
| $CH_2$ | Pyrazinyl | $NH-CH_2$ | Pyrimidinyl | $Z_1$: $CH_2-CF_3$ (meta) |
| $CH_2$ | Pyrazinyl | $NH-CH_2$ | Pyrimidinyl | $Z_1$: $CH_2-CF_3$ (ortho) |
| $CH_2$ | Pyrazinyl | $NH-CH_2$ | Pyrazinyl | None |
| $CH_2$ | Pyrazinyl | $NH-CH_2$ | Pyrazinyl | $Z_1$: F (para) |
| $CH_2$ | Pyrazinyl | $NH-CH_2$ | Pyrazinyl | $Z_1$: F (meta) |
| $CH_2$ | Pyrazinyl | $NH-CH_2$ | Pyrazinyl | $Z_1$: F (ortho) |
| $CH_2$ | Pyrazinyl | $NH-CH_2$ | Pyrazinyl | $Z_1$: F (para) $Z_2$: F (meta) |
| $CH_2$ | Pyrazinyl | $NH-CH_2$ | Pyrazinyl | $Z_1$: Cl (meta) |
| $CH_2$ | Pyrazinyl | $NH-CH_2$ | Pyrazinyl | $Z_1$: Cl (para) |
| $CH_2$ | Pyrazinyl | $NH-CH_2$ | Pyrazinyl | $Z_1$: Cl (para) $Z_2$: Cl (meta) |

TABLE 2-continued $$L^1-C^1-L^2-C^2-Z_p$$

[Structure: 7-azaindole (1H-pyrrolo[2,3-b]pyridine)]

| L¹ | C¹ | L² | C² | Z |
|---|---|---|---|---|
| CH₂ | Pyrazinyl | NH—CH₂ | Pyrazinyl | Z₁: F (para)<br>Z₂: Cl (meta) |
| CH₂ | Pyrazinyl | NH—CH₂ | Pyrazinyl | Z₁: Cl (para)<br>Z₂: F (meta) |
| CH₂ | Pyrazinyl | NH—CH₂ | Pyrazinyl | Z₁: CH₃ (para) |
| CH₂ | Pyrazinyl | NH—CH₂ | Pyrazinyl | Z₁: CH₃ (meta) |
| CH₂ | Pyrazinyl | NH—CH₂ | Pyrazinyl | Z₁: CH₃ (ortho) |
| CH₂ | Pyrazinyl | NH—CH₂ | Pyrazinyl | Z₁: CH₂—CH₃ (para) |
| CH₂ | Pyrazinyl | NH—CH₂ | Pyrazinyl | Z₁: CH₂—CH₃ (meta) |
| CH₂ | Pyrazinyl | NH—CH₂ | Pyrazinyl | Z₁: CH₂—CH₃ (ortho) |
| CH₂ | Pyrazinyl | NH—CH₂ | Pyrazinyl | Z₁: CH₂—CH₂—CH₃ or iPr (para) |
| CH₂ | Pyrazinyl | NH—CH₂ | Pyrazinyl | Z₁: CH₂—CH₂—CH₃ or iPr (meta) |
| CH₂ | Pyrazinyl | NH—CH₂ | Pyrazinyl | Z₁: CH₂—CH₂—CH₃ or iPr (ortho) |
| CH₂ | Pyrazinyl | NH—CH₂ | Pyrazinyl | Z₁: CH₂F (para) |
| CH₂ | Pyrazinyl | NH—CH₂ | Pyrazinyl | Z₁: CH₂F (meta) |
| CH₂ | Pyrazinyl | NH—CH₂ | Pyrazinyl | Z₁: CH₂F (ortho) |
| CH₂ | Pyrazinyl | NH—CH₂ | Pyrazinyl | Z₁: CHF₂ (para) |
| CH₂ | Pyrazinyl | NH—CH₂ | Pyrazinyl | Z₁: CHF₂ (meta) |
| CH₂ | Pyrazinyl | NH—CH₂ | Pyrazinyl | Z₁: CHF₂ (ortho) |
| CH₂ | Pyrazinyl | NH—CH₂ | Pyrazinyl | Z₁: CF₃ (para) |
| CH₂ | Pyrazinyl | NH—CH₂ | Pyrazinyl | Z₁: CF₃ (meta) |
| CH₂ | Pyrazinyl | NH—CH₂ | Pyrazinyl | Z₁: CF₃ (ortho) |
| CH₂ | Pyrazinyl | NH—CH₂ | Pyrazinyl | Z₁: CH₂—CH₂F (para) |
| CH₂ | Pyrazinyl | NH—CH₂ | Pyrazinyl | Z₁: CH₂—CH₂F (meta) |
| CH₂ | Pyrazinyl | NH—CH₂ | Pyrazinyl | Z₁: CH₂—CH₂F (ortho) |
| CH₂ | Pyrazinyl | NH—CH₂ | Pyrazinyl | Z₁: CH₂—CHF₂ (para) |
| CH₂ | Pyrazinyl | NH—CH₂ | Pyrazinyl | Z₁: CH₂—CHF₂ (meta) |
| CH₂ | Pyrazinyl | NH—CH₂ | Pyrazinyl | Z₁: CH₂—CHF₂ (ortho) |
| CH₂ | Pyrazinyl | NH—CH₂ | Pyrazinyl | Z₁: CH₂—CF₃ (para) |
| CH₂ | Pyrazinyl | NH—CH₂ | Pyrazinyl | Z₁: CH₂—CF₃ (meta) |
| CH₂ | Pyrazinyl | NH—CH₂ | Pyrazinyl | Z₁: CH₂—CF₃ (ortho) |
| CH₂ | Pyrazinyl | NH—CH₂ | Pyrrolyl | None |
| CH₂ | Pyrazinyl | NH—CH₂ | Pyrrolyl | Z₁: F (2) |
| CH₂ | Pyrazinyl | NH—CH₂ | Pyrrolyl | Z₁: F (3) |
| CH₂ | Pyrazinyl | NH—CH₂ | Pyrrolyl | Z₁: F (2)<br>Z₂: F (3) |
| CH₂ | Pyrazinyl | NH—CH₂ | Pyrrolyl | Z₁: Cl (2) |
| CH₂ | Pyrazinyl | NH—CH₂ | Pyrrolyl | Z₁: Cl (3) |
| CH₂ | Pyrazinyl | NH—CH₂ | Pyrrolyl | Z₁: Cl (2)<br>Z₂: Cl (3) |
| CH₂ | Pyrazinyl | NH—CH₂ | Pyrrolyl | Z₁: F (2)<br>Z₂: Cl (3) |
| CH₂ | Pyrazinyl | NH—CH₂ | Pyrrolyl | Z₁: Cl (2)<br>Z₂: F (3) |
| CH₂ | Pyrazinyl | NH—CH₂ | Pyrrolyl | Z₁: CH₃ (2) |
| CH₂ | Pyrazinyl | NH—CH₂ | Pyrrolyl | Z₁: CH₃ (3) |
| CH₂ | Pyrazinyl | NH—CH₂ | Pyrrolyl | Z₁: CH₂—CH₃ (2) |
| CH₂ | Pyrazinyl | NH—CH₂ | Pyrrolyl | Z₁: CH₂—CH₃ (3) |
| CH₂ | Pyrazinyl | NH—CH₂ | Pyrrolyl | Z₁: CH₂—CH₂—CH₃ or iPr (2) |
| CH₂ | Pyrazinyl | NH—CH₂ | Pyrrolyl | Z₁: CH₂—CH₂—CH₃ or iPr (3) |
| CH₂ | Pyrazinyl | NH—CH₂ | Pyrrolyl | Z₁: CH₂F (2) |
| CH₂ | Pyrazinyl | NH—CH₂ | Pyrrolyl | Z₁: CH₂F (3) |
| CH₂ | Pyrazinyl | NH—CH₂ | Pyrrolyl | Z₁: CHF₂ (2) |
| CH₂ | Pyrazinyl | NH—CH₂ | Pyrrolyl | Z₁: CHF₂ (3) |
| CH₂ | Pyrazinyl | NH—CH₂ | Pyrrolyl | Z₁: CF₃ (2) |
| CH₂ | Pyrazinyl | NH—CH₂ | Pyrrolyl | Z₁: CF₃ (3) |
| CH₂ | Pyrazinyl | NH—CH₂ | Pyrrolyl | Z₁: CH₂—CH₂F (2) |
| CH₂ | Pyrazinyl | NH—CH₂ | Pyrrolyl | Z₁: CH₂—CH₂F (3) |
| CH₂ | Pyrazinyl | NH—CH₂ | Pyrrolyl | Z₁: CH₂—CHF₂ (2) |
| CH₂ | Pyrazinyl | NH—CH₂ | Pyrrolyl | Z₁: CH₂—CHF₂ (3) |
| CH₂ | Pyrazinyl | NH—CH₂ | Pyrrolyl | Z₁: CH₂—CF₃ (2) |
| CH₂ | Pyrazinyl | NH—CH₂ | Pyrrolyl | Z₁: CH₂—CF₃ (3) |
| CH₂ | Pyrazinyl | NH—CH₂ | Imidazolyl | None |
| CH₂ | Pyrazinyl | NH—CH₂ | Imidazolyl | Z₁: F (2) |
| CH₂ | Pyrazinyl | NH—CH₂ | Imidazolyl | Z₁: F (3) |

TABLE 2-continued

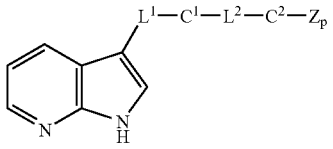

| L¹ | C¹ | L² | C² | Z |
|---|---|---|---|---|
| $CH_2$ | Pyrazinyl | $NH-CH_2$ | Imidazolyl | $Z_1$: F (2)<br>$Z_2$: F (3) |
| $CH_2$ | Pyrazinyl | $NH-CH_2$ | Imidazolyl | $Z_1$: Cl (2) |
| $CH_2$ | Pyrazinyl | $NH-CH_2$ | Imidazolyl | $Z_1$: Cl (3) |
| $CH_2$ | Pyrazinyl | $NH-CH_2$ | Imidazolyl | $Z_1$: Cl (2)<br>$Z_2$: Cl (3) |
| $CH_2$ | Pyrazinyl | $NH-CH_2$ | Imidazolyl | $Z_1$: F (2)<br>$Z_2$: Cl (3) |
| $CH_2$ | Pyrazinyl | $NH-CH_2$ | Imidazolyl | $Z_1$: Cl (2)<br>$Z_2$: F (3) |
| $CH_2$ | Pyrazinyl | $NH-CH_2$ | Imidazolyl | $Z_1$: $CH_3$ (2) |
| $CH_2$ | Pyrazinyl | $NH-CH_2$ | Imidazolyl | $Z_1$: $CH_3$ (3) |
| $CH_2$ | Pyrazinyl | $NH-CH_2$ | Imidazolyl | $Z_1$: $CH_2-CH_3$ (2) |
| $CH_2$ | Pyrazinyl | $NH-CH_2$ | Imidazolyl | $Z_1$: $CH_2-CH_3$ (3) |
| $CH_2$ | Pyrazinyl | $NH-CH_2$ | Imidazolyl | $Z_1$: $CH_2-CH_2-CH_3$ or iPr (2) |
| $CH_2$ | Pyrazinyl | $NH-CH_2$ | Imidazolyl | $Z_1$: $CH_2-CH_2-CH_3$ or iPr (3) |
| $CH_2$ | Pyrazinyl | $NH-CH_2$ | Imidazolyl | $Z_1$: $CH_2F$ (2) |
| $CH_2$ | Pyrazinyl | $NH-CH_2$ | Imidazolyl | $Z_1$: $CH_2F$ (3) |
| $CH_2$ | Pyrazinyl | $NH-CH_2$ | Imidazolyl | $Z_1$: $CHF_2$ (2) |
| $CH_2$ | Pyrazinyl | $NH-CH_2$ | Imidazolyl | $Z_1$: $CHF_2$ (3) |
| $CH_2$ | Pyrazinyl | $NH-CH_2$ | Imidazolyl | $Z_1$: $CF_3$ (2) |
| $CH_2$ | Pyrazinyl | $NH-CH_2$ | Imidazolyl | $Z_1$: $CF_3$ (3) |
| $CH_2$ | Pyrazinyl | $NH-CH_2$ | Imidazolyl | $Z_1$: $CH_2-CH_2F$ (2) |
| $CH_2$ | Pyrazinyl | $NH-CH_2$ | Imidazolyl | $Z_1$: $CH_2-CH_2F$ (3) |
| $CH_2$ | Pyrazinyl | $NH-CH_2$ | Imidazolyl | $Z_1$: $CH_2-CHF_2$ (2) |
| $CH_2$ | Pyrazinyl | $NH-CH_2$ | Imidazolyl | $Z_1$: $CH_2-CHF_2$ (3) |
| $CH_2$ | Pyrazinyl | $NH-CH_2$ | Imidazolyl | $Z_1$: $CH_2-CF_3$ (2) |
| $CH_2$ | Pyrazinyl | $NH-CH_2$ | Imidazolyl | $Z_1$: $CH_2-CF_3$ (3) |
| $CH_2$ | Pyrazinyl | $NH-CH_2$ | Furanyl | None |
| $CH_2$ | Pyrazinyl | $NH-CH_2$ | Furanyl | $Z_1$: F (2) |
| $CH_2$ | Pyrazinyl | $NH-CH_2$ | Furanyl | $Z_1$: F (3) |
| $CH_2$ | Pyrazinyl | $NH-CH_2$ | Furanyl | $Z_1$: F (2)<br>$Z_2$: F (3) |
| $CH_2$ | Pyrazinyl | $NH-CH_2$ | Furanyl | $Z_1$: Cl (2) |
| $CH_2$ | Pyrazinyl | $NH-CH_2$ | Furanyl | $Z_1$: Cl (3) |
| $CH_2$ | Pyrazinyl | $NH-CH_2$ | Furanyl | $Z_1$: Cl (2)<br>$Z_2$: Cl (3) |
| $CH_2$ | Pyrazinyl | $NH-CH_2$ | Furanyl | $Z_1$: F (2)<br>$Z_2$: Cl (3) |
| $CH_2$ | Pyrazinyl | $NH-CH_2$ | Furanyl | $Z_1$: Cl (2)<br>$Z_2$: F (3) |
| $CH_2$ | Pyrazinyl | $NH-CH_2$ | Furanyl | $Z_1$: $CH_3$ (2) |
| $CH_2$ | Pyrazinyl | $NH-CH_2$ | Furanyl | $Z_1$: $CH_3$ (3) |
| $CH_2$ | Pyrazinyl | $NH-CH_2$ | Furanyl | $Z_1$: $CH_2-CH_3$ (2) |
| $CH_2$ | Pyrazinyl | $NH-CH_2$ | Furanyl | $Z_1$: $CH_2-CH_3$ (3) |
| $CH_2$ | Pyrazinyl | $NH-CH_2$ | Furanyl | $Z_1$: $CH_2-CH_2-CH_3$ or iPr (2) |
| $CH_2$ | Pyrazinyl | $NH-CH_2$ | Furanyl | $Z_1$: $CH_2-CH_2-CH_3$ or iPr (3) |
| $CH_2$ | Pyrazinyl | $NH-CH_2$ | Furanyl | $Z_1$: $CH_2F$ (2) |
| $CH_2$ | Pyrazinyl | $NH-CH_2$ | Furanyl | $Z_1$: $CH_2F$ (3) |
| $CH_2$ | Pyrazinyl | $NH-CH_2$ | Furanyl | $Z_1$: $CHF_2$ (2) |
| $CH_2$ | Pyrazinyl | $NH-CH_2$ | Furanyl | $Z_1$: $CHF_2$ (3) |
| $CH_2$ | Pyrazinyl | $NH-CH_2$ | Furanyl | $Z_1$: $CF_3$ (2) |
| $CH_2$ | Pyrazinyl | $NH-CH_2$ | Furanyl | $Z_1$: $CF_3$ (3) |
| $CH_2$ | Pyrazinyl | $NH-CH_2$ | Furanyl | $Z_1$: $CH_2-CH_2F$ (2) |
| $CH_2$ | Pyrazinyl | $NH-CH_2$ | Furanyl | $Z_1$: $CH_2-CH_2F$ (3) |
| $CH_2$ | Pyrazinyl | $NH-CH_2$ | Furanyl | $Z_1$: $CH_2-CHF_2$ (2) |
| $CH_2$ | Pyrazinyl | $NH-CH_2$ | Furanyl | $Z_1$: $CH_2-CHF_2$ (3) |
| $CH_2$ | Pyrazinyl | $NH-CH_2$ | Furanyl | $Z_1$: $CH_2-CF_3$ (2) |
| $CH_2$ | Pyrazinyl | $NH-CH_2$ | Furanyl | $Z_1$: $CH_2-CF_3$ (3) |
| $CH_2$ | Pyrazinyl | $NH-CH_2$ | Oxazolyl | None |
| $CH_2$ | Pyrazinyl | $NH-CH_2$ | Oxazolyl | $Z_1$: F (2) |
| $CH_2$ | Pyrazinyl | $NH-CH_2$ | Oxazolyl | $Z_1$: F (3) |
| $CH_2$ | Pyrazinyl | $NH-CH_2$ | Oxazolyl | $Z_1$: F (2)<br>$Z_2$: F (3) |
| $CH_2$ | Pyrazinyl | $NH-CH_2$ | Oxazolyl | $Z_1$: Cl (2) |
| $CH_2$ | Pyrazinyl | $NH-CH_2$ | Oxazolyl | $Z_1$: Cl (3) |
| $CH_2$ | Pyrazinyl | $NH-CH_2$ | Oxazolyl | $Z_1$: Cl (2)<br>$Z_2$: Cl (3) |

TABLE 2-continued

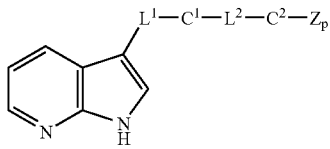

| $L^1$ | $C^1$ | $L^2$ | $C^2$ | Z |
|---|---|---|---|---|
| $CH_2$ | Pyrazinyl | $NH-CH_2$ | Oxazolyl | $Z_1$: F (2) |
| | | | | $Z_2$: Cl (3) |
| $CH_2$ | Pyrazinyl | $NH-CH_2$ | Oxazolyl | $Z_1$: Cl (2) |
| | | | | $Z_2$: F (3) |
| $CH_2$ | Pyrazinyl | $NH-CH_2$ | Oxazolyl | $Z_1$: $CH_3$ (2) |
| $CH_2$ | Pyrazinyl | $NH-CH_2$ | Oxazolyl | $Z_1$: $CH_3$ (3) |
| $CH_2$ | Pyrazinyl | $NH-CH_2$ | Oxazolyl | $Z_1$: $CH_2-CH_3$ (2) |
| $CH_2$ | Pyrazinyl | $NH-CH_2$ | Oxazolyl | $Z_1$: $CH_2-CH_3$ (3) |
| $CH_2$ | Pyrazinyl | $NH-CH_2$ | Oxazolyl | $Z_1$: $CH_2-CH_2-CH_3$ or iPr (2) |
| $CH_2$ | Pyrazinyl | $NH-CH_2$ | Oxazolyl | $Z_1$: $CH_2-CH_2-CH_3$ or iPr (3) |
| $CH_2$ | Pyrazinyl | $NH-CH_2$ | Oxazolyl | $Z_1$: $CH_2F$ (2) |
| $CH_2$ | Pyrazinyl | $NH-CH_2$ | Oxazolyl | $Z_1$: $CH_2F$ (3) |
| $CH_2$ | Pyrazinyl | $NH-CH_2$ | Oxazolyl | $Z_1$: $CHF_2$ (2) |
| $CH_2$ | Pyrazinyl | $NH-CH_2$ | Oxazolyl | $Z_1$: $CHF_2$ (3) |
| $CH_2$ | Pyrazinyl | $NH-CH_2$ | Oxazolyl | $Z_1$: $CF_3$ (2) |
| $CH_2$ | Pyrazinyl | $NH-CH_2$ | Oxazolyl | $Z_1$: $CF_3$ (3) |
| $CH_2$ | Pyrazinyl | $NH-CH_2$ | Oxazolyl | $Z_1$: $CH_2-CH_2F$ (2) |
| $CH_2$ | Pyrazinyl | $NH-CH_2$ | Oxazolyl | $Z_1$: $CH_2-CH_2F$ (3) |
| $CH_2$ | Pyrazinyl | $NH-CH_2$ | Oxazolyl | $Z_1$: $CH_2-CHF_2$ (2) |
| $CH_2$ | Pyrazinyl | $NH-CH_2$ | Oxazolyl | $Z_1$: $CH_2-CHF_2$ (3) |
| $CH_2$ | Pyrazinyl | $NH-CH_2$ | Oxazolyl | $Z_1$: $CH_2-CF_3$ (2) |
| $CH_2$ | Pyrazinyl | $NH-CH_2$ | Oxazolyl | $Z_1$: $CH_2-CF_3$ (3) |
| $CH_2$ | Pyrazinyl | $NH-CH_2$ | Thiophenyl | None |
| $CH_2$ | Pyrazinyl | $NH-CH_2$ | Thiophenyl | $Z_1$: F (2) |
| $CH_2$ | Pyrazinyl | $NH-CH_2$ | Thiophenyl | $Z_1$: F (3) |
| $CH_2$ | Pyrazinyl | $NH-CH_2$ | Thiophenyl | $Z_1$: F (2) |
| | | | | $Z_2$: F (3) |
| $CH_2$ | Pyrazinyl | $NH-CH_2$ | Thiophenyl | $Z_1$: Cl (2) |
| $CH_2$ | Pyrazinyl | $NH-CH_2$ | Thiophenyl | $Z_1$: Cl (3) |
| $CH_2$ | Pyrazinyl | $NH-CH_2$ | Thiophenyl | $Z_1$: Cl (2) |
| | | | | $Z_2$: Cl (3) |
| $CH_2$ | Pyrazinyl | $NH-CH_2$ | Thiophenyl | $Z_1$: F (2) |
| | | | | $Z_2$: Cl (3) |
| $CH_2$ | Pyrazinyl | $NH-CH_2$ | Thiophenyl | $Z_1$: Cl (2) |
| | | | | $Z_2$: F (3) |
| $CH_2$ | Pyrazinyl | $NH-CH_2$ | Thiophenyl | $Z_1$: $CH_3$ (2) |
| $CH_2$ | Pyrazinyl | $NH-CH_2$ | Thiophenyl | $Z_1$: $CH_3$ (3) |
| $CH_2$ | Pyrazinyl | $NH-CH_2$ | Thiophenyl | $Z_1$: $CH_2-CH_3$ (2) |
| $CH_2$ | Pyrazinyl | $NH-CH_2$ | Thiophenyl | $Z_1$: $CH_2-CH_3$ (3) |
| $CH_2$ | Pyrazinyl | $NH-CH_2$ | Thiophenyl | $Z_1$: $CH_2-CH_2-CH_3$ or iPr (2) |
| $CH_2$ | Pyrazinyl | $NH-CH_2$ | Thiophenyl | $Z_1$: $CH_2-CH_2-CH_3$ or iPr (3) |
| $CH_2$ | Pyrazinyl | $NH-CH_2$ | Thiophenyl | $Z_1$: $CH_2F$ (2) |
| $CH_2$ | Pyrazinyl | $NH-CH_2$ | Thiophenyl | $Z_1$: $CH_2F$ (3) |
| $CH_2$ | Pyrazinyl | $NH-CH_2$ | Thiophenyl | $Z_1$: $CHF_2$ (2) |
| $CH_2$ | Pyrazinyl | $NH-CH_2$ | Thiophenyl | $Z_1$: $CHF_2$ (3) |
| $CH_2$ | Pyrazinyl | $NH-CH_2$ | Thiophenyl | $Z_1$: $CF_3$ (2) |
| $CH_2$ | Pyrazinyl | $NH-CH_2$ | Thiophenyl | $Z_1$: $CF_3$ (3) |
| $CH_2$ | Pyrazinyl | $NH-CH_2$ | Thiophenyl | $Z_1$: $CH_2-CH_2F$ (2) |
| $CH_2$ | Pyrazinyl | $NH-CH_2$ | Thiophenyl | $Z_1$: $CH_2-CH_2F$ (3) |
| $CH_2$ | Pyrazinyl | $NH-CH_2$ | Thiophenyl | $Z_1$: $CH_2-CHF_2$ (2) |
| $CH_2$ | Pyrazinyl | $NH-CH_2$ | Thiophenyl | $Z_1$: $CH_2-CHF_2$ (3) |
| $CH_2$ | Pyrazinyl | $NH-CH_2$ | Thiophenyl | $Z_1$: $CH_2-CF_3$ (2) |
| $CH_2$ | Pyrazinyl | $NH-CH_2$ | Thiophenyl | $Z_1$: $CH_2-CF_3$ (3) |
| $CH_2$ | Pyrazinyl | $NH-CH_2$ | Thiazolyl | None |
| $CH_2$ | Pyrazinyl | $NH-CH_2$ | Thiazolyl | $Z_1$: F (2) |
| $CH_2$ | Pyrazinyl | $NH-CH_2$ | Thiazolyl | $Z_1$: F (3) |
| $CH_2$ | Pyrazinyl | $NH-CH_2$ | Thiazolyl | $Z_1$: F (2) |
| | | | | $Z_2$: F (3) |
| $CH_2$ | Pyrazinyl | $NH-CH_2$ | Thiazolyl | $Z_1$: Cl (2) |
| $CH_2$ | Pyrazinyl | $NH-CH_2$ | Thiazolyl | $Z_1$: Cl (3) |
| $CH_2$ | Pyrazinyl | $NH-CH_2$ | Thiazolyl | $Z_1$: Cl (2) |
| | | | | $Z_2$: Cl (3) |
| $CH_2$ | Pyrazinyl | $NH-CH_2$ | Thiazolyl | $Z_1$: F (2) |
| | | | | $Z_2$: Cl (3) |
| $CH_2$ | Pyrazinyl | $NH-CH_2$ | Thiazolyl | $Z_1$: Cl (2) |
| | | | | $Z_2$: F (3) |
| $CH_2$ | Pyrazinyl | $NH-CH_2$ | Thiazolyl | $Z_1$: $CH_3$ (2) |
| $CH_2$ | Pyrazinyl | $NH-CH_2$ | Thiazolyl | $Z_1$: $CH_3$ (3) |
| $CH_2$ | Pyrazinyl | $NH-CH_2$ | Thiazolyl | $Z_1$: $CH_2-CH_3$ (2) |

TABLE 2-continued

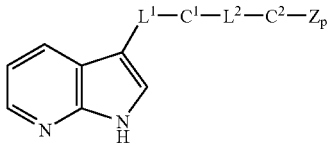

| L¹ | C¹ | L² | C² | Z |
|---|---|---|---|---|
| CH₂ | Pyrazinyl | NH—CH₂ | Thiazolyl | $Z_1$: CH₂—CH₃ (3) |
| CH₂ | Pyrazinyl | NH—CH₂ | Thiazolyl | $Z_1$: CH₂—CH₂—CH₃ or iPr (2) |
| CH₂ | Pyrazinyl | NH—CH₂ | Thiazolyl | $Z_1$: CH₂—CH₂—CH₃ or iPr (3) |
| CH₂ | Pyrazinyl | NH—CH₂ | Thiazolyl | $Z_1$: CH₂F (2) |
| CH₂ | Pyrazinyl | NH—CH₂ | Thiazolyl | $Z_1$: CH₂F (3) |
| CH₂ | Pyrazinyl | NH—CH₂ | Thiazolyl | $Z_1$: CHF₂ (2) |
| CH₂ | Pyrazinyl | NH—CH₂ | Thiazolyl | $Z_1$: CHF₂ (3) |
| CH₂ | Pyrazinyl | NH—CH₂ | Thiazolyl | $Z_1$: CF₃ (2) |
| CH₂ | Pyrazinyl | NH—CH₂ | Thiazolyl | $Z_1$: CF₃ (3) |
| CH₂ | Pyrazinyl | NH—CH₂ | Thiazolyl | $Z_1$: CH₂—CH₂F (2) |
| CH₂ | Pyrazinyl | NH—CH₂ | Thiazolyl | $Z_1$: CH₂—CH₂F (3) |
| CH₂ | Pyrazinyl | NH—CH₂ | Thiazolyl | $Z_1$: CH₂—CHF₂ (2) |
| CH₂ | Pyrazinyl | NH—CH₂ | Thiazolyl | $Z_1$: CH₂—CHF₂ (3) |
| CH₂ | Pyrazinyl | NH—CH₂ | Thiazolyl | $Z_1$: CH₂—CF₃ (2) |
| CH₂ | Pyrazinyl | NH—CH₂ | Thiazolyl | $Z_1$: CH₂—CF₃ (3) |
| CH₂ | Pyrazinyl | NH—C(O) | Phenyl | None |
| CH₂ | Pyrazinyl | NH—C(O) | Phenyl | $Z_1$: F (para) |
| CH₂ | Pyrazinyl | NH—C(O) | Phenyl | $Z_1$: F (meta) |
| CH₂ | Pyrazinyl | NH—C(O) | phenyl | $Z_1$: F (ortho) |
| CH₂ | Pyrazinyl | NH—C(O) | phenyl | $Z_1$: F (para)<br>$Z_2$: F (meta) |
| CH₂ | Pyrazinyl | NH—C(O) | Phenyl | $Z_1$: Cl (meta) |
| CH₂ | Pyrazinyl | NH—C(O) | Phenyl | $Z_1$: Cl (para) |
| CH₂ | Pyrazinyl | NH—C(O) | Phenyl | $Z_1$: Cl (para)<br>$Z_2$: Cl (meta) |
| CH₂ | Pyrazinyl | NH—C(O) | Phenyl | $Z_1$: F (para)<br>$Z_2$: Cl (meta) |
| CH₂ | Pyrazinyl | NH—C(O) | Phenyl | $Z_1$: Cl (para)<br>$Z_2$: F (meta) |
| CH₂ | Pyrazinyl | NH—C(O) | Phenyl | $Z_1$: CH₃ (para) |
| CH₂ | Pyrazinyl | NH—C(O) | Phenyl | $Z_1$: CH₃ (meta) |
| CH₂ | Pyrazinyl | NH—C(O) | Phenyl | $Z_1$: CH₃ (ortho) |
| CH₂ | Pyrazinyl | NH—C(O) | Phenyl | $Z_1$: CH₂—CH₃ (para) |
| CH₂ | Pyrazinyl | NH—C(O) | Phenyl | $Z_1$: CH₂—CH₃ (meta) |
| CH₂ | Pyrazinyl | NH—C(O) | Phenyl | $Z_1$: CH₂—CH₃ (ortho) |
| CH₂ | Pyrazinyl | NH—C(O) | Phenyl | $Z_1$: CH₂—CH₂—CH₃ or iPr (para) |
| CH₂ | Pyrazinyl | NH—C(O) | Phenyl | $Z_1$: CH₂—CH₂—CH₃ or iPr (meta) |
| CH₂ | Pyrazinyl | NH—C(O) | Phenyl | $Z_1$: CH₂—CH₂—CH₃ or iPr (ortho) |
| CH₂ | Pyrazinyl | NH—C(O) | Phenyl | $Z_1$: CH₂F (para) |
| CH₂ | Pyrazinyl | NH—C(O) | Phenyl | $Z_1$: CH₂F (meta) |
| CH₂ | Pyrazinyl | NH—C(O) | Phenyl | $Z_1$: CH₂F (ortho) |
| CH₂ | Pyrazinyl | NH—C(O) | Phenyl | $Z_1$: CHF₂ (para) |
| CH₂ | Pyrazinyl | NH—C(O) | Phenyl | $Z_1$: CHF₂ (meta) |
| CH₂ | Pyrazinyl | NH—C(O) | Phenyl | $Z_1$: CHF₂ (ortho) |
| CH₂ | Pyrazinyl | NH—C(O) | Phenyl | $Z_1$: CF₃ (para) |
| CH₂ | Pyrazinyl | NH—C(O) | Phenyl | $Z_1$: CF₃ (meta) |
| CH₂ | Pyrazinyl | NH—C(O) | Phenyl | $Z_1$: CF₃ (ortho) |
| CH₂ | Pyrazinyl | NH—C(O) | Phenyl | $Z_1$: CH₂—CH₂F (para) |
| CH₂ | Pyrazinyl | NH—C(O) | Phenyl | $Z_1$: CH₂—CH₂F (meta) |
| CH₂ | Pyrazinyl | NH—C(O) | Phenyl | $Z_1$: CH₂—CH₂F (ortho) |
| CH₂ | Pyrazinyl | NH—C(O) | Phenyl | $Z_1$: CH₂—CHF₂ (para) |
| CH₂ | Pyrazinyl | NH—C(O) | Phenyl | $Z_1$: CH₂—CHF₂ (meta) |
| CH₂ | Pyrazinyl | NH—C(O) | Phenyl | $Z_1$: CH₂—CHF₂ (ortho) |
| CH₂ | Pyrazinyl | NH—C(O) | Phenyl | $Z_1$: CH₂—CF₃ (para) |
| CH₂ | Pyrazinyl | NH—C(O) | Phenyl | $Z_1$: CH₂—CF₃ (meta) |
| CH₂ | Pyrazinyl | NH—C(O) | Phenyl | $Z_1$: CH₂—CF₃ (ortho) |
| CH₂ | Pyrazinyl | NH—C(O) | Pyridinyl | None |
| CH₂ | Pyrazinyl | NH—C(O) | Pyridinyl | $Z_1$: F (para) |
| CH₂ | Pyrazinyl | NH—C(O) | Pyridinyl | $Z_1$: F (meta) |
| CH₂ | Pyrazinyl | NH—C(O) | Pyridinyl | $Z_1$: F (ortho) |
| CH₂ | Pyrazinyl | NH—C(O) | Pyridinyl | $Z_1$: F (para)<br>$Z_2$: F (meta) |
| CH₂ | Pyrazinyl | NH—C(O) | Pyridinyl | $Z_1$: Cl (meta) |
| CH₂ | Pyrazinyl | NH—C(O) | Pyridinyl | $Z_1$: Cl (para) |
| CH₂ | Pyrazinyl | NH—C(O) | Pyridinyl | $Z_1$: Cl (para)<br>$Z_2$: Cl (meta) |

TABLE 2-continued

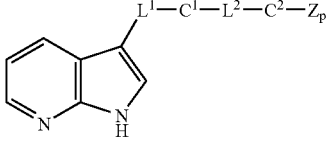

| $L^1$ | $C^1$ | $L^2$ | $C^2$ | Z |
|---|---|---|---|---|
| $CH_2$ | Pyrazinyl | NH—C(O) | Pyridinyl | $Z_1$: F (para)<br>$Z_2$: Cl (meta) |
| $CH_2$ | Pyrazinyl | NH—C(O) | Pyridinyl | $Z_1$: Cl (para)<br>$Z_2$: F (meta) |
| $CH_2$ | Pyrazinyl | NH—C(O) | Pyridinyl | $Z_1$: $CH_3$ (para) |
| $CH_2$ | Pyrazinyl | NH—C(O) | Pyridinyl | $Z_1$: $CH_3$ (meta) |
| $CH_2$ | Pyrazinyl | NH—C(O) | Pyridinyl | $Z_1$: $CH_3$ (ortho) |
| $CH_2$ | Pyrazinyl | NH—C(O) | Pyridinyl | $Z_1$: $CH_2$—$CH_3$ (para) |
| $CH_2$ | Pyrazinyl | NH—C(O) | Pyridinyl | $Z_1$: $CH_2$—$CH_3$ (meta) |
| $CH_2$ | Pyrazinyl | NH—C(O) | Pyridinyl | $Z_1$: $CH_2$—$CH_3$ (ortho) |
| $CH_2$ | Pyrazinyl | NH—C(O) | Pyridinyl | $Z_1$: $CH_2$—$CH_2$—$CH_3$ or iPr (para) |
| $CH_2$ | Pyrazinyl | NH—C(O) | Pyridinyl | $Z_1$: $CH_2$—$CH_2$—$CH_3$ or iPr (meta) |
| $CH_2$ | Pyrazinyl | NH—C(O) | Pyridinyl | $Z_1$: $CH_2$—$CH_2$—$CH_3$ or iPr (ortho) |
| $CH_2$ | Pyrazinyl | NH—C(O) | Pyridinyl | $Z_1$: $CH_2F$ (para) |
| $CH_2$ | Pyrazinyl | NH—C(O) | Pyridinyl | $Z_1$: $CH_2F$ (meta) |
| $CH_2$ | Pyrazinyl | NH—C(O) | Pyridinyl | $Z_1$: $CH_2F$ (ortho) |
| $CH_2$ | Pyrazinyl | NH—C(O) | Pyridinyl | $Z_1$: $CHF_2$ (para) |
| $CH_2$ | Pyrazinyl | NH—C(O) | Pyridinyl | $Z_1$: $CHF_2$ (meta) |
| $CH_2$ | Pyrazinyl | NH—C(O) | Pyridinyl | $Z_1$: $CHF_2$ (ortho) |
| $CH_2$ | Pyrazinyl | NH—C(O) | Pyridinyl | $Z_1$: $CF_3$ (para) |
| $CH_2$ | Pyrazinyl | NH—C(O) | Pyridinyl | $Z_1$: $CF_3$ (meta) |
| $CH_2$ | Pyrazinyl | NH—C(O) | Pyridinyl | $Z_1$: $CF_3$ (ortho) |
| $CH_2$ | Pyrazinyl | NH—C(O) | Pyridinyl | $Z_1$: $CH_2$—$CH_2F$ (para) |
| $CH_2$ | Pyrazinyl | NH—C(O) | Pyridinyl | $Z_1$: $CH_2$—$CH_2F$ (meta) |
| $CH_2$ | Pyrazinyl | NH—C(O) | Pyridinyl | $Z_1$: $CH_2$—$CH_2F$ (ortho) |
| $CH_2$ | Pyrazinyl | NH—C(O) | Pyridinyl | $Z_1$: $CH_2$—$CHF_2$ (para) |
| $CH_2$ | Pyrazinyl | NH—C(O) | Pyridinyl | $Z_1$: $CH_2$—$CHF_2$ (meta) |
| $CH_2$ | Pyrazinyl | NH—C(O) | Pyridinyl | $Z_1$: $CH_2$—$CHF_2$ (ortho) |
| $CH_2$ | Pyrazinyl | NH—C(O) | Pyridinyl | $Z_1$: $CH_2$—$CF_3$ (para) |
| $CH_2$ | Pyrazinyl | NH—C(O) | Pyridinyl | $Z_1$: $CH_2$—$CF_3$ (meta) |
| $CH_2$ | Pyrazinyl | NH—C(O) | Pyridinyl | $Z_1$: $CH_2$—$CF_3$ (ortho) |
| $CH_2$ | Pyrazinyl | NH—C(O) | Pyrimidinyl | None |
| $CH_2$ | Pyrazinyl | NH—C(O) | Pyrimidinyl | $Z_1$: F (para) |
| $CH_2$ | Pyrazinyl | NH—C(O) | Pyrimidinyl | $Z_1$: F (meta) |
| $CH_2$ | Pyrazinyl | NH—C(O) | Pyrimidinyl | $Z_1$: F (ortho) |
| $CH_2$ | Pyrazinyl | NH—C(O) | Pyrimidinyl | $Z_1$: F (para)<br>$Z_2$: F (meta) |
| $CH_2$ | Pyrazinyl | NH—C(O) | Pyrimidinyl | $Z_1$: Cl (meta) |
| $CH_2$ | Pyrazinyl | NH—C(O) | Pyrimidinyl | $Z_1$: Cl (para) |
| $CH_2$ | Pyrazinyl | NH—C(O) | Pyrimidinyl | $Z_1$: Cl (para)<br>$Z_2$: Cl (meta) |
| $CH_2$ | Pyrazinyl | NH—C(O) | Pyrimidinyl | $Z_1$: F (para)<br>$Z_2$: Cl (meta) |
| $CH_2$ | Pyrazinyl | NH—C(O) | Pyrimidinyl | $Z_1$: Cl (para)<br>$Z_2$: F (meta) |
| $CH_2$ | Pyrazinyl | NH—C(O) | Pyrimidinyl | $Z_1$: $CH_3$ (para) |
| $CH_2$ | Pyrazinyl | NH—C(O) | Pyrimidinyl | $Z_1$: $CH_3$ (meta) |
| $CH_2$ | Pyrazinyl | NH—C(O) | Pyrimidinyl | $Z_1$: $CH_3$ (ortho) |
| $CH_2$ | Pyrazinyl | NH—C(O) | Pyrimidinyl | $Z_1$: $CH_2$—$CH_3$ (para) |
| $CH_2$ | Pyrazinyl | NH—C(O) | Pyrimidinyl | $Z_1$: $CH_2$—$CH_3$ (meta) |
| $CH_2$ | Pyrazinyl | NH—C(O) | Pyrimidinyl | $Z_1$: $CH_2$—$CH_3$ (ortho) |
| $CH_2$ | Pyrazinyl | NH—C(O) | Pyrimidinyl | $Z_1$: $CH_2$—$CH_2$—$CH_3$ or iPr (para) |
| $CH_2$ | Pyrazinyl | NH—C(O) | Pyrimidinyl | $Z_1$: $CH_2$—$CH_2$—$CH_3$ or iPr (meta) |
| $CH_2$ | Pyrazinyl | NH—C(O) | Pyrimidinyl | $Z_1$: $CH_2$—$CH_2$—$CH_3$ or iPr (ortho) |
| $CH_2$ | Pyrazinyl | NH—C(O) | Pyrimidinyl | $Z_1$: $CH_2F$ (para) |
| $CH_2$ | Pyrazinyl | NH—C(O) | Pyrimidinyl | $Z_1$: $CH_2F$ (meta) |
| $CH_2$ | Pyrazinyl | NH—C(O) | Pyrimidinyl | $Z_1$: $CH_2F$ (ortho) |
| $CH_2$ | Pyrazinyl | NH—C(O) | Pyrimidinyl | $Z_1$: $CHF_2$ (para) |
| $CH_2$ | Pyrazinyl | NH—C(O) | Pyrimidinyl | $Z_1$: $CHF_2$ (meta) |
| $CH_2$ | Pyrazinyl | NH—C(O) | Pyrimidinyl | $Z_1$: $CHF_2$ (ortho) |
| $CH_2$ | Pyrazinyl | NH—C(O) | Pyrimidinyl | $Z_1$: $CF_3$ (para) |
| $CH_2$ | Pyrazinyl | NH—C(O) | Pyrimidinyl | $Z_1$: $CF_3$ (meta) |
| $CH_2$ | Pyrazinyl | NH—C(O) | Pyrimidinyl | $Z_1$: $CF_3$ (ortho) |

TABLE 2-continued

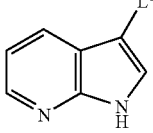

| L¹ | C¹ | L² | C² | Z |
|---|---|---|---|---|
| $CH_2$ | Pyrazinyl | NH—C(O) | Pyrimidinyl | $Z_1$: $CH_2$—$CH_2F$ (para) |
| $CH_2$ | Pyrazinyl | NH—C(O) | Pyrimidinyl | $Z_1$: $CH_2$—$CH_2F$ (meta) |
| $CH_2$ | Pyrazinyl | NH—C(O) | Pyrimidinyl | $Z_1$: $CH_2$—$CH_2F$ (ortho) |
| $CH_2$ | Pyrazinyl | NH—C(O) | Pyrimidinyl | $Z_1$: $CH_2$—$CHF_2$ (para) |
| $CH_2$ | Pyrazinyl | NH—C(O) | Pyrimidinyl | $Z_1$: $CH_2$—$CHF_2$ (meta) |
| $CH_2$ | Pyrazinyl | NH—C(O) | Pyrimidinyl | $Z_1$: $CH_2$—$CHF_2$ (ortho) |
| $CH_2$ | Pyrazinyl | NH—C(O) | Pyrimidinyl | $Z_1$: $CH_2$—$CF_3$ (para) |
| $CH_2$ | Pyrazinyl | NH—C(O) | Pyrimidinyl | $Z_1$: $CH_2$—$CF_3$ (meta) |
| $CH_2$ | Pyrazinyl | NH—C(O) | Pyrimidinyl | $Z_1$: $CH_2$—$CF_3$ (ortho) |
| $CH_2$ | Pyrazinyl | NH—C(O) | Pyrazinyl | None |
| $CH_2$ | Pyrazinyl | NH—C(O) | Pyrazinyl | $Z_1$: F (para) |
| $CH_2$ | Pyrazinyl | NH—C(O) | Pyrazinyl | $Z_1$: F (meta) |
| $CH_2$ | Pyrazinyl | NH—C(O) | Pyrazinyl | $Z_1$: F (ortho) |
| $CH_2$ | Pyrazinyl | NH—C(O) | Pyrazinyl | $Z_1$: F (para)<br>$Z_2$: F (meta) |
| $CH_2$ | Pyrazinyl | NH—C(O) | Pyrazinyl | $Z_1$: Cl (meta) |
| $CH_2$ | Pyrazinyl | NH—C(O) | Pyrazinyl | $Z_1$: Cl (para) |
| $CH_2$ | Pyrazinyl | NH—C(O) | Pyrazinyl | $Z_1$: Cl (para)<br>$Z_2$: Cl (meta) |
| $CH_2$ | Pyrazinyl | NH—C(O) | Pyrazinyl | $Z_1$: F (para)<br>$Z_2$: Cl (meta) |
| $CH_2$ | Pyrazinyl | NH—C(O) | Pyrazinyl | $Z_1$: Cl (para)<br>$Z_2$: F (meta) |
| $CH_2$ | Pyrazinyl | NH—C(O) | Pyrazinyl | $Z_1$: $CH_3$ (para) |
| $CH_2$ | Pyrazinyl | NH—C(O) | Pyrazinyl | $Z_1$: $CH_3$ (meta) |
| $CH_2$ | Pyrazinyl | NH—C(O) | Pyrazinyl | $Z_1$: $CH_3$ (ortho) |
| $CH_2$ | Pyrazinyl | NH—C(O) | Pyrazinyl | $Z_1$: $CH_2$—$CH_3$ (para) |
| $CH_2$ | Pyrazinyl | NH—C(O) | Pyrazinyl | $Z_1$: $CH_2$—$CH_3$ (meta) |
| $CH_2$ | Pyrazinyl | NH—C(O) | Pyrazinyl | $Z_1$: $CH_2$—$CH_3$ (ortho) |
| $CH_2$ | Pyrazinyl | NH—C(O) | Pyrazinyl | $Z_1$: $CH_2$—$CH_2$—$CH_3$ or iPr (para) |
| $CH_2$ | Pyrazinyl | NH—C(O) | Pyrazinyl | $Z_1$: $CH_2$—$CH_2$—$CH_3$ or iPr (meta) |
| $CH_2$ | Pyrazinyl | NH—C(O) | Pyrazinyl | $Z_1$: $CH_2$—$CH_2$—$CH_3$ or iPr (ortho) |
| $CH_2$ | Pyrazinyl | NH—C(O) | Pyrazinyl | $Z_1$: $CH_2F$ (para) |
| $CH_2$ | Pyrazinyl | NH—C(O) | Pyrazinyl | $Z_1$: $CH_2F$ (meta) |
| $CH_2$ | Pyrazinyl | NH—C(O) | Pyrazinyl | $Z_1$: $CH_2F$ (ortho) |
| $CH_2$ | Pyrazinyl | NH—C(O) | Pyrazinyl | $Z_1$: $CHF_2$ (para) |
| $CH_2$ | Pyrazinyl | NH—C(O) | Pyrazinyl | $Z_1$: $CHF_2$ (meta) |
| $CH_2$ | Pyrazinyl | NH—C(O) | Pyrazinyl | $Z_1$: $CHF_2$ (ortho) |
| $CH_2$ | Pyrazinyl | NH—C(O) | Pyrazinyl | $Z_1$: $CF_3$ (para) |
| $CH_2$ | Pyrazinyl | NH—C(O) | Pyrazinyl | $Z_1$: $CF_3$ (meta) |
| $CH_2$ | Pyrazinyl | NH—C(O) | Pyrazinyl | $Z_1$: $CF_3$ (ortho) |
| $CH_2$ | Pyrazinyl | NH—C(O) | Pyrazinyl | $Z_1$: $CH_2$—$CH_2F$ (para) |
| $CH_2$ | Pyrazinyl | NH—C(O) | Pyrazinyl | $Z_1$: $CH_2$—$CH_2F$ (meta) |
| $CH_2$ | Pyrazinyl | NH—C(O) | Pyrazinyl | $Z_1$: $CH_2$—$CH_2F$ (ortho) |
| $CH_2$ | Pyrazinyl | NH—C(O) | Pyrazinyl | $Z_1$: $CH_2$—$CHF_2$ (para) |
| $CH_2$ | Pyrazinyl | NH—C(O) | Pyrazinyl | $Z_1$: $CH_2$—$CHF_2$ (meta) |
| $CH_2$ | Pyrazinyl | NH—C(O) | Pyrazinyl | $Z_1$: $CH_2$—$CHF_2$ (ortho) |
| $CH_2$ | Pyrazinyl | NH—C(O) | Pyrazinyl | $Z_1$: $CH_2$—$CF_3$ (para) |
| $CH_2$ | Pyrazinyl | NH—C(O) | Pyrazinyl | $Z_1$: $CH_2$—$CF_3$ (meta) |
| $CH_2$ | Pyrazinyl | NH—C(O) | Pyrazinyl | $Z_1$: $CH_2$—$CF_3$ (ortho) |
| $CH_2$ | Pyrazinyl | NH—C(O) | Pyrrolyl | None |
| $CH_2$ | Pyrazinyl | NH—C(O) | Pyrrolyl | $Z_1$: F (2) |
| $CH_2$ | Pyrazinyl | NH—C(O) | Pyrrolyl | $Z_1$: F (3) |
| $CH_2$ | Pyrazinyl | NH—C(O) | Pyrrolyl | $Z_1$: F (2)<br>$Z_2$: F (3) |
| $CH_2$ | Pyrazinyl | NH—C(O) | Pyrrolyl | $Z_1$: Cl (2) |
| $CH_2$ | Pyrazinyl | NH—C(O) | Pyrrolyl | $Z_1$: Cl (3) |
| $CH_2$ | Pyrazinyl | NH—C(O) | Pyrrolyl | $Z_1$: Cl (2)<br>$Z_2$: Cl (3) |
| $CH_2$ | Pyrazinyl | NH—C(O) | Pyrrolyl | $Z_1$: F (2)<br>$Z_2$: Cl (3) |
| $CH_2$ | Pyrazinyl | NH—C(O) | Pyrrolyl | $Z_1$: Cl (2)<br>$Z_2$: F (3) |
| $CH_2$ | Pyrazinyl | NH—C(O) | Pyrrolyl | $Z_1$: $CH_3$ (2) |
| $CH_2$ | Pyrazinyl | NH—C(O) | Pyrrolyl | $Z_1$: $CH_3$ (3) |
| $CH_2$ | Pyrazinyl | NH—C(O) | Pyrrolyl | $Z_1$: $CH_2$—$CH_3$ (2) |

TABLE 2-continued

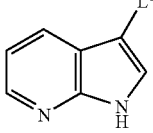

| L¹ | C¹ | L² | C² | Z |
|---|---|---|---|---|
| CH₂ | Pyrazinyl | NH—C(O) | Pyrrolyl | Z₁: CH₂—CH₃ (3) |
| CH₂ | Pyrazinyl | NH—C(O) | Pyrrolyl | Z₁: CH₂—CH₂—CH₃ or iPr (2) |
| CH₂ | Pyrazinyl | NH—C(O) | Pyrrolyl | Z₁: CH₂—CH₂—CH₃ or iPr (3) |
| CH₂ | Pyrazinyl | NH—C(O) | Pyrrolyl | Z₁: CH₂F (2) |
| CH₂ | Pyrazinyl | NH—C(O) | Pyrrolyl | Z₁: CH₂F (3) |
| CH₂ | Pyrazinyl | NH—C(O) | Pyrrolyl | Z₁: CHF₂ (2) |
| CH₂ | Pyrazinyl | NH—C(O) | Pyrrolyl | Z₁: CHF₂ (3) |
| CH₂ | Pyrazinyl | NH—C(O) | Pyrrolyl | Z₁: CF₃ (2) |
| CH₂ | Pyrazinyl | NH—C(O) | Pyrrolyl | Z₁: CF₃ (3) |
| CH₂ | Pyrazinyl | NH—C(O) | Pyrrolyl | Z₁: CH₂—CH₂F (2) |
| CH₂ | Pyrazinyl | NH—C(O) | Pyrrolyl | Z₁: CH₂—CH₂F (3) |
| CH₂ | Pyrazinyl | NH—C(O) | Pyrrolyl | Z₁: CH₂—CHF₂ (2) |
| CH₂ | Pyrazinyl | NH—C(O) | Pyrrolyl | Z₁: CH₂—CHF₂ (3) |
| CH₂ | Pyrazinyl | NH—C(O) | Pyrrolyl | Z₁: CH₂—CF₃ (2) |
| CH₂ | Pyrazinyl | NH—C(O) | Pyrrolyl | Z₁: CH₂—CF₃ (3) |
| CH₂ | Pyrazinyl | NH—C(O) | Imidazolyl | None |
| CH₂ | Pyrazinyl | NH—C(O) | Imidazolyl | Z₁: F (2) |
| CH₂ | Pyrazinyl | NH—C(O) | Imidazolyl | Z₁: F (3) |
| CH₂ | Pyrazinyl | NH—C(O) | Imidazolyl | Z₁: F (2) Z₂: F (3) |
| CH₂ | Pyrazinyl | NH—C(O) | Imidazolyl | Z₁: Cl (2) |
| CH₂ | Pyrazinyl | NH—C(O) | Imidazolyl | Z₁: Cl (3) |
| CH₂ | Pyrazinyl | NH—C(O) | Imidazolyl | Z₁: Cl (2) Z₂: Cl (3) |
| CH₂ | Pyrazinyl | NH—C(O) | Imidazolyl | Z₁: F (2) Z₂: Cl (3) |
| CH₂ | Pyrazinyl | NH—C(O) | Imidazolyl | Z₁: Cl (2) Z₂: F (3) |
| CH₂ | Pyrazinyl | NH—C(O) | Imidazolyl | Z₁: CH₃ (2) |
| CH₂ | Pyrazinyl | NH—C(O) | Imidazolyl | Z₁: CH₃ (3) |
| CH₂ | Pyrazinyl | NH—C(O) | Imidazolyl | Z₁: CH₂—CH₃ (2) |
| CH₂ | Pyrazinyl | NH—C(O) | Imidazolyl | Z₁: CH₂—CH₃ (3) |
| CH₂ | Pyrazinyl | NH—C(O) | Imidazolyl | Z₁: CH₂—CH₂—CH₃ or iPr (2) |
| CH₂ | Pyrazinyl | NH—C(O) | Imidazolyl | Z₁: CH₂—CH₂—CH₃ or iPr (3) |
| CH₂ | Pyrazinyl | NH—C(O) | Imidazolyl | Z₁: CH₂F (2) |
| CH₂ | Pyrazinyl | NH—C(O) | Imidazolyl | Z₁: CH₂F (3) |
| CH₂ | Pyrazinyl | NH—C(O) | Imidazolyl | Z₁: CHF₂ (2) |
| CH₂ | Pyrazinyl | NH—C(O) | Imidazolyl | Z₁: CHF₂ (3) |
| CH₂ | Pyrazinyl | NH—C(O) | Imidazolyl | Z₁: CF₃ (2) |
| CH₂ | Pyrazinyl | NH—C(O) | Imidazolyl | Z₁: CF₃ (3) |
| CH₂ | Pyrazinyl | NH—C(O) | Imidazolyl | Z₁: CH₂—CH₂F (2) |
| CH₂ | Pyrazinyl | NH—C(O) | Imidazolyl | Z₁: CH₂—CH₂F (3) |
| CH₂ | Pyrazinyl | NH—C(O) | Imidazolyl | Z₁: CH₂—CHF₂ (2) |
| CH₂ | Pyrazinyl | NH—C(O) | Imidazolyl | Z₁: CH₂—CHF₂ (3) |
| CH₂ | Pyrazinyl | NH—C(O) | Imidazolyl | Z₁: CH₂—CF₃ (2) |
| CH₂ | Pyrazinyl | NH—C(O) | Imidazolyl | Z₁: CH₂—CF₃ (3) |
| CH₂ | Pyrazinyl | NH—C(O) | Furanyl | None |
| CH₂ | Pyrazinyl | NH—C(O) | Furanyl | Z₁: F (2) |
| CH₂ | Pyrazinyl | NH—C(O) | Furanyl | Z₁: F (3) |
| CH₂ | Pyrazinyl | NH—C(O) | Furanyl | Z₁: F (2) Z₂: F (3) |
| CH₂ | Pyrazinyl | NH—C(O) | Furanyl | Z₁: Cl (2) |
| CH₂ | Pyrazinyl | NH—C(O) | Furanyl | Z₁: Cl (3) |
| CH₂ | Pyrazinyl | NH—C(O) | Furanyl | Z₁: Cl (2) Z₂: Cl (3) |
| CH₂ | Pyrazinyl | NH—C(O) | Furanyl | Z₁: F (2) Z₂: Cl (3) |
| CH₂ | Pyrazinyl | NH—C(O) | Furanyl | Z₁: Cl (2) Z₂: F (3) |
| CH₂ | Pyrazinyl | NH—C(O) | Furanyl | Z₁: CH₃ (2) |
| CH₂ | Pyrazinyl | NH—C(O) | Furanyl | Z₁: CH₃ (3) |
| CH₂ | Pyrazinyl | NH—C(O) | Furanyl | Z₁: CH₂—CH₃ (2) |
| CH₂ | Pyrazinyl | NH—C(O) | Furanyl | Z₁: CH₂—CH₃ (3) |
| CH₂ | Pyrazinyl | NH—C(O) | Furanyl | Z₁: CH₂—CH₂—CH₃ or iPr (2) |
| CH₂ | Pyrazinyl | NH—C(O) | Furanyl | Z₁: CH₂—CH₂—CH₃ or iPr (3) |
| CH₂ | Pyrazinyl | NH—C(O) | Furanyl | Z₁: CH₂F (2) |
| CH₂ | Pyrazinyl | NH—C(O) | Furanyl | Z₁: CH₂F (3) |
| CH₂ | Pyrazinyl | NH—C(O) | Furanyl | Z₁: CHF₂ (2) |
| CH₂ | Pyrazinyl | NH—C(O) | Furanyl | Z₁: CHF₂ (3) |

TABLE 2-continued $$L^1—C^1—L^2—C^2—Z_p$$

[7-azaindole structure with substitution at 3-position]

| $L^1$ | $C^1$ | $L^2$ | $C^2$ | Z |
|---|---|---|---|---|
| CH$_2$ | Pyrazinyl | NH—C(O) | Furanyl | $Z_1$: CF$_3$ (2) |
| CH$_2$ | Pyrazinyl | NH—C(O) | Furanyl | $Z_1$: CF$_3$ (3) |
| CH$_2$ | Pyrazinyl | NH—C(O) | Furanyl | $Z_1$: CH$_2$—CH$_2$F (2) |
| CH$_2$ | Pyrazinyl | NH—C(O) | Furanyl | $Z_1$: CH$_2$—CH$_2$F (3) |
| CH$_2$ | Pyrazinyl | NH—C(O) | Furanyl | $Z_1$: CH$_2$—CHF$_2$ (2) |
| CH$_2$ | Pyrazinyl | NH—C(O) | Furanyl | $Z_1$: CH$_2$—CHF$_2$ (3) |
| CH$_2$ | Pyrazinyl | NH—C(O) | Furanyl | $Z_1$: CH$_2$—CF$_3$ (2) |
| CH$_2$ | Pyrazinyl | NH—C(O) | Furanyl | $Z_1$: CH$_2$—CF$_3$ (3) |
| CH$_2$ | Pyrazinyl | NH—C(O) | Oxazolyl | None |
| CH$_2$ | Pyrazinyl | NH—C(O) | Oxazolyl | $Z_1$: F (2) |
| CH$_2$ | Pyrazinyl | NH—C(O) | Oxazolyl | $Z_1$: F (3) |
| CH$_2$ | Pyrazinyl | NH—C(O) | Oxazolyl | $Z_1$: F (2)<br>$Z_2$: F (3) |
| CH$_2$ | Pyrazinyl | NH—C(O) | Oxazolyl | $Z_1$: Cl (2) |
| CH$_2$ | Pyrazinyl | NH—C(O) | Oxazolyl | $Z_1$: Cl (3) |
| CH$_2$ | Pyrazinyl | NH—C(O) | Oxazolyl | $Z_1$: Cl (2)<br>$Z_2$: Cl (3) |
| CH$_2$ | Pyrazinyl | NH—C(O) | Oxazolyl | $Z_1$: F (2)<br>$Z_2$: Cl (3) |
| CH$_2$ | Pyrazinyl | NH—C(O) | Oxazolyl | $Z_1$: Cl (2)<br>$Z_2$: F (3) |
| CH$_2$ | Pyrazinyl | NH—C(O) | Oxazolyl | $Z_1$: CH$_3$ (2) |
| CH$_2$ | Pyrazinyl | NH—C(O) | Oxazolyl | $Z_1$: CH$_3$ (3) |
| CH$_2$ | Pyrazinyl | NH—C(O) | Oxazolyl | $Z_1$: CH$_2$—CH$_3$ (2) |
| CH$_2$ | Pyrazinyl | NH—C(O) | Oxazolyl | $Z_1$: CH$_2$—CH$_3$ (3) |
| CH$_2$ | Pyrazinyl | NH—C(O) | Oxazolyl | $Z_1$: CH$_2$—CH$_2$—CH$_3$ or iPr (2) |
| CH$_2$ | Pyrazinyl | NH—C(O) | Oxazolyl | $Z_1$: CH$_2$—CH$_2$—CH$_3$ or iPr (3) |
| CH$_2$ | Pyrazinyl | NH—C(O) | Oxazolyl | $Z_1$: CH$_2$F (2) |
| CH$_2$ | Pyrazinyl | NH—C(O) | Oxazolyl | $Z_1$: CH$_2$F (3) |
| CH$_2$ | Pyrazinyl | NH—C(O) | Oxazolyl | $Z_1$: CHF$_3$ (2) |
| CH$_2$ | Pyrazinyl | NH—C(O) | Oxazolyl | $Z_1$: CHF$_2$ (3) |
| CH$_2$ | Pyrazinyl | NH—C(O) | Oxazolyl | $Z_1$: CF$_3$ (2) |
| CH$_2$ | Pyrazinyl | NH—C(O) | Oxazolyl | $Z_1$: CF$_3$ (3) |
| CH$_2$ | Pyrazinyl | NH—C(O) | Oxazolyl | $Z_1$: CH$_2$—CH$_2$F (2) |
| CH$_2$ | Pyrazinyl | NH—C(O) | Oxazolyl | $Z_1$: CH$_2$—CH$_2$F (3) |
| CH$_2$ | Pyrazinyl | NH—C(O) | Oxazolyl | $Z_1$: CH$_2$—CHF$_2$ (2) |
| CH$_2$ | Pyrazinyl | NH—C(O) | Oxazolyl | $Z_1$: CH$_2$—CHF$_2$ (3) |
| CH$_2$ | Pyrazinyl | NH—C(O) | Oxazolyl | $Z_1$: CH$_2$—CF$_3$ (2) |
| CH$_2$ | Pyrazinyl | NH—C(O) | Oxazolyl | $Z_1$: CH$_2$—CF$_3$ (3) |
| CH$_2$ | Pyrazinyl | NH—C(O) | Thiophenyl | None |
| CH$_2$ | Pyrazinyl | NH—C(O) | Thiophenyl | $Z_1$: F (2) |
| CH$_2$ | Pyrazinyl | NH—C(O) | Thiophenyl | $Z_1$: F (3) |
| CH$_2$ | Pyrazinyl | NH—C(O) | Thiophenyl | $Z_1$: F (2)<br>$Z_2$: F (3) |
| CH$_2$ | Pyrazinyl | NH—C(O) | Thiophenyl | $Z_1$: Cl (2) |
| CH$_2$ | Pyrazinyl | NH—C(O) | Thiophenyl | $Z_1$: Cl (3) |
| CH$_2$ | Pyrazinyl | NH—C(O) | Thiophenyl | $Z_1$: Cl (2)<br>$Z_2$: Cl (3) |
| CH$_2$ | Pyrazinyl | NH—C(O) | Thiophenyl | $Z_1$: F (2)<br>$Z_2$: Cl (3) |
| CH$_2$ | Pyrazinyl | NH—C(O) | Thiophenyl | $Z_1$: Cl (2)<br>$Z_2$: F (3) |
| CH$_2$ | Pyrazinyl | NH—C(O) | Thiophenyl | $Z_1$: CH$_3$ (2) |
| CH$_2$ | Pyrazinyl | NH—C(O) | Thiophenyl | $Z_1$: CH$_3$ (3) |
| CH$_2$ | Pyrazinyl | NH—C(O) | Thiophenyl | $Z_1$: CH$_2$—CH$_3$ (2) |
| CH$_2$ | Pyrazinyl | NH—C(O) | Thiophenyl | $Z_1$: CH$_2$—CH$_3$ (3) |
| CH$_2$ | Pyrazinyl | NH—C(O) | Thiophenyl | $Z_1$: CH$_2$—CH$_2$—CH$_3$ or iPr (2) |
| CH$_2$ | Pyrazinyl | NH—C(O) | Thiophenyl | $Z_1$: CH$_2$—CH$_2$—CH$_3$ or iPr (3) |
| CH$_2$ | Pyrazinyl | NH—C(O) | Thiophenyl | $Z_1$: CH$_2$F (2) |
| CH$_2$ | Pyrazinyl | NH—C(O) | Thiophenyl | $Z_1$: CH$_2$F (3) |
| CH$_2$ | Pyrazinyl | NH—C(O) | Thiophenyl | $Z_1$: CHF$_2$ (2) |
| CH$_2$ | Pyrazinyl | NH—C(O) | Thiophenyl | $Z_1$: CHF$_2$ (3) |
| CH$_2$ | Pyrazinyl | NH—C(O) | Thiophenyl | $Z_1$: CF$_3$ (2) |
| CH$_2$ | Pyrazinyl | NH—C(O) | Thiophenyl | $Z_1$: CF$_3$ (3) |
| CH$_2$ | Pyrazinyl | NH—C(O) | Thiophenyl | $Z_1$: CH$_2$—CH$_2$F (2) |
| CH$_2$ | Pyrazinyl | NH—C(O) | Thiophenyl | $Z_1$: CH$_2$—CH$_2$F (3) |
| CH$_2$ | Pyrazinyl | NH—C(O) | Thiophenyl | $Z_1$: CH$_2$—CHF$_2$ (2) |
| CH$_2$ | Pyrazinyl | NH—C(O) | Thiophenyl | $Z_1$: CH$_2$—CHF$_2$ (3) |
| CH$_2$ | Pyrazinyl | NH—C(O) | Thiophenyl | $Z_1$: CH$_2$—CF$_3$ (2) |

TABLE 2-continued $$L^1-C^1-L^2-C^2-Z_p$$

[7-azaindole structure with substitution at 3-position]

| L¹ | C¹ | L² | C² | Z |
|---|---|---|---|---|
| CH₂ | Pyrazinyl | NH—C(O) | Thiophenyl | Z₁: CH₂—CF₃ (3) |
| CH₂ | Pyrazinyl | NH—C(O) | Thiazolyl | None |
| CH₂ | Pyrazinyl | NH—C(O) | Thiazolyl | Z₁: F (2) |
| CH₂ | Pyrazinyl | NH—C(O) | Thiazolyl | Z₁: F (3) |
| CH₂ | Pyrazinyl | NH—C(O) | Thiazolyl | Z₁: F (2)<br>Z₂: F (3) |
| CH₂ | Pyrazinyl | NH—C(O) | Thiazolyl | Z₁: Cl (2) |
| CH₂ | Pyrazinyl | NH—C(O) | Thiazolyl | Z₁: Cl (3) |
| CH₂ | Pyrazinyl | NH—C(O) | Thiazolyl | Z₁: Cl (2)<br>Z₂: Cl (3) |
| CH₂ | Pyrazinyl | NH—C(O) | Thiazolyl | Z₁: F (2)<br>Z₂: Cl (3) |
| CH₂ | Pyrazinyl | NH—C(O) | Thiazolyl | Z₁: Cl (2)<br>Z₂: F (3) |
| CH₂ | Pyrazinyl | NH—C(O) | Thiazolyl | Z₁: CH₃ (2) |
| CH₂ | Pyrazinyl | NH—C(O) | Thiazolyl | Z₁: CH₃ (3) |
| CH₂ | Pyrazinyl | NH—C(O) | Thiazolyl | Z₁: CH₂—CH₃ (2) |
| CH₂ | Pyrazinyl | NH—C(O) | Thiazolyl | Z₁: CH₂—CH₃ (3) |
| CH₂ | Pyrazinyl | NH—C(O) | Thiazolyl | Z₁: CH₂—CH₂—CH₃ or iPr (2) |
| CH₂ | Pyrazinyl | NH—C(O) | Thiazolyl | Z₁: CH₂—CH₂—CH₃ or iPr (3) |
| CH₂ | Pyrazinyl | NH—C(O) | Thiazolyl | Z₁: CH₂F (2) |
| CH₂ | Pyrazinyl | NH—C(O) | Thiazolyl | Z₁: CH₂F (3) |
| CH₂ | Pyrazinyl | NH—C(O) | Thiazolyl | Z₁: CHF₂ (2) |
| CH₂ | Pyrazinyl | NH—C(O) | Thiazolyl | Z₁: CHF₂ (3) |
| CH₂ | Pyrazinyl | NH—C(O) | Thiazolyl | Z₁: CF₃ (2) |
| CH₂ | Pyrazinyl | NH—C(O) | Thiazolyl | Z₁: CF₃ (3) |
| CH₂ | Pyrazinyl | NH—C(O) | Thiazolyl | Z₁: CH₂—CH₂F (2) |
| CH₂ | Pyrazinyl | NH—C(O) | Thiazolyl | Z₁: CH₂—CH₂F (3) |
| CH₂ | Pyrazinyl | NH—C(O) | Thiazolyl | Z₁: CH₂—CHF₂ (2) |
| CH₂ | Pyrazinyl | NH—C(O) | Thiazolyl | Z₁: CH₂—CHF₂ (3) |
| CH₂ | Pyrazinyl | NH—C(O) | Thiazolyl | Z₁: CH₂—CF₃ (2) |
| CH₂ | Pyrazinyl | NH—C(O) | Thiazolyl | Z₁: CH₂—CF₃ (3) |
| CH₂ | Pyrazinyl | NH—SO₂ | Phenyl | None |
| CH₂ | Pyrazinyl | NH—SO₂ | Phenyl | Z₁: F (para) |
| CH₂ | Pyrazinyl | NH—SO₂ | phenyl | Z₁: F (meta) |
| CH₂ | Pyrazinyl | NH—SO₂ | phenyl | Z₁: F (ortho) |
| CH₂ | Pyrazinyl | NH—SO₂ | phenyl | Z₁: F (para)<br>Z₂: F (meta) |
| CH₂ | Pyrazinyl | NH—SO₂ | Phenyl | Z₁: Cl (meta) |
| CH₂ | Pyrazinyl | NH—SO₂ | Phenyl | Z₁: Cl (para) |
| CH₂ | Pyrazinyl | NH—SO₂ | Phenyl | Z₁: Cl (para)<br>Z₂: Cl (meta) |
| CH₂ | Pyrazinyl | NH—SO₂ | Phenyl | Z₁: F (para)<br>Z₂: Cl (meta) |
| CH₂ | Pyrazinyl | NH—SO₂ | Phenyl | Z₁: Cl (para)<br>Z₂: F (meta) |
| CH₂ | Pyrazinyl | NH—SO₂ | Phenyl | Z₁: CH₃ (para) |
| CH₂ | Pyrazinyl | NH—SO₂ | Phenyl | Z₁: CH₃ (meta) |
| CH₂ | Pyrazinyl | NH—SO₂ | Phenyl | Z₁: CH₃ (ortho) |
| CH₂ | Pyrazinyl | NH—SO₂ | Phenyl | Z₁: CH₂—CH₃ (para) |
| CH₂ | Pyrazinyl | NH—SO₂ | Phenyl | Z₁: CH₂—CH₃ (meta) |
| CH₂ | Pyrazinyl | NH—SO₂ | Phenyl | Z₁: CH₂—CH₃ (ortho) |
| CH₂ | Pyrazinyl | NH—SO₂ | Phenyl | Z₁: CH₂—CH₂—CH₃ or iPr (para) |
| CH₂ | Pyrazinyl | NH—SO₂ | Phenyl | Z₁: CH₂—CH₂—CH₃ or iPr (meta) |
| CH₂ | Pyrazinyl | NH—SO₂ | Phenyl | Z₁: CH₂—CH₂—CH₃ or iPr (ortho) |
| CH₂ | Pyrazinyl | NH—SO₂ | Phenyl | Z₁: CH₂F (para) |
| CH₂ | Pyrazinyl | NH—SO₂ | Phenyl | Z₁: CH₂F (meta) |
| CH₂ | Pyrazinyl | NH—SO₂ | Phenyl | Z₁: CH₂F (ortho) |
| CH₂ | Pyrazinyl | NH—SO₂ | Phenyl | Z₁: CHF₂ (para) |
| CH₂ | Pyrazinyl | NH—SO₂ | Phenyl | Z₁: CHF₂ (meta) |
| CH₂ | Pyrazinyl | NH—SO₂ | Phenyl | Z₁: CHF₂ (ortho) |
| CH₂ | Pyrazinyl | NH—SO₂ | Phenyl | Z₁: CF₃ (para) |
| CH₂ | Pyrazinyl | NH—SO₂ | Phenyl | Z₁: CF₃ (meta) |
| CH₂ | Pyrazinyl | NH—SO₂ | Phenyl | Z₁: CF₃ (ortho) |
| CH₂ | Pyrazinyl | NH—SO₂ | Phenyl | Z₁: CH₂—CH₂F (para) |
| CH₂ | Pyrazinyl | NH—SO₂ | Phenyl | Z₁: CH₂—CH₂F (meta) |

TABLE 2-continued

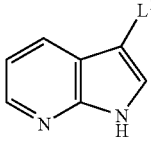

| L¹ | C¹ | L² | C² | Z |
|---|---|---|---|---|
| CH₂ | Pyrazinyl | NH—SO₂ | Phenyl | $Z_1$: CH₂—CH₂F (ortho) |
| CH₂ | Pyrazinyl | NH—SO₂ | Phenyl | $Z_1$: CH₂—CHF₂ (para) |
| CH₂ | Pyrazinyl | NH—SO₂ | Phenyl | $Z_1$: CH₂—CHF₂ (meta) |
| CH₂ | Pyrazinyl | NH—SO₂ | Phenyl | $Z_1$: CH₂—CHF₂ (ortho) |
| CH₂ | Pyrazinyl | NH—SO₂ | Phenyl | $Z_1$: CH₂—CF₃ (para) |
| CH₂ | Pyrazinyl | NH—SO₂ | Phenyl | $Z_1$: CH₂—CF₃ (meta) |
| CH₂ | Pyrazinyl | NH—SO₂ | Phenyl | $Z_1$: CH₂—CF₃ (ortho) |
| CH₂ | Pyrazinyl | NH—SO₂ | Pyridinyl | None |
| CH₂ | Pyrazinyl | NH—SO₂ | Pyridinyl | $Z_1$: F (para) |
| CH₂ | Pyrazinyl | NH—SO₂ | Pyridinyl | $Z_1$: F (meta) |
| CH₂ | Pyrazinyl | NH—SO₂ | Pyridinyl | $Z_1$: F (ortho) |
| CH₂ | Pyrazinyl | NH—SO₂ | Pyridinyl | $Z_1$: F (para)<br>$Z_2$: F (meta) |
| CH₂ | Pyrazinyl | NH—SO₂ | Pyridinyl | $Z_1$: Cl (meta) |
| CH₂ | Pyrazinyl | NH—SO₂ | Pyridinyl | $Z_1$: Cl (para) |
| CH₂ | Pyrazinyl | NH—SO₂ | Pyridinyl | $Z_1$: Cl (para)<br>$Z_2$: Cl (meta) |
| CH₂ | Pyrazinyl | NH—SO₂ | Pyridinyl | $Z_1$: F (para)<br>$Z_2$: Cl (meta) |
| CH₂ | Pyrazinyl | NH—SO₂ | Pyridinyl | $Z_1$: Cl (para)<br>$Z_2$: F (meta) |
| CH₂ | Pyrazinyl | NH—SO₂ | Pyridinyl | $Z_1$: CH₃ (para) |
| CH₂ | Pyrazinyl | NH—SO₂ | Pyridinyl | $Z_1$: CH₃ (meta) |
| CH₂ | Pyrazinyl | NH—SO₂ | Pyridinyl | $Z_1$: CH₃ (ortho) |
| CH₂ | Pyrazinyl | NH—SO₂ | Pyridinyl | $Z_1$: CH₂—CH₃ (para) |
| CH₂ | Pyrazinyl | NH—SO₂ | Pyridinyl | $Z_1$: CH₂—CH₃ (meta) |
| CH₂ | Pyrazinyl | NH—SO₂ | Pyridinyl | $Z_1$: CH₂—CH₃ (ortho) |
| CH₂ | Pyrazinyl | NH—SO₂ | Pyridinyl | $Z_1$: CH₂—CH₂—CH₃ or iPr (para) |
| CH₂ | Pyrazinyl | NH—SO₂ | Pyridinyl | $Z_1$: CH₂—CH₂—CH₃ or iPr (meta) |
| CH₂ | Pyrazinyl | NH—SO₂ | Pyridinyl | $Z_1$: CH₂—CH₂—CH₃ or iPr (ortho) |
| CH₂ | Pyrazinyl | NH—SO₂ | Pyridinyl | $Z_1$: CH₂F (para) |
| CH₂ | Pyrazinyl | NH—SO₂ | Pyridinyl | $Z_1$: CH₂F (meta) |
| CH₂ | Pyrazinyl | NH—SO₂ | Pyridinyl | $Z_1$: CH₂F (ortho) |
| CH₂ | Pyrazinyl | NH—SO₂ | Pyridinyl | $Z_1$: CHF₂ (para) |
| CH₂ | Pyrazinyl | NH—SO₂ | Pyridinyl | $Z_1$: CHF₂ (meta) |
| CH₂ | Pyrazinyl | NH—SO₂ | Pyridinyl | $Z_1$: CHF₂ (ortho) |
| CH₂ | Pyrazinyl | NH—SO₂ | Pyridinyl | $Z_1$: CF₃ (para) |
| CH₂ | Pyrazinyl | NH—SO₂ | Pyridinyl | $Z_1$: CF₃ (meta) |
| CH₂ | Pyrazinyl | NH—SO₂ | Pyridinyl | $Z_1$: CF₃ (ortho) |
| CH₂ | Pyrazinyl | NH—SO₂ | Pyridinyl | $Z_1$: CH₂—CH₂F (para) |
| CH₂ | Pyrazinyl | NH—SO₂ | Pyridinyl | $Z_1$: CH₂—CH₂F (meta) |
| CH₂ | Pyrazinyl | NH—SO₂ | Pyridinyl | $Z_1$: CH₂—CH₂F (ortho) |
| CH₂ | Pyrazinyl | NH—SO₂ | Pyridinyl | $Z_1$: CH₂—CHF₂ (para) |
| CH₂ | Pyrazinyl | NH—SO₂ | Pyridinyl | $Z_1$: CH₂—CHF₂ (meta) |
| CH₂ | Pyrazinyl | NH—SO₂ | Pyridinyl | $Z_1$: CH₂—CHF₂ (ortho) |
| CH₂ | Pyrazinyl | NH—SO₂ | Pyridinyl | $Z_1$: CH₂—CF₃ (para) |
| CH₂ | Pyrazinyl | NH—SO₂ | Pyridinyl | $Z_1$: CH₂—CF₃ (meta) |
| CH₂ | Pyrazinyl | NH—SO₂ | Pyridinyl | $Z_1$: CH₂—CF₃ (ortho) |
| CH₂ | Pyrazinyl | NH—SO₂ | Pyrimidinyl | None |
| CH₂ | Pyrazinyl | NH—SO₂ | Pyrimidinyl | $Z_1$: F (para) |
| CH₂ | Pyrazinyl | NH—SO₂ | Pyrimidinyl | $Z_1$: F (meta) |
| CH₂ | Pyrazinyl | NH—SO₂ | Pyrimidinyl | $Z_1$: F (ortho) |
| CH₂ | Pyrazinyl | NH—SO₂ | Pyrimidinyl | $Z_1$: F (para)<br>$Z_2$: F (meta) |
| CH₂ | Pyrazinyl | NH—SO₂ | Pyrimidinyl | $Z_1$: Cl (meta) |
| CH₂ | Pyrazinyl | NH—SO₂ | Pyrimidinyl | $Z_1$: Cl (para) |
| CH₂ | Pyrazinyl | NH—SO₂ | Pyrimidinyl | $Z_1$: Cl (para)<br>$Z_2$: Cl (meta) |
| CH₂ | Pyrazinyl | NH—SO₂ | Pyrimidinyl | $Z_1$: F (para)<br>$Z_2$: Cl (meta) |
| CH₂ | Pyrazinyl | NH—SO₂ | Pyrimidinyl | $Z_1$: Cl (para)<br>$Z_2$: F (meta) |
| CH₂ | Pyrazinyl | NH—SO₂ | Pyrimidinyl | $Z_1$: CH₃ (para) |
| CH₂ | Pyrazinyl | NH—SO₂ | Pyrimidinyl | $Z_1$: CH₃ (meta) |
| CH₂ | Pyrazinyl | NH—SO₂ | Pyrimidinyl | $Z_1$: CH₃ (ortho) |
| CH₂ | Pyrazinyl | NH—SO₂ | Pyrimidinyl | $Z_1$: CH₂—CH₃ (para) |

TABLE 2-continued

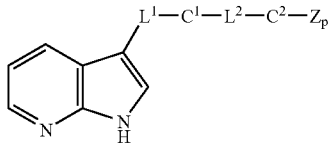

| $L^1$ | $C^1$ | $L^2$ | $C^2$ | Z |
|---|---|---|---|---|
| $CH_2$ | Pyrazinyl | $NH-SO_2$ | Pyrimidinyl | $Z_1$: $CH_2-CH_3$ (meta) |
| $CH_2$ | Pyrazinyl | $NH-SO_2$ | Pyrimidinyl | $Z_1$: $CH_2-CH_3$ (ortho) |
| $CH_2$ | Pyrazinyl | $NH-SO_2$ | Pyrimidinyl | $Z_1$: $CH_2-CH_2-CH_3$ or iPr (para) |
| $CH_2$ | Pyrazinyl | $NH-SO_2$ | Pyrimidinyl | $Z_1$: $CH_2-CH_2-CH_3$ or iPr (meta) |
| $CH_2$ | Pyrazinyl | $NH-SO_2$ | Pyrimidinyl | $Z_1$: $CH_2-CH_2-CH_3$ or iPr (ortho) |
| $CH_2$ | Pyrazinyl | $NH-SO_2$ | Pyrimidinyl | $Z_1$: $CH_2F$ (para) |
| $CH_2$ | Pyrazinyl | $NH-SO_2$ | Pyrimidinyl | $Z_1$: $CH_2F$ (meta) |
| $CH_2$ | Pyrazinyl | $NH-SO_2$ | Pyrimidinyl | $Z_1$: $CH_2F$ (ortho) |
| $CH_2$ | Pyrazinyl | $NH-SO_2$ | Pyrimidinyl | $Z_1$: $CHF_2$ (para) |
| $CH_2$ | Pyrazinyl | $NH-SO_2$ | Pyrimidinyl | $Z_1$: $CHF_2$ (meta) |
| $CH_2$ | Pyrazinyl | $NH-SO_2$ | Pyrimidinyl | $Z_1$: $CHF_2$ (ortho) |
| $CH_2$ | Pyrazinyl | $NH-SO_2$ | Pyrimidinyl | $Z_1$: $CF_3$ (para) |
| $CH_2$ | Pyrazinyl | $NH-SO_2$ | Pyrimidinyl | $Z_1$: $CF_3$ (meta) |
| $CH_2$ | Pyrazinyl | $NH-SO_2$ | Pyrimidinyl | $Z_1$: $CF_3$ (ortho) |
| $CH_2$ | Pyrazinyl | $NH-SO_2$ | Pyrimidinyl | $Z_1$: $CH_2-CH_2F$ (para) |
| $CH_2$ | Pyrazinyl | $NH-SO_2$ | Pyrimidinyl | $Z_1$: $CH_2-CH_2F$ (meta) |
| $CH_2$ | Pyrazinyl | $NH-SO_2$ | Pyrimidinyl | $Z_1$: $CH_2-CH_2F$ (ortho) |
| $CH_2$ | Pyrazinyl | $NH-SO_2$ | Pyrimidinyl | $Z_1$: $CH_2-CHF_2$ (para) |
| $CH_2$ | Pyrazinyl | $NH-SO_2$ | Pyrimidinyl | $Z_1$: $CH_2-CHF_2$ (meta) |
| $CH_2$ | Pyrazinyl | $NH-SO_2$ | Pyrimidinyl | $Z_1$: $CH_2-CHF_2$ (ortho) |
| $CH_2$ | Pyrazinyl | $NH-SO_2$ | Pyrimidinyl | $Z_1$: $CH_2-CF_3$ (para) |
| $CH_2$ | Pyrazinyl | $NH-SO_2$ | Pyrimidinyl | $Z_1$: $CH_2-CF_3$ (meta) |
| $CH_2$ | Pyrazinyl | $NH-SO_2$ | Pyrimidinyl | $Z_1$: $CH_2-CF_3$ (ortho) |
| $CH_2$ | Pyrazinyl | $NH-SO_2$ | Pyrazinyl | None |
| $CH_2$ | Pyrazinyl | $NH-SO_2$ | Pyrazinyl | $Z_1$: F (para) |
| $CH_2$ | Pyrazinyl | $NH-SO_2$ | Pyrazinyl | $Z_1$: F (meta) |
| $CH_2$ | Pyrazinyl | $NH-SO_2$ | Pyrazinyl | $Z_1$: F (ortho) |
| $CH_2$ | Pyrazinyl | $NH-SO_2$ | Pyrazinyl | $Z_1$: F (para) $Z_2$: F (meta) |
| $CH_2$ | Pyrazinyl | $NH-SO_2$ | Pyrazinyl | $Z_1$: Cl (meta) |
| $CH_2$ | Pyrazinyl | $NH-SO_2$ | Pyrazinyl | $Z_1$: Cl (para) |
| $CH_2$ | Pyrazinyl | $NH-SO_2$ | Pyrazinyl | $Z_1$: Cl (para) $Z_2$: Cl (meta) |
| $CH_2$ | Pyrazinyl | $NH-SO_2$ | Pyrazinyl | $Z_1$: F (para) $Z_2$: Cl (meta) |
| $CH_2$ | Pyrazinyl | $NH-SO_2$ | Pyrazinyl | $Z_1$: Cl (para) $Z_2$: F (meta) |
| $CH_2$ | Pyrazinyl | $NH-SO_2$ | Pyrazinyl | $Z_1$: $CH_3$ (para) |
| $CH_2$ | Pyrazinyl | $NH-SO_2$ | Pyrazinyl | $Z_1$: $CH_3$ (meta) |
| $CH_2$ | Pyrazinyl | $NH-SO_2$ | Pyrazinyl | $Z_1$: $CH_3$ (ortho) |
| $CH_2$ | Pyrazinyl | $NH-SO_2$ | Pyrazinyl | $Z_1$: $CH_2-CH_3$ (para) |
| $CH_2$ | Pyrazinyl | $NH-SO_2$ | Pyrazinyl | $Z_1$: $CH_2-CH_3$ (meta) |
| $CH_2$ | Pyrazinyl | $NH-SO_2$ | Pyrazinyl | $Z_1$: $CH_2-CH_3$ (ortho) |
| $CH_2$ | Pyrazinyl | $NH-SO_2$ | Pyrazinyl | $Z_1$: $CH_2-CH_2-CH_3$ or iPr (para) |
| $CH_2$ | Pyrazinyl | $NH-SO_2$ | Pyrazinyl | $Z_1$: $CH_2-CH_2-CH_3$ or iPr (meta) |
| $CH_2$ | Pyrazinyl | $NH-SO_2$ | Pyrazinyl | $Z_1$: $CH_2-CH_2-CH_3$ or iPr (ortho) |
| $CH_2$ | Pyrazinyl | $NH-SO_2$ | Pyrazinyl | $Z_1$: $CH_2F$ (para) |
| $CH_2$ | Pyrazinyl | $NH-SO_2$ | Pyrazinyl | $Z_1$: $CH_2F$ (meta) |
| $CH_2$ | Pyrazinyl | $NH-SO_2$ | Pyrazinyl | $Z_1$: $CH_2F$ (ortho) |
| $CH_2$ | Pyrazinyl | $NH-SO_2$ | Pyrazinyl | $Z_1$: $CHF_2$ (para) |
| $CH_2$ | Pyrazinyl | $NH-SO_2$ | Pyrazinyl | $Z_1$: $CHF_2$ (meta) |
| $CH_2$ | Pyrazinyl | $NH-SO_2$ | Pyrazinyl | $Z_1$: $CHF_2$ (ortho) |
| $CH_2$ | Pyrazinyl | $NH-SO_2$ | Pyrazinyl | $Z_1$: $CF_3$ (para) |
| $CH_2$ | Pyrazinyl | $NH-SO_2$ | Pyrazinyl | $Z_1$: $CF_3$ (meta) |
| $CH_2$ | Pyrazinyl | $NH-SO_2$ | Pyrazinyl | $Z_1$: $CF_3$ (ortho) |
| $CH_2$ | Pyrazinyl | $NH-SO_2$ | Pyrazinyl | $Z_1$: $CH_2-CH_2F$ (para) |
| $CH_2$ | Pyrazinyl | $NH-SO_2$ | Pyrazinyl | $Z_1$: $CH_2-CH_2F$ (meta) |
| $CH_2$ | Pyrazinyl | $NH-SO_2$ | Pyrazinyl | $Z_1$: $CH_2-CH_2F$ (ortho) |
| $CH_2$ | Pyrazinyl | $NH-SO_2$ | Pyrazinyl | $Z_1$: $CH_2-CHF_2$ (para) |
| $CH_2$ | Pyrazinyl | $NH-SO_2$ | Pyrazinyl | $Z_1$: $CH_2-CHF_2$ (meta) |
| $CH_2$ | Pyrazinyl | $NH-SO_2$ | Pyrazinyl | $Z_1$: $CH_2-CHF_2$ (ortho) |
| $CH_2$ | Pyrazinyl | $NH-SO_2$ | Pyrazinyl | $Z_1$: $CH_2-CF_3$ (para) |
| $CH_2$ | Pyrazinyl | $NH-SO_2$ | Pyrazinyl | $Z_1$: $CH_2-CF_3$ (meta) |

TABLE 2-continued

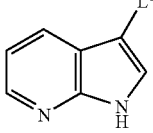

| $L^1$ | $C^1$ | $L^2$ | $C^2$ | Z |
|---|---|---|---|---|
| $CH_2$ | Pyrazinyl | $NH-SO_2$ | Pyrazinyl | $Z_1$: $CH_2-CF_3$ (ortho) |
| $CH_2$ | Pyrazinyl | $NH-SO_2$ | Pyrrolyl | None |
| $CH_2$ | Pyrazinyl | $NH-SO_2$ | Pyrrolyl | $Z_1$: F (2) |
| $CH_2$ | Pyrazinyl | $NH-SO_2$ | Pyrrolyl | $Z_1$: F (3) |
| $CH_2$ | Pyrazinyl | $NH-SO_2$ | Pyrrolyl | $Z_1$: F (2) |
| | | | | $Z_2$: F (3) |
| $CH_2$ | Pyrazinyl | $NH-SO_2$ | Pyrrolyl | $Z_1$: Cl (2) |
| $CH_2$ | Pyrazinyl | $NH-SO_2$ | Pyrrolyl | $Z_1$: Cl (3) |
| $CH_2$ | Pyrazinyl | $NH-SO_2$ | Pyrrolyl | $Z_1$: Cl (2) |
| | | | | $Z_2$: Cl (3) |
| $CH_2$ | Pyrazinyl | $NH-SO_2$ | Pyrrolyl | $Z_1$: F (2) |
| | | | | $Z_2$: Cl (3) |
| $CH_2$ | Pyrazinyl | $NH-SO_2$ | Pyrrolyl | $Z_1$: Cl (2) |
| | | | | $Z_2$: F (3) |
| $CH_2$ | Pyrazinyl | $NH-SO_2$ | Pyrrolyl | $Z_1$: $CH_3$ (2) |
| $CH_2$ | Pyrazinyl | $NH-SO_2$ | Pyrrolyl | $Z_1$: $CH_3$ (3) |
| $CH_2$ | Pyrazinyl | $NH-SO_2$ | Pyrrolyl | $Z_1$: $CH_2-CH_3$ (2) |
| $CH_2$ | Pyrazinyl | $NH-SO_2$ | Pyrrolyl | $Z_1$: $CH_2-CH_3$ (3) |
| $CH_2$ | Pyrazinyl | $NH-SO_2$ | Pyrrolyl | $Z_1$: $CH_2-CH_2-CH_3$ or iPr (2) |
| $CH_2$ | Pyrazinyl | $NH-SO_2$ | Pyrrolyl | $Z_1$: $CH_2-CH_2-CH_3$ or iPr (3) |
| $CH_2$ | Pyrazinyl | $NH-SO_2$ | Pyrrolyl | $Z_1$: $CH_2F$ (2) |
| $CH_2$ | Pyrazinyl | $NH-SO_2$ | Pyrrolyl | $Z_1$: $CH_2F$ (3) |
| $CH_2$ | Pyrazinyl | $NH-SO_2$ | Pyrrolyl | $Z_1$: $CHF_2$ (2) |
| $CH_2$ | Pyrazinyl | $NH-SO_2$ | Pyrrolyl | $Z_1$: $CHF_2$ (3) |
| $CH_2$ | Pyrazinyl | $NH-SO_2$ | Pyrrolyl | $Z_1$: $CF_3$ (2) |
| $CH_2$ | Pyrazinyl | $NH-SO_2$ | Pyrrolyl | $Z_1$: $CF_3$ (3) |
| $CH_2$ | Pyrazinyl | $NH-SO_2$ | Pyrrolyl | $Z_1$: $CH_2-CH_2F$ (2) |
| $CH_2$ | Pyrazinyl | $NH-SO_2$ | Pyrrolyl | $Z_1$: $CH_2-CH_2F$ (3) |
| $CH_2$ | Pyrazinyl | $NH-SO_2$ | Pyrrolyl | $Z_1$: $CH_2-CHF_2$ (2) |
| $CH_2$ | Pyrazinyl | $NH-SO_2$ | Pyrrolyl | $Z_1$: $CH_2-CHF_2$ (3) |
| $CH_2$ | Pyrazinyl | $NH-SO_2$ | Pyrrolyl | $Z_1$: $CH_2-CF_3$ (2) |
| $CH_2$ | Pyrazinyl | $NH-SO_2$ | Pyrrolyl | $Z_1$: $CH_2-CF_3$ (3) |
| $CH_2$ | Pyrazinyl | $NH-SO_2$ | Imidazolyl | None |
| $CH_2$ | Pyrazinyl | $NH-SO_2$ | Imidazolyl | $Z_1$: F (2) |
| $CH_2$ | Pyrazinyl | $NH-SO_2$ | Imidazolyl | $Z_1$: F (3) |
| $CH_2$ | Pyrazinyl | $NH-SO_2$ | Imidazolyl | $Z_1$: F (2) |
| | | | | $Z_2$: F (3) |
| $CH_2$ | Pyrazinyl | $NH-SO_2$ | Imidazolyl | $Z_1$: Cl (2) |
| $CH_2$ | Pyrazinyl | $NH-SO_2$ | Imidazolyl | $Z_1$: Cl (3) |
| $CH_2$ | Pyrazinyl | $NH-SO_2$ | Imidazolyl | $Z_1$: Cl (2) |
| | | | | $Z_2$: Cl (3) |
| $CH_2$ | Pyrazinyl | $NH-SO_2$ | Imidazolyl | $Z_1$: F (2) |
| | | | | $Z_2$: Cl (3) |
| $CH_2$ | Pyrazinyl | $NH-SO_2$ | Imidazolyl | $Z_1$: Cl (2) |
| | | | | $Z_2$: F (3) |
| $CH_2$ | Pyrazinyl | $NH-SO_2$ | Imidazolyl | $Z_1$: $CH_3$ (2) |
| $CH_2$ | Pyrazinyl | $NH-SO_2$ | Imidazolyl | $Z_1$: $CH_3$ (3) |
| $CH_2$ | Pyrazinyl | $NH-SO_2$ | Imidazolyl | $Z_1$: $CH_2-CH_3$ (2) |
| $CH_2$ | Pyrazinyl | $NH-SO_2$ | Imidazolyl | $Z_1$: $CH_2-CH_3$ (3) |
| $CH_2$ | Pyrazinyl | $NH-SO_2$ | Imidazolyl | $Z_1$: $CH_2-CH_2-CH_3$ or iPr (2) |
| $CH_2$ | Pyrazinyl | $NH-SO_2$ | Imidazolyl | $Z_1$: $CH_2-CH_2-CH_3$ or iPr (3) |
| $CH_2$ | Pyrazinyl | $NH-SO_2$ | Imidazolyl | $Z_1$: $CH_2F$ (2) |
| $CH_2$ | Pyrazinyl | $NH-SO_2$ | Imidazolyl | $Z_1$: $CH_2F$ (3) |
| $CH_2$ | Pyrazinyl | $NH-SO_2$ | Imidazolyl | $Z_1$: $CHF_2$ (2) |
| $CH_2$ | Pyrazinyl | $NH-SO_2$ | Imidazolyl | $Z_1$: $CHF_2$ (3) |
| $CH_2$ | Pyrazinyl | $NH-SO_2$ | Imidazolyl | $Z_1$: $CF_3$ (2) |
| $CH_2$ | Pyrazinyl | $NH-SO_2$ | Imidazolyl | $Z_1$: $CF_3$ (3) |
| $CH_2$ | Pyrazinyl | $NH-SO_2$ | Imidazolyl | $Z_1$: $CH_2-CH_2F$ (2) |
| $CH_2$ | Pyrazinyl | $NH-SO_2$ | Imidazolyl | $Z_1$: $CH_2-CH_2F$ (3) |
| $CH_2$ | Pyrazinyl | $NH-SO_2$ | Imidazolyl | $Z_1$: $CH_2-CHF_2$ (2) |
| $CH_2$ | Pyrazinyl | $NH-SO_2$ | Imidazolyl | $Z_1$: $CH_2-CHF_2$ (3) |
| $CH_2$ | Pyrazinyl | $NH-SO_2$ | Imidazolyl | $Z_1$: $CH_2-CF_3$ (2) |
| $CH_2$ | Pyrazinyl | $NH-SO_2$ | Imidazolyl | $Z_1$: $CH_2-CF_3$ (3) |
| $CH_2$ | Pyrazinyl | $NH-SO_2$ | Furanyl | None |
| $CH_2$ | Pyrazinyl | $NH-SO_2$ | Furanyl | $Z_1$: F (2) |
| $CH_2$ | Pyrazinyl | $NH-SO_2$ | Furanyl | $Z_1$: F (3) |
| $CH_2$ | Pyrazinyl | $NH-SO_2$ | Furanyl | $Z_1$: F (2) |
| | | | | $Z_2$: F (3) |
| $CH_2$ | Pyrazinyl | $NH-SO_2$ | Furanyl | $Z_1$: Cl (2) |

TABLE 2-continued

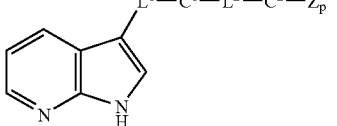

| L¹ | C¹ | L² | C² | Z |
|---|---|---|---|---|
| CH₂ | Pyrazinyl | NH—SO₂ | Furanyl | $Z_1$: Cl (3) |
| CH₂ | Pyrazinyl | NH—SO₂ | Furanyl | $Z_1$: Cl (2)<br>$Z_2$: Cl (3) |
| CH₂ | Pyrazinyl | NH—SO₂ | Furanyl | $Z_1$: F (2)<br>$Z_2$: Cl (3) |
| CH₂ | Pyrazinyl | NH—SO₂ | Furanyl | $Z_1$: Cl (2)<br>$Z_2$: F (3) |
| CH₂ | Pyrazinyl | NH—SO₂ | Furanyl | $Z_1$: CH₃ (2) |
| CH₂ | Pyrazinyl | NH—SO₂ | Furanyl | $Z_1$: CHF (3) |
| CH₂ | Pyrazinyl | NH—SO₂ | Furanyl | $Z_1$: CH₂—CH₃ (2) |
| CH₂ | Pyrazinyl | NH—SO₂ | Furanyl | $Z_1$: CH₂—CH₃ (3) |
| CH₂ | Pyrazinyl | NH—SO₂ | Furanyl | $Z_1$: CH₂—CH₂—CH₃ or iPr (2) |
| CH₂ | Pyrazinyl | NH—SO₂ | Furanyl | $Z_1$: CH₂—CH₂—CH₃ or iPr (3) |
| CH₂ | Pyrazinyl | NH—SO₂ | Furanyl | $Z_1$: CH₂F (2) |
| CH₂ | Pyrazinyl | NH—SO₂ | Furanyl | $Z_1$: CH₂F (3) |
| CH₂ | Pyrazinyl | NH—SO₂ | Furanyl | $Z_1$: CHF₂ (2) |
| CH₂ | Pyrazinyl | NH—SO₂ | Furanyl | $Z_1$: CHF₂ (3) |
| CH₂ | Pyrazinyl | NH—SO₂ | Furanyl | $Z_1$: CF₃ (2) |
| CH₂ | Pyrazinyl | NH—SO₂ | Furanyl | $Z_1$: CF₃ (3) |
| CH₂ | Pyrazinyl | NH—SO₂ | Furanyl | $Z_1$: CH₂—CH₂F (2) |
| CH₂ | Pyrazinyl | NH—SO₂ | Furanyl | $Z_1$: CH₂—CH₂F (3) |
| CH₂ | Pyrazinyl | NH—SO₂ | Furanyl | $Z_1$: CH₂—CHF₂ (2) |
| CH₂ | Pyrazinyl | NH—SO₂ | Furanyl | $Z_1$: CH₂—CHF₂ (3) |
| CH₂ | Pyrazinyl | NH—SO₂ | Furanyl | $Z_1$: CH₂—CF₃ (2) |
| CH₂ | Pyrazinyl | NH—SO₂ | Furanyl | $Z_1$: CH₂—CF₃ (3) |
| CH₂ | Pyrazinyl | NH—SO₂ | Oxazolyl | None |
| CH₂ | Pyrazinyl | NH—SO₂ | Oxazolyl | $Z_1$: F (2) |
| CH₂ | Pyrazinyl | NH—SO₂ | Oxazolyl | $Z_1$: F (3) |
| CH₂ | Pyrazinyl | NH—SO₂ | Oxazolyl | $Z_1$: F (2)<br>$Z_2$: F (3) |
| CH₂ | Pyrazinyl | NH—SO₂ | Oxazolyl | $Z_1$: Cl (2) |
| CH₂ | Pyrazinyl | NH—SO₂ | Oxazolyl | $Z_1$: Cl (3) |
| CH₂ | Pyrazinyl | NH—SO₂ | Oxazolyl | $Z_1$: Cl (2)<br>$Z_2$: Cl (3) |
| CH₂ | Pyrazinyl | NH—SO₂ | Oxazolyl | $Z_1$: F (2)<br>$Z_2$: Cl (3) |
| CH₂ | Pyrazinyl | NH—SO₂ | Oxazolyl | $Z_1$: Cl (2)<br>$Z_2$: F (3) |
| CH₂ | Pyrazinyl | NH—SO₂ | Oxazolyl | $Z_1$: CH₃ (2) |
| CH₂ | Pyrazinyl | NH—SO₂ | Oxazolyl | $Z_1$: CH₃ (3) |
| CH₂ | Pyrazinyl | NH—SO₂ | Oxazolyl | $Z_1$: CH₂—CH₃ (2) |
| CH₂ | Pyrazinyl | NH—SO₂ | Oxazolyl | $Z_1$: CH₂—CH₃ (3) |
| CH₂ | Pyrazinyl | NH—SO₂ | Oxazolyl | $Z_1$: CH₂—CH₂—CH₃ or iPr (2) |
| CH₂ | Pyrazinyl | NH—SO₂ | Oxazolyl | $Z_1$: CH₂—CH₂—CH₃ or iPr (3) |
| CH₂ | Pyrazinyl | NH—SO₂ | Oxazolyl | $Z_1$: CH₂F (2) |
| CH₂ | Pyrazinyl | NH—SO₂ | Oxazolyl | $Z_1$: CH₂F (3) |
| CH₂ | Pyrazinyl | NH—SO₂ | Oxazolyl | $Z_1$: CHF₂ (2) |
| CH₂ | Pyrazinyl | NH—SO₂ | Oxazolyl | $Z_1$: CHF₂ (3) |
| CH₂ | Pyrazinyl | NH—SO₂ | Oxazolyl | $Z_1$: CF₃ (2) |
| CH₂ | Pyrazinyl | NH—SO₂ | Oxazolyl | $Z_1$: CF₃ (3) |
| CH₂ | Pyrazinyl | NH—SO₂ | Oxazolyl | $Z_1$: CH₂—CH₂F (2) |
| CH₂ | Pyrazinyl | NH—SO₂ | Oxazolyl | $Z_1$: CH₂—CH₂F (3) |
| CH₂ | Pyrazinyl | NH—SO₂ | Oxazolyl | $Z_1$: CH₂—CHF₂ (2) |
| CH₂ | Pyrazinyl | NH—SO₂ | Oxazolyl | $Z_1$: CH₂—CHF₂ (3) |
| CH₂ | Pyrazinyl | NH—SO₂ | Oxazolyl | $Z_1$: CH₂—CF₃ (2) |
| CH₂ | Pyrazinyl | NH—SO₂ | Oxazolyl | $Z_1$: CH₂—CF₃ (3) |
| CH₂ | Pyrazinyl | NH—SO₂ | Thiophenyl | None |
| CH₂ | Pyrazinyl | NH—SO₂ | Thiophenyl | $Z_1$: F (2) |
| CH₂ | Pyrazinyl | NH—SO₂ | Thiophenyl | $Z_1$: F (3) |
| CH₂ | Pyrazinyl | NH—SO₂ | Thiophenyl | $Z_1$: F (2)<br>$Z_2$: F (3) |
| CH₂ | Pyrazinyl | NH—SO₂ | Thiophenyl | $Z_1$: Cl (2) |
| CH₂ | Pyrazinyl | NH—SO₂ | Thiophenyl | $Z_1$: Cl (3) |
| CH₂ | Pyrazinyl | NH—SO₂ | Thiophenyl | $Z_1$: Cl (2)<br>$Z_2$: Cl (3) |
| CH₂ | Pyrazinyl | NH—SO₂ | Thiophenyl | $Z_1$: F (2)<br>$Z_2$: Cl (3) |
| CH₂ | Pyrazinyl | NH—SO₂ | Thiophenyl | $Z_1$: Cl (2)<br>$Z_2$: F (3) |

TABLE 2-continued

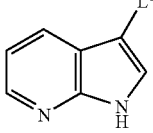

$L^1$—$C^1$—$L^2$—$C^2$—$Z_p$

| $L^1$ | $C^1$ | $L^2$ | $C^2$ | Z |
|---|---|---|---|---|
| CH$_2$ | Pyrazinyl | NH—SO$_2$ | Thiophenyl | $Z_1$: CH$_3$ (2) |
| CH$_2$ | Pyrazinyl | NH—SO$_2$ | Thiophenyl | $Z_1$: CH$_3$ (3) |
| CH$_2$ | Pyrazinyl | NH—SO$_2$ | Thiophenyl | $Z_1$: CH$_2$—CH$_3$ (2) |
| CH$_2$ | Pyrazinyl | NH—SO$_2$ | Thiophenyl | $Z_1$: CH$_2$—CH$_3$ (3) |
| CH$_2$ | Pyrazinyl | NH—SO$_2$ | Thiophenyl | $Z_1$: CH$_2$—CH$_2$—CH$_3$ or iPr (2) |
| CH$_2$ | Pyrazinyl | NH—SO$_2$ | Thiophenyl | $Z_1$: CH$_2$—CH$_2$—CH$_3$ or iPr (3) |
| CH$_2$ | Pyrazinyl | NH—SO$_2$ | Thiophenyl | $Z_1$: CH$_2$F (2) |
| CH$_2$ | Pyrazinyl | NH—SO$_2$ | Thiophenyl | $Z_1$: CH$_2$F (3) |
| CH$_2$ | Pyrazinyl | NH—SO$_2$ | Thiophenyl | $Z_1$: CHF$_2$ (2) |
| CH$_2$ | Pyrazinyl | NH—SO$_2$ | Thiophenyl | $Z_1$: CHF$_2$ (3) |
| CH$_2$ | Pyrazinyl | NH—SO$_2$ | Thiophenyl | $Z_1$: CF$_3$ (2) |
| CH$_2$ | Pyrazinyl | NH—SO$_2$ | Thiophenyl | $Z_1$: CF$_3$ (3) |
| CH$_2$ | Pyrazinyl | NH—SO$_2$ | Thiophenyl | $Z_1$: CH$_2$—CH$_2$F (2) |
| CH$_2$ | Pyrazinyl | NH—SO$_2$ | Thiophenyl | $Z_1$: CH$_2$—CH$_2$F (3) |
| CH$_2$ | Pyrazinyl | NH—SO$_2$ | Thiophenyl | $Z_1$: CH$_2$—CHF$_2$ (2) |
| CH$_2$ | Pyrazinyl | NH—SO$_2$ | Thiophenyl | $Z_1$: CH$_2$—CHF$_2$ (3) |
| CH$_2$ | Pyrazinyl | NH—SO$_2$ | Thiophenyl | $Z_1$: CH$_2$—CF$_3$ (2) |
| CH$_2$ | Pyrazinyl | NH—SO$_2$ | Thiophenyl | $Z_1$: CH$_2$—CF$_3$ (3) |
| CH$_2$ | Pyrazinyl | NH—SO$_2$ | Thiazolyl | None |
| CH$_2$ | Pyrazinyl | NH—SO$_2$ | Thiazolyl | $Z_1$: F (2) |
| CH$_2$ | Pyrazinyl | NH—SO$_2$ | Thiazolyl | $Z_1$: F (3) |
| CH$_2$ | Pyrazinyl | NH—SO$_2$ | Thiazolyl | $Z_1$: F (2) $Z_2$: F (3) |
| CH$_2$ | Pyrazinyl | NH—SO$_2$ | Thiazolyl | $Z_1$: Cl (2) |
| CH$_2$ | Pyrazinyl | NH—SO$_2$ | Thiazolyl | $Z_1$: Cl (3) |
| CH$_2$ | Pyrazinyl | NH—SO$_2$ | Thiazolyl | $Z_1$: Cl (2) $Z_2$: Cl (3) |
| CH$_2$ | Pyrazinyl | NH—SO$_2$ | Thiazolyl | $Z_1$: F (2) $Z_2$: Cl (3) |
| CH$_2$ | Pyrazinyl | NH—SO$_2$ | Thiazolyl | $Z_1$: Cl (2) $Z_2$: F (3) |
| CH$_2$ | Pyrazinyl | NH—SO$_2$ | Thiazolyl | $Z_1$: CH$_3$ (2) |
| CH$_2$ | Pyrazinyl | NH—SO$_2$ | Thiazolyl | $Z_1$: CH$_3$ (3) |
| CH$_2$ | Pyrazinyl | NH—SO$_2$ | Thiazolyl | $Z_1$: CH$_2$—CH$_3$ (2) |
| CH$_2$ | Pyrazinyl | NH—SO$_2$ | Thiazolyl | $Z_1$: CH$_2$—CH$_3$ (3) |
| CH$_2$ | Pyrazinyl | NH—SO$_2$ | Thiazolyl | $Z_1$: CH$_2$—CH$_2$—CH$_3$ or iPr (2) |
| CH$_2$ | Pyrazinyl | NH—SO$_2$ | Thiazolyl | $Z_1$: CH$_2$—CH$_2$—CH$_3$ or iPr (3) |
| CH$_2$ | Pyrazinyl | NH—SO$_2$ | Thiazolyl | $Z_1$: CH$_2$F (2) |
| CH$_2$ | Pyrazinyl | NH—SO$_2$ | Thiazolyl | $Z_1$: CH$_2$F (3) |
| CH$_2$ | Pyrazinyl | NH—SO$_2$ | Thiazolyl | $Z_1$: CHF$_2$ (2) |
| CH$_2$ | Pyrazinyl | NH—SO$_2$ | Thiazolyl | $Z_1$: CHF$_2$ (3) |
| CH$_2$ | Pyrazinyl | NH—SO$_2$ | Thiazolyl | $Z_1$: CF$_3$ (2) |
| CH$_2$ | Pyrazinyl | NH—SO$_2$ | Thiazolyl | $Z_1$: CF$_3$ (3) |
| CH$_2$ | Pyrazinyl | NH—SO$_2$ | Thiazolyl | $Z_1$: CH$_2$—CH$_2$F (2) |
| CH$_2$ | Pyrazinyl | NH—SO$_2$ | Thiazolyl | $Z_1$: CH$_2$—CH$_2$F (3) |
| CH$_2$ | Pyrazinyl | NH—SO$_2$ | Thiazolyl | $Z_1$: CH$_2$—CHF$_2$ (2) |
| CH$_2$ | Pyrazinyl | NH—SO$_2$ | Thiazolyl | $Z_1$: CH$_2$—CHF$_2$ (3) |
| CH$_2$ | Pyrazinyl | NH—SO$_2$ | Thiazolyl | $Z_1$: CH$_2$—CF$_3$ (2) |
| CH$_2$ | Pyrazinyl | NH—SO$_2$ | Thiazolyl | $Z_1$: CH$_2$—CF$_3$ (3) |
| CF$_2$ | pyridinyl | NH—CH$_2$ | Phenyl | None |
| CF$_2$ | pyridinyl | NH—CH$_2$ | Phenyl | $Z_1$: F (para) |
| CF$_2$ | pyridinyl | NH—CH$_2$ | phenyl | $Z_1$: F (meta) |
| CF$_2$ | pyridinyl | NH—CH$_2$ | phenyl | $Z_1$: F (ortho) |
| CF$_2$ | pyridinyl | NH—CH$_2$ | phenyl | $Z_1$: F (para) $Z_2$: F (meta) |
| CF$_2$ | Pyridinyl | NH—CH$_2$ | Phenyl | $Z_1$: Cl (meta) |
| CF$_2$ | Pyridinyl | NH—CH$_2$ | Phenyl | $Z_1$: Cl (para) |
| CF$_2$ | Pyridinyl | NH—CH$_2$ | Phenyl | $Z_1$: Cl (para) $Z_2$: Cl (meta) |
| CF$_2$ | Pyridinyl | NH—CH$_2$ | Phenyl | $Z_1$: F (para) $Z_2$: Cl (meta) |
| CF$_2$ | Pyridinyl | NH—CH$_2$ | Phenyl | $Z_1$: Cl (para) $Z_2$: F (meta) |
| CF$_2$ | Pyridinyl | NH—CH$_2$ | Phenyl | $Z_1$: CH$_3$ (para) |
| CF$_2$ | Pyridinyl | NH—CH$_2$ | Phenyl | $Z_1$: CH$_3$ (meta) |
| CF$_2$ | Pyridinyl | NH—CH$_2$ | Phenyl | $Z_1$: CH$_3$ (ortho) |
| CF$_2$ | Pyridinyl | NH—CH$_2$ | Phenyl | $Z_1$: CH$_2$—CH$_3$ (para) |
| CF$_2$ | Pyridinyl | NH—CH$_2$ | Phenyl | $Z_1$: CH$_2$—CH$_3$ (meta) |
| CF$_2$ | Pyridinyl | NH—CH$_2$ | Phenyl | $Z_1$: CH$_2$—CH$_3$ (ortho) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| CF₂ | Pyridinyl | NH—CH₂ | Phenyl | Z₁: CH₂—CH₂—CH₃ or iPr (para) |
| CF₂ | Pyridinyl | NH—CH₂ | Phenyl | Z₁: CH₂—CH₂—CH₃ or iPr (meta) |
| CF₂ | Pyridinyl | NH—CH₂ | Phenyl | Z₁: CH₂—CH₂—CH₃ or iPr (ortho) |
| CF₂ | Pyridinyl | NH—CH₂ | Phenyl | Z₁: CH₂F (para) |
| CF₂ | Pyridinyl | NH—CH₂ | Phenyl | Z₁: CH₂F (meta) |
| CF₂ | Pyridinyl | NH—CH₂ | Phenyl | Z₁: CH₂F (ortho) |
| CF₂ | Pyridinyl | NH—CH₂ | Phenyl | Z₁: CHF₂ (para) |
| CF₂ | Pyridinyl | NH—CH₂ | Phenyl | Z₁: CHF₂ (meta) |
| CF₂ | Pyridinyl | NH—CH₂ | Phenyl | Z₁: CHF₂ (ortho) |
| CF₂ | Pyridinyl | NH—CH₂ | Phenyl | Z₁: CF₃ (para) |
| CF₂ | Pyridinyl | NH—CH₂ | Phenyl | Z₁: CF₃ (meta) |
| CF₂ | Pyridinyl | NH—CH₂ | Phenyl | Z₁: CF₃ (ortho) |
| CF₂ | Pyridinyl | NH—CH₂ | Phenyl | Z₁: CH₂—CH₂F (para) |
| CF₂ | Pyridinyl | NH—CH₂ | Phenyl | Z₁: CH₂—CH₂F (meta) |
| CF₂ | Pyridinyl | NH—CH₂ | Phenyl | Z₁: CH₂—CH₂F (ortho) |
| CF₂ | Pyridinyl | NH—CH₂ | Phenyl | Z₁: CH₂—CHF₂ (para) |
| CF₂ | Pyridinyl | NH—CH₂ | Phenyl | Z₁: CH₂—CHF₂ (meta) |
| CF₂ | Pyridinyl | NH—CH₂ | Phenyl | Z₁: CH₂—CHF₂ (ortho) |
| CF₂ | Pyridinyl | NH—CH₂ | Phenyl | Z₁: CH₂—CF₃ (para) |
| CF₂ | Pyridinyl | NH—CH₂ | Phenyl | Z₁: CH₂—CF₃ (meta) |
| CF₂ | Pyridinyl | NH—CH₂ | Phenyl | Z₁: CH₂—CF₃ (ortho) |
| CF₂ | pyridinyl | NH—CH₂ | Pyridinyl | None |
| CF₂ | pyridinyl | NH—CH₂ | Pyridinyl | Z₁: F (para) |
| CF₂ | pyridinyl | NH—CH₂ | Pyridinyl | Z₁: F (meta) |
| CF₂ | pyridinyl | NH—CH₂ | Pyridinyl | Z₁: F (ortho) |
| CF₂ | pyridinyl | NH—CH₂ | Pyridinyl | Z₁: F (para) Z₂: F (meta) |
| CF₂ | Pyridinyl | NH—CH₂ | Pyridinyl | Z₁: Cl (meta) |
| CF₂ | Pyridinyl | NH—CH₂ | Pyridinyl | Z₁: Cl (para) |
| CF₂ | Pyridinyl | NH—CH₂ | Pyridinyl | Z₁: Cl (para) Z₂: Cl (meta) |
| CF₂ | Pyridinyl | NH—CH₂ | Pyridinyl | Z₁: F (para) Z₂: Cl (meta) |
| CF₂ | Pyridinyl | NH—CH₂ | Pyridinyl | Z₁: Cl (para) Z₂: F (meta) |
| CF₂ | Pyridinyl | NH—CH₂ | Pyridinyl | Z₁: CH₃ (para) |
| CF₂ | Pyridinyl | NH—CH₂ | Pyridinyl | Z₁: CH₃ (meta) |
| CF₂ | Pyridinyl | NH—CH₂ | Pyridinyl | Z₁: CH₃ (ortho) |
| CF₂ | Pyridinyl | NH—CH₂ | Pyridinyl | Z₁: CH₂—CH₃ (para) |
| CF₂ | Pyridinyl | NH—CH₂ | Pyridinyl | Z₁: CH₂—CH₃ (meta) |
| CF₂ | Pyridinyl | NH—CH₂ | Pyridinyl | Z₁: CH₂—CH₃ (ortho) |
| CF₂ | Pyridinyl | NH—CH₂ | Pyridinyl | Z₁: CH₂—CH₂—CH₃ or iPr (para) |
| CF₂ | Pyridinyl | NH—CH₂ | Pyridinyl | Z₁: CH₂—CH₂—CH₃ or iPr (meta) |
| CF₂ | Pyridinyl | NH—CH₂ | Pyridinyl | Z₁: CH₂—CH₂—CH₃ or iPr (ortho) |
| CF₂ | Pyridinyl | NH—CH₂ | Pyridinyl | Z₁: CH₂F (para) |
| CF₂ | Pyridinyl | NH—CH₂ | Pyridinyl | Z₁: CH₂F (meta) |
| CF₂ | Pyridinyl | NH—CH₂ | Pyridinyl | Z₁: CH₂F (ortho) |
| CF₂ | Pyridinyl | NH—CH₂ | Pyridinyl | Z₁: CHF₂ (para) |
| CF₂ | Pyridinyl | NH—CH₂ | Pyridinyl | Z₁: CHF₂ (meta) |
| CF₂ | Pyridinyl | NH—CH₂ | Pyridinyl | Z₁: CHF₂ (ortho) |
| CF₂ | Pyridinyl | NH—CH₂ | Pyridinyl | Z₁: CF₃ (para) |
| CF₂ | Pyridinyl | NH—CH₂ | Pyridinyl | Z₁: CF₃ (meta) |
| CF₂ | Pyridinyl | NH—CH₂ | Pyridinyl | Z₁: CF₃ (ortho) |
| CF₂ | Pyridinyl | NH—CH₂ | Pyridinyl | Z₁: CH₂—CH₂F (para) |
| CF₂ | Pyridinyl | NH—CH₂ | Pyridinyl | Z₁: CH₂—CH₂F (meta) |
| CF₂ | Pyridinyl | NH—CH₂ | Pyridinyl | Z₁: CH₂—CH₂F (ortho) |
| CF₂ | Pyridinyl | NH—CH₂ | Pyridinyl | Z₁: CH₂—CHF₂ (para) |
| CF₂ | Pyridinyl | NH—CH₂ | Pyridinyl | Z₁: CH₂—CHF₂ (meta) |
| CF₂ | Pyridinyl | NH—CH₂ | Pyridinyl | Z₁: CH₂—CHF₂ (ortho) |
| CF₂ | Pyridinyl | NH—CH₂ | Pyridinyl | Z₁: CH₂—CF₃ (para) |
| CF₂ | Pyridinyl | NH—CH₂ | Pyridinyl | Z₁: CH₂—CF₃ (meta) |
| CF₂ | Pyridinyl | NH—CH₂ | Pyridinyl | Z₁: CH₂—CF₃ (ortho) |
| CF₂ | pyridinyl | NH—CH₂ | Pyrimidinyl | None |

TABLE 2-continued $L^1-C^1-L^2-C^2-Z_p$

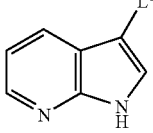

| $L^1$ | $C^1$ | $L^2$ | $C^2$ | Z |
|---|---|---|---|---|
| $CF_2$ | pyridinyl | $NH-CH_2$ | Pyrimidinyl | $Z_1$: F (para) |
| $CF_2$ | pyridinyl | $NH-CH_2$ | Pyrimidinyl | $Z_1$: F (meta) |
| $CF_2$ | pyridinyl | $NH-CH_2$ | Pyrimidinyl | $Z_1$: F (ortho) |
| $CF_2$ | pyridinyl | $NH-CH_2$ | Pyrimidinyl | $Z_1$: F (para) $Z_2$: F (meta) |
| $CF_2$ | Pyridinyl | $NH-CH_2$ | Pyrimidinyl | $Z_1$: Cl (meta) |
| $CF_2$ | Pyridinyl | $NH-CH_2$ | Pyrimidinyl | $Z_1$: Cl (para) |
| $CF_2$ | Pyridinyl | $NH-CH_2$ | Pyrimidinyl | $Z_1$: Cl (para) $Z_2$: Cl (meta) |
| $CF_2$ | Pyridinyl | $NH-CH_2$ | Pyrimidinyl | $Z_1$: F (para) $Z_2$: Cl (meta) |
| $CF_2$ | Pyridinyl | $NH-CH_2$ | Pyrimidinyl | $Z_1$: Cl (para) $Z_2$: F (meta) |
| $CF_2$ | Pyridinyl | $NH-CH_2$ | Pyrimidinyl | $Z_1$: $CH_3$ (para) |
| $CF_2$ | Pyridinyl | $NH-CH_2$ | Pyrimidinyl | $Z_1$: $CH_3$ (meta) |
| $CF_2$ | Pyridinyl | $NH-CH_2$ | Pyrimidinyl | $Z_1$: $CH_3$ (ortho) |
| $CF_2$ | Pyridinyl | $NH-CH_2$ | Pyrimidinyl | $Z_1$: $CH_2-CH_3$ (para) |
| $CF_2$ | Pyridinyl | $NH-CH_2$ | Pyrimidinyl | $Z_1$: $CH_2-CH_3$ (meta) |
| $CF_2$ | Pyridinyl | $NH-CH_2$ | Pyrimidinyl | $Z_1$: $CH_2-CH_3$ (ortho) |
| $CF_2$ | Pyridinyl | $NH-CH_2$ | Pyrimidinyl | $Z_1$: $CH_2-CH_2-CH_3$ or iPr (para) |
| $CF_2$ | Pyridinyl | $NH-CH_2$ | Pyrimidinyl | $Z_3$: $CH_2-CH_2-CH_3$ or iPr (meta) |
| $CF_2$ | Pyridinyl | $NH-CH_2$ | Pyrimidinyl | $Z_1$: $CH_2-CH_2-CH_3$ or iPr (ortho) |
| $CF_2$ | Pyridinyl | $NH-CH_2$ | Pyrimidinyl | $Z_1$: $CH_2F$ (para) |
| $CF_2$ | Pyridinyl | $NH-CH_2$ | Pyrimidinyl | $Z_1$: $CH_2F$ (meta) |
| $CF_2$ | Pyridinyl | $NH-CH_2$ | Pyrimidinyl | $Z_1$: $CH_2F$ (ortho) |
| $CF_2$ | Pyridinyl | $NH-CH_2$ | Pyrimidinyl | $Z_1$: $CHF_2$ (para) |
| $CF_2$ | Pyridinyl | $NH-CH_2$ | Pyrimidinyl | $Z_1$: $CHF_2$ (meta) |
| $CF_2$ | Pyridinyl | $NH-CH_2$ | Pyrimidinyl | $Z_1$: $CHF_2$ (ortho) |
| $CF_2$ | Pyridinyl | $NH-CH_2$ | Pyrimidinyl | $Z_1$: $CF_3$ (para) |
| $CF_2$ | Pyridinyl | $NH-CH_2$ | Pyrimidinyl | $Z_1$: $CF_3$ (meta) |
| $CF_2$ | Pyridinyl | $NH-CH_2$ | Pyrimidinyl | $Z_1$: $CF_3$ (ortho) |
| $CF_2$ | Pyridinyl | $NH-CH_2$ | Pyrimidinyl | $Z_1$: $CH_2-CH_2F$ (para) |
| $CF_2$ | Pyridinyl | $NH-CH_2$ | Pyrimidinyl | $Z_1$: $CH_2-CH_2F$ (meta) |
| $CF_2$ | Pyridinyl | $NH-CH_2$ | Pyrimidinyl | $Z_1$: $CH_2-CH_2F$ (ortho) |
| $CF_2$ | Pyridinyl | $NH-CH_2$ | Pyrimidinyl | $Z_1$: $CH_2-CHF_2$ (para) |
| $CF_2$ | Pyridinyl | $NH-CH_2$ | Pyrimidinyl | $Z_1$: $CH_2-CHF_2$ (meta) |
| $CF_2$ | Pyridinyl | $NH-CH_2$ | Pyrimidinyl | $Z_1$: $CH_2-CHF_2$ (ortho) |
| $CF_2$ | Pyridinyl | $NH-CH_2$ | Pyrimidinyl | $Z_1$: $CH_2-CF_3$ (para) |
| $CF_2$ | Pyridinyl | $NH-CH_2$ | Pyrimidinyl | $Z_1$: $CH_2-CF_3$ (meta) |
| $CF_2$ | Pyridinyl | $NH-CH_2$ | Pyrimidinyl | $Z_1$: $CH_2-CF_3$ (ortho) |
| $CF_2$ | pyridinyl | $NH-CH_2$ | Pyrazinyl | None |
| $CF_2$ | pyridinyl | $NH-CH_2$ | Pyrazinyl | $Z_1$: F (para) |
| $CF_2$ | pyridinyl | $NH-CH_2$ | Pyrazinyl | $Z_1$: F (meta) |
| $CF_2$ | pyridinyl | $NH-CH_2$ | Pyrazinyl | $Z_1$: F (ortho) |
| $CF_2$ | pyridinyl | $NH-CH_2$ | Pyrazinyl | $Z_1$: F (para) $Z_2$: F (meta) |
| $CF_2$ | Pyridinyl | $NH-CH_2$ | Pyrazinyl | $Z_1$: Cl (meta) |
| $CF_2$ | Pyridinyl | $NH-CH_2$ | Pyrazinyl | $Z_1$: Cl (para) |
| $CF_2$ | Pyridinyl | $NH-CH_2$ | Pyrazinyl | $Z_1$: Cl (para) $Z_2$: Cl (meta) |
| $CF_2$ | Pyridinyl | $NH-CH_2$ | Pyrazinyl | $Z_1$: F (para) $Z_2$: Cl (meta) |
| $CF_2$ | Pyridinyl | $NH-CH_2$ | Pyrazinyl | $Z_1$: Cl (para) $Z_2$: F (meta) |
| $CF_2$ | Pyridinyl | $NH-CH_2$ | Pyrazinyl | $Z_1$: $CH_3$ (para) |
| $CF_2$ | Pyridinyl | $NH-CH_2$ | Pyrazinyl | $Z_1$: $CH_3$ (meta) |
| $CF_2$ | Pyridinyl | $NH-CH_2$ | Pyrazinyl | $Z_1$: $CH_3$ (ortho) |
| $CF_2$ | Pyridinyl | $NH-CH_2$ | Pyrazinyl | $Z_1$: $CH_2-CH_3$ (para) |
| $CF_2$ | Pyridinyl | $NH-CH_2$ | Pyrazinyl | $Z_1$: $CH_2-CH_3$ (meta) |
| $CF_2$ | Pyridinyl | $NH-CH_2$ | Pyrazinyl | $Z_1$: $CH_2-CH_3$ (ortho) |
| $CF_2$ | Pyridinyl | $NH-CH_2$ | Pyrazinyl | $Z_1$: $CH_2-CH_2-CH_3$ or iPr (para) |
| $CF_2$ | Pyridinyl | $NH-CH_2$ | Pyrazinyl | $Z_1$: $CH_2-CH_2-CH_3$ or iPr (meta) |
| $CF_2$ | Pyridinyl | $NH-CH_2$ | Pyrazinyl | $Z_1$: $CH_2-CH_2-CH_3$ or iPr (ortho) |

TABLE 2-continued

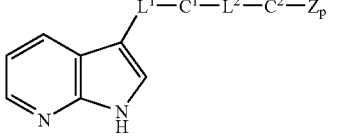

| L¹ | C¹ | L² | C² | Z |
|---|---|---|---|---|
| $CF_2$ | Pyridinyl | NH—CH$_2$ | Pyrazinyl | $Z_1$: CH$_2$F (para) |
| $CF_2$ | Pyridinyl | NH—CH$_2$ | Pyrazinyl | $Z_1$: CH$_2$F (meta) |
| $CF_2$ | Pyridinyl | NH—CH$_2$ | Pyrazinyl | $Z_1$: CH$_2$F (ortho) |
| $CF_2$ | Pyridinyl | NH—CH$_2$ | Pyrazinyl | $Z_1$: CHF$_2$ (para) |
| $CF_2$ | Pyridinyl | NH—CH$_2$ | Pyrazinyl | $Z_1$: CHF$_2$ (meta) |
| $CF_2$ | Pyridinyl | NH—CH$_2$ | Pyrazinyl | $Z_1$: CHF$_2$ (ortho) |
| $CF_2$ | Pyridinyl | NH—CH$_2$ | Pyrazinyl | $Z_1$: CF$_3$ (para) |
| $CF_2$ | Pyridinyl | NH—CH$_2$ | Pyrazinyl | $Z_1$: CF$_3$ (meta) |
| $CF_2$ | Pyridinyl | NH—CH$_2$ | Pyrazinyl | $Z_1$: CF$_3$ (ortho) |
| $CF_2$ | Pyridinyl | NH—CH$_2$ | Pyrazinyl | $Z_1$: CH$_2$—CH$_2$F (para) |
| $CF_2$ | Pyridinyl | NH—CH$_2$ | Pyrazinyl | $Z_1$: CH$_2$—CH$_2$F (meta) |
| $CF_2$ | Pyridinyl | NH—CH$_2$ | Pyrazinyl | $Z_1$: CH$_2$—CH$_2$F (ortho) |
| $CF_2$ | Pyridinyl | NH—CH$_2$ | Pyrazinyl | $Z_1$: CH$_2$—CHF$_2$ (para) |
| $CF_2$ | Pyridinyl | NH—CH$_2$ | Pyrazinyl | $Z_1$: CH$_2$—CHF$_2$ (meta) |
| $CF_2$ | Pyridinyl | NH—CH$_2$ | Pyrazinyl | $Z_1$: CH$_2$—CHF$_2$ (ortho) |
| $CF_2$ | Pyridinyl | NH—CH$_2$ | Pyrazinyl | $Z_1$: CH$_2$—CF$_3$ (para) |
| $CF_2$ | Pyridinyl | NH—CH$_2$ | Pyrazinyl | $Z_1$: CH$_2$—CF$_3$ (meta) |
| $CF_2$ | Pyridinyl | NH—CH$_2$ | Pyrazinyl | $Z_1$: CH$_2$—CF$_3$ (ortho) |
| $CF_2$ | pyridinyl | NH—CH$_2$ | Pyrrolyl | None |
| $CF_2$ | pyridinyl | NH—CH$_2$ | Pyrrolyl | $Z_1$: F (2) |
| $CF_2$ | pyridinyl | NH—CH$_2$ | Pyrrolyl | $Z_1$: F (3) |
| $CF_2$ | pyridinyl | NH—CH$_2$ | Pyrrolyl | $Z_1$: F (2) $Z_2$: F (3) |
| $CF_2$ | Pyridinyl | NH—CH$_2$ | Pyrrolyl | $Z_1$: Cl (2) |
| $CF_2$ | Pyridinyl | NH—CH$_2$ | Pyrrolyl | $Z_1$: Cl (3) |
| $CF_2$ | Pyridinyl | NH—CH$_2$ | Pyrrolyl | $Z_1$: Cl (2) $Z_2$: Cl (3) |
| $CF_2$ | Pyridinyl | NH—CH$_2$ | Pyrrolyl | $Z_1$: F (2) $Z_2$: Cl (3) |
| $CF_2$ | Pyridinyl | NH—CH$_2$ | Pyrrolyl | $Z_1$: Cl (2) $Z_2$: F (3) |
| $CF_2$ | Pyridinyl | NH—CH$_2$ | Pyrrolyl | $Z_1$: CH$_3$ (2) |
| $CF_2$ | Pyridinyl | NH—CH$_2$ | Pyrrolyl | $Z_1$: CH$_3$ (3) |
| $CF_2$ | Pyridinyl | NH—CH$_2$ | Pyrrolyl | $Z_1$: CH$_2$—CH$_3$ (2) |
| $CF_2$ | Pyridinyl | NH—CH$_2$ | Pyrrolyl | $Z_1$: CH$_2$—CH$_3$ (3) |
| $CF_2$ | Pyridinyl | NH—CH$_2$ | Pyrrolyl | $Z_1$: CH$_2$—CH$_2$—CH$_3$ or iPr (2) |
| $CF_2$ | Pyridinyl | NH—CH$_2$ | Pyrrolyl | $Z_1$: CH$_2$—CH$_2$—CH$_3$ or iPr (3) |
| $CF_2$ | Pyridinyl | NH—CH$_2$ | Pyrrolyl | $Z_1$: CH$_2$F (2) |
| $CF_2$ | Pyridinyl | NH—CH$_2$ | Pyrrolyl | $Z_1$: CH$_2$F (3) |
| $CF_2$ | Pyridinyl | NH—CH$_2$ | Pyrrolyl | $Z_1$: CHF$_2$ (2) |
| $CF_2$ | Pyridinyl | NH—CH$_2$ | Pyrrolyl | $Z_1$: CHF$_2$ (3) |
| $CF_2$ | Pyridinyl | NH—CH$_2$ | Pyrrolyl | $Z_1$: CF$_3$ (2) |
| $CF_2$ | Pyridinyl | NH—CH$_2$ | Pyrrolyl | $Z_1$: CF$_3$ (3) |
| $CF_2$ | Pyridinyl | NH—CH$_2$ | Pyrrolyl | $Z_1$: CH$_2$—CH$_2$F (2) |
| $CF_2$ | Pyridinyl | NH—CH$_2$ | Pyrrolyl | $Z_1$: CH$_2$—CH$_2$F (3) |
| $CF_2$ | Pyridinyl | NH—CH$_2$ | Pyrrolyl | $Z_1$: CH$_2$—CHF$_2$ (2) |
| $CF_2$ | Pyridinyl | NH—CH$_2$ | Pyrrolyl | $Z_1$: CH$_2$—CHF$_2$ (3) |
| $CF_2$ | Pyridinyl | NH—CH$_2$ | Pyrrolyl | $Z_1$: CH$_2$—CF$_3$ (2) |
| $CF_2$ | Pyridinyl | NH—CH$_2$ | Pyrrolyl | $Z_1$: CH$_2$—CF$_3$ (3) |
| $CF_2$ | pyridinyl | NH—CH$_2$ | Imidazolyl | None |
| $CF_2$ | pyridinyl | NH—CH$_2$ | Imidazolyl | $Z_1$: F (2) |
| $CF_2$ | pyridinyl | NH—CH$_2$ | Imidazolyl | $Z_1$: F (3) |
| $CF_2$ | pyridinyl | NH—CH$_2$ | Imidazolyl | $Z_1$: F (2) $Z_2$: F (3) |
| $CF_2$ | Pyridinyl | NH—CH$_2$ | Imidazolyl | $Z_1$: Cl (2) |
| $CF_2$ | Pyridinyl | NH—CH$_2$ | Imidazolyl | $Z_1$: Cl (3) |
| $CF_2$ | Pyridinyl | NH—CH$_2$ | Imidazolyl | $Z_1$: Cl (2) $Z_2$: Cl (3) |
| $CF_2$ | Pyridinyl | NH—CH$_2$ | Imidazolyl | $Z_1$: F (2) $Z_2$: Cl (3) |
| $CF_2$ | Pyridinyl | NH—CH$_2$ | Imidazolyl | $Z_1$: Cl (2) $Z_2$: F (3) |
| $CF_2$ | Pyridinyl | NH—CH$_2$ | Imidazolyl | $Z_1$: CH$_3$ (2) |
| $CF_2$ | Pyridinyl | NH—CH$_2$ | Imidazolyl | $Z_1$: CH$_3$ (3) |
| $CF_2$ | Pyridinyl | NH—CH$_2$ | Imidazolyl | $Z_1$: CH$_2$—CH$_3$ (2) |
| $CF_2$ | Pyridinyl | NH—CH$_2$ | Imidazolyl | $Z_1$: CH$_2$—CH$_3$ (3) |
| $CF_2$ | Pyridinyl | NH—CH$_2$ | Imidazolyl | $Z_1$: CH$_2$—CH$_2$—CH$_3$ or iPr (2) |
| $CF_2$ | Pyridinyl | NH—CH$_2$ | Imidazolyl | $Z_1$: CH$_2$—CH$_2$—CH$_3$ or iPr (3) |
| $CF_2$ | Pyridinyl | NH—CH$_2$ | Imidazolyl | $Z_1$: CH$_2$F (2) |

TABLE 2-continued

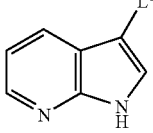

| L¹ | C¹ | L² | C² | Z |
|---|---|---|---|---|
| CF₂ | Pyridinyl | NH—CH₂ | Imidazolyl | $Z_1$: CH₂F (3) |
| CF₂ | Pyridinyl | NH—CH₂ | Imidazolyl | $Z_1$: CHF₂ (2) |
| CF₂ | Pyridinyl | NH—CH₂ | Imidazolyl | $Z_1$: CHF₂ (3) |
| CF₂ | Pyridinyl | NH—CH₂ | Imidazolyl | $Z_1$: CF₃ (2) |
| CF₂ | Pyridinyl | NH—CH₂ | Imidazolyl | $Z_1$: CF₃ (3) |
| CF₂ | Pyridinyl | NH—CH₂ | Imidazolyl | $Z_1$: CH₂—CH₂F (2) |
| CF₂ | Pyridinyl | NH—CH₂ | Imidazolyl | $Z_1$: CH₂—CH₂F (3) |
| CF₂ | Pyridinyl | NH—CH₂ | Imidazolyl | $Z_1$: CH₂—CHF₂ (2) |
| CF₂ | Pyridinyl | NH—CH₂ | Imidazolyl | $Z_1$: CH₂—CHF₂ (3) |
| CF₂ | Pyridinyl | NH—CH₂ | Imidazolyl | $Z_1$: CH₂—CF₃ (2) |
| CF₂ | Pyridinyl | NH—CH₂ | Imidazolyl | $Z_1$: CH₂—CF₃ (3) |
| CF₂ | pyridinyl | NH—CH₂ | Furanyl | None |
| CF₂ | pyridinyl | NH—CH₂ | Furanyl | $Z_1$: F (2) |
| CF₂ | pyridinyl | NH—CH₂ | Furanyl | $Z_1$: F (3) |
| CF₂ | pyridinyl | NH—CH₂ | Furanyl | $Z_1$: F (2)<br>$Z_2$: F (3) |
| CF₂ | Pyridinyl | NH—CH₂ | Furanyl | $Z_1$: Cl (2) |
| CF₂ | Pyridinyl | NH—CH₂ | Furanyl | $Z_1$: Cl (3) |
| CF₂ | Pyridinyl | NH—CH₂ | Furanyl | $Z_1$: Cl (2)<br>$Z_2$: Cl (3) |
| CF₂ | Pyridinyl | NH—CH₂ | Furanyl | $Z_1$: F (2)<br>$Z_2$: Cl (3) |
| CF₂ | Pyridinyl | NH—CH₂ | Furanyl | $Z_1$: Cl (2)<br>$Z_2$: F (3) |
| CF₂ | Pyridinyl | NH—CH₂ | Furanyl | $Z_1$: CH₃ (2) |
| CF₂ | Pyridinyl | NH—CH₂ | Furanyl | $Z_1$: CH₃ (3) |
| CF₂ | Pyridinyl | NH—CH₂ | Furanyl | $Z_1$: CH₂—CH₃ (2) |
| CF₂ | Pyridinyl | NH—CH₂ | Furanyl | $Z_1$: CH₂—CH₃ (3) |
| CF₂ | Pyridinyl | NH—CH₂ | Furanyl | $Z_1$: CH₂—CH₂—CH₃ or iPr (2) |
| CF₂ | Pyridinyl | NH—CH₂ | Furanyl | $Z_1$: CH₂—CH₂—CH₃ or iPr (3) |
| CF₂ | Pyridinyl | NH—CH₂ | Furanyl | $Z_1$: CH₂F (2) |
| CF₂ | Pyridinyl | NH—CH₂ | Furanyl | $Z_1$: CH₂F (3) |
| CF₂ | Pyridinyl | NH—CH₂ | Furanyl | $Z_1$: CHF₂ (2) |
| CF₂ | Pyridinyl | NH—CH₂ | Furanyl | $Z_1$: CHF₂ (3) |
| CF₂ | Pyridinyl | NH—CH₂ | Furanyl | $Z_1$: CF₃ (2) |
| CF₂ | Pyridinyl | NH—CH₂ | Furanyl | $Z_1$: CF₃ (3) |
| CF₂ | Pyridinyl | NH—CH₂ | Furanyl | $Z_1$: CH₂—CH₂F (2) |
| CF₂ | Pyridinyl | NH—CH₂ | Furanyl | $Z_1$: CH₂—CH₂F (3) |
| CF₂ | Pyridinyl | NH—CH₂ | Furanyl | $Z_1$: CH₂—CHF₂ (2) |
| CF₂ | Pyridinyl | NH—CH₂ | Furanyl | $Z_1$: CH₂—CHF₂ (3) |
| CF₂ | Pyridinyl | NH—CH₂ | Furanyl | $Z_1$: CH₂—CF₃ (2) |
| CF₂ | Pyridinyl | NH—CH₂ | Furanyl | $Z_1$: CH₂—CF₃ (3) |
| CF₂ | pyridinyl | NH—CH₂ | Oxazolyl | None |
| CF₂ | pyridinyl | NH—CH₂ | Oxazolyl | $Z_1$: F (2) |
| CF₂ | pyridinyl | NH—CH₂ | Oxazolyl | $Z_1$: F (3) |
| CF₂ | pyridinyl | NH—CH₂ | Oxazolyl | $Z_1$: F (2)<br>$Z_2$: F (3) |
| CF₂ | Pyridinyl | NH—CH₂ | Oxazolyl | $Z_1$: Cl (2) |
| CF₂ | Pyridinyl | NH—CH₂ | Oxazolyl | $Z_1$: Cl (3) |
| CF₂ | Pyridinyl | NH—CH₂ | Oxazolyl | $Z_1$: Cl (2)<br>$Z_2$: Cl (3) |
| CF₂ | Pyridinyl | NH—CH₂ | Oxazolyl | $Z_1$: F (2)<br>$Z_2$: Cl (3) |
| CF₂ | Pyridinyl | NH—CH₂ | Oxazolyl | $Z_1$: Cl (2)<br>$Z_2$: F (3) |
| CF₂ | Pyridinyl | NH—CH₂ | Oxazolyl | $Z_1$: CH₃ (2) |
| CF₂ | Pyridinyl | NH—CH₂ | Oxazolyl | $Z_1$: CH₃ (3) |
| CF₂ | Pyridinyl | NH—CH₂ | Oxazolyl | $Z_1$: CH₂—CH₃ (2) |
| CF₂ | Pyridinyl | NH—CH₂ | Oxazolyl | $Z_1$: CH₂—CH₃ (3) |
| CF₂ | Pyridinyl | NH—CH₂ | Oxazolyl | $Z_1$: CH₂—CH₂—CH₃ or iPr (2) |
| CF₂ | Pyridinyl | NH—CH₂ | Oxazolyl | $Z_1$: CH₂—CH₂—CH₃ or iPr (3) |
| CF₂ | Pyridinyl | NH—CH₂ | Oxazolyl | $Z_1$: CH₂F (2) |
| CF₂ | Pyridinyl | NH—CH₂ | Oxazolyl | $Z_1$: CH₂F (3) |
| CF₂ | Pyridinyl | NH—CH₂ | Oxazolyl | $Z_1$: CHF₂ (2) |
| CF₂ | Pyridinyl | NH—CH₂ | Oxazolyl | $Z_1$: CHF₂ (3) |
| CF₂ | Pyridinyl | NH—CH₂ | Oxazolyl | $Z_1$: CF₃ (2) |
| CF₂ | Pyridinyl | NH—CH₂ | Oxazolyl | $Z_1$: CF₃ (3) |
| CF₂ | Pyridinyl | NH—CH₂ | Oxazolyl | $Z_1$: CH₂—CH₂F (2) |
| CF₂ | Pyridinyl | NH—CH₂ | Oxazolyl | $Z_1$: CH₂—CH₂F (3) |

TABLE 2-continued

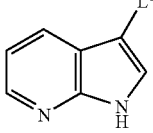

| L¹ | C¹ | L² | C² | Z |
|---|---|---|---|---|
| $CF_2$ | Pyridinyl | NH—$CH_2$ | Oxazolyl | $Z_1$: $CH_2$—$CHF_2$ (2) |
| $CF_2$ | Pyridinyl | NH—$CH_2$ | Oxazolyl | $Z_1$: $CH_2$—$CHF_2$ (3) |
| $CF_2$ | Pyridinyl | NH—$CH_2$ | Oxazolyl | $Z_1$: $CH_2$—$CF_3$ (2) |
| $CF_2$ | Pyridinyl | NH—$CH_2$ | Oxazolyl | $Z_1$: $CH_2$—$CF_3$ (3) |
| $CF_2$ | pyridinyl | NH—$CH_2$ | Thiophenyl | None |
| $CF_2$ | pyridinyl | NH—$CH_2$ | Thiophenyl | $Z_1$: F (2) |
| $CF_2$ | pyridinyl | NH—$CH_2$ | Thiophenyl | $Z_1$: F (3) |
| $CF_2$ | pyridinyl | NH—$CH_2$ | Thiophenyl | $Z_1$: F (2)<br>$Z_2$: F (3) |
| $CF_2$ | Pyridinyl | NH—$CH_2$ | Thiophenyl | $Z_1$: Cl (2) |
| $CF_2$ | Pyridinyl | NH—$CH_2$ | Thiophenyl | $Z_1$: Cl (3) |
| $CF_2$ | Pyridinyl | NH—$CH_2$ | Thiophenyl | $Z_1$: Cl (2)<br>$Z_2$: Cl (3) |
| $CF_2$ | Pyridinyl | NH—$CH_2$ | Thiophenyl | $Z_1$: F (2)<br>$Z_2$: Cl (3) |
| $CF_2$ | Pyridinyl | NH—$CH_2$ | Thiophenyl | $Z_1$: Cl (2)<br>$Z_2$: F (3) |
| $CF_2$ | Pyridinyl | NH—$CH_2$ | Thiophenyl | $Z_1$: $CH_3$ (2) |
| $CF_2$ | Pyridinyl | NH—$CH_2$ | Thiophenyl | $Z_1$: $CH_3$ (3) |
| $CF_2$ | Pyridinyl | NH—$CH_2$ | Thiophenyl | $Z_1$: $CH_2$—$CH_3$ (2) |
| $CF_2$ | Pyridinyl | NH—$CH_2$ | Thiophenyl | $Z_1$: $CH_2$—$CH_3$ (3) |
| $CF_2$ | Pyridinyl | NH—$CH_2$ | Thiophenyl | $Z_1$: $CH_2$—$CH_2$—$CH_3$ or iPr (2) |
| $CF_2$ | Pyridinyl | NH—$CH_2$ | Thiophenyl | $Z_1$: $CH_2$—$CH_2$—$CH_3$ or iPr (3) |
| $CF_2$ | Pyridinyl | NH—$CH_2$ | Thiophenyl | $Z_1$: $CH_2F$ (2) |
| $CF_2$ | Pyridinyl | NH—$CH_2$ | Thiophenyl | $Z_1$: $CH_2F$ (3) |
| $CF_2$ | Pyridinyl | NH—$CH_2$ | Thiophenyl | $Z_1$: $CHF_2$ (2) |
| $CF_2$ | Pyridinyl | NH—$CH_2$ | Thiophenyl | $Z_1$: $CHF_2$ (3) |
| $CF_2$ | Pyridinyl | NH—$CH_2$ | Thiophenyl | $Z_1$: $CF_3$ (2) |
| $CF_2$ | Pyridinyl | NH—$CH_2$ | Thiophenyl | $Z_1$: $CF_3$ (3) |
| $CF_2$ | Pyridinyl | NH—$CH_2$ | Thiophenyl | $Z_1$: $CH_2$—$CH_2F$ (2) |
| $CF_2$ | Pyridinyl | NH—$CH_2$ | Thiophenyl | $Z_1$: $CH_2$—$CH_2F$ (3) |
| $CF_2$ | Pyridinyl | NH—$CH_2$ | Thiophenyl | $Z_1$: $CH_2$—$CHF_2$ (2) |
| $CF_2$ | Pyridinyl | NH—$CH_2$ | Thiophenyl | $Z_1$: $CH_2$—$CHF_2$ (3) |
| $CF_2$ | Pyridinyl | NH—$CH_2$ | Thiophenyl | $Z_1$: $CH_2$—$CF_3$ (2) |
| $CF_2$ | Pyridinyl | NH—$CH_2$ | Thiophenyl | $Z_1$: $CH_2$—$CF_3$ (3) |
| $CF_2$ | pyridinyl | NH—$CH_2$ | Thiazolyl | None |
| $CF_2$ | pyridinyl | NH—$CH_2$ | Thiazolyl | $Z_1$: F (2) |
| $CF_2$ | pyridinyl | NH—$CH_2$ | Thiazolyl | $Z_1$: F (3) |
| $CF_2$ | pyridinyl | NH—$CH_2$ | Thiazolyl | $Z_1$: F (2)<br>$Z_2$: F (3) |
| $CF_2$ | Pyridinyl | NH—$CH_2$ | Thiazolyl | $Z_1$: Cl (2) |
| $CF_2$ | Pyridinyl | NH—$CH_2$ | Thiazolyl | $Z_1$: Cl (3) |
| $CF_2$ | Pyridinyl | NH—$CH_2$ | Thiazolyl | $Z_1$: Cl (2)<br>$Z_2$: Cl (3) |
| $CF_2$ | Pyridinyl | NH—$CH_2$ | Thiazolyl | $Z_1$: F (2)<br>$Z_2$: Cl (3) |
| $CF_2$ | Pyridinyl | NH—$CH_2$ | Thiazolyl | $Z_1$: Cl (2)<br>$Z_2$: F (3) |
| $CF_2$ | Pyridinyl | NH—$CH_2$ | Thiazolyl | $Z_1$: $CH_3$ (2) |
| $CF_2$ | Pyridinyl | NH—$CH_2$ | Thiazolyl | $Z_1$: $CH_3$ (3) |
| $CF_2$ | Pyridinyl | NH—$CH_2$ | Thiazolyl | $Z_1$: $CH_2$—$CH_3$ (2) |
| $CF_2$ | Pyridinyl | NH—$CH_2$ | Thiazolyl | $Z_1$: $CH_2$—$CH_3$ (3) |
| $CF_2$ | Pyridinyl | NH—$CH_2$ | Thiazolyl | $Z_1$: $CH_2$—$CH_2$—$CH_3$ or iPr (2) |
| $CF_2$ | Pyridinyl | NH—$CH_2$ | Thiazolyl | $Z_1$: $CH_2$—$CH_2$—$CH_3$ or iPr (3) |
| $CF_2$ | Pyridinyl | NH—$CH_2$ | Thiazolyl | $Z_1$: $CH_2F$ (2) |
| $CF_2$ | Pyridinyl | NH—$CH_2$ | Thiazolyl | $Z_1$: $CH_2F$ (3) |
| $CF_2$ | Pyridinyl | NH—$CH_2$ | Thiazolyl | $Z_1$: $CHF_2$ (2) |
| $CF_2$ | Pyridinyl | NH—$CH_2$ | Thiazolyl | $Z_1$: $CHF_2$ (3) |
| $CF_2$ | Pyridinyl | NH—$CH_2$ | Thiazolyl | $Z_1$: $CF_3$ (2) |
| $CF_2$ | Pyridinyl | NH—$CH_2$ | Thiazolyl | $Z_1$: $CF_3$ (3) |
| $CF_2$ | Pyridinyl | NH—$CH_2$ | Thiazolyl | $Z_1$: $CH_2$—$CH_2F$ (2) |
| $CF_2$ | Pyridinyl | NH—$CH_2$ | Thiazolyl | $Z_1$: $CH_2$—$CH_2F$ (3) |
| $CF_2$ | Pyridinyl | NH—$CH_2$ | Thiazolyl | $Z_1$: $CH_2$—$CHF_2$ (2) |
| $CF_2$ | Pyridinyl | NH—$CH_2$ | Thiazolyl | $Z_1$: $CH_2$—$CHF_2$ (3) |
| $CF_2$ | Pyridinyl | NH—$CH_2$ | Thiazolyl | $Z_1$: $CH_2$—$CF_3$ (2) |
| $CF_2$ | Pyridinyl | NH—$CH_2$ | Thiazolyl | $Z_1$: $CH_2$—$CF_3$ (3) |
| $CF_2$ | pyridinyl | NH—C(O) | Phenyl | None |
| $CF_2$ | pyridinyl | NH—C(O) | Phenyl | $Z_1$: F (para) |
| $CF_2$ | pyridinyl | NH—C(O) | phenyl | $Z_1$: F (meta) |

TABLE 2-continued

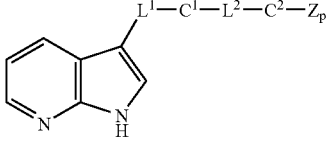

| L¹ | C¹ | L² | C² | Z |
|---|---|---|---|---|
| CF₂ | pyridinyl | NH—C(O) | phenyl | $Z_1$: F (ortho) |
| CF₂ | pyridinyl | NH—C(O) | phenyl | $Z_1$: F (para) |
| | | | | $Z_2$: F (meta) |
| CF₂ | Pyridinyl | NH—C(O) | Phenyl | $Z_1$: Cl (meta) |
| CF₂ | Pyridinyl | NH—C(O) | Phenyl | $Z_1$: Cl (para) |
| CF₂ | Pyridinyl | NH—C(O) | Phenyl | $Z_1$: Cl (para) |
| | | | | $Z_2$: Cl (meta) |
| CF₂ | Pyridinyl | NH—C(O) | Phenyl | $Z_1$: F (para) |
| | | | | $Z_2$: Cl (meta) |
| CF₂ | Pyridinyl | NH—C(O) | Phenyl | $Z_1$: Cl (para) |
| | | | | $Z_2$: F (meta) |
| CF₂ | Pyridinyl | NH—C(O) | Phenyl | $Z_1$: CHF (para) |
| CF₂ | Pyridinyl | NH—C(O) | Phenyl | $Z_1$: CH₃ (meta) |
| CF₂ | Pyridinyl | NH—C(O) | Phenyl | $Z_1$: CH₃ (ortho) |
| CF₂ | Pyridinyl | NH—C(O) | Phenyl | $Z_1$: CH₂—CH₃ (para) |
| CF₂ | Pyridinyl | NH—C(O) | Phenyl | $Z_1$: CH₂—CH₃ (meta) |
| CF₂ | Pyridinyl | NH—C(O) | Phenyl | $Z_1$: CH₂—CH₃ (ortho) |
| CF₂ | Pyridinyl | NH—C(O) | Phenyl | $Z_1$: CH₂—CH₂—CH₃ or iPr (para) |
| CF₂ | Pyridinyl | NH—C(O) | Phenyl | $Z_1$: CH₂—CH₂—CH₃ or iPr (meta) |
| CF₂ | Pyridinyl | NH—C(O) | Phenyl | $Z_1$: CH₂—CH₂—CH₃ or iPr (ortho) |
| CF₂ | Pyridinyl | NH—C(O) | Phenyl | $Z_1$: CH₂F (para) |
| CF₂ | Pyridinyl | NH—C(O) | Phenyl | $Z_1$: CH₂F (meta) |
| CF₂ | Pyridinyl | NH—C(O) | Phenyl | $Z_1$: CH₂F (ortho) |
| CF₂ | Pyridinyl | NH—C(O) | Phenyl | $Z_1$: CHF₂ (para) |
| CF₂ | Pyridinyl | NH—C(O) | Phenyl | $Z_1$: CHF₂ (meta) |
| CF₂ | Pyridinyl | NH—C(O) | Phenyl | $Z_1$: CHF₂ (ortho) |
| CF₂ | Pyridinyl | NH—C(O) | Phenyl | $Z_1$: CF₃ (para) |
| CF₂ | Pyridinyl | NH—C(O) | Phenyl | $Z_1$: CF₃ (meta) |
| CF₂ | Pyridinyl | NH—C(O) | Phenyl | $Z_1$: CF₃ (ortho) |
| CF₂ | Pyridinyl | NH—C(O) | Phenyl | $Z_1$: CH₂—CH₂F (para) |
| CF₂ | Pyridinyl | NH—C(O) | Phenyl | $Z_1$: CH₂—CH₂F (meta) |
| CF₂ | Pyridinyl | NH—C(O) | Phenyl | $Z_1$: CH₂—CH₂F (ortho) |
| CF₂ | Pyridinyl | NH—C(O) | Phenyl | $Z_1$: CH₂—CHF₂ (para) |
| CF₂ | Pyridinyl | NH—C(O) | Phenyl | $Z_1$: CH₂—CHF₂ (meta) |
| CF₂ | Pyridinyl | NH—C(O) | Phenyl | $Z_1$: CH₂—CHF₂ (ortho) |
| CF₂ | Pyridinyl | NH—C(O) | Phenyl | $Z_1$: CH₂—CF₃ (para) |
| CF₂ | Pyridinyl | NH—C(O) | Phenyl | $Z_1$: CH₂—CF₃ (meta) |
| CF₂ | Pyridinyl | NH—C(O) | Phenyl | $Z_1$: CH₂—CF₃ (ortho) |
| CF₂ | pyridinyl | NH—C(O) | Pyridinyl | None |
| CF₂ | pyridinyl | NH—C(O) | Pyridinyl | $Z_1$: F (para) |
| CF₂ | pyridinyl | NH—C(O) | Pyridinyl | $Z_1$: F (meta) |
| CF₂ | pyridinyl | NH—C(O) | Pyridinyl | $Z_1$: F (ortho) |
| CF₂ | pyridinyl | NH—C(O) | Pyridinyl | $Z_1$: F (para) |
| | | | | $Z_2$: F (meta) |
| CF₂ | Pyridinyl | NH—C(O) | Pyridinyl | $Z_1$: Cl (meta) |
| CF₂ | Pyridinyl | NH—C(O) | Pyridinyl | $Z_1$: Cl (para) |
| CF₂ | Pyridinyl | NH—C(O) | Pyridinyl | $Z_1$: Cl (para) |
| | | | | $Z_2$: Cl (meta) |
| CF₂ | Pyridinyl | NH—C(O) | Pyridinyl | $Z_1$: F (para) |
| | | | | $Z_2$: Cl (meta) |
| CF₂ | Pyridinyl | NH—C(O) | Pyridinyl | $Z_1$: Cl (para) |
| | | | | $Z_2$: F (meta) |
| CF₂ | Pyridinyl | NH—C(O) | Pyridinyl | $Z_1$: CH₃ (para) |
| CF₂ | Pyridinyl | NH—C(O) | Pyridinyl | $Z_1$: CH₃ (meta) |
| CF₂ | Pyridinyl | NH—C(O) | Pyridinyl | $Z_1$: CH₃ (ortho) |
| CF₂ | Pyridinyl | NH—C(O) | Pyridinyl | $Z_1$: CH₂—CH₃ (para) |
| CF₂ | Pyridinyl | NH—C(O) | Pyridinyl | $Z_1$: CH₂—CH₃ (meta) |
| CF₂ | Pyridinyl | NH—C(O) | Pyridinyl | $Z_1$: CH₂—CH₃ (ortho) |
| CF₂ | Pyridinyl | NH—C(O) | Pyridinyl | $Z_1$: CH₂—CH₂—CH₃ or iPr (para) |
| CF₂ | Pyridinyl | NH—C(O) | Pyridinyl | $Z_1$: CH₂—CH₂—CH₃ or iPr (meta) |
| CF₂ | Pyridinyl | NH—C(O) | Pyridinyl | $Z_1$: CH₂—CH₂—CH₃ or iPr (ortho) |
| CF₂ | Pyridinyl | NH—C(O) | Pyridinyl | $Z_1$: CH₂F (para) |
| CF₂ | Pyridinyl | NH—C(O) | Pyridinyl | $Z_1$: CH₂F (meta) |

TABLE 2-continued

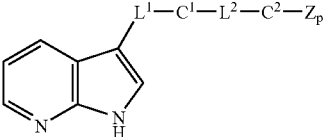

| L$^1$ | C$^1$ | L$^2$ | C$^2$ | Z |
|---|---|---|---|---|
| CF$_2$ | Pyridinyl | NH—C(O) | Pyridinyl | Z$_1$: CH$_2$F (ortho) |
| CF$_2$ | Pyridinyl | NH—C(O) | Pyridinyl | Z$_1$: CHF$_2$ (para) |
| CF$_2$ | Pyridinyl | NH—C(O) | Pyridinyl | Z$_1$: CHF$_2$ (meta) |
| CF$_2$ | Pyridinyl | NH—C(O) | Pyridinyl | Z$_1$: CHF$_2$ (ortho) |
| CF$_2$ | Pyridinyl | NH—C(O) | Pyridinyl | Z$_1$: CF$_3$ (para) |
| CF$_2$ | Pyridinyl | NH—C(O) | Pyridinyl | Z$_1$: CF$_3$ (meta) |
| CF$_2$ | Pyridinyl | NH—C(O) | Pyridinyl | Z$_1$: CF$_3$ (ortho) |
| CF$_2$ | Pyridinyl | NH—C(O) | Pyridinyl | Z$_1$: CH$_2$—CH$_2$F (para) |
| CF$_2$ | Pyridinyl | NH—C(O) | Pyridinyl | Z$_1$: CH$_2$—CH$_2$F (meta) |
| CF$_2$ | Pyridinyl | NH—C(O) | Pyridinyl | Z$_1$: CH$_2$—CH$_2$F (ortho) |
| CF$_2$ | Pyridinyl | NH—C(O) | Pyridinyl | Z$_1$: CH$_2$—CHF$_2$ (para) |
| CF$_2$ | Pyridinyl | NH—C(O) | Pyridinyl | Z$_1$: CH$_2$—CHF$_2$ (meta) |
| CF$_2$ | Pyridinyl | NH—C(O) | Pyridinyl | Z$_1$: CH$_2$—CHF$_2$ (ortho) |
| CF$_2$ | Pyridinyl | NH—C(O) | Pyridinyl | Z$_1$: CH$_2$—CF$_3$ (para) |
| CF$_2$ | Pyridinyl | NH—C(O) | Pyridinyl | Z$_1$: CH$_2$—CF$_3$ (meta) |
| CF$_2$ | Pyridinyl | NH—C(O) | Pyridinyl | Z$_1$: CH$_2$—CF$_3$ (ortho) |
| CF$_2$ | pyridinyl | NH—C(O) | Pyrimidinyl | None |
| CF$_2$ | pyridinyl | NH—C(O) | Pyrimidinyl | Z$_1$: F (para) |
| CF$_2$ | pyridinyl | NH—C(O) | Pyrimidinyl | Z$_1$: F (meta) |
| CF$_2$ | pyridinyl | NH—C(O) | Pyrimidinyl | Z$_1$: F (ortho) |
| CF$_2$ | pyridinyl | NH—C(O) | Pyrimidinyl | Z$_1$: F (para) Z$_2$: F (meta) |
| CF$_2$ | Pyridinyl | NH—C(O) | Pyrimidinyl | Z$_1$: Cl (meta) |
| CF$_2$ | Pyridinyl | NH—C(O) | Pyrimidinyl | Z$_1$: Cl (para) |
| CF$_2$ | Pyridinyl | NH—C(O) | Pyrimidinyl | Z$_1$: Cl (para) Z$_2$: Cl (meta) |
| CF$_2$ | Pyridinyl | NH—C(O) | Pyrimidinyl | Z$_1$: F (para) Z$_2$: Cl (meta) |
| CF$_2$ | Pyridinyl | NH—C(O) | Pyrimidinyl | Z$_1$: Cl (para) Z$_2$: F (meta) |
| CF$_2$ | Pyridinyl | NH—C(O) | Pyrimidinyl | Z$_1$: CH$_3$ (para) |
| CF$_2$ | Pyridinyl | NH—C(O) | Pyrimidinyl | Z$_1$: CH$_3$ (meta) |
| CF$_2$ | Pyridinyl | NH—C(O) | Pyrimidinyl | Z$_1$: CH$_3$ (ortho) |
| CF$_2$ | Pyridinyl | NH—C(O) | Pyrimidinyl | Z$_1$: CH$_2$—CH$_3$ (para) |
| CF$_2$ | Pyridinyl | NH—C(O) | Pyrimidinyl | Z$_1$: CH$_2$—CH$_3$ (meta) |
| CF$_2$ | Pyridinyl | NH—C(O) | Pyrimidinyl | Z$_1$: CH$_2$—CH$_3$ (ortho) |
| CF$_2$ | Pyridinyl | NH—C(O) | Pyrimidinyl | Z$_1$: CH$_2$—CH$_2$—CH$_3$ or iPr (para) |
| CF$_2$ | Pyridinyl | NH—C(O) | Pyrimidinyl | Z$_1$: CH$_2$—CH$_2$—CH$_3$ or iPr (meta) |
| CF$_2$ | Pyridinyl | NH—C(O) | Pyrimidinyl | Z$_1$: CH$_2$—CH$_2$—CH$_3$ or iPr (ortho) |
| CF$_2$ | Pyridinyl | NH—C(O) | Pyrimidinyl | Z$_1$: CH$_2$F (para) |
| CF$_2$ | Pyridinyl | NH—C(O) | Pyrimidinyl | Z$_1$: CH$_2$F (meta) |
| CF$_2$ | Pyridinyl | NH—C(O) | Pyrimidinyl | Z$_1$: CH$_2$F (ortho) |
| CF$_2$ | Pyridinyl | NH—C(O) | Pyrimidinyl | Z$_1$: CHF$_2$ (para) |
| CF$_2$ | Pyridinyl | NH—C(O) | Pyrimidinyl | Z$_1$: CHF$_2$ (meta) |
| CF$_2$ | Pyridinyl | NH—C(O) | Pyrimidinyl | Z$_1$: CHF$_2$ (ortho) |
| CF$_2$ | Pyridinyl | NH—C(O) | Pyrimidinyl | Z$_1$: CF$_3$ (para) |
| CF$_2$ | Pyridinyl | NH—C(O) | Pyrimidinyl | Z$_1$: CF$_3$ (meta) |
| CF$_2$ | Pyridinyl | NH—C(O) | Pyrimidinyl | Z$_1$: CF$_3$ (ortho) |
| CF$_2$ | Pyridinyl | NH—C(O) | Pyrimidinyl | Z$_1$: CH$_2$—CH$_2$F (para) |
| CF$_2$ | Pyridinyl | NH—C(O) | Pyrimidinyl | Z$_1$: CH$_2$—CH$_2$F (meta) |
| CF$_2$ | Pyridinyl | NH—C(O) | Pyrimidinyl | Z$_1$: CH$_2$—CH$_2$F (ortho) |
| CF$_2$ | Pyridinyl | NH—C(O) | Pyrimidinyl | Z$_1$: CH$_2$—CHF$_2$ (para) |
| CF$_2$ | Pyridinyl | NH—C(O) | Pyrimidinyl | Z$_1$: CH$_2$—CHF$_2$ (meta) |
| CF$_2$ | Pyridinyl | NH—C(O) | Pyrimidinyl | Z$_1$: CH$_2$—CHF$_2$ (ortho) |
| CF$_2$ | Pyridinyl | NH—C(O) | Pyrimidinyl | Z$_1$: CH$_2$—CF$_3$ (para) |
| CF$_2$ | Pyridinyl | NH—C(O) | Pyrimidinyl | Z$_1$: CH$_2$—CF$_3$ (meta) |
| CF$_2$ | Pyridinyl | NH—C(O) | Pyrimidinyl | Z$_1$: CH$_2$—CF$_3$ (ortho) |
| CF$_2$ | pyridinyl | NH—C(O) | Pyrazinyl | None |
| CF$_2$ | pyridinyl | NH—C(O) | Pyrazinyl | Z$_1$: F (para) |
| CF$_2$ | pyridinyl | NH—C(O) | Pyrazinyl | Z$_1$: F (meta) |
| CF$_2$ | pyridinyl | NH—C(O) | Pyrazinyl | Z$_1$: F (ortho) |
| CF$_2$ | pyridinyl | NH—C(O) | Pyrazinyl | Z$_1$: F (para) Z$_2$: F (meta) |
| CF$_2$ | Pyridinyl | NH—C(O) | Pyrazinyl | Z$_1$: Cl (meta) |
| CF$_2$ | Pyridinyl | NH—C(O) | Pyrazinyl | Z$_1$: Cl (para) |

TABLE 2-continued

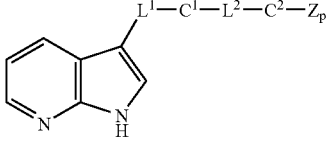

| L¹ | C¹ | L² | C² | Z |
|---|---|---|---|---|
| $CF_2$ | Pyridinyl | NH—C(O) | Pyrazinyl | $Z_1$: Cl (para) |
|  |  |  |  | $Z_2$: Cl (meta) |
| $CF_2$ | Pyridinyl | NH—C(O) | Pyrazinyl | $Z_1$: F (para) |
|  |  |  |  | $Z_2$: Cl (meta) |
| $CF_2$ | Pyridinyl | NH—C(O) | Pyrazinyl | $Z_1$: Cl (para) |
|  |  |  |  | $Z_2$: F (meta) |
| $CF_2$ | Pyridinyl | NH—C(O) | Pyrazinyl | $Z_1$: $CH_3$ (para) |
| $CF_2$ | Pyridinyl | NH—C(O) | Pyrazinyl | $Z_1$: $CH_3$ (meta) |
| $CF_2$ | Pyridinyl | NH—C(O) | Pyrazinyl | $Z_1$: $CH_3$ (ortho) |
| $CF_2$ | Pyridinyl | NH—C(O) | Pyrazinyl | $Z_1$: $CH_2$—$CH_3$ (para) |
| $CF_2$ | Pyridinyl | NH—C(O) | Pyrazinyl | $Z_1$: $CH_2$—$CH_3$ (meta) |
| $CF_2$ | Pyridinyl | NH—C(O) | Pyrazinyl | $Z_1$: $CH_2$—$CH_3$ (ortho) |
| $CF_2$ | Pyridinyl | NH—C(O) | Pyrazinyl | $Z_1$: $CH_2$—$CH_2$—$CH_3$ or iPr (para) |
| $CF_2$ | Pyridinyl | NH—C(O) | Pyrazinyl | $Z_1$: $CH_2$—$CH_2$—$CH_3$ or iPr (meta) |
| $CF_2$ | Pyridinyl | NH—C(O) | Pyrazinyl | $Z_1$: $CH_2$—$CH_2$—$CH_3$ or iPr (ortho) |
| $CF_2$ | Pyridinyl | NH—C(O) | Pyrazinyl | $Z_1$: $CH_2F$ (para) |
| $CF_2$ | Pyridinyl | NH—C(O) | Pyrazinyl | $Z_1$: $CH_2F$ (meta) |
| $CF_2$ | Pyridinyl | NH—C(O) | Pyrazinyl | $Z_1$: $CH_2F$ (ortho) |
| $CF_2$ | Pyridinyl | NH—C(O) | Pyrazinyl | $Z_1$: $CHF_2$ (para) |
| $CF_2$ | Pyridinyl | NH—C(O) | Pyrazinyl | $Z_1$: $CHF_2$ (meta) |
| $CF_2$ | Pyridinyl | NH—C(O) | Pyrazinyl | $Z_1$: $CHF_2$ (ortho) |
| $CF_2$ | Pyridinyl | NH—C(O) | Pyrazinyl | $Z_1$: $CF_3$ (para) |
| $CF_2$ | Pyridinyl | NH—C(O) | Pyrazinyl | $Z_1$: $CF_3$ (meta) |
| $CF_2$ | Pyridinyl | NH—C(O) | Pyrazinyl | $Z_1$: $CF_3$ (ortho) |
| $CF_2$ | Pyridinyl | NH—C(O) | Pyrazinyl | $Z_1$: $CH_2$—$CH_2F$ (para) |
| $CF_2$ | Pyridinyl | NH—C(O) | Pyrazinyl | $Z_1$: $CH_2$—$CH_2F$ (meta) |
| $CF_2$ | Pyridinyl | NH—C(O) | Pyrazinyl | $Z_1$: $CH_2$—$CH_2F$ (ortho) |
| $CF_2$ | Pyridinyl | NH—C(O) | Pyrazinyl | $Z_1$: $CH_2$—$CHF_2$ (para) |
| $CF_2$ | Pyridinyl | NH—C(O) | Pyrazinyl | $Z_1$: $CH_2$—$CHF_2$ (meta) |
| $CF_2$ | Pyridinyl | NH—C(O) | Pyrazinyl | $Z_1$: $CH_2$—$CHF_2$ (ortho) |
| $CF_2$ | Pyridinyl | NH—C(O) | Pyrazinyl | $Z_1$: $CH_2$—$CF_3$ (para) |
| $CF_2$ | Pyridinyl | NH—C(O) | Pyrazinyl | $Z_1$: $CH_2$—$CF_3$ (meta) |
| $CF_2$ | Pyridinyl | NH—C(O) | Pyrazinyl | $Z_1$: $CH_2$—$CF_3$ (ortho) |
| $CF_2$ | pyridinyl | NH—C(O) | Pyrrolyl | None |
| $CF_2$ | pyridinyl | NH—C(O) | Pyrrolyl | $Z_1$: F (2) |
| $CF_2$ | pyridinyl | NH—C(O) | Pyrrolyl | $Z_1$: F (3) |
| $CF_2$ | pyridinyl | NH—C(O) | Pyrrolyl | $Z_1$: F (2) |
|  |  |  |  | $Z_2$: F (3) |
| $CF_2$ | Pyridinyl | NH—C(O) | Pyrrolyl | $Z_1$: Cl (2) |
| $CF_2$ | Pyridinyl | NH—C(O) | Pyrrolyl | $Z_1$: Cl (3) |
| $CF_2$ | Pyridinyl | NH—C(O) | Pyrrolyl | $Z_1$: Cl (2) |
|  |  |  |  | $Z_2$: Cl (3) |
| $CF_2$ | Pyridinyl | NH—C(O) | Pyrrolyl | $Z_1$: F (2) |
|  |  |  |  | $Z_2$: Cl (3) |
| $CF_2$ | Pyridinyl | NH—C(O) | Pyrrolyl | $Z_1$: Cl (2) |
|  |  |  |  | $Z_2$: F (3) |
| $CF_2$ | Pyridinyl | NH—C(O) | Pyrrolyl | $Z_1$: $CH_3$ (2) |
| $CF_2$ | Pyridinyl | NH—C(O) | Pyrrolyl | $Z_1$: $CH_3$ (3) |
| $CF_2$ | Pyridinyl | NH—C(O) | Pyrrolyl | $Z_1$: $CH_2$—$CH_3$ (2) |
| $CF_2$ | Pyridinyl | NH—C(O) | Pyrrolyl | $Z_1$: $CH_2$—$CH_3$ (3) |
| $CF_2$ | Pyridinyl | NH—C(O) | Pyrrolyl | $Z_1$: $CH_2$—$CH_2$—$CH_3$ or iPr (2) |
| $CF_2$ | Pyridinyl | NH—C(O) | Pyrrolyl | $Z_1$: $CH_2$—$CH_2$—$CH_3$ or iPr (3) |
| $CF_2$ | Pyridinyl | NH—C(O) | Pyrrolyl | $Z_1$: $CH_2F$ (2) |
| $CF_2$ | Pyridinyl | NH—C(O) | Pyrrolyl | $Z_1$: $CH_2F$ (3) |
| $CF_2$ | Pyridinyl | NH—C(O) | Pyrrolyl | $Z_1$: $CHF_2$ (2) |
| $CF_2$ | Pyridinyl | NH—C(O) | Pyrrolyl | $Z_1$: $CHF_2$ (3) |
| $CF_2$ | Pyridinyl | NH—C(O) | Pyrrolyl | $Z_1$: $CF_3$ (2) |
| $CF_2$ | Pyridinyl | NH—C(O) | Pyrrolyl | $Z_1$: $CF_3$ (3) |
| $CF_2$ | Pyridinyl | NH—C(O) | Pyrrolyl | $Z_1$: $CH_2$—$CH_2F$ (2) |
| $CF_2$ | Pyridinyl | NH—C(O) | Pyrrolyl | $Z_1$: $CH_2$—$CH_2F$ (3) |
| $CF_2$ | Pyridinyl | NH—C(O) | Pyrrolyl | $Z_1$: $CH_2$—$CHF_2$ (2) |
| $CF_2$ | Pyridinyl | NH—C(O) | Pyrrolyl | $Z_1$: $CH_2$—$CHF_2$ (3) |
| $CF_2$ | Pyridinyl | NH—C(O) | Pyrrolyl | $Z_1$: $CH_2$—$CF_3$ (2) |
| $CF_2$ | Pyridinyl | NH—C(O) | Pyrrolyl | $Z_1$: $CH_2$—$CF_3$ (3) |
| $CF_2$ | pyridinyl | NH—C(O) | Imidazolyl | None |
| $CF_2$ | pyridinyl | NH—C(O) | Imidazolyl | $Z_1$: F (2) |

TABLE 2-continued

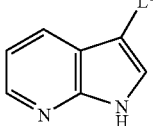

$$L^1\text{—}C^1\text{—}L^2\text{—}C^2\text{—}Z_p$$

| $L^1$ | $C^1$ | $L^2$ | $C^2$ | Z |
|---|---|---|---|---|
| $CF_2$ | pyridinyl | NH—C(O) | Imidazolyl | $Z_1$: F (3) |
| $CF_2$ | pyridinyl | NH—C(O) | Imidazolyl | $Z_1$: F (2) |
| | | | | $Z_2$: F (3) |
| $CF_2$ | Pyridinyl | NH—C(O) | Imidazolyl | $Z_1$: Cl (2) |
| $CF_2$ | Pyridinyl | NH—C(O) | Imidazolyl | $Z_1$: Cl (3) |
| $CF_2$ | Pyridinyl | NH—C(O) | Imidazolyl | $Z_1$: Cl (2) |
| | | | | $Z_2$: Cl (3) |
| $CF_2$ | Pyridinyl | NH—C(O) | Imidazolyl | $Z_1$: F (2) |
| | | | | $Z_2$: Cl (3) |
| $CF_2$ | Pyridinyl | NH—C(O) | Imidazolyl | $Z_1$: Cl (2) |
| | | | | $Z_2$: F (3) |
| $CF_2$ | Pyridinyl | NH—C(O) | Imidazolyl | $Z_1$: $CH_3$ (2) |
| $CF_2$ | Pyridinyl | NH—C(O) | Imidazolyl | $Z_1$: $CH_3$ (3) |
| $CF_2$ | Pyridinyl | NH—C(O) | Imidazolyl | $Z_1$: $CH_2$—$CH_3$ (2) |
| $CF_2$ | Pyridinyl | NH—C(O) | Imidazolyl | $Z_1$: $CH_2$—$CH_3$ (3) |
| $CF_2$ | Pyridinyl | NH—C(O) | Imidazolyl | $Z_1$: $CH_2$—$CH_2$—$CH_3$ or iPr (2) |
| $CF_2$ | Pyridinyl | NH—C(O) | Imidazolyl | $Z_1$: $CH_2$—$CH_2$—$CH_3$ or iPr (3) |
| $CF_2$ | Pyridinyl | NH—C(O) | Imidazolyl | $Z_1$: $CH_2F$ (2) |
| $CF_2$ | Pyridinyl | NH—C(O) | Imidazolyl | $Z_1$: $CH_2F$ (3) |
| $CF_2$ | Pyridinyl | NH—C(O) | Imidazolyl | $Z_1$: $CHF_2$ (2) |
| $CF_2$ | Pyridinyl | NH—C(O) | Imidazolyl | $Z_1$: $CHF_2$ (3) |
| $CF_2$ | Pyridinyl | NH—C(O) | Imidazolyl | $Z_1$: $CF_3$ (2) |
| $CF_2$ | Pyridinyl | NH—C(O) | Imidazolyl | $Z_1$: $CF_3$ (3) |
| $CF_2$ | Pyridinyl | NH—C(O) | Imidazolyl | $Z_1$: $CH_2$—$CH_2F$ (2) |
| $CF_2$ | Pyridinyl | NH—C(O) | Imidazolyl | $Z_1$: $CH_2$—$CH_2F$ (3) |
| $CF_2$ | Pyridinyl | NH—C(O) | Imidazolyl | $Z_1$: $CH_2$—$CHF_2$ (2) |
| $CF_2$ | Pyridinyl | NH—C(O) | Imidazolyl | $Z_1$: $CH_2$—$CHF_2$ (3) |
| $CF_2$ | Pyridinyl | NH—C(O) | Imidazolyl | $Z_1$: $CH_2$—$CF_3$ (2) |
| $CF_2$ | Pyridinyl | NH—C(O) | Imidazolyl | $Z_1$: $CH_2$—$CF_3$ (3) |
| $CF_2$ | pyridinyl | NH—C(O) | Furanyl | None |
| $CF_2$ | pyridinyl | NH—C(O) | Furanyl | $Z_1$: F (2) |
| $CF_2$ | pyridinyl | NH—C(O) | Furanyl | $Z_1$: F (3) |
| $CF_2$ | pyridinyl | NH—C(O) | Furanyl | $Z_1$: F (2) |
| $CF_2$ | Pyridinyl | NH—C(O) | Furanyl | $Z_1$: Cl (2) |
| $CF_2$ | Pyridinyl | NH—C(O) | Furanyl | $Z_1$: Cl (3) |
| $CF_2$ | Pyridinyl | NH—C(O) | Furanyl | $Z_1$: Cl (2) |
| | | | | $Z_2$: Cl (3) |
| $CF_2$ | Pyridinyl | NH—C(O) | Furanyl | $Z_1$: F (2) |
| | | | | $Z_2$: Cl (3) |
| $CF_2$ | Pyridinyl | NH—C(O) | Furanyl | $Z_1$: Cl (2) |
| | | | | $Z_2$: F (3) |
| $CF_2$ | Pyridinyl | NH—C(O) | Furanyl | $Z_1$: $CH_3$ (2) |
| $CF_2$ | Pyridinyl | NH—C(O) | Furanyl | $Z_1$: $CH_3$ (3) |
| $CF_2$ | Pyridinyl | NH—C(O) | Furanyl | $Z_1$: $CH_2$—$CH_3$ (2) |
| $CF_2$ | Pyridinyl | NH—C(O) | Furanyl | $Z_1$: $CH_2$—$CH_3$ (3) |
| $CF_2$ | Pyridinyl | NH—C(O) | Furanyl | $Z_1$: $CH_2$—$CH_2$—$CH_3$ or iPr (2) |
| $CF_2$ | Pyridinyl | NH—C(O) | Furanyl | $Z_1$: $CH_2$—$CH_2$—$CH_3$ or iPr (3) |
| $CF_2$ | Pyridinyl | NH—C(O) | Furanyl | $Z_1$: $CH_2F$ (2) |
| $CF_2$ | Pyridinyl | NH—C(O) | Furanyl | $Z_1$: $CH_2F$ (3) |
| $CF_2$ | Pyridinyl | NH—C(O) | Furanyl | $Z_1$: $CHF_2$ (2) |
| $CF_2$ | Pyridinyl | NH—C(O) | Furanyl | $Z_1$: $CHF_2$ (3) |
| $CF_2$ | Pyridinyl | NH—C(O) | Furanyl | $Z_1$: $CF_3$ (2) |
| $CF_2$ | Pyridinyl | NH—C(O) | Furanyl | $Z_1$: $CF_3$ (3) |
| $CF_2$ | Pyridinyl | NH—C(O) | Furanyl | $Z_1$: $CH_2$—$CH_2F$ (2) |
| $CF_2$ | Pyridinyl | NH—C(O) | Furanyl | $Z_1$: $CH_2$—$CH_2F$ (3) |
| $CF_2$ | Pyridinyl | NH—C(O) | Furanyl | $Z_1$: $CH_2$—$CHF_2$ (2) |
| $CF_2$ | Pyridinyl | NH—C(O) | Furanyl | $Z_1$: $CH_2$—$CHF_2$ (3) |
| $CF_2$ | Pyridinyl | NH—C(O) | Furanyl | $Z_1$: $CH_2$—$CF_3$ (2) |
| $CF_2$ | Pyridinyl | NH—C(O) | Furanyl | $Z_1$: $CH_2$—$CF_3$ (3) |
| $CF_2$ | pyridinyl | NH—C(O) | Oxazolyl | None |
| $CF_2$ | pyridinyl | NH—C(O) | Oxazolyl | $Z_1$: F (2) |
| $CF_2$ | pyridinyl | NH—C(O) | Oxazolyl | $Z_1$: F (3) |
| $CF_2$ | pyridinyl | NH—C(O) | Oxazolyl | $Z_1$: F (2) |
| | | | | $Z_2$: F (3) |
| $CF_2$ | Pyridinyl | NH—C(O) | Oxazolyl | $Z_1$: Cl (2) |
| $CF_2$ | Pyridinyl | NH—C(O) | Oxazolyl | $Z_1$: Cl (3) |
| $CF_2$ | Pyridinyl | NH—C(O) | Oxazolyl | $Z_1$: Cl (2) |
| | | | | $Z_2$: Cl (3) |

TABLE 2-continued

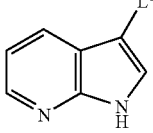

| L¹ | C¹ | L² | C² | Z |
|---|---|---|---|---|
| $CF_2$ | Pyridinyl | NH—C(O) | Oxazolyl | $Z_1$: F (2) |
| | | | | $Z_2$: Cl (3) |
| $CF_2$ | Pyridinyl | NH—C(O) | Oxazolyl | $Z_1$: Cl (2) |
| | | | | $Z_2$: F (3) |
| $CF_2$ | Pyridinyl | NH—C(O) | Oxazolyl | $Z_1$: $CH_3$ (2) |
| $CF_2$ | Pyridinyl | NH—C(O) | Oxazolyl | $Z_1$: $CH_3$ (3) |
| $CF_2$ | Pyridinyl | NH—C(O) | Oxazolyl | $Z_1$: $CH_2$—$CH_3$ (2) |
| $CF_2$ | Pyridinyl | NH—C(O) | Oxazolyl | $Z_1$: $CH_2$—$CH_3$ (3) |
| $CF_2$ | Pyridinyl | NH—C(O) | Oxazolyl | $Z_1$: $CH_2$—$CH_2$—$CH_3$ or iPr (2) |
| $CF_2$ | Pyridinyl | NH—C(O) | Oxazolyl | $Z_1$: $CH_2$—$CH_2$—$CH_3$ or iPr (3) |
| $CF_2$ | Pyridinyl | NH—C(O) | Oxazolyl | $Z_1$: $CH_2F$ (2) |
| $CF_2$ | Pyridinyl | NH—C(O) | Oxazolyl | $Z_1$: $CH_2F$ (3) |
| $CF_2$ | Pyridinyl | NH—C(O) | Oxazolyl | $Z_1$: $CHF_2$ (2) |
| $CF_2$ | Pyridinyl | NH—C(O) | Oxazolyl | $Z_1$: $CHF_2$ (3) |
| $CF_2$ | Pyridinyl | NH—C(O) | Oxazolyl | $Z_1$: $CF_3$ (2) |
| $CF_2$ | Pyridinyl | NH—C(O) | Oxazolyl | $Z_1$: $CF_3$ (3) |
| $CF_2$ | Pyridinyl | NH—C(O) | Oxazolyl | $Z_1$: $CH_2$—$CH_2F$ (2) |
| $CF_2$ | Pyridinyl | NH—C(O) | Oxazolyl | $Z_1$: $CH_2$—$CH_2F$ (3) |
| $CF_2$ | Pyridinyl | NH—C(O) | Oxazolyl | $Z_1$: $CH_2$—$CHF_2$ (2) |
| $CF_2$ | Pyridinyl | NH—C(O) | Oxazolyl | $Z_1$: $CH_2$—$CHF_2$ (3) |
| $CF_2$ | Pyridinyl | NH—C(O) | Oxazolyl | $Z_1$: $CH_2$—$CF_3$ (2) |
| $CF_2$ | Pyridinyl | NH—C(O) | Oxazolyl | $Z_1$: $CH_2$—$CF_3$ (3) |
| $CF_2$ | pyridinyl | NH—C(O) | Thiophenyl | None |
| $CF_2$ | pyridinyl | NH—C(O) | Thiophenyl | $Z_1$: F (2) |
| $CF_2$ | pyridinyl | NH—C(O) | Thiophenyl | $Z_1$: F (3) |
| $CF_2$ | pyridinyl | NH—C(O) | Thiophenyl | $Z_1$: F (2) |
| | | | | $Z_2$: F (3) |
| $CF_2$ | Pyridinyl | NH—C(O) | Thiophenyl | $Z_1$: Cl (2) |
| $CF_2$ | Pyridinyl | NH—C(O) | Thiophenyl | $Z_1$: Cl (3) |
| $CF_2$ | Pyridinyl | NH—C(O) | Thiophenyl | $Z_1$: Cl (2) |
| | | | | $Z_2$: Cl (3) |
| $CF_2$ | Pyridinyl | NH—C(O) | Thiophenyl | $Z_1$: F (2) |
| | | | | $Z_2$: Cl (3) |
| $CF_2$ | Pyridinyl | NH—C(O) | Thiophenyl | $Z_1$: Cl (2) |
| | | | | $Z_2$: F (3) |
| $CF_2$ | Pyridinyl | NH—C(O) | Thiophenyl | $Z_1$: $CH_3$ (2) |
| $CF_2$ | Pyridinyl | NH—C(O) | Thiophenyl | $Z_1$: $CH_3$ (3) |
| $CF_2$ | Pyridinyl | NH—C(O) | Thiophenyl | $Z_1$: $CH_2$—$CH_3$ (2) |
| $CF_2$ | Pyridinyl | NH—C(O) | Thiophenyl | $Z_1$: $CH_2$—$CH_3$ (3) |
| $CF_2$ | Pyridinyl | NH—C(O) | Thiophenyl | $Z_1$: $CH_2$—$CH_2$—$CH_3$ or iPr (2) |
| $CF_2$ | Pyridinyl | NH—C(O) | Thiophenyl | $Z_1$: $CH_2$—$CH_2$—$CH_3$ or iPr (3) |
| $CF_2$ | Pyridinyl | NH—C(O) | Thiophenyl | $Z_1$: $CH_2F$ (2) |
| $CF_2$ | Pyridinyl | NH—C(O) | Thiophenyl | $Z_1$: $CH_2F$ (3) |
| $CF_2$ | Pyridinyl | NH—C(O) | Thiophenyl | $Z_1$: $CHF_2$ (2) |
| $CF_2$ | Pyridinyl | NH—C(O) | Thiophenyl | $Z_1$: $CHF_2$ (3) |
| $CF_2$ | Pyridinyl | NH—C(O) | Thiophenyl | $Z_1$: $CF_3$ (2) |
| $CF_2$ | Pyridinyl | NH—C(O) | Thiophenyl | $Z_1$: $CF_3$ (3) |
| $CF_2$ | Pyridinyl | NH—C(O) | Thiophenyl | $Z_1$: $CH_2$—$CH_2F$ (2) |
| $CF_2$ | Pyridinyl | NH—C(O) | Thiophenyl | $Z_1$: $CH_2$—$CH_2F$ (3) |
| $CF_2$ | Pyridinyl | NH—C(O) | Thiophenyl | $Z_1$: $CH_2$—$CHF_2$ (2) |
| $CF_2$ | Pyridinyl | NH—C(O) | Thiophenyl | $Z_1$: $CH_2$—$CHF_2$ (3) |
| $CF_2$ | Pyridinyl | NH—C(O) | Thiophenyl | $Z_1$: $CH_2$—$CF_3$ (2) |
| $CF_2$ | Pyridinyl | NH—C(O) | Thiophenyl | $Z_1$: $CH_2$—$CF_3$ (3) |
| $CF_2$ | pyridinyl | NH—C(O) | Thiazolyl | None |
| $CF_2$ | pyridinyl | NH—C(O) | Thiazolyl | $Z_1$: F (2) |
| $CF_2$ | pyridinyl | NH—C(O) | Thiazolyl | $Z_1$: F (3) |
| $CF_2$ | pyridinyl | NH—C(O) | Thiazolyl | $Z_1$: F (2) |
| | | | | $Z_2$: F (3) |
| $CF_2$ | Pyridinyl | NH—C(O) | Thiazolyl | $Z_1$: Cl (2) |
| $CF_2$ | Pyridinyl | NH—C(O) | Thiazolyl | $Z_1$: Cl (3) |
| $CF_2$ | Pyridinyl | NH—C(O) | Thiazolyl | $Z_1$: Cl (2) |
| | | | | $Z_2$: Cl (3) |
| $CF_2$ | Pyridinyl | NH—C(O) | Thiazolyl | $Z_1$: F (2) |
| | | | | $Z_2$: Cl (3) |
| $CF_2$ | Pyridinyl | NH—C(O) | Thiazolyl | $Z_1$: Cl (2) |
| | | | | $Z_2$: F (3) |
| $CF_2$ | Pyridinyl | NH—C(O) | Thiazolyl | $Z_1$: $CH_3$ (2) |
| $CF_2$ | Pyridinyl | NH—C(O) | Thiazolyl | $Z_1$: $CH_3$ (3) |
| $CF_2$ | Pyridinyl | NH—C(O) | Thiazolyl | $Z_1$: $CH_2$—$CH_3$ (2) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| CF₂ | Pyridinyl | NH—C(O) | Thiazolyl | Z₁: CH₂—CH₃ (3) |
| CF₂ | Pyridinyl | NH—C(O) | Thiazolyl | Z₁: CH₂—CH₂—CH₃ or iPr (2) |
| CF₂ | Pyridinyl | NH—C(O) | Thiazolyl | Z₁: CH₂—CH₂—CH₃ or iPr (3) |
| CF₂ | Pyridinyl | NH—C(O) | Thiazolyl | Z₁: CH₂F (2) |
| CF₂ | Pyridinyl | NH—C(O) | Thiazolyl | Z₁: CH₂F (3) |
| CF₂ | Pyridinyl | NH—C(O) | Thiazolyl | Z₁: CHF₂ (2) |
| CF₂ | Pyridinyl | NH—C(O) | Thiazolyl | Z₁: CHF₂ (3) |
| CF₂ | Pyridinyl | NH—C(O) | Thiazolyl | Z₁: CF₃ (2) |
| CF₂ | Pyridinyl | NH—C(O) | Thiazolyl | Z₁: CF₃ (3) |
| CF₂ | Pyridinyl | NH—C(O) | Thiazolyl | Z₁: CH₂—CH₂F (2) |
| CF₂ | Pyridinyl | NH—C(O) | Thiazolyl | Z₁: CH₂—CH₂F (3) |
| CF₂ | Pyridinyl | NH—C(O) | Thiazolyl | Z₁: CH₂—CHF₂ (2) |
| CF₂ | Pyridinyl | NH—C(O) | Thiazolyl | Z₁: CH₂—CHF₂ (3) |
| CF₂ | Pyridinyl | NH—C(O) | Thiazolyl | Z₁: CH₂—CF₃ (2) |
| CF₂ | Pyridinyl | NH—C(O) | Thiazolyl | Z₁: CH₂—CF₃ (3) |
| CF₂ | pyridinyl | NH—SO₂ | Phenyl | None |
| CF₂ | pyridinyl | NH—SO₂ | Phenyl | Z₁: F (para) |
| CF₂ | pyridinyl | NH—SO₂ | phenyl | Z₁: F (meta) |
| CF₂ | pyridinyl | NH—SO₂ | phenyl | Z₁: F (ortho) |
| CF₂ | pyridinyl | NH—SO₂ | phenyl | Z₁: F (para)<br>Z₂: F (meta) |
| CF₂ | Pyridinyl | NH—SO₂ | Phenyl | Z₁: Cl (meta) |
| CF₂ | Pyridinyl | NH—SO₂ | Phenyl | Z₁: Cl (para) |
| CF₂ | Pyridinyl | NH—SO₂ | Phenyl | Z₁: Cl (para)<br>Z₂: Cl (meta) |
| CF₂ | Pyridinyl | NH—SO₂ | Phenyl | Z₁: F (para)<br>Z₂: Cl (meta) |
| CF₂ | Pyridinyl | NH—SO₂ | Phenyl | Z₁: Cl (para)<br>Z₂: F (meta) |
| CF₂ | Pyridinyl | NH—SO₂ | Phenyl | Z₁: CH₃ (para) |
| CF₂ | Pyridinyl | NH—SO₂ | Phenyl | Z₁: CH₃ (meta) |
| CF₂ | Pyridinyl | NH—SO₂ | Phenyl | Z₁: CH₃ (ortho) |
| CF₂ | Pyridinyl | NH—SO₂ | Phenyl | Z₁: CH₂—CH₃ (para) |
| CF₂ | Pyridinyl | NH—SO₂ | Phenyl | Z₁: CH₂—CH₃ (meta) |
| CF₂ | Pyridinyl | NH—SO₂ | Phenyl | Z₁: CH₂—CH₃ (ortho) |
| CF₂ | Pyridinyl | NH—SO₂ | Phenyl | Z₁: CH₂—CH₂—CH₃ or iPr (para) |
| CF₂ | Pyridinyl | NH—SO₂ | Phenyl | Z₁: CH₂—CH₂—CH₃ or iPr (meta) |
| CF₂ | Pyridinyl | NH—SO₂ | Phenyl | Z₁: CH₂—CH₂—CH₃ or iPr (ortho) |
| CF₂ | Pyridinyl | NH—SO₂ | Phenyl | Z₁: CH₂F (para) |
| CF₂ | Pyridinyl | NH—SO₂ | Phenyl | Z₁: CH₂F (meta) |
| CF₂ | Pyridinyl | NH—SO₂ | Phenyl | Z₁: CH₂F (ortho) |
| CF₂ | Pyridinyl | NH—SO₂ | Phenyl | Z₁: CHF₂ (para) |
| CF₂ | Pyridinyl | NH—SO₂ | Phenyl | Z₁: CHF₂ (meta) |
| CF₂ | Pyridinyl | NH—SO₂ | Phenyl | Z₁: CHF₂ (ortho) |
| CF₂ | Pyridinyl | NH—SO₂ | Phenyl | Z₁: CF₃ (para) |
| CF₂ | Pyridinyl | NH—SO₂ | Phenyl | Z₁: CF₃ (meta |
| CF₂ | Pyridinyl | NH—SO₂ | Phenyl | Z₁: CF₃ (ortho) |
| CF₂ | Pyridinyl | NH—SO₂ | Phenyl | Z₁: CH₂—CH₂F (para) |
| CF₂ | Pyridinyl | NH—SO₂ | Phenyl | Z₁: CH₂—CH₂F (meta) |
| CF₂ | Pyridinyl | NH—SO₂ | Phenyl | Z₁: CH₂—CH₂F (ortho) |
| CF₂ | Pyridinyl | NH—SO₂ | Phenyl | Z₁: CH₂—CHF₂ (para) |
| CF₂ | Pyridinyl | NH—SO₂ | Phenyl | Z₁: CH₂—CHF₂ (meta) |
| CF₂ | Pyridinyl | NH—SO₂ | Phenyl | Z₁: CH₂—CHF₂ (ortho) |
| CF₂ | Pyridinyl | NH—SO₂ | Phenyl | Z₁: CH₂—CF₃ (para) |
| CF₂ | Pyridinyl | NH—SO₂ | Phenyl | Z₁: CH₂—CF₃ (meta) |
| CF₂ | Pyridinyl | NH—SO₂ | Phenyl | Z₁: CH₂—CF₃ (ortho) |
| CF₂ | pyridinyl | NH—SO₂ | Pyridinyl | None |
| CF₂ | pyridinyl | NH—SO₂ | Pyridinyl | Z₁: F (para) |
| CF₂ | pyridinyl | NH—SO₂ | Pyridinyl | Z₁: F (meta) |
| CF₂ | pyridinyl | NH—SO₂ | Pyridinyl | Z₁: F (ortho) |
| CF₂ | pyridinyl | NH—SO₂ | Pyridinyl | Z₁: F (para) |
| CF₂ | pyridinyl | NH—SO₂ | Pyridinyl | Z₁: Cl (meta) |
| CF₂ | Pyridinyl | NH—SO₂ | Pyridinyl | Z₁: Cl (para) |
| CF₂ | Pyridinyl | NH—SO₂ | Pyridinyl | Z₁: Cl (para) |
| CF₂ | Pyridinyl | NH—SO₂ | Pyridinyl | Z₁: F (para) |
| CF₂ | Pyridinyl | NH—SO₂ | Pyridinyl | Z₁: Cl (para) |

TABLE 2-continued

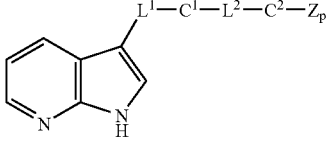

| $L^1$ | $C^1$ | $L^2$ | $C^2$ | Z |
|---|---|---|---|---|
| $CF_2$ | Pyridinyl | $NH-SO_2$ | Pyridinyl | $Z_1$: $CH_3$ (para) |
| $CF_2$ | Pyridinyl | $NH-SO_2$ | Pyridinyl | $Z_1$: $CH_3$ (meta) |
| $CF_2$ | Pyridinyl | $NH-SO_2$ | Pyridinyl | $Z_1$: $CH_3$ (ortho) |
| $CF_2$ | Pyridinyl | $NH-SO_2$ | Pyridinyl | $Z_1$: $CH_2-CH_3$ (para) |
| $CF_2$ | Pyridinyl | $NH-SO_2$ | Pyridinyl | $Z_1$: $CH_2-CH_3$ (meta) |
| $CF_2$ | Pyridinyl | $NH-SO_2$ | Pyridinyl | $Z_1$: $CH_2-CH_3$ (ortho) |
| $CF_2$ | Pyridinyl | $NH-SO_2$ | Pyridinyl | $Z_1$: $CH_2-CH_2-CH_3$ or iPr (para) |
| $CF_2$ | Pyridinyl | $NH-SO_2$ | Pyridinyl | $Z_1$: $CH_2-CH_2-CH_3$ or iPr (meta) |
| $CF_2$ | Pyridinyl | $NH-SO_2$ | Pyridinyl | $Z_1$: $CH_2-CH_2-CH_3$ or iPr (ortho) |
| $CF_2$ | Pyridinyl | $NH-SO_2$ | Pyridinyl | $Z_1$: $CH_2F$ (para) |
| $CF_2$ | Pyridinyl | $NH-SO_2$ | Pyridinyl | $Z_1$: $CH_2F$ (meta) |
| $CF_2$ | Pyridinyl | $NH-SO_2$ | Pyridinyl | $Z_1$: $CH_2F$ (ortho) |
| $CF_2$ | Pyridinyl | $NH-SO_2$ | Pyridinyl | $Z_1$: $CHF_2$ (para) |
| $CF_2$ | Pyridinyl | $NH-SO_2$ | Pyridinyl | $Z_1$: $CHF_2$ (meta) |
| $CF_2$ | Pyridinyl | $NH-SO_2$ | Pyridinyl | $Z_1$: $CHF_2$ (ortho) |
| $CF_2$ | Pyridinyl | $NH-SO_2$ | Pyridinyl | $Z_1$: $CF_3$ (para) |
| $CF_2$ | Pyridinyl | $NH-SO_2$ | Pyridinyl | $Z_1$: $CF_3$ (meta) |
| $CF_2$ | Pyridinyl | $NH-SO_2$ | Pyridinyl | $Z_1$: $CF_3$ (ortho) |
| $CF_2$ | Pyridinyl | $NH-SO_2$ | Pyridinyl | $Z_1$: $CH_2-CH_2F$ (para) |
| $CF_2$ | Pyridinyl | $NH-SO_2$ | Pyridinyl | $Z_1$: $CH_2-CH_2F$ (meta) |
| $CF_2$ | Pyridinyl | $NH-SO_2$ | Pyridinyl | $Z_1$: $CH_2-CH_2F$ (ortho) |
| $CF_2$ | Pyridinyl | $NH-SO_2$ | Pyridinyl | $Z_1$: $CH_2-CHF_2$ (para) |
| $CF_2$ | Pyridinyl | $NH-SO_2$ | Pyridinyl | $Z_1$: $CH_2-CHF_2$ (meta) |
| $CF_2$ | Pyridinyl | $NH-SO_2$ | Pyridinyl | $Z_1$: $CH_2-CHF_2$ (ortho) |
| $CF_2$ | Pyridinyl | $NH-SO_2$ | Pyridinyl | $Z_1$: $CH_2-CF_3$ (para) |
| $CF_2$ | Pyridinyl | $NH-SO_2$ | Pyridinyl | $Z_1$: $CH_2-CF_3$ (meta) |
| $CF_2$ | Pyridinyl | $NH-SO_2$ | Pyridinyl | $Z_1$: $CH_2-CF_3$ (ortho) |
| $CF_2$ | pyridinyl | $NH-SO_2$ | Pyrimidinyl | None |
| $CF_2$ | pyridinyl | $NH-SO_2$ | Pyrimidinyl | $Z_1$: F (para) |
| $CF_2$ | pyridinyl | $NH-SO_2$ | Pyrimidinyl | $Z_1$: F (meta) |
| $CF_2$ | pyridinyl | $NH-SO_2$ | Pyrimidinyl | $Z_1$: F (ortho) |
| $CF_2$ | pyridinyl | $NH-SO_2$ | Pyrimidinyl | $Z_1$: F (para) $Z_2$: F (meta) |
| $CF_2$ | Pyridinyl | $NH-SO_2$ | Pyrimidinyl | $Z_1$: Cl (meta) |
| $CF_2$ | Pyridinyl | $NH-SO_2$ | Pyrimidinyl | $Z_1$: Cl (para) |
| $CF_2$ | Pyridinyl | $NH-SO_2$ | Pyrimidinyl | $Z_1$: Cl (para) $Z_2$: Cl (meta) |
| $CF_2$ | Pyridinyl | $NH-SO_2$ | Pyrimidinyl | $Z_1$: F (para) $Z_2$: Cl (meta) |
| $CF_2$ | Pyridinyl | $NH-SO_2$ | Pyrimidinyl | $Z_1$: Cl (para) $Z_2$: F (meta) |
| $CF_2$ | Pyridinyl | $NH-SO_2$ | Pyrimidinyl | $Z_1$: $CH_3$ (para) |
| $CF_2$ | Pyridinyl | $NH-SO_2$ | Pyrimidinyl | $Z_1$: $CH_3$ (meta) |
| $CF_2$ | Pyridinyl | $NH-SO_2$ | Pyrimidinyl | $Z_1$: $CH_3$ (ortho) |
| $CF_2$ | Pyridinyl | $NH-SO_2$ | Pyrimidinyl | $Z_1$: $CH_2-CH_3$ (para) |
| $CF_2$ | Pyridinyl | $NH-SO_2$ | Pyrimidinyl | $Z_1$: $CH_2-CH_3$ (meta) |
| $CF_2$ | Pyridinyl | $NH-SO_2$ | Pyrimidinyl | $Z_1$: $CH_2-CH_3$ (ortho) |
| $CF_2$ | Pyridinyl | $NH-SO_2$ | Pyrimidinyl | $Z_1$: $CH_2-CH_2-CH_3$ or iPr (para) |
| $CF_2$ | Pyridinyl | $NH-SO_2$ | Pyrimidinyl | $Z_1$: $CH_2-CH_2-CH_3$ or iPr (meta) |
| $CF_2$ | Pyridinyl | $NH-SO_2$ | Pyrimidinyl | $Z_1$: $CH_2-CH_2-CH_3$ or iPr (ortho) |
| $CF_2$ | Pyridinyl | $NH-SO_2$ | Pyrimidinyl | $Z_1$: $CH_2F$ (para) |
| $CF_2$ | Pyridinyl | $NH-SO_2$ | Pyrimidinyl | $Z_1$: $CH_2F$ (meta) |
| $CF_2$ | Pyridinyl | $NH-SO_2$ | Pyrimidinyl | $Z_1$: $CH_2F$ (ortho) |
| $CF_2$ | Pyridinyl | $NH-SO_2$ | Pyrimidinyl | $Z_1$: $CHF_2$ (para) |
| $CF_2$ | Pyridinyl | $NH-SO_2$ | Pyrimidinyl | $Z_1$: $CHF_2$ (meta) |
| $CF_2$ | Pyridinyl | $NH-SO_2$ | Pyrimidinyl | $Z_1$: $CHF_2$ (ortho) |
| $CF_2$ | Pyridinyl | $NH-SO_2$ | Pyrimidinyl | $Z_1$: $CF_3$ (para) |
| $CF_2$ | Pyridinyl | $NH-SO_2$ | Pyrimidinyl | $Z_1$: $CF_3$ (meta) |
| $CF_2$ | Pyridinyl | $NH-SO_2$ | Pyrimidinyl | $Z_1$: $CF_3$ (ortho) |
| $CF_2$ | Pyridinyl | $NH-SO_2$ | Pyrimidinyl | $Z_1$: $CH_2-CH_2F$ (para) |
| $CF_2$ | Pyridinyl | $NH-SO_2$ | Pyrimidinyl | $Z_1$: $CH_2-CH_2F$ (meta) |
| $CF_2$ | Pyridinyl | $NH-SO_2$ | Pyrimidinyl | $Z_1$: $CH_2-CH_2F$ (ortho) |
| $CF_2$ | Pyridinyl | $NH-SO_2$ | Pyrimidinyl | $Z_1$: $CH_2-CHF_2$ (para) |

TABLE 2-continued

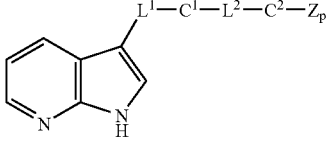

| L$^1$ | C$^1$ | L$^2$ | C$^2$ | Z |
|---|---|---|---|---|
| CF$_2$ | Pyridinyl | NH—SO$_2$ | Pyrimidinyl | Z$_1$: CH$_2$—CHF$_2$ (meta) |
| CF$_2$ | Pyridinyl | NH—SO$_2$ | Pyrimidinyl | Z$_1$: CH$_2$—CHF$_2$ (ortho) |
| CF$_2$ | Pyridinyl | NH—SO$_2$ | Pyrimidinyl | Z$_1$: CH$_2$—CF$_3$ (para) |
| CF$_2$ | Pyridinyl | NH—SO$_2$ | Pyrimidinyl | Z$_1$: CH$_2$—CF$_3$ (meta) |
| CF$_2$ | Pyridinyl | NH—SO$_2$ | Pyrimidinyl | Z$_1$: CH$_2$—CF$_3$ (ortho) |
| CF$_2$ | pyridinyl | NH—SO$_2$ | Pyrazinyl | None |
| CF$_2$ | pyridinyl | NH—SO$_2$ | Pyrazinyl | Z$_1$: F (para) |
| CF$_2$ | pyridinyl | NH—SO$_2$ | Pyrazinyl | Z$_1$: F (meta) |
| CF$_2$ | pyridinyl | NH—SO$_2$ | Pyrazinyl | Z$_1$: F (ortho) |
| CF$_2$ | pyridinyl | NH—SO$_2$ | Pyrazinyl | Z$_1$: F (para)<br>Z$_2$: F (meta) |
| CF$_2$ | Pyridinyl | NH—SO$_2$ | Pyrazinyl | Z$_1$: Cl (meta) |
| CF$_2$ | Pyridinyl | NH—SO$_2$ | Pyrazinyl | Z$_1$: Cl (para) |
| CF$_2$ | Pyridinyl | NH—SO$_2$ | Pyrazinyl | Z$_1$: Cl (para)<br>Z$_2$: Cl (meta) |
| CF$_2$ | Pyridinyl | NH—SO$_2$ | Pyrazinyl | Z$_1$: F (para)<br>Z$_2$: Cl (meta) |
| CF$_2$ | Pyridinyl | NH—SO$_2$ | Pyrazinyl | Z$_1$: Cl (para)<br>Z$_2$: F (meta) |
| CF$_2$ | Pyridinyl | NH—SO$_2$ | Pyrazinyl | Z$_1$: CH$_3$ (para) |
| CF$_2$ | Pyridinyl | NH—SO$_2$ | Pyrazinyl | Z$_1$: CH$_3$ (meta) |
| CF$_2$ | Pyridinyl | NH—SO$_2$ | Pyrazinyl | Z$_1$: CH$_3$ (ortho) |
| CF$_2$ | Pyridinyl | NH—SO$_2$ | Pyrazinyl | Z$_1$: CH$_2$—CH$_3$ (para) |
| CF$_2$ | Pyridinyl | NH—SO$_2$ | Pyrazinyl | Z$_1$: CH$_2$—CH$_3$ (meta) |
| CF$_2$ | Pyridinyl | NH—SO$_2$ | Pyrazinyl | Z$_1$: CH$_2$—CH$_3$ (ortho) |
| CF$_2$ | Pyridinyl | NH—SO$_2$ | Pyrazinyl | Z$_1$: CH$_2$—CH$_2$—CH$_3$ or iPr (para) |
| CF$_2$ | Pyridinyl | NH—SO$_2$ | Pyrazinyl | Z$_1$: CH$_2$—CH$_2$—CH$_3$ or iPr (meta) |
| CF$_2$ | Pyridinyl | NH—SO$_2$ | Pyrazinyl | Z$_1$: CH$_2$—CH$_2$—CH$_3$ or iPr (ortho) |
| CF$_2$ | Pyridinyl | NH—SO$_2$ | Pyrazinyl | Z$_1$: CH$_2$F (para) |
| CF$_2$ | Pyridinyl | NH—SO$_2$ | Pyrazinyl | Z$_1$: CH$_2$F (meta) |
| CF$_2$ | Pyridinyl | NH—SO$_2$ | Pyrazinyl | Z$_1$: CH$_2$F (ortho) |
| CF$_2$ | Pyridinyl | NH—SO$_2$ | Pyrazinyl | Z$_1$: CHF$_2$ (para) |
| CF$_2$ | Pyridinyl | NH—SO$_2$ | Pyrazinyl | Z$_1$: CHF$_2$ (meta) |
| CF$_2$ | Pyridinyl | NH—SO$_2$ | Pyrazinyl | Z$_1$: CHF$_2$ (ortho) |
| CF$_2$ | Pyridinyl | NH—SO$_2$ | Pyrazinyl | Z$_1$: CF$_3$ (para) |
| CF$_2$ | Pyridinyl | NH—SO$_2$ | Pyrazinyl | Z$_1$: CF$_3$ (meta) |
| CF$_2$ | Pyridinyl | NH—SO$_2$ | Pyrazinyl | Z$_1$: CF$_3$ (ortho) |
| CF$_2$ | Pyridinyl | NH—SO$_2$ | Pyrazinyl | Z$_1$: CH$_2$—CH$_2$F (para) |
| CF$_2$ | Pyridinyl | NH—SO$_2$ | Pyrazinyl | Z$_1$: CH$_2$—CH$_2$F (meta) |
| CF$_2$ | Pyridinyl | NH—SO$_2$ | Pyrazinyl | Z$_1$: CH$_2$—CH$_2$F (ortho) |
| CF$_2$ | Pyridinyl | NH—SO$_2$ | Pyrazinyl | Z$_1$: CH$_2$—CHF$_2$ (para) |
| CF$_2$ | Pyridinyl | NH—SO$_2$ | Pyrazinyl | Z$_1$: CH$_2$—CHF$_2$ (meta) |
| CF$_2$ | Pyridinyl | NH—SO$_2$ | Pyrazinyl | Z$_1$: CH$_2$—CHF$_2$ (ortho) |
| CF$_2$ | Pyridinyl | NH—SO$_2$ | Pyrazinyl | Z$_1$: CH$_2$—CF$_3$ (para) |
| CF$_2$ | Pyridinyl | NH—SO$_2$ | Pyrazinyl | Z$_1$: CH$_2$—CF$_3$ (meta) |
| CF$_2$ | Pyridinyl | NH—SO$_2$ | Pyrazinyl | Z$_1$: CH$_2$—CF$_3$ (ortho) |
| CF$_2$ | pyridinyl | NH—SO$_2$ | Pyrrolyl | None |
| CF$_2$ | pyridinyl | NH—SO$_2$ | Pyrrolyl | Z$_1$: F (2) |
| CF$_2$ | pyridinyl | NH—SO$_2$ | Pyrrolyl | Z$_1$: F (3) |
| CF$_2$ | pyridinyl | NH—SO$_2$ | Pyrrolyl | Z$_1$: F (2)<br>Z$_2$: F (3) |
| CF$_2$ | Pyridinyl | NH—SO$_2$ | Pyrrolyl | Z$_1$: Cl (2) |
| CF$_2$ | Pyridinyl | NH—SO$_2$ | Pyrrolyl | Z$_1$: Cl (3) |
| CF$_2$ | Pyridinyl | NH—SO$_2$ | Pyrrolyl | Z$_1$: Cl (2)<br>Z$_2$: Cl (3) |
| CF$_2$ | Pyridinyl | NH—SO$_2$ | Pyrrolyl | Z$_1$: F (2)<br>Z$_2$: Cl (3) |
| CF$_2$ | Pyridinyl | NH—SO$_2$ | Pyrrolyl | Z$_1$: Cl (2)<br>Z$_2$: F (3) |
| CF$_2$ | Pyridinyl | NH—SO$_2$ | Pyrrolyl | Z$_1$: CH$_3$ (2) |
| CF$_2$ | Pyridinyl | NH—SO$_2$ | Pyrrolyl | Z$_1$: CH$_3$ (3) |
| CF$_2$ | Pyridinyl | NH—SO$_2$ | Pyrrolyl | Z$_1$: CH$_2$—CH$_3$ (2) |
| CF$_2$ | Pyridinyl | NH—SO$_2$ | Pyrrolyl | Z$_1$: CH$_2$—CH$_3$ (3) |
| CF$_2$ | Pyridinyl | NH—SO$_2$ | Pyrrolyl | Z$_1$: CH$_2$—CH$_2$—CH$_3$ or iPr (2) |
| CF$_2$ | Pyridinyl | NH—SO$_2$ | Pyrrolyl | Z$_1$: CH$_2$—CH$_2$—CH$_3$ or iPr (3) |
| CF$_2$ | Pyridinyl | NH—SO$_2$ | Pyrrolyl | Z$_1$: CH$_2$F (2) |

TABLE 2-continued

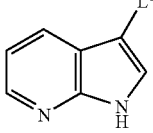

| L¹ | C¹ | L² | C² | Z |
|---|---|---|---|---|
| CF$_2$ | Pyridinyl | NH—SO$_2$ | Pyrrolyl | Z$_1$: CH$_2$F (3) |
| CF$_2$ | Pyridinyl | NH—SO$_2$ | Pyrrolyl | Z$_1$: CHF$_2$ (2) |
| CF$_2$ | Pyridinyl | NH—SO$_2$ | Pyrrolyl | Z$_1$: CHF$_2$ (3) |
| CF$_2$ | Pyridinyl | NH—SO$_2$ | Pyrrolyl | Z$_1$: CF$_3$ (2) |
| CF$_2$ | Pyridinyl | NH—SO$_2$ | Pyrrolyl | Z$_1$: CF$_3$ (3) |
| CF$_2$ | Pyridinyl | NH—SO$_2$ | Pyrrolyl | Z$_1$: CH$_2$—CH$_2$F (2) |
| CF$_2$ | Pyridinyl | NH—SO$_2$ | Pyrrolyl | Z$_1$: CH$_2$—CH$_2$F (3) |
| CF$_2$ | Pyridinyl | NH—SO$_2$ | Pyrrolyl | Z$_1$: CH$_2$—CHF$_2$ (2) |
| CF$_2$ | Pyridinyl | NH—SO$_2$ | Pyrrolyl | Z$_1$: CH$_2$—CHF$_2$ (3) |
| CF$_2$ | Pyridinyl | NH—SO$_2$ | Pyrrolyl | Z$_1$: CH$_2$—CF$_3$ (2) |
| CF$_2$ | Pyridinyl | NH—SO$_2$ | Pyrrolyl | Z$_1$: CH$_2$—CF$_3$ (3) |
| CF$_2$ | pyridinyl | NH—SO$_2$ | Imidazolyl | None |
| CF$_2$ | pyridinyl | NH—SO$_2$ | Imidazolyl | Z$_1$: F (2) |
| CF$_2$ | pyridinyl | NH—SO$_2$ | Imidazolyl | Z$_1$: F (3) |
| CF$_2$ | pyridinyl | NH—SO$_2$ | Imidazolyl | Z$_1$: F (2) Z$_2$: F (3) |
| CF$_2$ | Pyridinyl | NH—SO$_2$ | Imidazolyl | Z$_1$: Cl (2) |
| CF$_2$ | Pyridinyl | NH—SO$_2$ | Imidazolyl | Z$_1$: Cl (3) |
| CF$_2$ | Pyridinyl | NH—SO$_2$ | Imidazolyl | Z$_1$: Cl (2) Z$_2$: Cl (3) |
| CF$_2$ | Pyridinyl | NH—SO$_2$ | Imidazolyl | Z$_1$: F (2) Z$_2$: Cl (3) |
| CF$_2$ | Pyridinyl | NH—SO$_2$ | Imidazolyl | Z$_1$: Cl (2) Z$_2$: F (3) |
| CF$_2$ | Pyridinyl | NH—SO$_2$ | Imidazolyl | Z$_1$: CH$_3$ (2) |
| CF$_2$ | Pyridinyl | NH—SO$_2$ | Imidazolyl | Z$_1$: CH$_3$ (3) |
| CF$_2$ | Pyridinyl | NH—SO$_2$ | Imidazolyl | Z$_1$: CH$_2$—CH$_3$ (2) |
| CF$_2$ | Pyridinyl | NH—SO$_2$ | Imidazolyl | Z$_1$: CH$_2$—CH$_3$ (3) |
| CF$_2$ | Pyridinyl | NH—SO$_2$ | Imidazolyl | Z$_1$: CH$_2$—CH$_2$—CH$_3$ or iPr (2) |
| CF$_2$ | Pyridinyl | NH—SO$_2$ | Imidazolyl | Z$_1$: CH$_2$—CH$_2$—CH$_3$ or iPr (3) |
| CF$_2$ | Pyridinyl | NH—SO$_2$ | Imidazolyl | Z$_1$: CH$_2$F (2) |
| CF$_2$ | Pyridinyl | NH—SO$_2$ | Imidazolyl | Z$_1$: CH$_2$F (3) |
| CF$_2$ | Pyridinyl | NH—SO$_2$ | Imidazolyl | Z$_1$: CHF$_2$ (2) |
| CF$_2$ | Pyridinyl | NH—SO$_2$ | Imidazolyl | Z$_1$: CHF$_2$ (3) |
| CF$_2$ | Pyridinyl | NH—SO$_2$ | Imidazolyl | Z$_1$: CF$_3$ (2) |
| CF$_2$ | Pyridinyl | NH—SO$_2$ | Imidazolyl | Z$_1$: CF$_3$ (3) |
| CF$_2$ | Pyridinyl | NH—SO$_2$ | Imidazolyl | Z$_1$: CH$_2$—CH$_2$F (2) |
| CF$_2$ | Pyridinyl | NH—SO$_2$ | Imidazolyl | Z$_1$: CH$_2$—CH$_2$F (3) |
| CF$_2$ | Pyridinyl | NH—SO$_2$ | Imidazolyl | Z$_1$: CH$_2$—CHF$_2$ (2) |
| CF$_2$ | Pyridinyl | NH—SO$_2$ | Imidazolyl | Z$_1$: CH$_2$—CHF$_2$ (3) |
| CF$_2$ | Pyridinyl | NH—SO$_2$ | Imidazolyl | Z$_1$: CH$_2$—CF$_3$ (2) |
| CF$_2$ | Pyridinyl | NH—SO$_2$ | Imidazolyl | Z$_1$: CH$_2$—CF$_3$ (3) |
| CF$_2$ | pyridinyl | NH—SO$_2$ | Furanyl | None |
| CF$_2$ | pyridinyl | NH—SO$_2$ | Furanyl | Z$_1$: F (2) |
| CF$_2$ | pyridinyl | NH—SO$_2$ | Furanyl | Z$_1$: F (3) |
| CF$_2$ | pyridinyl | NH—SO$_2$ | Furanyl | Z$_1$: F (2) Z$_2$: F (3) |
| CF$_2$ | Pyridinyl | NH—SO$_2$ | Furanyl | Z$_1$: Cl (2) |
| CF$_2$ | Pyridinyl | NH—SO$_2$ | Furanyl | Z$_1$: Cl (3) |
| CF$_2$ | Pyridinyl | NH—SO$_2$ | Furanyl | Z$_1$: Cl (2) Z$_2$: Cl (3) |
| CF$_2$ | Pyridinyl | NH—SO$_2$ | Furanyl | Z$_1$: F (2) Z$_2$: Cl (3) |
| CF$_2$ | Pyridinyl | NH—SO$_2$ | Furanyl | Z$_1$: Cl (2) Z$_2$: F (3) |
| CF$_2$ | Pyridinyl | NH—SO$_2$ | Furanyl | Z$_1$: CH$_3$ (2) |
| CF$_2$ | Pyridinyl | NH—SO$_2$ | Furanyl | Z$_1$: CH$_3$ (3) |
| CF$_2$ | Pyridinyl | NH—SO$_2$ | Furanyl | Z$_1$: CH$_2$—CH$_3$ (2) |
| CF$_2$ | Pyridinyl | NH—SO$_2$ | Furanyl | Z$_1$: CH$_2$—CH$_3$ (3) |
| CF$_2$ | Pyridinyl | NH—SO$_2$ | Furanyl | Z$_1$: CH$_2$—CH$_2$—CH$_3$ or iPr (2) |
| CF$_2$ | Pyridinyl | NH—SO$_2$ | Furanyl | Z$_1$: CH$_2$—CH$_2$—CH$_3$ or iPr (3) |
| CF$_2$ | Pyridinyl | NH—SO$_2$ | Furanyl | Z$_1$: CH$_2$F (2) |
| CF$_2$ | Pyridinyl | NH—SO$_2$ | Furanyl | Z$_1$: CH$_2$F (3) |
| CF$_2$ | Pyridinyl | NH—SO$_2$ | Furanyl | Z$_1$: CHF$_2$ (2) |
| CF$_2$ | Pyridinyl | NH—SO$_2$ | Furanyl | Z$_1$: CHF$_2$ (3) |
| CF$_2$ | Pyridinyl | NH—SO$_2$ | Furanyl | Z$_1$: CF$_3$ (2) |
| CF$_2$ | Pyridinyl | NH—SO$_2$ | Furanyl | Z$_1$: CF$_3$ (3) |
| CF$_2$ | Pyridinyl | NH—SO$_2$ | Furanyl | Z$_1$: CH$_2$—CH$_2$F (2) |
| CF$_2$ | Pyridinyl | NH—SO$_2$ | Furanyl | Z$_1$: CH$_2$—CH$_2$F (3) |

TABLE 2-continued

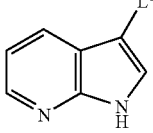

| L$^1$ | C$^1$ | L$^2$ | C$^2$ | Z |
|---|---|---|---|---|
| CF$_2$ | Pyridinyl | NH—SO$_2$ | Furanyl | Z$_1$: CH$_2$—CHF$_2$ (2) |
| CF$_2$ | Pyridinyl | NH—SO$_2$ | Furanyl | Z$_1$: CH$_2$—CHF$_2$ (3) |
| CF$_2$ | Pyridinyl | NH—SO$_2$ | Furanyl | Z$_1$: CH$_2$—CF$_3$ (2) |
| CF$_2$ | Pyridinyl | NH—SO$_2$ | Furanyl | Z$_1$: CH$_2$—CF$_3$ (3) |
| CF$_2$ | pyridinyl | NH—SO$_2$ | Oxazolyl | None |
| CF$_2$ | Pyridinyl | NH—SO$_2$ | Oxazolyl | Z$_1$: F (2) |
| CF$_2$ | pyridinyl | NH—SO$_2$ | Oxazolyl | Z$_1$: F (3) |
| CF$_2$ | pyridinyl | NH—SO$_2$ | Oxazolyl | Z$_1$: F (2) Z$_2$: F (3) |
| CF$_2$ | Pyridinyl | NH—SO$_2$ | Oxazolyl | Z$_1$: Cl (2) |
| CF$_2$ | Pyridinyl | NH—SO$_2$ | Oxazolyl | Z$_1$: Cl (3) |
| CF$_2$ | Pyridinyl | NH—SO$_2$ | Oxazolyl | Z$_1$: Cl (2) Z$_2$: Cl (3) |
| CF$_2$ | Pyridinyl | NH—SO$_2$ | Oxazolyl | Z$_1$: F (2) Z$_2$: Cl (3) |
| CF$_2$ | Pyridinyl | NH—SO$_2$ | Oxazolyl | Z$_1$: Cl (2) Z$_2$: F (3) |
| CF$_2$ | Pyridinyl | NH—SO$_2$ | Oxazolyl | Z$_1$: CH$_3$ (2) |
| CF$_2$ | Pyridinyl | NH—SO$_2$ | Oxazolyl | Z$_1$: CH$_3$ (3) |
| CF$_2$ | Pyridinyl | NH—SO$_2$ | Oxazolyl | Z$_1$: CH$_2$—CH$_3$ (2) |
| CF$_2$ | Pyridinyl | NH—SO$_2$ | Oxazolyl | Z$_1$: CH$_2$—CH$_3$ (3) |
| CF$_2$ | Pyridinyl | NH—SO$_2$ | Oxazolyl | Z$_1$: CH$_2$—CH$_2$—CH$_3$ or iPr (2) |
| CF$_2$ | Pyridinyl | NH—SO$_2$ | Oxazolyl | Z$_1$: CH$_2$—CH$_2$—CH$_3$ or iPr (3) |
| CF$_2$ | Pyridinyl | NH—SO$_2$ | Oxazolyl | Z$_1$: CH$_2$F (2) |
| CF$_2$ | Pyridinyl | NH—SO$_2$ | Oxazolyl | Z$_1$: CH$_2$F (3) |
| CF$_2$ | Pyridinyl | NH—SO$_2$ | Oxazolyl | Z$_1$: CHF$_2$ (2) |
| CF$_2$ | Pyridinyl | NH—SO$_2$ | Oxazolyl | Z$_1$: CHF$_2$ (3) |
| CF$_2$ | Pyridinyl | NH—SO$_2$ | Oxazolyl | Z$_1$: CF$_3$ (2) |
| CF$_2$ | Pyridinyl | NH—SO$_2$ | Oxazolyl | Z$_1$: CF$_3$ (3) |
| CF$_2$ | Pyridinyl | NH—SO$_2$ | Oxazolyl | Z$_1$: CH$_2$—CH$_2$F (2) |
| CF$_2$ | Pyridinyl | NH—SO$_2$ | Oxazolyl | Z$_1$: CH$_2$—CH$_2$F (3) |
| CF$_2$ | Pyridinyl | NH—SO$_2$ | Oxazolyl | Z$_1$: CH$_2$—CHF$_2$ (2) |
| CF$_2$ | Pyridinyl | NH—SO$_2$ | Oxazolyl | Z$_1$: CH$_2$—CHF$_2$ (3) |
| CF$_2$ | Pyridinyl | NH—SO$_2$ | Oxazolyl | Z$_1$: CH$_2$—CF$_3$ (2) |
| CF$_2$ | Pyridinyl | NH—SO$_2$ | Oxazolyl | Z$_1$: CH$_2$—CF$_3$ (3) |
| CF$_2$ | pyridinyl | NH—SO$_2$ | Thiophenyl | None |
| CF$_2$ | pyridinyl | NH—SO$_2$ | Thiophenyl | Z$_1$: F (2) |
| CF$_2$ | pyridinyl | NH—SO$_2$ | Thiophenyl | Z$_1$: F (3) |
| CF$_2$ | pyridinyl | NH—SO$_2$ | Thiophenyl | Z$_1$: F (2) Z$_2$: F (3) |
| CF$_2$ | Pyridinyl | NH—SO$_2$ | Thiophenyl | Z$_1$: Cl (2) |
| CF$_2$ | Pyridinyl | NH—SO$_2$ | Thiophenyl | Z$_1$: Cl (3) |
| CF$_2$ | Pyridinyl | NH—SO$_2$ | Thiophenyl | Z$_1$: Cl (2) Z$_2$: Cl (3) |
| CF$_2$ | Pyridinyl | NH—SO$_2$ | Thiophenyl | Z$_1$: F (2) Z$_2$: Cl (3) |
| CF$_2$ | Pyridinyl | NH—SO$_2$ | Thiophenyl | Z$_1$: Cl (2) Z$_2$: F (3) |
| CF$_2$ | Pyridinyl | NH—SO$_2$ | Thiophenyl | Z$_1$: CH$_3$ (2) |
| CF$_2$ | Pyridinyl | NH—SO$_2$ | Thiophenyl | Z$_1$: CH$_3$ (3) |
| CF$_2$ | Pyridinyl | NH—SO$_2$ | Thiophenyl | Z$_1$: CH$_2$—CH$_3$ (2) |
| CF$_2$ | Pyridinyl | NH—SO$_2$ | Thiophenyl | Z$_1$: CH$_2$—CH$_3$ (3) |
| CF$_2$ | Pyridinyl | NH—SO$_2$ | Thiophenyl | Z$_1$: CH$_2$—CH$_2$—CH$_3$ or iPr (2) |
| CF$_2$ | Pyridinyl | NH—SO$_2$ | Thiophenyl | Z$_1$: CH$_2$—CH$_2$—CH$_3$ or iPr (3) |
| CF$_2$ | Pyridinyl | NH—SO$_2$ | Thiophenyl | Z$_1$: CH$_2$F (2) |
| CF$_2$ | Pyridinyl | NH—SO$_2$ | Thiophenyl | Z$_1$: CH$_2$F (3) |
| CF$_2$ | Pyridinyl | NH—SO$_2$ | Thiophenyl | Z$_1$: CHF$_2$ (2) |
| CF$_2$ | Pyridinyl | NH—SO$_2$ | Thiophenyl | Z$_1$: CHF$_2$ (3) |
| CF$_2$ | Pyridinyl | NH—SO$_2$ | Thiophenyl | Z$_1$: CF$_3$ (2) |
| CF$_2$ | Pyridinyl | NH—SO$_2$ | Thiophenyl | Z$_1$: CF$_3$ (3) |
| CF$_2$ | Pyridinyl | NH—SO$_2$ | Thiophenyl | Z$_1$: CH$_2$—CH$_2$F (2) |
| CF$_2$ | Pyridinyl | NH—SO$_2$ | Thiophenyl | Z$_1$: CH$_2$—CH$_2$F (3) |
| CF$_2$ | Pyridinyl | NH—SO$_2$ | Thiophenyl | Z$_1$: CH$_2$—CHF$_2$ (2) |
| CF$_2$ | Pyridinyl | NH—SO$_2$ | Thiophenyl | Z$_1$: CH$_2$—CHF$_2$ (3) |
| CF$_2$ | Pyridinyl | NH—SO$_2$ | Thiophenyl | Z$_1$: CH$_2$—CF$_3$ (2) |
| CF$_2$ | Pyridinyl | NH—SO$_2$ | Thiophenyl | Z$_1$: CH$_2$—CF$_3$ (3) |
| CF$_2$ | pyridinyl | NH—SO$_2$ | Thiazolyl | None |
| CF$_2$ | pyridinyl | NH—SO$_2$ | Thiazolyl | Z$_1$: F (2) |
| CF$_2$ | pyridinyl | NH—SO$_2$ | Thiazolyl | Z$_1$: F (3) |

TABLE 2-continued

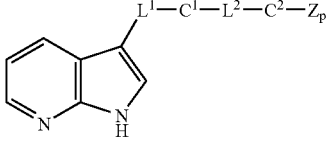

$L^1$—$C^1$—$L^2$—$C^2$—$Z_p$

| $L^1$ | $C^1$ | $L^2$ | $C^2$ | Z |
|---|---|---|---|---|
| $CF_2$ | pyridinyl | NH—$SO_2$ | Thiazolyl | $Z_1$: F (2)<br>$Z_2$: F (3) |
| $CF_2$ | Pyridinyl | NH—$SO_2$ | Thiazolyl | $Z_1$: Cl (2) |
| $CF_2$ | Pyridinyl | NH—$SO_2$ | Thiazolyl | $Z_1$: Cl (3) |
| $CF_2$ | Pyridinyl | NH—$SO_2$ | Thiazolyl | $Z_1$: Cl (2)<br>$Z_2$: Cl (3) |
| $CF_2$ | Pyridinyl | NH—$SO_2$ | Thiazolyl | $Z_1$: F (2)<br>$Z_2$: Cl (3) |
| $CF_2$ | Pyridinyl | NH—$SO_2$ | Thiazolyl | $Z_1$: Cl (2)<br>$Z_2$: F (3) |
| $CF_2$ | Pyridinyl | NH—$SO_2$ | Thiazolyl | $Z_1$: $CH_3$ (2) |
| $CF_2$ | Pyridinyl | NH—$SO_2$ | Thiazolyl | $Z_1$: $CH_3$ (3) |
| $CF_2$ | Pyridinyl | NH—$SO_2$ | Thiazolyl | $Z_1$: $CH_2$—$CH_3$ (2) |
| $CF_2$ | Pyridinyl | NH—$SO_2$ | Thiazolyl | $Z_1$: $CH_2$—$CH_3$ (3) |
| $CF_2$ | Pyridinyl | NH—$SO_2$ | Thiazolyl | $Z_1$: $CH_2$—$CH_2$—$CH_3$ or iPr (2) |
| $CF_2$ | Pyridinyl | NH—$SO_2$ | Thiazolyl | $Z_1$: $CH_2$—$CH_2$—$CH_3$ or iPr (3) |
| $CF_2$ | Pyridinyl | NH—$SO_2$ | Thiazolyl | $Z_1$: $CH_2F$ (2) |
| $CF_2$ | Pyridinyl | NH—$SO_2$ | Thiazolyl | $Z_1$: $CH_2F$ (3) |
| $CF_2$ | Pyridinyl | NH—$SO_2$ | Thiazolyl | $Z_1$: $CHF_2$ (2) |
| $CF_2$ | Pyridinyl | NH—$SO_2$ | Thiazolyl | $Z_1$: $CHF_2$ (3) |
| $CF_2$ | Pyridinyl | NH—$SO_2$ | Thiazolyl | $Z_1$: $CF_3$ (2) |
| $CF_2$ | Pyridinyl | NH—$SO_2$ | Thiazolyl | $Z_1$: $CF_3$ (3) |
| $CF_2$ | Pyridinyl | NH—$SO_2$ | Thiazolyl | $Z_1$: $CH_2$—$CH_2F$ (2) |
| $CF_2$ | Pyridinyl | NH—$SO_2$ | Thiazolyl | $Z_1$: $CH_2$—$CH_2F$ (3) |
| $CF_2$ | Pyridinyl | NH—$SO_2$ | Thiazolyl | $Z_1$: $CH_2$—$CHF_2$ (2) |
| $CF_2$ | Pyridinyl | NH—$SO_2$ | Thiazolyl | $Z_1$: $CH_2$—$CHF_2$ (3) |
| $CF_2$ | Pyridinyl | NH—$SO_2$ | Thiazolyl | $Z_1$: $CH_2$—$CF_3$ (2) |
| $CF_2$ | Pyridinyl | NH—$SO_2$ | Thiazolyl | $Z_1$: $CH_2$—$CF_3$ (3) |
| $CF_2$ | Pyrimidinyl | NH—$CH_2$ | Phenyl | None |
| $CF_2$ | Pyrimidinyl | NH—$CH_2$ | Phenyl | $Z_1$: F (para) |
| $CF_2$ | Pyrimidinyl | NH—$CH_2$ | phenyl | $Z_1$: F (meta) |
| $CF_2$ | Pyrimidinyl | NH—$CH_2$ | phenyl | $Z_1$: F (ortho) |
| $CF_2$ | Pyrimidinyl | NH—$CH_2$ | phenyl | $Z_1$: F (para)<br>$Z_2$: F (meta) |
| $CF_2$ | Pyrimidinyl | NH—$CH_2$ | Phenyl | $Z_1$: Cl (meta) |
| $CF_2$ | Pyrimidinyl | NH—$CH_2$ | Phenyl | $Z_1$: Cl (para) |
| $CF_2$ | Pyrimidinyl | NH—$CH_2$ | Phenyl | $Z_1$: Cl (para)<br>$Z_2$: Cl (meta) |
| $CF_2$ | Pyrimidinyl | NH—$CH_2$ | Phenyl | $Z_1$: F (para)<br>$Z_2$: Cl (meta) |
| $CF_2$ | Pyrimidinyl | NH—$CH_2$ | Phenyl | $Z_1$: Cl (para)<br>$Z_2$: F (meta) |
| $CF_2$ | Pyrimidinyl | NH—$CH_2$ | Phenyl | $Z_1$: $CH_3$ (para) |
| $CF_2$ | Pyrimidinyl | NH—$CH_2$ | Phenyl | $Z_1$: $CH_3$ (meta) |
| $CF_2$ | Pyrimidinyl | NH—$CH_2$ | Phenyl | $Z_1$: $CH_3$ (ortho) |
| $CF_2$ | Pyrimidinyl | NH—$CH_2$ | Phenyl | $Z_1$: $CH_2$—$CH_3$ (para) |
| $CF_2$ | Pyrimidinyl | NH—$CH_2$ | Phenyl | $Z_1$: $CH_2$—$CH_3$ (meta) |
| $CF_2$ | Pyrimidinyl | NH—$CH_2$ | Phenyl | $Z_1$: $CH_2$—$CH_3$ (ortho) |
| $CF_2$ | Pyrimidinyl | NH—$CH_2$ | Phenyl | $Z_1$: $CH_2$—$CH_2$—$CH_3$ or iPr (para) |
| $CF_2$ | Pyrimidinyl | NH—$CH_2$ | Phenyl | $Z_1$: $CH_2$—$CH_2$—$CH_3$ or iPr (meta) |
| $CF_2$ | Pyrimidinyl | NH—$CH_2$ | Phenyl | $Z_1$: $CH_2$—$CH_2$—$CH_3$ or iPr (ortho) |
| $CF_2$ | Pyrimidinyl | NH—$CH_2$ | Phenyl | $Z_1$: $CH_2F$ (para) |
| $CF_2$ | Pyrimidinyl | NH—$CH_2$ | Phenyl | $Z_1$: $CH_2F$ (meta) |
| $CF_2$ | Pyrimidinyl | NH—$CH_2$ | Phenyl | $Z_1$: $CH_2F$ (ortho) |
| $CF_2$ | Pyrimidinyl | NH—$CH_2$ | Phenyl | $Z_1$: $CHF_2$ (para) |
| $CF_2$ | Pyrimidinyl | NH—$CH_2$ | Phenyl | $Z_1$: $CHF_2$ (meta) |
| $CF_2$ | Pyrimidinyl | NH—$CH_2$ | Phenyl | $Z_1$: $CHF_2$ (ortho) |
| $CF_2$ | Pyrimidinyl | NH—$CH_2$ | Phenyl | $Z_1$: $CF_3$ (para) |
| $CF_2$ | Pyrimidinyl | NH—$CH_2$ | Phenyl | $Z_1$: $CF_3$ (meta) |
| $CF_2$ | Pyrimidinyl | NH—$CH_2$ | Phenyl | $Z_1$: $CF_3$ (ortho) |
| $CF_2$ | Pyrimidinyl | NH—$CH_2$ | Phenyl | $Z_1$: $CH_2$—$CH_2F$ (para) |
| $CF_2$ | Pyrimidinyl | NH—$CH_2$ | Phenyl | $Z_1$: $CH_2$—$CH_2F$ (meta) |
| $CF_2$ | Pyrimidinyl | NH—$CH_2$ | Phenyl | $Z_1$: $CH_2$—$CH_2F$ (ortho) |
| $CF_2$ | Pyrimidinyl | NH—$CH_2$ | Phenyl | $Z_1$: $CH_2$—$CHF_2$ (para) |
| $CF_2$ | Pyrimidinyl | NH—$CH_2$ | Phenyl | $Z_1$: $CH_2$—$CHF_2$ (meta) |
| $CF_2$ | Pyrimidinyl | NH—$CH_2$ | Phenyl | $Z_1$: $CH_2$—$CHF_2$ (ortho) |

TABLE 2-continued $$L^1\text{—}C^1\text{—}L^2\text{—}C^2\text{—}Z_p$$

(7-azaindole structure with L¹—C¹—L²—C²—Z_p at 3-position)

| L¹ | C¹ | L² | C² | Z |
|---|---|---|---|---|
| CF₂ | Pyrimidinyl | NH—CH₂ | Phenyl | Z₁: CH₂—CF₃ (para) |
| CF₂ | Pyrimidinyl | NH—CH₂ | Phenyl | Z₁: CH₂—CF₃ (meta) |
| CF₂ | Pyrimidinyl | NH—CH₂ | Phenyl | Z₁: CH₂—CF₃ (ortho) |
| CF₂ | Pyrimidinyl | NH—CH₂ | Pyridinyl | None |
| CF₂ | Pyrimidinyl | NH—CH₂ | Pyridinyl | Z₁: F (para) |
| CF₂ | Pyrimidinyl | NH—CH₂ | Pyridinyl | Z₁: F (meta) |
| CF₂ | Pyrimidinyl | NH—CH₂ | Pyridinyl | Z₁: F (ortho) |
| CF₂ | Pyrimidinyl | NH—CH₂ | Pyridinyl | Z₁: F (para) Z₂: F (meta) |
| CF₂ | Pyrimidinyl | NH—CH₂ | Pyridinyl | Z₁: Cl (meta) |
| CF₂ | Pyrimidinyl | NH—CH₂ | Pyridinyl | Z₁: Cl (para) |
| CF₂ | Pyrimidinyl | NH—CH₂ | Pyridinyl | Z₁: Cl (para) Z₂: Cl (meta) |
| CF₂ | Pyrimidinyl | NH—CH₂ | Pyridinyl | Z₁: F (para) Z₂: Cl (meta) |
| CF₂ | Pyrimidinyl | NH—CH₂ | Pyridinyl | Z₁: Cl (para) Z₂: F (meta) |
| CF₂ | Pyrimidinyl | NH—CH₂ | Pyridinyl | Z₁: CH₃ (para) |
| CF₂ | Pyrimidinyl | NH—CH₂ | Pyridinyl | Z₁: CH₃ (meta) |
| CF₂ | Pyrimidinyl | NH—CH₂ | Pyridinyl | Z₁: CH₃ (ortho) |
| CF₂ | Pyrimidinyl | NH—CH₂ | Pyridinyl | Z₁: CH₂—CH₃ (para) |
| CF₂ | Pyrimidinyl | NH—CH₂ | Pyridinyl | Z₁: CH₂—CH₃ (meta) |
| CF₂ | Pyrimidinyl | NH—CH₂ | Pyridinyl | Z₁: CH₂—CH₃ (ortho) |
| CF₂ | Pyrimidinyl | NH—CH₂ | Pyridinyl | Z₁: CH₂—CH₂—CH₃ or iPr (para) |
| CF₂ | Pyrimidinyl | NH—CH₂ | Pyridinyl | Z₁: CH₂—CH₂—CH₃ or iPr (meta) |
| CF₂ | Pyrimidinyl | NH—CH₂ | Pyridinyl | Z₁: CH₂—CH₂—CH₃ or iPr (ortho) |
| CF₂ | Pyrimidinyl | NH—CH₂ | Pyridinyl | Z₁: CH₂F (para) |
| CF₂ | Pyrimidinyl | NH—CH₂ | Pyridinyl | Z₁: CH₂F (meta) |
| CF₂ | Pyrimidinyl | NH—CH₂ | Pyridinyl | Z₁: CH₂F (ortho) |
| CF₂ | Pyrimidinyl | NH—CH₂ | Pyridinyl | Z₁: CHF₂ (para) |
| CF₂ | Pyrimidinyl | NH—CH₂ | Pyridinyl | Z₁: CHF₂ (meta) |
| CF₂ | Pyrimidinyl | NH—CH₂ | Pyridinyl | Z₁: CHF₂ (ortho) |
| CF₂ | Pyrimidinyl | NH—CH₂ | Pyridinyl | Z₁: CF₃ (para) |
| CF₂ | Pyrimidinyl | NH—CH₂ | Pyridinyl | Z₁: CF₃ (meta) |
| CF₂ | Pyrimidinyl | NH—CH₂ | Pyridinyl | Z₁: CF₃ (ortho) |
| CF₂ | Pyrimidinyl | NH—CH₂ | Pyridinyl | Z₁: CH₂—CH₂F (para) |
| CF₂ | Pyrimidinyl | NH—CH₂ | Pyridinyl | Z₁: CH₂—CH₂F (meta) |
| CF₂ | Pyrimidinyl | NH—CH₂ | Pyridinyl | Z₁: CH₂—CH₂F (ortho) |
| CF₂ | Pyrimidinyl | NH—CH₂ | Pyridinyl | Z₁: CH₂—CHF₂ (para) |
| CF₂ | Pyrimidinyl | NH—CH₂ | Pyridinyl | Z₁: CH₂—CHF₂ (meta) |
| CF₂ | Pyrimidinyl | NH—CH₂ | Pyridinyl | Z₁: CH₂—CHF₂ (ortho) |
| CF₂ | Pyrimidinyl | NH—CH₂ | Pyridinyl | Z₁: CH₂—CF₃ (para) |
| CF₂ | Pyrimidinyl | NH—CH₂ | Pyridinyl | Z₁: CH₂—CF₃ (meta) |
| CF₂ | Pyrimidinyl | NH—CH₂ | Pyridinyl | Z₁: CH₂—CF₃ (ortho) |
| CF₂ | Pyrimidinyl | NH—CH₂ | Pyrimidinyl | None |
| CF₂ | Pyrimidinyl | NH—CH₂ | Pyrimidinyl | Z₁: F (para) |
| CF₂ | Pyrimidinyl | NH—CH₂ | Pyrimidinyl | Z₁: F (meta) |
| CF₂ | Pyrimidinyl | NH—CH₂ | Pyrimidinyl | Z₁: F (ortho) |
| CF₂ | Pyrimidinyl | NH—CH₂ | Pyrimidinyl | Z₁: F (para) |
| CF₂ | Pyrimidinyl | NH—CH₂ | Pyrimidinyl | Z₁: Cl (meta) |
| CF₂ | Pyrimidinyl | NH—CH₂ | Pyrimidinyl | Z₁: Cl (para) |
| CF₂ | Pyrimidinyl | NH—CH₂ | Pyrimidinyl | Z₁: Cl (para) |
| CF₂ | Pyrimidinyl | NH—CH₂ | Pyrimidinyl | Z₁: F (para) Z₂: Cl (meta) |
| CF₂ | Pyrimidinyl | NH—CH₂ | Pyrimidinyl | Z₁: Cl (para) Z₂: F (meta) |
| CF₂ | Pyrimidinyl | NH—CH₂ | Pyrimidinyl | Z₁: CH₃ (para) |
| CF₂ | Pyrimidinyl | NH—CH₂ | Pyrimidinyl | Z₁: CH₃ (meta) |
| CF₂ | Pyrimidinyl | NH—CH₂ | Pyrimidinyl | Z₁: CH₃ (ortho) |
| CF₂ | Pyrimidinyl | NH—CH₂ | Pyrimidinyl | Z₁: CH₂—CH₃ (ara |
| CF₂ | Pyrimidinyl | NH—CH₂ | Pyrimidinyl | Z₁: CH₂—CH₃ (meta) |
| CF₂ | Pyrimidinyl | NH—CH₂ | Pyrimidinyl | Z₁: CH₂—CH₃ (ortho) |
| CF₂ | Pyrimidinyl | NH—CH₂ | Pyrimidinyl | Z₁: CH₂—CH₂—CH₃ or iPr (para) |
| CF₂ | Pyrimidinyl | NH—CH₂ | Pyrimidinyl | Z₁: CH₂—CH₂—CH₃ or iPr |
| CF₂ | Pyrimidinyl | NH—CH₂ | Pyrimidinyl | Z₁: CH₂—CH₂—CH₃ or iPr |

TABLE 2-continued $$L^1-C^1-L^2-C^2-Z_p$$

[Structure: 7-azaindole (1H-pyrrolo[2,3-b]pyridine) with substitution at 3-position]

| L¹ | C¹ | L² | C² | Z |
|---|---|---|---|---|
| CF₂ | Pyrimidinyl | NH—CH₂ | Pyrimidinyl | Z₁: CH₂F (para) |
| CF₂ | Pyrimidinyl | NH—CH₂ | Pyrimidinyl | Z₁: CH₂F (meta) |
| CF₂ | Pyrimidinyl | NH—CH₂ | Pyrimidinyl | Z₁: CH₂F (ortho) |
| CF₂ | Pyrimidinyl | NH—CH₂ | Pyrimidinyl | Z₁: CHF₂ (para) |
| CF₂ | Pyrimidinyl | NH—CH₂ | Pyrimidinyl | Z₁: CHF₂ (meta) |
| CF₂ | Pyrimidinyl | NH—CH₂ | Pyrimidinyl | Z₁: CHF₂ (ortho) |
| CF₂ | Pyrimidinyl | NH—CH₂ | Pyrimidinyl | Z₁: CF₃ (para) |
| CF₂ | Pyrimidinyl | NH—CH₂ | Pyrimidinyl | Z₁: CF₃ (meta) |
| CF₂ | Pyrimidinyl | NH—CH₂ | Pyrimidinyl | Z₁: CF₃ (ortho) |
| CF₂ | Pyrimidinyl | NH—CH₂ | Pyrimidinyl | Z₁: CH₂—CH₂F (para) |
| CF₂ | Pyrimidinyl | NH—CH₂ | Pyrimidinyl | Z₁: CH₂—CH₂F (meta) |
| CF₂ | Pyrimidinyl | NH—CH₂ | Pyrimidinyl | Z₁: CH₂—CH₂F (ortho) |
| CF₂ | Pyrimidinyl | NH—CH₂ | Pyrimidinyl | Z₁: CH₂—CHF₂ (para) |
| CF₂ | Pyrimidinyl | NH—CH₂ | Pyrimidinyl | Z₁: CH₂—CHF₂ (meta) |
| CF₂ | Pyrimidinyl | NH—CH₂ | Pyrimidinyl | Z₁: CH₂—CHF₂ (ortho) |
| CF₂ | Pyrimidinyl | NH—CH₂ | Pyrimidinyl | Z₁: CH₂—CF₃ (para) |
| CF₂ | Pyrimidinyl | NH—CH₂ | Pyrimidinyl | Z₁: CH₂—CF₃ (meta) |
| CF₂ | Pyrimidinyl | NH—CH₂ | Pyrimidinyl | Z₁: CH₂—CF₃ (ortho) |
| CF₂ | Pyrimidinyl | NH—CH₂ | Pyrazinyl | None |
| CF₂ | Pyrimidinyl | NH—CH₂ | Pyrazinyl | Z₁: F (para) |
| CF₂ | Pyrimidinyl | NH—CH₂ | Pyrazinyl | Z₁: F (meta) |
| CF₂ | Pyrimidinyl | NH—CH₂ | Pyrazinyl | Z₁: F (ortho) |
| CF₂ | Pyrimidinyl | NH—CH₂ | Pyrazinyl | Z₁: F (para)<br>Z₂: F (meta) |
| CF₂ | Pyrimidinyl | NH—CH₂ | Pyrazinyl | Z₁: Cl (meta) |
| CF₂ | Pyrimidinyl | NH—CH₂ | Pyrazinyl | Z₁: Cl (para) |
| CF₂ | Pyrimidinyl | NH—CH₂ | Pyrazinyl | Z₁: Cl (para)<br>Z₂: Cl (meta) |
| CF₂ | Pyrimidinyl | NH—CH₂ | Pyrazinyl | Z₁: F (para)<br>Z₂: Cl (meta) |
| CF₂ | Pyrimidinyl | NH—CH₂ | Pyrazinyl | Z₁: Cl (para)<br>Z₂: F (meta) |
| CF₂ | Pyrimidinyl | NH—CH₂ | Pyrazinyl | Z₁: CH₃ (para) |
| CF₂ | Pyrimidinyl | NH—CH₂ | Pyrazinyl | Z₁: CH₃ (meta) |
| CF₂ | Pyrimidinyl | NH—CH₂ | Pyrazinyl | Z₁: CH₃ (ortho) |
| CF₂ | Pyrimidinyl | NH—CH₂ | Pyrazinyl | Z₁: CH₂—CH₃ (para) |
| CF₂ | Pyrimidinyl | NH—CH₂ | Pyrazinyl | Z₁: CH₂—CH₃ (meta) |
| CF₂ | Pyrimidinyl | NH—CH₂ | Pyrazinyl | Z₁: CH₂—CH₃ (ortho) |
| CF₂ | Pyrimidinyl | NH—CH₂ | Pyrazinyl | Z₁: CH₂—CH₂—CH₃ or iPr (para) |
| CF₂ | Pyrimidinyl | NH—CH₂ | Pyrazinyl | Z₁: CH₂—CH₂—CH₃ or iPr (meta) |
| CF₂ | Pyrimidinyl | NH—CH₂ | Pyrazinyl | Z₁: CH₂—CH₂—CH₃ or iPr (ortho) |
| CF₂ | Pyrimidinyl | NH—CH₂ | Pyrazinyl | Z₁: CH₂F (para) |
| CF₂ | Pyrimidinyl | NH—CH₂ | Pyrazinyl | Z₁: CH₂F (meta) |
| CF₂ | Pyrimidinyl | NH—CH₂ | Pyrazinyl | Z₁: CH₂F (ortho) |
| CF₂ | Pyrimidinyl | NH—CH₂ | Pyrazinyl | Z₁: CHF₂ (para) |
| CF₂ | Pyrimidinyl | NH—CH₂ | Pyrazinyl | Z₁: CHF₂ (meta) |
| CF₂ | Pyrimidinyl | NH—CH₂ | Pyrazinyl | Z₁: CHF₂ (ortho) |
| CF₂ | Pyrimidinyl | NH—CH₂ | Pyrazinyl | Z₁: CF₃ (para) |
| CF₂ | Pyrimidinyl | NH—CH₂ | Pyrazinyl | Z₁: CF₃ (meta) |
| CF₂ | Pyrimidinyl | NH—CH₂ | Pyrazinyl | Z₁: CF₃ (ortho) |
| CF₂ | Pyrimidinyl | NH—CH₂ | Pyrazinyl | Z₁: CH₂—CH₂F (para) |
| CF₂ | Pyrimidinyl | NH—CH₂ | Pyrazinyl | Z₁: CH₂—CH₂F (meta) |
| CF₂ | Pyrimidinyl | NH—CH₂ | Pyrazinyl | Z₁: CH₂—CH₂F (ortho) |
| CF₂ | Pyrimidinyl | NH—CH₂ | Pyrazinyl | Z₁: CH₂—CHF₂ (para) |
| CF₂ | Pyrimidinyl | NH—CH₂ | Pyrazinyl | Z₁: CH₂—CUE2 (meta) |
| CF₂ | Pyrimidinyl | NH—CH₂ | Pyrazinyl | Z₁: CH₂—CHF₂ (ortho) |
| CF₂ | Pyrimidinyl | NH—CH₂ | Pyrazinyl | Z₁: CH₂—CF₃ (para) |
| CF₂ | Pyrimidinyl | NH—CH₂ | Pyrazinyl | Z₁: CH₂—CF₃ (meta) |
| CF₂ | Pyrimidinyl | NH—CH₂ | Pyrazinyl | Z₁: CH₂—CF3 (ortho) |
| CF₂ | Pyrimidinyl | NH—CH₂ | Pyrrolyl | None |
| CF₂ | Pyrimidinyl | NH—CH₂ | Pyrrolyl | Z₁: F (2) |
| CF₂ | Pyrimidinyl | NH—CH₂ | Pyrrolyl | Z₁: F (3) |
| CF₂ | Pyrimidinyl | NH—CH₂ | Pyrrolyl | Z₁: F (2)<br>Z₂: F (3) |
| CF₂ | Pyrimidinyl | NH—CH₂ | Pyrrolyl | Z₁: Cl (2) |

TABLE 2-continued

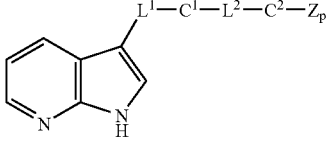

| $L^1$ | $C^1$ | $L^2$ | $C^2$ | Z |
|---|---|---|---|---|
| $CF_2$ | Pyrimidinyl | $NH-CH_2$ | Pyrrolyl | $Z_1$: Cl (3) |
| | | | | $Z_2$: Cl (3) |
| $CF_2$ | Pyrimidinyl | $NH-CH_2$ | Pyrrolyl | $Z_1$: F (2) |
| | | | | $Z_2$: Cl (3) |
| $CF_2$ | Pyrimidinyl | $NH-CH_2$ | Pyrrolyl | $Z_1$: Cl (2) |
| | | | | $Z_2$: F (3) |
| $CF_2$ | Pyrimidinyl | $NH-CH_2$ | Pyrrolyl | $Z_1$: $CH_3$ (2) |
| $CF_2$ | Pyrimidinyl | $NH-CH_2$ | Pyrrolyl | $Z_1$: $CH_3$ (3) |
| $CF_2$ | Pyrimidinyl | $NH-CH_2$ | Pyrrolyl | $Z_1$: $CH_2-CH_3$ (2) |
| $CF_2$ | Pyrimidinyl | $NH-CH_2$ | Pyrrolyl | $Z_1$: $CH_2-CH_3$ (3) |
| $CF_2$ | Pyrimidinyl | $NH-CH_2$ | Pyrrolyl | $Z_1$: $CH_2-CH_2-CH_3$ or iPr (2) |
| $CF_2$ | Pyrimidinyl | $NH-CH_2$ | Pyrrolyl | $Z_1$: $CH_2-CH_2-CH_3$ or iPr (3) |
| $CF_2$ | Pyrimidinyl | $NH-CH_2$ | Pyrrolyl | $Z_1$: $CH_2F$ (2) |
| $CF_2$ | Pyrimidinyl | $NH-CH_2$ | Pyrrolyl | $Z_1$: $CH_2F$ (3) |
| $CF_2$ | Pyrimidinyl | $NH-CH_2$ | Pyrrolyl | $Z_1$: $CHF_2$ (2) |
| $CF_2$ | Pyrimidinyl | $NH-CH_2$ | Pyrrolyl | $Z_1$: $CHF_2$ (3) |
| $CF_2$ | Pyrimidinyl | $NH-CH_2$ | Pyrrolyl | $Z_1$: $CF_3$ (2) |
| $CF_2$ | Pyrimidinyl | $NH-CH_2$ | Pyrrolyl | $Z_1$: $CF_3$ (3) |
| $CF_2$ | Pyrimidinyl | $NH-CH_2$ | Pyrrolyl | $Z_1$: $CH_2-CH_2F$ (2) |
| $CF_2$ | Pyrimidinyl | $NH-CH_2$ | Pyrrolyl | $Z_1$: $CH_2-CH_2F$ (3) |
| $CF_2$ | Pyrimidinyl | $NH-CH_2$ | Pyrrolyl | $Z_1$: $CH_2-CHF_2$ (2) |
| $CF_2$ | Pyrimidinyl | $NH-CH_2$ | Pyrrolyl | $Z_1$: $CH_2-CHF_2$ (3) |
| $CF_2$ | Pyrimidinyl | $NH-CH_2$ | Pyrrolyl | $Z_1$: $CH_2-CF_3$ (2) |
| $CF_2$ | Pyrimidinyl | $NH-CH_2$ | Pyrrolyl | $Z_1$: $CH_2-CF_3$ (3) |
| $CF_2$ | Pyrimidinyl | $NH-CH_2$ | Imidazolyl | None |
| $CF_2$ | Pyrimidinyl | $NH-CH_2$ | Imidazolyl | $Z_1$: F (2) |
| $CF_2$ | Pyrimidinyl | $NH-CH_2$ | Imidazolyl | $Z_1$: F (2) |
| | | | | $Z_2$: F (3) |
| $CF_2$ | Pyrimidinyl | $NH-CH_2$ | Imidazolyl | $Z_1$: Cl (2) |
| $CF_2$ | Pyrimidinyl | $NH-CH_2$ | Imidazolyl | $Z_1$: Cl (3) |
| | | | | $Z_2$: Cl (3) |
| $CF_2$ | Pyrimidinyl | $NH-CH_2$ | Imidazolyl | $Z_1$: F (2) |
| | | | | $Z_2$: Cl (3) |
| $CF_2$ | Pyrimidinyl | $NH-CH_2$ | Imidazolyl | $Z_1$: Cl (2) |
| | | | | $Z_1$: F(3) |
| $CF_2$ | Pyrimidinyl | $NH-CH_2$ | Imidazolyl | $Z_1$: $CH_3$ (2) |
| $CF_2$ | Pyrimidinyl | $NH-CH_2$ | Imidazolyl | $Z_1$: $CH_3$ (3) |
| $CF_2$ | Pyrimidinyl | $NH-CH_2$ | Imidazolyl | $Z_1$: $CH_2-CH_3$ (2) |
| $CF_2$ | Pyrimidinyl | $NH-CH_2$ | Imidazolyl | $Z_1$: $CH_2-CH_3$ (3) |
| $CF_2$ | Pyrimidinyl | $NH-CH_2$ | Imidazolyl | $Z_1$: $CH_2-CH_2-CH_3$ or iPr (2) |
| $CF_2$ | Pyrimidinyl | $NH-CH_2$ | Imidazolyl | $Z_1$: $CH_2-CH_2-CH_3$ or iPr (3) |
| $CF_2$ | Pyrimidinyl | $NH-CH_2$ | Imidazolyl | $Z_1$: $CH_2F$ (2) |
| $CF_2$ | Pyrimidinyl | $NH-CH_2$ | Imidazolyl | $Z_1$: $CH_2F$ (3) |
| $CF_2$ | Pyrimidinyl | $NH-CH_2$ | Imidazolyl | $Z_1$: $CHF_2$ (2) |
| $CF_2$ | Pyrimidinyl | $NH-CH_2$ | Imidazolyl | $Z_1$: $CHF_2$ (3) |
| $CF_2$ | Pyrimidinyl | $NH-CH_2$ | Imidazolyl | $Z_1$: $CF_3$ (2) |
| $CF_2$ | Pyrimidinyl | $NH-CH_2$ | Imidazolyl | $Z_1$: $CF_3$ (3) |
| $CF_2$ | Pyrimidinyl | $NH-CH_2$ | Imidazolyl | $Z_1$: $CH_2-CH_2F$ (2) |
| $CF_2$ | Pyrimidinyl | $NH-CH_2$ | Imidazolyl | $Z_1$: $CH_2-CH_2F$ (3) |
| $CF_2$ | Pyrimidinyl | $NH-CH_2$ | Imidazolyl | $Z_1$: $CH_2-CHF_2$ (2) |
| $CF_2$ | Pyrimidinyl | $NH-CH_2$ | Imidazolyl | $Z_1$: $CH_2-CHF_2$ (3) |
| $CF_2$ | Pyrimidinyl | $NH-CH_2$ | Imidazolyl | $Z_1$: $CH_2-CF_3$ (2) |
| $CF_2$ | Pyrimidinyl | $NH-CH_2$ | Inudazolyl | $Z_1$: $CH_2-CF_3$ (3) |
| $CF_2$ | Pyrimidinyl | $NH-CH_2$ | Furanyl | None |
| $CF_2$ | Pyrimidinyl | $NH-CH_2$ | Furanyl | $Z_1$: F (2) |
| $CF_2$ | Pyrimidinyl | $NH-CH_2$ | Furanyl | $Z_1$: F (3) |
| $CF_2$ | Pyrimidinyl | $NH-CH_2$ | Furanyl | $Z_1$: F (2) |
| | | | | $Z_2$: F (3) |
| $CF_2$ | Pyrimidinyl | $NH-CH_2$ | Furanyl | $Z_1$: Cl (2) |
| $CF_2$ | Pyrimidinyl | $NH-CH_2$ | Furanyl | $Z_1$: Cl (3) |
| $CF_2$ | Pyrimidinyl | $NH-CH_2$ | Furanyl | $Z_1$: Cl (2) |
| | | | | $Z_2$: Cl (3) |
| $CF_2$ | Pyrimidinyl | $NH-CH_2$ | Furanyl | $Z_1$: F (2) |
| | | | | $Z_2$: Cl (3) |
| $CF_2$ | Pyrimidinyl | $NH-CH_2$ | Furanyl | $Z_1$: Cl (2) |
| | | | | $Z_2$: F (3) |
| $CF_2$ | Pyrimidinyl | $NH-CH_2$ | Furanyl | $Z_1$: $CH_3$ (2) |
| $CF_2$ | Pyrimidinyl | $NH-CH_2$ | Furanyl | $Z_1$: $CH_3$ (3) |
| $CF_2$ | Pyrimidinyl | $NH-CH_2$ | Furanyl | $Z_1$: $CH_2-CH_3$ (2) |

TABLE 2-continued

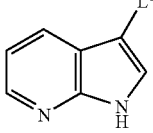

| $L^1$ | $C^1$ | $L^2$ | $C^2$ | Z |
|---|---|---|---|---|
| $CF_2$ | Pyrimidinyl | $NH-CH_2$ | Furanyl | $Z_1$: $CH_2-CH_3$ (3) |
| $CF_2$ | Pyrimidinyl | $NH-CH_2$ | Furanyl | $Z_1$: $CH_2-CH_2-CH_3$ or iPr (2) |
| $CF_2$ | Pyrimidinyl | $NH-CH_2$ | Furanyl | $Z_1$: $CH_2-CH_2-CH_3$ or iPr (3) |
| $CF_2$ | Pyrimidinyl | $NH-CH_2$ | Furanyl | $Z_1$: $CH_2F$ (2) |
| $CF_2$ | Pyrimidinyl | $NH-CH_2$ | Furanyl | $Z_1$: $CH_2F$ (3) |
| $CF_2$ | Pyrimidinyl | $NH-CH_2$ | Furanyl | $Z_1$: $CHF_2$ (2) |
| $CF_2$ | Pyrimidinyl | $NH-CH_2$ | Furanyl | $Z_1$: $CHF_2$ (3) |
| $CF_2$ | Pyrimidinyl | $NH-CH_2$ | Furanyl | $Z_1$: $CF_3$ (2) |
| $CF_2$ | Pyrimidinyl | $NH-CH_2$ | Furanyl | $Z_1$: $CF_3$ (3) |
| $CF_2$ | Pyrimidinyl | $NH-CH_2$ | Furanyl | $Z_1$: $CH_2-CH_2F$ (2) |
| $CF_2$ | Pyrimidinyl | $NH-CH_2$ | Furanyl | $Z_1$: $CH_2-CH_2F$ (3) |
| $CF_2$ | Pyrimidinyl | $NH-CH_2$ | Furanyl | $Z_1$: $CH_2-CHF_2$ (2) |
| $CF_2$ | Pyrimidinyl | $NH-CH_2$ | Furanyl | $Z_1$: $CH_2-CHF_2$ (3) |
| $CF_2$ | Pyrimidinyl | $NH-CH_2$ | Furanyl | $Z_1$: $CH_2-CF_3$ (2) |
| $CF_2$ | Pyrimidinyl | $NH-CH_2$ | Furanyl | $Z_1$: $CH_2-CF_3$ (3) |
| $CF_2$ | Pyrimidinyl | $NH-CH_2$ | Oxazolyl | None |
| $CF_2$ | Pyrimidinyl | $NH-CH_2$ | Oxazolyl | $Z_1$: F (2) |
| $CF_2$ | Pyrimidinyl | $NH-CH_2$ | Oxazolyl | $Z_1$: F (3) |
| $CF_2$ | Pyrimidinyl | $NH-CH_2$ | Oxazolyl | $Z_1$: F (2) $Z_2$: F (3) |
| $CF_2$ | Pyrimidinyl | $NH-CH_2$ | Oxazolyl | $Z_1$: Cl (2) |
| $CF_2$ | Pyrimidinyl | $NH-CH_2$ | Oxazolyl | $Z_1$: Cl (3) |
| $CF_2$ | Pyrimidinyl | $NH-CH_2$ | Oxazolyl | $Z_1$: Cl (2) $Z_2$: Cl (3) |
| $CF_2$ | Pyrimidinyl | $NH-CH_2$ | Oxazolyl | $Z_1$: F (2) $Z_2$: Cl (3) |
| $CF_2$ | Pyrimidinyl | $NH-CH_2$ | Oxazolyl | $Z_1$: Cl (2) $Z_2$: F (3) |
| $CF_2$ | Pyrimidinyl | $NH-CH_2$ | Oxazolyl | $Z_1$: $CH_3$ (2) |
| $CF_2$ | Pyrimidinyl | $NH-CH_2$ | Oxazolyl | $Z_1$: $CH_3$ (3) |
| $CF_2$ | Pyrimidinyl | $NH-CH_2$ | Oxazolyl | $Z_1$: $CH_2-CH_3$ (2) |
| $CF_2$ | Pyrimidinyl | $NH-CH_2$ | Oxazolyl | $Z_1$: $CH_2-CH_3$ (3) |
| $CF_2$ | Pyrimidinyl | $NH-CH_2$ | Oxazolyl | $Z_1$: $CH_2-CH_2-CH_3$ or iPr (2) |
| $CF_2$ | Pyrimidinyl | $NH-CH_2$ | Oxazolyl | $Z_1$: $CH_2-CH_2-CH_3$ or iPr (3) |
| $CF_2$ | Pyrimidinyl | $NH-CH_2$ | Oxazolyl | $Z_1$: $CH_2F$ (2) |
| $CF_2$ | Pyrimidinyl | $NH-CH_2$ | Oxazolyl | $Z_1$: $CH_2F$ (3) |
| $CF_2$ | Pyrimidinyl | $NH-CH_2$ | Oxazolyl | $Z_1$: $CHF_2$ (2) |
| $CF_2$ | Pyrimidinyl | $NH-CH_2$ | Oxazolyl | $Z_1$: $CHF_2$ (3) |
| $CF_2$ | Pyrimidinyl | $NH-CH_2$ | Oxazolyl | $Z_1$: $CF_3$ (2) |
| $CF_2$ | Pyrimidinyl | $NH-CH_2$ | Oxazolyl | $Z_1$: $CF_3$ (3) |
| $CF_2$ | Pyrimidinyl | $NH-CH_2$ | Oxazolyl | $Z_1$: $CH_2-CH_2F$ (2) |
| $CF_2$ | Pyrimidinyl | $NH-CH_2$ | Oxazolyl | $Z_1$: $CH_2-CH_2F$ (3) |
| $CF_2$ | Pyrimidinyl | $NH-CH_2$ | Oxazolyl | $Z_1$: $CH_2-CHF_2$ (2) |
| $CF_2$ | Pyrimidinyl | $NH-CH_2$ | Oxazolyl | $Z_1$: $CH_2-CHF_2$ (3) |
| $CF_2$ | Pyrimidinyl | $NH-CH_2$ | Oxazolyl | $Z_1$: $CH_2-CF_3$ (2) |
| $CF_2$ | Pyrimidinyl | $NH-CH_2$ | Oxazolyl | $Z_1$: $CH_2-CF_3$ (3) |
| $CF_2$ | Pyrimidinyl | $NH-CH_2$ | Thiophenyl | None |
| $CF_2$ | Pyrimidinyl | $NH-CH_2$ | Thiophenyl | $Z_1$: F (2) |
| $CF_2$ | Pyrimidinyl | $NH-CH_2$ | Thiophenyl | $Z_1$: F (3) |
| $CF_2$ | Pyrimidinyl | $NH-CH_2$ | Thiophenyl | $Z_1$: F (2) $Z_2$: F (3) |
| $CF_2$ | Pyrimidinyl | $NH-CH_2$ | Thiophenyl | $Z_1$: Cl (2) |
| $CF_2$ | Pyrimidinyl | $NH-CH_2$ | Thiophenyl | $Z_1$: Cl (3) |
| $CF_2$ | Pyrimidinyl | $NH-CH_2$ | Thiophenyl | $Z_1$: Cl (2) $Z_2$: Cl (3) |
| $CF_2$ | Pyrimidinyl | $NH-CH_2$ | Thiophenyl | $Z_1$: F (2) $Z_2$: Cl (3) |
| $CF_2$ | Pyrimidinyl | $NH-CH_2$ | Thiophenyl | $Z_1$: Cl (2) $Z_2$: F (3) |
| $CF_2$ | Pyrimidinyl | $NH-CH_2$ | Thiophenyl | $Z_1$: $CH_3$ (2) |
| $CF_2$ | Pyrimidinyl | $NH-CH_2$ | Thiophenyl | $Z_1$: $CH_3$ (3) |
| $CF_2$ | Pyrimidinyl | $NH-CH_2$ | Thiophenyl | $Z_1$: $CH_2-CH_3$ (2) |
| $CF_2$ | Pyrimidinyl | $NH-CH_2$ | Thiophenyl | $Z_1$: $CH_2-CH_3$ (3) |
| $CF_2$ | Pyrimidinyl | $NH-CH_2$ | Thiophenyl | $Z_1$: $CH_2-CH_2-CH_3$ or iPr (2) |
| $CF_2$ | Pyrimidinyl | $NH-CH_2$ | Thiophenyl | $Z_1$: $CH_2-CH_2-CH_3$ or iPr (3) |
| $CF_2$ | Pyrimidinyl | $NH-CH_2$ | Thiophenyl | $Z_1$: $CH_2F$ (2) |
| $CF_2$ | Pyrimidinyl | $NH-CH_2$ | Thiophenyl | $Z_1$: $CH_2F$ (3) |
| $CF_2$ | Pyrimidinyl | $NH-CH_2$ | Thiophenyl | $Z_1$: $CHF_2$ (2) |
| $CF_2$ | Pyrimidinyl | $NH-CH_2$ | Thiophenyl | $Z_1$: $CHF_2$ (3) |

TABLE 2-continued

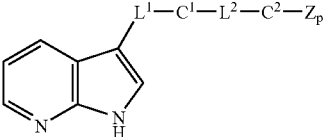

| L¹ | C¹ | L² | C² | Z |
|---|---|---|---|---|
| $CF_2$ | Pyrimidinyl | $NH-CH_2$ | Thiophenyl | $Z_1$: $CF_3$ (2) |
| $CF_2$ | Pyrimidinyl | $NH-CH_2$ | Thiophenyl | $Z_1$: $CF_3$ (3) |
| $CF_2$ | Pyrimidinyl | $NH-CH_2$ | Thiophenyl | $Z_1$: $CH_2-CH_2F$ (2) |
| $CF_2$ | Pyrimidinyl | $NH-CH_2$ | Thiophenyl | $Z_1$: $CH_2-CH_2F$ (3) |
| $CF_2$ | Pyrimidinyl | $NH-CH_2$ | Thiophenyl | $Z_1$: $CH_2-CHF_2$ (2) |
| $CF_2$ | Pyrimidinyl | $NH-CH_2$ | Thiophenyl | $Z_1$: $CH_2-CHF_2$ (3) |
| $CF_2$ | Pyrimidinyl | $NH-CH_2$ | Thiophenyl | $Z_1$: $CH_2-CF_3$ (2) |
| $CF_2$ | Pyrimidinyl | $NH-CH_2$ | Thiophenyl | $Z_1$: $CH_2-CF_3$ (3) |
| $CF_2$ | Pyrimidinyl | $NH-CH_2$ | Thiazolyl | None |
| $CF_2$ | Pyrimidinyl | $NH-CH_2$ | Thiazolyl | $Z_1$: F (2) |
| $CF_2$ | Pyrimidinyl | $NH-CH_2$ | Thiazolyl | $Z_1$: F (3) |
| $CF_2$ | Pyrimidinyl | $NH-CH_2$ | Thiazolyl | $Z_1$: F (2)<br>$Z_2$: F (3) |
| $CF_2$ | Pyrimidinyl | $NH-CH_2$ | Thiazolyl | $Z_1$: Cl (2) |
| $CF_2$ | Pyrimidinyl | $NH-CH_2$ | Thiazolyl | $Z_1$: Cl (3) |
| $CF_2$ | Pyrimidinyl | $NH-CH_2$ | Thiazolyl | $Z_1$: Cl (2)<br>$Z_2$: Cl (3) |
| $CF_2$ | Pyrimidinyl | $NH-CH_2$ | Thiazolyl | $Z_1$: F (2)<br>$Z_2$: Cl (3) |
| $CF_2$ | Pyrimidinyl | $NH-CH_2$ | Thiazolyl | $Z_1$: Cl (2)<br>$Z_2$: F (3) |
| $CF_2$ | Pyrimidinyl | $NH-CH_2$ | Thiazolyl | $Z_1$: $CH_3$ (2) |
| $CF_2$ | Pyrimidinyl | $NH-CH_2$ | Thiazolyl | $Z_1$: $CH_3$ (3) |
| $CF_2$ | Pyrimidinyl | $NH-CH_2$ | Thiazolyl | $Z_1$: $CH_2-CH_3$ (2) |
| $CF_2$ | Pyrimidinyl | $NH-CH_2$ | Thiazolyl | $Z_1$: $CH_2-CH_3$ (3) |
| $CF_2$ | Pyrimidinyl | $NH-CH_2$ | Thiazolyl | $Z_1$: $CH_2-CH_2-CH_3$ or iPr (2) |
| $CF_2$ | Pyrimidinyl | $NH-CH_2$ | Thiazolyl | $Z_1$: $CH_2-CH_2-CH_3$ or iPr (3) |
| $CF_2$ | Pyrimidinyl | $NH-CH_2$ | Thiazolyl | $Z_1$: $CH_2F$ (2) |
| $CF_2$ | Pyrimidinyl | $NH-CH_2$ | Thiazolyl | $Z_1$: $CH_2F$ (3) |
| $CF_2$ | Pyrimidinyl | $NH-CH_2$ | Thiazolyl | $Z_1$: $CHF_2$ (2) |
| $CF_2$ | Pyrimidinyl | $NH-CH_2$ | Thiazolyl | $Z_1$: $CHF_2$ (3) |
| $CF_2$ | Pyrimidinyl | $NH-CH_2$ | Thiazolyl | $Z_1$: $CF_3$ (2) |
| $CF_2$ | Pyrimidinyl | $NH-CH_2$ | Thiazolyl | $Z_1$: $CF_3$ (3) |
| $CF_2$ | Pyrimidinyl | $NH-CH_2$ | Thiazolyl | $Z_1$: $CH_2-CH_2F$ (2) |
| $CF_2$ | Pyrimidinyl | $NH-CH_2$ | Thiazolyl | $Z_1$: $CH_2-CH_2F$ (3) |
| $CF_2$ | Pyrimidinyl | $NH-CH_2$ | Thiazolyl | $Z_1$: $CH_2-CHF_2$ (2) |
| $CF_2$ | Pyrimidinyl | $NH-CH_2$ | Thiazolyl | $Z_1$: $CH_2-CHF_2$ (3) |
| $CF_2$ | Pyrimidinyl | $NH-CH_2$ | Thiazolyl | $Z_1$: $CH_2-CF_3$ (2) |
| $CF_2$ | Pyrimidinyl | $NH-CH_2$ | Thiazolyl | $Z_1$: $CH_2-CF_3$ (3) |
| $CF_2$ | Pyrimidinyl | $NH-C(O)$ | Phenyl | None |
| $CF_2$ | Pyrimidinyl | $NH-C(O)$ | Phenyl | $Z_1$: F (para) |
| $CF_2$ | Pyrimidinyl | $NH-C(O)$ | phenyl | $Z_1$: F (meta) |
| $CF_2$ | Pyrimidinyl | $NH-C(O)$ | phenyl | $Z_1$: F (ortho) |
| $CF_2$ | Pyrimidinyl | $NH-C(O)$ | phenyl | $Z_1$: F (para)<br>$Z_2$: F (meta) |
| $CF_2$ | Pyrimidinyl | $NH-C(O)$ | Phenyl | $Z_1$: Cl (meta) |
| $CF_2$ | Pyrimidinyl | $NH-C(O)$ | Phenyl | $Z_1$: Cl (para) |
| $CF_2$ | Pyrimidinyl | $NH-C(O)$ | Phenyl | $Z_1$: Cl (para)<br>$Z_2$: Cl (meta) |
| $CF_2$ | Pyrimidinyl | $NH-C(O)$ | Phenyl | $Z_1$: F (para)<br>$Z_2$: Cl (meta) |
| $CF_2$ | Pyrimidinyl | $NH-C(O)$ | Phenyl | $Z_1$: Cl (para)<br>$Z_2$: F (meta) |
| $CF_2$ | Pyrimidinyl | $NH-C(O)$ | Phenyl | $Z_1$: $CH_3$ (para) |
| $CF_2$ | Pyrimidinyl | $NH-C(O)$ | Phenyl | $Z_1$: $CH_3$ (meta) |
| $CF_2$ | Pyrimidinyl | $NH-C(O)$ | Phenyl | $Z_1$: $CH_3$ (ortho) |
| $CF_2$ | Pyrimidinyl | $NH-C(O)$ | Phenyl | $Z_1$: $CH_2-CH_3$ (para) |
| $CF_2$ | Pyrimidinyl | $NH-C(O)$ | Phenyl | $Z_1$: $CH_2-CH_3$ (meta) |
| $CF_2$ | Pyrimidinyl | $NH-C(O)$ | Phenyl | $Z_1$: $CH_2-CH_3$ (ortho) |
| $CF_2$ | Pyrimidinyl | $NH-C(O)$ | Phenyl | $Z_1$: $CH_2-CH_2-CH_3$ or iPr (para) |
| $CF_2$ | Pyrimidinyl | $NH-C(O)$ | Phenyl | $Z_1$: $CH_2-CH_2-CH_3$ or iPr (meta) |
| $CF_2$ | Pyrimidinyl | $NH-C(O)$ | Phenyl | $Z_1$: $CH_2-CH_2-CH_3$ or iPr (ortho) |
| $CF_2$ | Pyrimidinyl | $NH-C(O)$ | Phenyl | $Z_1$: $CH_2F$ (para) |
| $CF_2$ | Pyrimidinyl | $NH-C(O)$ | Phenyl | $Z_1$: $CH_2F$ (meta) |
| $CF_2$ | Pyrimidinyl | $NH-C(O)$ | Phenyl | $Z_1$: $CH_2F$ (ortho) |
| $CF_2$ | Pyrimidinyl | $NH-C(O)$ | Phenyl | $Z_1$: $CHF_2$ (para) |

TABLE 2-continued

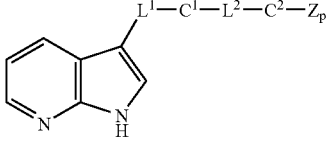

| L$^1$ | C$^1$ | L$^2$ | C$^2$ | Z |
|---|---|---|---|---|
| CF$_2$ | Pyrimidinyl | NH—C(O) | Phenyl | Z$_1$: CHF$_2$ (meta) |
| CF$_2$ | Pyrimidinyl | NH—C(O) | Phenyl | Z$_1$: CHF$_2$ (ortho) |
| CF$_2$ | Pyrimidinyl | NH—C(O) | Phenyl | Z$_1$: CF$_3$ (para) |
| CF$_2$ | Pyrimidinyl | NH—C(O) | Phenyl | Z$_1$: CF$_3$ (meta) |
| CF$_2$ | Pyrimidinyl | NH—C(O) | Phenyl | Z$_1$: CF$_3$ (ortho) |
| CF$_2$ | Pyrimidinyl | NH—C(O) | Phenyl | Z$_1$: CH$_2$—CH$_2$F (para) |
| CF$_2$ | Pyrimidinyl | NH—C(O) | Phenyl | Z$_1$: CH$_2$—CH$_2$F (meta) |
| CF$_2$ | Pyrimidinyl | NH—C(O) | Phenyl | Z$_1$: CH$_2$—CH$_2$F (ortho) |
| CF$_2$ | Pyrimidinyl | NH—C(O) | Phenyl | Z$_1$: CH$_2$—CHF$_2$ (para) |
| CF$_2$ | Pyrimidinyl | NH—C(O) | Phenyl | Z$_1$: CH$_2$—CHF$_2$ (meta) |
| CF$_2$ | Pyrimidinyl | NH—C(O) | Phenyl | Z$_1$: CH$_2$—CHF$_2$ (ortho) |
| CF$_2$ | Pyrimidinyl | NH—C(O) | Phenyl | Z$_1$: CH$_2$—CF$_3$ (para) |
| CF$_2$ | Pyrimidinyl | NH—C(O) | Phenyl | Z$_1$: CH$_2$—CF$_3$ (meta) |
| CF$_2$ | Pyrimidinyl | NH—C(O) | Phenyl | Z$_1$: CH$_2$—CF$_3$ (ortho) |
| CF$_2$ | Pyrimidinyl | NH—C(O) | Pyridinyl | None |
| CF$_2$ | Pyrimidinyl | NH—C(O) | Pyridinyl | Z$_1$: F (para) |
| CF$_2$ | Pyrimidinyl | NH—C(O) | Pyridinyl | Z$_1$: F (meta) |
| CF$_2$ | Pyrimidinyl | NH—C(O) | Pyridinyl | Z$_1$: F (ortho) |
| CF$_2$ | Pyrimidinyl | NH—C(O) | Pyridinyl | Z$_1$: F (para)<br>Z$_2$: F (meta) |
| CF$_2$ | Pyrimidinyl | NH—C(O) | Pyridinyl | Z$_1$: Cl (meta) |
| CF$_2$ | Pyrimidinyl | NH—C(O) | Pyridinyl | Z$_1$: Cl (para) |
| CF$_2$ | Pyrimidinyl | NH—C(O) | Pyridinyl | Z$_1$: Cl (para)<br>Z$_2$: Cl (meta) |
| CF$_2$ | Pyrimidinyl | NH—C(O) | Pyridinyl | Z$_1$: F (para)<br>Z$_2$: Cl (meta) |
| CF$_2$ | Pyrimidinyl | NH—C(O) | Pyridinyl | Z$_1$: Cl (para)<br>Z$_2$: F (meta) |
| CF$_2$ | Pyrimidinyl | NH—C(O) | Pyridinyl | Z$_1$: CH$_3$ (para) |
| CF$_2$ | Pyrimidinyl | NH—C(O) | Pyridinyl | Z$_1$: CH$_3$ (meta) |
| CF$_2$ | Pyrimidinyl | NH—C(O) | Pyridinyl | Z$_1$: CH$_3$ (ortho) |
| CF$_2$ | Pyrimidinyl | NH—C(O) | Pyridinyl | Z$_1$: CH$_2$—CH$_3$ (para) |
| CF$_2$ | Pyrimidinyl | NH—C(O) | Pyridinyl | Z$_1$: CH$_2$—CH$_3$ (meta) |
| CF$_2$ | Pyrimidinyl | NH—C(O) | Pyridinyl | Z$_1$: CH$_2$—CH$_3$ (ortho) |
| CF$_2$ | Pyrimidinyl | NH—C(O) | Pyridinyl | Z$_1$: CH$_2$—CH$_2$—CH$_3$ or iPr (para) |
| CF$_2$ | Pyrimidinyl | NH—C(O) | Pyridinyl | Z$_1$: CH$_2$—CH$_2$—CH$_3$ or iPr (meta) |
| CF$_2$ | Pyrimidinyl | NH—C(O) | Pyridinyl | Z$_1$: CH$_2$—CH$_2$—CH$_3$ or iPr (ortho) |
| CF$_2$ | Pyrimidinyl | NH—C(O) | Pyridinyl | Z$_1$: CH$_2$F (para) |
| CF$_2$ | Pyrimidinyl | NH—C(O) | Pyridinyl | Z$_1$: CH$_2$F (meta) |
| CF$_2$ | Pyrimidinyl | NH—C(O) | Pyridinyl | Z$_1$: CH$_2$F (ortho) |
| CF$_2$ | Pyrimidinyl | NH—C(O) | Pyridinyl | Z$_1$: CHF$_2$ (para) |
| CF$_2$ | Pyrimidinyl | NH—C(O) | Pyridinyl | Z$_1$: CHF$_2$ (meta) |
| CF$_2$ | Pyrimidinyl | NH—C(O) | Pyridinyl | Z$_1$: CHF$_2$ (ortho) |
| CF$_2$ | Pyrimidinyl | NH—C(O) | Pyridinyl | Z$_1$: CF$_3$ (para) |
| CF$_2$ | Pyrimidinyl | NH—C(O) | Pyridinyl | Z$_1$: CF$_3$ (meta) |
| CF$_2$ | Pyrimidinyl | NH—C(O) | Pyridinyl | Z$_1$: CF$_3$ (ortho) |
| CF$_2$ | Pyrimidinyl | NH—C(O) | Pyridinyl | Z$_1$: CH$_2$—CH$_2$F (para) |
| CF$_2$ | Pyrimidinyl | NH—C(O) | Pyridinyl | Z$_1$: CH$_2$—CH$_2$F (meta) |
| CF$_2$ | Pyrimidinyl | NH—C(O) | Pyridinyl | Z$_1$: CH$_2$—CH$_2$F (ortho) |
| CF$_2$ | Pyrimidinyl | NH—C(O) | Pyridinyl | Z$_1$: CH$_2$—CHF$_2$ (para) |
| CF$_2$ | Pyrimidinyl | NH—C(O) | Pyridinyl | Z$_1$: CH$_2$—CHF$_2$ (meta) |
| CF$_2$ | Pyrimidinyl | NH—C(O) | Pyridinyl | Z$_1$: CH$_2$—CHF$_2$ (ortho) |
| CF$_2$ | Pyrimidinyl | NH—C(O) | Pyridinyl | Z$_1$: CH$_2$—CF$_3$ (para) |
| CF$_2$ | Pyrimidinyl | NH—C(O) | Pyridinyl | Z$_1$: CH$_2$—CF$_3$ (meta) |
| CF$_2$ | Pyrimidinyl | NH—C(O) | Pyridinyl | Z$_1$: CH$_2$—CF$_3$ (ortho) |
| CF$_2$ | Pyrimidinyl | NH—C(O) | Pyrimidinyl | None |
| CF$_2$ | Pyrimidinyl | NH—C(O) | Pyrimidinyl | Z$_1$: F (para) |
| CF$_2$ | Pyrimidinyl | NH—C(O) | Pyrimidinyl | Z$_1$: F (meta) |
| CF$_2$ | Pyrimidinyl | NH—C(O) | Pyrimidinyl | Z$_1$: F (ortho) |
| CF$_2$ | Pyrimidinyl | NH—C(O) | Pyrimidinyl | Z$_1$: F (para)<br>Z$_2$: F (meta) |
| CF$_2$ | Pyrimidinyl | NH—C(O) | Pyrimidinyl | Z$_1$: Cl (meta) |
| CF$_2$ | Pyrimidinyl | NH—C(O) | Pyrimidinyl | Z$_1$: Cl (para) |
| CF$_2$ | Pyrimidinyl | NH—C(O) | Pyrimidinyl | Z$_1$: Cl (para)<br>Z$_2$: Cl (meta) |

TABLE 2-continued

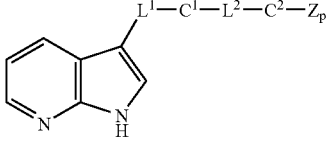

| $L^1$ | $C^1$ | $L^2$ | $C^2$ | Z |
|---|---|---|---|---|
| $CF_2$ | Pyrimidinyl | NH—C(O) | Pyrimidinyl | $Z_1$: F (para) |
| | | | | $Z_2$: Cl (meta) |
| $CF_2$ | Pyrimidinyl | NH—C(O) | Pyrimidinyl | $Z_1$: Cl (para) |
| | | | | $Z_2$: F (meta) |
| $CF_2$ | Pyrimidinyl | NH—C(O) | Pyrimidinyl | $Z_1$: $CH_3$ (para) |
| $CF_2$ | Pyrimidinyl | NH—C(O) | Pyrimidinyl | $Z_1$: $CH_3$ (meta) |
| $CF_2$ | Pyrimidinyl | NH—C(O) | Pyrimidinyl | $Z_1$: $CH_3$ (ortho) |
| $CF_2$ | Pyrimidinyl | NH—C(O) | Pyrimidinyl | $Z_1$: $CH_2$—$CH_3$ (para) |
| $CF_2$ | Pyrimidinyl | NH—C(O) | Pyrimidinyl | $Z_1$: $CH_2$—$CH_3$ (meta) |
| $CF_2$ | Pyrimidinyl | NH—C(O) | Pyrimidinyl | $Z_1$: $CH_2$—$CH_3$ (ortho) |
| $CF_2$ | Pyrimidinyl | NH—C(O) | Pyrimidinyl | $Z_1$: $CH_2$—$CH_2$—$CH_3$ or iPr (para) |
| $CF_2$ | Pyrimidinyl | NH—C(O) | Pyrimidinyl | $Z_1$: $CH_2$—$CH_2$—$CH_3$ or iPr (meta) |
| $CF_2$ | Pyrimidinyl | NH—C(O) | Pyrimidinyl | $Z_1$: $CH_2$—$CH_2$—$CH_3$ or iPr (ortho) |
| $CF_2$ | Pyrimidinyl | NH—C(O) | Pyrimidinyl | $Z_1$: $CH_2F$ (para) |
| $CF_2$ | Pyrimidinyl | NH—C(O) | Pyrimidinyl | $Z_1$: $CH_2F$ (meta) |
| $CF_2$ | Pyrimidinyl | NH—C(O) | Pyrimidinyl | $Z_1$: $CH_2F$ (ortho) |
| $CF_2$ | Pyrimidinyl | NH—C(O) | Pyrimidinyl | $Z_1$: $CHF_2$ (para) |
| $CF_2$ | Pyrimidinyl | NH—C(O) | Pyrimidinyl | $Z_1$: $CHF_2$ (meta) |
| $CF_2$ | Pyrimidinyl | NH—C(O) | Pyrimidinyl | $Z_1$: $CHF_2$ (ortho) |
| $CF_2$ | Pyrimidinyl | NH—C(O) | Pyrimidinyl | $Z_1$: $CF_3$ (para) |
| $CF_2$ | Pyrimidinyl | NH—C(O) | Pyrimidinyl | $Z_1$: $CF_3$ (meta) |
| $CF_2$ | Pyrimidinyl | NH—C(O) | Pyrimidinyl | $Z_1$: $CF_3$ (ortho) |
| $CF_2$ | Pyrimidinyl | NH—C(O) | Pyrimidinyl | $Z_1$: $CH_2$—$CH_2F$ (para) |
| $CF_2$ | Pyrimidinyl | NH—C(O) | Pyrimidinyl | $Z_1$: $CH_2$—$CH_2F$ (meta) |
| $CF_2$ | Pyrimidinyl | NH—C(O) | Pyrimidinyl | $Z_1$: $CH_2$—$CH_2F$ (ortho) |
| $CF_2$ | Pyrimidinyl | NH—C(O) | Pyrimidinyl | $Z_1$: $CH_2$—$CHF_2$ (para) |
| $CF_2$ | Pyrimidinyl | NH—C(O) | Pyrimidinyl | $Z_1$: $CH_2$—$CHF_2$ (meta) |
| $CF_2$ | Pyrimidinyl | NH—C(O) | Pyrimidinyl | $Z_1$: $CH_2$—$CHF_2$ (ortho) |
| $CF_2$ | Pyrimidinyl | NH—C(O) | Pyrimidinyl | $Z_1$: $CH_2$—$CF_3$ (para) |
| $CF_2$ | Pyrimidinyl | NH—C(O) | Pyrimidinyl | $Z_1$: $CH_2$—$CF_3$ (meta) |
| $CF_2$ | Pyrimidinyl | NH—C(O) | Pyrimidinyl | $Z_1$: $CH_2$—$CF_3$ (ortho) |
| $CF_2$ | Pyrimidinyl | NH—C(O) | Pyrazinyl | None |
| $CF_2$ | Pyrimidinyl | NH—C(O) | Pyrazinyl | $Z_1$: F (para) |
| $CF_2$ | Pyrimidinyl | NH—C(O) | Pyrazinyl | $Z_1$: F (meta) |
| $CF_2$ | Pyrimidinyl | NH—C(O) | Pyrazinyl | $Z_1$: F (ortho) |
| $CF_2$ | Pyrimidinyl | NH—C(O) | Pyrazinyl | $Z_1$: F (para) |
| | | | | $Z_2$: F (meta) |
| $CF_2$ | Pyrimidinyl | NH—C(O) | Pyrazinyl | $Z_1$: Cl (meta) |
| $CF_2$ | Pyrimidinyl | NH—C(O) | Pyrazinyl | $Z_1$: Cl (para) |
| $CF_2$ | Pyrimidinyl | NH—C(O) | Pyrazinyl | $Z_1$: Cl (para) |
| | | | | $Z_2$: Cl (meta) |
| $CF_2$ | Pyrimidinyl | NH—C(O) | Pyrazinyl | $Z_1$: F (para) |
| | | | | $Z_2$: Cl (meta) |
| $CF_2$ | Pyrimidinyl | NH—C(O) | Pyrazinyl | $Z_1$: Cl (para) |
| | | | | $Z_2$: F (meta) |
| $CF_2$ | Pyrimidinyl | NH—C(O) | Pyrazinyl | $Z_1$: $CH_3$ (para) |
| $CF_2$ | Pyrimidinyl | NH—C(O) | Pyrazinyl | $Z_1$: $CH_3$ (meta) |
| $CF_2$ | Pyrimidinyl | NH—C(O) | Pyrazinyl | $Z_1$: $CH_3$ (ortho) |
| $CF_2$ | Pyrimidinyl | NH—C(O) | Pyrazinyl | $Z_1$: $CH_2$—$CH_3$ (para) |
| $CF_2$ | Pyrimidinyl | NH—C(O) | Pyrazinyl | $Z_1$: $CH_2$—$CH_3$ (meta) |
| $CF_2$ | Pyrimidinyl | NH—C(O) | Pyrazinyl | $Z_1$: $CH_2$—$CH_3$ (ortho) |
| $CF_2$ | Pyrimidinyl | NH—C(O) | Pyrazinyl | $Z_1$: $CH_2$—$CH_2$—$CH_3$ or iPr (para) |
| $CF_2$ | Pyrimidinyl | NH—C(O) | Pyrazinyl | $Z_1$: $CH_2$—$CH_2$—$CH_3$ or iPr |
| $CF_2$ | Pyrimidinyl | NH—C(O) | Pyrazinyl | $Z_1$: $CH_2$—$CH_2$—$CH_3$ or iPr |
| $CF_2$ | Pyrimidinyl | NH—C(O) | Pyrazinyl | $Z_1$: $CH_2F$ (para) |
| $CF_2$ | Pyrimidinyl | NH—C(O) | Pyrazinyl | $Z_1$: $CH_2F$ (meta) |
| $CF_2$ | Pyrimidinyl | NH—C(O) | Pyrazinyl | $Z_1$: $CH_2F$ (ortho) |
| $CF_2$ | Pyrimidinyl | NH—C(O) | Pyrazinyl | $Z_1$: $CHF_2$ (para) |
| $CF_2$ | Pyrimidinyl | NH—C(O) | Pyrazinyl | $Z_1$: $CHF_2$ (meta) |
| $CF_2$ | Pyrimidinyl | NH—C(O) | Pyrazinyl | $Z_1$: $CHF_2$ (ortho) |
| $CF_2$ | Pyrimidinyl | NH—C(O) | Pyrazinyl | $Z_1$: $CF_3$ (para) |
| $CF_2$ | Pyrimidinyl | NH—C(O) | Pyrazinyl | $Z_1$: $CF_3$ (meta) |
| $CF_2$ | Pyrimidinyl | NH—C(O) | Pyrazinyl | $Z_1$: $CF_3$ (ortho) |
| $CF_2$ | Pyrimidinyl | NH—C(O) | Pyrazinyl | $Z_1$: $CH_2$—$CH_2F$ (para) |
| $CF_2$ | Pyrimidinyl | NH—C(O) | Pyrazinyl | $Z_1$: $CH_2$—$CH_2F$ (meta) |

TABLE 2-continued

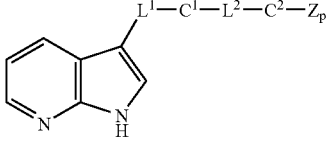

| L¹ | C¹ | L² | C² | Z |
|---|---|---|---|---|
| $CF_2$ | Pyrimidinyl | NH—C(O) | Pyrazinyl | $Z_1$: $CH_2$—$CH_2F$ (ortho) |
| $CF_2$ | Pyrimidinyl | NH—C(O) | Pyrazinyl | $Z_1$: $CH_2$—$CHF_2$ (para) |
| $CF_2$ | Pyrimidinyl | NH—C(O) | Pyrazinyl | $Z_1$: $CH_2$—$CHF_2$ (meta) |
| $CF_2$ | Pyrimidinyl | NH—C(O) | Pyrazinyl | $Z_1$: $CH_2$—$CHF_2$ (ortho) |
| $CF_2$ | Pyrimidinyl | NH—C(O) | Pyrazinyl | $Z_1$: $CH_2$—$CF_3$ (para) |
| $CF_2$ | Pyrimidinyl | NH—C(O) | Pyrazinyl | $Z_1$: $CH_2$—$CF_3$ (meta) |
| $CF_2$ | Pyrimidinyl | NH—C(O) | Pyrazinyl | $Z_1$: $CH_2$—$CF_3$ (ortho) |
| $CF_2$ | Pyrimidinyl | NH—C(O) | Pyrrolyl | None |
| $CF_2$ | Pyrimidinyl | NH—C(O) | Pyrrolyl | $Z_1$: F (2) |
| $CF_2$ | Pyrimidinyl | NH—C(O) | Pyrrolyl | $Z_1$: F (3) |
| $CF_2$ | Pyrimidinyl | NH—C(O) | Pyrrolyl | $Z_1$: F (2) |
|  |  |  |  | $Z_2$: F (3) |
| $CF_2$ | Pyrimidinyl | NH—C(O) | Pyrrolyl | $Z_1$: Cl (2) |
| $CF_2$ | Pyrimidinyl | NH—C(O) | Pyrrolyl | $Z_1$: Cl (3) |
| $CF_2$ | Pyrimidinyl | NH—C(O) | Pyrrolyl | $Z_1$: Cl (2) |
|  |  |  |  | $Z_2$: Cl (3) |
| $CF_2$ | Pyrimidinyl | NH—C(O) | Pyrrolyl | $Z_1$: F (2) |
|  |  |  |  | $Z_2$: Cl (3) |
| $CF_2$ | Pyrimidinyl | NH—C(O) | Pyrrolyl | $Z_1$: Cl (2) |
|  |  |  |  | $Z_2$: F (3) |
| $CF_2$ | Pyrimidinyl | NH—C(O) | Pyrrolyl | $Z_1$: $CH_3$ (2) |
| $CF_2$ | Pyrimidinyl | NH—C(O) | Pyrrolyl | $Z_1$: $CH_3$ (3) |
| $CF_2$ | Pyrimidinyl | NH—C(O) | Pyrrolyl | $Z_1$: $CH_2$—$CH_3$ (2) |
| $CF_2$ | Pyrimidinyl | NH—C(O) | Pyrrolyl | $Z_1$: $CH_2$—$CH_3$ (3) |
| $CF_2$ | Pyrimidinyl | NH—C(O) | Pyrrolyl | $Z_1$: $CH_2$—$CH_2$—$CH_3$ or iPr (2) |
| $CF_2$ | Pyrimidinyl | NH—C(O) | Pyrrolyl | $Z_1$: $CH_2$—$CH_2$—$CH_3$ or iPr (3) |
| $CF_2$ | Pyrimidinyl | NH—C(O) | Pyrrolyl | $Z_1$: $CH_2F$ (2) |
| $CF_2$ | Pyrimidinyl | NH—C(O) | Pyrrolyl | $Z_1$: $CH_2F$ (3) |
| $CF_2$ | Pyrimidinyl | NH—C(O) | Pyrrolyl | $Z_1$: $CHF_2$ (2) |
| $CF_2$ | Pyrimidinyl | NH—C(O) | Pyrrolyl | $Z_1$: $CHF_2$ (3) |
| $CF_2$ | Pyrimidinyl | NH—C(O) | Pyrrolyl | $Z_1$: $CF_3$ (2) |
| $CF_2$ | Pyrimidinyl | NH—C(O) | Pyrrolyl | $Z_1$: $CF_3$ (3) |
| $CF_2$ | Pyrimidinyl | NH—C(O) | Pyrrolyl | $Z_1$: $CH_2$—$CH_2F$ (2) |
| $CF_2$ | Pyrimidinyl | NH—C(O) | Pyrrolyl | $Z_1$: $CH_2$—$CH_2F$ (3) |
| $CF_2$ | Pyrimidinyl | NH—C(O) | Pyrrolyl | $Z_1$: $CH_2$—$CHF_2$ (2) |
| $CF_2$ | Pyrimidinyl | NH—C(O) | Pyrrolyl | $Z_1$: $CH_2$—$CHF_2$ (3) |
| $CF_2$ | Pyrimidinyl | NH—C(O) | Pyrrolyl | $Z_1$: $CH_2$—$CF_3$ (2) |
| $CF_2$ | Pyrimidinyl | NH—C(O) | Pyrrolyl | $Z_1$: $CH_2$—$CF_3$ (3) |
| $CF_2$ | Pyrimidinyl | NH—C(O) | Imidazolyl | None |
| $CF_2$ | Pyrimidinyl | NH—C(O) | Imidazolyl | $Z_1$: F (2) |
| $CF_2$ | Pyrimidinyl | NH—C(O) | Imidazolyl | $Z_1$: F (2) |
|  |  |  |  | $Z_2$: F (3) |
| $CF_2$ | Pyrimidinyl | NH—C(O) | Imidazolyl | $Z_1$: Cl (2) |
| $CF_2$ | Pyrimidinyl | NH—C(O) | Imidazolyl | $Z_1$: Cl (3) |
| $CF_2$ | Pyrimidinyl | NH—C(O) | Imidazolyl | $Z_1$: Cl (2) |
|  |  |  |  | $Z_2$: Cl (3) |
| $CF_2$ | Pyrimidinyl | NH—C(O) | Imidazolyl | $Z_1$: F (2) |
|  |  |  |  | $Z_2$: F (3) |
| $CF_2$ | Pyrimidinyl | NH—C(O) | Imidazolyl | $Z_1$: $CH_3$ (2) |
| $CF_2$ | Pyrimidinyl | NH—C(O) | Imidazolyl | $Z_1$: $CH_3$ (3) |
| $CF_2$ | Pyrimidinyl | NH—C(O) | Imidazolyl | $Z_1$: $CH_2$—$CH_3$ (2) |
| $CF_2$ | Pyrimidinyl | NH—C(O) | Imidazolyl | $Z_1$: $CH_2$—$CH_3$ (3) |
| $CF_2$ | Pyrimidinyl | NH—C(O) | Imidazolyl | $Z_1$: $CH_2$—$CH_2$—$CH_3$ or iPr (2) |
| $CF_2$ | Pyrimidinyl | NH—C(O) | Imidazolyl | $Z_1$: $CH_2$—$CH_2$—$CH_3$ or iPr (3) |
| $CF_2$ | Pyrimidinyl | NH—C(O) | Imidazolyl | $Z_1$: $CH_2F$ (2) |
| $CF_2$ | Pyrimidinyl | NH—C(O) | Imidazolyl | $Z_1$: $CH_2F$ (3) |
| $CF_2$ | Pyrimidinyl | NH—C(O) | Imidazolyl | $Z_1$: $CHF_2$ (2) |
| $CF_2$ | Pyrimidinyl | NH—C(O) | Imidazolyl | $Z_1$: $CHF_2$ (3) |
| $CF_2$ | Pyrimidinyl | NH—C(O) | Imidazolyl | $Z_1$: $CF_3$ (2) |
| $CF_2$ | Pyrimidinyl | NH—C(O) | Imidazolyl | $Z_1$: $CF_3$ (3) |
| $CF_2$ | Pyrimidinyl | NH—C(O) | Imidazolyl | $Z_1$: $CH_2$—$CH_2F$ (2) |
| $CF_2$ | Pyrimidinyl | NH—C(O) | Imidazolyl | $Z_1$: $CH_2$—$CH_2F$ (3) |
| $CF_2$ | Pyrimidinyl | NH—C(O) | Imidazolyl | $Z_1$: $CH_2$—$CHF_2$ (2) |
| $CF_2$ | Pyrimidinyl | NH—C(O) | Imidazolyl | $Z_1$: $CH_2$—$CHF_2$ (3) |
| $CF_2$ | Pyrimidinyl | NH—C(O) | Imidazolyl | $Z_1$: $CH_2$—$CF_3$ (2) |
| $CF_2$ | Pyrimidinyl | NH—C(O) | Imidazolyl | $Z_1$: $CH_2$—$CF_3$ (3) |
| $CF_2$ | Pyrimidinyl | NH—C(O) | Furanyl | None |
| $CF_2$ | Pyrimidinyl | NH—C(O) | Furanyl | $Z_1$: F (2) |
| $CF_2$ | Pyrimidinyl | NH—C(O) | Furanyl | $Z_1$: F (3) |

TABLE 2-continued $$L^1-C^1-L^2-C^2-Z_p$$

attached to 7-azaindole (1H-pyrrolo[2,3-b]pyridine) at the 3-position

| L¹ | C¹ | L² | C² | Z |
|---|---|---|---|---|
| CF₂ | Pyrimidinyl | NH—C(O) | Furanyl | $Z_1$: F (2)<br>$Z_2$: F (3) |
| CF₂ | Pyrimidinyl | NH—C(O) | Furanyl | $Z_1$: Cl (2) |
| CF₂ | Pyrimidinyl | NH—C(O) | Furanyl | $Z_1$: Cl (3) |
| CF₂ | Pyrimidinyl | NH—C(O) | Furanyl | $Z_1$: Cl (2)<br>$Z_2$: Cl (3) |
| CF₂ | Pyrimidinyl | NH—C(O) | Furanyl | $Z_1$: Cl (2)<br>$Z_2$: F (3) |
| CF₂ | Pyrimidinyl | NH—C(O) | Furanyl | $Z_1$: CH₃ (2) |
| CF₂ | Pyrimidinyl | NH—C(O) | Furanyl | $Z_1$: CH₃ (3) |
| CF₂ | Pyrimidinyl | NH—C(O) | Furanyl | $Z_1$: CH₂—CH₃ (2) |
| CF₂ | Pyrimidinyl | NH—C(O) | Furanyl | $Z_1$: CH₂—CH₃ (3) |
| CF₂ | Pyrimidinyl | NH—C(O) | Furanyl | $Z_1$: CH₂—CH₂—CH₃ or iPr (2) |
| CF₂ | Pyrimidinyl | NH—C(O) | Furanyl | $Z_1$: CH₂—CH₂—CH₃ or iPr (3) |
| CF₂ | Pyrimidinyl | NH—C(O) | Furanyl | $Z_1$: CH₂F (2) |
| CF₂ | Pyrimidinyl | NH—C(O) | Furanyl | $Z_1$: CH₂F (3) |
| CF₂ | Pyrimidinyl | NH—C(O) | Furanyl | $Z_1$: ClTE2 (2) |
| CF₂ | Pyrimidinyl | NH—C(O) | Furanyl | $Z_1$: CHF₂ (3) |
| CF₂ | Pyrimidinyl | NH—C(O) | Furanyl | $Z_1$: CF₃ (2) |
| CF₂ | Pyrimidinyl | NH—C(O) | Furanyl | $Z_1$: CF₃ (3) |
| CF₂ | Pyrimidinyl | NH—C(O) | Furanyl | $Z_1$: CH₂—CH₂F (2) |
| CF₂ | Pyrimidinyl | NH—C(O) | Furanyl | $Z_1$: CH₂—CH₂F (3) |
| CF₂ | Pyrimidinyl | NH—C(O) | Furanyl | $Z_1$: CH₂—CHF₂ (2) |
| CF₂ | Pyrimidinyl | NH—C(O) | Furanyl | $Z_1$: CH₂—CHF₂ (3) |
| CF₂ | Pyrimidinyl | NH—C(O) | Furanyl | $Z_1$: CH₂—CF₃ (2) |
| CF₂ | Pyrimidinyl | NH—C(O) | Furanyl | $Z_1$: CH₂—CF₃ (3) |
| CF₂ | Pyrimidinyl | NH—C(O) | Oxazolyl | None |
| CF₂ | Pyrimidinyl | NH—C(O) | Oxazolyl | $Z_1$: F (2) |
| CF₂ | Pyrimidinyl | NH—C(O) | Oxazolyl | $Z_1$: F (3) |
| CF₂ | Pyrimidinyl | NH—C(O) | Oxazolyl | $Z_1$: F (2)<br>$Z_2$: F (3) |
| CF₂ | Pyrimidinyl | NH—C(O) | Oxazolyl | $Z_1$: Cl (2) |
| CF₂ | Pyrimidinyl | NH—C(O) | Oxazolyl | $Z_1$: Cl (3) |
| CF₂ | Pyrimidinyl | NH—C(O) | Oxazolyl | $Z_1$: Cl (2)<br>$Z_2$: Cl (3) |
| CF₂ | Pyrimidinyl | NH—C(O) | Oxazolyl | $Z_1$: F (2)<br>$Z_2$: Cl (3) |
| CF₂ | Pyrimidinyl | NH—C(O) | Oxazolyl | $Z_1$: Cl (2)<br>$Z_2$: F (3) |
| CF₂ | Pyrimidinyl | NH—C(O) | Oxazolyl | $Z_1$: CH₃ (2) |
| CF₂ | Pyrimidinyl | NH—C(O) | Oxazolyl | $Z_1$: CH₃ (3) |
| CF₂ | Pyrimidinyl | NH—C(O) | Oxazolyl | $Z_1$: CH₂—CH₃ (2) |
| CF₂ | Pyrimidinyl | NH—C(O) | Oxazolyl | $Z_1$: CH₂—CH₃ (3) |
| CF₂ | Pyrimidinyl | NH—C(O) | Oxazolyl | $Z_1$: CH₂—CH₂—CH₃ or iPr (2) |
| CF₂ | Pyrimidinyl | NH—C(O) | Oxazolyl | $Z_1$: CH₂—CH₂—CH₃ or iPr (3) |
| CF₂ | Pyrimidinyl | NH—C(O) | Oxazolyl | $Z_1$: CH₂F (2) |
| CF₂ | Pyrimidinyl | NH—C(O) | Oxazolyl | $Z_1$: CH₂F (3) |
| CF₂ | Pyrimidinyl | NH—C(O) | Oxazolyl | $Z_1$: CHF₂ (2) |
| CF₂ | Pyrimidinyl | NH—C(O) | Oxazolyl | $Z_1$: CHF₂ (3) |
| CF₂ | Pyrimidinyl | NH—C(O) | Oxazolyl | $Z_1$: CF₃ (2) |
| CF₂ | Pyrimidinyl | NH—C(O) | Oxazolyl | $Z_1$: CF₃ (3) |
| CF₂ | Pyrimidinyl | NH—C(O) | Oxazolyl | $Z_1$: CH₂—CH₂F (2) |
| CF₂ | Pyrimidinyl | NH—C(O) | Oxazolyl | $Z_1$: CH₂—CH₂F (3) |
| CF₂ | Pyrimidinyl | NH—C(O) | Oxazolyl | $Z_1$: CH₂—CHF₂ (2) |
| CF₂ | Pyrimidinyl | NH—C(O) | Oxazolyl | $Z_1$: CH₂—CHF₂ (3) |
| CF₂ | Pyrimidinyl | NH—C(O) | Oxazolyl | $Z_1$: CH₂—CF₃ (2) |
| CF₂ | Pyrimidinyl | NH—C(O) | Oxazolyl | $Z_1$: CH₂—CF₃ (3) |
| CF₂ | Pyrimidinyl | NH—C(O) | Thiophenyl | None |
| CF₂ | Pyrimidinyl | NH—C(O) | Thiophenyl | $Z_1$: F (2) |
| CF₂ | Pyrimidinyl | NH—C(O) | Thiophenyl | $Z_1$: F (3) |
| CF₂ | Pyrimidinyl | NH—C(O) | Thiophenyl | $Z_1$: F (2)<br>$Z_2$: F (3) |
| CF₂ | Pyrimidinyl | NH—C(O) | Thiophenyl | $Z_1$: Cl (2) |
| CF₂ | Pyrimidinyl | NH—C(O) | Thiophenyl | $Z_1$: Cl (3) |
| CF₂ | Pyrimidinyl | NH—C(O) | Thiophenyl | $Z_1$: Cl (2)<br>$Z_2$: Cl (3) |
| CF₂ | Pyrimidinyl | NH—C(O) | Thiophenyl | $Z_1$: F (2)<br>$Z_2$: Cl (3) |

TABLE 2-continued

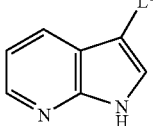

$$L^1-C^1-L^2-C^2-Z_p$$

| $L^1$ | $C^1$ | $L^2$ | $C^2$ | Z |
|---|---|---|---|---|
| $CF_2$ | Pyrimidinyl | NH—C(O) | Thiophenyl | $Z_1$: Cl (2) |
| | | | | $Z_2$: F (3) |
| $CF_2$ | Pyrimidinyl | NH—C(O) | Thiophenyl | $Z_1$: $CH_3$ (2) |
| $CF_2$ | Pyrimidinyl | NH—C(O) | Thiophenyl | $Z_1$: $CH_3$ (3) |
| $CF_2$ | Pyrimidinyl | NH—C(O) | Thiophenyl | $Z_1$: $CH_2$—$CH_3$ (2) |
| $CF_2$ | Pyrimidinyl | NH—C(O) | Thiophenyl | $Z_1$: $CHrCH_3$ (3) |
| $CF_2$ | Pyrimidinyl | NH—C(O) | Thiophenyl | $Z_1$: $CH_2$—$CH_2$—$CH_3$ or iPr (2) |
| $CF_2$ | Pyrimidinyl | NH—C(O) | Thiophenyl | $Z_1$: $CH_2$—$CH_2$—$CH_3$ or iPr (3) |
| $CF_2$ | Pyrimidinyl | NH—C(O) | Thiophenyl | $Z_1$: $CH_2F$ (2) |
| $CF_2$ | Pyrimidinyl | NH—C(O) | Thiophenyl | $Z_1$: $CH_2F$ (3) |
| $CF_2$ | Pyrimidinyl | NH—C(O) | Thiophenyl | $Z_1$: $CHF_2$ (2) |
| $CF_2$ | Pyrimidinyl | NH—C(O) | Thiophenyl | $Z_1$: $CHF_2$ (3) |
| $CF_2$ | Pyrimidinyl | NH—C(O) | Thiophenyl | $Z_1$: $CF_3$ (2) |
| $CF_2$ | Pyrimidinyl | NH—C(O) | Thiophenyl | $Z_1$: $CF_3$ (3) |
| $CF_2$ | Pyrimidinyl | NH—C(O) | Thiophenyl | $Z_1$: $CH_2$—$CH_2F$ (2) |
| $CF_2$ | Pyrimidinyl | NH—C(O) | Thiophenyl | $Z_1$: $CH_2$—$CH_2F$ (3) |
| $CF_2$ | Pyrimidinyl | NH—C(O) | Thiophenyl | $Z_1$: $CH_2$—$CHF_2$ (2) |
| $CF_2$ | Pyrimidinyl | NH—C(O) | Thiophenyl | $Z_1$: $CH_2$—$CHF_2$ (3) |
| $CF_2$ | Pyrimidinyl | NH—C(O) | Thiophenyl | $Z_1$: $CH_2$—$CF_3$ (2) |
| $CF_2$ | Pyrimidinyl | NH—C(O) | Thiophenyl | $Z_1$: $CH_2$—$CF_3$ (3) |
| $CF_2$ | Pyrimidinyl | NH—C(O) | Thiazolyl | None |
| $CF_2$ | Pyrimidinyl | NH—C(O) | Thiazolyl | $Z_1$: F (2) |
| $CF_2$ | Pyrimidinyl | NH—C(O) | Thiazolyl | $Z_1$: F (3) |
| $CF_2$ | Pyrimidinyl | NH—C(O) | Thiazolyl | $Z_1$: F (2) |
| $CF_2$ | Pyrimidinyl | NH—C(O) | Thiazolyl | $Z_1$: Cl (2) |
| $CF_2$ | Pyrimidinyl | NH—C(O) | Thiazolyl | $Z_1$: Cl (3) |
| $CF_2$ | Pyrimidinyl | NH—C(O) | Thiazolyl | $Z_1$: Cl (2) |
| | | | | $Z_2$: Cl (3) |
| $CF_2$ | Pyrimidinyl | NH—C(O) | Thiazolyl | $Z_1$: F (2) |
| | | | | $Z_2$: Cl (3) |
| $CF_2$ | Pyrimidinyl | NH—C(O) | Thiazolyl | $Z_1$: Cl (2) |
| | | | | $Z_2$: F (3) |
| $CF_2$ | Pyrimidinyl | NH—C(O) | Thiazolyl | $Z_1$: $CH_3$ (2) |
| $CF_2$ | Pyrimidinyl | NH—C(O) | Thiazolyl | $Z_1$: $CH_3$ (3) |
| $CF_2$ | Pyrimidinyl | NH—C(O) | Thiazolyl | $Z_1$: $CH_2$—$CH_3$ (2) |
| $CF_2$ | Pyrimidinyl | NH—C(O) | Thiazolyl | $Z_1$: $CH_2$—$CH_3$ (3) |
| $CF_2$ | Pyrimidinyl | NH—C(O) | Thiazolyl | $Z_1$: $CH_2$—$CH_2$—$CH_3$ or iPr (2) |
| $CF_2$ | Pyrimidinyl | NH—C(O) | Thiazolyl | $Z_1$: $CH_2$—$CH_2$—$CH_3$ or iPr (3) |
| $CF_2$ | Pyrimidinyl | NH—C(O) | Thiazolyl | $Z_1$: $CH_2F$ (2) |
| $CF_2$ | Pyrimidinyl | NH—C(O) | Thiazolyl | $Z_1$: $CH_2F$ (3) |
| $CF_2$ | Pyrimidinyl | NH—C(O) | Thiazolyl | $Z_1$: $CHF_2$ (2) |
| $CF_2$ | Pyrimidinyl | NH—C(O) | Thiazolyl | $Z_1$: $CHF_2$ (3) |
| $CF_2$ | Pyrimidinyl | NH—C(O) | Thiazolyl | $Z_1$: $CF_3$ (2) |
| $CF_2$ | Pyrimidinyl | NH—C(O) | Thiazolyl | $Z_1$: $CF_3$ (3) |
| $CF_2$ | Pyrimidinyl | NH—C(O) | Thiazolyl | $Z_1$: $CH_2$—$CH_2F$ (2) |
| $CF_2$ | Pyrimidinyl | NH—C(O) | Thiazolyl | $Z_1$: $CH_2$—$CH_2F$ (3) |
| $CF_2$ | Pyrimidinyl | NH—C(O) | Thiazolyl | $Z_1$: $CH_2$—$CHF_2$ (2) |
| $CF_2$ | Pyrimidinyl | NH—C(O) | Thiazolyl | $Z_1$: $CH_2$—$CHF_2$ (3) |
| $CF_2$ | Pyrmnudinyl | NH—C(O) | Thiazolyl | $Z_1$: $CH_2$—$CF_3$ (2) |
| $CF_2$ | Pyrimidinyl | NH—C(O) | Thiazolyl | $Z_1$: $CH_2$—$CF_3$ (3) |
| $CF_2$ | Pyrimidinyl | NH—$SO_2$ | Phenyl | None |
| $CF_2$ | Pyrimidinyl | NH—$SO_2$ | Phenyl | $Z_1$: F (para) |
| $CF_2$ | Pyrimidinyl | NH—$SO_2$ | phenyl | $Z_1$: F (meta) |
| $CF_2$ | Pyrimidinyl | NH—$SO_2$ | phenyl | $Z_1$: F (ortho) |
| $CF_2$ | Pyrimidinyl | NH—$SO_2$ | phenyl | $Z_1$: F (para) |
| | | | | $Z_2$: F (meta) |
| $CF_2$ | Pyrimidinyl | NH—$SO_2$ | Phenyl | $Z_1$: Cl (meta) |
| $CF_2$ | Pyrimidinyl | NH—$SO_2$ | Phenyl | $Z_1$: Cl (para) |
| $CF_2$ | Pyrimidinyl | NH—$SO_2$ | Phenyl | $Z_1$: Cl (para) |
| | | | | $Z_2$: Cl (meta) |
| $CF_2$ | Pyrimidinyl | NH—$SO_2$ | Phenyl | $Z_1$: F (para) |
| | | | | $Z_2$: Cl (meta) |
| $CF_2$ | Pyrimidinyl | NH—$SO_2$ | Phenyl | $Z_1$: Cl (para) |
| | | | | $Z_2$: F (meta) |
| $CF_2$ | Pyrimidinyl | NH—$SO_2$ | Phenyl | $Z_1$: $CH_3$ (para) |
| $CF_2$ | Pyrimidinyl | NH—$SO_2$ | Phenyl | $Z_1$: $CH_3$ (meta) |
| $CF_2$ | Pyrimidinyl | NH—$SO_2$ | Phenyl | $Z_1$: $CH_3$ (ortho) |
| $CF_2$ | Pyrimidinyl | NH—$SO_2$ | Phenyl | $Z_1$: $CH_2$—$CH_3$ (para) |
| $CF_2$ | Pyrimidinyl | NH—$SO_2$ | Phenyl | $Z_1$: $CH_2$—$CH_3$ (meta) |

TABLE 2-continued

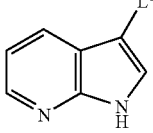

| L¹ | C¹ | L² | C² | Z |
|---|---|---|---|---|
| $CF_2$ | Pyrimidinyl | NH—$SO_2$ | Phenyl | $Z_1$: $CH_2$—$CH_3$ (ortho) |
| $CF_2$ | Pyrimidinyl | NH—$SO_2$ | Phenyl | $Z_1$: $CH_2$—$CH_2$—$CH_3$ or iPr (para) |
| $CF_2$ | Pyrimidinyl | NH—$SO_2$ | Phenyl | $Z_1$: $CH_2$—$CH_2$—$CH_3$ or iPr (meta) |
| $CF_2$ | Pyrimidinyl | NH—$SO_2$ | Phenyl | $Z_1$: $CH_2$—$CH_2$—$CH_3$ or iPr (ortho) |
| $CF_2$ | Pyrimidinyl | NH—$SO_2$ | Phenyl | $Z_1$: $CH_2F$ (para) |
| $CF_2$ | Pyrimidinyl | NH—$SO_2$ | Phenyl | $Z_1$: $CH_2F$ (meta) |
| $CF_2$ | Pyrimidinyl | NH—$SO_2$ | Phenyl | $Z_1$: $CH_2F$ (ortho) |
| $CF_2$ | Pyrimidinyl | NH—$SO_2$ | Phenyl | $Z_1$: $CHF_2$ (para) |
| $CF_2$ | Pyrimidinyl | NH—$SO_2$ | Phenyl | $Z_1$: $CHF_2$ (meta) |
| $CF_2$ | Pyrimidinyl | NH—$SO_2$ | Phenyl | $Z_1$: $CHF_2$ (ortho) |
| $CF_2$ | Pyrimidinyl | NH—$SO_2$ | Phenyl | $Z_1$: $CF_3$ (para) |
| $CF_2$ | Pyrimidinyl | NH—$SO_2$ | Phenyl | $Z_1$: $CF_3$ (meta) |
| $CF_2$ | Pyrimidinyl | NH—$SO_2$ | Phenyl | $Z_1$: $CF_3$ (ortho) |
| $CF_2$ | Pyrimidinyl | NH—$SO_2$ | Phenyl | $Z_1$: $CH_2$—$CH_2F$ (para) |
| $CF_2$ | Pyrimidinyl | NH—$SO_2$ | Phenyl | $Z_1$: $CH_2$—$CH_2F$ (meta) |
| $CF_2$ | Pyrimidinyl | NH—$SO_2$ | Phenyl | $Z_1$: $CH_2$—$CH_2F$ (ortho) |
| $CF_2$ | Pyrimidinyl | NH—$SO_2$ | Phenyl | $Z_1$: $CH_2$—$CHF_2$ (para) |
| $CF_2$ | Pyrimidinyl | NH—$SO_2$ | Phenyl | $Z_1$: $CH_2$—$CHF_2$ (meta) |
| $CF_2$ | Pyrimidinyl | NH—$SO_2$ | Phenyl | $Z_1$: $CH_2$—$CHF_2$ (ortho) |
| $CF_2$ | Pyrimidinyl | NH—$SO_2$ | Phenyl | $Z_1$: $CH_2$—$CF_3$ (para) |
| $CF_2$ | Pyrimidinyl | NH—$SO_2$ | Phenyl | $Z_1$: $CH_2$—$CF_3$ (meta) |
| $CF_2$ | Pyrimidinyl | NH—$SO_2$ | Phenyl | $Z_1$: $CH_2$—$CF_3$ (ortho) |
| $CF_2$ | Pyrimidinyl | NH—$SO_2$ | Pyridinyl | None |
| $CF_2$ | Pyrimidinyl | NH—$SO_2$ | Pyridinyl | $Z_1$: F (para) |
| $CF_2$ | Pyrimidinyl | NH—$SO_2$ | Pyridinyl | $Z_1$: F (meta) |
| $CF_2$ | Pyrimidinyl | NH—$SO_2$ | Pyridinyl | $Z_1$: F (ortho) |
| $CF_2$ | Pyrimidinyl | NH—$SO_2$ | Pyridinyl | $Z_1$: F (para) $Z_2$: F (meta) |
| $CF_2$ | Pyrimidinyl | NH—$SO_2$ | Pyridinyl | $Z_1$: Cl (meta) |
| $CF_2$ | Pyrimidinyl | NH—$SO_2$ | Pyridinyl | $Z_1$: Cl (para) |
| $CF_2$ | Pyrimidinyl | NH—$SO_2$ | Pyridinyl | $Z_1$: Cl (para) $Z_2$: Cl (meta) |
| $CF_2$ | Pyrimidinyl | NH—$SO_2$ | Pyridinyl | $Z_1$: F (para) $Z_2$: Cl (meta) |
| $CF_2$ | Pyrimidinyl | NH—$SO_2$ | Pyridinyl | $Z_1$: Cl (para) $Z_2$: F (meta) |
| $CF_2$ | Pyrimidinyl | NH—$SO_2$ | Pyridinyl | $Z_1$: $CH_3$ (para) |
| $CF_2$ | Pyrimidinyl | NH—$SO_2$ | Pyridinyl | $Z_1$: $CH_3$ (meta) |
| $CF_2$ | Pyrimidinyl | NH—$SO_2$ | Pyridinyl | $Z_1$: $CH_3$ (ortho) |
| $CF_2$ | Pyrimidinyl | NH—$SO_2$ | Pyridinyl | $Z_1$: $CH_2$—$CH_3$ (para) |
| $CF_2$ | Pyrimidinyl | NH—$SO_2$ | Pyridinyl | $Z_1$: $CH_2$—$CH_3$ (meta) |
| $CF_2$ | Pyrimidinyl | NH—$SO_2$ | Pyridinyl | $Z_1$: $CH_2$—$CH_3$ (ortho) |
| $CF_2$ | Pyrimidinyl | NH—$SO_2$ | Pyridinyl | $Z_1$: $CH_2$—$CH_2$—$CH_3$ or iPr (para) |
| $CF_2$ | Pyrimidinyl | NH—$SO_2$ | Pyridinyl | $Z_1$: $CH_2$—$CH_2$—$CH_3$ or iPr (meta) |
| $CF_2$ | Pyrimidinyl | NH—$SO_2$ | Pyridinyl | $Z_1$: $CH_2$—$CH_2$—$CH_3$ or iPr (ortho) |
| $CF_2$ | Pyrimidinyl | NH—$SO_2$ | Pyridinyl | $Z_1$: $CH_2F$ (para) |
| $CF_2$ | Pyrimidinyl | NH—$SO_2$ | Pyridinyl | $Z_1$: $CH_2F$ (meta) |
| $CF_2$ | Pyrimidinyl | NH—$SO_2$ | Pyridinyl | $Z_1$: $CH_2F$ (ortho) |
| $CF_2$ | Pyrimidinyl | NH—$SO_2$ | Pyridinyl | $Z_1$: $CHF_2$ (para) |
| $CF_2$ | Pyrimidinyl | NH—$SO_2$ | Pyridinyl | $Z_1$: $CHF_2$ (meta) |
| $CF_2$ | Pyrimidinyl | NH—$SO_2$ | Pyridinyl | $Z_1$: $CHF_2$ (ortho) |
| $CF_2$ | Pyrimidinyl | NH—$SO_2$ | Pyridinyl | $Z_1$: $CF_3$ (para) |
| $CF_2$ | Pyrimidinyl | NH—$SO_2$ | Pyridinyl | $Z_1$: $CF_3$ (meta) |
| $CF_2$ | Pyrimidinyl | NH—$SO_2$ | Pyridinyl | $Z_1$: $CF_3$ (ortho) |
| $CF_2$ | Pyrimidinyl | NH—$SO_2$ | Pyridinyl | $Z_1$: $CH_2$—$CH_2F$ (para) |
| $CF_2$ | Pyrimidinyl | NH—$SO_2$ | Pyridinyl | $Z_1$: $CH_2$—$CH_2F$ (meta) |
| $CF_2$ | Pyrimidinyl | NH—$SO_2$ | Pyridinyl | $Z_1$: $CHr$ $CH_2F$ (ortho) |
| $CF_2$ | Pyrimidinyl | NH—$SO_2$ | Pyridinyl | $Z_1$: $CH_2$—$CHF_2$ (para) |
| $CF_2$ | Pyrimidinyl | NH—$SO_2$ | Pyridinyl | $Z_1$: $CH_2$—$CHF_2$ (meta) |
| $CF_2$ | Pyrimidinyl | NH—$SO_2$ | Pyridinyl | $Z_1$: $CH_2$—$CHF_2$ (ortho) |
| $CF_2$ | Pyrimidinyl | NH—$SO_2$ | Pyridinyl | $Z_1$: $CH_2$—$CF_3$ (para) |
| $CF_2$ | Pyrimidinyl | NH—$SO_2$ | Pyridinyl | $Z_1$: $CH_2$—$CF_3$ (meta) |
| $CF_2$ | Pyrimidinyl | NH—$SO_2$ | Pyridinyl | $Z_1$: $CH_2$—$CF_3$ (ortho) |

TABLE 2-continued

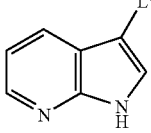

| $L^1$ | $C^1$ | $L^2$ | $C^2$ | Z |
|---|---|---|---|---|
| $CF_2$ | Pyrimidinyl | NH—$SO_2$ | Pyrimidinyl | None |
| $CF_2$ | Pyrimidinyl | NH—$SO_2$ | Pyrimidinyl | $Z_1$: F (para) |
| $CF_2$ | Pyrimidinyl | NH—$SO_2$ | Pyrimidinyl | $Z_1$: F (meta) |
| $CF_2$ | Pyrimidinyl | NH—$SO_2$ | Pyrimidinyl | $Z_1$: F (ortho) |
| $CF_2$ | Pyrimidinyl | NH—$SO_2$ | Pyrimidinyl | $Z_1$: F (para) $Z_2$: F (meta) |
| $CF_2$ | Pyrimidinyl | NH—$SO_2$ | Pyrimidinyl | $Z_1$: Cl (meta) |
| $CF_2$ | Pyrimidinyl | NH—$SO_2$ | Pyrimidinyl | $Z_1$: Cl (para) |
| $CF_2$ | Pyrimidinyl | NH—$SO_2$ | Pyrimidinyl | $Z_1$: Cl (para) $Z_2$: Cl (meta) |
| $CF_2$ | Pyrimidinyl | NH—$SO_2$ | Pyrimidinyl | $Z_1$: F (para) $Z_2$: Cl (meta) |
| $CF_2$ | Pyrimidinyl | NH—$SO_2$ | Pyrimidinyl | $Z_1$: Cl (para) $Z_2$: F (meta) |
| $CF_2$ | Pyrimidinyl | NH—$SO_2$ | Pyrimidinyl | $Z_1$: $CH_3$ (para) |
| $CF_2$ | Pyrimidinyl | NH—$SO_2$ | Pyrimidinyl | $Z_1$: $CH_3$ (meta) |
| $CF_2$ | Pyrimidinyl | NH—$SO_2$ | Pyrimidinyl | $Z_1$: $CH_3$ (ortho) |
| $CF_2$ | Pyrimidinyl | NH—$SO_2$ | Pyrimidinyl | $Z_1$: $CH_2$—$CH_3$ (para) |
| $CF_2$ | Pyrimidinyl | NH—$SO_2$ | Pyrimidinyl | $Z_1$: $CH_2$—$CH_3$ (meta) |
| $CF_2$ | Pyrimidinyl | NH—$SO_2$ | Pyrimidinyl | $Z_1$: $CH_2$—$CH_3$ (ortho) |
| $CF_2$ | Pyrimidinyl | NH—$SO_2$ | Pyrimidinyl | $Z_1$: $CH_2$—$CH_2$—$CH_3$ or iPr (para) |
| $CF_2$ | Pyrimidinyl | NH—$SO_2$ | Pyrimidinyl | $Z_1$: $CH_2$—$CH_2$—$CH_3$ or iPr (meta) |
| $CF_2$ | Pyrimidinyl | NH—$SO_2$ | Pyrimidinyl | $Z_1$: $CH_2$—$CH_2$—$CH_3$ or iPr (ortho) |
| $CF_2$ | Pyrimidinyl | NH—$SO_2$ | Pyrimidinyl | $Z_1$: $CH_2$F (para) |
| $CF_2$ | Pyrimidinyl | NH—$SO_2$ | Pyrimidinyl | $Z_1$: $CH_2$F (meta) |
| $CF_2$ | Pyrimidinyl | NH—$SO_2$ | Pyrimidinyl | $Z_1$: $CH_2$F (ortho) |
| $CF_2$ | Pyrimidinyl | NH—$SO_2$ | Pyrimidinyl | $Z_1$: $CHF_2$ (para) |
| $CF_2$ | Pyrimidinyl | NH—$SO_2$ | Pyrimidinyl | $Z_1$: $CHF_2$ (meta) |
| $CF_2$ | Pyrimidinyl | NH—$SO_2$ | Pyrimidinyl | $Z_1$: $CHF_2$ (ortho) |
| $CF_2$ | Pyrimidinyl | NH—$SO_2$ | Pyrimidinyl | $Z_1$: $CF_3$ (para) |
| $CF_2$ | Pyrimidinyl | NH—$SO_2$ | Pyrimidinyl | $Z_1$: $CF_3$ (meta) |
| $CF_2$ | Pyrimidinyl | NH—$SO_2$ | Pyrimidinyl | $Z_1$: $CF_3$ (ortho) |
| $CF_2$ | Pyrimidinyl | NH—$SO_2$ | Pyrimidinyl | $Z_1$: $CH_2$—$CH_2$F (para) |
| $CF_2$ | Pyrimidinyl | NH—$SO_2$ | Pyrimidinyl | $Z_1$: $CH_2$—$CH_2$F (meta) |
| $CF_2$ | Pyrimidinyl | NH—$SO_2$ | Pyrimidinyl | $Z_1$: $CH_2$—$CH_2$F (ortho) |
| $CF_2$ | Pyrimidinyl | NH—$SO_2$ | Pyrimidinyl | $Z_1$: $CH_2$—$CHF_2$ (para) |
| $CF_2$ | Pyrimidinyl | NH—$SO_2$ | Pyrimidinyl | $Z_1$: $CH_2$—$CHF_2$ (meta) |
| $CF_2$ | Pyrimidinyl | NH—$SO_2$ | Pyrimidinyl | $Z_1$: $CH_2$—$CHF_2$ (ortho) |
| $CF_2$ | Pyrimidinyl | NH—$SO_2$ | Pyrimidinyl | $Z_1$: $CH_2$—$CF_3$ (para) |
| $CF_2$ | Pyrimidinyl | NH—$SO_2$ | Pyrimidinyl | $Z_1$: $CH_2$—$CF_3$ (meta) |
| $CF_2$ | Pyrimidinyl | NH—$SO_2$ | Pyrimidinyl | $Z_1$: $CH_2$—$CF_3$ (ortho) |
| $CF_2$ | Pyrimidinyl | NH—$SO_2$ | Pyrazinyl | None |
| $CF_2$ | Pyrimidinyl | NH—$SO_2$ | Pyrazinyl | $Z_1$: F (para) |
| $CF_2$ | Pyrimidinyl | NH—$SO_2$ | Pyrazinyl | $Z_1$: F (meta) |
| $CF_2$ | Pyrimidinyl | NH—$SO_2$ | Pyrazinyl | $Z_1$: F (ortho) |
| $CF_2$ | Pyrimidinyl | NH—$SO_2$ | Pyrazinyl | $Z_1$: F (para) $Z_2$: F (meta) |
| $CF_2$ | Pyrimidinyl | NH—$SO_2$ | Pyrazinyl | $Z_1$: Cl (meta) |
| $CF_2$ | Pyrimidinyl | NH—$SO_2$ | Pyrazinyl | $Z_1$: Cl (para) |
| $CF_2$ | Pyrimidinyl | NH—$SO_2$ | Pyrazinyl | $Z_1$: Cl (para) $Z_2$: Cl (meta) |
| $CF_2$ | Pyrimidinyl | NH—$SO_2$ | Pyrazinyl | $Z_1$: F (para) $Z_2$: Cl (meta) |
| $CF_2$ | Pyrimidinyl | NH—$SO_2$ | Pyrazinyl | $Z_1$: Cl (para) $Z_2$: F (meta) |
| $CF_2$ | Pyrimidinyl | NH—$SO_2$ | Pyrazinyl | $Z_1$: $CH_3$ (para) |
| $CF_2$ | Pyrimidinyl | NH—$SO_2$ | Pyrazinyl | $Z_1$: $CH_3$ (meta) |
| $CF_2$ | Pyrimidinyl | NH—$SO_2$ | Pyrazinyl | $Z_1$: $CH_3$ (ortho) |
| $CF_2$ | Pyrimidinyl | NH—$SO_2$ | Pyrazinyl | $Z_1$: $CH_2$—$CH_3$ (para) |
| $CF_2$ | Pyrimidinyl | NH—$SO_2$ | Pyrazinyl | $Z_1$: $CH_2$—$CH_3$ (meta) |
| $CF_2$ | Pyrimidinyl | NH—$SO_2$ | Pyrazinyl | $Z_1$: $CH_2$—$CH_3$ (ortho) |
| $CF_2$ | Pyrimidinyl | NH—$SO_2$ | Pyrazinyl | $Z_1$: $CH_2$—$CH_2$—$CH_3$ or iPr (para) |
| $CF_2$ | Pyrimidinyl | NH—$SO_2$ | Pyrazinyl | $Z_1$: $CH_2$—$CH_2$—$CH_3$ or iPr |
| $CF_2$ | Pyrimidinyl | NH—$SO_2$ | Pyrazinyl | $Z_1$: $CH_2$—$CH_2$—$CH_3$ or iPr |
| $CF_2$ | Pyrimidinyl | NH—$SO_2$ | Pyrazinyl | $Z_1$: $CH_2$F (para) |

TABLE 2-continued

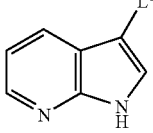

| L¹ | C¹ | L² | C² | Z |
|---|---|---|---|---|
| CF₂ | Pyrimidinyl | NH—SO₂ | Pyrazinyl | Z₁: CH₂F (meta) |
| CF₂ | Pyrimidinyl | NH—SO₂ | Pyrazinyl | Z₁: CH₂F (ortho) |
| CF₂ | Pyrimidinyl | NH—SO₂ | Pyrazinyl | Z₁: CHF₂ (para) |
| CF₂ | Pyrimidinyl | NH—SO₂ | Pyrazinyl | Z₁: CHF₂ (meta) |
| CF₂ | Pyrimidinyl | NH—SO₂ | Pyrazinyl | Z₁: CHF₂ (ortho) |
| CF₂ | Pyrimidinyl | NH—SO₂ | Pyrazinyl | Z₁: CF₃ (para) |
| CF₂ | Pyrimidinyl | NH—SO₂ | Pyrazinyl | Z₁: CF₃ (meta) |
| CF₂ | Pyrimidinyl | NH—SO₂ | Pyrazinyl | Z₁: CF₃ (ortho) |
| CF₂ | Pyrimidinyl | NH—SO₂ | Pyrazinyl | Z₁: CH₂—CH₂F (para) |
| CF₂ | Pyrimidinyl | NH—SO₂ | Pyrazinyl | Z₁: CH₂—CH₂F (meta) |
| CF₂ | Pyrimidinyl | NH—SO₂ | Pyrazinyl | Z₁: CH₂—CH₂F (ortho) |
| CF₂ | Pyrimidinyl | NH—SO₂ | Pyrazinyl | Z₁: CH₂—CHF₂ (para) |
| CF₂ | Pyrimidinyl | NH—SO₂ | Pyrazinyl | Z₁: CH₂—CHF₂ (meta) |
| CF₂ | Pyrimidinyl | NH—SO₂ | Pyrazinyl | Z₁: CH₂—CHF₂ (ortho) |
| CF₂ | Pyrimidinyl | NH—SO₂ | Pyrazinyl | Z₁: CH₂—CF₃ (para) |
| CF₂ | Pyrimidinyl | NH—SO₂ | Pyrazinyl | Z₁: CH₂—CF₃ (meta) |
| CF₂ | Pyrimidinyl | NH—SO₂ | Pyrazinyl | Z₁: CH₂—CF₃ (ortho) |
| CF₂ | Pyrimidinyl | NH—SO₂ | Pyrrolyl | None |
| CF₂ | Pyrimidinyl | NH—SO₂ | Pyrrolyl | Z₁: F (2) |
| CF₂ | Pyrimidinyl | NH—SO₂ | Pyrrolyl | Z₁: F (3) |
| CF₂ | Pyrimidinyl | NH—SO₂ | Pyrrolyl | Z₁: F (2)<br>Z₂: F (3) |
| CF₂ | Pyrimidinyl | NH—SO₂ | Pyrrolyl | Z₁: Cl (2) |
| CF₂ | Pyrimidinyl | NH—SO₂ | Pyrrolyl | Z₁: Cl (3) |
| CF₂ | Pyrimidinyl | NH—SO₂ | Pyrrolyl | Z₁: Cl (2)<br>Z₂: Cl (3) |
| CF₂ | Pyrimidinyl | NH—SO₂ | Pyrrolyl | Z₁: Cl (2)<br>Z₂: F (3) |
| CF₂ | Pyrimidinyl | NH—SO₂ | Pyrrolyl | Z₁: CH₃ (2) |
| CF₂ | Pyrimidinyl | NH—SO₂ | Pyrrolyl | Z₁: CH₃ (3) |
| CF₂ | Pyrimidinyl | NH—SO₂ | Pyrrolyl | Z₁: CH₂—CH₃ (2) |
| CF₂ | Pyrimidinyl | NH—SO₂ | Pyrrolyl | Z₁: CH₂—CH₃ (3) |
| CF₂ | Pyrimidinyl | NH—SO₂ | Pyrrolyl | Z₁: CH₂—CH₂—CH₃ or iPr (2) |
| CF₂ | Pyrimidinyl | NH—SO₂ | Pyrrolyl | Z₁: CH₂—CH₂—CH₃ or iPr (3) |
| CF₂ | Pyrimidinyl | NH—SO₂ | Pyrrolyl | Z₁: CH₂F (2) |
| CF₂ | Pyrimidinyl | NH—SO₂ | Pyrrolyl | Z₁: CH₂F (3) |
| CF₂ | Pyrimidinyl | NH—SO₂ | Pyrrolyl | Z₁: CHF₂ (2) |
| CF₂ | Pyrimidinyl | NH—SO₂ | Pyrrolyl | Z₁: CHF₂ (3) |
| CF₂ | Pyrimidinyl | NH—SO₂ | Pyrrolyl | Z₁: CF₃ (2) |
| CF₂ | Pyrimidinyl | NH—SO₂ | Pyrrolyl | Z₁: CF₃ (3) |
| CF₂ | Pyrimidinyl | NH—SO₂ | Pyrrolyl | Z₁: CH₂—CH₂F (2) |
| CF₂ | Pyrimidinyl | NH—SO₂ | Pyrrolyl | Z₁: CH₂—CH₂F (3) |
| CF₂ | Pyrimidinyl | NH—SO₂ | Pyrrolyl | Z₁: CH₂—CHF₂ (2) |
| CF₂ | Pyrimidinyl | NH—SO₂ | Pyrrolyl | Z₁: CH₂—CHF₂ (3) |
| CF₂ | Pyrimidinyl | NH—SO₂ | Pyrrolyl | Z₁: CH₂—CF₃ (2) |
| CF₂ | Pyrimidinyl | NH—SO₂ | Pyrrolyl | Z₁: CH₂—CF₃ (3) |
| CF₂ | Pyrimidinyl | NH—SO₂ | Imidazolyl | None |
| CF₂ | Pyrimidinyl | NH—SO₂ | Imidazolyl | Z₁: F (2) |
| CF₂ | Pyrimidinyl | NH—SO₂ | Imidazolyl | Z₁: F (3) |
| CF₂ | Pyrimidinyl | NH—SO₂ | Imidazolyl | Z₁: F (2)<br>Z₂: F (3) |
| CF₂ | Pyrimidinyl | NH—SO₂ | Imidazolyl | Z₁: Cl (2) |
| CF₂ | Pyrimidinyl | NH—SO₂ | Imidazolyl | Z₁: Cl (3)<br>Z₂: Cl (3) |
| CF₂ | Pyrimidinyl | NH—SO₂ | Imidazolyl | Z₁: F (2)<br>Z₂: F (3) |
| CF₂ | Pyrimidinyl | NH—SO₂ | Imidazolyl | Z₁: CH₃ (2) |
| CF₂ | Pyrimidinyl | NH—SO₂ | Imidazolyl | Z₁: CH₃ (3) |
| CF₂ | Pyrimidinyl | NH—SO₂ | Imidazolyl | Z₁: CH₂—CH₃ (2) |
| CF₂ | Pyrimidinyl | NH—SO₂ | Imidazolyl | Z₁: CH₂—CH₃ (3) |
| CF₂ | Pyrimidinyl | NH—SO₂ | Imidazolyl | Z₁: CH₂—CH₂—CH₃ or iPr (2) |
| CF₂ | Pyrimidinyl | NH—SO₂ | Imidazolyl | Z₁: CH₂—CH₂—CH₃ or iPr (3) |
| CF₂ | Pyrimidinyl | NH—SO₂ | Imidazolyl | Z₁: CH₂F (2) |
| CF₂ | Pyrimidinyl | NH—SO₂ | Imidazolyl | Z₁: CH₂F (3) |
| CF₂ | Pyrimidinyl | NH—SO₂ | Imidazolyl | Z₁: CHF₂ (2) |
| CF₂ | Pyrimidinyl | NH—SO₂ | Imidazolyl | Z₁: CHF₂ (3) |
| CF₂ | Pyrimidinyl | NH—SO₂ | Imidazolyl | Z₁: CF₃ (2) |
| CF₂ | Pyrimidinyl | NH—SO₂ | Imidazolyl | Z₁: CF₃ (3) |
| CF₂ | Pyrimidinyl | NH—SO₂ | Imidazolyl | Z₁: CH₂—CH₂F (2) |

TABLE 2-continued $$L^1-C^1-L^2-C^2-Z_p$$

attached to 7-azaindole (3-position)

| L¹ | C¹ | L² | C² | Z |
|---|---|---|---|---|
| CF₂ | Pyrimidinyl | NH—SO₂ | Imidazolyl | Z₁: CH₂—CH₂F (3) |
| CF₂ | Pyrimidinyl | NH—SO₂ | Imidazolyl | Z₁: CH₂—CHF₂ (2) |
| CF₂ | Pyrimidinyl | NH—SO₂ | Imidazolyl | Z₁: CH₂—CHF₂ (3) |
| CF₂ | Pyrimidinyl | NH—SO₂ | Imidazolyl | Z₁: CH₂—CF₃ (2) |
| CF₂ | Pyrimidinyl | NH—SO₂ | Imidazolyl | Z₁: CH₂—CF₃ (3) |
| CF₂ | Pyrimidinyl | NH—SO₂ | Furanyl | None |
| CF₂ | Pyrimidinyl | NH—SO₂ | Furanyl | Z₁: F (2) |
| CF₂ | Pyrimidinyl | NH—SO₂ | Furanyl | Z₁: F (3) |
| CF₂ | Pyrimidinyl | NH—SO₂ | Furanyl | Z₁: F (2) Z₂: F (3) |
| CF₂ | Pyrimidinyl | NH—SO₂ | Furanyl | Z₁: Cl (2) |
| CF₂ | Pyrimidinyl | NH—SO₂ | Furanyl | Z₁: Cl (3) |
| CF₂ | Pyrimidinyl | NH—SO₂ | Furanyl | Z₁: Cl (2) Z₂: Cl (3) |
| CF₂ | Pyrimidinyl | NH—SO₂ | Furanyl | Z₁: F (2) Z₂: F (3) |
| CF₂ | Pyrimidinyl | NH—SO₂ | Furanyl | Z₁: CH₃ (2) |
| CF₂ | Pyrimidinyl | NH—SO₂ | Furanyl | Z₁: CH₃ (3) |
| CF₂ | Pyrimidinyl | NH—SO₂ | Furanyl | Z₁: CH₂—CH₃ (2) |
| CF₂ | Pyrimidinyl | NH—SO₂ | Furanyl | Z₁: CH₂—CH₃ (3) |
| CF₂ | Pyrimidinyl | NH—SO₂ | Furanyl | Z₁: CH₂—CH₂—CH₃ or iPr (2) |
| CF₂ | Pyrimidinyl | NH—SO₂ | Furanyl | Z₁: CH₂—CH₂—CH₃ or iPr (3) |
| CF₂ | Pyrimidinyl | NH—SO₂ | Furanyl | Z₁: CH₂F (2) |
| CF₂ | Pyrimidinyl | NH—SO₂ | Furanyl | Z₁: CH₂F (3) |
| CF₂ | Pyrimidinyl | NH—SO₂ | Furanyl | Z₁: CHF₂ (2) |
| CF₂ | Pyrimidinyl | NH—SO₂ | Furanyl | Z₁: CHF₂ (3) |
| CF₂ | Pyrimidinyl | NH—SO₂ | Furanyl | Z₁: CF₃ (2) |
| CF₂ | Pyrimidinyl | NH—SO₂ | Furanyl | Z₁: CF₃ (3) |
| CF₂ | Pyrimidinyl | NH—SO₂ | Furanyl | Z₁: CH₂—CH₂F (2) |
| CF₂ | Pyrimidinyl | NH—SO₂ | Furanyl | Z₁: CH₂—CH₂F (3) |
| CF₂ | Pyrimidinyl | NH—SO₂ | Furanyl | Z₁: CH₂—CHF₂ (2) |
| CF₂ | Pyrimidinyl | NH—SO₂ | Furanyl | Z₁: CH₂—CHF₂ (3) |
| CF₂ | Pyrimidinyl | NH—SO₂ | Furanyl | Z₁: CH₂—CF₃ (2) |
| CF₂ | Pyrimidinyl | NH—SO₂ | Furanyl | Z₁: CH₂—CF₃ (3) |
| CF₂ | Pyrimidinyl | NH—SO₂ | Oxazolyl | None |
| CF₂ | Pyrimidinyl | NH—SO₂ | Oxazolyl | Z₁: F (2) |
| CF₂ | Pyrimidinyl | NH—SO₂ | Oxazolyl | Z₁: F (3) |
| CF₂ | Pyrimidinyl | NH—SO₂ | Oxazolyl | Z₁: Cl (2) |
| CF₂ | Pyrimidinyl | NH—SO₂ | Oxazolyl | Z₁: Cl (3) |
| CF₂ | Pyrimidinyl | NH—SO₂ | Oxazolyl | Z₁: Cl (2) Z₂: Cl (3) |
| CF₂ | Pyrimidinyl | NH—SO₂ | Oxazolyl | Z₁: F (2) Z₂: Cl (3) |
| CF₂ | Pyrimidinyl | NH—SO₂ | Oxazolyl | Z₁: Cl (2) Z₂: F (3) |
| CF₂ | Pyrimidinyl | NH—SO₂ | Oxazolyl | Z₁: CH₃ (2) |
| CF₂ | Pyrimidinyl | NH—SO₂ | Oxazolyl | Z₁: CH₃ (3) |
| CF₂ | Pyrimidinyl | NH—SO₂ | Oxazolyl | Z₁: CH₂—CH₃ (2) |
| CF₂ | Pyrimidinyl | NH—SO₂ | Oxazolyl | Z₁: CH₂—CH₃ (3) |
| CF₂ | Pyrimidinyl | NH—SO₂ | Oxazolyl | Z₁: CH₂—CH₂—CH₃ or iPr (2) |
| CF₂ | Pyrimidinyl | NH—SO₂ | Oxazolyl | Z₁: CH₂—CH₂—CH₃ or iPr (3) |
| CF₂ | Pyrimidinyl | NH—SO₂ | Oxazolyl | Z₁: CH₂F (2) |
| CF₂ | Pyrimidinyl | NH—SO₂ | Oxazolyl | Z₁: CH₂F (3) |
| CF₂ | Pyrimidinyl | NH—SO₂ | Oxazolyl | Z₁: CHF₂ (2) |
| CF₂ | Pyrimidinyl | NH—SO₂ | Oxazolyl | Z₁: CHF₂ (3) |
| CF₂ | Pyrimidinyl | NH—SO₂ | Oxazolyl | Z₁: CF₃ (2) |
| CF₂ | Pyrimidinyl | NH—SO₂ | Oxazolyl | Z₁: CF₃ (3) |
| CF₂ | Pyrimidinyl | NH—SO₂ | Oxazolyl | Z₁: CH₂—CH₂F (2) |
| CF₂ | Pyrimidinyl | NH—SO₂ | Oxazolyl | Z₁: CH₂—CH₂F (3) |
| CF₂ | Pyrimidinyl | NH—SO₂ | Oxazolyl | Z₁: CH₂—CHF₂ (2) |
| CF₂ | Pyrimidinyl | NH—SO₂ | Oxazolyl | Z₁: CH₂—CHF₂ (3) |
| CF₂ | Pyrimidinyl | NH—SO₂ | Oxazolyl | Z₁: CH₂—CF₃ (2) |
| CF₂ | Pyrimidinyl | NH—SO₂ | Oxazolyl | Z₁: CH₂—CF₂ (3) |
| CF₂ | Pyrimidinyl | NH—SO₂ | Thiophenyl | None |
| CF₂ | Pyrimidinyl | NH—SO₂ | Thiophenyl | Z₁: F (2) |
| CF₂ | Pyrimidinyl | NH—SO₂ | Thiophenyl | Z₁: F (3) |
| CF₂ | Pyrimidinyl | NH—SO₂ | Thiophenyl | Z₁: F (2) Z₂: F (3) |
| CF₂ | Pyrimidinyl | NH—SO₂ | Thiophenyl | Z₁: Cl (2) |

TABLE 2-continued

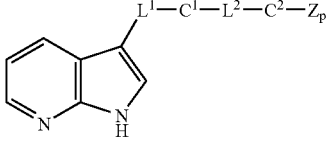

| L$^1$ | C$^1$ | L$^2$ | C$^2$ | Z |
|---|---|---|---|---|
| CF$_2$ | Pyrimidinyl | NH—SO$_2$ | Thiophenyl | Z$_1$: Cl (3) |
| CF$_2$ | Pyrimidinyl | NH—SO$_2$ | Thiophenyl | Z$_1$: F (2) |
|  |  |  |  | Z$_2$: Cl (3) |
| CF$_2$ | Pyrimidinyl | NH—SO$_2$ | Thiophenyl | Z$_1$: Cl (2) |
|  |  |  |  | Z$_2$: F (3) |
| CF$_2$ | Pyrimidinyl | NH—SO$_2$ | Thiophenyl | Z$_1$: CH$_3$ (2) |
| CF$_2$ | Pyrimidinyl | NH—SO$_2$ | Thiophenyl | Z$_1$: CH$_3$ (3) |
| CF$_2$ | Pyrimidinyl | NH—SO$_2$ | Thiophenyl | Z$_1$: CH$_2$—CH$_3$ (2) |
| CF$_2$ | Pyrimidinyl | NH—SO$_2$ | Thiophenyl | Z$_1$: CH$_2$—CH$_3$ (3) |
| CF$_2$ | Pyrimidinyl | NH—SO$_2$ | Thiophenyl | Z$_1$: CH$_2$—CH$_2$—CH$_3$ or iPr (2) |
| CF$_2$ | Pyrimidinyl | NH—SO$_2$ | Thiophenyl | Z$_1$: CH$_2$—CH$_2$—CH$_3$ or iPr (3) |
| CF$_2$ | Pyrimidinyl | NH—SO$_2$ | Thiophenyl | Z$_1$: CH$_2$F (2) |
| CF$_2$ | Pyrimidinyl | NH—SO$_2$ | Thiophenyl | Z$_1$: CH$_2$F (3) |
| CF$_2$ | Pyrimidinyl | NH—SO$_2$ | Thiophenyl | Z$_1$: CHF$_2$ (2) |
| CF$_2$ | Pyrimidinyl | NH—SO$_2$ | Thiophenyl | Z$_1$: CHF$_2$ (3) |
| CF$_2$ | Pyrimidinyl | NH—SO$_2$ | Thiophenyl | Z$_1$: CF$_3$ (2) |
| CF$_2$ | Pyrimidinyl | NH—SO$_2$ | Thiophenyl | Z$_1$: CF$_3$ (3) |
| CF$_2$ | Pyrimidinyl | NH—SO$_2$ | Thiophenyl | Z$_1$: CH$_2$—CH$_2$F (2) |
| CF$_2$ | Pyrimidinyl | NH—SO$_2$ | Thiophenyl | Z$_1$: CH$_2$—CH$_2$F (3) |
| CF$_2$ | Pyrimidinyl | NH—SO$_2$ | Thiophenyl | Z$_1$: CH$_2$—CHF$_2$ (2) |
| CF$_2$ | Pyrimidinyl | NH—SO$_2$ | Thiophenyl | Z$_1$: CH$_2$—CHF$_2$ (3) |
| CF$_2$ | Pyrimidinyl | NH—SO$_2$ | Thiophenyl | Z$_1$: CH$_2$—CF$_3$ (2) |
| CF$_2$ | Pyrimidinyl | NH—SO$_2$ | Thiophenyl | Z$_1$: CH$_2$—CF$_3$ (3) |
| CF$_2$ | Pyrimidinyl | NH—SO$_2$ | Thiazolyl | None |
| CF$_2$ | Pyrimidinyl | NH—SO$_2$ | Thiazolyl | Z$_1$: F (2) |
| CF$_2$ | Pyrimidinyl | NH—SO$_2$ | Thiazolyl | Z$_1$: F (3) |
|  |  |  |  | Z$_2$: F (3) |
| CF$_2$ | Pyrimidinyl | NH—SO$_2$ | Thiazolyl | Z$_1$: Cl (2) |
| CF$_2$ | Pyrimidinyl | NH—SO$_2$ | Thiazolyl | Z$_1$: Cl (3) |
| CF$_2$ | Pyrimidinyl | NH—SO$_2$ | Thiazolyl | Z$_1$: Cl (2) |
|  |  |  |  | Z$_2$: Cl (3) |
| CF$_2$ | Pyrimidinyl | NH—SO$_2$ | Thiazolyl | Z$_1$: F (2) |
|  |  |  |  | Z$_2$: Cl (3) |
| CF$_2$ | Pyrimidinyl | NH—SO$_2$ | Thiazolyl | Z$_1$: Cl (2) |
|  |  |  |  | Z$_2$: F (3) |
| CF$_2$ | Pyrimidinyl | NH—SO$_2$ | Thiazolyl | Z$_1$: CH$_3$ (2) |
| CF$_2$ | Pyrimidinyl | NH—SO$_2$ | Thiazolyl | Z$_1$: CH$_3$ (3) |
| CF$_2$ | Pyrimidinyl | NH—SO$_2$ | Thiazolyl | Z$_1$: CH$_2$—CH$_3$ (2) |
| CF$_2$ | Pyrimidinyl | NH—SO$_2$ | Thiazolyl | Z$_1$: CH$_2$—CH$_3$ (3) |
| CF$_2$ | Pyrimidinyl | NH—SO$_2$ | Thiazolyl | Z$_1$: CH$_2$—CH$_2$—CH$_3$ or iPr (2) |
| CF$_2$ | Pyrimidinyl | NH—SO$_2$ | Thiazolyl | Z$_1$: CH$_2$—CH$_2$—CH$_3$ or iPr (3) |
| CF$_2$ | Pyrimidinyl | NH—SO$_2$ | Thiazolyl | Z$_1$: CH$_2$F (2) |
| CF$_2$ | Pyrimidinyl | NH—SO$_2$ | Thiazolyl | Z$_1$: CH$_2$F (3) |
| CF$_2$ | Pyrimidinyl | NH—SO$_2$ | Thiazolyl | Z$_1$: CHF$_2$ (2) |
| CF$_2$ | Pyrimidinyl | NH—SO$_2$ | Thiazolyl | Z$_1$: CHIF$_2$ (3) |
| CF$_2$ | Pyrimidinyl | NH—SO$_2$ | Thiazolyl | Z$_1$: CF$_3$ (2) |
| CF$_2$ | Pyrimidinyl | NH—SO$_2$ | Thiazolyl | Z$_1$: CF$_3$ (3) |
| CF$_2$ | Pyrimidinyl | NH—SO$_2$ | Thiazolyl | Z$_1$: CH$_2$—CH$_2$F (2) |
| CF$_2$ | Pyrimidinyl | NH—SO$_2$ | Thiazolyl | Z$_1$: CH$_2$—CH$_2$F (3) |
| CF$_2$ | Pyrimidinyl | NH—SO$_2$ | Thiazolyl | Z$_1$: CH$_2$—CHF$_2$ (2) |
| CF$_2$ | Pyrimidinyl | NH—SO$_2$ | Thiazolyl | Z$_1$: CH$_2$—CHF$_2$ (3) |
| CF$_2$ | Pyrimidinyl | NH—SO$_2$ | Thiazolyl | Z$_1$: CH$_2$—CF$_3$ (2) |
| CF$_2$ | Pyrimidinyl | NH—SO$_2$ | Thiazolyl | Z$_1$: CH$_2$—CF$_3$ (3) |
| CF$_2$ | Pyrazinyl | NH—CH$_2$ | Phenyl | None |
| CF$_2$ | Pyrazinyl | NH—CH$_2$ | Phenyl | Z$_1$: F (para) |
| CF$_2$ | Pyrazinyl | NH—CH$_2$ | phenyl | Z$_1$: F (meta) |
| CF$_2$ | Pyrazinyl | NH—CH$_2$ | phenyl | Z$_1$: F (ortho) |
| CF$_2$ | Pyrazinyl | NH—CH$_2$ | phenyl | Z$_1$: F (para) |
|  |  |  |  | Z$_2$: F (meta) |
| CF$_2$ | Pyrazinyl | NH—CH$_2$ | Phenyl | Z$_1$: Cl (meta) |
| CF$_2$ | Pyrazinyl | NH—CH$_2$ | Phenyl | Z$_1$: Cl (para) |
| CF$_2$ | Pyrazinyl | NH—CH$_2$ | Phenyl | Z$_1$: Cl (para) |
|  |  |  |  | Z$_2$: Cl (meta) |
| CF$_2$ | Pyrazinyl | NH—CH$_2$ | Phenyl | Z$_1$: F (para) |
|  |  |  |  | Z$_2$: Cl (meta) |
| CF$_2$ | Pyrazinyl | NH—CH$_2$ | Phenyl | Z$_1$: Cl (para) |
|  |  |  |  | Z$_2$: F (meta) |
| CF$_2$ | Pyrazinyl | NH—CH$_2$ | Phenyl | Z$_1$: CH$_3$ (para) |
| CF$_2$ | Pyrazinyl | NH—CH$_2$ | Phenyl | Z$_1$: CH$_3$ (meta) |

TABLE 2-continued $$L^1-C^1-L^2-C^2-Z_p$$

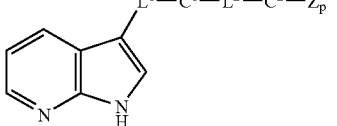

| L¹ | C¹ | L² | C² | Z |
|---|---|---|---|---|
| CF₂ | Pyrazinyl | NH—CH₂ | Phenyl | Z₁: CH₃ (ortho) |
| CF₂ | Pyrazinyl | NH—CH₂ | Phenyl | Z₁: CH₂—CH₃ (para) |
| CF₂ | Pyrazinyl | NH—CH₂ | Phenyl | Z₁: CH₂—CH₃ (meta) |
| CF₂ | Pyrazinyl | NH—CH₂ | Phenyl | Z₁: CH₂—CH₃ (ortho) |
| CF₂ | Pyrazinyl | NH—CH₂ | Phenyl | Z₁: CH₂—CH₂—CH₃ or iPr (para) |
| CF₂ | Pyrazinyl | NH—CH₂ | Phenyl | Z₁: CH₂—CH₂—CH₃ or iPr (meta) |
| CF₂ | Pyrazinyl | NH—CH₂ | Phenyl | Z₁: CH₂—CH₂—CH₃ or iPr (ortho) |
| CF₂ | Pyrazinyl | NH—CH₂ | Phenyl | Z₁: CH₂F (para) |
| CF₂ | Pyrazinyl | NH—CH₂ | Phenyl | Z₁: CH₂F (meta) |
| CF₂ | Pyrazinyl | NH—CH₂ | Phenyl | Z₁: CH₂F (ortho) |
| CF₂ | Pyrazinyl | NH—CH₂ | Phenyl | Z₁: CHF₂ (para) |
| CF₂ | Pyrazinyl | NH—CH₂ | Phenyl | Z₁: CHF₂ (meta) |
| CF₂ | Pyrazinyl | NH—CH₂ | Phenyl | Z₁: CHF₂ (ortho) |
| CF₂ | Pyrazinyl | NH—CH₂ | Phenyl | Z₁: CF₃ (para) |
| CF₂ | Pyrazinyl | NH—CH₂ | Phenyl | Z₁: CF₃ (meta) |
| CF₂ | Pyrazinyl | NH—CH₂ | Phenyl | Z₁: CF₃ (ortho) |
| CF₂ | Pyrazinyl | NH—CH₂ | Phenyl | Z₁: CH₂—CH₂F (para) |
| CF₂ | Pyrazinyl | NH—CH₂ | Phenyl | Z₁: CH₂—CH₂F (meta) |
| CF₂ | Pyrazinyl | NH—CH₂ | Phenyl | Z₁: CH₂—CH₂F (ortho) |
| CF₂ | Pyrazinyl | NH—CH₂ | Phenyl | Z₁: CH₂—CHF₂ (para) |
| CF₂ | Pyrazinyl | NH—CH₂ | Phenyl | Z₁: CH₂—CHF₂ (meta) |
| CF₂ | Pyrazinyl | NH—CH₂ | Phenyl | Z₁: CH₂—CHF₂ (ortho) |
| CF₂ | Pyrazinyl | NH—CH₂ | Phenyl | Z₁: CH₂—CF₃ (para) |
| CF₂ | Pyrazinyl | NH—CH₂ | Phenyl | Z₁: CH₂—CF₃ (meta) |
| CF₂ | Pyrazinyl | NH—CH₂ | Phenyl | Z₁: CH₂—CF₃ (ortho) |
| CF₂ | Pyrazinyl | NH—CH₂ | Pyridinyl | None |
| CF₂ | Pyrazinyl | NH—CH₂ | Pyridinyl | Z₁: F (para) |
| CF₂ | Pyrazinyl | NH—CH₂ | Pyridinyl | Z₁: F (meta) |
| CF₂ | Pyrazinyl | NH—CH₂ | Pyridinyl | Z₁: F (ortho) |
| CF₂ | Pyrazinyl | NH—CH₂ | Pyridinyl | Z₁: F (para) |
| CF₂ | Pyrazinyl | NH—CH₂ | Pyridinyl | Z₁: Cl (meta) |
| CF₂ | Pyrazinyl | NH—CH₂ | Pyridinyl | Z₁: Cl (para) |
| CF₂ | Pyrazinyl | NH—CH₂ | Pyridinyl | Z₁: Cl (para) Z₂: Cl (meta) |
| CF₂ | Pyrazinyl | NH—CH₂ | Pyridinyl | Z₁: F (para) Z₂: Cl (meta) |
| CF₂ | Pyrazinyl | NH—CH₂ | Pyridinyl | Z₁: Cl (para) Z₂: F (meta) |
| CF₂ | Pyrazinyl | NH—CH₂ | Pyridinyl | Z₁: CH₃ (para) |
| CF₂ | Pyrazinyl | NH—CH₂ | Pyridinyl | Z₁: CH₃ (meta) |
| CF₂ | Pyrazinyl | NH—CH₂ | Pyridinyl | Z₁: CH₃ (ortho) |
| CF₂ | Pyrazinyl | NH—CH₂ | Pyridinyl | Z₁: CH₂—CH₃ (para) |
| CF₂ | Pyrazinyl | NH—CH₂ | Pyridinyl | Z₁: CH₂—CH₃ (meta) |
| CF₂ | Pyrazinyl | NH—CH₂ | Pyridinyl | Z₁: CH₂—CH₃ (ortho) |
| CF₂ | Pyrazinyl | NH—CH₂ | Pyridinyl | Z₁: CH₂—CH₂—CH₃ or iPr (para) |
| CF₂ | Pyrazinyl | NH—CH₂ | Pyridinyl | Z₁: CH₂—CH₂—CH₃ or iPr (meta) |
| CF₂ | Pyrazinyl | NH—CH₂ | Pyridinyl | Z₁: CH₂—CH₂—CH₃ or iPr (ortho) |
| CF₂ | Pyrazinyl | NH—CH₂ | Pyridinyl | Z₁: CH₂F (para) |
| CF₂ | Pyrazinyl | NH—CH₂ | Pyridinyl | Z₁: CH₂F (meta) |
| CF₂ | Pyrazinyl | NH—CH₂ | Pyridinyl | Z₁: CH₂F (ortho) |
| CF₂ | Pyrazinyl | NH—CH₂ | Pyridinyl | Z₁: CHF₂ (para) |
| CF₂ | Pyrazinyl | NH—CH₂ | Pyridinyl | Z₁: CHF₂ (meta) |
| CF₂ | Pyrazinyl | NH—CH₂ | Pyridinyl | Z₁: CHF₂ (ortho) |
| CF₂ | Pyrazinyl | NH—CH₂ | Pyridinyl | Z₁: CF₃ (para) |
| CF₂ | Pyrazinyl | NH—CH₂ | Pyridinyl | Z₁: CF₃ (meta) |
| CF₂ | Pyrazinyl | NH—CH₂ | Pyridinyl | Z₁: CF₃ (ortho) |
| CF₂ | Pyrazinyl | NH—CH₂ | Pyridinyl | Z₁: CH₂—CH₂F (para) |
| CF₂ | Pyrazinyl | NH—CH₂ | Pyridinyl | Z₁: CH₂—CH₂F (meta) |
| CF₂ | Pyrazinyl | NH—CH₂ | Pyridinyl | Z₁: CH₂—CH₂F (ortho) |
| CF₂ | Pyrazinyl | NH—CH₂ | Pyridinyl | Z₁: CH₂—CHF₂ (para) |
| CF₂ | Pyrazinyl | NH—CH₂ | Pyridinyl | Z₁: CH₂—CHF₂ (meta) |
| CF₂ | Pyrazinyl | NH—CH₂ | Pyridinyl | Z₁: CH₂—CHF₂ (ortho) |
| CF₂ | Pyrazinyl | NH—CH₂ | Pyridinyl | Z₁: CH₂—CF₃ (para) |

TABLE 2-continued $$L^1-C^1-L^2-C^2-Z_p$$

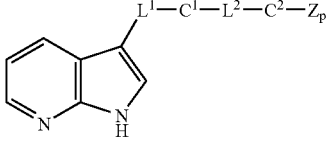

| L¹ | C¹ | L² | C² | Z |
|---|---|---|---|---|
| CF₂ | Pyrazinyl | NH—CH₂ | Pyridinyl | Z₁: CH₂—CF₃ (meta) |
| CF₂ | Pyrazinyl | NH—CH₂ | Pyridinyl | Z₁: CH₂—CF₃ (ortho) |
| CF₂ | Pyrazinyl | NH—CH₂ | Pyrimidinyl | None |
| CF₂ | Pyrazinyl | NH—CH₂ | Pyrimidinyl | Z₁: F (para) |
| CF₂ | Pyrazinyl | NH—CH₂ | Pyrimidinyl | Z₁: F (meta) |
| CF₂ | Pyrazinyl | NH—CH₂ | Pyrimidinyl | Z₁: F (ortho) |
| CF₂ | Pyrazinyl | NH—CH₂ | Pyrimidinyl | Z₁: F (para)<br>Z₂: F (meta) |
| CF₂ | Pyrazinyl | NH—CH₂ | Pyrimidinyl | Z₁: Cl (meta) |
| CF₂ | Pyrazinyl | NH—CH₂ | Pyrimidinyl | Z₁: Cl (para) |
| CF₂ | Pyrazinyl | NH—CH₂ | Pyrimidinyl | Z₁: Cl (para)<br>Z₂: Cl (meta) |
| CF₂ | Pyrazinyl | NH—CH₂ | Pyrimidinyl | Z₁: F (para)<br>Z₂: Cl (meta) |
| CF₂ | Pyrazinyl | NH—CH₂ | Pyrimidinyl | Z₁: Cl (para)<br>Z₂: F (meta) |
| CF₂ | Pyrazinyl | NH—CH₂ | Pyrimidinyl | Z₁: CH₃ (para) |
| CF₂ | Pyrazinyl | NH—CH₂ | Pyrimidinyl | Z₁: CH₃ (meta) |
| CF₂ | Pyrazinyl | NH—CH₂ | Pyrimidinyl | Z₁: CH₃ (ortho) |
| CF₂ | Pyrazinyl | NH—CH₂ | Pyrimidinyl | Z₁: CH₂—CH₃ (para) |
| CF₂ | Pyrazinyl | NH—CH₂ | Pyrimidinyl | Z₁: CH₂—CH₃ (meta) |
| CF₂ | Pyrazinyl | NH—CH₂ | Pyrimidinyl | Z₁: CH₂—CH₃ (ortho) |
| CF₂ | Pyrazinyl | NH—CH₂ | Pyrimidinyl | Z₁: CH₂—CH₂—CH₃ or iPr (para) |
| CF₂ | Pyrazinyl | NH—CH₂ | Pyrimidinyl | Z₁: CH₂—CH₂—CH₃ or iPr (meta) |
| CF₂ | Pyrazinyl | NH—CH₂ | Pyrimidinyl | Z₁: CH₂—CH₂—CH₃ or iPr (ortho) |
| CF₂ | Pyrazinyl | NH—CH₂ | Pyrimidinyl | Z₁: CH₂F (para) |
| CF₂ | Pyrazinyl | NH—CH₂ | Pyrimidinyl | Z₁: CH₂F (meta) |
| CF₂ | Pyrazinyl | NH—CH₂ | Pyrimidinyl | Z₁: CH₂F (ortho) |
| CF₂ | Pyrazinyl | NH—CH₂ | Pyrimidinyl | Z₁: CHF₂ (para) |
| CF₂ | Pyrazinyl | NH—CH₂ | Pyrimidinyl | Z₁: CHF₂ (meta) |
| CF₂ | Pyrazinyl | NH—CH₂ | Pyrimidinyl | Z₁: CHF₂ (ortho) |
| CF₂ | Pyrazinyl | NH—CH₂ | Pyrimidinyl | Z₁: CF₃ (para) |
| CF₂ | Pyrazinyl | NH—CH₂ | Pyrimidinyl | Z₁: CF₃ (meta) |
| CF₂ | Pyrazinyl | NH—CH₂ | Pyrimidinyl | Z₁: CF₃ (ortho) |
| CF₂ | Pyrazinyl | NH—CH₂ | Pyrimidinyl | Z₁: CH₂—CH₂F (para) |
| CF₂ | Pyrazinyl | NH—CH₂ | Pyrimidinyl | Z₁: CH₂—CH₂F (meta) |
| CF₂ | Pyrazinyl | NH—CH₂ | Pyrimidinyl | Z₁: CH₂—CH₂F (ortho) |
| CF₂ | Pyrazinyl | NH—CH₂ | Pyrimidinyl | Z₁: CH₂—CHF₂ (para) |
| CF₂ | Pyrazinyl | NH—CH₂ | Pyrimidinyl | Z₁: CH₂—CHF₂ (meta) |
| CF₂ | Pyrazinyl | NH—CH₂ | Pyrimidinyl | Z₁: CH₂—CHF₂ (ortho) |
| CF₂ | Pyrazinyl | NH—CH₂ | Pyrimidinyl | Z₁: CH₂—CF₃ (para) |
| CF₂ | Pyrazinyl | NH—CH₂ | Pyrimidinyl | Z₁: CH₂—CF₃ (meta) |
| CF₂ | Pyrazinyl | NH—CH₂ | Pyrimidinyl | Z₁: CH₂—CF₃ (ortho) |
| CF₂ | Pyrazinyl | NH—CH₂ | Pyrazinyl | None |
| CF₂ | Pyrazinyl | NH—CH₂ | Pyrazinyl | Z₁: F (para) |
| CF₂ | Pyrazinyl | NH—CH₂ | Pyrazinyl | Z₁: F (meta) |
| CF₂ | Pyrazinyl | NH—CH₂ | Pyrazinyl | Z₁: F (ortho) |
| CF₂ | Pyrazinyl | NH—CH₂ | Pyrazinyl | Z₁: F (para)<br>Z₂: F (meta) |
| CF₂ | Pyrazinyl | NH—CH₂ | Pyrazinyl | Z₁: Cl (meta) |
| CF₂ | Pyrazinyl | NH—CH₂ | Pyrazinyl | Z₁: Cl (para) |
| CF₂ | Pyrazinyl | NH—CH₂ | Pyrazinyl | Z₁: Cl (para)<br>Z₂: Cl (meta) |
| CF₂ | Pyrazinyl | NH—CH₂ | Pyrazinyl | Z₁: F (para)<br>Z₂: Cl (meta) |
| CF₂ | Pyrazinyl | NH—CH₂ | Pyrazinyl | Z₁: Cl (para)<br>Z₂: F (meta) |
| CF₂ | Pyrazinyl | NH—CH₂ | Pyrazinyl | Z₁: CH₃ (para) |
| CF₂ | Pyrazinyl | NH—CH₂ | Pyrazinyl | Z₁: CH₃ (meta) |
| CF₂ | Pyrazinyl | NH—CH₂ | Pyrazinyl | Z₁: CH₃ (ortho) |
| CF₂ | Pyrazinyl | NH—CH₂ | Pyrazinyl | Z₁: CH₂—CH₃ (para) |
| CF₂ | Pyrazinyl | NH—CH₂ | Pyrazinyl | Z₁: CH₂—CH₃ (meta) |
| CF₂ | Pyrazinyl | NH—CH₂ | Pyrazinyl | Z₁: CH₂—CH₃ (ortho) |
| CF₂ | Pyrazinyl | NH—CH₂ | Pyrazinyl | Z₁: CH₂—CH₂—CH₃ or iPr (para) |

TABLE 2-continued

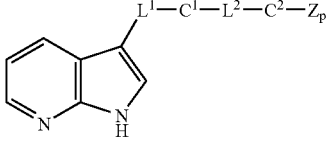

| L¹ | C¹ | L² | C² | Z |
|---|---|---|---|---|
| CF₂ | Pyrazinyl | NH—CH₂ | Pyrazinyl | Z₁: CH₂—CH₂—CH₃ or iPr (meta) |
| CF₂ | Pyrazinyl | NH—CH₂ | Pyrazinyl | Z₁: CH₂—CH₂—CH₃ or iPr (ortho) |
| CF₂ | Pyrazinyl | NH—CH₂ | Pyrazinyl | Z₁: CH₂F (para) |
| CF₂ | Pyrazinyl | NH—CH₂ | Pyrazinyl | Z₁: CH₂F (meta) |
| CF₂ | Pyrazinyl | NH—CH₂ | Pyrazinyl | Z₁: CH₂F (ortho) |
| CF₂ | Pyrazinyl | NH—CH₂ | Pyrazinyl | Z₁: CHF₂ (para) |
| CF₂ | Pyrazinyl | NH—CH₂ | Pyrazinyl | Z₁: CHF₂ (meta) |
| CF₂ | Pyrazinyl | NH—CH₂ | Pyrazinyl | Z₁: CHF₂ (ortho) |
| CF₂ | Pyrazinyl | NH—CH₂ | Pyrazinyl | Z₁: CF₃ (para) |
| CF₂ | Pyrazinyl | NH—CH₂ | Pyrazinyl | Z₁: CF₃ (meta) |
| CF₂ | Pyrazinyl | NH—CH₂ | Pyrazinyl | Z₁: CF₃ (ortho) |
| CF₂ | Pyrazinyl | NH—CH₂ | Pyrazinyl | Z₁: CH₂—CH₂F (para) |
| CF₂ | Pyrazinyl | NH—CH₂ | Pyrazinyl | Z₁: CH₂—CH₂F (meta) |
| CF₂ | Pyrazinyl | NH—CH₂ | Pyrazinyl | Z₁: CH₂—CH₂F (ortho) |
| CF₂ | Pyrazinyl | NH—CH₂ | Pyrazinyl | Z₁: CH₂—CHF₂ (para) |
| CF₂ | Pyrazinyl | NH—CH₂ | Pyrazinyl | Z₁: CH₂—CHF₂ (meta) |
| CF₂ | Pyrazinyl | NH—CH₂ | Pyrazinyl | Z₁: CH₂—CHF₂ (ortho) |
| CF₂ | Pyrazinyl | NH—CH₂ | Pyrazinyl | Z₁: CH₂—CF₃ (para) |
| CF₂ | Pyrazinyl | NH—CH₂ | Pyrazinyl | Z₁: CH₂—CF₃ (meta) |
| CF₂ | Pyrazinyl | NH—CH₂ | Pyrazinyl | Z₁: CH₂—CF₃ (ortho) |
| CF₂ | Pyrazinyl | NH—CH₂ | Pyrrolyl | None |
| CF₂ | Pyrazinyl | NH—CH₂ | Pyrrolyl | Z₁: F (2) |
| CF₂ | Pyrazinyl | NH—CH₂ | Pyrrolyl | Z₁: F (3) |
| CF₂ | Pyrazinyl | NH—CH₂ | Pyrrolyl | Z₁: F (2) Z₂: F (3) |
| CF₂ | Pyrazinyl | NH—CH₂ | Pyrrolyl | Z₁: Cl (2) |
| CF₂ | Pyrazinyl | NH—CH₂ | Pyrrolyl | Z₁: Cl (3) |
| CF₂ | Pyrazinyl | NH—CH₂ | Pyrrolyl | Z₁: Cl (2) Z₂: Cl (3) |
| CF₂ | Pyrazinyl | NH—CH₂ | Pyrrolyl | Z₁: F (2) Z₂: Cl (3) |
| CF₂ | Pyrazinyl | NH—CH₂ | Pyrrolyl | Z₁: Cl (2) Z₂: F (3) |
| CF₂ | Pyrazinyl | NH—CH₂ | Pyrrolyl | Z₁: CH₃ (2) |
| CF₂ | Pyrazinyl | NH—CH₂ | Pyrrolyl | Z₁: CH₃ (3) |
| CF₂ | Pyrazinyl | NH—CH₂ | Pyrrolyl | Z₁: CH₂—CH₃ (2) |
| CF₂ | Pyrazinyl | NH—CH₂ | Pyrrolyl | Z₁: CH₂—CH₃ (3) |
| CF₂ | Pyrazinyl | NH—CH₂ | Pyrrolyl | Z₁: CH₂—CH₂—CH₃ or iPr (2) |
| CF₂ | Pyrazinyl | NH—CH₂ | Pyrrolyl | Z₁: CH₂—CH₂—CH₃ or iPr (3) |
| CF₂ | Pyrazinyl | NH—CH₂ | Pyrrolyl | Z₁: CH₂F (2) |
| CF₂ | Pyrazinyl | NH—CH₂ | Pyrrolyl | Z₁: CH₂F (3) |
| CF₂ | Pyrazinyl | NH—CH₂ | Pyrrolyl | Z₁: CHLF₂ (2) |
| CF₂ | Pyrazinyl | NH—CH₂ | Pyrrolyl | Z₁: CHF₂ (3) |
| CF₂ | Pyrazinyl | NH—CH₂ | Pyrrolyl | Z₁: CF₃ (2) |
| CF₂ | Pyrazinyl | NH—CH₂ | Pyrrolyl | Z₁: CF₃ (3) |
| CF₂ | Pyrazinyl | NH—CH₂ | Pyrrolyl | Z₁: CH₂—CH₂F (2) |
| CF₂ | Pyrazinyl | NH—CH₂ | Pyrrolyl | Z₁: CH₂—CH₂F (3) |
| CF₂ | Pyrazinyl | NH—CH₂ | Pyrrolyl | Z₁: CH₂—CHF₂ (2) |
| CF₂ | Pyrazinyl | NH—CH₂ | Pyrrolyl | Z₁: CH₂—CHF₂ (3) |
| CF₂ | Pyrazinyl | NH—CH₂ | Pyrrolyl | Z₁: CH₂—CF₃ (2) |
| CF₂ | Pyrazinyl | NH—CH₂ | Pyrrolyl | Z₁: CH₂—CF₃ (3) |
| CF₂ | Pyrazinyl | NH—CH₂ | Imidazolyl | None |
| CF₂ | Pyrazinyl | NH—CH₂ | Imidazolyl | Z₁: F (2) |
| CF₂ | Pyrazinyl | NH—CH₂ | Imidazolyl | Z₁: F (3) |
| CF₂ | Pyrazinyl | NH—CH₂ | Imidazolyl | Z₁: F (2) Z₂: F (3) |
| CF₂ | Pyrazinyl | NH—CH₂ | Imidazolyl | Z₁: Cl (2) |
| CF₂ | Pyrazinyl | NH—CH₂ | Imidazolyl | Z₁: Cl (3) |
| CF₂ | Pyrazinyl | NH—CH₂ | Imidazolyl | Z₁: Cl (2) Z₂: Cl (3) |
| CF₂ | Pyrazinyl | NH—CH₂ | Imidazolyl | Z₁: F (2) Z₂: Cl (3) |
| CF₂ | Pyrazinyl | NH—CH₂ | Imidazolyl | Z₁: Cl (2) Z₂: F (3) |
| CF₂ | Pyrazinyl | NH—CH₂ | Imidazolyl | Z₁: CH₃ (2) |
| CF₂ | Pyrazinyl | NH—CH₂ | Imidazolyl | Z₁: CH₃ (3) |
| CF₂ | Pyrazinyl | NH—CH₂ | Imidazolyl | Z₁: CH₂—CH₃ (2) |

TABLE 2-continued

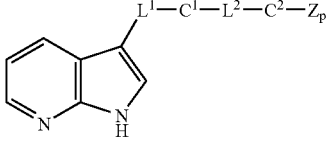

| L¹ | C¹ | L² | C² | Z |
|---|---|---|---|---|
| $CF_2$ | Pyrazinyl | NH—$CH_2$ | Imidazolyl | $Z_1$: $CH_2$—$CH_3$ (3) |
| $CF_2$ | Pyrazinyl | NH—$CH_2$ | Imidazolyl | $Z_1$: $CH_2$—$CH_2$—$CH_3$ or iPr (2) |
| $CF_2$ | Pyrazinyl | NH—$CH_2$ | Imidazolyl | $Z_1$: $CH_2$—$CH_2$—$CH_3$ or iPr (3) |
| $CF_2$ | Pyrazinyl | NH—$CH_2$ | Imidazolyl | $Z_1$: $CH_2F$ (2) |
| $CF_2$ | Pyrazinyl | NH—$CH_2$ | Imidazolyl | $Z_1$: $CH_2F$ (3) |
| $CF_2$ | Pyrazinyl | NH—$CH_2$ | Imidazolyl | $Z_1$: $CHF_2$ (2) |
| $CF_2$ | Pyrazinyl | NH—$CH_2$ | Imidazolyl | $Z_1$: $CHF_2$ (3) |
| $CF_2$ | Pyrazinyl | NH—$CH_2$ | Imidazolyl | $Z_1$: $CF_3$ (2) |
| $CF_2$ | Pyrazinyl | NH—$CH_2$ | Imidazolyl | $Z_1$: $CF_3$ (3) |
| $CF_2$ | Pyrazinyl | NH—$CH_2$ | Imidazolyl | $Z_1$: $CH_2$—$CH_2F$ (2) |
| $CF_2$ | Pyrazinyl | NH—$CH_2$ | Imidazolyl | $Z_1$: $CH_2$—$CH_2F$ (3) |
| $CF_2$ | Pyrazinyl | NH—$CH_2$ | Imidazolyl | $Z_1$: $CH_2$—$CHF_2$ (2) |
| $CF_2$ | Pyrazinyl | NH—$CH_2$ | Imidazolyl | $Z_1$: $CH_2$—$CHF_2$ (3) |
| $CF_2$ | Pyrazinyl | NH—$CH_2$ | Imidazolyl | $Z_1$: $CH_2$—$CF_3$ (2) |
| $CF_2$ | Pyrazinyl | NH—$CH_2$ | Imidazolyl | $Z_1$: $CH_2$—$CF_3$ (3) |
| $CF_2$ | Pyrazinyl | NH—$CH_2$ | Furanyl | None |
| $CF_2$ | Pyrazinyl | NH—$CH_2$ | Furanyl | $Z_1$: F (2) |
| $CF_2$ | Pyrazinyl | NH—$CH_2$ | Furanyl | $Z_1$: F (3) |
| $CF_2$ | Pyrazinyl | NH—$CH_2$ | Furanyl | $Z_1$: Cl (2) |
| $CF_2$ | Pyrazinyl | NH—$CH_2$ | Furanyl | $Z_1$: Cl (3) |
| $CF_2$ | Pyrazinyl | NH—$CH_2$ | Furanyl | $Z_1$: Cl (2) $Z_2$: Cl (3) |
| $CF_2$ | Pyrazinyl | NH—$CH_2$ | Furanyl | $Z_1$: Cl (2) $Z_2$: Cl (3) |
| $CF_2$ | Pyrazinyl | NH—$CH_2$ | Furanyl | $Z_1$: Cl (2) $Z_2$: F (3) |
| $CF_2$ | Pyrazinyl | NH—$CH_2$ | Furanyl | $Z_1$: $CH_3$ (2) |
| $CF_2$ | Pyrazinyl | NH—$CH_2$ | Furanyl | $Z_1$: $CH_3$ (3) |
| $CF_2$ | Pyrazinyl | NH—$CH_2$ | Furanyl | $Z_1$: $CH_2$—$CH_3$ (2) |
| $CF_2$ | Pyrazinyl | NH—$CH_2$ | Furanyl | $Z_1$: $CH_2$—$CH_3$ (3) |
| $CF_2$ | Pyrazinyl | NH—$CH_2$ | Furanyl | $Z_1$: $CH_2$—$CH_2$—$CH_3$ or iPr (2) |
| $CF_2$ | Pyrazinyl | NH—$CH_2$ | Furanyl | $Z_1$: $CH_2$—$CH_2$—$CH_3$ or iPr (3) |
| $CF_2$ | Pyrazinyl | NH—$CH_2$ | Furanyl | $Z_1$: $CH_2F$ (2) |
| $CF_2$ | Pyrazinyl | NH—$CH_2$ | Furanyl | $Z_1$: $CH_2F$ (3) |
| $CF_2$ | Pyrazinyl | NH—$CH_2$ | Furanyl | $Z_1$: $CHF_2$ (2) |
| $CF_2$ | Pyrazinyl | NH—$CH_2$ | Furanyl | $Z_1$: $CHF_2$ (3) |
| $CF_2$ | Pyrazinyl | NH—$CH_2$ | Furanyl | $Z_1$: $CF_3$ (2) |
| $CF_2$ | Pyrazinyl | NH—$CH_2$ | Furanyl | $Z_1$: $CF_3$ (3) |
| $CF_2$ | Pyrazinyl | NH—$CH_2$ | Furanyl | $Z_1$: $CH_2$—$CH_2F$ (2) |
| $CF_2$ | Pyrazinyl | NH—$CH_2$ | Furanyl | $Z_1$: $CH_2$—$CH_2F$ (3) |
| $CF_2$ | Pyrazinyl | NH—$CH_2$ | Furanyl | $Z_1$: $CH_2$—$CHF_2$ (2) |
| $CF_2$ | Pyrazinyl | NH—$CH_2$ | Furanyl | $Z_1$: $CH_2$—$CHF_2$ (3) |
| $CF_2$ | Pyrazinyl | NH—$CH_2$ | Furanyl | $Z_1$: $CH_2$—$CF_3$ (2) |
| $CF_2$ | Pyrazinyl | NH—$CH_2$ | Furanyl | $Z_1$: $CH_2$—$CF_3$ (3) |
| $CF_2$ | Pyrazinyl | NH—$CH_2$ | Oxazolyl | None |
| $CF_2$ | Pyrazinyl | NH—$CH_2$ | Oxazolyl | $Z_1$: F (2) |
| $CF_2$ | Pyrazinyl | NH—$CH_2$ | Oxazolyl | $Z_1$: F (3) |
| $CF_2$ | Pyrazinyl | NH—$CH_2$ | Oxazolyl | $Z_1$: F (2) $Z_2$: F (3) |
| $CF_2$ | Pyrazinyl | NH—$CH_2$ | Oxazolyl | $Z_1$: Cl (2) |
| $CF_2$ | Pyrazinyl | NH—$CH_2$ | Oxazolyl | $Z_1$: Cl (3) |
| $CF_2$ | Pyrazinyl | NH—$CH_2$ | Oxazolyl | $Z_1$: Cl (2) $Z_2$: Cl (3) |
| $CF_2$ | Pyrazinyl | NH—$CH_2$ | Oxazolyl | $Z_1$: F (2) $Z_2$: Cl (3) |
| $CF_2$ | Pyrazinyl | NH—$CH_2$ | Oxazolyl | $Z_1$: Cl (2) $Z_2$: F (3) |
| $CF_2$ | Pyrazinyl | NH—$CH_2$ | Oxazolyl | $Z_1$: $CH_3$ (2) |
| $CF_2$ | Pyrazinyl | NH—$CH_2$ | Oxazolyl | $Z_1$: $CH_3$ (3) |
| $CF_2$ | Pyrazinyl | NH—$CH_2$ | Oxazolyl | $Z_1$: $CH_2$—$CH_3$ (2) |
| $CF_2$ | Pyrazinyl | NH—$CH_2$ | Oxazolyl | $Z_1$: $CH_2$—$CH_3$ (3) |
| $CF_2$ | Pyrazinyl | NH—$CH_2$ | Oxazolyl | $Z_1$: $CH_2$—$CH_2$—$CH_3$ or iPr (2) |
| $CF_2$ | Pyrazinyl | NH—$CH_2$ | Oxazolyl | $Z_1$: $CH_2$—$CH_2$—$CH_3$ or iPr (3) |
| $CF_2$ | Pyrazinyl | NH—$CH_2$ | Oxazolyl | $Z_1$: $CH_2F$ (2) |
| $CF_2$ | Pyrazinyl | NH—$CH_2$ | Oxazolyl | $Z_1$: $CH_2F$ (3) |
| $CF_2$ | Pyrazinyl | NH—$CH_2$ | Oxazolyl | $Z_1$: $CHF_2$ (2) |
| $CF_2$ | Pyrazinyl | NH—$CH_2$ | Oxazolyl | $Z_1$: $CHF_2$ (3) |
| $CF_2$ | Pyrazinyl | NH—$CH_2$ | Oxazolyl | $Z_1$: $CF_3$ (2) |
| $CF_2$ | Pyrazinyl | NH—$CH_2$ | Oxazolyl | $Z_1$: $CF_3$ (3) |

TABLE 2-continued $$L^1-C^1-L^2-C^2-Z_p$$

[7-azaindole structure with L¹–C¹–L²–C²–Zp substituent at position 3]

| L¹ | C¹ | L² | C² | Z |
|---|---|---|---|---|
| CF₂ | Pyrazinyl | NH—CH₂ | Oxazolyl | Z₁: CH₂—CH₂F (2) |
| CF₂ | Pyrazinyl | NH—CH₂ | Oxazolyl | Z₁: CH₂—CH₂F (3) |
| CF₂ | Pyrazinyl | NH—CH₂ | Oxazolyl | Z₁: CH₂—CHF₂ (2) |
| CF₂ | Pyrazinyl | NH—CH₂ | Oxazolyl | Z₁: CH₂—CHF₂ (3) |
| CF₂ | Pyrazinyl | NH—CH₂ | Oxazolyl | Z₁: CH₂—CF₃ (2) |
| CF₂ | Pyrazinyl | NH—CH₂ | Oxazolyl | Z₁: CH₂—CF₃ (3) |
| CF₂ | Pyrazinyl | NH—CH₂ | Thiophenyl | None |
| CF₂ | Pyrazinyl | NH—CH₂ | Thiophenyl | Z₁: F (2) |
| CF₂ | Pyrazinyl | NH—CH₂ | Thiophenyl | Z₁: F (3) |
| CF₂ | Pyrazinyl | NH—CH₂ | Thiophenyl | Z₁: F (2) Z₂: F (3) |
| CF₂ | Pyrazinyl | NH—CH₂ | Thiophenyl | Z₁: Cl (2) |
| CF₂ | Pyrazinyl | NH—CH₂ | Thiophenyl | Z₁: Cl (3) |
| CF₂ | Pyrazinyl | NH—CH₂ | Thiophenyl | Z₁: Cl (2) Z₂: Cl (3) |
| CF₂ | Pyrazinyl | NH—CH₂ | Thiophenyl | Z₁: F (2) Z₂: Cl (3) |
| CF₂ | Pyrazinyl | NH—CH₂ | Thiophenyl | Z₁: Cl (2) Z₂: F (3) |
| CF₂ | Pyrazinyl | NH—CH₂ | Thiophenyl | Z₁: CH₃ (2) |
| CF₂ | Pyrazinyl | NH—CH₂ | Thiophenyl | Z₁: CH₃ (3) |
| CF₂ | Pyrazinyl | NH—CH₂ | Thiophenyl | Z₁: CH₂—CH₃ (2) |
| CF₂ | Pyrazinyl | NH—CH₂ | Thiophenyl | Z₁: CH₂—CH₃ (3) |
| CF₂ | Pyrazinyl | NH—CH₂ | Thiophenyl | Z₁: CH₂—CH₂—CH₃ or iPr (2) |
| CF₂ | Pyrazinyl | NH—CH₂ | Thiophenyl | Z₁: CH₂—CH₂—CH₃ or iPr (3) |
| CF₂ | Pyrazinyl | NH—CH₂ | Thiophenyl | Z₁: CH₂F (2) |
| CF₂ | Pyrazinyl | NH—CH₂ | Thiophenyl | Z₁: CH₂F (3) |
| CF₂ | Pyrazinyl | NH—CH₂ | Thiophenyl | Z₁: CHF₂ (2) |
| CF₂ | Pyrazinyl | NH—CH₂ | Thiophenyl | Z₂: CHF₂ (3) |
| CF₂ | Pyrazinyl | NH—CH₂ | Thiophenyl | Z₁: CF₃ (2) |
| CF₂ | Pyrazinyl | NH—CH₂ | Thiophenyl | Z₁: CF₃ (3) |
| CF₂ | Pyrazinyl | NH—CH₂ | Thiophenyl | Z₁: CH₂—CH₂F (2) |
| CF₂ | Pyrazinyl | NH—CH₂ | Thiophenyl | Z₁: CH₂—CH₂F (3) |
| CF₂ | Pyrazinyl | NH—CH₂ | Thiophenyl | Z₁: CH₂—CHF₂ (2) |
| CF₂ | Pyrazinyl | NH—CH₂ | Thiophenyl | Z₁: CH₂—CHF₂ (3) |
| CF₂ | Pyrazinyl | NH—CH₂ | Thiophenyl | Z₁: CH₂—CF₃ (2) |
| CF₂ | Pyrazinyl | NH—CH₂ | Thiophenyl | Z₁: CH₂—CF₃ (3) |
| CF₂ | Pyrazinyl | NH—CH₂ | Thiazolyl | None |
| CF₂ | Pyrazinyl | NH—CH₂ | Thiazolyl | Z₁: F (2) |
| CF₂ | Pyrazinyl | NH—CH₂ | Thiazolyl | Z₁: F (3) |
| CF₂ | Pyrazinyl | NH—CH₂ | Thiazolyl | Z₁: F (2) Z₂: F (3) |
| CF₂ | Pyrazinyl | NH—CH₂ | Thiazolyl | Z₁: Cl (2) |
| CF₂ | Pyrazinyl | NH—CH₂ | Thiazolyl | Z₁: Cl (3) |
| CF₂ | Pyrazinyl | NH—CH₂ | Thiazolyl | Z₁: Cl (2) Z₂: Cl (3) |
| CF₂ | Pyrazinyl | NH—CH₂ | Thiazolyl | Z₁: F (2) Z₂: Cl (3) |
| CF₂ | Pyrazinyl | NH—CH₂ | Thiazolyl | Z₁: Cl (2) Z₂: F (3) |
| CF₂ | Pyrazinyl | NH—CH₂ | Thiazolyl | Z₁: CH₃ (2) |
| CF₂ | Pyrazinyl | NH—CH₂ | Thiazolyl | Z₁: CH₃ (3) |
| CF₂ | Pyrazinyl | NH—CH₂ | Thiazolyl | Z₁: CH₂—CH₃ (2) |
| CF₂ | Pyrazinyl | NH—CH₂ | Thiazolyl | Z₁: CH₂—CH₃ (3) |
| CF₂ | Pyrazinyl | NH—CH₂ | Thiazolyl | Z₁: CH₂—CH₂—CH₃ or iPr (2) |
| CF₂ | Pyrazinyl | NH—CH₂ | Thiazolyl | Z₁: CH₂—CH₂—CH₃ or iPr (3) |
| CF₂ | Pyrazinyl | NH—CH₂ | Thiazolyl | Z₁: CH₂F (2) |
| CF₂ | Pyrazinyl | NH—CH₂ | Thiazolyl | Z₁: CH₂F (3) |
| CF₂ | Pyrazinyl | NH—CH₂ | Thiazolyl | Z₁: CHF₂ (2) |
| CF₂ | Pyrazinyl | NH—CH₂ | Thiazolyl | Z₁: CHF₂ (3) |
| CF₂ | Pyrazinyl | NH—CH₂ | Thiazolyl | Z₁: CF₃ (2) |
| CF₂ | Pyrazinyl | NH—CH₂ | Thiazolyl | Z₁: CF₃ (3) |
| CF₂ | Pyrazinyl | NH—CH₂ | Thiazolyl | Z₁: CH₂—CH₂F (2) |
| CF₂ | Pyrazinyl | NH—CH₂ | Thiazolyl | Z₁: CH₂—CH₂F (3) |
| CF₂ | Pyrazinyl | NH—CH₂ | Thiazolyl | Z₁: CH₂—CHF₂ (2) |
| CF₂ | Pyrazinyl | NH—CH₂ | Thiazolyl | Z₁: CH₂—CHF₂ (3) |
| CF₂ | Pyrazinyl | NH—CH₂ | Thiazolyl | Z₁: CH₂—CF₃ (2) |
| CF₂ | Pyrazinyl | NH—CH₂ | Thiazolyl | Z₁: CH₂—CF₃ (3) |
| CF₂ | Pyrazinyl | NH—C(O) | Phenyl | None |

TABLE 2-continued

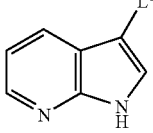

| L$^1$ | C$^1$ | L$^2$ | C$^2$ | Z |
|---|---|---|---|---|
| CF$_2$ | Pyrazinyl | NH—C(O) | Phenyl | Z$_1$: F (para) |
| CF$_2$ | Pyrazinyl | NH—C(O) | phenyl | Z$_1$: F (meta) |
| CF$_2$ | Pyrazinyl | NH—C(O) | phenyl | Z$_1$: F (ortho) |
| CF$_2$ | Pyrazinyl | NH—C(O) | phenyl | Z$_1$: F (para) Z$_2$: F (meta) |
| CF$_2$ | Pyrazinyl | NH—C(O) | Phenyl | Z$_1$: Cl (meta) |
| CF$_2$ | Pyrazinyl | NH—C(O) | Phenyl | Z$_1$: Cl (para) |
| CF$_2$ | Pyrazinyl | NH—C(O) | Phenyl | Z$_1$: Cl (para) Z$_2$: Cl (meta) |
| CF$_2$ | Pyrazinyl | NH—C(O) | Phenyl | Z$_1$: F (para) Z$_2$: Cl (meta) |
| CF$_2$ | Pyrazinyl | NH—C(O) | Phenyl | Z$_1$: Cl (para) Z$_2$: F (meta) |
| CF$_2$ | Pyrazinyl | NH—C(O) | Phenyl | Z$_1$: CH$_3$ (para) |
| CF$_2$ | Pyrazinyl | NH—C(O) | Phenyl | Z$_1$: CH$_3$ (meta) |
| CF$_2$ | Pyrazinyl | NH—C(O) | Phenyl | Z$_1$: CH$_3$ (ortho) |
| CF$_2$ | Pyrazinyl | NH—C(O) | Phenyl | Z$_1$: CH$_2$—CH$_3$ (para) |
| CF$_2$ | Pyrazinyl | NH—C(O) | Phenyl | Z$_1$: CH$_2$—CH$_3$ (meta) |
| CF$_2$ | Pyrazinyl | NH—C(O) | Phenyl | Z$_1$: CH$_2$—CH$_3$ (ortho) |
| CF$_2$ | Pyrazinyl | NH—C(O) | Phenyl | Z$_1$: CH$_2$—CH$_2$—CH$_3$ or iPr (para) |
| CF$_2$ | Pyrazinyl | NH—C(O) | Phenyl | Z$_1$: CH$_2$—CH$_2$—CH$_3$ or iPr (meta) |
| CF$_2$ | Pyrazinyl | NH—C(O) | Phenyl | Z$_1$: CH$_2$—CH$_2$—CH$_3$ or iPr (ortho) |
| CF$_2$ | Pyrazinyl | NH—C(O) | Phenyl | Z$_1$: CH$_2$F (para) |
| CF$_2$ | Pyrazinyl | NH—C(O) | Phenyl | Z$_1$: CH$_2$F (meta) |
| CF$_2$ | Pyrazinyl | NH—C(O) | Phenyl | Z$_1$: CH$_2$F (ortho) |
| CF$_2$ | Pyrazinyl | NH—C(O) | Phenyl | Z$_1$: CHF$_2$ (para) |
| CF$_2$ | Pyrazinyl | NH—C(O) | Phenyl | Z$_1$: CHF$_2$ (meta) |
| CF$_2$ | Pyrazinyl | NH—C(O) | Phenyl | Z$_1$: CHF$_2$ (ortho) |
| CF$_2$ | Pyrazinyl | NH—C(O) | Phenyl | Z$_1$: CF$_3$ (para) |
| CF$_2$ | Pyrazinyl | NH—C(O) | Phenyl | Z$_1$: CF$_3$ (meta) |
| CF$_2$ | Pyrazinyl | NH—C(O) | Phenyl | Z$_1$: CF$_3$ (ortho) |
| CF$_2$ | Pyrazinyl | NH—C(O) | Phenyl | Z$_1$: CH$_2$—CH$_2$F (para) |
| CF$_2$ | Pyrazinyl | NH—C(O) | Phenyl | Z$_1$: CH$_2$—CH$_2$F (meta) |
| CF$_2$ | Pyrazinyl | NH—C(O) | Phenyl | Z$_1$: CH$_2$—CH$_2$F (ortho) |
| CF$_2$ | Pyrazinyl | NH—C(O) | Phenyl | Z$_1$: CH$_2$—CHF$_2$ (para) |
| CF$_2$ | Pyrazinyl | NH—C(O) | Phenyl | Z$_1$: CH$_2$—CHF$_2$ (meta) |
| CF$_2$ | Pyrazinyl | NH—C(O) | Phenyl | Z$_1$: CH$_2$—CHF$_2$ (ortho) |
| CF$_2$ | Pyrazinyl | NH—C(O) | Phenyl | Z$_1$: CH$_2$—CF$_3$ (para) |
| CF$_2$ | Pyrazinyl | NH—C(O) | Phenyl | Z$_1$: CH$_2$—CF$_3$ (meta) |
| CF$_2$ | Pyrazinyl | NH—C(O) | Phenyl | Z$_1$: CH$_2$—CF$_3$ (ortho) |
| CF$_2$ | Pyrazinyl | NH—C(O) | Pyridinyl | None |
| CF$_2$ | Pyrazinyl | NH—C(O) | Pyridinyl | Z$_1$: F (para) |
| CF$_2$ | Pyrazinyl | NH—C(O) | Pyridinyl | Z$_1$: F (meta) |
| CF$_2$ | Pyrazinyl | NH—C(O) | Pyridinyl | Z$_1$: F (ortho) |
| CF$_2$ | Pyrazinyl | NH—C(O) | Pyridinyl | Z$_1$: F (para) Z$_2$: F (meta) |
| CF$_2$ | Pyrazinyl | NH—C(O) | Pyridinyl | Z$_1$: Cl (meta) |
| CF$_2$ | Pyrazinyl | NH—C(O) | Pyridinyl | Z$_1$: Cl (para) |
| CF$_2$ | Pyrazinyl | NH—C(O) | Pyridinyl | Z$_1$: Cl (para) Z$_2$: Cl (meta) |
| CF$_2$ | Pyrazinyl | NH—C(O) | Pyridinyl | Z$_1$: F (para) Z$_2$: Cl (meta) |
| CF$_2$ | Pyrazinyl | NH—C(O) | Pyridinyl | Z$_1$: Cl (para) Z$_2$: F (meta) |
| CF$_2$ | Pyrazinyl | NH—C(O) | Pyridinyl | Z$_1$: CH$_3$ (para) |
| CF$_2$ | Pyrazinyl | NH—C(O) | Pyridinyl | Z$_1$: CH$_3$ (meta) |
| CF$_2$ | Pyrazinyl | NH—C(O) | Pyridinyl | Z$_1$: CH$_3$ (ortho) |
| CF$_2$ | Pyrazinyl | NH—C(O) | Pyridinyl | Z$_1$: CH$_2$—CH$_3$ (para) |
| CF$_2$ | Pyrazinyl | NH—C(O) | Pyridinyl | Z$_1$: CH$_2$—CH$_3$ (meta) |
| CF$_2$ | Pyrazinyl | NH—C(O) | Pyridinyl | Z$_1$: CH$_2$—CH$_3$ (ortho) |
| CF$_2$ | Pyrazinyl | NH—C(O) | Pyridinyl | Z$_1$: CH$_2$—CH$_2$—CH$_3$ or iPr (para) |
| CF$_2$ | Pyrazinyl | NH—C(O) | Pyridinyl | Z$_1$: CH$_2$—CH$_2$—CH$_3$ or iPr (meta) |
| CF$_2$ | Pyrazinyl | NH—C(O) | Pyridinyl | Z$_1$: CH$_2$—CH$_2$—CH$_3$ or iPr (ortho) |

TABLE 2-continued

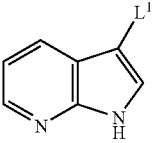

| L¹ | C¹ | L² | C² | Z |
|---|---|---|---|---|
| $CF_2$ | Pyrazinyl | NH—C(O) | Pyridinyl | $Z_1$: $CH_2F$ (para) |
| $CF_2$ | Pyrazinyl | NH—C(O) | Pyridinyl | $Z_1$: $CH_2F$ (meta) |
| $CF_2$ | Pyrazinyl | NH—C(O) | Pyridinyl | $Z_1$: $CH_2F$ (ortho) |
| $CF_2$ | Pyrazinyl | NH—C(O) | Pyridinyl | $Z_1$: $CHF_2$ (para) |
| $CF_2$ | Pyrazinyl | NH—C(O) | Pyridinyl | $Z_1$: $CHF_2$ (meta) |
| $CF_2$ | Pyrazinyl | NH—C(O) | Pyridinyl | $Z_1$: $CHF_2$ (ortho) |
| $CF_2$ | Pyrazinyl | NH—C(O) | Pyridinyl | $Z_1$: $CF_3$ (para) |
| $CF_2$ | Pyrazinyl | NH—C(O) | Pyridinyl | $Z_1$: $CF_3$ (meta) |
| $CF_2$ | Pyrazinyl | NH—C(O) | Pyridinyl | $Z_1$: $CF_3$ (ortho) |
| $CF_2$ | Pyrazinyl | NH—C(O) | Pyridinyl | $Z_1$: $CH_2$—$CH_2F$ (para) |
| $CF_2$ | Pyrazinyl | NH—C(O) | Pyridinyl | $Z_1$: $CH_2$—$CH_2F$ (meta) |
| $CF_2$ | Pyrazinyl | NH—C(O) | Pyridinyl | $Z_1$: $CH_2$—$CH_2F$ (ortho) |
| $CF_2$ | Pyrazinyl | NH—C(O) | Pyridinyl | $Z_1$: $CH_2$—$CHF_2$ (para) |
| $CF_2$ | Pyrazinyl | NH—C(O) | Pyridinyl | $Z_1$: $CH_2$—$CHF_2$ (meta) |
| $CF_2$ | Pyrazinyl | NH—C(O) | Pyridinyl | $Z_1$: $CH_2$—$CHF_2$ (ortho) |
| $CF_2$ | Pyrazinyl | NH—C(O) | Pyridinyl | $Z_1$: $CH_2$—$CF_3$ (para) |
| $CF_2$ | Pyrazinyl | NH—C(O) | Pyridinyl | $Z_1$: $CH_2$—$CF_3$ (meta) |
| $CF_2$ | Pyrazinyl | NH—C(O) | Pyridinyl | $Z_1$: $CH_2$—$CF_3$ (ortho) |
| $CF_2$ | Pyrazinyl | NH—C(O) | Pyrimidinyl | None |
| $CF_2$ | Pyrazinyl | NH—C(O) | Pyrimidinyl | $Z_1$: F (para) |
| $CF_2$ | Pyrazinyl | NH—C(O) | Pyrimidinyl | $Z_1$: F (meta) |
| $CF_2$ | Pyrazinyl | NH—C(O) | Pyrimidinyl | $Z_1$: F (ortho) |
| $CF_2$ | Pyrazinyl | NH—C(O) | Pyrimidinyl | $Z_1$: F (para)<br>$Z_2$: F (meta) |
| $CF_2$ | Pyrazinyl | NH—C(O) | Pyrimidinyl | $Z_1$: Cl (meta) |
| $CF_2$ | Pyrazinyl | NH—C(O) | Pyrimidinyl | $Z_1$: Cl (para) |
| $CF_2$ | Pyrazinyl | NH—C(O) | Pyrimidinyl | $Z_1$: Cl (para)<br>$Z_2$: Cl (meta) |
| $CF_2$ | Pyrazinyl | NH—C(O) | Pyrimidinyl | $Z_1$: F (para)<br>$Z_2$: Cl (meta) |
| $CF_2$ | Pyrazinyl | NH—C(O) | Pyrimidinyl | $Z_1$: Cl (para)<br>$Z_2$: F (meta) |
| $CF_2$ | Pyrazinyl | NH—C(O) | Pyrimidinyl | $Z_1$: $CH_3$ (para) |
| $CF_2$ | Pyrazinyl | NH—C(O) | Pyrimidinyl | $Z_1$: $CH_3$ (meta) |
| $CF_2$ | Pyrazinyl | NH—C(O) | Pyrimidinyl | $Z_1$: $CH_3$ (ortho) |
| $CF_2$ | Pyrazinyl | NH—C(O) | Pyrimidinyl | $Z_1$: $CH_2$—$CH_3$ (para) |
| $CF_2$ | Pyrazinyl | NH—C(O) | Pyrimidinyl | $Z_1$: $CH_2$—$CH_3$ (meta) |
| $CF_2$ | Pyrazinyl | NH—C(O) | Pyrimidinyl | $Z_1$: $CH_2$—$CH_3$ (ortho) |
| $CF_2$ | Pyrazinyl | NH—C(O) | Pyrimidinyl | $Z_1$: $CH_2$—$CH_2$—$CH_3$ or iPr (para) |
| $CF_2$ | Pyrazinyl | NH—C(O) | Pyrimidinyl | $Z_1$: $CH_2$—$CH_2$—$CH_3$ or iPr (meta) |
| $CF_2$ | Pyrazinyl | NH—C(O) | Pyrimidinyl | $Z_1$: $CH_2$—$CH_2$—$CH_3$ or iPr (ortho) |
| $CF_2$ | Pyrazinyl | NH—C(O) | Pyrimidinyl | $Z_1$: $CH_2F$ (para) |
| $CF_2$ | Pyrazinyl | NH—C(O) | Pyrimidinyl | $Z_1$: $CH_2F$ (meta) |
| $CF_2$ | Pyrazinyl | NH—C(O) | Pyrimidinyl | $Z_1$: $CH_2F$ (ortho) |
| $CF_2$ | Pyrazinyl | NH—C(O) | Pyrimidinyl | $Z_1$: $CHF_2$ (para) |
| $CF_2$ | Pyrazinyl | NH—C(O) | Pyrimidinyl | $Z_1$: $CHF_2$ (meta) |
| $CF_2$ | Pyrazinyl | NH—C(O) | Pyrimidinyl | $Z_1$: $CHF_2$ (ortho) |
| $CF_2$ | Pyrazinyl | NH—C(O) | Pyrimidinyl | $Z_1$: $CF_3$ (para) |
| $CF_2$ | Pyrazinyl | NH—C(O) | Pyrimidinyl | $Z_1$: $CF_3$ (meta) |
| $CF_2$ | Pyrazinyl | NH—C(O) | Pyrimidinyl | $Z_1$: $CF_3$ (ortho) |
| $CF_2$ | Pyrazinyl | NH—C(O) | Pyrimidinyl | $Z_1$: $CH_2$—$CH_2F$ (para) |
| $CF_2$ | Pyrazinyl | NH—C(O) | Pyrimidinyl | $Z_1$: $CH_2$—$CH_2F$ (meta) |
| $CF_2$ | Pyrazinyl | NH—C(O) | Pyrimidinyl | $Z_1$: $CH_2$—$CH_2F$ (ortho) |
| $CF_2$ | Pyrazinyl | NH—C(O) | Pyrimidinyl | $Z_1$: $CH_2$—$CHF_2$ (para) |
| $CF_2$ | Pyrazinyl | NH—C(O) | Pyrimidinyl | $Z_1$: $CH_2$—$CHF_2$ (meta) |
| $CF_2$ | Pyrazinyl | NH—C(O) | Pyrimidinyl | $Z_1$: $CH_2$—$CHF_2$ (ortho) |
| $CF_2$ | Pyrazinyl | NH—C(O) | Pyrimidinyl | $Z_1$: $CH_2$—$CF_3$ (para) |
| $CF_2$ | Pyrazinyl | NH—C(O) | Pyrimidinyl | $Z_1$: $CH_2$—$CF_3$ (meta) |
| $CF_2$ | Pyrazinyl | NH—C(O) | Pyrimidinyl | $Z_1$: $CH_2$—$CF_3$ (ortho) |
| $CF_2$ | Pyrazinyl | NH—C(O) | Pyrazinyl | None |
| $CF_2$ | Pyrazinyl | NH—C(O) | Pyrazinyl | $Z_1$: F (para) |
| $CF_2$ | Pyrazinyl | NH—C(O) | Pyrazinyl | $Z_1$: F (meta) |
| $CF_2$ | Pyrazinyl | NH—C(O) | Pyrazinyl | $Z_1$: F (ortho) |
| $CF_2$ | Pyrazinyl | NH—C(O) | Pyrazinyl | $Z_1$: F (para)<br>$Z_2$: F (meta) |
| $CF_2$ | Pyrazinyl | NH—C(O) | Pyrazinyl | $Z_1$: Cl (meta) |

TABLE 2-continued

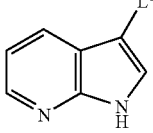

| L¹ | C¹ | L² | C² | Z |
|---|---|---|---|---|
| $CF_2$ | Pyrazinyl | NH—C(O) | Pyrazinyl | $Z_1$: Cl (para) |
| $CF_2$ | Pyrazinyl | NH—C(O) | Pyrazinyl | $Z_1$: Cl (para)<br>$Z_2$: Cl (meta) |
| $CF_2$ | Pyrazinyl | NH—C(O) | Pyrazinyl | $Z_1$: F (para)<br>$Z_2$: Cl (meta) |
| $CF_2$ | Pyrazinyl | NH—C(O) | Pyrazinyl | $Z_1$: Cl (para)<br>$Z_2$: F (meta) |
| $CF_2$ | Pyrazinyl | NH—C(O) | Pyrazinyl | $Z_1$: $CH_3$ (para) |
| $CF_2$ | Pyrazinyl | NH—C(O) | Pyrazinyl | $Z_1$: $CH_3$ (meta) |
| $CF_2$ | Pyrazinyl | NH—C(O) | Pyrazinyl | $Z_1$: $CH_3$ (ortho) |
| $CF_2$ | Pyrazinyl | NH—C(O) | Pyrazinyl | $Z_1$: $CH_2$—$CH_3$ (para) |
| $CF_2$ | Pyrazinyl | NH—C(O) | Pyrazinyl | $Z_1$: $CH_2$—$CH_3$ (meta) |
| $CF_2$ | Pyrazinyl | NH—C(O) | Pyrazinyl | $Z_1$: $CH_2$—$CH_3$ (ortho) |
| $CF_2$ | Pyrazinyl | NH—C(O) | Pyrazinyl | $Z_1$: $CH_2$—$CH_2$—$CH_3$ or iPr (para) |
| $CF_2$ | Pyrazinyl | NH—C(O) | Pyrazinyl | $Z_1$: $CH_2$—$CH_2$—$CH_3$ or iPr (meta) |
| $CF_2$ | Pyrazinyl | NH—C(O) | Pyrazinyl | $Z_1$: $CH_2$—$CH_2$—$CH_3$ or iPr (ortho) |
| $CF_2$ | Pyrazinyl | NH—C(O) | Pyrazinyl | $Z_1$: $CH_2F$ (para) |
| $CF_2$ | Pyrazinyl | NH—C(O) | Pyrazinyl | $Z_1$: $CH_2F$ (meta) |
| $CF_2$ | Pyrazinyl | NH—C(O) | Pyrazinyl | $Z_1$: $CH_2F$ (ortho) |
| $CF_2$ | Pyrazinyl | NH—C(O) | Pyrazinyl | $Z_1$: $CHF_2$ (para) |
| $CF_2$ | Pyrazinyl | NH—C(O) | Pyrazinyl | $Z_1$: $CHF_2$ (meta) |
| $CF_2$ | Pyrazinyl | NH—C(O) | Pyrazinyl | $Z_1$: $CHF_2$ (ortho) |
| $CF_2$ | Pyrazinyl | NH—C(O) | Pyrazinyl | $Z_1$: $CF_3$ (para) |
| $CF_2$ | Pyrazinyl | NH—C(O) | Pyrazinyl | $Z_1$: $CF_3$ (meta) |
| $CF_2$ | Pyrazinyl | NH—C(O) | Pyrazinyl | $Z_1$: $CF_3$ (ortho) |
| $CF_2$ | Pyrazinyl | NH—C(O) | Pyrazinyl | $Z_1$: $CH_2$—$CH_2F$ (para) |
| $CF_2$ | Pyrazinyl | NH—C(O) | Pyrazinyl | $Z_1$: $CH_2$—$CH_2F$ (meta) |
| $CF_2$ | Pyrazinyl | NH—C(O) | Pyrazinyl | $Z_1$: $CH_2$—$CH_2F$ (ortho) |
| $CF_2$ | Pyrazinyl | NH—C(O) | Pyrazinyl | $Z_1$: $CH_2$—$CHF_2$ (para) |
| $CF_2$ | Pyrazinyl | NH—C(O) | Pyrazinyl | $Z_1$: $CH_2$—$CHF_2$ (meta) |
| $CF_2$ | Pyrazinyl | NH—C(O) | Pyrazinyl | $Z_1$: $CH_2$—$CHF_2$ (ortho) |
| $CF_2$ | Pyrazinyl | NH—C(O) | Pyrazinyl | $Z_1$: $CH_2$—$CF_3$ (para) |
| $CF_2$ | Pyrazinyl | NH—C(O) | Pyrazinyl | $Z_1$: $CH_2$—$CF_3$ (meta) |
| $CF_2$ | Pyrazinyl | NH—C(O) | Pyrazinyl | $Z_1$: $CH_2$—$CF_3$ (ortho) |
| $CF_2$ | Pyrazinyl | NH—C(O) | Pyrrolyl | None |
| $CF_2$ | Pyrazinyl | NH—C(O) | Pyrrolyl | $Z_1$: F (2) |
| $CF_2$ | Pyrazinyl | NH—C(O) | Pyrrolyl | $Z_1$: F (3) |
| $CF_2$ | Pyrazinyl | NH—C(O) | Pyrrolyl | $Z_1$: F (2)<br>$Z_2$: F (3) |
| $CF_2$ | Pyrazinyl | NH—C(O) | Pyrrolyl | $Z_1$: Cl (2) |
| $CF_2$ | Pyrazinyl | NH—C(O) | Pyrrolyl | $Z_1$: Cl (3) |
| $CF_2$ | Pyrazinyl | NH—C(O) | Pyrrolyl | $Z_1$: Cl (2)<br>$Z_2$: Cl (3) |
| $CF_2$ | Pyrazinyl | NH—C(O) | Pyrrolyl | $Z_1$: F (2)<br>$Z_2$: Cl (3) |
| $CF_2$ | Pyrazinyl | NH—C(O) | Pyrrolyl | $Z_1$: Cl (2)<br>$Z_2$: F (3) |
| $CF_2$ | Pyrazinyl | NH—C(O) | Pyrrolyl | $Z_1$: $CH_3$ (2) |
| $CF_2$ | Pyrazinyl | NH—C(O) | Pyrrolyl | $Z_1$: $CH_3$ (3) |
| $CF_2$ | Pyrazinyl | NH—C(O) | Pyrrolyl | $Z_1$: $CH_2$—$CH_3$ (2) |
| $CF_2$ | Pyrazinyl | NH—C(O) | Pyrrolyl | $Z_1$: $CH_2$—$CH_3$ (3) |
| $CF_2$ | Pyrazinyl | NH—C(O) | Pyrrolyl | $Z_1$: $CH_2$—$CH_2$—$CH_3$ or iPr (2) |
| $CF_2$ | Pyrazinyl | NH—C(O) | Pyrrolyl | $Z_1$: $CH_2$—$CH_2$—$CH_3$ or iPr (3) |
| $CF_2$ | Pyrazinyl | NH—C(O) | Pyrrolyl | $Z_1$: $CH_2F$ (2) |
| $CF_2$ | Pyrazinyl | NH—C(O) | Pyrrolyl | $Z_1$: $CH_2F$ (3) |
| $CF_2$ | Pyrazinyl | NH—C(O) | Pyrrolyl | $Z_1$: $CHF_2$ (2) |
| $CF_2$ | Pyrazinyl | NH—C(O) | Pyrrolyl | $Z_1$: $CHF_2$ (3) |
| $CF_2$ | Pyrazinyl | NH—C(O) | Pyrrolyl | $Z_1$: $CF_3$ (2) |
| $CF_2$ | Pyrazinyl | NH—C(O) | Pyrrolyl | $Z_1$: $CF_3$ (3) |
| $CF_2$ | Pyrazinyl | NH—C(O) | Pyrrolyl | $Z_1$: $CH_2$—$CH_2F$ (2) |
| $CF_2$ | Pyrazinyl | NH—C(O) | Pyrrolyl | $Z_1$: $CH_2$—$CH_2F$ (3) |
| $CF_2$ | Pyrazinyl | NH—C(O) | Pyrrolyl | $Z_1$: $CH_2$—$CHF_2$ (2) |
| $CF_2$ | Pyrazinyl | NH—C(O) | Pyrrolyl | $Z_1$: $CH_2$—$CHF_2$ (3) |
| $CF_2$ | Pyrazinyl | NH—C(O) | Pyrrolyl | $Z_1$: $CH_2$—$CF_3$ (2) |
| $CF_2$ | Pyrazinyl | NH—C(O) | Pyrrolyl | $Z_1$: $CH_2$—$CF_3$ (3) |
| $CF_2$ | Pyrazinyl | NH—C(O) | Imidazolyl | None |

TABLE 2-continued

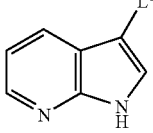

$$L^1-C^1-L^2-C^2-Z_p$$

| $L^1$ | $C^1$ | $L^2$ | $C^2$ | Z |
|---|---|---|---|---|
| $CF_2$ | Pyrazinyl | NH—C(O) | Imidazolyl | $Z_1$: F (2) |
| $CF_2$ | Pyrazinyl | NH—C(O) | Imidazolyl | $Z_1$: F (3) |
| $CF_2$ | Pyrazinyl | NH—C(O) | Imidazolyl | $Z_1$: F (2) |
| | | | | $Z_2$: F (3) |
| $CF_2$ | Pyrazinyl | NH—C(O) | Imidazolyl | $Z_1$: Cl (2) |
| $CF_2$ | Pyrazinyl | NH—C(O) | Imidazolyl | $Z_1$: Cl (3) |
| $CF_2$ | Pyrazinyl | NH—C(O) | Imidazolyl | $Z_1$: Cl (2) |
| | | | | $Z_2$: Cl (3) |
| $CF_2$ | Pyrazinyl | NH—C(O) | Imidazolyl | $Z_1$: F (2) |
| | | | | $Z_2$: Cl (3) |
| $CF_2$ | Pyrazinyl | NH—C(O) | Imidazolyl | $Z_1$: Cl (2) |
| | | | | $Z_2$: F (3) |
| $CF_2$ | Pyrazinyl | NH—C(O) | Imidazolyl | $Z_1$: $CH_3$ (2) |
| $CF_2$ | Pyrazinyl | NH—C(O) | Imidazolyl | $Z_1$: $CH_3$ (3) |
| $CF_2$ | Pyrazinyl | NH—C(O) | Imidazolyl | $Z_1$: $CH_2$—$CH_3$ (2) |
| $CF_2$ | Pyrazinyl | NH—C(O) | Imidazolyl | $Z_1$: $CH_2$—$CH_3$ (3) |
| $CF_2$ | Pyrazinyl | NH—C(O) | Imidazolyl | $Z_1$: $CH_2$—$CH_2$—$CH_3$ or iPr (2) |
| $CF_2$ | Pyrazinyl | NH—C(O) | Imidazolyl | $Z_1$: $CH_2$—$CH_2$—$CH_3$ or iPr (3) |
| $CF_2$ | Pyrazinyl | NH—C(O) | Imidazolyl | $Z_1$: $CH_2F$ (2) |
| $CF_2$ | Pyrazinyl | NH—C(O) | Imidazolyl | $Z_1$: $CH_2F$ (3) |
| $CF_2$ | Pyrazinyl | NH—C(O) | Imidazolyl | $Z_1$: $CHF_2$ (2) |
| $CF_2$ | Pyrazinyl | NH—C(O) | Imidazolyl | $Z_1$: $CHF_2$ (3) |
| $CF_2$ | Pyrazinyl | NH—C(O) | Imidazolyl | $Z_1$: $CF_3$ (2) |
| $CF_2$ | Pyrazinyl | NH—C(O) | Imidazolyl | $Z_1$: $CF_3$ (3) |
| $CF_2$ | Pyrazinyl | NH—C(O) | Imidazolyl | $Z_1$: $CH_2$—$CH_2F$ (2) |
| $CF_2$ | Pyrazinyl | NH—C(O) | Imidazolyl | $Z_1$: $CH_2$—$CH_2F$ (3) |
| $CF_2$ | Pyrazinyl | NH—C(O) | Imidazolyl | $Z_1$: $CH_2$—$CHF_2$ (2) |
| $CF_2$ | Pyrazinyl | NH—C(O) | Imidazolyl | $Z_1$: $CH_2$—$CHF_2$ (3) |
| $CF_2$ | Pyrazinyl | NH—C(O) | Imidazolyl | $Z_1$: $CH_2$—$CF_3$ (2) |
| $CF_2$ | Pyrazinyl | NH—C(O) | Imidazolyl | $Z_1$: $CH_2$—$CF_3$ (3) |
| $CF_2$ | Pyrazinyl | NH—C(O) | Furanyl | None |
| $CF_2$ | Pyrazinyl | NH—C(O) | Furanyl | $Z_1$: F (2) |
| $CF_2$ | Pyrazinyl | NH—C(O) | Furanyl | $Z_1$: F (3) |
| $CF_2$ | Pyrazinyl | NH—C(O) | Furanyl | $Z_1$: F (2) |
| | | | | $Z_2$: F (3) |
| $CF_2$ | Pyrazinyl | NH—C(O) | Furanyl | $Z_1$: Cl (2) |
| $CF_2$ | Pyrazinyl | NH—C(O) | Furanyl | $Z_1$: Cl (3) |
| $CF_2$ | Pyrazinyl | NH—C(O) | Furanyl | $Z_1$: Cl (2) |
| | | | | $Z_2$: Cl (3) |
| $CF_2$ | Pyrazinyl | NH—C(O) | Furanyl | $Z_1$: F (2) |
| | | | | $Z_2$: Cl (3) |
| $CF_2$ | Pyrazinyl | NH—C(O) | Furanyl | $Z_1$: Cl (2) |
| | | | | $Z_2$: F (3) |
| $CF_2$ | Pyrazinyl | NH—C(O) | Furanyl | $Z_1$: $CH_3$ (2) |
| $CF_2$ | Pyrazinyl | NH—C(O) | Furanyl | $Z_1$: $CH_3$ (3) |
| $CF_2$ | Pyrazinyl | NH—C(O) | Furanyl | $Z_1$: $CH_2$—$CH_3$ (2) |
| $CF_2$ | Pyrazinyl | NH—C(O) | Furanyl | $Z_1$: $CH_2$—$CH_3$ (3) |
| $CF_2$ | Pyrazinyl | NH—C(O) | Furanyl | $Z_1$: $CH_2$—$CH_2$—$CH_3$ or iPr (2) |
| $CF_2$ | Pyrazinyl | NH—C(O) | Furanyl | $Z_1$: $CH_2$—$CH_2$—$CH_3$ or iPr (3) |
| $CF_2$ | Pyrazinyl | NH—C(O) | Furanyl | $Z_1$: $CH_2F$ (2) |
| $CF_2$ | Pyrazinyl | NH—C(O) | Furanyl | $Z_1$: $CH_2F$ (3) |
| $CF_2$ | Pyrazinyl | NH—C(O) | Furanyl | $Z_1$: $CHF_2$ (2) |
| $CF_2$ | Pyrazinyl | NH—C(O) | Furanyl | $Z_1$: $CHF_2$ (3) |
| $CF_2$ | Pyrazinyl | NH—C(O) | Furanyl | $Z_1$: $CF_3$ (2) |
| $CF_2$ | Pyrazinyl | NH—C(O) | Furanyl | $Z_1$: $CF_3$ (3) |
| $CF_2$ | Pyrazinyl | NH—C(O) | Furanyl | $Z_1$: $CH_2$—$CH_2F$ (2) |
| $CF_2$ | Pyrazinyl | NH—C(O) | Furanyl | $Z_1$: $CH_2$—$CH_2F$ (3) |
| $CF_2$ | Pyrazinyl | NH—C(O) | Furanyl | $Z_1$: $CH_2$—$CHF_2$ (2) |
| $CF_2$ | Pyrazinyl | NH—C(O) | Furanyl | $Z_1$: $CH_2$—$CHF_2$ (3) |
| $CF_2$ | Pyrazinyl | NH—C(O) | Furanyl | $Z_1$: $CH_2$—$CF_3$ (2) |
| $CF_2$ | Pyrazinyl | NH—C(O) | Furanyl | $Z_1$: $CH_2$—$CF_3$ (3) |
| $CF_2$ | Pyrazinyl | NH—C(O) | Oxazolyl | None |
| $CF_2$ | Pyrazinyl | NH—C(O) | Oxazolyl | $Z_1$: F (2) |
| $CF_2$ | Pyrazinyl | NH—C(O) | Oxazolyl | $Z_1$: F (3) |
| $CF_2$ | Pyrazinyl | NH—C(O) | Oxazolyl | $Z_1$: F (2) |
| | | | | $Z_2$: F (3) |
| $CF_2$ | Pyrazinyl | NH—C(O) | Oxazolyl | $Z_1$: Cl (2) |
| $CF_2$ | Pyrazinyl | NH—C(O) | Oxazolyl | $Z_1$: Cl (3) |

TABLE 2-continued $$L^1-C^1-L^2-C^2-Z_p$$

(7-azaindole core structure)

| L¹ | C¹ | L² | C² | Z |
|---|---|---|---|---|
| CF₂ | Pyrazinyl | NH—C(O) | Oxazolyl | $Z_1$: Cl (2)<br>$Z_2$: Cl (3) |
| CF₂ | Pyrazinyl | NH—C(O) | Oxazolyl | $Z_1$: F (2)<br>$Z_2$: Cl (3) |
| CF₂ | Pyrazinyl | NH—C(O) | Oxazolyl | $Z_1$: Cl (2)<br>$Z_2$: F (3) |
| CF₂ | Pyrazinyl | NH—C(O) | Oxazolyl | $Z_1$: CH₃ (2) |
| CF₂ | Pyrazinyl | NH—C(O) | Oxazolyl | $Z_1$: CH₃ (3) |
| CF₂ | Pyrazinyl | NH—C(O) | Oxazolyl | $Z_1$: CH₂—CH₃ (2) |
| CF₂ | Pyrazinyl | NH—C(O) | Oxazolyl | $Z_1$: CH₂—CH₃ (3) |
| CF₂ | Pyrazinyl | NH—C(O) | Oxazolyl | $Z_1$: CH₂—CH₂—CH₃ or iPr (2) |
| CF₂ | Pyrazinyl | NH—C(O) | Oxazolyl | $Z_1$: CH₂—CH₂—CH₃ or iPr (3) |
| CF₂ | Pyrazinyl | NH—C(O) | Oxazolyl | $Z_1$: CH₂F (2) |
| CF₂ | Pyrazinyl | NH—C(O) | Oxazolyl | $Z_1$: CH₂F (3) |
| CF₂ | Pyrazinyl | NH—C(O) | Oxazolyl | $Z_1$: CHF₂ (2) |
| CF₂ | Pyrazinyl | NH—C(O) | Oxazolyl | $Z_1$: CHF₂ (3) |
| CF₂ | Pyrazinyl | NH—C(O) | Oxazolyl | $Z_1$: CF₃ (2) |
| CF₂ | Pyrazinyl | NH—C(O) | Oxazolyl | $Z_1$: CF₃ (3) |
| CF₂ | Pyrazinyl | NH—C(O) | Oxazolyl | $Z_1$: CH₂—CH₂F (2) |
| CF₂ | Pyrazinyl | NH—C(O) | Oxazolyl | $Z_1$: CH₂—CH₂F (3) |
| CF₂ | Pyrazinyl | NH—C(O) | Oxazolyl | $Z_1$: CH₂—CHF₂ (2) |
| CF₂ | Pyrazinyl | NH—C(O) | Oxazolyl | $Z_1$: CH₂—CHF₂ (3) |
| CF₂ | Pyrazinyl | NH—C(O) | Oxazolyl | $Z_1$: CH₂—CF₃ (2) |
| CF₂ | Pyrazinyl | NH—C(O) | Oxazolyl | $Z_1$: CH₂—CF₃ (3) |
| CF₂ | Pyrazinyl | NH—C(O) | Thiophenyl | None |
| CF₂ | Pyrazinyl | NH—C(O) | Thiophenyl | $Z_1$: F (2) |
| CF₂ | Pyrazinyl | NH—C(O) | Thiophenyl | $Z_1$: F (3) |
| CF₂ | Pyrazinyl | NH—C(O) | Thiophenyl | $Z_1$: F (2)<br>$Z_2$: F (3) |
| CF₂ | Pyrazinyl | NH—C(O) | Thiophenyl | $Z_1$: Cl (2) |
| CF₂ | Pyrazinyl | NH—C(O) | Thiophenyl | $Z_1$: Cl (3) |
| CF₂ | Pyrazinyl | NH—C(O) | Thiophenyl | $Z_1$: Cl (2)<br>$Z_2$: Cl (3) |
| CF₂ | Pyrazinyl | NH—C(O) | Thiophenyl | $Z_1$: F (2)<br>$Z_2$: Cl (3) |
| CF₂ | Pyrazinyl | NH—C(O) | Thiophenyl | $Z_1$: Cl (2)<br>$Z_2$: F (3) |
| CF₂ | Pyrazinyl | NH—C(O) | Thiophenyl | $Z_1$: CH₃ (2) |
| CF₂ | Pyrazinyl | NH—C(O) | Thiophenyl | $Z_1$: CH₃ (3) |
| CF₂ | Pyrazinyl | NH—C(O) | Thiophenyl | $Z_1$: CH₂—CH₃ (2) |
| CF₂ | Pyrazinyl | NH—C(O) | Thiophenyl | $Z_1$: CH₂—CH₃ (3) |
| CF₂ | Pyrazinyl | NH—C(O) | Thiophenyl | $Z_1$: CH₂—CH₂—CH₃ or iPr (2) |
| CF₂ | Pyrazinyl | NH—C(O) | Thiophenyl | $Z_1$: CH₂—CH₂—CH₃ or iPr (3) |
| CF₂ | Pyrazinyl | NH—C(O) | Thiophenyl | $Z_1$: CH₂F (2) |
| CF₂ | Pyrazinyl | NH—C(O) | Thiophenyl | $Z_1$: CH₂F (3) |
| CF₂ | Pyrazinyl | NH—C(O) | Thiophenyl | $Z_1$: CHF₂ (2) |
| CF₂ | Pyrazinyl | NH—C(O) | Thiophenyl | $Z_1$: CHF₂ (3) |
| CF₂ | Pyrazinyl | NH—C(O) | Thiophenyl | $Z_1$: CF₃ (2) |
| CF₂ | Pyrazinyl | NH—C(O) | Thiophenyl | $Z_1$: CF₃ (3) |
| CF₂ | Pyrazinyl | NH—C(O) | Thiophenyl | $Z_1$: CH₂—CH₂F (2) |
| CF₂ | Pyrazinyl | NH—C(O) | Thiophenyl | $Z_1$: CH₂—CH₂F (3) |
| CF₂ | Pyrazinyl | NH—C(O) | Thiophenyl | $Z_1$: CH₂—CHF₂ (2) |
| CF₂ | Pyrazinyl | NH—C(O) | Thiophenyl | $Z_1$: CH₂—CHF₂ (3) |
| CF₂ | Pyrazinyl | NH—C(O) | Thiophenyl | $Z_1$: CH₂—CF₃ (2) |
| CF₂ | Pyrazinyl | NH—C(O) | Thiophenyl | $Z_1$: CH₂—CF₃ (3) |
| CF₂ | Pyrazinyl | NH—C(O) | Thiazolyl | None |
| CF₂ | Pyrazinyl | NH—C(O) | Thiazolyl | $Z_1$: F (2) |
| CF₂ | Pyrazinyl | NH—C(O) | Thiazolyl | $Z_1$: F (3) |
| CF₂ | Pyrazinyl | NH—C(O) | Thiazolyl | $Z_1$: F (2)<br>$Z_2$: F (3) |
| CF₂ | Pyrazinyl | NH—C(O) | Thiazolyl | $Z_1$: Cl (2) |
| CF₂ | Pyrazinyl | NH—C(O) | Thiazolyl | $Z_1$: Cl (3) |
| CF₂ | Pyrazinyl | NH—C(O) | Thiazolyl | $Z_1$: Cl (2)<br>$Z_2$: Cl (3) |
| CF₂ | Pyrazinyl | NH—C(O) | Thiazolyl | $Z_1$: F (2)<br>$Z_2$: Cl (3) |
| CF₂ | Pyrazinyl | NH—C(O) | Thiazolyl | $Z_1$: Cl (2)<br>$Z_2$: F (3) |
| CF₂ | Pyrazinyl | NH—C(O) | Thiazolyl | $Z_1$: CH₃ (2) |

TABLE 2-continued

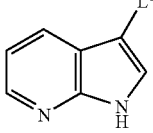

| L¹ | C¹ | L² | C² | Z |
|---|---|---|---|---|
| CF₂ | Pyrazinyl | NH—C(O) | Thiazolyl | $Z_1$: CH₃ (3) |
| CF₂ | Pyrazinyl | NH—C(O) | Thiazolyl | $Z_1$: CH₂—CH₃ (2) |
| CF₂ | Pyrazinyl | NH—C(O) | Thiazolyl | $Z_1$: CH₂—CH₃ (3) |
| CF₂ | Pyrazinyl | NH—C(O) | Thiazolyl | $Z_1$: CH₂—CH₂—CH₃ or iPr (2) |
| CF₂ | Pyrazinyl | NH—C(O) | Thiazolyl | $Z_1$: CH₂—CH₂—CH₃ or iPr (3) |
| CF₂ | Pyrazinyl | NH—C(O) | Thiazolyl | $Z_1$: CH₂F (2) |
| CF₂ | Pyrazinyl | NH—C(O) | Thiazolyl | $Z_1$: CH₂F (3) |
| CF₂ | Pyrazinyl | NH—C(O) | Thiazolyl | $Z_1$: CHF₂ (2) |
| CF₂ | Pyrazinyl | NH—C(O) | Thiazolyl | $Z_1$: CHF₂ (3) |
| CF₂ | Pyrazinyl | NH—C(O) | Thiazolyl | $Z_1$: CF₃ (2) |
| CF₂ | Pyrazinyl | NH—C(O) | Thiazolyl | $Z_1$: CF₃ (3) |
| CF₂ | Pyrazinyl | NH—C(O) | Thiazolyl | $Z_1$: CH₂—CH₂F (2) |
| CF₂ | Pyrazinyl | NH—C(O) | Thiazolyl | $Z_1$: CH₂—CH₂F (3) |
| CF₂ | Pyrazinyl | NH—C(O) | Thiazolyl | $Z_1$: CH₂—CHF₂ (2) |
| CF₂ | Pyrazinyl | NH—C(O) | Thiazolyl | $Z_1$: CH₂—CHF₂ (3) |
| CF₂ | Pyrazinyl | NH—C(O) | Thiazolyl | $Z_1$: CH₂—CF₃ (2) |
| CF₂ | Pyrazinyl | NH—C(O) | Thiazolyl | $Z_1$: CH₂—CF₃ (3) |
| CF₂ | Pyrazinyl | NH—SO₂ | Phenyl | None |
| CF₂ | Pyrazinyl | NH—SO₂ | Phenyl | $Z_1$: F (para) |
| CF₂ | Pyrazinyl | NH—SO₂ | phenyl | $Z_1$: F (meta) |
| CF₂ | Pyrazinyl | NH—SO₂ | phenyl | $Z_1$: F (ortho) |
| CF₂ | Pyrazinyl | NH—SO₂ | phenyl | $Z_1$: F (para)<br>$Z_2$: F (meta) |
| CF₂ | Pyrazinyl | NH—SO₂ | Phenyl | $Z_1$: Cl (meta) |
| CF₂ | Pyrazinyl | NH—SO₂ | Phenyl | $Z_1$: Cl (para) |
| CF₂ | Pyrazinyl | NH—SO₂ | Phenyl | $Z_1$: Cl (para)<br>$Z_2$: Cl (meta) |
| CF₂ | Pyrazinyl | NH—SO₂ | Phenyl | $Z_1$: F (para)<br>$Z_2$: Cl (meta) |
| CF₂ | Pyrazinyl | NH—SO₂ | Phenyl | $Z_1$: Cl (para)<br>$Z_2$: F (meta) |
| CF₂ | Pyrazinyl | NH—SO₂ | Phenyl | $Z_1$: CH₃ (para) |
| CF₂ | Pyrazinyl | NH—SO₂ | Phenyl | $Z_1$: CH₃ (meta) |
| CF₂ | Pyrazinyl | NH—SO₂ | Phenyl | $Z_1$: CH₃ (ortho) |
| CF₂ | Pyrazinyl | NH—SO₂ | Phenyl | $Z_1$: CH₂—CH₃ (para) |
| CF₂ | Pyrazinyl | NH—SO₂ | Phenyl | $Z_1$: CH₂—CH₂ (meta) |
| CF₂ | Pyrazinyl | NH—SO₂ | Phenyl | $Z_1$: CH₂—CH₃ (ortho) |
| CF₂ | Pyrazinyl | NH—SO₂ | Phenyl | $Z_1$: CH₂—CH₂—CH₃ or iPr (para) |
| CF₂ | Pyrazinyl | NH—SO₂ | Phenyl | $Z_1$: CH₂—CH₂—CH₃ or iPr (meta) |
| CF₂ | Pyrazinyl | NH—SO₂ | Phenyl | $Z_1$: CH₂—CH₂—CH₃ or iPr (ortho) |
| CF₂ | Pyrazinyl | NH—SO₂ | Phenyl | $Z_1$: CH₂F (para) |
| CF₂ | Pyrazinyl | NH—SO₂ | Phenyl | $Z_1$: CH₂F (meta) |
| CF₂ | Pyrazinyl | NH—SO₂ | Phenyl | $Z_1$: CH₂F (ortho) |
| CF₂ | Pyrazinyl | NH—SO₂ | Phenyl | $Z_1$: CHF₂ (para) |
| CF₂ | Pyrazinyl | NH—SO₂ | Phenyl | $Z_1$: CHF₂ (meta) |
| CF₂ | Pyrazinyl | NH—SO₂ | Phenyl | $Z_1$: CHF₂ (ortho) |
| CF₂ | Pyrazinyl | NH—SO₂ | Phenyl | $Z_1$: CF₃ (para) |
| CF₂ | Pyrazinyl | NH—SO₂ | Phenyl | $Z_1$: CF₃ (meta) |
| CF₂ | Pyrazinyl | NH—SO₂ | Phenyl | $Z_1$: CF₃ (ortho) |
| CF₂ | Pyrazinyl | NH—SO₂ | Phenyl | $Z_1$: CH₂—CH₂F (para) |
| CF₂ | Pyrazinyl | NH—SO₂ | Phenyl | $Z_1$: CH₂—CH₂F (meta) |
| CF₂ | Pyrazinyl | NH—SO₂ | Phenyl | $Z_1$: CH₂—CH₂F (ortho) |
| CF₂ | Pyrazinyl | NH—SO₂ | Phenyl | $Z_1$: CH₂—CHF₂ (para) |
| CF₂ | Pyrazinyl | NH—SO₂ | Phenyl | $Z_1$: CH₂—CHF₂ (meta) |
| CF₂ | Pyrazinyl | NH—SO₂ | Phenyl | $Z_1$: CH₂—CHF₂ (ortho) |
| CF₂ | Pyrazinyl | NH—SO₂ | Phenyl | $Z_1$: CH₂—CF₃ (para) |
| CF₂ | Pyrazinyl | NH—SO₂ | Phenyl | $Z_1$: CH₂—CF₃ (meta) |
| CF₂ | Pyrazinyl | NH—SO₂ | Phenyl | $Z_1$: CH₂—CF₃ (ortho) |
| CF₂ | Pyrazinyl | NH—SO₂ | Pyridinyl | None |
| CF₂ | Pyrazinyl | NH—SO₂ | Pyridinyl | $Z_1$: F (para) |
| CF₂ | Pyrazinyl | NH—SO₂ | Pyridinyl | $Z_1$: F (meta) |
| CF₂ | Pyrazinyl | NH—SO₂ | Pyridinyl | $Z_1$: F (ortho) |
| CF₂ | Pyrazinyl | NH—SO₂ | Pyridinyl | $Z_1$: F (para)<br>$Z_2$: F (meta) |
| CF₂ | Pyrazinyl | NH—SO₂ | Pyridinyl | $Z_1$: Cl (meta) |
| CF₂ | Pyrazinyl | NH—SO₂ | Pyridinyl | $Z_1$: Cl (para) |

TABLE 2-continued

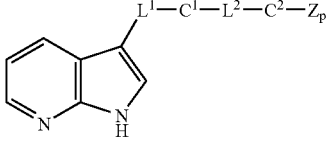

| L¹ | C¹ | L² | C² | Z |
|---|---|---|---|---|
| $CF_2$ | Pyrazinyl | $NH-SO_2$ | Pyridinyl | $Z_1$: Cl (para) |
|  |  |  |  | $Z_2$: Cl (meta) |
| $CF_2$ | Pyrazinyl | $NH-SO_2$ | Pyridinyl | $Z_1$: F (para) |
|  |  |  |  | $Z_2$: Cl (meta) |
| $CF_2$ | Pyrazinyl | $NH-SO_2$ | Pyridinyl | $Z_1$: Cl (para) |
|  |  |  |  | $Z_2$: F (meta) |
| $CF_2$ | Pyrazinyl | $NH-SO_2$ | Pyridinyl | $Z_1$: $CH_3$ (para) |
| $CF_2$ | Pyrazinyl | $NH-SO_2$ | Pyridinyl | $Z_1$: $CH_3$ (meta) |
| $CF_2$ | Pyrazinyl | $NH-SO_2$ | Pyridinyl | $Z_1$: $CH_3$ (ortho) |
| $CF_2$ | Pyrazinyl | $NH-SO_2$ | Pyridinyl | $Z_1$: $CH_2-CH_3$ (para) |
| $CF_2$ | Pyrazinyl | $NH-SO_2$ | Pyridinyl | $Z_1$: $CH_2-CH_3$ (meta) |
| $CF_2$ | Pyrazinyl | $NH-SO_2$ | Pyridinyl | $Z_1$: $CH_2-CH_3$ (ortho) |
| $CF_2$ | Pyrazinyl | $NH-SO_2$ | Pyridinyl | $Z_1$: $CH_2-CH_2-CH_3$ or iPr (para) |
| $CF_2$ | Pyrazinyl | $NH-SO_2$ | Pyridinyl | $Z_1$: $CH_2-CH_2-CH_3$ or iPr (meta) |
| $CF_2$ | Pyrazinyl | $NH-SO_2$ | Pyridinyl | $Z_1$: $CH_2-CH_2-CH_3$ or iPr (ortho) |
| $CF_2$ | Pyrazinyl | $NH-SO_2$ | Pyridinyl | $Z_1$: $CH_2F$ (para) |
| $CF_2$ | Pyrazinyl | $NH-SO_2$ | Pyridinyl | $Z_1$: $CH_2F$ (meta) |
| $CF_2$ | Pyrazinyl | $NH-SO_2$ | Pyridinyl | $Z_1$: $CH_2F$ (ortho) |
| $CF_2$ | Pyrazinyl | $NH-SO_2$ | Pyridinyl | $Z_1$: $CHF_2$ (para) |
| $CF_2$ | Pyrazinyl | $NH-SO_2$ | Pyridinyl | $Z_1$: $CHF_2$ (meta) |
| $CF_2$ | Pyrazinyl | $NH-SO_2$ | Pyridinyl | $Z_1$: $CHF_2$ (ortho) |
| $CF_2$ | Pyrazinyl | $NH-SO_2$ | Pyridinyl | $Z_1$: $CF_3$ (para) |
| $CF_2$ | Pyrazinyl | $NH-SO_2$ | Pyridinyl | $Z_1$: $CF_3$ (meta) |
| $CF_2$ | Pyrazinyl | $NH-SO_2$ | Pyridinyl | $Z_1$: $CF_3$ (ortho) |
| $CF_2$ | Pyrazinyl | $NH-SO_2$ | Pyridinyl | $Z_1$: $CH_2-CH_2F$ (para) |
| $CF_2$ | Pyrazinyl | $NH-SO_2$ | Pyridinyl | $Z_1$: $CH_2-CH_2F$ (meta) |
| $CF_2$ | Pyrazinyl | $NH-SO_2$ | Pyridinyl | $Z_1$: $CH_2-CH_2F$ (ortho) |
| $CF_2$ | Pyrazinyl | $NH-SO_2$ | Pyridinyl | $Z_1$: $CH_2-CHF_2$ (para) |
| $CF_2$ | Pyrazinyl | $NH-SO_2$ | Pyridinyl | $Z_1$: $CH_2-CHF_2$ (meta) |
| $CF_2$ | Pyrazinyl | $NH-SO_2$ | Pyridinyl | $Z_1$: $CH_2-CHF_2$ (ortho) |
| $CF_2$ | Pyrazinyl | $NH-SO_2$ | Pyridinyl | $Z_1$: $CH_2-CF_3$ (para) |
| $CF_2$ | Pyrazinyl | $NH-SO_2$ | Pyridinyl | $Z_1$: $CH_2-CF_3$ (meta) |
| $CF_2$ | Pyrazinyl | $NH-SO_2$ | Pyridinyl | $Z_1$: $CH_2-CF_3$ (ortho) |
| $CF_2$ | Pyrazinyl | $NH-SO_2$ | Pyrimidinyl | None |
| $CF_2$ | Pyrazinyl | $NH-SO_2$ | Pyrimidinyl | $Z_1$: F (para) |
| $CF_2$ | Pyrazinyl | $NH-SO_2$ | Pyrimidinyl | $Z_1$: F (meta) |
| $CF_2$ | Pyrazinyl | $NH-SO_2$ | Pyrimidinyl | $Z_1$: F (ortho) |
| $CF_2$ | Pyrazinyl | $NH-SO_2$ | Pyrimidinyl | $Z_1$: F (para) |
|  |  |  |  | $Z_2$: F (meta) |
| $CF_2$ | Pyrazinyl | $NH-SO_2$ | Pyrimidinyl | $Z_1$: Cl (meta) |
| $CF_2$ | Pyrazinyl | $NH-SO_2$ | Pyrimidinyl | $Z_1$: Cl (para) |
|  |  |  |  | $Z_2$: Cl (meta) |
| $CF_2$ | Pyrazinyl | $NH-SO_2$ | Pyrimidinyl | $Z_1$: F (para) |
|  |  |  |  | $Z_2$: Cl (meta) |
| $CF_2$ | Pyrazinyl | $NH-SO_2$ | Pyrimidinyl | $Z_1$: Cl (para) |
|  |  |  |  | $Z_2$: F (meta) |
| $CF_2$ | Pyrazinyl | $NH-SO_2$ | Pyrimidinyl | $Z_1$: $CH_3$ (para) |
| $CF_2$ | Pyrazinyl | $NH-SO_2$ | Pyrimidinyl | $Z_1$: $CH_3$ (meta) |
| $CF_2$ | Pyrazinyl | $NH-SO_2$ | Pyrimidinyl | $Z_1$: $CH_3$ (ortho) |
| $CF_2$ | Pyrazinyl | $NH-SO_2$ | Pyrimidinyl | $Z_1$: $CH_2-CH_3$ (para) |
| $CF_2$ | Pyrazinyl | $NH-SO_2$ | Pyrimidinyl | $Z_1$: $CH_2-CH_3$ (meta) |
| $CF_2$ | Pyrazinyl | $NH-SO_2$ | Pyrimidinyl | $Z_1$: $CH_2-CH_3$ (ortho) |
| $CF_2$ | Pyrazinyl | $NH-SO_2$ | Pyrimidinyl | $Z_1$: $CH_2-CH_2-CH_3$ or iPr (para) |
| $CF_2$ | Pyrazinyl | $NH-SO_2$ | Pyrimidinyl | $Z_1$: $CH_2-CH_2-CH_3$ or iPr (meta) |
| $CF_2$ | Pyrazinyl | $NH-SO_2$ | Pyrimidinyl | $Z_1$: $CH_2-CH_2-CH_3$ or iPr (ortho) |
| $CF_2$ | Pyrazinyl | $NH-SO_2$ | Pyrimidinyl | $Z_1$: $CH_2F$ (para) |
| $CF_2$ | Pyrazinyl | $NH-SO_2$ | Pyrimidinyl | $Z_1$: $CH_2F$ (meta) |
| $CF_2$ | Pyrazinyl | $NH-SO_2$ | Pyrimidinyl | $Z_1$: $CH_2F$ (ortho) |
| $CF_2$ | Pyrazinyl | $NH-SO_2$ | Pyrimidinyl | $Z_1$: $CHF_2$ (para) |
| $CF_2$ | Pyrazinyl | $NH-SO_2$ | Pyrimidinyl | $Z_1$: $CHF_2$ (meta) |
| $CF_2$ | Pyrazinyl | $NH-SO_2$ | Pyrimidinyl | $Z_1$: $CHF_2$ (ortho) |
| $CF_2$ | Pyrazinyl | $NH-SO_2$ | Pyrimidinyl | $Z_1$: $CF_3$ (para) |

TABLE 2-continued

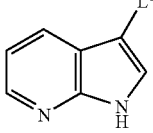

| $L^1$ | $C^1$ | $L^2$ | $C^2$ | Z |
|---|---|---|---|---|
| $CF_2$ | Pyrazinyl | $NH-SO_2$ | Pyrimidinyl | $Z_1$: $CF_3$ (meta) |
| $CF_2$ | Pyrazinyl | $NH-SO_2$ | Pyrimidinyl | $Z_1$: $CF_3$ (ortho) |
| $CF_2$ | Pyrazinyl | $NH-SO_2$ | Pyrimidinyl | $Z_1$: $CH_2-CH_2F$ (para) |
| $CF_2$ | Pyrazinyl | $NH-SO_2$ | Pyrimidinyl | $Z_1$: $CH_2-CH_2F$ (meta) |
| $CF_2$ | Pyrazinyl | $NH-SO_2$ | Pyrimidinyl | $Z_1$: $CH_2-CH_2F$ (ortho) |
| $CF_2$ | Pyrazinyl | $NH-SO_2$ | Pyrimidinyl | $Z_1$: $CH_2-CHF_2$ (para) |
| $CF_2$ | Pyrazinyl | $NH-SO_2$ | Pyrimidinyl | $Z_1$: $CH_2-CHF_2$ (meta) |
| $CF_2$ | Pyrazinyl | $NH-SO_2$ | Pyrimidinyl | $Z_1$: $CH_2-CHF_2$ (ortho) |
| $CF_2$ | Pyrazinyl | $NH-SO_2$ | Pyrimidinyl | $Z_1$: $CH_2-CF_3$ (para) |
| $CF_2$ | Pyrazinyl | $NH-SO_2$ | Pyrimidinyl | $Z_1$: $CH_2-CF_3$ (meta) |
| $CF_2$ | Pyrazinyl | $NH-SO_2$ | Pyrimidinyl | $Z_1$: $CH_2-CF_3$ (ortho) |
| $CF_2$ | Pyrazinyl | $NH-SO_2$ | Pyrazinyl | None |
| $CF_2$ | Pyrazinyl | $NH-SO_2$ | Pyrazinyl | $Z_1$: F (para) |
| $CF_2$ | Pyrazinyl | $NH-SO_2$ | Pyrazinyl | $Z_1$: F (meta) |
| $CF_2$ | Pyrazinyl | $NH-SO_2$ | Pyrazinyl | $Z_1$: F (ortho) |
| $CF_2$ | Pyrazinyl | $NH-SO_2$ | Pyrazinyl | $Z_1$: F (para) $Z_2$: F (meta) |
| $CF_2$ | Pyrazinyl | $NH-SO_2$ | Pyrazinyl | $Z_1$: Cl (meta) |
| $CF_2$ | Pyrazinyl | $NH-SO_2$ | Pyrazinyl | $Z_1$: Cl (para) |
| $CF_2$ | Pyrazinyl | $NH-SO_2$ | Pyrazinyl | $Z_1$: Cl (para) $Z_2$: Cl (meta) |
| $CF_2$ | Pyrazinyl | $NH-SO_2$ | Pyrazinyl | $Z_1$: F (para) $Z_2$: Cl (meta) |
| $CF_2$ | Pyrazinyl | $NH-SO_2$ | Pyrazinyl | $Z_1$: Cl (para) $Z_2$: F (meta) |
| $CF_2$ | Pyrazinyl | $NH-SO_2$ | Pyrazinyl | $Z_1$: $CH_3$ (para) |
| $CF_2$ | Pyrazinyl | $NH-SO_2$ | Pyrazinyl | $Z_1$: $CH_3$ (meta) |
| $CF_2$ | Pyrazinyl | $NH-SO_2$ | Pyrazinyl | $Z_1$: $CH_3$ (ortho) |
| $CF_2$ | Pyrazinyl | $NH-SO_2$ | Pyrazinyl | $Z_1$: $CH_2-CH_3$ (para) |
| $CF_2$ | Pyrazinyl | $NH-SO_2$ | Pyrazinyl | $Z_1$: $CH_2-CH_3$ (meta) |
| $CF_2$ | Pyrazinyl | $NH-SO_2$ | Pyrazinyl | $Z_1$: $CH_2-CH_3$ (ortho) |
| $CF_2$ | Pyrazinyl | $NH-SO_2$ | Pyrazinyl | $Z_1$: $CH_2-CH_2-CH_3$ or iPr (para) |
| $CF_2$ | Pyrazinyl | $NH-SO_2$ | Pyrazinyl | $Z_1$: $CH_2-CH_2-CH_3$ or iPr (meta) |
| $CF_2$ | Pyrazinyl | $NH-SO_2$ | Pyrazinyl | $Z_1$: $CH_2-CH_2-CH_3$ or iPr (ortho) |
| $CF_2$ | Pyrazinyl | $NH-SO_2$ | Pyrazinyl | $Z_1$: $CH_2F$ (para) |
| $CF_2$ | Pyrazinyl | $NH-SO_2$ | Pyrazinyl | $Z_1$: $CH_2F$ (meta) |
| $CF_2$ | Pyrazinyl | $NH-SO_2$ | Pyrazinyl | $Z_1$: $CH_2F$ (ortho) |
| $CF_2$ | Pyrazinyl | $NH-SO_2$ | Pyrazinyl | $Z_1$: $CHF_2$ (para) |
| $CF_2$ | Pyrazinyl | $NH-SO_2$ | Pyrazinyl | $Z_1$: $CHF_2$ (meta) |
| $CF_2$ | Pyrazinyl | $NH-SO_2$ | Pyrazinyl | $Z_1$: $CHF_2$ (ortho) |
| $CF_2$ | Pyrazinyl | $NH-SO_2$ | Pyrazinyl | $Z_1$: $CF_3$ (para) |
| $CF_2$ | Pyrazinyl | $NH-SO_2$ | Pyrazinyl | $Z_1$: $CF_3$ (meta) |
| $CF_2$ | Pyrazinyl | $NH-SO_2$ | Pyrazinyl | $Z_1$: $CF_3$ (ortho) |
| $CF_2$ | Pyrazinyl | $NH-SO_2$ | Pyrazinyl | $Z_1$: $CH_2-CH_2F$ (para) |
| $CF_2$ | Pyrazinyl | $NH-SO_2$ | Pyrazinyl | $Z_1$: $CH_2-CH_2F$ (meta) |
| $CF_2$ | Pyrazinyl | $NH-SO_2$ | Pyrazinyl | $Z_1$: $CH_2-CH_2F$ (ortho) |
| $CF_2$ | Pyrazinyl | $NH-SO_2$ | Pyrazinyl | $Z_1$: $CH_2-CHF_2$ (para) |
| $CF_2$ | Pyrazinyl | $NH-SO_2$ | Pyrazinyl | $Z_1$: $CH_2-CHF_2$ (meta) |
| $CF_2$ | Pyrazinyl | $NH-SO_2$ | Pyrazinyl | $Z_1$: $CH_2-CHF_2$ (ortho) |
| $CF_2$ | Pyrazinyl | $NH-SO_2$ | Pyrazinyl | $Z_1$: $CH_2-CF_3$ (para) |
| $CF_2$ | Pyrazinyl | $NH-SO_2$ | Pyrazinyl | $Z_1$: $CH_2-CF_3$ (meta) |
| $CF_2$ | Pyrazinyl | $NH-SO_2$ | Pyrazinyl | $Z_1$: $CH_2-CF_3$ (ortho) |
| $CF_2$ | Pyrazinyl | $NH-SO_2$ | Pyrrolyl | None |
| $CF_2$ | Pyrazinyl | $NH-SO_2$ | Pyrrolyl | $Z_1$: F (2) |
| $CF_2$ | Pyrazinyl | $NH-SO_2$ | Pyrrolyl | $Z_1$: F (3) |
| $CF_2$ | Pyrazinyl | $NH-SO_2$ | Pyrrolyl | $Z_1$: F (2) $Z_2$: F (3) |
| $CF_2$ | Pyrazinyl | $NH-SO_2$ | Pyrrolyl | $Z_1$: Cl (2) |
| $CF_2$ | Pyrazinyl | $NH-SO_2$ | Pyrrolyl | $Z_1$: Cl (3) |
| $CF_2$ | Pyrazinyl | $NH-SO_2$ | Pyrrolyl | $Z_1$: Cl (2) $Z_2$: Cl (3) |
| $CF_2$ | Pyrazinyl | $NH-SO_2$ | Pyrrolyl | $Z_1$: F (2) $Z_2$: Cl (3) |
| $CF_2$ | Pyrazinyl | $NH-SO_2$ | Pyrrolyl | $Z_1$: Cl (2) $Z_2$: F (3) |
| $CF_2$ | Pyrazinyl | $NH-SO_2$ | Pyrrolyl | $Z_1$: $CH_3$ (2) |

TABLE 2-continued $$L^1-C^1-L^2-C^2-Z_p$$

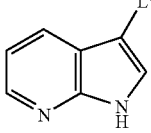

| L¹ | C¹ | L² | C² | Z |
|---|---|---|---|---|
| CF₂ | Pyrazinyl | NH—SO₂ | Pyrrolyl | Z₁: CH₃ (3) |
| CF₂ | Pyrazinyl | NH—SO₂ | Pyrrolyl | Z₁: CH₂—CH₃ (2) |
| CF₂ | Pyrazinyl | NH—SO₂ | Pyrrolyl | Z₁: CH₂—CH₃ (3) |
| CF₂ | Pyrazinyl | NH—SO₂ | Pyrrolyl | Z₁: CH₂—CH₂—CH₃ or iPr (2) |
| CF₂ | Pyrazinyl | NH—SO₂ | Pyrrolyl | Z₁: CH₂—CH₂—CH₃ or iPr (3) |
| CF₂ | Pyrazinyl | NH—SO₂ | Pyrrolyl | Z₁: CH₂F (2) |
| CF₂ | Pyrazinyl | NH—SO₂ | Pyrrolyl | Z₁: CH₂F (3) |
| CF₂ | Pyrazinyl | NH—SO₂ | Pyrrolyl | Z₁: CHF₂ (2) |
| CF₂ | Pyrazinyl | NH—SO₂ | Pyrrolyl | Z₁: CHF₂ (3) |
| CF₂ | Pyrazinyl | NH—SO₂ | Pyrrolyl | Z₁: CF₃ (2) |
| CF₂ | Pyrazinyl | NH—SO₂ | Pyrrolyl | Z₁: CF₃ (3) |
| CF₂ | Pyrazinyl | NH—SO₂ | Pyrrolyl | Z₁: CH₂—CH₂F (2) |
| CF₂ | Pyrazinyl | NH—SO₂ | Pyrrolyl | Z₁: CH₂—CH₂F (3) |
| CF₂ | Pyrazinyl | NH—SO₂ | Pyrrolyl | Z₁: CH₂—CHF₂ (2) |
| CF₂ | Pyrazinyl | NH—SO₂ | Pyrrolyl | Z₁: CH₂—CHF₂ (3) |
| CF₂ | Pyrazinyl | NH—SO₂ | Pyrrolyl | Z₁: CH₂—CF₃ (2) |
| CF₂ | Pyrazinyl | NH—SO₂ | Pyrrolyl | Z₁: CH₂—CF₃ (3) |
| CF₂ | Pyrazinyl | NH—SO₂ | Imidazolyl | None |
| CF₂ | Pyrazinyl | NH—SO₂ | Imidazolyl | Z₁: F (2) |
| CF₂ | Pyrazinyl | NH—SO₂ | Imidazolyl | Z₁: F (3) |
| CF₂ | Pyrazinyl | NH—SO₂ | Imidazolyl | Z₁: F (2) <br> Z₂: F (3) |
| CF₂ | Pyrazinyl | NH—SO₂ | Imidazolyl | Z₁: Cl (2) |
| CF₂ | Pyrazinyl | NH—SO₂ | Imidazolyl | Z₁: Cl (3) |
| CF₂ | Pyrazinyl | NH—SO₂ | Imidazolyl | Z₁: Cl (2) <br> Z₂: Cl (3) |
| CF₂ | Pyrazinyl | NH—SO₂ | Imidazolyl | Z₁: F (2) <br> Z₂: Cl (3) |
| CF₂ | Pyrazinyl | NH—SO₂ | Imidazolyl | Z₁: Cl (2) <br> Z₂: F (3) |
| CF₂ | Pyrazinyl | NH—SO₂ | Imidazolyl | Z₁: CH₃ (2) |
| CF₂ | Pyrazinyl | NH—SO₂ | Imidazolyl | Z₁: CH₃ (3) |
| CF₂ | Pyrazinyl | NH—SO₂ | Imidazolyl | Z₁: CH₂—CH₃ (2) |
| CF₂ | Pyrazinyl | NH—SO₂ | Imidazolyl | Z₁: CH₂—CH₃ (3) |
| CF₂ | Pyrazinyl | NH—SO₂ | Imidazolyl | Z₁: CH₂—CH₂—CH₃ or iPr (2) |
| CF₂ | Pyrazinyl | NH—SO₂ | Imidazolyl | Z₁: CH₂—CH₂—CH₃ or iPr (3) |
| CF₂ | Pyrazinyl | NH—SO₂ | Imidazolyl | Z₁: CH₂F (2) |
| CF₂ | Pyrazinyl | NH—SO₂ | Imidazolyl | Z₁: CH₂F (3) |
| CF₂ | Pyrazinyl | NH—SO₂ | Imidazolyl | Z₁: CHF₂ (2) |
| CF₂ | Pyrazinyl | NH—SO₂ | Imidazolyl | Z₁: CHF₂ (3) |
| CF₂ | Pyrazinyl | NH—SO₂ | Imidazolyl | Z₁: CF₃ (2) |
| CF₂ | Pyrazinyl | NH—SO₂ | Imidazolyl | Z₁: CF₃ (3) |
| CF₂ | Pyrazinyl | NH—SO₂ | Imidazolyl | Z₁: CH₂—CH₂F (2) |
| CF₂ | Pyrazinyl | NH—SO₂ | Imidazolyl | Z₁: CH₂—CH₂F (3) |
| CF₂ | Pyrazinyl | NH—SO₂ | Imidazolyl | Z₁: CH₂—CHF₂ (2) |
| CF₂ | Pyrazinyl | NH—SO₂ | Imidazolyl | Z₁: CH₂—CHF₂ (3) |
| CF₂ | Pyrazinyl | NH—SO₂ | Imidazolyl | Z₁: CH₂—CF₃ (2) |
| CF₂ | Pyrazinyl | NH—SO₂ | Imidazolyl | Z₁: CH₂—CF₃ (3) |
| CF₂ | Pyrazinyl | NH—SO₂ | Furanyl | None |
| CF₂ | Pyrazinyl | NH—SO₂ | Furanyl | Z₁: F (2) |
| CF₂ | Pyrazinyl | NH—SO₂ | Furanyl | Z₁: F (3) |
| CF₂ | Pyrazinyl | NH—SO₂ | Furanyl | Z₂: F (3) |
| CF₂ | Pyrazinyl | NH—SO₂ | Furanyl | Z₁: Cl (2) |
| CF₂ | Pyrazinyl | NH—SO₂ | Furanyl | Z₁: Cl (3) |
| CF₂ | Pyrazinyl | NH—SO₂ | Furanyl | Z₁: Cl (2) <br> Z₂: Cl (3) |
| CF₂ | Pyrazinyl | NH—SO₂ | Furanyl | Z₁: F (2) <br> Z₂: Cl (3) |
| CF₂ | Pyrazinyl | NH—SO₂ | Furanyl | Z₁: Cl (2) <br> Z₂: F (3) |
| CF₂ | Pyrazinyl | NH—SO₂ | Furanyl | Z₁: CH₃ (2) |
| CF₂ | Pyrazinyl | NH—SO₂ | Furanyl | Z₁: CH₃ (3) |
| CF₂ | Pyrazinyl | NH—SO₂ | Furanyl | Z₁: CH₂—CH₃ (2) |
| CF₂ | Pyrazinyl | NH—SO₂ | Furanyl | Z₁: CH₂—CH₃ (3) |
| CF₂ | Pyrazinyl | NH—SO₂ | Furanyl | Z₁: CH₂—CH₂—CH₃ or iPr (2) |
| CF₂ | Pyrazinyl | NH—SO₂ | Furanyl | Z₁: CH₂—CH₂—CH₃ or iPr (3) |
| CF₂ | Pyrazinyl | NH—SO₂ | Furanyl | Z₁: CH₂F (2) |
| CF₂ | Pyrazinyl | NH—SO₂ | Furanyl | Z₁: CH₂F (3) |
| CF₂ | Pyrazinyl | NH—SO₂ | Furanyl | Z₁: CHF₂ (2) |

TABLE 2-continued

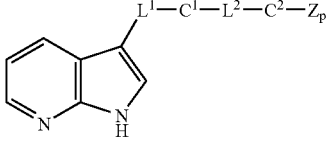

| L¹ | C¹ | L² | C² | Z |
|---|---|---|---|---|
| $CF_2$ | Pyrazinyl | $NH-SO_2$ | Furanyl | $Z_1$: $CHF_2$ (3) |
| $CF_2$ | Pyrazinyl | $NH-SO_2$ | Furanyl | $Z_1$: $CF_3$ (2) |
| $CF_2$ | Pyrazinyl | $NH-SO_2$ | Furanyl | $Z_1$: $CF_3$ (3) |
| $CF_2$ | Pyrazinyl | $NH-SO_2$ | Furanyl | $Z_1$: $CH_2-CH_2F$ (2) |
| $CF_2$ | Pyrazinyl | $NH-SO_2$ | Furanyl | $Z_1$: $CH_2-CH_2F$ (3) |
| $CF_2$ | Pyrazinyl | $NH-SO_2$ | Furanyl | $Z_1$: $CH_2-CHF_2$ (2) |
| $CF_2$ | Pyrazinyl | $NH-SO_2$ | Furanyl | $Z_1$: $CH_2-CHF_2$ (3) |
| $CF_2$ | Pyrazinyl | $NH-SO_2$ | Furanyl | $Z_1$: $CH_2-CF_3$ (2) |
| $CF_2$ | Pyrazinyl | $NH-SO_2$ | Furanyl | $Z_1$: $CH_2-CF_3$ (3) |
| $CF_2$ | Pyrazinyl | $NH-SO_2$ | Oxazolyl | None |
| $CF_2$ | Pyrazinyl | $NH-SO_2$ | Oxazolyl | $Z_1$: F (2) |
| $CF_2$ | Pyrazinyl | $NH-SO_2$ | Oxazolyl | $Z_1$: F (3) |
| $CF_2$ | Pyrazinyl | $NH-SO_2$ | Oxazolyl | $Z_1$: F (2)<br>$Z_2$: F (3) |
| $CF_2$ | Pyrazinyl | $NH-SO_2$ | Oxazolyl | $Z_1$: Cl (2) |
| $CF_2$ | Pyrazinyl | $NH-SO_2$ | Oxazolyl | $Z_1$: Cl (3) |
| $CF_2$ | Pyrazinyl | $NH-SO_2$ | Oxazolyl | $Z_1$: Cl (2)<br>$Z_2$: Cl (3) |
| $CF_2$ | Pyrazinyl | $NH-SO_2$ | Oxazolyl | $Z_1$: F (2)<br>$Z_2$: Cl (3) |
| $CF_2$ | Pyrazinyl | $NH-SO_2$ | Oxazolyl | $Z_1$: Cl (2)<br>$Z_2$: F (3) |
| $CF_2$ | Pyrazinyl | $NH-SO_2$ | Oxazolyl | $Z_1$: $CH_3$ (2) |
| $CF_2$ | Pyrazinyl | $NH-SO_2$ | Oxazolyl | $Z_1$: $CH_3$ (3) |
| $CF_2$ | Pyrazinyl | $NH-SO_2$ | Oxazolyl | $Z_1$: $CH_2-CH_3$ (2) |
| $CF_2$ | Pyrazinyl | $NH-SO_2$ | Oxazolyl | $Z_1$: $CH_2-CH_3$ (3) |
| $CF_2$ | Pyrazinyl | $NH-SO_2$ | Oxazolyl | $Z_1$: $CH_2-CH_2-CH_3$ or iPr (2) |
| $CF_2$ | Pyrazinyl | $NH-SO_2$ | Oxazolyl | $Z_1$: $CH_2-CH_2-CH_3$ or iPr (3) |
| $CF_2$ | Pyrazinyl | $NH-SO_2$ | Oxazolyl | $Z_1$: $CH_2F$ (2) |
| $CF_2$ | Pyrazinyl | $NH-SO_2$ | Oxazolyl | $Z_1$: $CH_2F$ (3) |
| $CF_2$ | Pyrazinyl | $NH-SO_2$ | Oxazolyl | $Z_1$: $CHF_2$ (2) |
| $CF_2$ | Pyrazinyl | $NH-SO_2$ | Oxazolyl | $Z_1$: $CHF_2$ (3) |
| $CF_2$ | Pyrazinyl | $NH-SO_2$ | Oxazolyl | $Z_1$: $CF_3$ (2) |
| $CF_2$ | Pyrazinyl | $NH-SO_2$ | Oxazolyl | $Z_1$: $CF_3$ (3) |
| $CF_2$ | Pyrazinyl | $NH-SO_2$ | Oxazolyl | $Z_1$: $CH_2-CH_2F$ (2) |
| $CF_2$ | Pyrazinyl | $NH-SO_2$ | Oxazolyl | $Z_1$: $CH_2-CH_2F$ (3) |
| $CF_2$ | Pyrazinyl | $NH-SO_2$ | Oxazolyl | $Z_1$: $CH_2-CHF_2$ (2) |
| $CF_2$ | Pyrazinyl | $NH-SO_2$ | Oxazolyl | $Z_1$: $CH_2-CHF_2$ (3) |
| $CF_2$ | Pyrazinyl | $NH-SO_2$ | Oxazolyl | $Z_1$: $CH_2-CF_3$ (2) |
| $CF_2$ | Pyrazinyl | $NH-SO_2$ | Oxazolyl | $Z_1$: $CH_2-CF_3$ (3) |
| $CF_2$ | Pyrazinyl | $NH-SO_2$ | Thiophenyl | None |
| $CF_2$ | Pyrazinyl | $NH-SO_2$ | Thiophenyl | $Z_1$: F (2) |
| $CF_2$ | Pyrazinyl | $NH-SO_2$ | Thiophenyl | $Z_1$: F (3) |
| $CF_2$ | Pyrazinyl | $NH-SO_2$ | Thiophenyl | $Z_1$: F (2)<br>$Z_2$: F (3) |
| $CF_2$ | Pyrazinyl | $NH-SO_2$ | Thiophenyl | $Z_1$: Cl (2) |
| $CF_2$ | Pyrazinyl | $NH-SO_2$ | Thiophenyl | $Z_1$: Cl (3) |
| $CF_2$ | Pyrazinyl | $NH-SO_2$ | Thiophenyl | $Z_1$: Cl (2)<br>$Z_2$: Cl (3) |
| $CF_2$ | Pyrazinyl | $NH-SO_2$ | Thiophenyl | $Z_1$: F (2)<br>$Z_2$: Cl (3) |
| $CF_2$ | Pyrazinyl | $NH-SO_2$ | Thiophenyl | $Z_1$: Cl (2)<br>$Z_2$: F (3) |
| $CF_2$ | Pyrazinyl | $NH-SO_2$ | Thiophenyl | $Z_1$: $CH_3$ (2) |
| $CF_2$ | Pyrazinyl | $NH-SO_2$ | Thiophenyl | $Z_1$: $CH_3$ (3) |
| $CF_2$ | Pyrazinyl | $NH-SO_2$ | Thiophenyl | $Z_1$: $CH_2-CH_3$ (2) |
| $CF_2$ | Pyrazinyl | $NH-SO_2$ | Thiophenyl | $Z_1$: $CH_2-CH_3$ (3) |
| $CF_2$ | Pyrazinyl | $NH-SO_2$ | Thiophenyl | $Z_1$: $CH_2-CH_2-CH_3$ or iPr (2) |
| $CF_2$ | Pyrazinyl | $NH-SO_2$ | Thiophenyl | $Z_1$: $CH_2-CH_2-CH_3$ or iPr (3) |
| $CF_2$ | Pyrazinyl | $NH-SO_2$ | Thiophenyl | $Z_1$: $CH_2F$ (2) |
| $CF_2$ | Pyrazinyl | $NH-SO_2$ | Thiophenyl | $Z_1$: $CH_2F$ (3) |
| $CF_2$ | Pyrazinyl | $NH-SO_2$ | Thiophenyl | $Z_1$: $CHF_2$ (2) |
| $CF_2$ | Pyrazinyl | $NH-SO_2$ | Thiophenyl | $Z_1$: $CHF_2$ (3) |
| $CF_2$ | Pyrazinyl | $NH-SO_2$ | Thiophenyl | $Z_1$: $CF_3$ (2) |
| $CF_2$ | Pyrazinyl | $NH-SO_2$ | Thiophenyl | $Z_1$: $CF_3$ (3) |
| $CF_2$ | Pyrazinyl | $NH-SO_2$ | Thiophenyl | $Z_1$: $CH_2-CH_2F$ (2) |
| $CF_2$ | Pyrazinyl | $NH-SO_2$ | Thiophenyl | $Z_1$: $CH_2-CH_2F$ (3) |
| $CF_2$ | Pyrazinyl | $NH-SO_2$ | Thiophenyl | $Z_1$: $CH_2-CHF_2$ (2) |
| $CF_2$ | Pyrazinyl | $NH-SO_2$ | Thiophenyl | $Z_1$: $CH_2-CHF_2$ (3) |

TABLE 2-continued

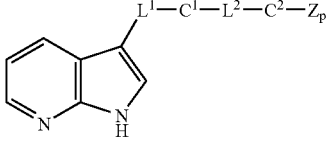

$$L^1-C^1-L^2-C^2-Z_p$$

| $L^1$ | $C^1$ | $L^2$ | $C^2$ | Z |
|---|---|---|---|---|
| $CF_2$ | Pyrazinyl | NH—$SO_2$ | Thiophenyl | $Z_1$: $CH_2$—$CF_3$ (2) |
| $CF_2$ | Pyrazinyl | NH—$SO_2$ | Thiophenyl | $Z_1$: $CH_2$—$CF_3$ (3) |
| $CF_2$ | Pyrazinyl | NH—$SO_2$ | Thiazolyl | None |
| $CF_2$ | Pyrazinyl | NH—$SO_2$ | Thiazolyl | $Z_1$: F (2) |
| $CF_2$ | Pyrazinyl | NH—$SO_2$ | Thiazolyl | $Z_1$: F (3) |
| $CF_2$ | Pyrazinyl | NH—$SO_2$ | Thiazolyl | $Z_1$: F (2)<br>$Z_2$: F (3) |
| $CF_2$ | Pyrazinyl | NH—$SO_2$ | Thiazolyl | $Z_1$: Cl (2) |
| $CF_2$ | Pyrazinyl | NH—$SO_2$ | Thiazolyl | $Z_1$: Cl (3) |
| $CF_2$ | Pyrazinyl | NH—$SO_2$ | Thiazolyl | $Z_1$: Cl (2)<br>$Z_2$: Cl (3) |
| $CF_2$ | Pyrazinyl | NH—$SO_2$ | Thiazolyl | $Z_1$: F (2)<br>$Z_2$: Cl (3) |
| $CF_2$ | Pyrazinyl | NH—$SO_2$ | Thiazolyl | $Z_1$: Cl (2)<br>$Z_2$: F (3) |
| $CF_2$ | Pyrazinyl | NH—$SO_2$ | Thiazolyl | $Z_1$: $CH_3$ (2) |
| $CF_2$ | Pyrazinyl | NH—$SO_2$ | Thiazolyl | $Z_1$: $CH_3$ (3) |
| $CF_2$ | Pyrazinyl | NH—$SO_2$ | Thiazolyl | $Z_1$: $CH_2$—$CH_3$ (2) |
| $CF_2$ | Pyrazinyl | NH—$SO_2$ | Thiazolyl | $Z_1$: $CH_2$—$CH_3$ (3) |
| $CF_2$ | Pyrazinyl | NH—$SO_2$ | Thiazolyl | $Z_1$: $CH_2$—$CH_2$—$CH_3$ or iPr (2) |
| $CF_2$ | Pyrazinyl | NH—$SO_2$ | Thiazolyl | $Z_1$: $CH_2$—$CH_2$—$CH_3$ or iPr (3) |
| $CF_2$ | Pyrazinyl | NH—$SO_2$ | Thiazolyl | $Z_1$: $CH_2F$ (2) |
| $CF_2$ | Pyrazinyl | NH—$SO_2$ | Thiazolyl | $Z_1$: $CH_2F$ (3) |
| $CF_2$ | Pyrazinyl | NH—$SO_2$ | Thiazolyl | $Z_1$: $CHF_2$ (2) |
| $CF_2$ | Pyrazinyl | NH—$SO_2$ | Thiazolyl | $Z_1$: $CHF_2$ (3) |
| $CF_2$ | Pyrazinyl | NH—$SO_2$ | Thiazolyl | $Z_1$: $CF_3$ (2) |
| $CF_2$ | Pyrazinyl | NH—$SO_2$ | Thiazolyl | $Z_1$: $CF_3$ (3) |
| $CF_2$ | Pyrazinyl | NH—$SO_2$ | Thiazolyl | $Z_1$: $CH_2$—$CH_2F$ (2) |
| $CF_2$ | Pyrazinyl | NH—$SO_2$ | Thiazolyl | $Z_1$: $CH_2$—$CH_2F$ (3) |
| $CF_2$ | Pyrazinyl | NH—$SO_2$ | Thiazolyl | $Z_1$: $CH_2$—$CHF_2$ (2) |
| $CF_2$ | Pyrazinyl | NH—$SO_2$ | Thiazolyl | $Z_1$: $CH_2$—$CHF_2$ (3) |
| $CF_2$ | Pyrazinyl | NH—$SO_2$ | Thiazolyl | $Z_1$: $CH_2$—$CF_3$ (2) |
| $CF_2$ | Pyrazinyl | NH—$SO_2$ | Thiazolyl | $Z_1$: $CH_2$—$CF_3$ (3) |
| S | pyridinyl | NH—$CH_2$ | Phenyl | None |
| S | pyridinyl | NH—$CH_2$ | Phenyl | $Z_1$: F (para) |
| S | pyridinyl | NH—$CH_2$ | phenyl | $Z_1$: F (meta) |
| S | pyridinyl | NH—$CH_2$ | phenyl | $Z_1$: F (ortho) |
| S | pyridinyl | NH—$CH_2$ | phenyl | $Z_1$: F (para)<br>$Z_2$: F (meta) |
| S | Pyridinyl | NH—$CH_2$ | Phenyl | $Z_1$: Cl (meta) |
| S | Pyridinyl | NH—$CH_2$ | Phenyl | $Z_1$: Cl (para) |
| S | Pyridinyl | NH—$CH_2$ | Phenyl | $Z_1$: Cl (para)<br>$Z_2$: Cl (meta) |
| S | Pyridinyl | NH—$CH_2$ | Phenyl | $Z_1$: F (para)<br>$Z_2$: Cl (meta) |
| S | Pyridinyl | NH—$CH_2$ | Phenyl | $Z_1$: Cl (para)<br>$Z_2$: F (meta) |
| S | Pyridinyl | NH—$CH_2$ | Phenyl | $Z_1$: $CH_3$ (para) |
| S | Pyridinyl | NH—$CH_2$ | Phenyl | $Z_1$: $CH_3$ (meta) |
| S | Pyridinyl | NH—$CH_2$ | Phenyl | $Z_1$: $CH_3$ (ortho) |
| S | Pyridinyl | NH—$CH_2$ | Phenyl | $Z_1$: $CH_2$—$CH_3$ (para) |
| S | Pyridinyl | NH—$CH_2$ | Phenyl | $Z_1$: $CH_2$—$CH_3$ (meta) |
| S | Pyridinyl | NH—$CH_2$ | Phenyl | $Z_1$: $CH_2$—$CH_3$ (ortho) |
| S | Pyridinyl | NH—$CH_2$ | Phenyl | $Z_1$: $CH_2$—$CH_2$—$CH_3$ or iPr (para) |
| S | Pyridinyl | NH—$CH_2$ | Phenyl | $Z_1$: $CH_2$—$CH_2$—$CH_3$ or iPr (meta) |
| S | Pyridinyl | NH—$CH_2$ | Phenyl | $Z_1$: $CH_2$—$CH_2$—$CH_3$ or iPr (ortho) |
| S | Pyridinyl | NH—$CH_2$ | Phenyl | $Z_1$: $CH_2F$ (para) |
| S | Pyridinyl | NH—$CH_2$ | Phenyl | $Z_1$: $CH_2F$ (meta) |
| S | Pyridinyl | NH—$CH_2$ | Phenyl | $Z_1$: $CH_2F$ (ortho) |
| S | Pyridinyl | NH—$CH_2$ | Phenyl | $Z_1$: $CHF_2$ (para) |
| S | Pyridinyl | NH—$CH_2$ | Phenyl | $Z_1$: $CHF_2$ (meta) |
| S | Pyridinyl | NH—$CH_2$ | Phenyl | $Z_1$: $CHF_2$ (ortho) |
| S | Pyridinyl | NH—$CH_2$ | Phenyl | $Z_1$: $CF_3$ (para) |
| S | Pyridinyl | NH—$CH_2$ | Phenyl | $Z_1$: $CF_3$ (meta) |
| S | Pyridinyl | NH—$CH_2$ | Phenyl | $Z_1$: $CF_3$ (ortho) |
| S | Pyridinyl | NH—$CH_2$ | Phenyl | $Z_1$: $CH_2$—$CH_2F$ (para) |

TABLE 2-continued

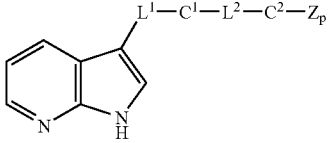

| L¹ | C¹ | L² | C² | Z |
|---|---|---|---|---|
| S | Pyridinyl | NH—CH₂ | Phenyl | $Z_1$: CH₂—CH₂F (meta) |
| S | Pyridinyl | NH—CH₂ | Phenyl | $Z_1$: CH₂—CH₂F (ortho) |
| S | Pyridinyl | NH—CH₂ | Phenyl | $Z_1$: CH₂—CHF₂ (para) |
| S | Pyridinyl | NH—CH₂ | Phenyl | $Z_1$: CH₂—CHF₂ (meta) |
| S | Pyridinyl | NH—CH₂ | Phenyl | $Z_1$: CH₂—CHF₂ (ortho) |
| S | Pyridinyl | NH—CH₂ | Phenyl | $Z_1$: CH₂—CF₃ (para) |
| S | Pyridinyl | NH—CH₂ | Phenyl | $Z_1$: CH₂—CF₃ (meta) |
| S | Pyridinyl | NH—CH₂ | Phenyl | $Z_1$: CH₂—CF₃ (ortho) |
| S | pyridinyl | NH—CH₂ | Pyridinyl | None |
| S | pyridinyl | NH—CH₂ | Pyridinyl | $Z_1$: F (para) |
| S | pyridinyl | NH—CH₂ | Pyridinyl | $Z_1$: F (meta) |
| S | pyridinyl | NH—CH₂ | Pyridinyl | $Z_1$: F (ortho) |
| S | pyridinyl | NH—CH₂ | Pyridinyl | $Z_1$: F (para) $Z_2$: F (meta) |
| S | Pyridinyl | NH—CH₂ | Pyridinyl | $Z_1$: Cl (meta) |
| S | Pyridinyl | NH—CH₂ | Pyridinyl | $Z_1$: Cl (para) |
| S | Pyridinyl | NH—CH₂ | Pyridinyl | $Z_1$: Cl (para) $Z_2$: Cl (meta) |
| S | Pyridinyl | NH—CH₂ | Pyridinyl | $Z_1$: F (para) $Z_2$: Cl (meta) |
| S | Pyridinyl | NH—CH₂ | Pyridinyl | $Z_1$: Cl (para) $Z_2$: F (meta) |
| S | Pyridinyl | NH—CH₂ | Pyridinyl | $Z_1$: CH₃ (para) |
| S | Pyridinyl | NH—CH₂ | Pyridinyl | $Z_1$: CH₃ (meta) |
| S | Pyridinyl | NH—CH₂ | Pyridinyl | $Z_1$: CH₃ (ortho) |
| S | Pyridinyl | NH—CH₂ | Pyridinyl | $Z_1$: CH₂—CH₃ (para) |
| S | Pyridinyl | NH—CH₂ | Pyridinyl | $Z_1$: CH₂—CH₃ (meta) |
| S | Pyridinyl | NH—CH₂ | Pyridinyl | $Z_1$: CH₂—CH₃ (ortho) |
| S | Pyridinyl | NH—CH₂ | Pyridinyl | $Z_1$: CH₂—CH₂—CH₃ or iPr (para) |
| S | Pyridinyl | NH—CH₂ | Pyridinyl | $Z_1$: CH₂—CH₂—CH₃ or iPr (meta) |
| S | Pyridinyl | NH—CH₂ | Pyridinyl | $Z_1$: CH₂—CH₂—CH₃ or iPr (ortho) |
| S | Pyridinyl | NH—CH₂ | Pyridinyl | $Z_1$: CH₂F (para) |
| S | Pyridinyl | NH—CH₂ | Pyridinyl | $Z_1$: CH₂F (meta) |
| S | Pyridinyl | NH—CH₂ | Pyridinyl | $Z_1$: CH₂F (ortho) |
| S | Pyridinyl | NH—CH₂ | Pyridinyl | $Z_1$: CHF₂ (para) |
| S | Pyridinyl | NH—CH₂ | Pyridinyl | $Z_1$: CHF₂ (meta) |
| S | Pyridinyl | NH—CH₂ | Pyridinyl | $Z_1$: CHF₂ (ortho) |
| S | Pyridinyl | NH—CH₂ | Pyridinyl | $Z_1$: CF₃ (para) |
| S | Pyridinyl | NH—CH₂ | Pyridinyl | $Z_1$: CF₃ (meta) |
| S | Pyridinyl | NH—CH₂ | Pyridinyl | $Z_1$: CF₃ (ortho) |
| S | Pyridinyl | NH—CH₂ | Pyridinyl | $Z_1$: CH₂—CH₂F (para) |
| S | Pyridinyl | NH—CH₂ | Pyridinyl | $Z_1$: CH₂—CH₂F (meta) |
| S | Pyridinyl | NH—CH₂ | Pyridinyl | $Z_1$: CH₂—CH₂F (ortho) |
| S | Pyridinyl | NH—CH₂ | Pyridinyl | $Z_1$: CH₂—CHF₂ (para) |
| S | Pyridinyl | NH—CH₂ | Pyridinyl | $Z_1$: CH₂—CHF₂ (meta) |
| S | Pyridinyl | NH—CH₂ | Pyridinyl | $Z_1$: CH₂—CHF₂ (ortho) |
| S | Pyridinyl | NH—CH₂ | Pyridinyl | $Z_1$: CH₂—CF₃ (para) |
| S | Pyridinyl | NH—CH₂ | Pyridinyl | $Z_1$: CH₂—CF₃ (meta) |
| S | Pyridinyl | NH—CH₂ | Pyridinyl | $Z_1$: CH₂—CF₃ (ortho) |
| S | pyridinyl | NH—CH₂ | Pyrimidinyl | None |
| S | pyridinyl | NH—CH₂ | Pyrimidinyl | $Z_1$: F (para) |
| S | pyridinyl | NH—CH₂ | Pyrimidinyl | $Z_1$: F (meta) |
| S | pyridinyl | NH—CH₂ | Pyrimidinyl | $Z_1$: F (ortho) |
| S | pyridinyl | NH—CH₂ | Pyrimidinyl | $Z_1$: F (para) $Z_2$: F (meta) |
| S | Pyridinyl | NH—CH₂ | Pyrimidinyl | $Z_1$: Cl (meta) |
| S | Pyridinyl | NH—CH₂ | Pyrimidinyl | $Z_1$: Cl (para) |
| S | Pyridinyl | NH—CH₂ | Pyrimidinyl | $Z_1$: Cl (para) $Z_2$: Cl (meta) |
| S | Pyridinyl | NH—CH₂ | Pyrimidinyl | $Z_1$: F (para) $Z_2$: Cl (meta) |
| S | Pyridinyl | NH—CH₂ | Pyrimidinyl | $Z_1$: Cl (para) $Z_2$: F (meta) |
| S | Pyridinyl | NH—CH₂ | Pyrimidinyl | $Z_1$: CH₃ (para) |
| S | Pyridinyl | NH—CH₂ | Pyrimidinyl | $Z_1$: CH₃ (meta) |
| S | Pyridinyl | NH—CH₂ | Pyrimidinyl | $Z_1$: CH₃ (ortho) |

TABLE 2-continued

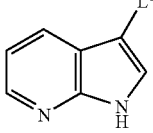

| L¹ | C¹ | L² | C² | Z |
|---|---|---|---|---|
| S | Pyridinyl | NH—CH₂ | Pyrimidinyl | $Z_1$: CH₂—CH₃ (para) |
| S | Pyridinyl | NH—CH₂ | Pyrimidinyl | $Z_1$: CH₂—CH₃ (meta) |
| S | Pyridinyl | NH—CH₂ | Pyrimidinyl | $Z_1$: CH₂—CH₃ (ortho) |
| S | Pyridinyl | NH—CH₂ | Pyrimidinyl | $Z_1$: CH₂—CH₂—CH₃ or iPr (para) |
| S | Pyridinyl | NH—CH₂ | Pyrimidinyl | $Z_1$: CH₂—CH₂—CH₃ or iPr (meta) |
| S | Pyridinyl | NH—CH₂ | Pyrimidinyl | $Z_1$: CH₂—CH₂—CH₃ or iPr (ortho) |
| S | Pyridinyl | NH—CH₂ | Pyrimidinyl | $Z_1$: CH₂F (para) |
| S | Pyridinyl | NH—CH₂ | Pyrimidinyl | $Z_1$: CH₂F (meta) |
| S | Pyridinyl | NH—CH₂ | Pyrimidinyl | $Z_1$: CH₂F (ortho) |
| S | Pyridinyl | NH—CH₂ | Pyrimidinyl | $Z_1$: CHF₂ (para) |
| S | Pyridinyl | NH—CH₂ | Pyrimidinyl | $Z_1$: CHF₂ (meta) |
| S | Pyridinyl | NH—CH₂ | Pyrimidinyl | $Z_1$: CHF₂ (ortho) |
| S | Pyridinyl | NH—CH₂ | Pyrimidinyl | $Z_1$: CF₃ (para) |
| S | Pyridinyl | NH—CH₂ | Pyrimidinyl | $Z_1$: CF₃ (meta) |
| S | Pyridinyl | NH—CH₂ | Pyrimidinyl | $Z_1$: CF₃ (ortho) |
| S | Pyridinyl | NH—CH₂ | Pyrimidinyl | $Z_1$: CH₂—CH₂F (para) |
| S | Pyridinyl | NH—CH₂ | Pyrimidinyl | $Z_1$: CH₂—CH₂F (meta) |
| S | Pyridinyl | NH—CH₂ | Pyrimidinyl | $Z_1$: CH₂—CH₂F (ortho) |
| S | Pyridinyl | NH—CH₂ | Pyrimidinyl | $Z_1$: CH₂—CHF₂ (para) |
| S | Pyridinyl | NH—CH₂ | Pyrimidinyl | $Z_1$: CH₂—CHF₂ (meta) |
| S | Pyridinyl | NH—CH₂ | Pyrimidinyl | $Z_1$: CH₂—CHF₂ (ortho) |
| S | Pyridinyl | NH—CH₂ | Pyrimidinyl | $Z_1$: CH₂—CF₃ (para) |
| S | Pyridinyl | NH—CH₂ | Pyrimidinyl | $Z_1$: CH₂—CF₃ (meta) |
| S | Pyridinyl | NH—CH₂ | Pyrimidinyl | $Z_1$: CH₂—CF₃ (ortho) |
| S | pyridinyl | NH—CH₂ | Pyrazinyl | None |
| S | pyridinyl | NH—CH₂ | Pyrazinyl | $Z_1$: F (para) |
| S | pyridinyl | NH—CH₂ | Pyrazinyl | $Z_1$: F (meta) |
| S | pyridinyl | NH—CH₂ | Pyrazinyl | $Z_1$: F (ortho) |
| S | pyridinyl | NH—CH₂ | Pyrazinyl | $Z_1$: F (para) $Z_2$: F (meta) |
| S | Pyridinyl | NH—CH₂ | Pyrazinyl | $Z_1$: Cl (meta) |
| S | Pyridinyl | NH—CH₂ | Pyrazinyl | $Z_1$: Cl (para) |
| S | Pyridinyl | NH—CH₂ | Pyrazinyl | $Z_1$: Cl (para) $Z_2$: Cl (meta) |
| S | Pyridinyl | NH—CH₂ | Pyrazinyl | $Z_1$: F (para) $Z_2$: Cl (meta) |
| S | Pyridinyl | NH—CH₂ | Pyrazinyl | $Z_1$: Cl (para) $Z_2$: F (meta) |
| S | Pyridinyl | NH—CH₂ | Pyrazinyl | $Z_1$: CH₃ (para) |
| S | Pyridinyl | NH—CH₂ | Pyrazinyl | $Z_1$: CH₃ (meta) |
| S | Pyridinyl | NH—CH₂ | Pyrazinyl | $Z_1$: CH₃ (ortho) |
| S | Pyridinyl | NH—CH₂ | Pyrazinyl | $Z_1$: CH₂—CH₃ (para) |
| S | Pyridinyl | NH—CH₂ | Pyrazinyl | $Z_1$: CH₂—CH₃ (meta) |
| S | Pyridinyl | NH—CH₂ | Pyrazinyl | $Z_1$: CH₂—CH₃ (ortho) |
| S | Pyridinyl | NH—CH₂ | Pyrazinyl | $Z_1$: CH₂—CH₂—CH₃ or iPr (para) |
| S | Pyridinyl | NH—CH₂ | Pyrazinyl | $Z_1$: CH₂—CH₂—CH₃ or iPr (meta) |
| S | Pyridinyl | NH—CH₂ | Pyrazinyl | $Z_1$: CH₂—CH₂—CH₃ or iPr (ortho) |
| S | Pyridinyl | NH—CH₂ | Pyrazinyl | $Z_1$: CH₂F (para) |
| S | Pyridinyl | NH—CH₂ | Pyrazinyl | $Z_1$: CH₂F (meta) |
| S | Pyridinyl | NH—CH₂ | Pyrazinyl | $Z_1$: CH₂F (ortho) |
| S | Pyridinyl | NH—CH₂ | Pyrazinyl | $Z_1$: CHF₂ (para) |
| S | Pyridinyl | NH—CH₂ | Pyrazinyl | $Z_1$: CHF₂ (meta) |
| S | Pyridinyl | NH—CH₂ | Pyrazinyl | $Z_1$: CHF₂ (ortho) |
| S | Pyridinyl | NH—CH₂ | Pyrazinyl | $Z_1$: CF₃ (para) |
| S | Pyridinyl | NH—CH₂ | Pyrazinyl | $Z_1$: CF₃ (meta) |
| S | Pyridinyl | NH—CH₂ | Pyrazinyl | $Z_1$: CF₃ (ortho) |
| S | Pyridinyl | NH—CH₂ | Pyrazinyl | $Z_1$: CH₂—CH₂F (para) |
| S | Pyridinyl | NH—CH₂ | Pyrazinyl | $Z_1$: CH₂—CH₂F (meta) |
| S | Pyridinyl | NH—CH₂ | Pyrazinyl | $Z_1$: CH₂—CH₂F (ortho) |
| S | Pyridinyl | NH—CH₂ | Pyrazinyl | $Z_1$: CH₂—CHF₂ (para) |
| S | Pyridinyl | NH—CH₂ | Pyrazinyl | $Z_1$: CH₂—CHF₂ (meta) |
| S | Pyridinyl | NH—CH₂ | Pyrazinyl | $Z_1$: CH₂—CHF₂ (ortho) |
| S | Pyridinyl | NH—CH₂ | Pyrazinyl | $Z_1$: CH₂—CF₃ (para) |

TABLE 2-continued

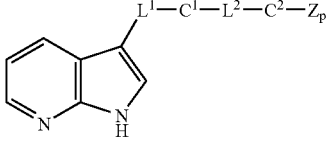

| L¹ | C¹ | L² | C² | Z |
|---|---|---|---|---|
| S | Pyridinyl | NH—CH₂ | Pyrazinyl | $Z_1$: CH₂—CF₃ (meta) |
| S | Pyridinyl | NH—CH₂ | Pyrazinyl | $Z_1$: CH₂—CF₃ (ortho) |
| S | pyridinyl | NH—CH₂ | Pyrrolyl | None |
| S | pyridinyl | NH—CH₂ | Pyrrolyl | $Z_1$: F (2) |
| S | pyridinyl | NH—CH₂ | Pyrrolyl | $Z_1$: F (3) |
| S | pyridinyl | NH—CH₂ | Pyrrolyl | $Z_1$: F (2) $Z_2$: F (3) |
| S | Pyridinyl | NH—CH₂ | Pyrrolyl | $Z_1$: Cl (2) |
| S | Pyridinyl | NH—CH₂ | Pyrrolyl | $Z_1$: Cl (3) |
| S | Pyridinyl | NH—CH₂ | Pyrrolyl | $Z_1$: Cl (2) $Z_2$: Cl (3) |
| S | Pyridinyl | NH—CH₂ | Pyrrolyl | $Z_1$: F (2) $Z_2$: Cl (3) |
| S | Pyridinyl | NH—CH₂ | Pyrrolyl | $Z_1$: Cl (2) $Z_2$: F (3) |
| S | Pyridinyl | NH—CH₂ | Pyrrolyl | $Z_1$: CH₃ (2) |
| S | Pyridinyl | NH—CH₂ | Pyrrolyl | $Z_1$: CH₃ (3) |
| S | Pyridinyl | NH—CH₂ | Pyrrolyl | $Z_1$: CH₂—CH₃ (2) |
| S | Pyridinyl | NH—CH₂ | Pyrrolyl | $Z_1$: CH₂—CH₃ (3) |
| S | Pyridinyl | NH—CH₂ | Pyrrolyl | $Z_1$: CH₂—CH₂—CH₃ or iPr (2) |
| S | Pyridinyl | NH—CH₂ | Pyrrolyl | $Z_1$: CH₂—CH₂—CH₃ or iPr (3) |
| S | Pyridinyl | NH—CH₂ | Pyrrolyl | $Z_1$: CH₂F (2) |
| S | Pyridinyl | NH—CH₂ | Pyrrolyl | $Z_1$: CH₂F (3) |
| S | Pyridinyl | NH—CH₂ | Pyrrolyl | $Z_1$: CHF₂ (2) |
| S | Pyridinyl | NH—CH₂ | Pyrrolyl | $Z_1$: CHF₂ (3) |
| S | Pyridinyl | NH—CH₂ | Pyrrolyl | $Z_1$: CF₃ (2) |
| S | Pyridinyl | NH—CH₂ | Pyrrolyl | $Z_1$: CF₃ (3) |
| S | Pyridinyl | NH—CH₂ | Pyrrolyl | $Z_1$: CH₂—CH₂F (2) |
| S | Pyridinyl | NH—CH₂ | Pyrrolyl | $Z_1$: CH₂—CH₂F (3) |
| S | Pyridinyl | NH—CH₂ | Pyrrolyl | $Z_1$: CH₂—CHF₂ (2) |
| S | Pyridinyl | NH—CH₂ | Pyrrolyl | $Z_1$: CH₂—CHF₂ (3) |
| S | Pyridinyl | NH—CH₂ | Pyrrolyl | $Z_1$: CH₂—CF₃ (2) |
| S | Pyridinyl | NH—CH₂ | Pyrrolyl | $Z_1$: CH₂—CF₃ (3) |
| S | pyridinyl | NH—CH₂ | Imidazolyl | None |
| S | pyridinyl | NH—CH₂ | Imidazolyl | $Z_1$: F (2) |
| S | pyridinyl | NH—CH₂ | Imidazolyl | $Z_1$: F (3) |
| S | pyridinyl | NH—CH₂ | Imidazolyl | $Z_1$: F (2) $Z_2$: F (3) |
| S | Pyridinyl | NH—CH₂ | Imidazolyl | $Z_1$: Cl (2) |
| S | Pyridinyl | NH—CH₂ | Imidazolyl | $Z_1$: Cl (3) |
| S | Pyridinyl | NH—CH₂ | Imidazolyl | $Z_1$: Cl (2) $Z_2$: Cl (3) |
| S | Pyridinyl | NH—CH₂ | Imidazolyl | $Z_1$: F (2) $Z_2$: Cl (3) |
| S | Pyridinyl | NH—CH₂ | Imidazolyl | $Z_1$: Cl (2) $Z_2$: F (3) |
| S | Pyridinyl | NH—CH₂ | Imidazolyl | $Z_1$: CH₃ (2) |
| S | Pyridinyl | NH—CH₂ | Imidazolyl | $Z_1$: CH₃ (3) |
| S | Pyridinyl | NH—CH₂ | Imidazolyl | $Z_1$: CH₂—CH₃ (2) |
| S | Pyridinyl | NH—CH₂ | Imidazolyl | $Z_1$: CH₂—CH₃ (3) |
| S | Pyridinyl | NH—CH₂ | Imidazolyl | $Z_1$: CH₂—CH₂—CH₃ or iPr (2) |
| S | Pyridinyl | NH—CH₂ | Imidazolyl | $Z_1$: CH₂—CH₂—CH₃ or iPr (3) |
| S | Pyridinyl | NH—CH₂ | Imidazolyl | $Z_1$: CH₂F (2) |
| S | Pyridinyl | NH—CH₂ | Imidazolyl | $Z_1$: CH₂F (3) |
| S | Pyridinyl | NH—CH₂ | Imidazolyl | $Z_1$: CHF₂ (2) |
| S | Pyridinyl | NH—CH₂ | Imidazolyl | $Z_1$: CHF₂ (3) |
| S | Pyridinyl | NH—CH₂ | Imidazolyl | $Z_1$: CF₃ (2) |
| S | Pyridinyl | NH—CH₂ | Imidazolyl | $Z_1$: CF₃ (3) |
| S | Pyridinyl | NH—CH₂ | Imidazolyl | $Z_1$: CH₂—CH₂F (2) |
| S | Pyridinyl | NH—CH₂ | Imidazolyl | $Z_1$: CH₂—CH₂F (3) |
| S | Pyridinyl | NH—CH₂ | Imidazolyl | $Z_1$: CH₂—CHF₂ (2) |
| S | Pyridinyl | NH—CH₂ | Imidazolyl | $Z_1$: CH₂—CHF₂ (3) |
| S | Pyridinyl | NH—CH₂ | Imidazolyl | $Z_1$: CH₂—CF₃ (2) |
| S | Pyridinyl | NH—CH₂ | Imidazolyl | $Z_1$: CH₂—CF₃ (3) |
| S | pyridinyl | NH—CH₂ | Furanyl | None |
| S | pyridinyl | NH—CH₂ | Furanyl | $Z_1$: F (2) |
| S | pyridinyl | NH—CH₂ | Furanyl | $Z_1$: F (3) |
| S | pyridinyl | NH—CH₂ | Furanyl | $Z_1$: F (2) $Z_2$: F (3) |

TABLE 2-continued

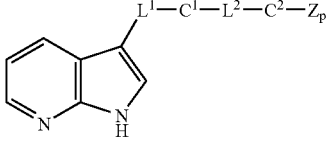

| $L^1$ | $C^1$ | $L^2$ | $C^2$ | Z |
|---|---|---|---|---|
| S | Pyridinyl | NH—CH$_2$ | Furanyl | $Z_1$: Cl (2) |
| S | Pyridinyl | NH—CH$_2$ | Furanyl | $Z_1$: Cl (3) |
| S | Pyridinyl | NH—CH$_2$ | Furanyl | $Z_1$: Cl (2) |
|   |   |   |   | $Z_2$: Cl (3) |
| S | Pyridinyl | NH—CH$_2$ | Furanyl | $Z_1$: F (2) |
|   |   |   |   | $Z_2$: Cl (3) |
| S | Pyridinyl | NH—CH$_2$ | Furanyl | $Z_1$: Cl (2) |
|   |   |   |   | $Z_2$: F (3) |
| S | Pyridinyl | NH—CH$_2$ | Furanyl | $Z_1$: CH$_3$ (2) |
| S | Pyridinyl | NH—CH$_2$ | Furanyl | $Z_1$: CH$_3$ (3) |
| S | Pyridinyl | NH—CH$_2$ | Furanyl | $Z_1$: CH$_2$—CH$_3$ (2) |
| S | Pyridinyl | NH—CH$_2$ | Furanyl | $Z_1$: CH$_2$—CH$_3$ (3) |
| S | Pyridinyl | NH—CH$_2$ | Furanyl | $Z_1$: CH$_2$—CH$_2$—CH$_3$ or iPr (2) |
| S | Pyridinyl | NH—CH$_2$ | Furanyl | $Z_1$: CH$_2$—CH$_2$—CH$_3$ or iPr (3) |
| S | Pyridinyl | NH—CH$_2$ | Furanyl | $Z_1$: CH$_2$F (2) |
| S | Pyridinyl | NH—CH$_2$ | Furanyl | $Z_1$: CH$_2$F (3) |
| S | Pyridinyl | NH—CH$_2$ | Furanyl | $Z_1$: CHF$_2$ (2) |
| S | Pyridinyl | NH—CH$_2$ | Furanyl | $Z_1$: CHF$_2$ (3) |
| S | Pyridinyl | NH—CH$_2$ | Furanyl | $Z_1$: CF$_3$ (2) |
| S | Pyridinyl | NH—CH$_2$ | Furanyl | $Z_1$: CF$_3$ (3) |
| S | Pyridinyl | NH—CH$_2$ | Furanyl | $Z_1$: CH$_2$—CH$_2$F (2) |
| S | Pyridinyl | NH—CH$_2$ | Furanyl | $Z_1$: CH$_2$—CH$_2$F (3) |
| S | Pyridinyl | NH—CH$_2$ | Furanyl | $Z_1$: CH$_2$—CHF$_2$ (2) |
| S | Pyridinyl | NH—CH$_2$ | Furanyl | $Z_1$: CH$_2$—CHF$_2$ (3) |
| S | Pyridinyl | NH—CH$_2$ | Furanyl | $Z_1$: CH$_2$—CF$_3$ (2) |
| S | Pyridinyl | NH—CH$_2$ | Furanyl | $Z_1$: CH$_2$—CF$_3$ (3) |
| S | pyridinyl | NH—CH$_2$ | Oxazolyl | None |
| S | pyridinyl | NH—CH$_2$ | Oxazolyl | $Z_1$: F (2) |
| S | pyridinyl | NH—CH$_2$ | Oxazolyl | $Z_1$: F (3) |
| S | pyridinyl | NH—CH$_2$ | Oxazolyl | $Z_1$: F (2) |
|   |   |   |   | $Z_2$: F (3) |
| S | Pyridinyl | NH—CH$_2$ | Oxazolyl | $Z_1$: Cl (2) |
| S | Pyridinyl | NH—CH$_2$ | Oxazolyl | $Z_1$: Cl (3) |
| S | Pyridinyl | NH—CH$_2$ | Oxazolyl | $Z_1$: Cl (2) |
|   |   |   |   | $Z_2$: Cl (3) |
| S | Pyridinyl | NH—CH$_2$ | Oxazolyl | $Z_1$: F (2) |
|   |   |   |   | $Z_2$: Cl (3) |
| S | Pyridinyl | NH—CH$_2$ | Oxazolyl | $Z_1$: Cl (2) |
|   |   |   |   | $Z_2$: F (3) |
| S | Pyridinyl | NH—CH$_2$ | Oxazolyl | $Z_1$: CH$_3$ (2) |
| S | Pyridinyl | NH—CH$_2$ | Oxazolyl | $Z_1$: CH$_3$ (3) |
| S | Pyridinyl | NH—CH$_2$ | Oxazolyl | $Z_1$: CH$_2$—CH$_3$ (2) |
| S | Pyridinyl | NH—CH$_2$ | Oxazolyl | $Z_1$: CH$_2$—CH$_3$ (3) |
| S | Pyridinyl | NH—CH$_2$ | Oxazolyl | $Z_1$: CH$_2$—CH$_2$—CH$_3$ or iPr (2) |
| S | Pyridinyl | NH—CH$_2$ | Oxazolyl | $Z_1$: CH$_2$—CH$_2$—CH$_3$ or iPr (3) |
| S | Pyridinyl | NH—CH$_2$ | Oxazolyl | $Z_1$: CH$_2$F (2) |
| S | Pyridinyl | NH—CH$_2$ | Oxazolyl | $Z_1$: CH$_2$F (3) |
| S | Pyridinyl | NH—CH$_2$ | Oxazolyl | $Z_1$: CHF$_2$ (2) |
| S | Pyridinyl | NH—CH$_2$ | Oxazolyl | $Z_1$: CHF$_2$ (3) |
| S | Pyridinyl | NH—CH$_2$ | Oxazolyl | $Z_1$: CF$_3$ (2) |
| S | Pyridinyl | NH—CH$_2$ | Oxazolyl | $Z_1$: CF$_3$ (3) |
| S | Pyridinyl | NH—CH$_2$ | Oxazolyl | $Z_1$: CH$_2$—CH$_2$F (2) |
| S | Pyridinyl | NH—CH$_2$ | Oxazolyl | $Z_1$: CH$_2$—CH$_2$F (3) |
| S | Pyridinyl | NH—CH$_2$ | Oxazolyl | $Z_1$: CH$_2$—CHF$_2$ (2) |
| S | Pyridinyl | NH—CH$_2$ | Oxazolyl | $Z_1$: CH$_2$—CHF$_2$ (3) |
| S | Pyridinyl | NH—CH$_2$ | Oxazolyl | $Z_1$: CH$_2$—CF$_3$ (2) |
| S | Pyridinyl | NH—CH$_2$ | Oxazolyl | $Z_1$: CH$_2$—CF$_3$ (3) |
| S | pyridinyl | NH—CH$_2$ | Thiophenyl | None |
| S | pyridinyl | NH—CH$_2$ | Thiophenyl | $Z_1$: F (2) |
| S | pyridinyl | NH—CH$_2$ | Thiophenyl | $Z_1$: F (3) |
| S | pyridinyl | NH—CH$_2$ | Thiophenyl | $Z_1$: F (2) |
|   |   |   |   | $Z_2$: F (3) |
| S | Pyridinyl | NH—CH$_2$ | Thiophenyl | $Z_1$: Cl (2) |
| S | Pyridinyl | NH—CH$_2$ | Thiophenyl | $Z_1$: Cl (3) |
| S | Pyridinyl | NH—CH$_2$ | Thiophenyl | $Z_1$: Cl (2) |
|   |   |   |   | $Z_2$: Cl (3) |
| S | Pyridinyl | NH—CH$_2$ | Thiophenyl | $Z_1$: F (2) |
|   |   |   |   | $Z_2$: Cl (3) |

TABLE 2-continued

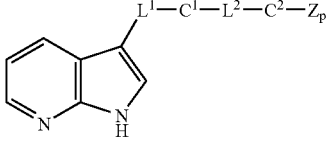

| $L^1$ | $C^1$ | $L^2$ | $C^2$ | Z |
|---|---|---|---|---|
| S | Pyridinyl | NH—CH$_2$ | Thiophenyl | $Z_1$: Cl (2) |
|   |           |           |            | $Z_2$: F (3) |
| S | Pyridinyl | NH—CH$_2$ | Thiophenyl | $Z_1$: CH$_3$ (2) |
| S | Pyridinyl | NH—CH$_2$ | Thiophenyl | $Z_1$: CH$_3$ (3) |
| S | Pyridinyl | NH—CH$_2$ | Thiophenyl | $Z_1$: CH$_2$—CH$_3$ (2) |
| S | Pyridinyl | NH—CH$_2$ | Thiophenyl | $Z_1$: CH$_2$—CH$_3$ (3) |
| S | Pyridinyl | NH—CH$_2$ | Thiophenyl | $Z_1$: CH$_2$—CH$_2$—CH$_3$ or iPr (2) |
| S | Pyridinyl | NH—CH$_2$ | Thiophenyl | $Z_1$: CH$_2$—CH$_2$—CH$_3$ or iPr (3) |
| S | Pyridinyl | NH—CH$_2$ | Thiophenyl | $Z_1$: CH$_2$F (2) |
| S | Pyridinyl | NH—CH$_2$ | Thiophenyl | $Z_1$: CH$_2$F (3) |
| S | Pyridinyl | NH—CH$_2$ | Thiophenyl | $Z_1$: CHF$_2$ (2) |
| S | Pyridinyl | NH—CH$_2$ | Thiophenyl | $Z_1$: CHF$_2$ (3) |
| S | Pyridinyl | NH—CH$_2$ | Thiophenyl | $Z_1$: CF$_3$ (2) |
| S | Pyridinyl | NH—CH$_2$ | Thiophenyl | $Z_1$: CF$_3$ (3) |
| S | Pyridinyl | NH—CH$_2$ | Thiophenyl | $Z_1$: CH$_2$—CH$_2$F (2) |
| S | Pyridinyl | NH—CH$_2$ | Thiophenyl | $Z_1$: CH$_2$—CH$_2$F (3) |
| S | Pyridinyl | NH—CH$_2$ | Thiophenyl | $Z_1$: CH$_2$—CHF$_2$ (2) |
| S | Pyridinyl | NH—CH$_2$ | Thiophenyl | $Z_1$: CH$_2$—CHF$_2$ (3) |
| S | Pyridinyl | NH—CH$_2$ | Thiophenyl | $Z_1$: CH$_2$—CF$_3$ (2) |
| S | Pyridinyl | NH—CH$_2$ | Thiophenyl | $Z_1$: CH$_2$—CF$_3$ (3) |
| S | pyridinyl | NH—CH$_2$ | Thiazolyl | None |
| S | pyridinyl | NH—CH$_2$ | Thiazolyl | $Z_1$: F (2) |
| S | pyridinyl | NH—CH$_2$ | Thiazolyl | $Z_1$: F (3) |
| S | pyridinyl | NH—CH$_2$ | Thiazolyl | $Z_1$: F (2) |
|   |           |           |            | $Z_2$: F (3) |
| S | Pyridinyl | NH—CH$_2$ | Thiazolyl | $Z_1$: Cl (2) |
| S | Pyridinyl | NH—CH$_2$ | Thiazolyl | $Z_1$: Cl (3) |
| S | Pyridinyl | NH—CH$_2$ | Thiazolyl | $Z_1$: Cl (2) |
|   |           |           |            | $Z_2$: Cl (3) |
| S | Pyridinyl | NH—CH$_2$ | Thiazolyl | $Z_1$: F (2) |
|   |           |           |            | $Z_2$: Cl (3) |
| S | Pyridinyl | NH—CH$_2$ | Thiazolyl | $Z_1$: Cl (2) |
|   |           |           |            | $Z_2$: F (3) |
| S | Pyridinyl | NH—CH$_2$ | Thiazolyl | $Z_1$: CH$_3$ (2) |
| S | Pyridinyl | NH—CH$_2$ | Thiazolyl | $Z_1$: CH$_3$ (3) |
| S | Pyridinyl | NH—CH$_2$ | Thiazolyl | $Z_1$: CH$_2$—CH$_3$ (2) |
| S | Pyridinyl | NH—CH$_2$ | Thiazolyl | $Z_1$: CH$_2$—CH$_3$ (3) |
| S | Pyridinyl | NH—CH$_2$ | Thiazolyl | $Z_1$: CH$_2$—CH$_2$—CH$_3$ or iPr (2) |
| S | Pyridinyl | NH—CH$_2$ | Thiazolyl | $Z_1$: CH$_2$—CH$_2$—CH$_3$ or iPr (3) |
| S | Pyridinyl | NH—CH$_2$ | Thiazolyl | $Z_1$: CH$_2$F (2) |
| S | Pyridinyl | NH—CH$_2$ | Thiazolyl | $Z_1$: CH$_2$F (3) |
| S | Pyridinyl | NH—CH$_2$ | Thiazolyl | $Z_1$: CHF$_2$ (2) |
| S | Pyridinyl | NH—CH$_2$ | Thiazolyl | $Z_1$: CHF$_2$ (3) |
| S | Pyridinyl | NH—CH$_2$ | Thiazolyl | $Z_1$: CF$_3$ (2) |
| S | Pyridinyl | NH—CH$_2$ | Thiazolyl | $Z_1$: CF$_3$ (3) |
| S | Pyridinyl | NH—CH$_2$ | Thiazolyl | $Z_1$: CH$_2$—CH$_2$F (2) |
| S | Pyridinyl | NH—CH$_2$ | Thiazolyl | $Z_1$: CH$_2$—CH$_2$F (3) |
| S | Pyridinyl | NH—CH$_2$ | Thiazolyl | $Z_1$: CH$_2$—CHF$_2$ (2) |
| S | Pyridinyl | NH—CH$_2$ | Thiazolyl | $Z_1$: CH$_2$—CHF$_2$ (3) |
| S | Pyridinyl | NH—CH$_2$ | Thiazolyl | $Z_1$: CH$_2$—CF$_3$ (2) |
| S | Pyridinyl | NH—CH$_2$ | Thiazolyl | $Z_1$: CH$_2$—CF$_3$ (3) |
| S | pyridinyl | NH—C(O) | Phenyl | None |
| S | pyridinyl | NH—C(O) | Phenyl | $Z_1$: F (para) |
| S | pyridinyl | NH—C(O) | phenyl | $Z_1$: F (meta) |
| S | pyridinyl | NH—C(O) | phenyl | $Z_1$: F (ortho) |
| S | pyridinyl | NH—C(O) | phenyl | $Z_1$: F (para) |
|   |           |         |        | $Z_2$: F (meta) |
| S | Pyridinyl | NH—C(O) | Phenyl | $Z_1$: Cl (meta) |
| S | Pyridinyl | NH—C(O) | Phenyl | $Z_1$: Cl (para) |
| S | Pyridinyl | NH—C(O) | Phenyl | $Z_1$: Cl (para) |
|   |           |         |        | $Z_2$: Cl (meta) |
| S | Pyridinyl | NH—C(O) | Phenyl | $Z_1$: F (para) |
|   |           |         |        | $Z_2$: Cl (meta) |
| S | Pyridinyl | NH—C(O) | Phenyl | $Z_1$: Cl (para) |
|   |           |         |        | $Z_2$: F (meta) |
| S | Pyridinyl | NH—C(O) | Phenyl | $Z_1$: CH$_3$ (para) |
| S | Pyridinyl | NH—C(O) | Phenyl | $Z_1$: CH$_3$ (meta) |
| S | Pyridinyl | NH—C(O) | Phenyl | $Z_1$: CH$_3$ (ortho) |
| S | Pyridinyl | NH—C(O) | Phenyl | $Z_1$: CH$_2$—CH$_3$ (para) |

TABLE 2-continued

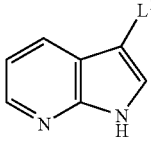

| L¹ | C¹ | L² | C² | Z |
|---|---|---|---|---|
| S | Pyridinyl | NH—C(O) | Phenyl | $Z_1$: $CH_2$—$CH_3$ (meta) |
| S | Pyridinyl | NH—C(O) | Phenyl | $Z_1$: $CH_2$—$CH_3$ (ortho) |
| S | Pyridinyl | NH—C(O) | Phenyl | $Z_1$: $CH_2$—$CH_2$—$CH_3$ or iPr (para) |
| S | Pyridinyl | NH—C(O) | Phenyl | $Z_1$: $CH_2$—$CH_2$—$CH_3$ or iPr (meta) |
| S | Pyridinyl | NH—C(O) | Phenyl | $Z_1$: $CH_2$—$CH_2$—$CH_3$ or iPr (ortho) |
| S | Pyridinyl | NH—C(O) | Phenyl | $Z_1$: $CH_2F$ (para) |
| S | Pyridinyl | NH—C(O) | Phenyl | $Z_1$: $CH_2F$ (meta) |
| S | Pyridinyl | NH—C(O) | Phenyl | $Z_1$: $CH_2F$ (ortho) |
| S | Pyridinyl | NH—C(O) | Phenyl | $Z_1$: $CHF_2$ (para) |
| S | Pyridinyl | NH—C(O) | Phenyl | $Z_1$: $CHF_2$ (meta) |
| S | Pyridinyl | NH—C(O) | Phenyl | $Z_1$: $CHF_2$ (ortho) |
| S | Pyridinyl | NH—C(O) | Phenyl | $Z_1$: $CF_3$ (para) |
| S | Pyridinyl | NH—C(O) | Phenyl | $Z_1$: $CF_3$ (meta) |
| S | Pyridinyl | NH—C(O) | Phenyl | $Z_1$: $CF_3$ (ortho) |
| S | Pyridinyl | NH—C(O) | Phenyl | $Z_1$: $CH_2$—$CH_2F$ (para) |
| S | Pyridinyl | NH—C(O) | Phenyl | $Z_1$: $CH_2$—$CH_2F$ (meta) |
| S | Pyridinyl | NH—C(O) | Phenyl | $Z_1$: $CH_2$—$CH_2F$ (ortho) |
| S | Pyridinyl | NH—C(O) | Phenyl | $Z_1$: $CH_2$—$CHF_2$ (para) |
| S | Pyridinyl | NH—C(O) | Phenyl | $Z_1$: $CH_2$—$CHF_2$ (meta) |
| S | Pyridinyl | NH—C(O) | Phenyl | $Z_1$: $CH_2$—$CHF_2$ (ortho) |
| S | Pyridinyl | NH—C(O) | Phenyl | $Z_1$: $CH_2$—$CF_3$ (para) |
| S | Pyridinyl | NH—C(O) | Phenyl | $Z_1$: $CH_2$—$CF_3$ (meta) |
| S | Pyridinyl | NH—C(O) | Phenyl | $Z_1$: $CH_2$—$CF_3$ (ortho) |
| S | pyridinyl | NH—C(O) | Pyridinyl | None |
| S | pyridinyl | NH—C(O) | Pyridinyl | $Z_1$: F (para) |
| S | pyridinyl | NH—C(O) | Pyridinyl | $Z_1$: F (meta) |
| S | pyridinyl | NH—C(O) | Pyridinyl | $Z_1$: F (ortho) |
| S | pyridinyl | NH—C(O) | Pyridinyl | $Z_1$: F (para) $Z_2$: F (meta) |
| S | Pyridinyl | NH—C(O) | Pyridinyl | $Z_1$: Cl (meta) |
| S | Pyridinyl | NH—C(O) | Pyridinyl | $Z_1$: Cl (para) |
| S | Pyridinyl | NH—C(O) | Pyridinyl | $Z_1$: Cl (para) $Z_2$: Cl (meta) |
| S | Pyridinyl | NH—C(O) | Pyridinyl | $Z_1$: F (para) $Z_2$: Cl (meta) |
| S | Pyridinyl | NH—C(O) | Pyridinyl | $Z_1$: Cl (para) $Z_2$: F (meta) |
| S | Pyridinyl | NH—C(O) | Pyridinyl | $Z_1$: $CH_3$ (para) |
| S | Pyridinyl | NH—C(O) | Pyridinyl | $Z_1$: $CH_3$ (meta) |
| S | Pyridinyl | NH—C(O) | Pyridinyl | $Z_1$: $CH_3$ (ortho) |
| S | Pyridinyl | NH—C(O) | Pyridinyl | $Z_1$: $CH_2$—$CH_3$ (para) |
| S | Pyridinyl | NH—C(O) | Pyridinyl | $Z_1$: $CH_2$—$CH_3$ (meta) |
| S | Pyridinyl | NH—C(O) | Pyridinyl | $Z_1$: $CH_2$—$CH_3$ (ortho) |
| S | Pyridinyl | NH—C(O) | Pyridinyl | $Z_1$: $CH_2$—$CH_2$—$CH_3$ or iPr (para) |
| S | Pyridinyl | NH—C(O) | Pyridinyl | $Z_1$: $CH_2$—$CH_2$—$CH_3$ or iPr (meta) |
| S | Pyridinyl | NH—C(O) | Pyridinyl | $Z_1$: $CH_2$—$CH_2$—$CH_3$ or iPr (ortho) |
| S | Pyridinyl | NH—C(O) | Pyridinyl | $Z_1$: $CH_2F$ (para) |
| S | Pyridinyl | NH—C(O) | Pyridinyl | $Z_1$: $CH_2F$ (meta) |
| S | Pyridinyl | NH—C(O) | Pyridinyl | $Z_1$: $CH_2F$ (ortho) |
| S | Pyridinyl | NH—C(O) | Pyridinyl | $Z_1$: $CHF_2$ (para) |
| S | Pyridinyl | NH—C(O) | Pyridinyl | $Z_1$: $CHF_2$ (meta) |
| S | Pyridinyl | NH—C(O) | Pyridinyl | $Z_1$: $CHF_2$ (ortho) |
| S | Pyridinyl | NH—C(O) | Pyridinyl | $Z_1$: $CF_3$ (para) |
| S | Pyridinyl | NH—C(O) | Pyridinyl | $Z_1$: $CF_3$ (meta) |
| S | Pyridinyl | NH—C(O) | Pyridinyl | $Z_1$: $CF_3$ (ortho) |
| S | Pyridinyl | NH—C(O) | Pyridinyl | $Z_1$: $CH_2$—$CH_2F$ (para) |
| S | Pyridinyl | NH—C(O) | Pyridinyl | $Z_1$: $CH_2$—$CH_2F$ (meta) |
| S | Pyridinyl | NH—C(O) | Pyridinyl | $Z_1$: $CH_2$—$CH_2F$ (ortho) |
| S | Pyridinyl | NH—C(O) | Pyridinyl | $Z_1$: $CH_2$—$CHF_2$ (para) |
| S | Pyridinyl | NH—C(O) | Pyridinyl | $Z_1$: $CH_2$—$CHF_2$ (meta) |
| S | Pyridinyl | NH—C(O) | Pyridinyl | $Z_1$: $CH_2$—$CHF_2$ (ortho) |
| S | Pyridinyl | NH—C(O) | Pyridinyl | $Z_1$: $CH_2$—$CF_3$ (para) |
| S | Pyridinyl | NH—C(O) | Pyridinyl | $Z_1$: $CH_2$—$CF_3$ (meta) |

TABLE 2-continued

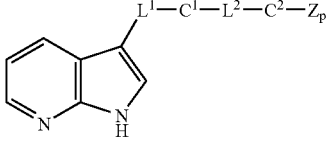

| L¹ | C¹ | L² | C² | Z |
|---|---|---|---|---|
| S | Pyridinyl | NH—C(O) | Pyridinyl | $Z_1$: $CH_2$—$CF_3$ (ortho) |
| S | pyridinyl | NH—C(O) | Pyrimidinyl | None |
| S | pyridinyl | NH—C(O) | Pyrimidinyl | $Z_1$: F (para) |
| S | pyridinyl | NH—C(O) | Pyrimidinyl | $Z_1$: F (meta) |
| S | pyridinyl | NH—C(O) | Pyrimidinyl | $Z_1$: F (ortho) |
| S | pyridinyl | NH—C(O) | Pyrimidinyl | $Z_1$: F (para) $Z_2$: F (meta) |
| S | Pyridinyl | NH—C(O) | Pyrimidinyl | $Z_1$: Cl (meta) |
| S | Pyridinyl | NH—C(O) | Pyrimidinyl | $Z_1$: Cl (para) |
| S | Pyridinyl | NH—C(O) | Pyrimidinyl | $Z_1$: Cl (para) $Z_2$: Cl (meta) |
| S | Pyridinyl | NH—C(O) | Pyrimidinyl | $Z_1$: F (para) $Z_2$: Cl (meta) |
| S | Pyridinyl | NH—C(O) | Pyrimidinyl | $Z_1$: Cl (para) $Z_2$: F (meta) |
| S | Pyridinyl | NH—C(O) | Pyrimidinyl | $Z_1$: $CH_3$ (para) |
| S | Pyridinyl | NH—C(O) | Pyrimidinyl | $Z_1$: $CH_3$ (meta) |
| S | Pyridinyl | NH—C(O) | Pyrimidinyl | $Z_1$: $CH_3$ (ortho) |
| S | Pyridinyl | NH—C(O) | Pyrimidinyl | $Z_1$: $CH_2$—$CH_3$ (para) |
| S | Pyridinyl | NH—C(O) | Pyrimidinyl | $Z_1$: $CH_2$—$CH_3$ (meta) |
| S | Pyridinyl | NH—C(O) | Pyrimidinyl | $Z_1$: $CH_2$—$CH_3$ (ortho) |
| S | Pyridinyl | NH—C(O) | Pyrimidinyl | $Z_1$: $CH_2$—$CH_2$—$CH_3$ or iPr (para) |
| S | Pyridinyl | NH—C(O) | Pyrimidinyl | $Z_1$: $CH_2$—$CH_2$—$CH_3$ or iPr (meta) |
| S | Pyridinyl | NH—C(O) | Pyrimidinyl | $Z_1$: $CH_2$—$CH_2$—$CH_3$ or iPr (ortho) |
| S | Pyridinyl | NH—C(O) | Pyrimidinyl | $Z_1$: $CH_2F$ (para) |
| S | Pyridinyl | NH—C(O) | Pyrimidinyl | $Z_1$: $CH_2F$ (meta) |
| S | Pyridinyl | NH—C(O) | Pyrimidinyl | $Z_1$: $CH_2F$ (ortho) |
| S | Pyridinyl | NH—C(O) | Pyrimidinyl | $Z_1$: $CHF_2$ (para) |
| S | Pyridinyl | NH—C(O) | Pyrimidinyl | $Z_1$: $CHF_2$ (meta) |
| S | Pyridinyl | NH—C(O) | Pyrimidinyl | $Z_1$: $CHF_2$ (ortho) |
| S | Pyridinyl | NH—C(O) | Pyrimidinyl | $Z_1$: $CF_3$ (para) |
| S | Pyridinyl | NH—C(O) | Pyrimidinyl | $Z_1$: $CF_3$ (meta) |
| S | Pyridinyl | NH—C(O) | Pyrimidinyl | $Z_1$: $CF_3$ (ortho) |
| S | Pyridinyl | NH—C(O) | Pyrimidinyl | $Z_1$: $CH_2$—$CH_2F$ (para) |
| S | Pyridinyl | NH—C(O) | Pyrimidinyl | $Z_1$: $CH_2$—$CH_2F$ (meta) |
| S | Pyridinyl | NH—C(O) | Pyrimidinyl | $Z_1$: $CH_2$—$CH_2F$ (ortho) |
| S | Pyridinyl | NH—C(O) | Pyrimidinyl | $Z_1$: $CH_2$—$CHF_2$ (para) |
| S | Pyridinyl | NH—C(O) | Pyrimidinyl | $Z_1$: $CH_2$—$CHF_2$ (meta) |
| S | Pyridinyl | NH—C(O) | Pyrimidinyl | $Z_1$: $CH_2$—$CHF_2$ (ortho) |
| S | Pyridinyl | NH—C(O) | Pyrimidinyl | $Z_1$: $CH_2$—$CF_3$ (para) |
| S | Pyridinyl | NH—C(O) | Pyrimidinyl | $Z_1$: $CH_2$—$CF_3$ (meta) |
| S | Pyridinyl | NH—C(O) | Pyrimidinyl | $Z_1$: $CH_2$—$CF_3$ (ortho) |
| S | pyridinyl | NH—C(O) | Pyrazinyl | None |
| S | pyridinyl | NH—C(O) | Pyrazinyl | $Z_1$: F (para) |
| S | pyridinyl | NH—C(O) | Pyrazinyl | $Z_1$: F (meta) |
| S | pyridinyl | NH—C(O) | Pyrazinyl | $Z_1$: F (ortho) |
| S | pyridinyl | NH—C(O) | Pyrazinyl | $Z_1$: F (para) $Z_2$: F (meta) |
| S | Pyridinyl | NH—C(O) | Pyrazinyl | $Z_1$: Cl (meta) |
| S | Pyridinyl | NH—C(O) | Pyrazinyl | $Z_1$: Cl (para) |
| S | Pyridinyl | NH—C(O) | Pyrazinyl | $Z_1$: Cl (para) $Z_2$: Cl (meta) |
| S | Pyridinyl | NH—C(O) | Pyrazinyl | $Z_1$: F (para) $Z_2$: Cl (meta) |
| S | Pyridinyl | NH—C(O) | Pyrazinyl | $Z_1$: Cl (para) $Z_2$: F (meta) |
| S | Pyridinyl | NH—C(O) | Pyrazinyl | $Z_1$: $CH_3$ (para) |
| S | Pyridinyl | NH—C(O) | Pyrazinyl | $Z_1$: $CH_3$ (meta) |
| S | Pyridinyl | NH—C(O) | Pyrazinyl | $Z_1$: $CH_3$ (ortho) |
| S | Pyridinyl | NH—C(O) | Pyrazinyl | $Z_1$: $CH_2$—$CH_3$ (para) |
| S | Pyridinyl | NH—C(O) | Pyrazinyl | $Z_1$: $CH_2$—$CH_3$ (meta) |
| S | Pyridinyl | NH—C(O) | Pyrazinyl | $Z_1$: $CH_2$—$CH_3$ (ortho) |
| S | Pyridinyl | NH—C(O) | Pyrazinyl | $Z_1$: $CH_2$—$CH_2$—$CH_3$ or iPr (para) |
| S | Pyridinyl | NH—C(O) | Pyrazinyl | $Z_1$: $CH_2$—$CH_2$—$CH_3$ or iPr (meta) |

TABLE 2-continued

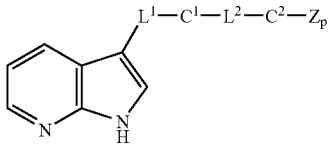

| $L^1$ | $C^1$ | $L^2$ | $C^2$ | Z |
|---|---|---|---|---|
| S | Pyridinyl | NH—C(O) | Pyrazinyl | $Z_1$: $CH_2$—$CH_2$—$CH_3$ or iPr (ortho) |
| S | Pyridinyl | NH—C(O) | Pyrazinyl | $Z_1$: $CH_2F$ (para) |
| S | Pyridinyl | NH—C(O) | Pyrazinyl | $Z_1$: $CH_2F$ (meta) |
| S | Pyridinyl | NH—C(O) | Pyrazinyl | $Z_1$: $CH_2F$ (ortho) |
| S | Pyridinyl | NH—C(O) | Pyrazinyl | $Z_1$: $CHF_2$ (para) |
| S | Pyridinyl | NH—C(O) | Pyrazinyl | $Z_1$: $CHF_2$ (meta) |
| S | Pyridinyl | NH—C(O) | Pyrazinyl | $Z_1$: $CHF_2$ (ortho) |
| S | Pyridinyl | NH—C(O) | Pyrazinyl | $Z_1$: $CF_3$ (para) |
| S | Pyridinyl | NH—C(O) | Pyrazinyl | $Z_1$: $CF_3$ (meta) |
| S | Pyridinyl | NH—C(O) | Pyrazinyl | $Z_1$: $CF_3$ (ortho) |
| S | Pyridinyl | NH—C(O) | Pyrazinyl | $Z_1$: $CH_2$—$CH_2F$ (para) |
| S | Pyridinyl | NH—C(O) | Pyrazinyl | $Z_1$: $CH_2$—$CH_2F$ (meta) |
| S | Pyridinyl | NH—C(O) | Pyrazinyl | $Z_1$: $CH_2$—$CH_2F$ (ortho) |
| S | Pyridinyl | NH—C(O) | Pyrazinyl | $Z_1$: $CH_2$—$CHF_2$ (para) |
| S | Pyridinyl | NH—C(O) | Pyrazinyl | $Z_1$: $CH_2$—$CHF_2$ (meta) |
| S | Pyridinyl | NH—C(O) | Pyrazinyl | $Z_1$: $CH_2$—$CHF_2$ (ortho) |
| S | Pyridinyl | NH—C(O) | Pyrazinyl | $Z_1$: $CH_2$—$CF_3$ (para) |
| S | Pyridinyl | NH—C(O) | Pyrazinyl | $Z_1$: $CH_2$—$CF_3$ (meta) |
| S | Pyridinyl | NH—C(O) | Pyrazinyl | $Z_1$: $CH_2$—$CF_3$ (ortho) |
| S | pyridinyl | NH—C(O) | Pyrrolyl | None |
| S | pyridinyl | NH—C(O) | Pyrrolyl | $Z_1$: F (2) |
| S | pyridinyl | NH—C(O) | Pyrrolyl | $Z_1$: F (3) |
| S | pyridinyl | NH—C(O) | Pyrrolyl | $Z_1$: F (2)<br>$Z_2$: F (3) |
| S | Pyridinyl | NH—C(O) | Pyrrolyl | $Z_1$: Cl (2) |
| S | Pyridinyl | NH—C(O) | Pyrrolyl | $Z_1$: Cl (3) |
| S | Pyridinyl | NH—C(O) | Pyrrolyl | $Z_1$: Cl (2)<br>$Z_2$: Cl (3) |
| S | Pyridinyl | NH—C(O) | Pyrrolyl | $Z_1$: F (2)<br>$Z_2$: Cl (3) |
| S | Pyridinyl | NH—C(O) | Pyrrolyl | $Z_1$: Cl (2)<br>$Z_2$: F (3) |
| S | Pyridinyl | NH—C(O) | Pyrrolyl | $Z_1$: $CH_3$ (2) |
| S | Pyridinyl | NH—C(O) | Pyrrolyl | $Z_1$: $CH_3$ (3) |
| S | Pyridinyl | NH—C(O) | Pyrrolyl | $Z_1$: $CH_2$—$CH_3$ (2) |
| S | Pyridinyl | NH—C(O) | Pyrrolyl | $Z_1$: $CH_2$—$CH_3$ (3) |
| S | Pyridinyl | NH—C(O) | Pyrrolyl | $Z_1$: $CH_2$—$CH_2$—$CH_3$ or iPr (2) |
| S | Pyridinyl | NH—C(O) | Pyrrolyl | $Z_1$: $CH_2$—$CH_2$—$CH_3$ or iPr (3) |
| S | Pyridinyl | NH—C(O) | Pyrrolyl | $Z_1$: $CH_2F$ (2) |
| S | Pyridinyl | NH—C(O) | Pyrrolyl | $Z_1$: $CH_2F$ (3) |
| S | Pyridinyl | NH—C(O) | Pyrrolyl | $Z_1$: $CHF_2$ (2) |
| S | Pyridinyl | NH—C(O) | Pyrrolyl | $Z_1$: $CHF_2$ (3) |
| S | Pyridinyl | NH—C(O) | Pyrrolyl | $Z_1$: $CF_3$ (2) |
| S | Pyridinyl | NH—C(O) | Pyrrolyl | $Z_1$: $CF_3$ (3) |
| S | Pyridinyl | NH—C(O) | Pyrrolyl | $Z_1$: $CH_2$—$CH_2F$ (2) |
| S | Pyridinyl | NH—C(O) | Pyrrolyl | $Z_1$: $CH_2$—$CH_2F$ (3) |
| S | Pyridinyl | NH—C(O) | Pyrrolyl | $Z_1$: $CH_2$—$CHF_2$ (2) |
| S | Pyridinyl | NH—C(O) | Pyrrolyl | $Z_1$: $CH_2$—$CHF_2$ (3) |
| S | Pyridinyl | NH—C(O) | Pyrrolyl | $Z_1$: $CH_2$—$CF_3$ (2) |
| S | Pyridinyl | NH—C(O) | Pyrrolyl | $Z_1$: $CH_2$—$CF_3$ (3) |
| S | pyridinyl | NH—C(O) | Imidazolyl | None |
| S | pyridinyl | NH—C(O) | Imidazolyl | $Z_1$: F (2) |
| S | pyridinyl | NH—C(O) | Imidazolyl | $Z_1$: F (3) |
| S | pyridinyl | NH—C(O) | Imidazolyl | $Z_1$: F (2)<br>$Z_2$: F (3) |
| S | Pyridinyl | NH—C(O) | Imidazolyl | $Z_1$: Cl (2) |
| S | Pyridinyl | NH—C(O) | Imidazolyl | $Z_1$: Cl (3) |
| S | Pyridinyl | NH—C(O) | Imidazolyl | $Z_1$: Cl (2)<br>$Z_2$: Cl (3) |
| S | Pyridinyl | NH—C(O) | Imidazolyl | $Z_1$: F (2)<br>$Z_2$: Cl (3) |
| S | Pyridinyl | NH—C(O) | Imidazolyl | $Z_1$: Cl (2)<br>$Z_2$: F (3) |
| S | Pyridinyl | NH—C(O) | Imidazolyl | $Z_1$: $CH_3$ (2) |
| S | Pyridinyl | NH—C(O) | Imidazolyl | $Z_1$: $CH_3$ (3) |
| S | Pyridinyl | NH—C(O) | Imidazolyl | $Z_1$: $CH_2$—$CH_3$ (2) |
| S | Pyridinyl | NH—C(O) | Imidazolyl | $Z_1$: $CH_2$—$CH_3$ (3) |
| S | Pyridinyl | NH—C(O) | Imidazolyl | $Z_1$: $CH_2$—$CH_2$—$CH_3$ or iPr (2) |

TABLE 2-continued

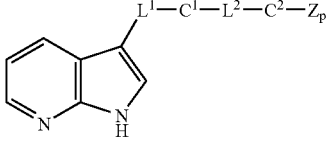

| $L^1$ | $C^1$ | $L^2$ | $C^2$ | Z |
|---|---|---|---|---|
| S | Pyridinyl | NH—C(O) | Imidazolyl | $Z_1$: $CH_2$—$CH_2$—$CH_3$ or iPr (3) |
| S | Pyridinyl | NH—C(O) | Imidazolyl | $Z_1$: $CH_2F$ (2) |
| S | Pyridinyl | NH—C(O) | Imidazolyl | $Z_1$: $CH_2F$ (3) |
| S | Pyridinyl | NH—C(O) | Imidazolyl | $Z_1$: $CHF_2$ (2) |
| S | Pyridinyl | NH—C(O) | Imidazolyl | $Z_1$: $CHF_2$ (3) |
| S | Pyridinyl | NH—C(O) | Imidazolyl | $Z_1$: $CF_3$ (2) |
| S | Pyridinyl | NH—C(O) | Imidazolyl | $Z_1$: $CF_3$ (3) |
| S | Pyridinyl | NH—C(O) | Imidazolyl | $Z_1$: $CH_2$—$CH_2F$ (2) |
| S | Pyridinyl | NH—C(O) | Imidazolyl | $Z_1$: $CH_2$—$CH_2F$ (3) |
| S | Pyridinyl | NH—C(O) | Imidazolyl | $Z_1$: $CH_2$—$CHF_2$ (2) |
| S | Pyridinyl | NH—C(O) | Imidazolyl | $Z_1$: $CH_2$—$CHF_2$ (3) |
| S | Pyridinyl | NH—C(O) | Imidazolyl | $Z_1$: $CH_2$—$CF_3$ (2) |
| S | Pyridinyl | NH—C(O) | Imidazolyl | $Z_1$: $CH_2$—$CF_3$ (3) |
| S | pyridinyl | NH—C(O) | Furanyl | None |
| S | pyridinyl | NH—C(O) | Furanyl | $Z_1$: F (2) |
| S | pyridinyl | NH—C(O) | Furanyl | $Z_1$: F (3) |
| S | pyridinyl | NH—C(O) | Furanyl | $Z_1$: F (2) $Z_2$: F (3) |
| S | Pyridinyl | NH—C(O) | Furanyl | $Z_1$: Cl (2) |
| S | Pyridinyl | NH—C(O) | Furanyl | $Z_1$: Cl (3) |
| S | Pyridinyl | NH—C(O) | Furanyl | $Z_1$: Cl (2) $Z_2$: Cl (3) |
| S | Pyridinyl | NH—C(O) | Furanyl | $Z_1$: F (2) $Z_2$: Cl (3) |
| S | Pyridinyl | NH—C(O) | Furanyl | $Z_1$: Cl (2) $Z_2$: F (3) |
| S | Pyridinyl | NH—C(O) | Furanyl | $Z_1$: $CH_3$ (2) |
| S | Pyridinyl | NH—C(O) | Furanyl | $Z_1$: $CH_3$ (3) |
| S | Pyridinyl | NH—C(O) | Furanyl | $Z_1$: $CH_2$—$CH_3$ (2) |
| S | Pyridinyl | NH—C(O) | Furanyl | $Z_1$: $CH_2$—$CH_3$ (3) |
| S | Pyridinyl | NH—C(O) | Furanyl | $Z_1$: $CH_2$—$CH_2$—$CH_3$ or iPr (2) |
| S | Pyridinyl | NH—C(O) | Furanyl | $Z_1$: $CH_2$—$CH_2$—$CH_3$ or iPr (3) |
| S | Pyridinyl | NH—C(O) | Furanyl | $Z_1$: $CH_2F$ (2) |
| S | Pyridinyl | NH—C(O) | Furanyl | $Z_1$: $CH_2F$ (3) |
| S | Pyridinyl | NH—C(O) | Furanyl | $Z_1$: $CHF_2$ (2) |
| S | Pyridinyl | NH—C(O) | Furanyl | $Z_1$: $CHF_2$ (3) |
| S | Pyridinyl | NH—C(O) | Furanyl | $Z_1$: $CF_3$ (2) |
| S | Pyridinyl | NH—C(O) | Furanyl | $Z_1$: $CF_3$ (3) |
| S | Pyridinyl | NH—C(O) | Furanyl | $Z_1$: $CH_2$—$CH_2F$ (2) |
| S | Pyridinyl | NH—C(O) | Furanyl | $Z_1$: $CH_2$—$CH_2F$ (3) |
| S | Pyridinyl | NH—C(O) | Furanyl | $Z_1$: $CH_2$—$CHF_2$ (2) |
| S | Pyridinyl | NH—C(O) | Furanyl | $Z_1$: $CH_2$—$CHF_2$ (3) |
| S | Pyridinyl | NH—C(O) | Furanyl | $Z_1$: $CH_2$—$CF_3$ (2) |
| S | Pyridinyl | NH—C(O) | Furanyl | $Z_1$: $CH_2$—$CF_3$ (3) |
| S | pyridinyl | NH—C(O) | Oxazolyl | None |
| S | pyridinyl | NH—C(O) | Oxazolyl | $Z_1$: F (2) |
| S | pyridinyl | NH—C(O) | Oxazolyl | $Z_1$: F (3) |
| S | pyridinyl | NH—C(O) | Oxazolyl | $Z_1$: F (2) $Z_2$: F (3) |
| S | Pyridinyl | NH—C(O) | Oxazolyl | $Z_1$: Cl (2) |
| S | Pyridinyl | NH—C(O) | Oxazolyl | $Z_1$: Cl (3) |
| S | Pyridinyl | NH—C(O) | Oxazolyl | $Z_1$: Cl (2) $Z_2$: Cl (3) |
| S | Pyridinyl | NH—C(O) | Oxazolyl | $Z_1$: F (2) $Z_2$: Cl (3) |
| S | Pyridinyl | NH—C(O) | Oxazolyl | $Z_1$: Cl (2) $Z_2$: F (3) |
| S | Pyridinyl | NH—C(O) | Oxazolyl | $Z_1$: $CH_3$ (2) |
| S | Pyridinyl | NH—C(O) | Oxazolyl | $Z_1$: $CH_3$ (3) |
| S | Pyridinyl | NH—C(O) | Oxazolyl | $Z_1$: $CH_2$—$CH_3$ (2) |
| S | Pyridinyl | NH—C(O) | Oxazolyl | $Z_1$: $CH_2$—$CH_3$ (3) |
| S | Pyridinyl | NH—C(O) | Oxazolyl | $Z_1$: $CH_2$—$CH_2$—$CH_3$ or iPr (2) |
| S | Pyridinyl | NH—C(O) | Oxazolyl | $Z_1$: $CH_2$—$CH_2$—$CH_3$ or iPr (3) |
| S | Pyridinyl | NH—C(O) | Oxazolyl | $Z_1$: $CH_2F$ (2) |
| S | Pyridinyl | NH—C(O) | Oxazolyl | $Z_1$: $CH_2F$ (3) |
| S | Pyridinyl | NH—C(O) | Oxazolyl | $Z_1$: $CHF_2$ (2) |
| S | Pyridinyl | NH—C(O) | Oxazolyl | $Z_1$: $CHF_2$ (3) |
| S | Pyridinyl | NH—C(O) | Oxazolyl | $Z_1$: $CF_3$ (2) |
| S | Pyridinyl | NH—C(O) | Oxazolyl | $Z_1$: $CF_3$ (3) |

TABLE 2-continued

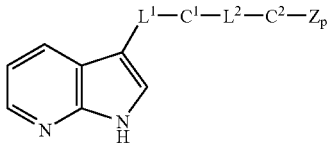

| L¹ | C¹ | L² | C² | Z |
|---|---|---|---|---|
| S | Pyridinyl | NH—C(O) | Oxazolyl | $Z_1$: $CH_2$—$CH_2F$ (2) |
| S | Pyridinyl | NH—C(O) | Oxazolyl | $Z_1$: $CH_2$—$CH_2F$ (3) |
| S | Pyridinyl | NH—C(O) | Oxazolyl | $Z_1$: $CH_2$—$CHF_2$ (2) |
| S | Pyridinyl | NH—C(O) | Oxazolyl | $Z_1$: $CH_2$—$CHF_2$ (3) |
| S | Pyridinyl | NH—C(O) | Oxazolyl | $Z_1$: $CH_2$—$CF_3$ (2) |
| S | Pyridinyl | NH—C(O) | Oxazolyl | $Z_1$: $CH_2$—$CF_3$ (3) |
| S | pyridinyl | NH—C(O) | Thiophenyl | None |
| S | pyridinyl | NH—C(O) | Thiophenyl | $Z_1$: F (2) |
| S | pyridinyl | NH—C(O) | Thiophenyl | $Z_1$: F (3) |
| S | pyridinyl | NH—C(O) | Thiophenyl | $Z_1$: F (2) $Z_2$: F (3) |
| S | Pyridinyl | NH—C(O) | Thiophenyl | $Z_1$: Cl (2) |
| S | Pyridinyl | NH—C(O) | Thiophenyl | $Z_1$: Cl (3) |
| S | Pyridinyl | NH—C(O) | Thiophenyl | $Z_1$: Cl (2) $Z_2$: Cl (3) |
| S | Pyridinyl | NH—C(O) | Thiophenyl | $Z_1$: F (2) $Z_2$: Cl (3) |
| S | Pyridinyl | NH—C(O) | Thiophenyl | $Z_1$: Cl (2) $Z_2$: F (3) |
| S | Pyridinyl | NH—C(O) | Thiophenyl | $Z_1$: $CH_3$ (2) |
| S | Pyridinyl | NH—C(O) | Thiophenyl | $Z_1$: $CH_3$ (3) |
| S | Pyridinyl | NH—C(O) | Thiophenyl | $Z_1$: $CH_2$—$CH_3$ (2) |
| S | Pyridinyl | NH—C(O) | Thiophenyl | $Z_1$: $CH_2$—$CH_3$ (3) |
| S | Pyridinyl | NH—C(O) | Thiophenyl | $Z_1$: $CH_2$—$CH_2$—$CH_3$ or iPr (2) |
| S | Pyridinyl | NH—C(O) | Thiophenyl | $Z_1$: $CH_2$—$CH_2$—$CH_3$ or iPr (3) |
| S | Pyridinyl | NH—C(O) | Thiophenyl | $Z_1$: $CH_2F$ (2) |
| S | Pyridinyl | NH—C(O) | Thiophenyl | $Z_1$: $CH_2F$ (3) |
| S | Pyridinyl | NH—C(O) | Thiophenyl | $Z_1$: $CHF_2$ (2) |
| S | Pyridinyl | NH—C(O) | Thiophenyl | $Z_1$: $CHF_2$ (3) |
| S | Pyridinyl | NH—C(O) | Thiophenyl | $Z_1$: $CF_3$ (2) |
| S | Pyridinyl | NH—C(O) | Thiophenyl | $Z_1$: $CF_3$ (3) |
| S | Pyridinyl | NH—C(O) | Thiophenyl | $Z_1$: $CH_2$—$CH_2F$ (2) |
| S | Pyridinyl | NH—C(O) | Thiophenyl | $Z_1$: $CH_2$—$CH_2F$ (3) |
| S | Pyridinyl | NH—C(O) | Thiophenyl | $Z_1$: $CH_2$—$CHF_2$ (2) |
| S | Pyridinyl | NH—C(O) | Thiophenyl | $Z_1$: $CH_2$—$CHF_2$ (3) |
| S | Pyridinyl | NH—C(O) | Thiophenyl | $Z_1$: $CH_2$—$CF_3$ (2) |
| S | Pyridinyl | NH—C(O) | Thiophenyl | $Z_1$: $CH_2$—$CF_3$ (3) |
| S | pyridinyl | NH—C(O) | Thiazolyl | None |
| S | pyridinyl | NH—C(O) | Thiazolyl | $Z_1$: F (2) |
| S | pyridinyl | NH—C(O) | Thiazolyl | $Z_1$: F (3) |
| S | pyridinyl | NH—C(O) | Thiazolyl | $Z_1$: F (2) $Z_2$: F (3) |
| S | Pyridinyl | NH—C(O) | Thiazolyl | $Z_1$: Cl (2) |
| S | Pyridinyl | NH—C(O) | Thiazolyl | $Z_1$: Cl (3) |
| S | Pyridinyl | NH—C(O) | Thiazolyl | $Z_1$: Cl (2) $Z_2$: Cl (3) |
| S | Pyridinyl | NH—C(O) | Thiazolyl | $Z_1$: F (2) $Z_2$: Cl (3) |
| S | Pyridinyl | NH—C(O) | Thiazolyl | $Z_1$: Cl (2) $Z_2$: F (3) |
| S | Pyridinyl | NH—C(O) | Thiazolyl | $Z_1$: $CH_3$ (2) |
| S | Pyridinyl | NH—C(O) | Thiazolyl | $Z_1$: $CH_3$ (3) |
| S | Pyridinyl | NH—C(O) | Thiazolyl | $Z_1$: $CH_2$—$CH_3$ (2) |
| S | Pyridinyl | NH—C(O) | Thiazolyl | $Z_1$: $CH_2$—$CH_3$ (3) |
| S | Pyridinyl | NH—C(O) | Thiazolyl | $Z_1$: $CH_2$—$CH_2$—$CH_3$ or iPr (2) |
| S | Pyridinyl | NH—C(O) | Thiazolyl | $Z_1$: $CH_2$—$CH_2$—$CH_3$ or iPr (3) |
| S | Pyridinyl | NH—C(O) | Thiazolyl | $Z_1$: $CH_2F$ (2) |
| S | Pyridinyl | NH—C(O) | Thiazolyl | $Z_1$: $CH_2F$ (3) |
| S | Pyridinyl | NH—C(O) | Thiazolyl | $Z_1$: $CHF_2$ (2) |
| S | Pyridinyl | NH—C(O) | Thiazolyl | $Z_1$: $CHF_2$ (3) |
| S | Pyridinyl | NH—C(O) | Thiazolyl | $Z_1$: $CF_3$ (2) |
| S | Pyridinyl | NH—C(O) | Thiazolyl | $Z_1$: $CF_3$ (3) |
| S | Pyridinyl | NH—C(O) | Thiazolyl | $Z_1$: $CH_2$—$CH_2F$ (2) |
| S | Pyridinyl | NH—C(O) | Thiazolyl | $Z_1$: $CH_2$—$CH_2F$ (3) |
| S | Pyridinyl | NH—C(O) | Thiazolyl | $Z_1$: $CH_2$—$CHF_2$ (2) |
| S | Pyridinyl | NH—C(O) | Thiazolyl | $Z_1$: $CH_2$—$CHF_2$ (3) |
| S | Pyridinyl | NH—C(O) | Thiazolyl | $Z_1$: $CH_2$—$CF_3$ (2) |
| S | Pyridinyl | NH—C(O) | Thiazolyl | $Z_1$: $CH_2$—$CF_3$ (3) |
| S | pyridinyl | NH—$SO_2$ | Phenyl | None |

TABLE 2-continued

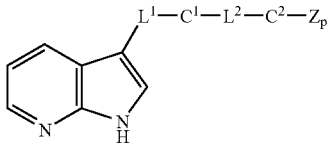

| L¹ | C¹ | L² | C² | Z |
|---|---|---|---|---|
| S | pyridinyl | NH—SO$_2$ | Phenyl | $Z_1$: F (para) |
| S | pyridinyl | NH—SO$_2$ | phenyl | $Z_1$: F (meta) |
| S | pyridinyl | NH—SO$_2$ | phenyl | $Z_1$: F (ortho) |
| S | pyridinyl | NH—SO$_2$ | phenyl | $Z_1$: F (para) $Z_2$: F (meta) |
| S | Pyridinyl | NH—SO$_2$ | Phenyl | $Z_1$: Cl (meta) |
| S | Pyridinyl | NH—SO$_2$ | Phenyl | $Z_1$: Cl (para) |
| S | Pyridinyl | NH—SO$_2$ | Phenyl | $Z_1$: Cl (para) $Z_2$: Cl (meta) |
| S | Pyridinyl | NH—SO$_2$ | Phenyl | $Z_1$: F (para) $Z_2$: Cl (meta) |
| S | Pyridinyl | NH—SO$_2$ | Phenyl | $Z_1$: Cl (para) $Z_2$: F (meta) |
| S | Pyridinyl | NH—SO$_2$ | Phenyl | $Z_1$: CH$_3$ (para) |
| S | Pyridinyl | NH—SO$_2$ | Phenyl | $Z_1$: CH$_3$ (meta) |
| S | Pyridinyl | NH—SO$_2$ | Phenyl | $Z_1$: CH$_3$ (ortho) |
| S | Pyridinyl | NH—SO$_2$ | Phenyl | $Z_1$: CH$_2$—CH$_3$ (para) |
| S | Pyridinyl | NH—SO$_2$ | Phenyl | $Z_1$: CH$_2$—CH$_3$ (meta) |
| S | Pyridinyl | NH—SO$_2$ | Phenyl | $Z_1$: CH$_2$—CH$_3$ (ortho) |
| S | Pyridinyl | NH—SO$_2$ | Phenyl | $Z_1$: CH$_2$—CH$_2$—CH$_3$ or iPr (para) |
| S | Pyridinyl | NH—SO$_2$ | Phenyl | $Z_1$: CH$_2$—CH$_2$—CH$_3$ or iPr (meta) |
| S | Pyridinyl | NH—SO$_2$ | Phenyl | $Z_1$: CH$_2$—CH$_2$—CH$_3$ or iPr (ortho) |
| S | Pyridinyl | NH—SO$_2$ | Phenyl | $Z_1$: CH$_2$F (para) |
| S | Pyridinyl | NH—SO$_2$ | Phenyl | $Z_1$: CH$_2$F (meta) |
| S | Pyridinyl | NH—SO$_2$ | Phenyl | $Z_1$: CH$_2$F (ortho) |
| S | Pyridinyl | NH—SO$_2$ | Phenyl | $Z_1$: CHF$_2$ (para) |
| S | Pyridinyl | NH—SO$_2$ | Phenyl | $Z_1$: CHF$_2$ (meta) |
| S | Pyridinyl | NH—SO$_2$ | Phenyl | $Z_1$: CHF$_2$ (ortho) |
| S | Pyridinyl | NH—SO$_2$ | Phenyl | $Z_1$: CF$_3$ (para) |
| S | Pyridinyl | NH—SO$_2$ | Phenyl | $Z_1$: CF$_3$ (meta) |
| S | Pyridinyl | NH—SO$_2$ | Phenyl | $Z_1$: CF$_3$ (ortho) |
| S | Pyridinyl | NH—SO$_2$ | Phenyl | $Z_1$: CH$_2$—CH$_2$F (para) |
| S | Pyridinyl | NH—SO$_2$ | Phenyl | $Z_1$: CH$_2$—CH$_2$F (meta) |
| S | Pyridinyl | NH—SO$_2$ | Phenyl | $Z_1$: CH$_2$—CH$_2$F (ortho) |
| S | Pyridinyl | NH—SO$_2$ | Phenyl | $Z_1$: CH$_2$—CHF$_2$ (para) |
| S | Pyridinyl | NH—SO$_2$ | Phenyl | $Z_1$: CH$_2$—CHF$_2$ (meta) |
| S | Pyridinyl | NH—SO$_2$ | Phenyl | $Z_1$: CH$_2$—CHF$_2$ (ortho) |
| S | Pyridinyl | NH—SO$_2$ | Phenyl | $Z_1$: CH$_2$—CF$_3$ (para) |
| S | Pyridinyl | NH—SO$_2$ | Phenyl | $Z_1$: CH$_2$—CF$_3$ (meta) |
| S | Pyridinyl | NH—SO$_2$ | Phenyl | $Z_1$: CH$_2$—CF$_3$ (ortho) |
| S | pyridinyl | NH—SO$_2$ | Pyridinyl | None |
| S | pyridinyl | NH—SO$_2$ | Pyridinyl | $Z_1$: F (para) |
| S | pyridinyl | NH—SO$_2$ | Pyridinyl | $Z_1$: F (meta) |
| S | pyridinyl | NH—SO$_2$ | Pyridinyl | $Z_1$: F (ortho) |
| S | pyridinyl | NH—SO$_2$ | Pyridinyl | $Z_1$: F (para) $Z_2$: F (meta) |
| S | Pyridinyl | NH—SO$_2$ | Pyridinyl | $Z_1$: Cl (meta) |
| S | Pyridinyl | NH—SO$_2$ | Pyridinyl | $Z_1$: Cl (para) |
| S | Pyridinyl | NH—SO$_2$ | Pyridinyl | $Z_1$: Cl (para) $Z_2$: Cl (meta) |
| S | Pyridinyl | NH—SO$_2$ | Pyridinyl | $Z_1$: F (para) $Z_2$: Cl (meta) |
| S | Pyridinyl | NH—SO$_2$ | Pyridinyl | $Z_1$: Cl (para) $Z_2$: F (meta) |
| S | Pyridinyl | NH—SO$_2$ | Pyridinyl | $Z_1$: CH$_3$ (para) |
| S | Pyridinyl | NH—SO$_2$ | Pyridinyl | $Z_1$: CH$_3$ (meta) |
| S | Pyridinyl | NH—SO$_2$ | Pyridinyl | $Z_1$: CH$_3$ (ortho) |
| S | Pyridinyl | NH—SO$_2$ | Pyridinyl | $Z_1$: CH$_2$—CH$_3$ (para) |
| S | Pyridinyl | NH—SO$_2$ | Pyridinyl | $Z_1$: CH$_2$—CH$_3$ (meta) |
| S | Pyridinyl | NH—SO$_2$ | Pyridinyl | $Z_1$: CH$_2$—CH$_3$ (ortho) |
| S | Pyridinyl | NH—SO$_2$ | Pyridinyl | $Z_1$: CH$_2$—CH$_2$—CH$_3$ or iPr (para) |
| S | Pyridinyl | NH—SO$_2$ | Pyridinyl | $Z_1$: CH$_2$—CH$_2$—CH$_3$ or iPr (meta) |
| S | Pyridinyl | NH—SO$_2$ | Pyridinyl | $Z_1$: CH$_2$—CH$_2$—CH$_3$ or iPr (ortho) |

TABLE 2-continued

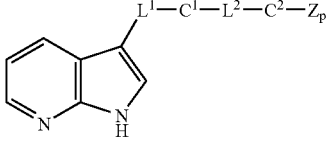

| L¹ | C¹ | L² | C² | Z |
|---|---|---|---|---|
| S | Pyridinyl | NH—SO$_2$ | Pyridinyl | Z$_1$: CH$_2$F (para) |
| S | Pyridinyl | NH—SO$_2$ | Pyridinyl | Z$_1$: CH$_2$F (meta) |
| S | Pyridinyl | NH—SO$_2$ | Pyridinyl | Z$_1$: CH$_2$F (ortho) |
| S | Pyridinyl | NH—SO$_2$ | Pyridinyl | Z$_1$: CHF$_2$ (para) |
| S | Pyridinyl | NH—SO$_2$ | Pyridinyl | Z$_1$: CHF$_2$ (meta) |
| S | Pyridinyl | NH—SO$_2$ | Pyridinyl | Z$_1$: CHF$_2$ (ortho) |
| S | Pyridinyl | NH—SO$_2$ | Pyridinyl | Z$_1$: CF$_3$ (para) |
| S | Pyridinyl | NH—SO$_2$ | Pyridinyl | Z$_1$: CF$_3$ (meta) |
| S | Pyridinyl | NH—SO$_2$ | Pyridinyl | Z$_1$: CF$_3$ (ortho) |
| S | Pyridinyl | NH—SO$_2$ | Pyridinyl | Z$_1$: CH$_2$—CH$_2$F (para) |
| S | Pyridinyl | NH—SO$_2$ | Pyridinyl | Z$_1$: CH$_2$—CH$_2$F (meta) |
| S | Pyridinyl | NH—SO$_2$ | Pyridinyl | Z$_1$: CH$_2$—CH$_2$F (ortho) |
| S | Pyridinyl | NH—SO$_2$ | Pyridinyl | Z$_1$: CH$_2$—CHF$_2$ (para) |
| S | Pyridinyl | NH—SO$_2$ | Pyridinyl | Z$_1$: CH$_2$—CHF$_2$ (meta) |
| S | Pyridinyl | NH—SO$_2$ | Pyridinyl | Z$_1$: CH$_2$—CHF$_2$ (ortho) |
| S | Pyridinyl | NH—SO$_2$ | Pyridinyl | Z$_1$: CH$_2$—CF$_3$ (para) |
| S | Pyridinyl | NH—SO$_2$ | Pyridinyl | Z$_1$: CH$_2$—CF$_3$ (meta) |
| S | Pyridinyl | NH—SO$_2$ | Pyridinyl | Z$_1$: CH$_2$—CF$_3$ (ortho) |
| S | pyridinyl | NH—SO$_2$ | Pyrimidinyl | None |
| S | pyridinyl | NH—SO$_2$ | Pyrimidinyl | Z$_1$: F (para) |
| S | pyridinyl | NH—SO$_2$ | Pyrimidinyl | Z$_1$: F (meta) |
| S | pyridinyl | NH—SO$_2$ | Pyrimidinyl | Z$_1$: F (ortho) |
| S | pyridinyl | NH—SO$_2$ | Pyrimidinyl | Z$_1$: F (para) Z$_2$: F (meta) |
| S | Pyridinyl | NH—SO$_2$ | Pyrimidinyl | Z$_1$: Cl (meta) |
| S | Pyridinyl | NH—SO$_2$ | Pyrimidinyl | Z$_1$: Cl (para) |
| S | Pyridinyl | NH—SO$_2$ | Pyrimidinyl | Z$_1$: Cl (para) Z$_2$: Cl (meta) |
| S | Pyridinyl | NH—SO$_2$ | Pyrimidinyl | Z$_1$: F (para) Z$_2$: Cl (meta) |
| S | Pyridinyl | NH—SO$_2$ | Pyrimidinyl | Z$_1$: Cl (para) Z$_2$: F (meta) |
| S | Pyridinyl | NH—SO$_2$ | Pyrimidinyl | Z$_1$: CH$_3$ (para) |
| S | Pyridinyl | NH—SO$_2$ | Pyrimidinyl | Z$_1$: CH$_3$ (meta) |
| S | Pyridinyl | NH—SO$_2$ | Pyrimidinyl | Z$_1$: CH$_3$ (ortho) |
| S | Pyridinyl | NH—SO$_2$ | Pyrimidinyl | Z$_1$: CH$_2$—CH$_3$ (para) |
| S | Pyridinyl | NH—SO$_2$ | Pyrimidinyl | Z$_1$: CH$_2$—CH$_3$ (meta) |
| S | Pyridinyl | NH—SO$_2$ | Pyrimidinyl | Z$_1$: CH$_2$—CH$_3$ (ortho) |
| S | Pyridinyl | NH—SO$_2$ | Pyrimidinyl | Z$_1$: CH$_2$—CH$_2$—CH$_3$ or iPr (para) |
| S | Pyridinyl | NH—SO$_2$ | Pyrimidinyl | Z$_1$: CH$_2$—CH$_2$—CH$_3$ or iPr (meta) |
| S | Pyridinyl | NH—SO$_2$ | Pyrimidinyl | Z$_1$: CH$_2$—CH$_2$—CH$_3$ or iPr (ortho) |
| S | Pyridinyl | NH—SO$_2$ | Pyrimidinyl | Z$_1$: CH$_2$F (para) |
| S | Pyridinyl | NH—SO$_2$ | Pyrimidinyl | Z$_1$: CH$_2$F (meta) |
| S | Pyridinyl | NH—SO$_2$ | Pyrimidinyl | Z$_1$: CH$_2$F (ortho) |
| S | Pyridinyl | NH—SO$_2$ | Pyrimidinyl | Z$_1$: CHF$_2$ (para) |
| S | Pyridinyl | NH—SO$_2$ | Pyrimidinyl | Z$_1$: CHF$_2$ (meta) |
| S | Pyridinyl | NH—SO$_2$ | Pyrimidinyl | Z$_1$: CHF$_2$ (ortho) |
| S | Pyridinyl | NH—SO$_2$ | Pyrimidinyl | Z$_1$: CF$_3$ (para) |
| S | Pyridinyl | NH—SO$_2$ | Pyrimidinyl | Z$_1$: CF$_3$ (meta) |
| S | Pyridinyl | NH—SO$_2$ | Pyrimidinyl | Z$_1$: CF$_3$ (ortho) |
| S | Pyridinyl | NH—SO$_2$ | Pyrimidinyl | Z$_1$: CH$_2$—CH$_2$F (para) |
| S | Pyridinyl | NH—SO$_2$ | Pyrimidinyl | Z$_1$: CH$_2$—CH$_2$F (meta) |
| S | Pyridinyl | NH—SO$_2$ | Pyrimidinyl | Z$_1$: CH$_2$—CH$_2$F (ortho) |
| S | Pyridinyl | NH—SO$_2$ | Pyrimidinyl | Z$_1$: CH$_2$—CHF$_2$ (para) |
| S | Pyridinyl | NH—SO$_2$ | Pyrimidinyl | Z$_1$: CH$_2$—CHF$_2$ (meta) |
| S | Pyridinyl | NH—SO$_2$ | Pyrimidinyl | Z$_1$: CH$_2$—CHF$_2$ (ortho) |
| S | Pyridinyl | NH—SO$_2$ | Pyrimidinyl | Z$_1$: CH$_2$—CF$_3$ (para) |
| S | Pyridinyl | NH—SO$_2$ | Pyrimidinyl | Z$_1$: CH$_2$—CF$_3$ (meta) |
| S | Pyridinyl | NH—SO$_2$ | Pyrimidinyl | Z$_1$: CH$_2$—CF$_3$ (ortho) |
| S | pyridinyl | NH—SO$_2$ | Pyrazinyl | None |
| S | pyridinyl | NH—SO$_2$ | Pyrazinyl | Z$_1$: F (para) |
| S | pyridinyl | NH—SO$_2$ | Pyrazinyl | Z$_1$: F (meta) |
| S | pyridinyl | NH—SO$_2$ | Pyrazinyl | Z$_1$: F (ortho) |
| S | pyridinyl | NH—SO$_2$ | Pyrazinyl | Z$_1$: F (para) Z$_2$: F (meta) |
| S | Pyridinyl | NH—SO$_2$ | Pyrazinyl | Z$_1$:. Cl (meta) |

TABLE 2-continued

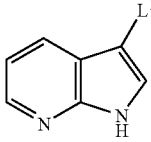

| L¹ | C¹ | L² | C² | Z |
|---|---|---|---|---|
| S | Pyridinyl | NH—SO₂ | Pyrazinyl | $Z_1$: Cl (para) |
| S | Pyridinyl | NH—SO₂ | Pyrazinyl | $Z_1$: Cl (para) $Z_2$: Cl (meta) |
| S | Pyridinyl | NH—SO₂ | Pyrazinyl | $Z_1$: F (para) $Z_2$: Cl (meta) |
| S | Pyridinyl | NH—SO₂ | Pyrazinyl | $Z_1$: Cl (para) $Z_2$: F (meta) |
| S | Pyridinyl | NH—SO₂ | Pyrazinyl | $Z_1$: CH₃ (para) |
| S | Pyridinyl | NH—SO₂ | Pyrazinyl | $Z_1$: CH₃ (meta) |
| S | Pyridinyl | NH—SO₂ | Pyrazinyl | $Z_1$: CH₃ (ortho) |
| S | Pyridinyl | NH—SO₂ | Pyrazinyl | $Z_1$: CH₂—CH₃ (para) |
| S | Pyridinyl | NH—SO₂ | Pyrazinyl | $Z_1$: CH₂—CH₃ (meta) |
| S | Pyridinyl | NH—SO₂ | Pyrazinyl | $Z_1$: CH₂—CH₃ (ortho) |
| S | Pyridinyl | NH—SO₂ | Pyrazinyl | $Z_1$: CH₂—CH₂—CH₃ or iPr (para) |
| S | Pyridinyl | NH—SO₂ | Pyrazinyl | $Z_1$: CH₂—CH₂—CH₃ or iPr (meta) |
| S | Pyridinyl | NH—SO₂ | Pyrazinyl | $Z_1$: CH₂—CH₂—CH₃ or iPr (ortho) |
| S | Pyridinyl | NH—SO₂ | Pyrazinyl | $Z_1$: CH₂F (para) |
| S | Pyridinyl | NH—SO₂ | Pyrazinyl | $Z_1$: CH₂F (meta) |
| S | Pyridinyl | NH—SO₂ | Pyrazinyl | $Z_1$: CH₂F (ortho) |
| S | Pyridinyl | NH—SO₂ | Pyrazinyl | $Z_1$: CHF₂ (para) |
| S | Pyridinyl | NH—SO₂ | Pyrazinyl | $Z_1$: CHF₂ (meta) |
| S | Pyridinyl | NH—SO₂ | Pyrazinyl | $Z_1$: CHF₂ (ortho) |
| S | Pyridinyl | NH—SO₂ | Pyrazinyl | $Z_1$: CF₃ (para) |
| S | Pyridinyl | NH—SO₂ | Pyrazinyl | $Z_1$: CF₃ (meta) |
| S | Pyridinyl | NH—SO₂ | Pyrazinyl | $Z_1$: CF₃ (ortho) |
| S | Pyridinyl | NH—SO₂ | Pyrazinyl | $Z_1$: CH₂—CH₂F (para) |
| S | Pyridinyl | NH—SO₂ | Pyrazinyl | $Z_1$: CH₂—CH₂F (meta) |
| S | Pyridinyl | NH—SO₂ | Pyrazinyl | $Z_1$: CH₂—CH₂F (ortho) |
| S | Pyridinyl | NH—SO₂ | Pyrazinyl | $Z_1$: CH₂—CHF₂ (para) |
| S | Pyridinyl | NH—SO₂ | Pyrazinyl | $Z_1$: CH₂—CHF₂ (meta) |
| S | Pyridinyl | NH—SO₂ | Pyrazinyl | $Z_1$: CH₂—CHF₂ (ortho) |
| S | Pyridinyl | NH—SO₂ | Pyrazinyl | $Z_1$: CH₂—CF₃ (para) |
| S | Pyridinyl | NH—SO₂ | Pyrazinyl | $Z_1$: CH₂—CF₃ (meta) |
| S | Pyridinyl | NH—SO₂ | Pyrazinyl | $Z_1$: CH₂—CF₃ (ortho) |
| S | pyridinyl | NH—SO₂ | Pyrrolyl | None |
| S | pyridinyl | NH—SO₂ | Pyrrolyl | $Z_1$: F (2) |
| S | pyridinyl | NH—SO₂ | Pyrrolyl | $Z_1$: F (3) |
| S | pyridinyl | NH—SO₂ | Pyrrolyl | $Z_1$: F (2) $Z_2$: F (3) |
| S | Pyridinyl | NH—SO₂ | Pyrrolyl | $Z_1$: Cl (2) |
| S | Pyridinyl | NH—SO₂ | Pyrrolyl | $Z_1$: Cl (3) |
| S | Pyridinyl | NH—SO₂ | Pyrrolyl | $Z_1$: Cl (2) $Z_2$: Cl (3) |
| S | Pyridinyl | NH—SO₂ | Pyrrolyl | $Z_1$: F (2) $Z_2$: Cl (3) |
| S | Pyridinyl | NH—SO₂ | Pyrrolyl | $Z_1$: Cl (2) $Z_2$: F (3) |
| S | Pyridinyl | NH—SO₂ | Pyrrolyl | $Z_1$: CH₃ (2) |
| S | Pyridinyl | NH—SO₂ | Pyrrolyl | $Z_1$: CH₃ (3) |
| S | Pyridinyl | NH—SO₂ | Pyrrolyl | $Z_1$: CH₂—CH₃ (2) |
| S | Pyridinyl | NH—SO₂ | Pyrrolyl | $Z_1$: CH₂—CH₃ (3) |
| S | Pyridinyl | NH—SO₂ | Pyrrolyl | $Z_1$: CH₂—CH₂—CH₃ or iPr (2) |
| S | Pyridinyl | NH—SO₂ | Pyrrolyl | $Z_1$: CH₂—CH₂—CH₃ or iPr (3) |
| S | Pyridinyl | NH—SO₂ | Pyrrolyl | $Z_1$: CH₂F (2) |
| S | Pyridinyl | NH—SO₂ | Pyrrolyl | $Z_1$: CH₂F (3) |
| S | Pyridinyl | NH—SO₂ | Pyrrolyl | $Z_1$: CHF₂ (2) |
| S | Pyridinyl | NH—SO₂ | Pyrrolyl | $Z_1$: CHF₂ (3) |
| S | Pyridinyl | NH—SO₂ | Pyrrolyl | $Z_1$: CF₃ (2) |
| S | Pyridinyl | NH—SO₂ | Pyrrolyl | $Z_1$: CF₃ (3) |
| S | Pyridinyl | NH—SO₂ | Pyrrolyl | $Z_1$: CH₂—CH₂F (2) |
| S | Pyridinyl | NH—SO₂ | Pyrrolyl | $Z_1$: CH₂—CH₂F (3) |
| S | Pyridinyl | NH—SO₂ | Pyrrolyl | $Z_1$: CH₂—CHF₂ (2) |
| S | Pyridinyl | NH—SO₂ | Pyrrolyl | $Z_1$: CH₂—CHF₂ (3) |
| S | Pyridinyl | NH—SO₂ | Pyrrolyl | $Z_1$: CH₂—CF₃ (2) |
| S | Pyridinyl | NH—SO₂ | Pyrrolyl | $Z_1$: CH₂—CF₃ (3) |
| S | pyridinyl | NH—SO₂ | Imidazolyl | None |

TABLE 2-continued

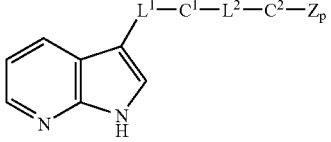

| L¹ | C¹ | L² | C² | Z |
|---|---|---|---|---|
| S | pyridinyl | NH—SO₂ | Imidazolyl | $Z_1$: F (2) |
| S | pyridinyl | NH—SO₂ | Imidazolyl | $Z_1$: F (3) |
| S | pyridinyl | NH—SO₂ | Imidazolyl | $Z_1$: F (2) $Z_2$: F (3) |
| S | Pyridinyl | NH—SO₂ | Imidazolyl | $Z_1$: Cl (2) |
| S | Pyridinyl | NH—SO₂ | Imidazolyl | $Z_1$: Cl (3) |
| S | Pyridinyl | NH—SO₂ | Imidazolyl | $Z_1$: Cl (2) $Z_2$: Cl (3) |
| S | Pyridinyl | NH—SO₂ | Imidazolyl | $Z_1$: F (2) $Z_2$: Cl (3) |
| S | Pyridinyl | NH—SO₂ | Imidazolyl | $Z_1$: Cl (2) $Z_2$: F (3) |
| S | Pyridinyl | NH—SO₂ | Imidazolyl | $Z_1$: CH₃ (2) |
| S | Pyridinyl | NH—SO₂ | Imidazolyl | $Z_1$: CH₃ (3) |
| S | Pyridinyl | NH—SO₂ | Imidazolyl | $Z_1$: CH₂—CH₃ (2) |
| S | Pyridinyl | NH—SO₂ | Imidazolyl | $Z_1$: CH₂—CH₃ (3) |
| S | Pyridinyl | NH—SO₂ | Imidazolyl | $Z_1$: CH₂—CH₂—CH₃ or iPr (2) |
| S | Pyridinyl | NH—SO₂ | Imidazolyl | $Z_1$: CH₂—CH₂—CH₃ or iPr (3) |
| S | Pyridinyl | NH—SO₂ | Imidazolyl | $Z_1$: CH₂F (2) |
| S | Pyridinyl | NH—SO₂ | Imidazolyl | $Z_1$: CH₂F (3) |
| S | Pyridinyl | NH—SO₂ | Imidazolyl | $Z_1$: CHF₂ (2) |
| S | Pyridinyl | NH—SO₂ | Imidazolyl | $Z_1$: CHF₂ (3) |
| S | Pyridinyl | NH—SO₂ | Imidazolyl | $Z_1$: CF₃ (2) |
| S | Pyridinyl | NH—SO₂ | Imidazolyl | $Z_1$: CF₃ (3) |
| S | Pyridinyl | NH—SO₂ | Imidazolyl | $Z_1$: CH₂—CH₂F (2) |
| S | Pyridinyl | NH—SO₂ | Imidazolyl | $Z_1$: CH₂—CH₂F (3) |
| S | Pyridinyl | NH—SO₂ | Imidazolyl | $Z_1$: CH₂—CHF₂ (2) |
| S | Pyridinyl | NH—SO₂ | Imidazolyl | $Z_1$: CH₂—CHF₂ (3) |
| S | Pyridinyl | NH—SO₂ | Imidazolyl | $Z_1$: CH₂—CF₃ (2) |
| S | Pyridinyl | NH—SO₂ | Imidazolyl | $Z_1$: CH₂—CF₃ (3) |
| S | pyridinyl | NH—SO₂ | Furanyl | None |
| S | pyridinyl | NH—SO₂ | Furanyl | $Z_1$: F (2) |
| S | pyridinyl | NH—SO₂ | Furanyl | $Z_1$: F (3) |
| S | pyridinyl | NH—SO₂ | Furanyl | $Z_1$: F (2) $Z_2$: F (3) |
| S | Pyridinyl | NH—SO₂ | Furanyl | $Z_1$: Cl (2) |
| S | Pyridinyl | NH—SO₂ | Furanyl | $Z_1$: Cl (3) |
| S | Pyridinyl | NH—SO₂ | Furanyl | $Z_1$: Cl (2) $Z_2$: Cl (3) |
| S | Pyridinyl | NH—SO₂ | Furanyl | $Z_1$: F (2) $Z_2$: Cl (3) |
| S | Pyridinyl | NH—SO₂ | Furanyl | $Z_1$: Cl (2) $Z_2$: F (3) |
| S | Pyridinyl | NH—SO₂ | Furanyl | $Z_1$: CH₃ (2) |
| S | Pyridinyl | NH—SO₂ | Furanyl | $Z_1$: CH₃ (3) |
| S | Pyridinyl | NH—SO₂ | Furanyl | $Z_1$: CH₂—CH₃ (2) |
| S | Pyridinyl | NH—SO₂ | Furanyl | $Z_1$: CH₂—CH₃ (3) |
| S | Pyridinyl | NH—SO₂ | Furanyl | $Z_1$: CH₂—CH₂—CH₃ or iPr (2) |
| S | Pyridinyl | NH—SO₂ | Furanyl | $Z_1$: CH₂—CH₂—CH₃ or iPr (3) |
| S | Pyridinyl | NH—SO₂ | Furanyl | $Z_1$: CH₂F (2) |
| S | Pyridinyl | NH—SO₂ | Furanyl | $Z_1$: CH₂F (3) |
| S | Pyridinyl | NH—SO₂ | Furanyl | $Z_1$: CHF₂ (2) |
| S | Pyridinyl | NH—SO₂ | Furanyl | $Z_1$: CHF₂ (3) |
| S | Pyridinyl | NH—SO₂ | Furanyl | $Z_1$: CF₃ (2) |
| S | Pyridinyl | NH—SO₂ | Furanyl | $Z_1$: CF₃ (3) |
| S | Pyridinyl | NH—SO₂ | Furanyl | $Z_1$: CH₂—CH₂F (2) |
| S | Pyridinyl | NH—SO₂ | Furanyl | $Z_1$: CH₂—CH₂F (3) |
| S | Pyridinyl | NH—SO₂ | Furanyl | $Z_1$: CH₂—CHF₂ (2) |
| S | Pyridinyl | NH—SO₂ | Furanyl | $Z_1$: CH₂—CHF₂ (3) |
| S | Pyridinyl | NH—SO₂ | Furanyl | $Z_1$: CH₂—CF₃ (2) |
| S | Pyridinyl | NH—SO₂ | Furanyl | $Z_1$: CH₂—CF₃ (3) |
| S | pyridinyl | NH—SO₂ | Oxazolyl | None |
| S | pyridinyl | NH—SO₂ | Oxazolyl | $Z_1$: F (2) |
| S | pyridinyl | NH—SO₂ | Oxazolyl | $Z_1$: F (3) |
| S | pyridinyl | NH—SO₂ | Oxazolyl | $Z_1$: F (2) $Z_2$: F (3) |
| S | Pyridinyl | NH—SO₂ | Oxazolyl | $Z_1$: Cl (2) |
| S | Pyridinyl | NH—SO₂ | Oxazolyl | $Z_1$: Cl (3) |

TABLE 2-continued

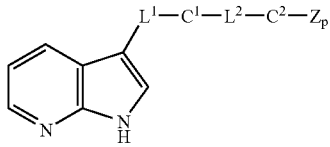

| $L^1$ | $C^1$ | $L^2$ | $C^2$ | Z |
|---|---|---|---|---|
| S | Pyridinyl | NH—SO$_2$ | Oxazolyl | $Z_1$: Cl (2) |
|   |   |   |   | $Z_2$: Cl (3) |
| S | Pyridinyl | NH—SO$_2$ | Oxazolyl | $Z_1$: F (2) |
|   |   |   |   | $Z_2$: Cl (3) |
| S | Pyridinyl | NH—SO$_2$ | Oxazolyl | $Z_1$: Cl (2) |
|   |   |   |   | $Z_2$: F (3) |
| S | Pyridinyl | NH—SO$_2$ | Oxazolyl | $Z_1$: CH$_3$ (2) |
| S | Pyridinyl | NH—SO$_2$ | Oxazolyl | $Z_1$: CH$_3$ (3) |
| S | Pyridinyl | NH—SO$_2$ | Oxazolyl | $Z_1$: CH$_2$—CH$_3$ (2) |
| S | Pyridinyl | NH—SO$_2$ | Oxazolyl | $Z_1$: CH$_2$—CH$_3$ (3) |
| S | Pyridinyl | NH—SO$_2$ | Oxazolyl | $Z_1$: CH$_2$—CH$_2$—CH$_3$ or iPr (2) |
| S | Pyridinyl | NH—SO$_2$ | Oxazolyl | $Z_1$: CH$_2$—CH$_2$—CH$_3$ or iPr (3) |
| S | Pyridinyl | NH—SO$_2$ | Oxazolyl | $Z_1$: CH$_2$F (2) |
| S | Pyridinyl | NH—SO$_2$ | Oxazolyl | $Z_1$: CH$_2$F (3) |
| S | Pyridinyl | NH—SO$_2$ | Oxazolyl | $Z_1$: CHF$_2$ (2) |
| S | Pyridinyl | NH—SO$_2$ | Oxazolyl | $Z_1$: CHF$_2$ (3) |
| S | Pyridinyl | NH—SO$_2$ | Oxazolyl | $Z_1$: CF$_3$ (2) |
| S | Pyridinyl | NH—SO$_2$ | Oxazolyl | $Z_1$: CF$_3$ (3) |
| S | Pyridinyl | NH—SO$_2$ | Oxazolyl | $Z_1$: CH$_2$—CH$_2$F (2) |
| S | Pyridinyl | NH—SO$_2$ | Oxazolyl | $Z_1$: CH$_2$—CH$_2$F (3) |
| S | Pyridinyl | NH—SO$_2$ | Oxazolyl | $Z_1$: CH$_2$—CHF$_2$ (2) |
| S | Pyridinyl | NH—SO$_2$ | Oxazolyl | $Z_1$: CH$_2$—CHF$_2$ (3) |
| S | Pyridinyl | NH—SO$_2$ | Oxazolyl | $Z_1$: CH$_2$—CF$_3$ (2) |
| S | Pyridinyl | NH—SO$_2$ | Oxazolyl | $Z_1$: CH$_2$—CF$_3$ (3) |
| S | pyridinyl | NH—SO$_2$ | Thiophenyl | None |
| S | pyridinyl | NH—SO$_2$ | Thiophenyl | $Z_1$: F (2) |
| S | pyridinyl | NH—SO$_2$ | Thiophenyl | $Z_1$: F (3) |
| S | pyridinyl | NH—SO$_2$ | Thiophenyl | $Z_1$: F (2) |
|   |   |   |   | $Z_2$: F (3) |
| S | Pyridinyl | NH—SO$_2$ | Thiophenyl | $Z_1$: Cl (2) |
| S | Pyridinyl | NH—SO$_2$ | Thiophenyl | $Z_1$: Cl (3) |
| S | Pyridinyl | NH—SO$_2$ | Thiophenyl | $Z_1$: Cl (2) |
|   |   |   |   | $Z_2$: Cl (3) |
| S | Pyridinyl | NH—SO$_2$ | Thiophenyl | $Z_1$: F (2) |
|   |   |   |   | $Z_2$: Cl (3) |
| S | Pyridinyl | NH—SO$_2$ | Thiophenyl | $Z_1$: Cl (2) |
|   |   |   |   | $Z_2$: F (3) |
| S | Pyridinyl | NH—SO$_2$ | Thiophenyl | $Z_1$: CH$_3$ (2) |
| S | Pyridinyl | NH—SO$_2$ | Thiophenyl | $Z_1$: CH$_3$ (3) |
| S | Pyridinyl | NH—SO$_2$ | Thiophenyl | $Z_1$: CH$_2$—CH$_3$ (2) |
| S | Pyridinyl | NH—SO$_2$ | Thiophenyl | $Z_1$: CH$_2$—CH$_3$ (3) |
| S | Pyridinyl | NH—SO$_2$ | Thiophenyl | $Z_1$: CH$_2$—CH$_2$—CH$_3$ or iPr (2) |
| S | Pyridinyl | NH—SO$_2$ | Thiophenyl | $Z_1$: CH$_2$—CH$_2$—CH$_3$ or iPr (3) |
| S | Pyridinyl | NH—SO$_2$ | Thiophenyl | $Z_1$: CH$_2$F (2) |
| S | Pyridinyl | NH—SO$_2$ | Thiophenyl | $Z_1$: CH$_2$F (3) |
| S | Pyridinyl | NH—SO$_2$ | Thiophenyl | $Z_1$: CHF$_2$ (2) |
| S | Pyridinyl | NH—SO$_2$ | Thiophenyl | $Z_1$: CHF$_2$ (3) |
| S | Pyridinyl | NH—SO$_2$ | Thiophenyl | $Z_1$: CF$_3$ (2) |
| S | Pyridinyl | NH—SO$_2$ | Thiophenyl | $Z_1$: CF$_3$ (3) |
| S | Pyridinyl | NH—SO$_2$ | Thiophenyl | $Z_1$: CH$_2$—CH$_2$F (2) |
| S | Pyridinyl | NH—SO$_2$ | Thiophenyl | $Z_1$: CH$_2$—CH$_2$F (3) |
| S | Pyridinyl | NH—SO$_2$ | Thiophenyl | $Z_1$: CH$_2$—CHF$_2$ (2) |
| S | Pyridinyl | NH—SO$_2$ | Thiophenyl | $Z_1$: CH$_2$—CHF$_2$ (3) |
| S | Pyridinyl | NH—SO$_2$ | Thiophenyl | $Z_1$: CH$_2$—CF$_3$ (2) |
| S | Pyridinyl | NH—SO$_2$ | Thiophenyl | $Z_1$: CH$_2$—CF$_3$ (3) |
| S | pyridinyl | NH—SO$_2$ | Thiazolyl | None |
| S | pyridinyl | NH—SO$_2$ | Thiazolyl | $Z_1$: F (2) |
| S | pyridinyl | NH—SO$_2$ | Thiazolyl | $Z_1$: F (3) |
| S | pyridinyl | NH—SO$_2$ | Thiazolyl | $Z_1$: F (2) |
|   |   |   |   | $Z_2$: F (3) |
| S | Pyridinyl | NH—SO$_2$ | Thiazolyl | $Z_1$: Cl (2) |
| S | Pyridinyl | NH—SO$_2$ | Thiazolyl | $Z_1$: Cl (3) |
| S | Pyridinyl | NH—SO$_2$ | Thiazolyl | $Z_1$: Cl (2) |
|   |   |   |   | $Z_2$: Cl (3) |
| S | Pyridinyl | NH—SO$_2$ | Thiazolyl | $Z_1$: F (2) |
|   |   |   |   | $Z_2$: Cl (3) |
| S | Pyridinyl | NH—SO$_2$ | Thiazolyl | $Z_1$: Cl (2) |
|   |   |   |   | $Z_2$: F (3) |
| S | Pyridinyl | NH—SO$_2$ | Thiazolyl | $Z_1$: CH$_3$ (2) |

TABLE 2-continued

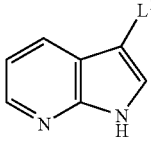

| L¹ | C¹ | L² | C² | Z |
|---|---|---|---|---|
| S | Pyridinyl | NH—SO₂ | Thiazolyl | $Z_1$: $CH_3$ (3) |
| S | Pyridinyl | NH—SO₂ | Thiazolyl | $Z_1$: $CH_2$—$CH_3$ (2) |
| S | Pyridinyl | NH—SO₂ | Thiazolyl | $Z_1$: $CH_2$—$CH_3$ (3) |
| S | Pyridinyl | NH—SO₂ | Thiazolyl | $Z_1$: $CH_2$—$CH_2$—$CH_3$ or iPr (2) |
| S | Pyridinyl | NH—SO₂ | Thiazolyl | $Z_1$: $CH_2$—$CH_2$—$CH_3$ or iPr (3) |
| S | Pyridinyl | NH—SO₂ | Thiazolyl | $Z_1$: $CH_2F$ (2) |
| S | Pyridinyl | NH—SO₂ | Thiazolyl | $Z_1$: $CH_2F$ (3) |
| S | Pyridinyl | NH—SO₂ | Thiazolyl | $Z_1$: $CHF_2$ (2) |
| S | Pyridinyl | NH—SO₂ | Thiazolyl | $Z_1$: $CHF_2$ (3) |
| S | Pyridinyl | NH—SO₂ | Thiazolyl | $Z_1$: $CF_3$ (2) |
| S | Pyridinyl | NH—SO₂ | Thiazolyl | $Z_1$: $CF_3$ (3) |
| S | Pyridinyl | NH—SO₂ | Thiazolyl | $Z_1$: $CH_2$—$CH_2F$ (2) |
| S | Pyridinyl | NH—SO₂ | Thiazolyl | $Z_1$: $CH_2$—$CH_2F$ (3) |
| S | Pyridinyl | NH—SO₂ | Thiazolyl | $Z_1$: $CH_2$—$CHF_2$ (2) |
| S | Pyridinyl | NH—SO₂ | Thiazolyl | $Z_1$: $CH_2$—$CHF_2$ (3) |
| S | Pyridinyl | NH—SO₂ | Thiazolyl | $Z_1$: $CH_2$—$CF_3$ (2) |
| S | Pyridinyl | NH—SO₂ | Thiazolyl | $Z_1$: $CH_2$—$CF_3$ (3) |
| S | Pyrimidinyl | NH—CH₂ | Phenyl | None |
| S | Pyrimidinyl | NH—CH₂ | Phenyl | $Z_1$: F (para) |
| S | Pyrimidinyl | NH—CH₂ | phenyl | $Z_1$: F (meta) |
| S | Pyrimidinyl | NH—CH₂ | phenyl | $Z_1$: F (ortho) |
| S | Pyrimidinyl | NH—CH₂ | phenyl | $Z_1$: F (para) $Z_2$: F (meta) |
| S | Pyrimidinyl | NH—CH₂ | Phenyl | $Z_1$: Cl (meta) |
| S | Pyrimidinyl | NH—CH₂ | Phenyl | $Z_1$: Cl (para) $Z_2$: Cl (meta) |
| S | Pyrimidinyl | NH—CH₂ | Phenyl | $Z_1$: F (para) $Z_2$: Cl (meta) |
| S | Pyrimidinyl | NH—CH₂ | Phenyl | $Z_1$: Cl (para) $Z_2$: F (meta) |
| S | Pyrimidinyl | NH—CH₂ | Phenyl | $Z_1$: $CH_3$ (para) |
| S | Pyrimidinyl | NH—CH₂ | Phenyl | $Z_1$: $CH_3$ (meta) |
| S | Pyrimidinyl | NH—CH₂ | Phenyl | $Z_1$: $CH_3$ (ortho) |
| S | Pyrimidinyl | NH—CH₂ | Phenyl | $Z_1$: $CH_2$—$CH_3$ (para) |
| S | Pyrimidinyl | NH—CH₂ | Phenyl | $Z_1$: $CH_2$—$CH_3$ (meta) |
| S | Pyrimidinyl | NH—CH₂ | Phenyl | $Z_1$: $CH_2$—$CH_3$ (ortho) |
| S | Pyrimidinyl | NH—CH₂ | Phenyl | $Z_1$: $CH_2$—$CH_2$—$CH_3$ or iPr (para) |
| S | Pyrimidinyl | NH—CH₂ | Phenyl | $Z_1$: $CH_2$—$CH_2$—$CH_3$ or iPr (meta) |
| S | Pyrimidinyl | NH—CH₂ | Phenyl | $Z_1$: $CH_2$—$CH_2$—$CH_3$ or iPr (ortho) |
| S | Pyrimidinyl | NH—CH₂ | Phenyl | $Z_1$: $CH_2F$ (para) |
| S | Pyrimidinyl | NH—CH₂ | Phenyl | $Z_1$: $CH_2F$ (meta) |
| S | Pyrimidinyl | NH—CH₂ | Phenyl | $Z_1$: $CH_2F$ (ortho) |
| S | Pyrimidinyl | NH—CH₂ | Phenyl | $Z_1$: $CHF_2$ (para) |
| S | Pyrimidinyl | NH—CH₂ | Phenyl | $Z_1$: $CHF_2$ (meta) |
| S | Pyrimidinyl | NH—CH₂ | Phenyl | $Z_1$: $CHF_2$ (ortho) |
| S | Pyrimidinyl | NH—CH₂ | Phenyl | $Z_1$: $CF_3$ (para) |
| S | Pyrimidinyl | NH—CH₂ | Phenyl | $Z_1$: $CF_3$ (meta) |
| S | Pyrimidinyl | NH—CH₂ | Phenyl | $Z_1$: $CF_3$ (ortho) |
| S | Pyrimidinyl | NH—CH₂ | Phenyl | $Z_1$: $CH_2$—$CH_2F$ (para) |
| S | Pyrimidinyl | NH—CH₂ | Phenyl | $Z_1$: $CH_2$—$CH_2F$ (meta) |
| S | Pyrimidinyl | NH—CH₂ | Phenyl | $Z_1$: $CH_2$—$CH_2F$ (ortho) |
| S | Pyrimidinyl | NH—CH₂ | Phenyl | $Z_1$: $CH_2$—$CHF_2$ (para) |
| S | Pyrimidinyl | NH—CH₂ | Phenyl | $Z_1$: $CH_2$—$CHF_2$ (meta) |
| S | Pyrimidinyl | NH—CH₂ | Phenyl | $Z_1$: $CH_2$—$CHF_2$ (ortho) |
| S | Pyrimidinyl | NH—CH₂ | Phenyl | $Z_1$: $CH_2$—$CF_3$ (para) |
| S | Pyrimidinyl | NH—CH₂ | Phenyl | $Z_1$: $CH_2$—$CF_3$ (meta) |
| S | Pyrimidinyl | NH—CH₂ | Phenyl | $Z_1$: $CH_2$—$CF_3$ (ortho) |
| S | Pyrimidinyl | NH—CH₂ | Pyridinyl | None |
| S | Pyrimidinyl | NH—CH₂ | Pyridinyl | $Z_1$: F (para) |
| S | Pyrimidinyl | NH—CH₂ | Pyridinyl | $Z_1$: F (meta) |
| S | Pyrimidinyl | NH—CH₂ | Pyridinyl | $Z_1$: F (ortho) |
| S | Pyrimidinyl | NH—CH₂ | Pyridinyl | $Z_1$: F (para) $Z_2$: F (meta) |
| S | Pyrimidinyl | NH—CH₂ | Pyridinyl | $Z_1$: Cl (meta) |
| S | Pyrimidinyl | NH—CH₂ | Pyridinyl | $Z_1$: Cl (para) |

TABLE 2-continued

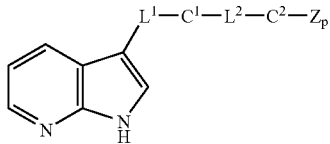

| L$^1$ | C$^1$ | L$^2$ | C$^2$ | Z |
|---|---|---|---|---|
| S | Pyrimidinyl | NH—CH$_2$ | Pyridinyl | Z$_1$: Cl (para)<br>Z$_2$: Cl (meta) |
| S | Pyrimidinyl | NH—CH$_2$ | Pyridinyl | Z$_1$: F (para)<br>Z$_2$: Cl (meta) |
| S | Pyrimidinyl | NH—CH$_2$ | Pyridinyl | Z$_1$: Cl (para)<br>Z$_2$: F (meta) |
| S | Pyrimidinyl | NH—CH$_2$ | Pyridinyl | Z$_1$: CH$_3$ (para) |
| S | Pyrimidinyl | NH—CH$_2$ | Pyridinyl | Z$_1$: CH$_3$ (meta) |
| S | Pyrimidinyl | NH—CH$_2$ | Pyridinyl | Z$_1$: CH$_3$ (ortho) |
| S | Pyrimidinyl | NH—CH$_2$ | Pyridinyl | Z$_1$: CH$_2$—CH$_3$ (para) |
| S | Pyrimidinyl | NH—CH$_2$ | Pyridinyl | Z$_1$: CH$_2$—CH$_3$ (meta) |
| S | Pyrimidinyl | NH—CH$_2$ | Pyridinyl | Z$_1$: CH$_2$—CH$_3$ (ortho) |
| S | Pyrimidinyl | NH—CH$_2$ | Pyridinyl | Z$_1$: CH$_2$—CH$_2$—CH$_3$ or iPr (para) |
| S | Pyrimidinyl | NH—CH$_2$ | Pyridinyl | Z$_1$: CH$_2$—CH$_2$—CH$_3$ or iPr (meta) |
| S | Pyrimidinyl | NH—CH$_2$ | Pyridinyl | Z$_1$: CH$_2$—CH$_2$—CH$_3$ or iPr (ortho) |
| S | Pyrimidinyl | NH—CH$_2$ | Pyridinyl | Z$_1$: CH$_2$F (para) |
| S | Pyrimidinyl | NH—CH$_2$ | Pyridinyl | Z$_1$: CH$_2$F (meta) |
| S | Pyrimidinyl | NH—CH$_2$ | Pyridinyl | Z$_1$: CH$_2$F (ortho) |
| S | Pyrimidinyl | NH—CH$_2$ | Pyridinyl | Z$_1$: CHF$_2$ (para) |
| S | Pyrimidinyl | NH—CH$_2$ | Pyridinyl | Z$_1$: CHF$_2$ (meta) |
| S | Pyrimidinyl | NH—CH$_2$ | Pyridinyl | Z$_1$: CHF$_2$ (ortho) |
| S | Pyrimidinyl | NH—CH$_2$ | Pyridinyl | Z$_1$: CF$_3$ (para) |
| S | Pyrimidinyl | NH—CH$_2$ | Pyridinyl | Z$_1$: CF$_3$ (meta) |
| S | Pyrimidinyl | NH—CH$_2$ | Pyridinyl | Z$_1$: CF$_3$ (ortho) |
| S | Pyrimidinyl | NH—CH$_2$ | Pyridinyl | Z$_1$: CH$_2$—CH$_2$F (para) |
| S | Pyrimidinyl | NH—CH$_2$ | Pyridinyl | Z$_1$: CH$_2$—CH$_2$F (meta) |
| S | Pyrimidinyl | NH—CH$_2$ | Pyridinyl | Z$_1$: CH$_2$—CH$_2$F (ortho) |
| S | Pyrimidinyl | NH—CH$_2$ | Pyridinyl | Z$_1$: CH$_2$—CHF$_2$ (para) |
| S | Pyrimidinyl | NH—CH$_2$ | Pyridinyl | Z$_1$: CH$_2$—CHF$_2$ (meta) |
| S | Pyrimidinyl | NH—CH$_2$ | Pyridinyl | Z$_1$: CH$_2$—CHF$_2$ (ortho) |
| S | Pyrimidinyl | NH—CH$_2$ | Pyridinyl | Z$_1$: CH$_2$—CF$_3$ (para) |
| S | Pyrimidinyl | NH—CH$_2$ | Pyridinyl | Z$_1$: CH$_2$—CF$_3$ (meta) |
| S | Pyrimidinyl | NH—CH$_2$ | Pyridinyl | Z$_1$: CH$_2$—CF$_3$ (ortho) |
| S | Pyrimidinyl | NH—CH$_2$ | Pyrimidinyl | None |
| S | Pyrimidinyl | NH—CH$_2$ | Pyrimidinyl | Z$_1$: F (para) |
| S | Pyrimidinyl | NH—CH$_2$ | Pyrimidinyl | Z$_1$: F (meta) |
| S | Pyrimidinyl | NH—CH$_2$ | Pyrimidinyl | Z$_1$: F (ortho) |
| S | Pyrimidinyl | NH—CH$_2$ | Pyrimidinyl | Z$_1$: F (para)<br>Z$_2$: F (meta) |
| S | Pyrimidinyl | NH—CH$_2$ | Pyrimidinyl | Z$_1$: Cl (meta) |
| S | Pyrimidinyl | NH—CH$_2$ | Pyrimidinyl | Z$_1$: Cl (para) |
| S | Pyrimidinyl | NH—CH$_2$ | Pyrimidinyl | Z$_1$: Cl (para)<br>Z$_2$: Cl (meta) |
| S | Pyrimidinyl | NH—CH$_2$ | Pyrimidinyl | Z$_1$: Cl (meta)<br>Z$_2$: Cl (meta) |
| S | Pyrimidinyl | NH—CH$_2$ | Pyrimidinyl | Z$_1$: Cl (para)<br>Z$_2$: F (meta) |
| S | Pyrimidinyl | NH—CH$_2$ | Pyrimidinyl | Z$_1$: CH$_3$ (para) |
| S | Pyrimidinyl | NH—CH$_2$ | Pyrimidinyl | Z$_1$: CH$_3$ (meta) |
| S | Pyrimidinyl | NH—CH$_2$ | Pyrimidinyl | Z$_1$: CH$_3$ (ortho) |
| S | Pyrimidinyl | NH—CH$_2$ | Pyrimidinyl | Z$_1$: CH$_2$—CH$_3$ (para) |
| S | Pyrimidinyl | NH—CH$_2$ | Pyrimidinyl | Z$_1$: CH$_2$—CH$_3$ (meta) |
| S | Pyrimidinyl | NH—CH$_2$ | Pyrimidinyl | Z$_1$: CH$_2$—CH$_3$ (ortho) |
| S | Pyrimidinyl | NH—CH$_2$ | Pyrimidinyl | Z$_1$: CH$_2$—CH$_2$—CH$_3$ or iPr (para) |
| S | Pyrimidinyl | NH—CH$_2$ | Pyrimidinyl | Z$_1$: CH$_2$—CH$_2$—CH$_3$ or iPr (meta) |
| S | Pyrimidinyl | NH—CH$_2$ | Pyrimidinyl | Z$_1$: CH$_2$—CH$_2$—CH$_3$ or iPr (ortho) |
| S | Pyrimidinyl | NH—CH$_2$ | Pyrimidinyl | Z$_1$: CH$_2$F (para) |
| S | Pyrimidinyl | NH—CH$_2$ | Pyrimidinyl | Z$_1$: CH$_2$F (meta) |
| S | Pyrimidinyl | NH—CH$_2$ | Pyrimidinyl | Z$_1$: CH$_2$F (ortho) |
| S | Pyrimidinyl | NH—CH$_2$ | Pyrimidinyl | Z$_1$: CHF$_2$ (para) |
| S | Pyrimidinyl | NH—CH$_2$ | Pyrimidinyl | Z$_1$: CHF$_2$ (meta) |
| S | Pyrimidinyl | NH—CH$_2$ | Pyrimidinyl | Z$_1$: CHF$_2$ (ortho) |
| S | Pyrimidinyl | NH—CH$_2$ | Pyrimidinyl | Z$_1$: CF$_3$ (para) |

TABLE 2-continued

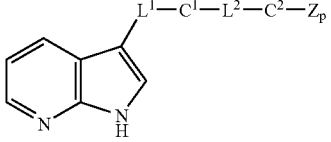

| L$^1$ | C$^1$ | L$^2$ | C$^2$ | Z |
|---|---|---|---|---|
| S | Pyrimidinyl | NH—CH$_2$ | Pyrimidinyl | Z$_1$: CF$_3$ (meta) |
| S | Pyrimidinyl | NH—CH$_2$ | Pyrimidinyl | Z$_1$: CF$_3$ (ortho) |
| S | Pyrimidinyl | NH—CH$_2$ | Pyrimidinyl | Z$_1$: CH$_2$—CH$_2$F (para) |
| S | Pyrimidinyl | NH—CH$_2$ | Pyrimidinyl | Z$_1$: CH$_2$—CH$_2$F (meta) |
| S | Pyrimidinyl | NH—CH$_2$ | Pyrimidinyl | Z$_1$: CH$_2$—CH$_2$F (ortho) |
| S | Pyrimidinyl | NH—CH$_2$ | Pyrimidinyl | Z$_1$: CH$_2$—CHF$_2$ (para) |
| S | Pyrimidinyl | NH—CH$_2$ | Pyrimidinyl | Z$_1$: CH$_2$—CHF$_2$ (meta) |
| S | Pyrimidinyl | NH—CH$_2$ | Pyrimidinyl | Z$_1$: CH$_2$—CHF$_2$ (ortho) |
| S | Pyrimidinyl | NH—CH$_2$ | Pyrimidinyl | Z$_1$: CH$_2$—CF$_3$ (para) |
| S | Pyrimidinyl | NH—CH$_2$ | Pyrimidinyl | Z$_1$: CH$_2$—CF$_3$ (meta) |
| S | Pyrimidinyl | NH—CH$_2$ | Pyrimidinyl | Z$_1$: CH$_2$—CF$_3$ (ortho) |
| S | Pyrimidinyl | NH—CH$_2$ | Pyrazinyl | None |
| S | Pyrimidinyl | NH—CH$_2$ | Pyrazinyl | Z$_1$: F (para) |
| S | Pyrimidinyl | NH—CH$_2$ | Pyrazinyl | Z$_1$: F (meta) |
| S | Pyrimidinyl | NH—CH$_2$ | Pyrazinyl | Z$_1$: F (ortho) |
| S | Pyrimidinyl | NH—CH$_2$ | Pyrazinyl | Z$_1$: F (para) Z$_2$: F (meta) |
| S | Pyrimidinyl | NH—CH$_2$ | Pyrazinyl | Z$_1$: Cl (meta) |
| S | Pyrimidinyl | NH—CH$_2$ | Pyrazinyl | Z$_1$: Cl (para) |
| S | Pyrimidinyl | NH—CH$_2$ | Pyrazinyl | Z$_1$: Cl (para) Z$_2$: Cl (meta) |
| S | Pyrimidinyl | NH—CH$_2$ | Pyrazinyl | Z$_1$: F (para) Z$_2$: Cl (meta) |
| S | Pyrimidinyl | NH—CH$_2$ | Pyrazinyl | Z$_1$: Cl (para) Z$_2$: F (meta) |
| S | Pyrimidinyl | NH—CH$_2$ | Pyrazinyl | Z$_1$: CH$_3$ (para) |
| S | Pyrimidinyl | NH—CH$_2$ | Pyrazinyl | Z$_1$: CH$_3$ (meta) |
| S | Pyrimidinyl | NH—CH$_2$ | Pyrazinyl | Z$_1$: CH$_3$ (ortho) |
| S | Pyrimidinyl | NH—CH$_2$ | Pyrazinyl | Z$_1$: CH$_2$—CH$_3$ (para) |
| S | Pyrimidinyl | NH—CH$_2$ | Pyrazinyl | Z$_1$: CH$_2$—CH$_3$ (meta) |
| S | Pyrimidinyl | NH—CH$_2$ | Pyrazinyl | Z$_1$: CH$_2$—CH$_3$ (ortho) |
| S | Pyrimidinyl | NH—CH$_2$ | Pyrazinyl | Z$_1$: CH$_2$—CH$_2$—CH$_3$ or iPr (para) |
| S | Pyrmildinyl | NH—CH$_2$ | Pyrazinyl | Z$_1$: CH$_2$—CH$_2$—CH$_3$ or iPr (meta) |
| S | Pyrimidinyl | NH—CH$_2$ | Pyrazinyl | Z$_1$: CH$_2$—CH$_2$—CH$_3$ or iPr (ortho) |
| S | Pyrimidinyl | NH—CH$_2$ | Pyrazinyl | Z$_1$: CH$_2$F (para) |
| S | Pyrimidinyl | NH—CH$_2$ | Pyrazinyl | Z$_1$: CH$_2$F (meta) |
| S | Pyrimidinyl | NH—CH$_2$ | Pyrazinyl | Z$_1$: CH$_2$F (ortho) |
| S | Pyrimidinyl | NH—CH$_2$ | Pyrazinyl | Z$_1$: CHF$_2$ (para) |
| S | Pyrimidinyl | NH—CH$_2$ | Pyrazinyl | Z$_1$: CHF$_2$ (meta) |
| S | Pyrimidinyl | NH—CH$_2$ | Pyrazinyl | Z$_1$: CHF$_2$ (ortho) |
| S | Pyrimidinyl | NH—CH$_2$ | Pyrazinyl | Z$_1$: CF$_3$ (para) |
| S | Pyrimidinyl | NH—CH$_2$ | Pyrazinyl | Z$_1$: CF$_3$ (meta) |
| S | Pyrimidinyl | NH—CH$_2$ | Pyrazinyl | Z$_1$: CF$_3$ (ortho) |
| S | Pyrimidinyl | NH—CH$_2$ | Pyrazinyl | Z$_1$: CH$_2$—CH$_2$F (para) |
| S | Pyrimidinyl | NH—CH$_2$ | Pyrazinyl | Z$_1$: CH$_2$—CH$_2$F (meta) |
| S | Pyrimidinyl | NH—CH$_2$ | Pyrazinyl | Z$_1$: CH$_2$—CH$_2$F (ortho) |
| S | Pyrimidinyl | NH—CH$_2$ | Pyrazinyl | Z$_1$: CH$_2$—CHF$_2$ (para) |
| S | Pyrimidinyl | NH—CH$_2$ | Pyrazinyl | Z$_1$: CH$_2$—CHF$_2$ (meta) |
| S | Pyrimidinyl | NH—CH$_2$ | Pyrazinyl | Z$_1$: CH$_2$—CHF$_2$ (ortho) |
| S | Pyrimidinyl | NH—CH$_2$ | Pyrazinyl | Z$_1$: CH$_2$—CF$_3$ (para) |
| S | Pyrimidinyl | NH—CH$_2$ | Pyrazinyl | Z$_1$: CH$_2$—CF$_3$ (meta) |
| S | Pyrimidinyl | NH—CH$_2$ | Pyrazinyl | Z$_1$: CH$_2$—CF$_3$ (ortho) |
| S | Pyrimidinyl | NH—CH$_2$ | Pyrrolyl | None |
| S | Pyrimidinyl | NH—CH$_2$ | Pyrrolyl | Z$_1$: F (2) |
| S | Pyrimidinyl | NH—CH$_2$ | Pyrrolyl | Z$_1$: F (3) |
| S | Pyrimidinyl | NH—CH$_2$ | Pyrrolyl | Z$_1$: F (2) Z$_2$: F (3) |
| S | Pyrimidinyl | NH—CH$_2$ | Pyrrolyl | Z$_1$: Cl (2) |
| S | Pyrimidinyl | NH—CH$_2$ | Pyrrolyl | Z$_1$: Cl (3) |
| S | Pyrimidinyl | NH—CH$_2$ | Pyrrolyl | Z$_1$: Cl (2) Z$_2$: Cl (3) |
| S | Pyrimidinyl | NH—CH$_2$ | Pyrrolyl | Z$_1$: F (2) Z$_2$: Cl (3) |
| S | Pyrimidinyl | NH—CH$_2$ | Pyrrolyl | Z$_1$: Cl (2) Z$_2$: F (3) |
| S | Pyrimidinyl | NH—CH$_2$ | Pyrrolyl | Z$_1$: CH$_3$ (2) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| S | Pyrimidinyl | NH—CH₂ | Pyrrolyl | $Z_1$: CH₃ (3) |
| S | Pyrimidinyl | NH—CH₂ | Pyrrolyl | $Z_1$: CH₂—CH₃ (2) |
| S | Pyrimidinyl | NH—CH₂ | Pyrrolyl | $Z_1$: CH₂—CH₃ (3) |
| S | Pyrimidinyl | NH—CH₂ | Pyrrolyl | $Z_1$: CH₂—CH₂—CH₃ or iPr (2) |
| S | Pyrimidinyl | NH—CH₂ | Pyrrolyl | $Z_1$: CH₂—CH₂—CH₃ or iPr (3) |
| S | Pyrimidinyl | NH—CH₂ | Pyrrolyl | $Z_1$: CH₂F (2) |
| S | Pyrimidinyl | NH—CH₂ | Pyrrolyl | $Z_1$: CH₂F (3) |
| S | Pyrimidinyl | NH—CH₂ | Pyrrolyl | $Z_1$: CHF₂ (2) |
| S | Pyrimidinyl | NH—CH₂ | Pyrrolyl | $Z_1$: CHF₂ (3) |
| S | Pyrimidinyl | NH—CH₂ | Pyrrolyl | $Z_1$: CF₃ (2) |
| S | Pyrimidinyl | NH—CH₂ | Pyrrolyl | $Z_1$: CF₃ (3) |
| S | Pyrimidinyl | NH—CH₂ | Pyrrolyl | $Z_1$: CH₂—CH₂F (2) |
| S | Pyrimidinyl | NH—CH₂ | Pyrrolyl | $Z_1$: CH₂—CH₂F (3) |
| S | Pyrimidinyl | NH—CH₂ | Pyrrolyl | $Z_1$: CH₂—CHF₂ (2) |
| S | Pyrimidinyl | NH—CH₂ | Pyrrolyl | $Z_1$: CH₂—CHF₂ (3) |
| S | Pyrimidinyl | NH—CH₂ | Pyrrolyl | $Z_1$: CH₂—CF₃ (2) |
| S | Pyrimidinyl | NH—CH₂ | Pyrrolyl | $Z_1$: CH₂—CF₃ (3) |
| S | Pyrimidinyl | NH—CH₂ | Imidazolyl | None |
| S | Pyrimidinyl | NH—CH₂ | Imidazolyl | $Z_1$: F (2) |
| S | Pyrimiduiyl | NH—CH₂ | Imidazolyl | $Z_1$: F (3) |
| S | Pyrimidinyl | NH—CH₂ | Imidazolyl | $Z_1$: F (2)<br>$Z_2$: F (3) |
| S | Pyrimidinyl | NH—CH₂ | Imidazolyl | $Z_1$: Cl (2) |
| S | Pyrimidinyl | NH—CH₂ | Imidazolyl | $Z_1$: Cl (3) |
| S | Pyrimidinyl | NH—CH₂ | Imidazolyl | $Z_1$: Cl (2)<br>$Z_2$: Cl (3) |
| S | Pyrimidinyl | NH—CH₂ | Imidazolyl | $Z_1$: F (2)<br>$Z_2$: Cl (3) |
| S | Pyrimidinyl | NH—CH₂ | Imidazolyl | $Z_1$: Cl (2)<br>$Z_2$: F (3) |
| S | Pyrimidinyl | NH—CH₂ | Imidazolyl | $Z_1$: CH₃ (2) |
| S | Pyrimidinyl | NH—CH₂ | Imidazolyl | $Z_1$: CH₃ (3) |
| S | Pyrimidinyl | NH—CH₂ | Imidazolyl | $Z_1$: CH₂—CH₃ (2) |
| S | Pyrimidinyl | NH—CH₂ | Imidazolyl | $Z_1$: CH₂—CH₃ (3) |
| S | Pyrimidinyl | NH—CH₂ | Imidazolyl | $Z_1$: CH₂—CH₂—CH₃ or iPr (2) |
| S | Pyrimidinyl | NH—CH₂ | Imidazolyl | $Z_1$: CH₂—CH₂—CH₃ or iPr (3) |
| S | Pyrimidinyl | NH—CH₂ | Imidazolyl | $Z_1$: CH₂F (2) |
| S | Pyrimidinyl | NH—CH₂ | Imidazolyl | $Z_1$: CH₂F (3) |
| S | Pyrimidinyl | NH—CH₂ | Imidazolyl | $Z_1$: CHF₂ (2) |
| S | Pyrimidinyl | NH—CH₂ | Imidazolyl | $Z_1$: CHF₂ (3) |
| S | Pyrimidinyl | NH—CH₂ | Imidazolyl | $Z_1$: CF₃ (2) |
| S | Pyrimidinyl | NH—CH₂ | Imidazolyl | $Z_1$: CF₃ (3) |
| S | Pyrimidinyl | NH—CH₂ | Imidazolyl | $Z_1$: CH₂—CH₂F (2) |
| S | Pyrimidinyl | NH—CH₂ | Imidazolyl | $Z_1$: CH₂—CH₂F (3) |
| S | Pyrimidinyl | NH—CH₂ | Imidazolyl | $Z_1$: CH₂—CHF₂ (2) |
| S | Pyrimidinyl | NH—CH₂ | Imidazolyl | $Z_1$: CH₂—CHF₂ (3) |
| S | Pyrimidinyl | NH—CH₂ | Imidazolyl | $Z_1$: CH₂—CF₃ (2) |
| S | Pyrimidinyl | NH—CH₂ | Imidazolyl | $Z_1$: CH₂—CF₃ (3) |
| S | Pyrimidinyl | NH—CH₂ | Furanyl | None |
| S | Pyrimidinyl | NH—CH₂ | Furanyl | $Z_1$: F (2) |
| S | Pyrimidinyl | NH—CH₂ | Furanyl | $Z_1$: F (3) |
| S | Pyrimidinyl | NH—CH₂ | Furanyl | $Z_1$: F (2)<br>$Z_2$: F (3) |
| S | Pyrimidinyl | NH—CH₂ | Furanyl | $Z_1$: Cl (2) |
| S | Pyrimidinyl | NH—CH₂ | Furanyl | $Z_1$: Cl (3) |
| S | Pyrimidinyl | NH—CH₂ | Furanyl | $Z_1$: Cl (2)<br>$Z_2$: Cl (3) |
| S | Pyrimidinyl | NH—CH₂ | Furanyl | $Z_1$: F (2)<br>$Z_2$: Cl (3) |
| S | Pyrimidinyl | NH—CH₂ | Furanyl | $Z_1$: Cl (2)<br>$Z_2$: F (3) |
| S | Pyrimidinyl | NH—CH₂ | Furanyl | $Z_1$: CH₃ (2) |
| S | Pyrimidinyl | NH—CH₂ | Furanyl | $Z_1$: CH₃ (3) |
| S | Pyrimidinyl | NH—CH₂ | Furanyl | $Z_1$: CH₂—CH₃ (2) |
| S | Pyrimidinyl | NH—CH₂ | Furanyl | $Z_1$: CH₂—CH₃ (3) |
| S | Pyrimidinyl | NH—CH₂ | Furanyl | $Z_1$: CH₂—CH₂—CH₃ or iPr (2) |
| S | Pyrimidinyl | NH—CH₂ | Furanyl | $Z_1$: CH₂—CH₂—CH₃ or iPr (3) |
| S | Pyrimidinyl | NH—CH₂ | Furanyl | $Z_1$: CH₂F (2) |
| S | Pyrimidinyl | NH—CH₂ | Furanyl | $Z_1$: CH₂F (3) |

TABLE 2-continued $$L^1-C^1-L^2-C^2-Z_p$$

[7-azaindole structure with substituent at 3-position]

| L¹ | C¹ | L² | C² | Z |
|---|---|---|---|---|
| S | Pyrimidinyl | NH—CH₂ | Furanyl | Z₁: CHF₂ (2) |
| S | Pyrimidinyl | NH—CH₂ | Furanyl | Z₁: CHF₂ (3) |
| S | Pyrimidinyl | NH—CH₂ | Furanyl | Z₁: CF₃ (2) |
| S | Pyrimidinyl | NH—CH₂ | Furanyl | Z₁: CF₃ (3) |
| S | Pyrimidinyl | NH—CH₂ | Furanyl | Z₁: CH₂—CH₂F (2) |
| S | Pyrimidinyl | NH—CH₂ | Furanyl | Z₁: CH₂—CH₂F (3) |
| S | Pyrimidinyl | NH—CH₂ | Furanyl | Z₁: CH₂—CHF₂ (2) |
| S | Pyrimidinyl | NH—CH₂ | Furanyl | Z₁: CH₂—CHF₂ (3) |
| S | Pyrimidinyl | NH—CH₂ | Furanyl | Z₁: CH₂—CF₃ (2) |
| S | Pyrimidinyl | NH—CH₂ | Furanyl | Z₁: CH₂—CF₃ (3) |
| S | Pyrimidinyl | NH—CH₂ | Oxazolyl | None |
| S | Pyrimidinyl | NH—CH₂ | Oxazolyl | Z₁: F (2) |
| S | Pyrimidinyl | NH—CH₂ | Oxazolyl | Z₁: F (3) |
| S | Pyrimidinyl | NH—CH₂ | Oxazolyl | Z₁: F (2)<br>Z₂: F (3) |
| S | Pyrimidinyl | NH—CH₂ | Oxazolyl | Z₁: Cl (2) |
| S | Pyrimidinyl | NH—CH₂ | Oxazolyl | Z₁: Cl (3) |
| S | Pyrimidinyl | NH—CH₂ | Oxazolyl | Z₁: Cl (2)<br>Z₂: Cl (3) |
| S | Pyrimidinyl | NH—CH₂ | Oxazolyl | Z₁: F (2)<br>Z₂: Cl (3) |
| S | Pyrimidinyl | NH—CH₂ | Oxazolyl | Z₁: Cl (2)<br>Z₂: F (3) |
| S | Pyrimidinyl | NH—CH₂ | Oxazolyl | Z₁: CH₃ (2) |
| S | Pyrimidinyl | NH—CH₂ | Oxazolyl | Z₁: CH₃ (3) |
| S | Pyrimidinyl | NH—CH₂ | Oxazolyl | Z₁: CH₂—CH₃ (2) |
| S | Pyrimidinyl | NH—CH₂ | Oxazolyl | Z₁: CH₂—CH₃ (3) |
| S | Pyrimidinyl | NH—CH₂ | Oxazolyl | Z₁: CH₂—CH₂—CH₃ or iPr (2) |
| S | Pyrimidinyl | NH—CH₂ | Oxazolyl | Z₁: CH₂—CH₂—CH₃ or iPr (3) |
| S | Pyrimidinyl | NH—CH₂ | Oxazolyl | Z₁: CH₂F (2) |
| S | Pyrimidinyl | NH—CH₂ | Oxazolyl | Z₁: CH₂F (3) |
| S | Pyrimidinyl | NH—CH₂ | Oxazolyl | Z₁: CHF₂ (2) |
| S | Pyrimidinyl | NH—CH₂ | Oxazolyl | Z₁: CHF₂ (3) |
| S | Pyrimidinyl | NH—CH₂ | Oxazolyl | Z₁: CF₃ (2) |
| S | Pyrimidinyl | NH—CH₂ | Oxazolyl | Z₁: CF₃ (3) |
| S | Pyrimidinyl | NH—CH₂ | Oxazolyl | Z₁: CH₂—CH₂F (2) |
| S | Pyrimidinyl | NH—CH₂ | Oxazolyl | Z₁: CH₂—CH₂F (3) |
| S | Pyrimidinyl | NH—CH₂ | Oxazolyl | Z₁: CH₂—CHF₂ (2) |
| S | Pyrimidinyl | NH—CH₂ | Oxazolyl | Z₁: CH₂—CHF₂ (3) |
| S | Pyrimidinyl | NH—CH₂ | Oxazolyl | Z₁: CH₂—CF₃ (2) |
| S | Pyrimidinyl | NH—CH₂ | Oxazolyl | Z₁: CH₂—CF₃ (3) |
| S | Pyrimidinyl | NH—CH₂ | Thiophenyl | None |
| S | Pyrimidinyl | NH—CH₂ | Thiophenyl | Z₁: F (2) |
| S | Pyrimidinyl | NH—CH₂ | Thiophenyl | Z₁: F (3) |
| S | Pyrimidinyl | NH—CH₂ | Thiophenyl | Z₁: F (2)<br>Z₂: F (3) |
| S | Pyrimidinyl | NH—CH₂ | Thiophenyl | Z₁: Cl (2) |
| S | Pyrimidinyl | NH—CH₂ | Thiophenyl | Z₁: Cl (3) |
| S | Pyrimidinyl | NH—CH₂ | Thiophenyl | Z₁: Cl (2)<br>Z₂: Cl (3) |
| S | Pyrimidinyl | NH—CH₂ | Thiophenyl | Z₁: F (2)<br>Z₂: Cl (3) |
| S | Pyrimidinyl | NH—CH₂ | Thiophenyl | Z₁: Cl (2)<br>Z₂: F (3) |
| S | Pyrimidinyl | NH—CH₂ | Thiophenyl | Z₁: CH₃ (2) |
| S | Pyrimidinyl | NH—CH₂ | Thiophenyl | Z₁: CH₃ (3) |
| S | Pyrimidinyl | NH—CH₂ | Thiophenyl | Z₁: CH₂—CH₃ (2) |
| S | Pyrimidinyl | NH—CH₂ | Thiophenyl | Z₁: CH₂—CH₃ (3) |
| S | Pyrimidinyl | NH—CH₂ | Thiophenyl | Z₁: CH₂—CH₂—CH₃ or iPr (2) |
| S | Pyrimidinyl | NH—CH₂ | Thiophenyl | Z₁: CH₂—CH₂—CH₃ or iPr (3) |
| S | Pyrimidinyl | NH—CH₂ | Thiophenyl | Z₁: CH₂F (2) |
| S | Pyrimidinyl | NH—CH₂ | Thiophenyl | Z₁: CH₂F (3) |
| S | Pyrimidinyl | NH—CH₂ | Thiophenyl | Z₁: CHF₂ (2) |
| S | Pyrimidinyl | NH—CH₂ | Thiophenyl | Z₁: CHF₂ (3) |
| S | Pyrimidinyl | NH—CH₂ | Thiophenyl | Z₁: CF₃ (2) |
| S | Pyrimidinyl | NH—CH₂ | Thiophenyl | Z₁: CF₃ (3) |
| S | Pyrimidinyl | NH—CH₂ | Thiophenyl | Z₁: CH₂—CH₂F (2) |
| S | Pyrimidinyl | NH—CH₂ | Thiophenyl | Z₁: CH₂—CH₂F (3) |
| S | Pyrimidinyl | NH—CH₂ | Thiophenyl | Z₁: CH₂—CHF₂ (2) |

TABLE 2-continued

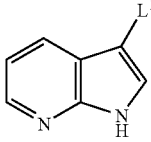

| L¹ | C¹ | L² | C² | Z |
|---|---|---|---|---|
| S | Pyrimidinyl | NH—CH₂ | Thiophenyl | $Z_1$: CH₂—CHF₂ (3) |
| S | Pyrimidinyl | NH—CH₂ | Thiophenyl | $Z_1$: CH₂—CF₃ (2) |
| S | Pyrimidinyl | NH—CH₂ | Thiophenyl | $Z_1$: CH₂—CF₃ (3) |
| S | Pyrimidinyl | NH—CH₂ | Thiazolyl | None |
| S | Pyrimidinyl | NH—CH₂ | Thiazolyl | $Z_1$: F (2) |
| S | Pyrimidinyl | NH—CH₂ | Thiazolyl | $Z_1$: F (3) |
| S | Pyrimidinyl | NH—CH₂ | Thiazolyl | $Z_1$: F (2) $Z_2$: F (3) |
| S | Pyrimidinyl | NH—CH₂ | Thiazolyl | $Z_1$: Cl (2) |
| S | Pyrimidinyl | NH—CH₂ | Thiazolyl | $Z_1$: Cl (3) |
| S | Pyrimidinyl | NH—CH₂ | Thiazolyl | $Z_1$: Cl (2) $Z_2$: Cl (3) |
| S | Pyrimidinyl | NH—CH₂ | Thiazolyl | $Z_1$: F (2) $Z_2$: Cl (3) |
| S | Pyrimidinyl | NH—CH₂ | Thiazolyl | $Z_1$: Cl (2) $Z_2$: F (3) |
| S | Pyrimidinyl | NH—CH₂ | Thiazolyl | $Z_1$: CH₃ (2) |
| S | Pyrimidinyl | NH—CH₂ | Thiazolyl | $Z_1$: CH₃ (3) |
| S | Pyrimidinyl | NH—CH₂ | Thiazolyl | $Z_1$: CH₂—CH₃ (2) |
| S | Pyrimidinyl | NH—CH₂ | Thiazolyl | $Z_1$: CH₂—CH₃ (3) |
| S | Pyrimidinyl | NH—CH₂ | Thiazolyl | $Z_1$: CH₂—CH₂—CH₃ or iPr (2) |
| S | Pyrimidinyl | NH—CH₂ | Thiazolyl | $Z_1$: CH₂—CH₂—CH₃ or iPr (3) |
| S | Pyrimidinyl | NH—CH₂ | Thiazolyl | $Z_1$: CH₂F (2) |
| S | Pyrimidinyl | NH—CH₂ | Thiazolyl | $Z_1$: CH₂F (3) |
| S | Pyrimidinyl | NH—CH₂ | Thiazolyl | $Z_1$: CHF₂ (2) |
| S | Pyrimidinyl | NH—CH₂ | Thiazolyl | $Z_1$: CHF₂ (3) |
| S | Pyrimidinyl | NH—CH₂ | Thiazolyl | $Z_1$: CF₃ (2) |
| S | Pyrimidinyl | NH—CH₂ | Thiazolyl | $Z_1$: CF₃ (3) |
| S | Pyrimidinyl | NH—CH₂ | Thiazolyl | $Z_1$: CH₂—CH₂F (2) |
| S | Pyrimidinyl | NH—CH₂ | Thiazolyl | $Z_1$: CH₂—CH₂F (3) |
| S | Pyrimidinyl | NH—CH₂ | Thiazolyl | $Z_1$: CH₂—CHF₂ (2) |
| S | Pyrimidinyl | NH—CH₂ | Thiazolyl | $Z_1$: CH₂—CHF₂ (3) |
| S | Pyrimidinyl | NH—CH₂ | Thiazolyl | $Z_1$: CH₂—CF₃ (2) |
| S | Pyrimidinyl | NH—CH₂ | Thiazolyl | $Z_1$: CH₂—CF₃ (3) |
| S | Pyrimidinyl | NH—C(O) | Phenyl | None |
| S | Pyrimidinyl | NH—C(O) | Phenyl | $Z_1$: F (para) |
| S | Pyrimidinyl | NH—C(O) | phenyl | $Z_1$: F (meta) |
| S | Pyrimidinyl | NH—C(O) | phenyl | $Z_1$: F (ortho) |
| S | Pyrimidinyl | NH—C(O) | phenyl | $Z_1$: F (para) $Z_2$: F (meta) |
| S | Pyrimidinyl | NH—C(O) | Phenyl | $Z_1$: Cl (meta) |
| S | Pyrimidinyl | NH—C(O) | Phenyl | $Z_1$: Cl (para) |
| S | Pyrimidinyl | NH—C(O) | Phenyl | $Z_1$: Cl (para) $Z_2$: Cl (meta) |
| S | Pyrimidinyl | NH—C(O) | Phenyl | $Z_1$: F (para) $Z_2$: Cl (meta) |
| S | Pyrimidinyl | NH—C(O) | Phenyl | $Z_1$: Cl (para) $Z_2$: F (meta) |
| S | Pyrimidinyl | NH—C(O) | Phenyl | $Z_1$: CHF (para) |
| S | Pyrimidinyl | NH—C(O) | Phenyl | $Z_1$: CH₃ (meta) |
| S | Pyrimidinyl | NH—C(O) | Phenyl | $Z_1$: CH₃ (ortho) |
| S | Pyrimidinyl | NH—C(O) | Phenyl | $Z_1$: CH₂—CH₃ (para) |
| S | Pyrimidinyl | NH—C(O) | Phenyl | $Z_1$: CH₂—CH₃ (meta) |
| S | Pyrimidinyl | NH—C(O) | Phenyl | $Z_1$: CH₂—CH₃ (ortho) |
| S | Pyrimidinyl | NH—C(O) | Phenyl | $Z_1$: CH₂—CH₂—CH₃ or iPr (para) |
| S | Pyrimidinyl | NH—C(O) | Phenyl | $Z_1$: CH₂—CH₂—CH₃ or iPr (meta) |
| S | Pyrimidinyl | NH—C(O) | Phenyl | $Z_1$: CH₂—CH₂—CH₃ or iPr (ortho) |
| S | Pyrimidinyl | NH—C(O) | Phenyl | $Z_1$: CH₂F (para) |
| S | Pyrimidinyl | NH—C(O) | Phenyl | $Z_1$: CH₂F (meta) |
| S | Pyrimidinyl | NH—C(O) | Phenyl | $Z_1$: CH₂F (ortho) |
| S | Pyrimidinyl | NH—C(O) | Phenyl | $Z_1$: CHF₂ (para) |
| S | Pyrimidinyl | NH—C(O) | Phenyl | $Z_1$: CHF₂ (meta) |
| S | Pyrimidinyl | NH—C(O) | Phenyl | $Z_1$: CHF₂ (ortho) |
| S | Pyrimidinyl | NH—C(O) | Phenyl | $Z_1$: CF₃ (para) |
| S | Pyrimidinyl | NH—C(O) | Phenyl | $Z_1$: CF₃ (meta) |
| S | Pyrimidinyl | NH—C(O) | Phenyl | $Z_1$: CF₃ (ortho) |

TABLE 2-continued

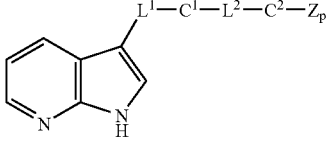

| L¹ | C¹ | L² | C² | Z |
|---|---|---|---|---|
| S | Pyrimidinyl | NH—C(O) | Phenyl | $Z_1$: $CH_2$—$CH_2F$ (para) |
| S | Pyrimidinyl | NH—C(O) | Phenyl | $Z_1$: $CH_2$—$CH_2F$ (meta) |
| S | Pyrimidinyl | NH—C(O) | Phenyl | $Z_1$: $CH_2$—$CH_2F$ (ortho) |
| S | Pyrimidinyl | NH—C(O) | Phenyl | $Z_1$: $CH_2$—$CHF_2$ (para) |
| S | Pyrimidinyl | NH—C(O) | Phenyl | $Z_1$: $CH_2$—$CHF_2$ (meta) |
| S | Pyrimidinyl | NH—C(O) | Phenyl | $Z_1$: $CH_2$—$CHF_2$ (ortho) |
| S | Pyrimidinyl | NH—C(O) | Phenyl | $Z_1$: $CH_2$—$CF_3$ (para) |
| S | Pyrimidinyl | NH—C(O) | Phenyl | $Z_1$: $CH_2$—$CF_3$ (meta) |
| S | Pyrimidinyl | NH—C(O) | Phenyl | $Z_1$: $CH_2$—$CF_3$ (ortho) |
| S | Pyrimidinyl | NH—C(O) | Pyridinyl | None |
| S | Pyrimidinyl | NH—C(O) | Pyridinyl | $Z_1$: F (para) |
| S | Pyrimidinyl | NH—C(O) | Pyridinyl | $Z_1$: F (meta) |
| S | Pyrimidinyl | NH—C(O) | Pyridinyl | $Z_1$: F (ortho) |
| S | Pyrimidinyl | NH—C(O) | Pyridinyl | $Z_1$: F (para)<br>$Z_2$: F (meta) |
| S | Pyrimidinyl | NH—C(O) | Pyridinyl | $Z_1$: Cl (meta) |
| S | Pyrimidinyl | NH—C(O) | Pyridinyl | $Z_1$: Cl (para) |
| S | Pyrimidinyl | NH—C(O) | Pyridinyl | $Z_1$: Cl (para)<br>$Z_2$: Cl (meta) |
| S | Pyrimidinyl | NH—C(O) | Pyridinyl | $Z_1$: F (para)<br>$Z_2$: Cl (meta) |
| S | Pyrimidinyl | NH—C(O) | Pyridinyl | $Z_1$: Cl (para)<br>$Z_2$: F (meta) |
| S | Pyrimidinyl | NH—C(O) | Pyridinyl | $Z_1$: $CH_3$ (para) |
| S | Pyrimidinyl | NH—C(O) | Pyridinyl | $Z_1$: $CH_3$ (meta) |
| S | Pyrimidinyl | NH—C(O) | Pyridinyl | $Z_1$: $CH_3$ (ortho) |
| S | Pyrimidinyl | NH—C(O) | Pyridinyl | $Z_1$: $CH_2$—$CH_3$ (para) |
| S | Pyrimidinyl | NH—C(O) | Pyridinyl | $Z_1$: $CH_2$—$CH_3$ (meta) |
| S | Pyrimidinyl | NH—C(O) | Pyridinyl | $Z_1$: $CH_2$—$CH_3$ (ortho) |
| S | Pyrimidinyl | NH—C(O) | Pyridinyl | $Z_1$: $CH_2$—$CH_2$—$CH_3$ or iPr (para) |
| S | Pyrimidinyl | NH—C(O) | Pyridinyl | $Z_1$: $CH_2$—$CH_2$—$CH_3$ or iPr (meta) |
| S | Pyrimidinyl | NH—C(O) | Pyridinyl | $Z_1$: $CH_2$—$CH_2$—$CH_3$ or iPr (ortho) |
| S | Pyrimidinyl | NH—C(O) | Pyridinyl | $Z_1$: $CH_2F$ (para) |
| S | Pyrimidinyl | NH—C(O) | Pyridinyl | $Z_1$: $CH_2F$ (meta) |
| S | Pyrimidinyl | NH—C(O) | Pyridinyl | $Z_1$: $CH_2F$ (ortho) |
| S | Pyrimidinyl | NH—C(O) | Pyridinyl | $Z_1$: $CHF_2$ (para) |
| S | Pyrimidinyl | NH—C(O) | Pyridinyl | $Z_1$: $CHF_2$ (meta) |
| S | Pyrimidinyl | NH—C(O) | Pyridinyl | $Z_1$: $CHF_2$ (ortho) |
| S | Pyrimidinyl | NH—C(O) | Pyridinyl | $Z_1$: $CF_3$ (para) |
| S | Pyrimidinyl | NH—C(O) | Pyridinyl | $Z_1$: $CF_3$ (meta) |
| S | Pyrimidinyl | NH—C(O) | Pyridinyl | $Z_1$: $CF_3$ (ortho) |
| S | Pyrimidinyl | NH—C(O) | Pyridinyl | $Z_1$: $CH_2$—$CH_2F$ (para) |
| S | Pyrimidinyl | NH—C(O) | Pyridinyl | $Z_1$: $CH_2$—$CH_2F$ (meta) |
| S | Pyrimidinyl | NH—C(O) | Pyridinyl | $Z_1$: $CH_2$—$CH_2F$ (ortho) |
| S | Pyrimidinyl | NH—C(O) | Pyridinyl | $Z_1$: $CH_2$—$CHF_2$ (para) |
| S | Pyrimidinyl | NH—C(O) | Pyridinyl | $Z_1$: $CH_2$—$CHF_2$ (meta) |
| S | Pyrimidinyl | NH—C(O) | Pyridinyl | $Z_1$: $CH_2$—$CHF_2$ (ortho) |
| S | Pyrimidinyl | NH—C(O) | Pyridinyl | $Z_1$: $CH_2$—$CF_3$ (para) |
| S | Pyrimidinyl | NH—C(O) | Pyridinyl | $Z_1$: $CH_2$—$CF_3$ (meta) |
| S | Pyrimidinyl | NH—C(O) | Pyridinyl | $Z_1$: $CH_2$—$CF_3$ (ortho) |
| S | Pyrimidinyl | NH—C(O) | Pyrimidinyl | None |
| S | Pyrimidinyl | NH—C(O) | Pyrimidinyl | $Z_1$: F (para) |
| S | Pyrimidinyl | NH—C(O) | Pyrimidinyl | $Z_1$: F (meta) |
| S | Pyrimidinyl | NH—C(O) | Pyrimidinyl | $Z_1$: F (ortho) |
| S | Pyrimidinyl | NH—C(O) | Pyrimidinyl | $Z_1$: F (para)<br>$Z_2$: F (meta) |
| S | Pyrimidinyl | NH—C(O) | Pyrimidinyl | $Z_1$: Cl (meta) |
| S | Pyrimidinyl | NH—C(O) | Pyrimidinyl | $Z_1$: Cl (para) |
| S | Pyrimidinyl | NH—C(O) | Pyrimidinyl | $Z_1$: Cl (para)<br>$Z_2$: Cl (meta) |
| S | Pyrimidinyl | NH—C(O) | Pyrimiinyl | $Z_1$: F (para)<br>$Z_2$: Cl (meta) |
| S | Pyrimidinyl | NH—C(O) | Pyrimidinyl | $Z_1$: Cl (para)<br>$Z_2$: F (meta) |
| S | Pyrimidinyl | NH—C(O) | Pyrimidinyl | $Z_1$: $CH_3$ (para) |
| S | Pyrimidinyl | NH—C(O) | Pyrimidinyl | $Z_1$: $CH_3$ (meta) |

TABLE 2-continued

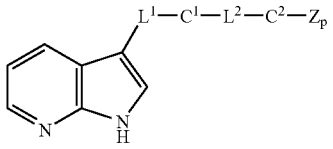

| L$^1$ | C$^1$ | L$^2$ | C$^2$ | Z |
|---|---|---|---|---|
| S | Pyrimidinyl | NH—C(O) | Pyrimidinyl | Z$_1$: CH$_3$ (ortho) |
| S | Pyrimidinyl | NH—C(O) | Pyrimidinyl | Z$_1$: CH$_2$—CH$_3$ (para) |
| S | Pyrimidinyl | NH—C(O) | Pyrimidinyl | Z$_1$: CH$_2$—CH$_3$ (meta) |
| S | Pyrimidinyl | NH—C(O) | Pyrimidinyl | Z$_1$: CH$_2$—CH$_3$ (ortho) |
| S | Pyrimidinyl | NH—C(O) | Pyrimidinyl | Z$_1$: CH$_2$—CH$_2$—CH$_3$ or iPr (para) |
| S | Pyrimidinyl | NH—C(O) | Pyrimidinyl | Z$_1$: CH$_2$—CH$_2$—CH$_3$ or iPr (meta) |
| S | Pyrimidinyl | NH—C(O) | Pyrimidinyl | Z$_1$: CH$_2$—CH$_2$—CH$_3$ or iPr (ortho) |
| S | Pyrimidinyl | NH—C(O) | Pyrimidinyl | Z$_1$: CH$_2$F (para) |
| S | Pyrimidinyl | NH—C(O) | Pyrimidinyl | Z$_1$: CH$_2$F (meta) |
| S | Pyrimidinyl | NH—C(O) | Pyrimidinyl | Z$_1$: CH$_2$F (ortho) |
| S | Pyrimidinyl | NH—C(O) | Pyrimidinyl | Z$_1$: CHF$_2$ (para) |
| S | Pyrimidinyl | NH—C(O) | Pyrimidinyl | Z$_1$: CHF$_2$ (meta) |
| S | Pyrimidinyl | NH—C(O) | Pyrimidinyl | Z$_1$: CHF$_2$ (ortho) |
| S | Pyrimidinyl | NH—C(O) | Pyrimidinyl | Z$_1$: CF$_3$ (para) |
| S | Pyrimidinyl | NH—C(O) | Pyrimidinyl | Z$_1$: CF$_3$ (meta) |
| S | Pyrimidinyl | NH—C(O) | Pyrimidinyl | Z$_1$: CF$_3$ (ortho) |
| S | Pyrimidinyl | NH—C(O) | Pyrimidinyl | Z$_1$: CH$_2$—CH$_2$F (para) |
| S | Pyrimidinyl | NH—C(O) | Pyrimidinyl | Z$_1$: CH$_2$—CH$_2$F (meta) |
| S | Pyrimidinyl | NH—C(O) | Pyrimidinyl | Z$_1$: CH$_2$—CH$_2$F (ortho) |
| S | Pyrimidinyl | NH—C(O) | Pyrimidinyl | Z$_1$: CH$_2$—CHF$_2$ (para) |
| S | Pyrimidinyl | NH—C(O) | Pyrimidinyl | Z$_1$: CH$_2$—CHF$_2$ (meta) |
| S | Pyrimidinyl | NH—C(O) | Pyrimidinyl | Z$_1$: CH$_2$—CHF$_2$ (ortho) |
| S | Pyrimidinyl | NH—C(O) | Pyrimidinyl | Z$_1$: CH$_2$—CF$_3$ (para) |
| S | Pyrimidinyl | NH—C(O) | Pyrimidinyl | Z$_1$: CH$_2$—CF$_3$ (meta) |
| S | Pyrimidinyl | NH—C(O) | Pyrimidinyl | Z$_1$: CH$_2$—CF$_3$ (ortho) |
| S | Pyrimidinyl | NH—C(O) | Pyrazinyl | None |
| S | Pyrimidinyl | NH—C(O) | Pyrazinyl | Z$_1$: F (para) |
| S | Pyrimidinyl | NH—C(O) | Pyrazinyl | Z$_1$: F (meta) |
| S | Pyrimidinyl | NH—C(O) | Pyrazinyl | Z$_1$: F (ortho) |
| S | Pyrimidinyl | NH—C(O) | Pyrazinyl | Z$_1$: F (para) Z$_2$: F (meta) |
| S | Pynnildinyl | NH—C(O) | Pyrazinyl | Z$_1$: Cl (meta) |
| S | Pyrimidinyl | NH—C(O) | Pyrazinyl | Z$_1$: Cl (para) |
| S | Pyrimidinyl | NH—C(O) | Pyrazinyl | Z$_1$: Cl (para) Z$_2$: Cl (meta) |
| S | Pyrimidinyl | NH—C(O) | Pyrazinyl | Z$_1$: F (para) Z$_2$: Cl (meta) |
| S | Pyrimidinyl | NH—C(O) | Pyrazinyl | Z$_1$: Cl (para) Z$_2$: F (meta) |
| S | Pyrimidinyl | NH—C(O) | Pyrazinyl | Z$_1$: CH$_3$ (para) |
| S | Pyrimidinyl | NH—C(O) | Pyrazinyl | Z$_1$: CH$_3$ (meta) |
| S | Pyrimidinyl | NH—C(O) | Pyrazinyl | Z$_1$: CH$_3$ (ortho) |
| S | Pyrimidinyl | NH—C(O) | Pyrazinyl | Z$_1$: CH$_2$—CH$_3$ (para) |
| S | Pyrimidinyl | NH—C(O) | Pyrazinyl | Z$_1$: CH$_2$—CH$_3$ (meta) |
| S | Pyrimidinyl | NH—C(O) | Pyrazinyl | Z$_1$: CH$_2$—CH$_3$ (ortho) |
| S | Pyrimidinyl | NH—C(O) | Pyrazinyl | Z$_1$: CH$_2$—CH$_2$—CH$_3$ or iPr (para) |
| S | Pyrimidinyl | NH—C(O) | Pyrazinyl | Z$_2$: CH$_2$—CH$_2$—CH$_3$ or iPr (meta) |
| S | Pyrimidinyl | NH—C(O) | Pyrazinyl | Z$_1$: CH$_2$—CH$_2$—CH$_3$ or iPr (ortho) |
| S | Pyrimidinyl | NH—C(O) | Pyrazinyl | Z$_1$: CH$_2$F (para) |
| S | Pyrimidinyl | NH—C(O) | Pyrazinyl | Z$_1$: CH$_2$F (meta) |
| S | Pyrimidinyl | NH—C(O) | Pyrazinyl | Z$_1$: CH$_2$F (ortho) |
| S | Pyrimidinyl | NH—C(O) | Pyrazinyl | Z$_1$: CHF$_2$ (para) |
| S | Pyrimidinyl | NH—C(O) | Pyrazinyl | Z$_1$: CHF$_2$ (meta) |
| S | Pyrimidinyl | NH—C(O) | Pyrazinyl | Z$_1$: CHF$_2$ (ortho) |
| S | Pyrimidinyl | NH—C(O) | Pyrazinyl | Z$_1$: CF$_3$ (para) |
| S | Pyrimidinyl | NH—C(O) | Pyrazinyl | Z$_1$: CF$_3$ (meta) |
| S | Pyrimidinyl | NH—C(O) | Pyrazinyl | Z$_1$: CF3 (ortho) |
| S | Pyrimidinyl | NH—C(O) | Pyrazinyl | Z$_1$: CH$_2$—CH$_2$F (para) |
| S | Pyrimidinyl | NH—C(O) | Pyrazinyl | Z$_1$: CH$_2$—CH$_2$F (meta) |
| S | Pyrimidinyl | NH—C(O) | Pyrazinyl | Z$_1$: CH$_2$—CH$_2$F (ortho) |
| S | Pyrimidinyl | NH—C(O) | Pyrazinyl | Z$_1$: CH$_2$—CHF$_2$ (para) |
| S | Pyrimidinyl | NH—C(O) | Pyrazinyl | Z$_1$: CH$_2$—CHF$_2$ (meta) |
| S | Pyrimidinyl | NH—C(O) | Pyrazinyl | Z$_1$: CH$_2$—CHF$_2$ (ortho) |

TABLE 2-continued

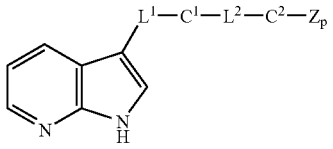

| L¹ | C¹ | L² | C² | Z |
|---|---|---|---|---|
| S | Pyrimidinyl | NH—C(O) | Pyrazinyl | $Z_1$: $CH_2$—$CF_3$ (para) |
| S | Pyrimidinyl | NH—C(O) | Pyrazinyl | $Z_1$: $CH_2$—$CF_3$ (meta) |
| S | Pyrimidinyl | NH—C(O) | Pyrazinyl | $Z_1$: $CH_2$—$CF_3$ (ortho) |
| S | Pyrimidinyl | NH—C(O) | Pyrrolyl | None |
| S | Pyrimidinyl | NH—C(O) | Pyrrolyl | $Z_1$: F (2) |
| S | Pyrimidinyl | NH—C(O) | Pyrrolyl | $Z_1$: F (3) |
| S | Pyrimidinyl | NH—C(O) | Pyrrolyl | $Z_1$: F (2) $Z_2$: F (3) |
| S | Pyrimidinyl | NH—C(O) | Pyrrolyl | $Z_1$: Cl (2) |
| S | Pyrimidinyl | NH—C(O) | Pyrrolyl | $Z_1$: Cl (3) |
| S | Pyrimidinyl | NH—C(O) | Pyrrolyl | $Z_1$: Cl (2) $Z_2$: Cl (3) |
| S | Pyrimidinyl | NH—C(O) | Pyrrolyl | $Z_1$: F (2) $Z_2$: Cl (3) |
| S | Pyrimidinyl | NH—C(O) | Pyrrolyl | $Z_1$: Cl (2) $Z_2$: F (3) |
| S | Pyrimidinyl | NH—C(O) | Pyrrolyl | $Z_1$: $CH_3$ (2) |
| S | Pyrimidinyl | NH—C(O) | Pyrrolyl | $Z_1$: $CH_3$ (3) |
| S | Pyrimidinyl | NH—C(O) | Pyrrolyl | $Z_1$: $CH_2$—$CH_3$ (2) |
| S | Pyrimidinyl | NH—C(O) | Pyrrolyl | $Z_1$: $CH_2$—$CH_3$ (3) |
| S | Pyrimidinyl | NH—C(O) | Pyrrolyl | $Z_1$: $CH_2$—$CH_2$—$CH_3$ or iPr (2) |
| S | Pyrimidinyl | NH—C(O) | Pyrrolyl | $Z_1$: $CH_2$—$CH_2$—$CH_3$ or iPr (3) |
| S | Pyrimidinyl | NH—C(O) | Pyrrolyl | $Z_1$: $CH_2F$ (2) |
| S | Pyrimidinyl | NH—C(O) | Pyrrolyl | $Z_1$: $CH_2F$ (3) |
| S | Pyrimidinyl | NH—C(O) | Pyrrolyl | $Z_1$: $CHF_2$ (2) |
| S | Pyrimidinyl | NH—C(O) | Pyrrolyl | $Z_1$: $CHF_2$ (3) |
| S | Pyrimidinyl | NH—C(O) | Pyrrolyl | $Z_1$: $CF_3$ (2) |
| S | Pyrimidinyl | NH—C(O) | Pyrrolyl | $Z_1$: $CF_3$ (3) |
| S | Pyrimidinyl | NH—C(O) | Pyrrolyl | $Z_1$: $CH_2$—$CH_2F$ (2) |
| S | Pyrimidinyl | NH—C(O) | Pyrrolyl | $Z_1$: $CH_2$—$CH_2F$ (3) |
| S | Pyrimidinyl | NH—C(O) | Pyrrolyl | $Z_1$: $CH_2$—$CHF_2$ (2) |
| S | Pyrimidinyl | NH—C(O) | Pyrrolyl | $Z_1$: $CH_2$—$CHF_2$ (3) |
| S | Pyrimidinyl | NH—C(O) | Pyrrolyl | $Z_1$: $CH_2$—$CF_3$ (2) |
| S | Pyrimidinyl | NH—C(O) | Pyrrolyl | $Z_1$: $CH_2$—$CF_3$ (3) |
| S | Pyrimiidinyl | NH—C(O) | Imidazolyl | None |
| S | Pyrimidinyl | NH—C(O) | Imidazolyl | $Z_1$: F (2) |
| S | Pyrimidinyl | NH—C(O) | Imidazolyl | $Z_1$: F (3) |
| S | Pyrimidinyl | NH—C(O) | Imidazolyl | $Z_1$: F (2) $Z_2$: F (3) |
| S | Pyrimidinyl | NH—C(O) | Imidazolyl | $Z_1$: Cl (2) |
| S | Pyrimidinyl | NH—C(O) | Imidazolyl | $Z_1$: Cl (3) |
| S | Pyrimidinyl | NH—C(O) | Imidazolyl | $Z_1$: Cl (2) $Z_2$: Cl (3) |
| S | Pyrimidinyl | NH—C(O) | Imidazolyl | $Z_1$: F (2) $Z_2$: Cl (3) |
| S | Pyrimidinyl | NH—C(O) | Imidazolyl | $Z_1$: Cl (2) $Z_2$: F (3) |
| S | Pyrimidinyl | NH—C(O) | Imidazolyl | $Z_1$: $CH_3$ (2) |
| S | Pyrimidinyl | NH—C(O) | Imidazolyl | $Z_1$: $CH_3$ (3) |
| S | Pyrimidinyl | NH—C(O) | Imidazolyl | $Z_1$: $CH_2$—$CH_3$ (2) |
| S | Pyrimidinyl | NH—C(O) | Imidazolyl | $Z_1$: $CH_2$—$CH_3$ (3) |
| S | Pyrimidinyl | NH—C(O) | Imidazolyl | $Z_1$: $CH_2$—$CH_2$—$CH_3$ or iPr (2) |
| S | Pyrimidinyl | NH—C(O) | Imidazolyl | $Z_1$: $CH_2$—$CH_2$—$CH_3$ or iPr (3) |
| S | Pyrimidinyl | NH—C(O) | Imidazolyl | $Z_1$: $CH_2F$ (2) |
| S | Pyrimidinyl | NH—C(O) | Imidazolyl | $Z_1$: $CH_2F$ (3) |
| S | Pyrimidinyl | NH—C(O) | Imidazolyl | $Z_1$: $CHF_2$ (2) |
| S | Pyrimidinyl | NH—C(O) | Imidazolyl | $Z_1$: $CHF_2$ (3) |
| S | Pyrimidinyl | NH—C(O) | Imidazolyl | $Z_1$: $CF_3$ (2) |
| S | Pyrimidinyl | NH—C(O) | Imidazolyl | $Z_1$: $CF_3$ (3) |
| S | Pyrimidinyl | NH—C(O) | Imidazolyl | $Z_1$: $CH_2$—$CH_2F$ (2) |
| S | Pyrimidinyl | NH—C(O) | Imidazolyl | $Z_1$: $CH_2$—$CH_2F$ (3) |
| S | Pyrimidinyl | NH—C(O) | Imidazolyl | $Z_1$: $CH_2$—$CHF_2$ (2) |
| S | Pyrimidinyl | NH—C(O) | Imidazolyl | $Z_1$: $CH_2$—$CHF_2$ (3) |
| S | Pyrimidinyl | NH—C(O) | Imidazolyl | $Z_1$: $CH_2$—$CF_3$ (2) |
| S | Pyrimidinyl | NH—C(O) | Imidazolyl | $Z_1$: $CH_2$—$CF_3$ (3) |
| S | Pyrimidinyl | NH—C(O) | Furanyl | None |
| S | Pyrimidinyl | NH—C(O) | Furanyl | $Z_1$: F (2) |
| S | Pyrimidinyl | NH—C(O) | Furanyl | $Z_1$: F (3) |

TABLE 2-continued

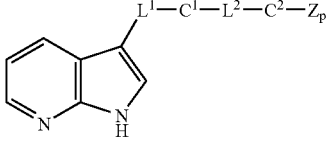

L¹—C¹—L²—C²—Z_p

| L¹ | C¹ | L² | C² | Z |
|---|---|---|---|---|
| S | Pyrimidinyl | NH—C(O) | Furanyl | $Z_1$: F (2)<br>$Z_2$: F (3) |
| S | Pyrimidinyl | NH—C(O) | Furanyl | $Z_1$: Cl (2) |
| S | Pyrimidinyl | NH—C(O) | Furanyl | $Z_1$: Cl (3) |
| S | Pyrimidinyl | NH—C(O) | Furanyl | $Z_1$: Cl (2)<br>$Z_2$: Cl (3) |
| S | Pyrimidinyl | NH—C(O) | Furanyl | $Z_1$: F (2)<br>$Z_2$: Cl (3) |
| S | Pyrimidinyl | NH—C(O) | Furanyl | $Z_1$: Cl (2)<br>$Z_2$: F (3) |
| S | Pyrimidinyl | NH—C(O) | Furanyl | $Z_1$: $CH_3$ (2) |
| S | Pyrimidinyl | NH—C(O) | Furanyl | $Z_1$: $CH_3$ (3) |
| S | Pyrimidinyl | NH—C(O) | Furanyl | $Z_1$: $CH_2$—$CH_3$ (2) |
| S | Pyrimidinyl | NH—C(O) | Furanyl | $Z_1$: $CH_2$—$CH_3$ (3) |
| S | Pyrimidinyl | NH—C(O) | Furanyl | $Z_1$: $CH_2$—$CH_2$—$CH_3$ or iPr (2) |
| S | Pyrimidinyl | NH—C(O) | Furanyl | $Z_1$: $CH_2$—$CH_2$—$CH_3$ or iPr (3) |
| S | Pyrimidinyl | NH—C(O) | Furanyl | $Z_1$: $CH_2F$ (2) |
| S | Pyrimidinyl | NH—C(O) | Furanyl | $Z_1$: $CH_2F$ (3) |
| S | Pyrimidinyl | NH—C(O) | Furanyl | $Z_1$: $CHF_2$ (2) |
| S | Pyrimidinyl | NH—C(O) | Furanyl | $Z_1$: $CHF_2$ (3) |
| S | Pyrimidinyl | NH—C(O) | Furanyl | $Z_1$: $CF_3$ (2) |
| S | Pyrimidinyl | NH—C(O) | Furanyl | $Z_1$: $CF_3$ (3) |
| S | Pyrimidinyl | NH—C(O) | Furanyl | $Z_1$: $CH_2$—$CH_2F$ (2) |
| S | Pyrimidinyl | NH—C(O) | Furanyl | $Z_1$: $CH_2$—$CH_2F$ (3) |
| S | Pyrimidinyl | NH—C(O) | Furanyl | $Z_1$: $CH_2$—$CHF_2$ (2) |
| S | Pyrimidinyl | NH—C(O) | Furanyl | $Z_1$: $CH_2$—$CHF_2$ (3) |
| S | Pyrimidinyl | NH—C(O) | Furanyl | $Z_1$: $CH_2$—$CF_3$ (2) |
| S | Pyrimidinyl | NH—C(O) | Furanyl | $Z_1$: $CH_2$—$CF_3$ (3) |
| S | Pyrimidinyl | NH—C(O) | Oxazolyl | None |
| S | Pyrimidinyl | NH—C(O) | Oxazolyl | $Z_1$: F (2) |
| S | Pyrimidinyl | NH—C(O) | Oxazolyl | $Z_1$: F (3) |
| S | Pyrimidinyl | NH—C(O) | Oxazolyl | $Z_1$: F (2)<br>$Z_2$: F (3) |
| S | Pyrimidinyl | NH—C(O) | Oxazolyl | $Z_1$: Cl (2) |
| S | Pyrimidinyl | NH—C(O) | Oxazolyl | $Z_1$: Cl (3) |
| S | Pyrimidinyl | NH—C(O) | Oxazolyl | $Z_1$: Cl (2)<br>$Z_2$: Cl (3) |
| S | Pyrimidinyl | NH—C(O) | Oxazolyl | $Z_1$: F (2)<br>$Z_2$: Cl (3) |
| S | Pyrimidinyl | NH—C(O) | Oxazolyl | $Z_1$: Cl (2)<br>$Z_2$: F (3) |
| S | Pyrimidinyl | NH—C(O) | Oxazolyl | $Z_1$: $CH_3$ (2) |
| S | Pyrimidinyl | NH—C(O) | Oxazolyl | $Z_1$: $CH_3$ (3) |
| S | Pyrimidinyl | NH—C(O) | Oxazolyl | $Z_1$: $CH_2$—$CH_3$ (2) |
| S | Pyrimidinyl | NH—C(O) | Oxazolyl | $Z_1$: $CH_2$—$CH_3$ (3) |
| S | Pyrimidinyl | NH—C(O) | Oxazolyl | $Z_1$: $CH_2$—$CH_2$—$CH_3$ or iPr (2) |
| S | Pyrimidinyl | NH—C(O) | Oxazolyl | $Z_1$: $CH_2$—$CH_2$—$CH_3$ or iPr (3) |
| S | Pyrimidinyl | NH—C(O) | Oxazolyl | $Z_1$: $CH_2F$ (2) |
| S | Pyrimidinyl | NH—C(O) | Oxazolyl | $Z_1$: $CH_2F$ (3) |
| S | Pyrimidinyl | NH—C(O) | Oxazolyl | $Z_1$: $CHF_2$ (2) |
| S | Pyrimidinyl | NH—C(O) | Oxazolyl | $Z_1$: $CHF_2$ (3) |
| S | Pyrimidinyl | NH—C(O) | Oxazolyl | $Z_1$: $CF_3$ (2) |
| S | Pyrimidinyl | NH—C(O) | Oxazolyl | $Z_1$: $CF_3$ (3) |
| S | Pyrimidinyl | NH—C(O) | Oxazolyl | $Z_1$: $CH_2$—$CH_2F$ (2) |
| S | Pyrimidinyl | NH—C(O) | Oxazolyl | $Z_1$: $CH_2$—$CH_2F$ (3) |
| S | Pyrimidinyl | NH—C(O) | Oxazolyl | $Z_1$: $CH_2$—$CHF_2$ (2) |
| S | Pyrimidinyl | NH—C(O) | Oxazolyl | $Z_1$: $CH_2$—$CHF_2$ (3) |
| S | Pyrimidinyl | NH—C(O) | Oxazolyl | $Z_1$: $CH_2$—$CF_3$ (2) |
| S | Pyrimidinyl | NH—C(O) | Oxazolyl | $Z_1$: $CH_2$—$CF_3$ (3) |
| S | Pyrimidinyl | NH—C(O) | Thiophenyl | None |
| S | Pyrimidinyl | NH—C(O) | Thiophenyl | $Z_1$: F (2) |
| S | Pyrimidinyl | NH—C(O) | Thiophenyl | $Z_1$: F (3) |
| S | Pyrimidinyl | NH—C(O) | Thiophenyl | $Z_1$: F (2)<br>$Z_2$: F (3) |
| S | Pyrimidinyl | NH—C(O) | Thiophenyl | $Z_1$: Cl (2) |
| S | Pyrimidinyl | NH—C(O) | Thiophenyl | $Z_1$: Cl (3) |
| S | Pyrimidinyl | NH—C(O) | Thiophenyl | $Z_1$: Cl (2)<br>$Z_2$: Cl (3) |

TABLE 2-continued

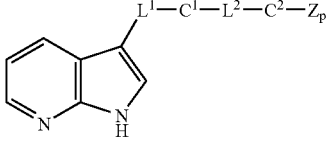

$L^1$—$C^1$—$L^2$—$C^2$—$Z_p$

| $L^1$ | $C^1$ | $L^2$ | $C^2$ | Z |
|---|---|---|---|---|
| S | Pyrimidinyl | NH—C(O) | Thiophenyl | $Z_1$: F (2)<br>$Z_2$: Cl (3) |
| S | Pyrimidinyl | NH—C(O) | Thiophenyl | $Z_1$: Cl (2)<br>$Z_2$: F (3) |
| S | Pyrimidinyl | NH—C(O) | Thiophenyl | $Z_1$: $CH_3$ (2) |
| S | Pyrimidinyl | NH—C(O) | Thiophenyl | $Z_1$: $CH_3$ (3) |
| S | Pyrimidinyl | NH—C(O) | Thiophenyl | $Z_1$: $CH_2$—$CH_3$ (2) |
| S | Pyrimidinyl | NH—C(O) | Thiophenyl | $Z_1$: $CH_2$—$CH_3$ (3) |
| S | Pyrimidinyl | NH—C(O) | Thiophenyl | $Z_1$: $CH_2$—$CH_2$—$CH_3$ or iPr (2) |
| S | Pyrimidinyl | NH—C(O) | Thiophenyl | $Z_1$: $CH_2$—$CH_2$—$CH_3$ or iPr (3) |
| S | Pyrimidinyl | NH—C(O) | Thiophenyl | $Z_1$: $CH_2F$ (2) |
| S | Pyrimidinyl | NH—C(O) | Thiophenyl | $Z_1$: $CH_2F$ (3) |
| S | Pyrimidinyl | NH—C(O) | Thiophenyl | $Z_1$: $CHF_2$ (2) |
| S | Pyrimidinyl | NH—C(O) | Thiophenyl | $Z_2$: $CHF_2$ (3) |
| S | Pyrimidinyl | NH—C(O) | Thiophenyl | $Z_1$: $CF_3$ (2) |
| S | Pyrimidinyl | NH—C(O) | Thiophenyl | $Z_1$: $CF_3$ (3) |
| S | Pyrimidinyl | NH—C(O) | Thiophenyl | $Z_1$: $CH_2$—$CH_2F$ (2) |
| S | Pyrimidinyl | NH—C(O) | Thiophenyl | $Z_1$: $CH_2$—$CH_2F$ (3) |
| S | Pyrimidinyl | NH—C(O) | Thiophenyl | $Z_1$: $CH_2$—$CHF_2$ (2) |
| S | Pyrimidinyl | NH—C(O) | Thiophenyl | $Z_1$: $CH_2$—$CHF_2$ (3) |
| S | Pyrimidinyl | NH—C(O) | Thiophenyl | $Z_1$: $CH_2$—$CF_3$ (2) |
| S | Pyrimidinyl | NH—C(O) | Thiophenyl | $Z_1$: $CH_2$—$CF_3$ (3) |
| S | Pyrimidinyl | NH—C(O) | Thiazolyl | None |
| S | Pyrimidinyl | NH—C(O) | Thiazolyl | $Z_1$: F (2) |
| S | Pyrimidinyl | NH—C(O) | Thiazolyl | $Z_1$: F (3) |
| S | Pyrimidinyl | NH—C(O) | Thiazolyl | $Z_1$: F (2)<br>$Z_2$: F (3) |
| S | Pyrimidinyl | NH—C(O) | Thiazolyl | $Z_1$: Cl (2) |
| S | Pyrimidinyl | NH—C(O) | Thiazolyl | $Z_1$: Cl (3) |
| S | Pyrimidinyl | NH—C(O) | Thiazolyl | $Z_1$: Cl (2)<br>$Z_2$: Cl (3) |
| S | Pyrimidinyl | NH—C(O) | Thiazolyl | $Z_1$: F (2)<br>$Z_2$: Cl (3) |
| S | Pyrimidinyl | NH—C(O) | Thiazolyl | $Z_1$: Cl (2)<br>$Z_2$: F (3) |
| S | Pyrimidinyl | NH—C(O) | Thiazolyl | $Z_1$: $CH_3$ (2) |
| S | Pyrimidinyl | NH—C(O) | Thiazolyl | $Z_1$: $CH_3$ (3) |
| S | Pyrimidinyl | NH—C(O) | Thiazolyl | $Z_1$: $CH_2$—$CH_3$ (2) |
| S | Pyrimidinyl | NH—C(O) | Thiazolyl | $Z_1$: $CH_2$—$CH_3$ (3) |
| S | Pyrimidinyl | NH—C(O) | Thiazolyl | $Z_1$: $CH_2$—$CH_2$—$CH_3$ or iPr (2) |
| S | Pyrimidinyl | NH—C(O) | Thiazolyl | $Z_1$: $CH_2$—$CH_2$—$CH_3$ or iPr (3) |
| S | Pyrimidinyl | NH—C(O) | Thiazolyl | $Z_1$: $CH_2F$ (2) |
| S | Pyrimidinyl | NH—C(O) | Thiazolyl | $Z_1$: $CH_2F$ (3) |
| S | Pyrimidinyl | NH—C(O) | Thiazolyl | $Z_1$: $CHF_2$ (2) |
| S | Pyrimidinyl | NH—C(O) | Thiazolyl | $Z_1$: $CHF_2$ (3) |
| S | Pyrimidinyl | NH—C(O) | Thiazolyl | $Z_1$: $CF_3$ (2) |
| S | Pyrimidinyl | NH—C(O) | Thiazolyl | $Z_1$: $CF_3$ (3) |
| S | Pyrimidinyl | NH—C(O) | Thiazolyl | $Z_1$: $CH_2$—$CH_2F$ (2) |
| S | Pyrimidinyl | NH—C(O) | Thiazolyl | $Z_1$: $CH_2$—$CH_2F$ (3) |
| S | Pyrimidinyl | NH—C(O) | Thiazolyl | $Z_1$: $CH_2$—$CHF_2$ (2) |
| S | Pyrimidinyl | NH—C(O) | Thiazolyl | $Z_1$: $CH_2$—$CHF_2$ (3) |
| S | Pyrimidinyl | NH—C(O) | Thiazolyl | $Z_1$: $CH_2$—$CF_3$ (2) |
| S | Pyrimidinyl | NH—C(O) | Thiazolyl | $Z_1$: $CH_2$—$CF_3$ (3) |
| S | Pyrimidinyl | NH—$SO_2$ | Phenyl | None |
| S | Pyrimidinyl | NH—$SO_2$ | Phenyl | $Z_1$: F (para) |
| S | Pyrimidinyl | NH—$SO_2$ | phenyl | $Z_1$: F (meta) |
| S | Pyrimidinyl | NH—$SO_2$ | phenyl | $Z_1$: F (ortho) |
| S | Pyrimidinyl | NH—$SO_2$ | phenyl | $Z_1$: F (para)<br>$Z_2$: F (meta) |
| S | Pyrimidinyl | NH—$SO_2$ | Phenyl | $Z_1$: Cl (meta) |
| S | Pyrimidinyl | NH—$SO_2$ | Phenyl | $Z_1$: Cl (para) |
| S | Pyrimidinyl | NH—$SO_2$ | Phenyl | $Z_1$: Cl (para)<br>$Z_2$: Cl (meta) |
| S | Pyrimidinyl | NH—$SO_2$ | Phenyl | $Z_1$: F (para)<br>$Z_2$: Cl (meta) |
| S | Pyrimidinyl | NH—$SO_2$ | Phenyl | $Z_1$: Cl (para)<br>$Z_2$: F (meta) |
| S | Pyrimidinyl | NH—$SO_2$ | Phenyl | $Z_1$: $CH_3$ (para) |
| S | Pyrimidinyl | NH—$SO_2$ | Phenyl | $Z_1$: $CH_3$ (meta) |

TABLE 2-continued

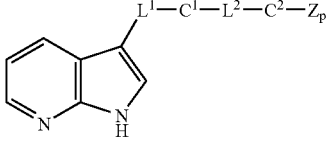

| L$^1$ | C$^1$ | L$^2$ | C$^2$ | Z |
|---|---|---|---|---|
| S | Pyrimidinyl | NH—SO$_2$ | Phenyl | Z$_1$: CH$_3$ (ortho) |
| S | Pyrimidinyl | NH—SO$_2$ | Phenyl | Z$_1$: CH$_2$—CH$_3$ (para) |
| S | Pyrimidinyl | NH—SO$_2$ | Phenyl | Z$_1$: CH$_2$—CH$_3$ (meta) |
| S | Pyrimidinyl | NH—SO$_2$ | Phenyl | Z$_1$: CH$_2$—CH$_3$ (ortho) |
| S | Pyrimidinyl | NH—SO$_2$ | Phenyl | Z$_1$: CH$_2$—CH$_2$—CH$_3$ or iPr (para) |
| S | Pyrimidinyl | NH—SO$_2$ | Phenyl | Z$_1$: CH$_2$—CH$_2$—CH$_3$ or iPr (meta) |
| S | Pyrimidinyl | NH—SO$_2$ | Phenyl | Z$_1$: CH$_2$—CH$_2$—CH$_3$ or iPr (ortho) |
| S | Pyrimidinyl | NH—SO$_2$ | Phenyl | Z$_1$: CH$_2$F (para) |
| S | Pyrimidinyl | NH—SO$_2$ | Phenyl | Z$_1$: CH$_2$F (meta) |
| S | Pyrimidinyl | NH—SO$_2$ | Phenyl | Z$_1$: CH$_2$F (ortho) |
| S | Pyrimidinyl | NH—SO$_2$ | Phenyl | Z$_1$: CHF$_2$ (para) |
| S | Pyrimidinyl | NH—SO$_2$ | Phenyl | Z$_1$: CHF$_2$ (meta) |
| S | Pyrimidinyl | NH—SO$_2$ | Phenyl | Z$_1$: CHF$_2$ (ortho) |
| S | Pyrimidinyl | NH—SO$_2$ | Phenyl | Z$_1$: CF$_3$ (para) |
| S | Pyrimidinyl | NH—SO$_2$ | Phenyl | Z$_1$: CF$_3$ (meta) |
| S | Pyrimidinyl | NH—SO$_2$ | Phenyl | Z$_1$: CF$_3$ (ortho) |
| S | Pyrimidinyl | NH—SO$_2$ | Phenyl | Z$_1$: CH$_2$—CH$_2$F (para) |
| S | Pyrimidinyl | NH—SO$_2$ | Phenyl | Z$_1$: CH$_2$—CH$_2$F (meta) |
| S | Pyrimidinyl | NH—SO$_2$ | Phenyl | Z$_1$: CH$_2$—CH$_2$F (ortho) |
| S | Pyrimidinyl | NH—SO$_2$ | Phenyl | Z$_1$: CH$_2$—CHF$_2$ (para) |
| S | Pyrimidinyl | NH—SO$_2$ | Phenyl | Z$_1$: CH$_2$—CHF$_2$ (meta) |
| S | Pyrimidinyl | NH—SO$_2$ | Phenyl | Z$_1$: CH$_2$—CHF$_2$ (ortho) |
| S | Pyrimidinyl | NH—SO$_2$ | Phenyl | Z$_1$: CH$_2$—CF$_3$ (para) |
| S | Pyrimidinyl | NH—SO$_2$ | Phenyl | Z$_1$: CH$_2$—CF$_3$ (meta) |
| S | Pyrimidinyl | NH—SO$_2$ | Phenyl | Z$_1$: CH$_2$—CF$_3$ (ortho) |
| S | Pyrimidinyl | NH—SO$_2$ | Pyridinyl | None |
| S | Pyrimidinyl | NH—SO$_2$ | Pyridinyl | Z$_1$: F (para) |
| S | Pyrimidinyl | NH—SO$_2$ | Pyridinyl | Z$_1$: F (meta) |
| S | Pyrimidinyl | NH—SO$_2$ | Pyridinyl | Z$_1$: F (ortho) |
| S | Pyrimidinyl | NH—SO$_2$ | Pyridinyl | Z$_1$: F (para) Z$_2$: F (meta) |
| S | Pyrimidinyl | NH—SO$_2$ | Pyridinyl | Z$_1$: Cl (meta) |
| S | Pyrimidinyl | NH—SO$_2$ | Pyridinyl | Z$_1$: Cl (para) |
| S | Pyrimidinyl | NH—SO$_2$ | Pyridinyl | Z$_1$: Cl (para) Z$_2$: Cl (meta) |
| S | Pyrimidinyl | NH—SO$_2$ | Pyridinyl | Z$_1$: F (para) Z$_2$: Cl (meta) |
| S | Pyrimidinyl | NH—SO$_2$ | Pyridinyl | Z$_1$: Cl (para) Z$_2$: F (meta) |
| S | Pyrimidinyl | NH—SO$_2$ | Pyridinyl | Z$_1$: CH$_3$ (para) |
| S | Pyrimidinyl | NH—SO$_2$ | Pyridinyl | Z$_1$: CH$_3$ (meta) |
| S | Pyrimidinyl | NH—SO$_2$ | Pyridinyl | Z$_1$: CH$_3$ (ortho) |
| S | Pyrimidinyl | NH—SO$_2$ | Pyridinyl | Z$_1$: CH$_2$—CH$_3$ (para) |
| S | Pyrimidinyl | NH—SO$_2$ | Pyridinyl | Z$_1$: CH$_2$—CH$_3$ (meta) |
| S | Pyrimidinyl | NH—SO$_2$ | Pyridinyl | Z$_1$: CH$_2$—CH$_3$ (ortho) |
| S | Pyrimidinyl | NH—SO$_2$ | Pyridinyl | Z$_1$: CH$_2$—CH$_2$—CH$_3$ or iPr (para) |
| S | Pyrimidinyl | NH—SO$_2$ | Pyridinyl | Z$_1$: CH$_2$—CH$_2$—CH$_3$ or iPr (meta) |
| S | Pyrimidinyl | NH—SO$_2$ | Pyridinyl | Z$_1$: CH$_2$—CH$_2$—CH$_3$ or iPr (ortho) |
| S | Pyrimidinyl | NH—SO$_2$ | Pyridinyl | Z$_1$: CH$_2$F (para) |
| S | Pyrimidinyl | NH—SO$_2$ | Pyridinyl | Z$_1$: CH$_2$F (meta) |
| S | Pyrimidinyl | NH—SO$_2$ | Pyridinyl | Z$_1$: CH$_2$F (ortho) |
| S | Pyrimidinyl | NH—SO$_2$ | Pyridinyl | Z$_1$: CHF$_2$ (para) |
| S | Pyrimidinyl | NH—SO$_2$ | Pyridinyl | Z$_1$: CHF$_2$ (meta) |
| S | Pyrimidinyl | NH—SO$_2$ | Pyridinyl | Z$_1$: CHF$_2$ (ortho) |
| S | Pyrimidinyl | NH—SO$_2$ | Pyridinyl | Z$_1$: CF$_3$ (para) |
| S | Pyrimidinyl | NH—SO$_2$ | Pyridinyl | Z$_1$: CF$_3$ (meta) |
| S | Pyrimidinyl | NH—SO$_2$ | Pyridinyl | Z$_1$: CF$_3$ (ortho) |
| S | Pyrimidinyl | NH—SO$_2$ | Pyridinyl | Z$_1$: CH$_2$—CH$_2$F (para) |
| S | Pyrimidinyl | NH—SO$_2$ | Pyridinyl | Z$_1$: CH$_2$—CH$_2$F (meta) |
| S | Pyrimidinyl | NH—SO$_2$ | Pyridinyl | Z$_1$: CH$_2$—CH$_2$F (ortho) |
| S | Pyrimidinyl | NH—SO$_2$ | Pyridinyl | Z$_1$: CH$_2$—CHF$_2$ (para) |
| S | Pyrimidinyl | NH—SO$_2$ | Pyridinyl | Z$_1$: CH$_2$—CHF$_2$ (meta) |
| S | Pyrimidinyl | NH—SO$_2$ | Pyridinyl | Z$_1$: CH$_2$—CHF$_2$ (ortho) |

TABLE 2-continued $$L^1-C^1-L^2-C^2-Z_p$$

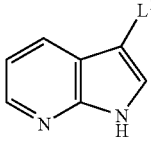

| L¹ | C¹ | L² | C² | Z |
|---|---|---|---|---|
| S | Pyrimidinyl | NH—SO$_2$ | Pyridinyl | Z$_1$: CH$_2$—CF$_3$ (para) |
| S | Pyrimidinyl | NH—SO$_2$ | Pyridinyl | Z$_1$: CH$_2$—CF$_3$ (meta) |
| S | Pyrimidinyl | NH—SO$_2$ | Pyridinyl | Z$_1$: CH$_2$—CF$_3$ (ortho) |
| S | Pyrimidinyl | NH—SO$_2$ | Pyrimidinyl | None |
| S | Pyrimidinyl | NH—SO$_2$ | Pyrimidinyl | Z$_1$: F (para) |
| S | Pyrimidinyl | NH—SO$_2$ | Pyrimidinyl | Z$_1$: F (meta) |
| S | Pyrimidinyl | NH—SO$_2$ | Pyrimidinyl | Z$_1$: F (ortho) |
| S | Pyrimidinyl | NH—SO$_2$ | Pyrimidinyl | Z$_1$: F (para) Z$_2$: F (meta) |
| S | Pyrimidinyl | NH—SO$_2$ | Pyrimidinyl | Z$_1$: Cl (meta) |
| S | Pyrimidinyl | NH—SO$_2$ | Pyrimidinyl | Z$_1$: Cl (para) |
| S | Pyrimidinyl | NH—SO$_2$ | Pyrimidinyl | Z$_1$: Cl (para) Z$_2$: Cl (meta) |
| S | Pyrimidinyl | NH—SO$_2$ | Pyrimidinyl | Z$_1$: F (para) Z$_2$: Cl (meta) |
| S | Pyrimidinyl | NH—SO$_2$ | Pyrimidinyl | Z$_1$: Cl (para) Z$_2$: F (meta) |
| S | Pyrimidinyl | NH—SO$_2$ | Pyrimidinyl | Z$_1$: CH$_3$ (para) |
| S | Pyrimidinyl | NH—SO$_2$ | Pyrimidinyl | Z$_1$: CH$_3$ (meta) |
| S | Pyrimidinyl | NH—SO$_2$ | Pyrimidinyl | Z$_1$: CH$_3$ (ortho) |
| S | Pyrimidinyl | NH—SO$_2$ | Pyrimidinyl | Z$_1$: CH$_2$—CH$_3$ (para) |
| S | Pyrimidinyl | NH—SO$_2$ | Pyrimidinyl | Z$_1$: CH$_2$—CH$_3$ (meta) |
| S | Pyrimidinyl | NH—SO$_2$ | Pyrimidinyl | Z$_1$: CH$_2$—CH$_3$ (ortho) |
| S | Pyrimidinyl | NH—SO$_2$ | Pyrimidinyl | Z$_1$: CH$_2$—CH$_2$—CH$_3$ or iPr (para) |
| S | Pyrimidinyl | NH—SO$_2$ | Pyrimidinyl | Z$_1$: CH$_2$—CH$_2$—CH$_3$ or iPr (meta) |
| S | Pyrimidinyl | NH—SO$_2$ | Pyrimidinyl | Z$_1$: CH$_2$—CH$_2$—CH$_3$ or iPr (ortho) |
| S | Pyrimidinyl | NH—SO$_2$ | Pyrimidinyl | Z$_1$: CH$_2$F (para) |
| S | Pyrimidinyl | NH—SO$_2$ | Pyrimidinyl | Z$_1$: CH$_2$F (meta) |
| S | Pyrimidinyl | NH—SO$_2$ | Pyrimidinyl | Z$_1$: CH$_2$F (ortho) |
| S | Pyrimidinyl | NH—SO$_2$ | Pyrimidinyl | Z$_1$: CHF$_2$ (para) |
| S | Pyrimidinyl | NH—SO$_2$ | Pyrimidinyl | Z$_1$: CHF$_2$ (meta) |
| S | Pyrimidinyl | NH—SO$_2$ | Pyrimidinyl | Z$_1$: CHF$_2$ (ortho) |
| S | Pyrimidinyl | NH—SO$_2$ | Pyrimidinyl | Z$_1$: CF$_3$ (para) |
| S | Pyrimidinyl | NH—SO$_2$ | Pyrimidinyl | Z$_1$: CF$_3$ (meta) |
| S | Pyrimidinyl | NH—SO$_2$ | Pyrimidinyl | Z$_1$: CF$_3$ (ortho) |
| S | Pyrimidinyl | NH—SO$_2$ | Pyrimidinyl | Z$_1$: CH$_2$—CH$_2$F (para) |
| S | Pyrimidinyl | NH—SO$_2$ | Pyrimidinyl | Z$_1$: CH$_2$—CH$_2$F (meta) |
| S | Pyrimidinyl | NH—SO$_2$ | Pyrimidinyl | Z$_1$: CH$_2$—CH$_2$F (ortho) |
| S | Pyrimidinyl | NH—SO$_2$ | Pyrimidinyl | Z$_1$: CH$_2$—CHF$_2$ (para) |
| S | Pyrimidinyl | NH—SO$_2$ | Pyrimidinyl | Z$_1$: CH$_2$—CHF$_2$ (meta) |
| S | Pyrimidinyl | NH—SO$_2$ | Pyrimidinyl | Z$_1$: CH$_2$—CHF$_2$ (ortho) |
| S | Pyrimidinyl | NH—SO$_2$ | Pyrimidinyl | Z$_1$: CH$_2$—CF$_3$ (para) |
| S | Pyrimidinyl | NH—SO$_2$ | Pyrimidinyl | Z$_1$: CH$_2$—CF$_3$ (meta) |
| S | Pyrimidinyl | NH—SO$_2$ | Pyrimidinyl | Z$_1$: CH$_2$—CF$_3$ (ortho) |
| S | Pyrimidinyl | NH—SO$_2$ | Pyrazinyl | None |
| S | Pyrimidinyl | NH—SO$_2$ | Pyrazinyl | Z$_1$: F (para) |
| S | Pyrimidinyl | NH—SO$_2$ | Pyrazinyl | Z$_1$: F (meta) |
| S | Pyrimidinyl | NH—SO$_2$ | Pyrazinyl | Z$_1$: F (ortho) |
| S | Pyrimidinyl | NH—SO$_2$ | Pyrazinyl | Z$_1$: F (para) Z$_2$: F (meta) |
| S | Pyrimidinyl | NH—SO$_2$ | Pyrazinyl | Z$_1$: Cl (meta) |
| S | Pyrimidinyl | NH—SO$_2$ | Pyrazinyl | Z$_1$: Cl (para) |
| S | Pyrimidinyl | NH—SO$_2$ | Pyrazinyl | Z$_1$: Cl (para) Z$_2$: Cl (meta) |
| S | Pyrimidinyl | NH—SO$_2$ | Pyrazinyl | Z$_1$: F (para) Z$_2$: Cl (meta) |
| S | Pyrimidinyl | NH—SO$_2$ | Pyrazinyl | Z$_1$: Cl (para) Z$_2$: F (meta) |
| S | Pyrimidinyl | NH—SO$_2$ | Pyrazinyl | Z$_1$: CH$_3$ (para) |
| S | Pyrimidinyl | NH—SO$_2$ | Pyrazinyl | Z$_1$: CH$_3$ (meta) |
| S | Pyrimidinyl | NH—SO$_2$ | Pyrazinyl | Z$_1$: CH$_3$ (ortho) |
| S | Pyrimidinyl | NH—SO$_2$ | Pyrazinyl | Z$_1$: CH$_2$—CH$_3$ (para) |
| S | Pyrimidinyl | NH—SO$_2$ | Pyrazinyl | Z$_1$: CH$_2$—CH$_3$ (meta) |
| S | Pyrimidinyl | NH—SO$_2$ | Pyrazinyl | Z$_1$: CH$_2$—CH$_3$ (ortho) |
| S | Pyrimidinyl | NH—SO$_2$ | Pyrazinyl | Z$_1$: CH$_2$—CH$_2$—CH$_3$ or iPr (para) |

TABLE 2-continued

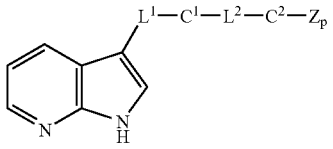

| L¹ | C¹ | L² | C² | Z |
|---|---|---|---|---|
| S | Pyrimidinyl | NH—SO$_2$ | Pyrazinyl | Z$_1$: CH$_2$—CH$_2$—CH$_3$ or iPr (meta) |
| S | Pyrimidinyl | NH—SO$_2$ | Pyrazinyl | Z$_1$: CH$_2$—CH$_2$—CH$_3$ or iPr (ortho) |
| S | Pyrimidinyl | NH—SO$_2$ | Pyrazinyl | Z$_1$: CH$_2$F (para) |
| S | Pyrimidinyl | NH—SO$_2$ | Pyrazinyl | Z$_1$: CH$_2$F (meta) |
| S | Pyrimidinyl | NH—SO$_2$ | Pyrazinyl | Z$_1$: CH$_2$F (ortho) |
| S | Pyrimidinyl | NH—SO$_2$ | Pyrazinyl | Z$_1$: CHF$_2$ (para) |
| S | Pyrimidinyl | NH—SO$_2$ | Pyrazinyl | Z$_1$: CHF$_2$ (meta) |
| S | Pyrimidinyl | NH—SO$_2$ | Pyrazinyl | Z$_1$: CHF$_2$ (ortho) |
| S | Pyrimidinyl | NH—SO$_2$ | Pyrazinyl | Z$_1$: CF$_3$ (para) |
| S | Pyrimidinyl | NH—SO$_2$ | Pyrazinyl | Z$_1$: CF$_3$ (meta) |
| S | Pyrimidinyl | NH—SO$_2$ | Pyrazinyl | Z$_1$: CF$_3$ (ortho) |
| S | Pyrimidinyl | NH—SO$_2$ | Pyrazinyl | Z$_1$: CH$_2$—CH$_2$F (para) |
| S | Pyrimidinyl | NH—SO$_2$ | Pyrazinyl | Z$_1$: CH$_2$—CH$_2$F (meta) |
| S | Pyrimidinyl | NH—SO$_2$ | Pyrazinyl | Z$_1$: CH$_2$—CH$_2$F (ortho) |
| S | Pyrimidinyl | NH—SO$_2$ | Pyrazinyl | Z$_1$: CH$_2$—CHF$_2$ (para) |
| S | Pyrimidinyl | NH—SO$_2$ | Pyrazinyl | Z$_1$: CH$_2$—CHF$_2$ (meta) |
| S | Pyrimidinyl | NH—SO$_2$ | Pyrazinyl | Z$_1$: CH$_2$—CHF$_2$ (ortho) |
| S | Pyrimidinyl | NH—SO$_2$ | Pyrazinyl | Z$_1$: CH$_2$—CF$_3$ (para) |
| S | Pyrimidinyl | NH—SO$_2$ | Pyrazinyl | Z$_1$: CH$_2$—CF$_3$ (meta) |
| S | Pyrimidinyl | NH—SO$_2$ | Pyrazinyl | Z$_1$: CH$_2$—CF$_3$ (ortho) |
| S | Pyrimidinyl | NH—SO$_2$ | Pyrrolyl | None |
| S | Pyrimidinyl | NH—SO$_2$ | Pyrrolyl | Z$_1$: F (2) |
| S | Pyrimidinyl | NH—SO$_2$ | Pyrrolyl | Z$_1$: F (3) |
| S | Pyrimidinyl | NH—SO$_2$ | Pyrrolyl | Z$_1$: F (2) Z$_2$: F (3) |
| S | Pyrimidinyl | NH—SO$_2$ | Pyrrolyl | Z$_1$: Cl (2) |
| S | Pyrimidinyl | NH—SO$_2$ | Pyrrolyl | Z$_1$: Cl (3) |
| S | Pyrimidinyl | NH—SO$_2$ | Pyrrolyl | Z$_1$: Cl (2) Z$_2$: Cl (3) |
| S | Pyrimidinyl | NH—SO$_2$ | Pyrrolyl | Z$_1$: F (2) Z$_2$: Cl (3) |
| S | Pyrimidinyl | NH—SO$_2$ | Pyrrolyl | Z$_1$: Cl (2) Z$_2$: F (3) |
| S | Pyrimidinyl | NH—SO$_2$ | Pyrrolyl | Z$_1$: CH$_3$ (2) |
| S | Pyrimidinyl | NH—SO$_2$ | Pyrrolyl | Z$_1$: CH$_3$ (3) |
| S | Pyrimidinyl | NH—SO$_2$ | Pyrrolyl | Z$_1$: CH$_2$—CH$_3$ (2) |
| S | Pyrimidinyl | NH—SO$_2$ | Pyrrolyl | Z$_1$: CH$_2$—CH$_3$ (3) |
| S | Pyrimidinyl | NH—SO$_2$ | Pyrrolyl | Z$_1$: CH$_2$—CH$_2$—CH$_3$ or iPr (2) |
| S | Pyrimidinyl | NH—SO$_2$ | Pyrrolyl | Z$_1$: CH$_2$—CH$_2$—CH$_3$ or iPr (3) |
| S | Pyrimidinyl | NH—SO$_2$ | Pyrrolyl | Z$_1$: CH$_2$F (2) |
| S | Pyrimidinyl | NH—SO$_2$ | Pyrrolyl | Z$_1$: CH$_2$F (3) |
| S | Pyrimidinyl | NH—SO$_2$ | Pyrrolyl | Z$_1$: CHF$_2$ (2) |
| S | Pyrimidinyl | NH—SO$_2$ | Pyrrolyl | Z$_1$: CHF$_2$ (3) |
| S | Pyrimidinyl | NH—SO$_2$ | Pyrrolyl | Z$_1$: CF$_3$ (2) |
| S | Pyrimidinyl | NH—SO$_2$ | Pyrrolyl | Z$_1$: CF$_3$ (3) |
| S | Pyrimidinyl | NH—SO$_2$ | Pyrrolyl | Z$_1$: CH$_2$—CH$_2$F (2) |
| S | Pyrimidinyl | NH—SO$_2$ | Pyrrolyl | Z$_1$: CH$_2$—CH$_2$F (3) |
| S | Pyrimidinyl | NH—SO$_2$ | Pyrrolyl | Z$_1$: CH$_2$—CHF$_2$ (2) |
| S | Pyrimidinyl | NH—SO$_2$ | Pyrrolyl | Z$_1$: CH$_2$—CHF$_2$ (3) |
| S | Pyrimidinyl | NH—SO$_2$ | Pyrrolyl | Z$_1$: CH$_2$—CF$_3$ (2) |
| S | Pyrimidinyl | NH—SO$_2$ | Pyrrolyl | Z$_1$: CH$_2$—CF$_3$ (3) |
| S | Pyrimidinyl | NH—SO$_2$ | Imidazolyl | None |
| S | Pyrimidinyl | NH—SO$_2$ | Imidazolyl | Z$_1$: F (2) |
| S | Pyrimidinyl | NH—SO$_2$ | Imidazolyl | Z$_1$: F (3) |
| S | Pyrimidinyl | NH—SO$_2$ | Imidazolyl | Z$_1$: F (2) Z$_2$: F (3) |
| S | Pyrimidinyl | NH—SO$_2$ | Imidazolyl | Z$_1$: Cl (2) |
| S | Pyrimidinyl | NH—SO$_2$ | Imidazolyl | Z$_1$: Cl (3) |
| S | Pyrimidinyl | NH—SO$_2$ | Imidazolyl | Z$_1$: Cl (2) Z$_2$: Cl (3) |
| S | Pyrimidinyl | NH—SO$_2$ | Imidazolyl | Z$_1$: F (2) Z$_2$: Cl (3) |
| S | Pyrimidinyl | NH—SO$_2$ | Imidazolyl | Z$_1$: Cl (2) Z$_2$: F (3) |
| S | Pyrimidinyl | NH—SO$_2$ | Imidazolyl | Z$_1$: CH$_3$ (2) |
| S | Pyrimidinyl | NH—SO$_2$ | Imidazolyl | Z$_1$: CH$_3$ (3) |
| S | Pyrimidinyl | NH—SO$_2$ | Imidazolyl | Z$_1$: CH$_2$—CH$_3$ (2) |

TABLE 2-continued

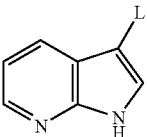

| L¹ | C¹ | L² | C² | Z |
|---|---|---|---|---|
| S | Pyrimidinyl | NH—SO₂ | Imidazolyl | $Z_1$: CH₂—CH₃ (3) |
| S | Pyrimidinyl | NH—SO₂ | Imidazolyl | $Z_1$: CH₂—CH₂—CH₃ or iPr (2) |
| S | Pyrimidinyl | NH—SO₂ | Imidazolyl | $Z_1$: CH₂—CH₂—CH₃ or iPr (3) |
| S | Pyrimidinyl | NH—SO₂ | Imidazolyl | $Z_1$: CH₂F (2) |
| S | Pyrimidinyl | NH—SO₂ | Imidazolyl | $Z_1$: CH₂F (3) |
| S | Pyrimidinyl | NH—SO₂ | Imidazolyl | $Z_1$: CHF₂ (2) |
| S | Pyrimidinyl | NH—SO₂ | Imidazolyl | $Z_1$: CHF₂ (3) |
| S | Pyrimidinyl | NH—SO₂ | Imidazolyl | $Z_1$: CF₃ (2) |
| S | Pyrimidinyl | NH—SO₂ | Imidazolyl | $Z_1$: CF₃ (3) |
| S | Pyrimidinyl | NH—SO₂ | Imidazolyl | $Z_1$: CH₂—CH₂F (2) |
| S | Pyrimidinyl | NH—SO₂ | Imidazolyl | $Z_1$: CH₂—CH₂F (3) |
| S | Pyrimidinyl | NH—SO₂ | Imidazolyl | $Z_1$: CH₂—CHF₂ (2) |
| S | Pyrimidinyl | NH—SO₂ | Imidazolyl | $Z_1$: CH₂—CHF₂ (3) |
| S | Pyrimidinyl | NH—SO₂ | Imidazolyl | $Z_1$: CH₂—CF₃ (2) |
| S | Pyrimidinyl | NH—SO₂ | Imidazolyl | $Z_1$: CH₂—CF₃ (3) |
| S | Pyrimidinyl | NH—SO₂ | Furanyl | None |
| S | Pyrimidinyl | NH—SO₂ | Furanyl | $Z_1$: F (2) |
| S | Pyrimidinyl | NH—SO₂ | Furanyl | $Z_1$: F (3) |
| S | Pyrimidinyl | NH—SO₂ | Furanyl | $Z_1$: F (2)<br>$Z_2$: F (3) |
| S | Pyrimidinyl | NH—SO₂ | Furanyl | $Z_1$: Cl (2) |
| S | Pyrimidinyl | NH—SO₂ | Furanyl | $Z_1$: Cl (3) |
| S | Pyrimidinyl | NH—SO₂ | Furanyl | $Z_1$: Cl (2)<br>$Z_2$: Cl (3) |
| S | Pyrimidinyl | NH—SO₂ | Furanyl | $Z_1$: F (2)<br>$Z_2$: Cl (3) |
| S | Pyrimidinyl | NH—SO₂ | Furanyl | $Z_1$: Cl (2)<br>$Z_2$: F (3) |
| S | Pyrimidinyl | NH—SO₂ | Furanyl | $Z_1$: CH₃ (2) |
| S | Pyrimidinyl | NH—SO₂ | Furanyl | $Z_1$: CH₃ (3) |
| S | Pyrimidinyl | NH—SO₂ | Furanyl | $Z_1$: CH₂—CH₃ (2) |
| S | Pyrimidinyl | NH—SO₂ | Furanyl | $Z_1$: CH₂—CH₃ (3) |
| S | Pyrimidinyl | NH—SO₂ | Furanyl | $Z_1$: CH₂—CH₂—CH₃ or iPr (2) |
| S | Pyrimidinyl | NH—SO₂ | Furanyl | $Z_1$: CH₂—CH₂—CH₃ or iPr (3) |
| S | Pyrimidinyl | NH—SO₂ | Furanyl | $Z_1$: CH₂F (2) |
| S | Pyrimidinyl | NH—SO₂ | Furanyl | $Z_1$: CH₂F (3) |
| S | Pyrimidinyl | NH—SO₂ | Furanyl | $Z_1$: CHF₂ (2) |
| S | Pyrimidinyl | NH—SO₂ | Furanyl | $Z_1$: CHF₂ (3) |
| S | Pyrimidinyl | NH—SO₂ | Furanyl | $Z_1$: CF₃ (2) |
| S | Pyrimidinyl | NH—SO₂ | Furanyl | $Z_1$: CF₃ (3) |
| S | Pyrimidinyl | NH—SO₂ | Furanyl | $Z_1$: CH₂—CH₂F (2) |
| S | Pyrimidinyl | NH—SO₂ | Furanyl | $Z_1$: CH₂—CH₂F (3) |
| S | Pyrimidinyl | NH—SO₂ | Furanyl | $Z_1$: CH₂—CHF₂ (2) |
| S | Pyrimidinyl | NH—SO₂ | Furanyl | $Z_1$: CH₂—CHF₂ (3) |
| S | Pyrimidinyl | NH—SO₂ | Furanyl | $Z_1$: CH₂—CF₃ (2) |
| S | Pyrimidinyl | NH—SO₂ | Furanyl | $Z_1$: CH₂—CF₃ (3) |
| S | Pyrimidinyl | NH—SO₂ | Oxazolyl | None |
| S | Pyrimidinyl | NH—SO₂ | Oxazolyl | $Z_1$: F (2) |
| S | Pyrimidinyl | NH—SO₂ | Oxazolyl | $Z_1$: F (3) |
| S | Pyrimidinyl | NH—SO₂ | Oxazolyl | $Z_1$: F (2)<br>$Z_2$: F (3) |
| S | Pyrimidinyl | NH—SO₂ | Oxazolyl | $Z_1$: Cl (2) |
| S | Pyrimidinyl | NH—SO₂ | Oxazolyl | $Z_1$: Cl (3) |
| S | Pyrimidinyl | NH—SO₂ | Oxazolyl | $Z_1$: Cl (2)<br>$Z_2$: Cl (3) |
| S | Pyrimidinyl | NH—SO₂ | Oxazolyl | $Z_1$: F (2)<br>$Z_2$: Cl (3) |
| S | Pyrimidinyl | NH—SO₂ | Oxazolyl | $Z_1$: Cl (2)<br>$Z_2$: F (3) |
| S | Pyrimidinyl | NH—SO₂ | Oxazolyl | $Z_1$: CH₃ (2) |
| S | Pyrimidinyl | NH—SO₂ | Oxazolyl | $Z_1$: CH₃ (3) |
| S | Pyrimidinyl | NH—SO₂ | Oxazolyl | $Z_1$: CH₂—CH₃ (2) |
| S | Pyrimidinyl | NH—SO₂ | Oxazolyl | $Z_1$: CH₂—CH₃ (3) |
| S | Pyrimidinyl | NH—SO₂ | Oxazolyl | $Z_1$: CH₂—CH₂—CH₃ or iPr (2) |
| S | Pyrimidinyl | NH—SO₂ | Oxazolyl | $Z_1$: CH₂—CH₂—CH₃ or iPr (3) |
| S | Pyrimidinyl | NH—SO₂ | Oxazolyl | $Z_1$: CH₂F (2) |
| S | Pyrimidinyl | NH—SO₂ | Oxazolyl | $Z_1$: CH₂F (3) |
| S | Pyrimidinyl | NH—SO₂ | Oxazolyl | $Z_1$: CHF₂ (2) |
| S | Pyrimidinyl | NH—SO₂ | Oxazolyl | $Z_1$: CHF₂ (3) |

TABLE 2-continued

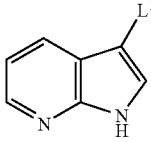

| L¹ | C¹ | L² | C² | Z |
|---|---|---|---|---|
| S | Pyrimidinyl | NH—SO₂ | Oxazolyl | $Z_1$: $CF_3$ (2) |
| S | Pyrimidinyl | NH—SO₂ | Oxazolyl | $Z_1$: $CF_3$ (3) |
| S | Pyrimidinyl | NH—SO₂ | Oxazolyl | $Z_1$: $CH_2$—$CH_2F$ (2) |
| S | Pyrimidinyl | NH—SO₂ | Oxazolyl | $Z_1$: $CH_2$—$CH_2F$ (3) |
| S | Pyrimidinyl | NH—SO₂ | Oxazolyl | $Z_1$: $CH_2$—$CHF_2$ (2) |
| S | Pyrimidinyl | NH—SO₂ | Oxazolyl | $Z_1$: $CH_2$—$CHF_2$ (3) |
| S | Pyrimidinyl | NH—SO₂ | Oxazolyl | $Z_1$: $CH_2$—$CF_3$ (2) |
| S | Pyrimidinyl | NH—SO₂ | Oxazolyl | $Z_1$: $CH_2$—$CF_3$ (3) |
| S | Pyrimidinyl | NH—SO₂ | Thiophenyl | None |
| S | Pyrimidinyl | NH—SO₂ | Thiophenyl | $Z_1$: F (2) |
| S | Pyrimidinyl | NH—SO₂ | Thiophenyl | $Z_1$: F (3) |
| S | Pyrimidinyl | NH—SO₂ | Thiophenyl | $Z_1$: F (2)<br>$Z_2$: F (3) |
| S | Pyrimidinyl | NH—SO₂ | Thiophenyl | $Z_1$: Cl (2) |
| S | Pyrimidinyl | NH—SO₂ | Thiophenyl | $Z_1$: Cl (3) |
| S | Pyrimidinyl | NH—SO₂ | Thiophenyl | $Z_1$: Cl (2)<br>$Z_2$: Cl (3) |
| S | Pyrimidinyl | NH—SO₂ | Thiophenyl | $Z_1$: F (2)<br>$Z_2$: Cl (3) |
| S | Pyrimidinyl | NH—SO₂ | Thiophenyl | $Z_1$: Cl (2)<br>$Z_2$: F (3) |
| S | Pyrimidinyl | NH—SO₂ | Thiophenyl | $Z_1$: $CH_3$ (2) |
| S | Pyrimidinyl | NH—SO₂ | Thiophenyl | $Z_1$: $CH_3$ (3) |
| S | Pyrimidinyl | NH—SO₂ | Thiophenyl | $Z_1$: $CH_2$—$CH_3$ (2) |
| S | Pyrimidinyl | NH—SO₂ | Thiophenyl | $Z_1$: $CH_2$—$CH_3$ (3) |
| S | Pyrimidinyl | NH—SO₂ | Thiophenyl | $Z_1$: $CH_2$—$CH_2$—$CH_3$ or iPr (2) |
| S | Pyrimidinyl | NH—SO₂ | Thiophenyl | $Z_1$: $CH_2$—$CH_2$—$CH_3$ or iPr (3) |
| S | Pyrimidinyl | NH—SO₂ | Thiophenyl | $Z_1$: $CH_2F$ (2) |
| S | Pyrimidinyl | NH—SO₂ | Thiophenyl | $Z_1$: $CH_2F$ (3) |
| S | Pyrimidinyl | NH—SO₂ | Thiophenyl | $Z_1$: $CHF_2$ (2) |
| S | Pyrimidinyl | NH—SO₂ | Thiophenyl | $Z_1$: $CHF_2$ (3) |
| S | Pyrimidinyl | NH—SO₂ | Thiophenyl | $Z_1$: $CF_3$ (2) |
| S | Pyrimidinyl | NH—SO₂ | Thiophenyl | $Z_1$: $CF_3$ (3) |
| S | Pyrimidinyl | NH—SO₂ | Thiophenyl | $Z_1$: $CH_2$—$CH_2F$ (2) |
| S | Pyrimidinyl | NH—SO₂ | Thiophenyl | $Z_1$: $CH_2$—$CH_2F$ (3) |
| S | Pyrimidinyl | NH—SO₂ | Thiophenyl | $Z_1$: $CH_2$—$CHF_2$ (2) |
| S | Pyrimidinyl | NH—SO₂ | Thiophenyl | $Z_1$: $CH_2$—$CHF_2$ (3) |
| S | Pyrimidinyl | NH—SO₂ | Thiophenyl | $Z_1$: $CH_2$—$CF_3$ (2) |
| S | Pyrimidinyl | NH—SO₂ | Thiophenyl | $Z_1$: $CH_2$—$CF_3$ (3) |
| S | Pyrimidinyl | NH—SO₂ | Thiazolyl | None |
| S | Pyrimidinyl | NH—SO₂ | Thiazolyl | $Z_1$: F (2) |
| S | Pyrimidinyl | NH—SO₂ | Thiazolyl | $Z_1$: F (3) |
| S | Pyrimidinyl | NH—SO₂ | Thiazolyl | $Z_1$: F (2)<br>$Z_2$: F (3) |
| S | Pyrimidinyl | NH—SO₂ | Thiazolyl | $Z_1$: Cl (2) |
| S | Pyrimidinyl | NH—SO₂ | Thiazolyl | $Z_1$: Cl (3) |
| S | Pyrimidinyl | NH—SO₂ | Thiazolyl | $Z_1$: Cl (2)<br>$Z_2$: Cl (3) |
| S | Pyrimidinyl | NH—SO₂ | Thiazolyl | $Z_1$: F (2)<br>$Z_2$: Cl (3) |
| S | Pyrimidinyl | NH—SO₂ | Thiazolyl | $Z_1$: Cl (2)<br>$Z_2$: F (3) |
| S | Pyrimidinyl | NH—SO₂ | Thiazolyl | $Z_1$: $CH_3$ (2) |
| S | Pyrimidinyl | NH—SO₂ | Thiazolyl | $Z_1$: $CH_3$ (3) |
| S | Pyrimidinyl | NH—SO₂ | Thiazolyl | $Z_1$: $CH_2$—$CH_3$ (2) |
| S | Pyrimidinyl | NH—SO₂ | Thiazolyl | $Z_1$: $CH_2$—$CH_3$ (3) |
| S | Pyrimidinyl | NH—SO₂ | Thiazolyl | $Z_1$: $CH_2$—$CH_2$—$CH_3$ or iPr (2) |
| S | Pyrimidinyl | NH—SO₂ | Thiazolyl | $Z_1$: $CH_2$—$CH_2$—$CH_3$ or iPr (3) |
| S | Pyrimidinyl | NH—SO₂ | Thiazolyl | $Z_1$: $CH_2F$ (2) |
| S | Pyrimidinyl | NH—SO₂ | Thiazolyl | $Z_1$: $CH_2F$ (3) |
| S | Pyrimidinyl | NH—SO₂ | Thiazolyl | $Z_1$: $CHF_2$ (2) |
| S | Pyrimidinyl | NH—SO₂ | Thiazolyl | $Z_1$: $CHF_2$ (3) |
| S | Pyrimidinyl | NH—SO₂ | Thiazolyl | $Z_1$: $CF_3$ (2) |
| S | Pyrimidinyl | NH—SO₂ | Thiazolyl | $Z_1$: $CF_3$ (3) |
| S | Pyrimidinyl | NH—SO₂ | Thiazolyl | $Z_1$: $CH_2$—$CH_2F$ (2) |
| S | Pyrimidinyl | NH—SO₂ | Thiazolyl | $Z_1$: $CH_2$—$CH_2F$ (3) |
| S | Pyrimidinyl | NH—SO₂ | Thiazolyl | $Z_1$: $CH_2$—$CHF_2$ (2) |
| S | Pyrimidinyl | NH—SO₂ | Thiazolyl | $Z_1$: $CH_2$—$CHF_2$ (3) |
| S | Pyrimidinyl | NH—SO₂ | Thiazolyl | $Z_1$: $CH_2$—$CF_3$ (2) |

TABLE 2-continued

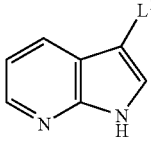

| L$^1$ | C$^1$ | L$^2$ | C$^2$ | Z |
|---|---|---|---|---|
| S | Pyrimidinyl | NH—SO$_2$ | Thiazolyl | Z$_1$: CH$_2$—CF$_3$ (3) |
| S | Pyrazinyl | NH—CH$_2$ | Phenyl | None |
| S | Pyrazinyl | NH—CH$_2$ | Phenyl | Z$_1$: F (para) |
| S | Pyrazinyl | NH—CH$_2$ | phenyl | Z$_1$: F (meta) |
| S | Pyrazinyl | NH—CH$_2$ | phenyl | Z$_1$: F (ortho) |
| S | Pyrazinyl | NH—CH$_2$ | phenyl | Z$_1$: F (para)<br>Z$_2$: F (meta) |
| S | Pyrazinyl | NH—CH$_2$ | Phenyl | Z$_1$: Cl (meta) |
| S | Pyrazinyl | NH—CH$_2$ | Phenyl | Z$_1$: Cl (para) |
| S | Pyrazinyl | NH—CH$_2$ | Phenyl | Z$_1$: Cl (para)<br>Z$_2$: Cl (meta) |
| S | Pyrazinyl | NH—CH$_2$ | Phenyl | Z$_1$: F (para)<br>Z$_2$: Cl (meta) |
| S | Pyrazinyl | NH—CH$_2$ | Phenyl | Z$_1$: Cl (para)<br>Z$_2$: F (meta) |
| S | Pyrazinyl | NH—CH$_2$ | Phenyl | Z$_1$: CH$_3$ (para) |
| S | Pyrazinyl | NH—CH$_2$ | Phenyl | Z$_1$: CH$_3$ (meta) |
| S | Pyrazinyl | NH—CH$_2$ | Phenyl | Z$_1$: CH$_3$ (ortho) |
| S | Pyrazinyl | NH—CH$_2$ | Phenyl | Z$_1$: CH$_2$—CH$_3$ (para) |
| S | Pyrazinyl | NH—CH$_2$ | Phenyl | Z$_1$: CH$_2$—CH$_3$ (meta) |
| S | Pyrazinyl | NH—CH$_2$ | Phenyl | Z$_1$: CH$_2$—CH$_3$ (ortho) |
| S | Pyrazinyl | NH—CH$_2$ | Phenyl | Z$_1$: CH$_2$—CH$_2$—CH$_3$ or iPr (para) |
| S | Pyrazinyl | NH—CH$_2$ | Phenyl | Z$_1$: CH$_2$—CH$_2$—CH$_3$ or iPr (meta) |
| S | Pyrazinyl | NH—CH$_2$ | Phenyl | Z$_1$: CH$_2$—CH$_2$—CH$_3$ or iPr (ortho) |
| S | Pyrazinyl | NH—CH$_2$ | Phenyl | Z$_1$: CH$_2$F (para) |
| S | Pyrazinyl | NH—CH$_2$ | Phenyl | Z$_1$: CH$_2$F (meta) |
| S | Pyrazinyl | NH—CH$_2$ | Phenyl | Z$_1$: CH$_2$F (ortho) |
| S | Pyrazinyl | NH—CH$_2$ | Phenyl | Z$_1$: CHF$_2$ (para) |
| S | Pyrazinyl | NH—CH$_2$ | Phenyl | Z$_1$: CHF$_2$ (meta) |
| S | Pyrazinyl | NH—CH$_2$ | Phenyl | Z$_1$: CHF$_2$ (ortho) |
| S | Pyrazinyl | NH—CH$_2$ | Phenyl | Z$_1$: CF$_3$ (para) |
| S | Pyrazinyl | NH—CH$_2$ | Phenyl | Z$_1$: CF$_3$ (meta) |
| S | Pyrazinyl | NH—CH$_2$ | Phenyl | Z$_1$: CF$_3$ (ortho) |
| S | Pyrazinyl | NH—CH$_2$ | Phenyl | Z$_1$: CH$_2$—CH$_2$F (para) |
| S | Pyrazinyl | NH—CH$_2$ | Phenyl | Z$_1$: CH$_2$—CH$_2$F (meta) |
| S | Pyrazinyl | NH—CH$_2$ | Phenyl | Z$_1$: CH$_2$—CH$_2$F (ortho) |
| S | Pyrazinyl | NH—CH$_2$ | Phenyl | Z$_1$: CH$_2$—CHF$_2$ (para) |
| S | Pyrazinyl | NH—CH$_2$ | Phenyl | Z$_1$: CH$_2$—CHF$_2$ (meta) |
| S | Pyrazinyl | NH—CH$_2$ | Phenyl | Z$_1$: CH$_2$—CHF$_2$ (ortho) |
| S | Pyrazinyl | NH—CH$_2$ | Phenyl | Z$_1$: CH$_2$—CF$_3$ (para) |
| S | Pyrazinyl | NH—CH$_2$ | Phenyl | Z$_1$: CH$_2$—CF$_3$ (meta) |
| S | Pyrazinyl | NH—CH$_2$ | Phenyl | Z$_1$: CH$_2$—CF$_3$ (ortho) |
| S | Pyrazinyl | NH—CH$_2$ | Pyridinyl | None |
| S | Pyrazinyl | NH—CH$_2$ | Pyridinyl | Z$_1$: F (para) |
| S | Pyrazinyl | NH—CH$_2$ | Pyridinyl | Z$_1$: F (meta) |
| S | Pyrazinyl | NH—CH$_2$ | Pyridinyl | Z$_1$: F (ortho) |
| S | Pyrazinyl | NH—CH$_2$ | Pyridinyl | Z$_1$: F (para)<br>Z$_2$: F (meta) |
| S | Pyrazinyl | NH—CH$_2$ | Pyridinyl | Z$_1$: Cl (meta) |
| S | Pyrazinyl | NH—CH$_2$ | Pyridinyl | Z$_1$: Cl (para) |
| S | Pyrazinyl | NH—CH$_2$ | Pyridinyl | Z$_1$: Cl (para)<br>Z$_2$: Cl (meta) |
| S | Pyrazinyl | NH—CH$_2$ | Pyridinyl | Z$_1$: F (para)<br>Z$_2$: Cl (meta) |
| S | Pyrazinyl | NH—CH$_2$ | Pyridinyl | Z$_1$: Cl (para)<br>Z$_2$: F (meta) |
| S | Pyrazinyl | NH—CH$_2$ | Pyridinyl | Z$_1$: CH$_3$ (para) |
| S | Pyrazinyl | NH—CH$_2$ | Pyridinyl | Z$_1$: CH$_3$ (meta) |
| S | Pyrazinyl | NH—CH$_2$ | Pyridinyl | Z$_1$: CH$_3$ (ortho) |
| S | Pyrazinyl | NH—CH$_2$ | Pyridinyl | Z$_1$: CH$_2$—CH$_3$ (para) |
| S | Pyrazinyl | NH—CH$_2$ | Pyridinyl | Z$_1$: CH$_2$—CH$_3$ (meta) |
| S | Pyrazinyl | NH—CH$_2$ | Pyridinyl | Z$_1$: CH$_2$—CH$_3$ (ortho) |
| S | Pyrazinyl | NH—CH$_2$ | Pyridinyl | Z$_1$: CH$_2$—CH$_2$—CH$_3$ or iPr (para) |
| S | Pyrazinyl | NH—CH$_2$ | Pyridinyl | Z$_1$: CH$_2$—CH$_2$—CH$_3$ or iPr (meta) |

TABLE 2-continued

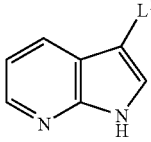

| L¹ | C¹ | L² | C² | Z |
|---|---|---|---|---|
| S | Pyrazinyl | NH—CH₂ | Pyridinyl | $Z_1$: CH₂—CH₂—CH₃ or iPr (ortho) |
| S | Pyrazinyl | NH—CH₂ | Pyridinyl | $Z_1$: CH₂F (para) |
| S | Pyrazinyl | NH—CH₂ | Pyridinyl | $Z_1$: CH₂F (meta) |
| S | Pyrazinyl | NH—CH₂ | Pyridinyl | $Z_1$: CH₂F (ortho) |
| S | Pyrazinyl | NH—CH₂ | Pyridinyl | $Z_1$: CHF₂ (para) |
| S | Pyrazinyl | NH—CH₂ | Pyridinyl | $Z_1$: CHF₂ (meta) |
| S | Pyrazinyl | NH—CH₂ | Pyridinyl | $Z_1$: CHF₂ (ortho) |
| S | Pyrazinyl | NH—CH₂ | Pyridinyl | $Z_1$: CF₃ (para) |
| S | Pyrazinyl | NH—CH₂ | Pyridinyl | $Z_1$: CF₃ (meta) |
| S | Pyrazinyl | NH—CH₂ | Pyridinyl | $Z_1$: CF₃ (ortho) |
| S | Pyrazinyl | NH—CH₂ | Pyridinyl | $Z_1$: CH₂—CH₂F (para) |
| S | Pyrazinyl | NH—CH₂ | Pyridinyl | $Z_1$: CH₂—CH₂F (meta) |
| S | Pyrazinyl | NH—CH₂ | Pyridinyl | $Z_1$: CH₂—CH₂F (ortho) |
| S | Pyrazinyl | NH—CH₂ | Pyridinyl | $Z_1$: CH₂—CHF₂ (para) |
| S | Pyrazinyl | NH—CH₂ | Pyridinyl | $Z_1$: CH₂—CHF₂ (meta) |
| S | Pyrazinyl | NH—CH₂ | Pyridinyl | $Z_1$: CH₂—CHF₂ (ortho) |
| S | Pyrazinyl | NH—CH₂ | Pyridinyl | $Z_1$: CH₂—CF₃ (para) |
| S | Pyrazinyl | NH—CH₂ | Pyridinyl | $Z_1$: CH₂—CF₃ (meta) |
| S | Pyrazinyl | NH—CH₂ | Pyridinyl | $Z_1$: CH₂—CF₃ (ortho) |
| S | Pyrazinyl | NH—CH₂ | Pyrimidinyl | None |
| S | Pyrazinyl | NH—CH₂ | Pyrimidinyl | $Z_1$: F (para) |
| S | Pyrazinyl | NH—CH₂ | Pyrimidinyl | $Z_1$: F (meta) |
| S | Pyrazinyl | NH—CH₂ | Pyrimidinyl | $Z_1$: F (ortho) |
| S | Pyrazinyl | NH—CH₂ | Pyrimidinyl | $Z_1$: F (para) $Z_2$: F (meta) |
| S | Pyrazinyl | NH—CH₂ | Pyrimidinyl | $Z_1$: Cl (meta) |
| S | Pyrazinyl | NH—CH₂ | Pyrimidinyl | $Z_1$: Cl (para) |
| S | Pyrazinyl | NH—CH₂ | Pyrimidinyl | $Z_1$: Cl (para) $Z_2$: Cl (meta) |
| S | Pyrazinyl | NH—CH₂ | Pyrimidinyl | $Z_1$: F (para) $Z_2$: Cl (meta) |
| S | Pyrazinyl | NH—CH₂ | Pyrimidinyl | $Z_1$: Cl (para) $Z_2$: F (meta) |
| S | Pyrazinyl | NH—CH₂ | Pyrimidinyl | $Z_1$: CH₃ (para) |
| S | Pyrazinyl | NH—CH₂ | Pyrimidinyl | $Z_1$: CH₃ (meta) |
| S | Pyrazinyl | NH—CH₂ | Pyrimidinyl | $Z_1$: CH₃ (ortho) |
| S | Pyrazinyl | NH—CH₂ | Pyrimidinyl | $Z_1$: CH₂—CH₃ (para) |
| S | Pyrazinyl | NH—CH₂ | Pyrimidinyl | $Z_1$: CH₂—CH₃ (meta) |
| S | Pyrazinyl | NH—CH₂ | Pyrimidinyl | $Z_1$: CH₂—CH₃ (ortho) |
| S | Pyrazinyl | NH—CH₂ | Pyrimidinyl | $Z_1$: CH₂—CH₂—CH₃ or iPr (para) |
| S | Pyrazinyl | NH—CH₂ | Pyrimidinyl | $Z_1$: CH₂—CH₂—CH₃ or iPr (meta) |
| S | Pyrazinyl | NH—CH₂ | Pyrimidinyl | $Z_1$: CH₂—CH₂—CH₃ or iPr (ortho) |
| S | Pyrazinyl | NH—CH₂ | Pyrimidinyl | $Z_1$: CH₂F (para) |
| S | Pyrazinyl | NH—CH₂ | Pyrimidinyl | $Z_1$: CH₂F (meta) |
| S | Pyrazinyl | NH—CH₂ | Pyrimidinyl | $Z_1$: CH₂F (ortho) |
| S | Pyrazinyl | NH—CH₂ | Pyrimidinyl | $Z_1$: CHF₂ (para) |
| S | Pyrazinyl | NH—CH₂ | Pyrimidinyl | $Z_1$: CHF₂ (meta) |
| S | Pyrazinyl | NH—CH₂ | Pyrimidinyl | $Z_1$: CHF₂ (ortho) |
| S | Pyrazinyl | NH—CH₂ | Pyrimidinyl | $Z_1$: CF₃ (para) |
| S | Pyrazinyl | NH—CH₂ | Pyrimidinyl | $Z_1$: CF₃ (meta) |
| S | Pyrazinyl | NH—CH₂ | Pyrimidinyl | $Z_1$: CF₃ (ortho) |
| S | Pyrazinyl | NH—CH₂ | Pyrimidinyl | $Z_1$: CH₂—CH₂F (para) |
| S | Pyrazinyl | NH—CH₂ | Pyrimidinyl | $Z_1$: CH₂—CH₂F (meta) |
| S | Pyrazinyl | NH—CH₂ | Pyrimidinyl | $Z_1$: CH₂—CH₂F (ortho) |
| S | Pyrazinyl | NH—CH₂ | Pyrimidinyl | $Z_1$: CH₂—CHF₂ (para) |
| S | Pyrazinyl | NH—CH₂ | Pyrimidinyl | $Z_1$: CH₂—CHF₂ (meta) |
| S | Pyrazinyl | NH—CH₂ | Pyrimidinyl | $Z_1$: CH₂—CHF₂ (ortho) |
| S | Pyrazinyl | NH—CH₂ | Pyrimidinyl | $Z_1$: CH₂—CF₃ (para) |
| S | Pyrazinyl | NH—CH₂ | Pyrimidinyl | $Z_1$: CH₂—CF₃ (meta) |
| S | Pyrazinyl | NH—CH₂ | Pyrimidinyl | $Z_1$: CH₂—CF₃ (ortho) |
| S | Pyrazinyl | NH—CH₂ | Pyrazinyl | None |
| S | Pyrazinyl | NH—CH₂ | Pyrazinyl | $Z_1$: F (para) |
| S | Pyrazinyl | NH—CH₂ | Pyrazinyl | $Z_1$: F (meta) |
| S | Pyrazinyl | NH—CH₂ | Pyrazinyl | $Z_1$: F (ortho) |

TABLE 2-continued $$L^1-C^1-L^2-C^2-Z_p$$

(7-azaindole structure with L¹—C¹—L²—C²—Zp substituent at 3-position)

| L¹ | C¹ | L² | C² | Z |
|---|---|---|---|---|
| S | Pyrazinyl | NH—CH₂ | Pyrazinyl | Z₁: F (para) |
|   |   |   |   | Z₂: F (meta) |
| S | Pyrazinyl | NH—CH₂ | Pyrazinyl | Z₁: Cl (meta) |
| S | Pyrazinyl | NH—CH₂ | Pyrazinyl | Z₁: Cl (para) |
| S | Pyrazinyl | NH—CH₂ | Pyrazinyl | Z₁: Cl (para) |
|   |   |   |   | Z₂: Cl (meta) |
| S | Pyrazinyl | NH—CH₂ | Pyrazinyl | Z₁: F (para) |
|   |   |   |   | Z₂: Cl (meta) |
| S | Pyrazinyl | NH—CH₂ | Pyrazinyl | Z₁: Cl (para) |
|   |   |   |   | Z₂: F (meta) |
| S | Pyrazinyl | NH—CH₂ | Pyrazinyl | Z₁: CH₃ (para) |
| S | Pyrazinyl | NH—CH₂ | Pyrazinyl | Z₁: CH₃ (meta) |
| S | Pyrazinyl | NH—CH₂ | Pyrazinyl | Z₁: CH₃ (ortho) |
| S | Pyrazinyl | NH—CH₂ | Pyrazinyl | Z₁: CH₂—CH₃ (para) |
| S | Pyrazinyl | NH—CH₂ | Pyrazinyl | Z₁: CH₂—CH₃ (meta) |
| S | Pyrazinyl | NH—CH₂ | Pyrazinyl | Z₁: CH₂—CH₃ (ortho) |
| S | Pyrazinyl | NH—CH₂ | Pyrazinyl | Z₁: CH₂—CH₂—CH₃ or iPr (para) |
| S | Pyrazinyl | NH—CH₂ | Pyrazinyl | Z₁: CH₂—CH₂—CH₃ or iPr (meta) |
| S | Pyrazinyl | NH—CH₂ | Pyrazinyl | Z₁: CH₂—CH₂—CH₃ or iPr (ortho) |
| S | Pyrazinyl | NH—CH₂ | Pyrazinyl | Z₁: CH₂F (para) |
| S | Pyrazinyl | NH—CH₂ | Pyrazinyl | Z₁: CH₂F (meta) |
| S | Pyrazinyl | NH—CH₂ | Pyrazinyl | Z₁: CH₂F (ortho) |
| S | Pyrazinyl | NH—CH₂ | Pyrazinyl | Z₁: CHF₂ (para) |
| S | Pyrazinyl | NH—CH₂ | Pyrazinyl | Z₁: CHF₂ (meta) |
| S | Pyrazinyl | NH—CH₂ | Pyrazinyl | Z₁: CHF₂ (ortho) |
| S | Pyrazinyl | NH—CH₂ | Pyrazinyl | Z₁: CF₃ (para) |
| S | Pyrazinyl | NH—CH₂ | Pyrazinyl | Z₁: CF₃ (meta) |
| S | Pyrazinyl | NH—CH₂ | Pyrazinyl | Z₁: CF₃ (ortho) |
| S | Pyrazinyl | NH—CH₂ | Pyrazinyl | Z₁: CH₂—CH₂F (para) |
| S | Pyrazinyl | NH—CH₂ | Pyrazinyl | Z₁: CH₂—CH₂F (meta |
| S | Pyrazinyl | NH—CH₂ | Pyrazinyl | Z₁: CH₂—CH₂F (ortho) |
| S | Pyrazinyl | NH—CH₂ | Pyrazinyl | Z₁: CH₂—CHF₂ (para) |
| S | Pyrazinyl | NH—CH₂ | Pyrazinyl | Z₁: CH₂—CHF₂ (meta) |
| S | Pyrazinyl | NH—CH₂ | Pyrazinyl | Z₁: CH₂—CHF₂ (ortho) |
| S | Pyrazinyl | NH—CH₂ | Pyrazinyl | Z₁: CH₂—CF₃ (para) |
| S | Pyrazinyl | NH—CH₂ | Pyrazinyl | Z₁: CH₂—CF₃ (meta) |
| S | Pyrazinyl | NH—CH₂ | Pyrazinyl | Z₁: CH₂—CF₃ (ortho) |
| S | Pyrazinyl | NH—CH₂ | Pyrrolyl | None |
| S | Pyrazinyl | NH—CH₂ | Pyrrolyl | Z₁: F (2) |
| S | Pyrazinyl | NH—CH₂ | Pyrrolyl | Z₁: F (3) |
| S | Pyrazinyl | NH—CH₂ | Pyrrolyl | Z₁: F (2) |
|   |   |   |   | Z₂: F (3) |
| S | Pyrazinyl | NH—CH₂ | Pyrrolyl | Z₁: Cl (2) |
| S | Pyrazinyl | NH—CH₂ | Pyrrolyl | Z₁: Cl (3) |
| S | Pyrazinyl | NH—CH₂ | Pyrrolyl | Z₁: Cl (2) |
|   |   |   |   | Z₂: Cl (3) |
| S | Pyrazinyl | NH—CH₂ | Pyrrolyl | Z₁: F (2) |
|   |   |   |   | Z₂: Cl (3) |
| S | Pyrazinyl | NH—CH₂ | Pyrrolyl | Z₁: Cl (2) |
|   |   |   |   | Z₂: F (3) |
| S | Pyrazinyl | NH—CH₂ | Pyrrolyl | Z₁: CH₃ (2) |
| S | Pyrazinyl | NH—CH₂ | Pyrrolyl | Z₁: CH₃ (3) |
| S | Pyrazinyl | NH—CH₂ | Pyrrolyl | Z₁: CH₂—CH₃ (2) |
| S | Pyrazinyl | NH—CH₂ | Pyrrolyl | Z₁: CH₂—CH₃ (3) |
| S | Pyrazinyl | NH—CH₂ | Pyrrolyl | Z₁: CH₂—CH₂—CH₃ or iPr (2) |
| S | Pyrazinyl | NH—CH₂ | Pyrrolyl | Z₁: CH₂—CH₂—CH₃ or iPr (3) |
| S | Pyrazinyl | NH—CH₂ | Pyrrolyl | Z₁: CH₂F (2) |
| S | Pyrazinyl | NH—CH₂ | Pyrrolyl | Z₁: CH₂F (3) |
| S | Pyrazinyl | NH—CH₂ | Pyrrolyl | Z₁: CHF₂ (2) |
| S | Pyrazinyl | NH—CH₂ | Pyrrolyl | Z₁: CHF₂ (3) |
| S | Pyrazinyl | NH—CH₂ | Pyrrolyl | Z₁: CF₃ (2) |
| S | Pyrazinyl | NH—CH₂ | Pyrrolyl | Z₁: CF₃ (3) |
| S | Pyrazinyl | NH—CH₂ | Pyrrolyl | Z₁: CH₂—CH₂F (2) |
| S | Pyrazinyl | NH—CH₂ | Pyrrolyl | Z₁: CH₂—CH₂F (3) |
| S | Pyrazinyl | NH—CH₂ | Pyrrolyl | Z₁: CH₂—CHF₂ (2) |
| S | Pyrazinyl | NH—CH₂ | Pyrrolyl | Z₁: CH₂—CHF₂ (3) |

TABLE 2-continued $$L^1-C^1-L^2-C^2-Z_p$$

(7-azaindole core structure)

| $L^1$ | $C^1$ | $L^2$ | $C^2$ | Z |
|---|---|---|---|---|
| S | Pyrazinyl | NH—CH$_2$ | Pyrrolyl | $Z_1$: CH$_2$—CF$_3$ (2) |
| S | Pyrazinyl | NH—CH$_2$ | Pyrrolyl | $Z_1$: CH$_2$—CF$_3$ (3) |
| S | Pyrazinyl | NH—CH$_2$ | Imidazolyl | None |
| S | Pyrazinyl | NH—CH$_2$ | Imidazolyl | $Z_1$: F (2) |
| S | Pyrazinyl | NH—CH$_2$ | Imidazolyl | $Z_1$: F (3) |
| S | Pyrazinyl | NH—CH$_2$ | Imidazolyl | $Z_1$: F (2) <br> $Z_2$: F (3) |
| S | Pyrazinyl | NH—CH$_2$ | Imidazolyl | $Z_1$: Cl (2) |
| S | Pyrazinyl | NH—CH$_2$ | Imidazolyl | $Z_1$: Cl (3) |
| S | Pyrazinyl | NH—CH$_2$ | Imidazolyl | $Z_1$: Cl (2) <br> $Z_2$: Cl (3) |
| S | Pyrazinyl | NH—CH$_2$ | Imidazolyl | $Z_1$: F (2) <br> $Z_2$: Cl (3) |
| S | Pyrazinyl | NH—CH$_2$ | Imidazolyl | $Z_1$: Cl (2) <br> $Z_2$: F (3) |
| S | Pyrazinyl | NH—CH$_2$ | Imidazolyl | $Z_1$: CH$_3$ (2) |
| S | Pyrazinyl | NH—CH$_2$ | Imidazolyl | $Z_1$: CH$_3$ (3) |
| S | Pyrazinyl | NH—CH$_2$ | Imidazolyl | $Z_1$: CH$_2$—CH$_3$ (2) |
| S | Pyrazinyl | NH—CH$_2$ | Imidazolyl | $Z_1$: CH$_2$—CH$_3$ (3) |
| S | Pyrazinyl | NH—CH$_2$ | Imidazolyl | $Z_1$: CH$_2$—CH$_2$—CH$_3$ or iPr (2) |
| S | Pyrazinyl | NH—CH$_2$ | Imidazolyl | $Z_1$: CH$_2$—CH$_2$—CH$_3$ or iPr (3) |
| S | Pyrazinyl | NH—CH$_2$ | Imidazolyl | $Z_1$: CH$_2$F (2) |
| S | Pyrazinyl | NH—CH$_2$ | Imidazolyl | $Z_1$: CH$_2$F (3) |
| S | Pyrazinyl | NH—CH$_2$ | Imidazolyl | $Z_1$: CHF$_2$ (2) |
| S | Pyrazinyl | NH—CH$_2$ | Imidazolyl | $Z_1$: CHF$_2$ (3) |
| S | Pyrazinyl | NH—CH$_2$ | Imidazolyl | $Z_1$: CF$_3$ (2) |
| S | Pyrazinyl | NH—CH$_2$ | Imidazolyl | $Z_1$: CF$_3$ (3) |
| S | Pyrazinyl | NH—CH$_2$ | Imidazolyl | $Z_1$: CH$_2$—CH$_2$F (2) |
| S | Pyrazinyl | NH—CH$_2$ | Imidazolyl | $Z_1$: CH$_2$—CH$_2$F (3) |
| S | Pyrazinyl | NH—CH$_2$ | Imidazolyl | $Z_1$: CH$_2$—CHF$_2$ (2) |
| S | Pyrazinyl | NH—CH$_2$ | Imidazolyl | $Z_1$: CH$_2$—CHF$_2$ (3) |
| S | Pyrazinyl | NH—CH$_2$ | Imidazolyl | $Z_1$: CH$_2$—CF$_3$ (2) |
| S | Pyrazinyl | NH—CH$_2$ | Imidazolyl | $Z_1$: CH$_2$—CF$_3$ (3) |
| S | Pyrazinyl | NH—CH$_2$ | Furanyl | None |
| S | Pyrazinyl | NH—CH$_2$ | Furanyl | $Z_1$: F (2) |
| S | Pyrazinyl | NH—CH$_2$ | Furanyl | $Z_1$: F (3) |
| S | Pyrazinyl | NH—CH$_2$ | Furanyl | $Z_1$: F (2) <br> $Z_2$: F (3) |
| S | Pyrazinyl | NH—CH$_2$ | Furanyl | $Z_1$: Cl (2) |
| S | Pyrazinyl | NH—CH$_2$ | Furanyl | $Z_1$: Cl (3) |
| S | Pyrazinyl | NH—CH$_2$ | Furanyl | $Z_1$: Cl (2) <br> $Z_2$: Cl (3) |
| S | Pyrazinyl | NH—CH$_2$ | Furanyl | $Z_1$: F (2) <br> $Z_2$: Cl (3) |
| S | Pyrazinyl | NH—CH$_2$ | Furanyl | $Z_1$: Cl (2) <br> $Z_2$: F (3) |
| S | Pyrazinyl | NH—CH$_2$ | Furanyl | $Z_1$: CH$_3$ (2) |
| S | Pyrazinyl | NH—CH$_2$ | Furanyl | $Z_1$: CH$_3$ (3) |
| S | Pyrazinyl | NH—CH$_2$ | Furanyl | $Z_1$: CH$_2$—CH$_3$ (2) |
| S | Pyrazinyl | NH—CH$_2$ | Furanyl | $Z_1$: CH$_2$—CH$_3$ (3) |
| S | Pyrazinyl | NH—CH$_2$ | Furanyl | $Z_1$: CH$_2$—CH$_2$—CH$_3$ or iPr (2) |
| S | Pyrazinyl | NH—CH$_2$ | Furanyl | $Z_1$: CH$_2$—CH$_2$—CH$_3$ or iPr (3) |
| S | Pyrazinyl | NH—CH$_2$ | Furanyl | $Z_1$: CH$_2$F (2) |
| S | Pyrazinyl | NH—CH$_2$ | Furanyl | $Z_1$: CH$_2$F (3) |
| S | Pyrazinyl | NH—CH$_2$ | Furanyl | $Z_1$: CHF$_2$ (2) |
| S | Pyrazinyl | NH—CH$_2$ | Furanyl | $Z_1$: CHF$_2$ (3) |
| S | Pyrazinyl | NH—CH$_2$ | Furanyl | $Z_1$: CF$_3$ (2) |
| S | Pyrazinyl | NH—CH$_2$ | Furanyl | $Z_1$: CF$_3$ (3) |
| S | Pyrazinyl | NH—CH$_2$ | Furanyl | $Z_1$: CH$_2$—CH$_2$F (2) |
| S | Pyrazinyl | NH—CH$_2$ | Furanyl | $Z_1$: CH$_2$—CH$_2$F (3) |
| S | Pyrazinyl | NH—CH$_2$ | Furanyl | $Z_1$: CH$_2$—CHF$_2$ (2) |
| S | Pyrazinyl | NH—CH$_2$ | Furanyl | $Z_1$: CH$_2$—CHF$_2$ (3) |
| S | Pyrazinyl | NH—CH$_2$ | Furanyl | $Z_1$: CH$_2$—CF$_3$ (2) |
| S | Pyrazinyl | NH—CH$_2$ | Furanyl | $Z_1$: CH$_2$—CF$_3$ (3) |
| S | Pyrazinyl | NH—CH$_2$ | Oxazolyl | None |
| S | Pyrazinyl | NH—CH$_2$ | Oxazolyl | $Z_1$: F (2) |
| S | Pyrazinyl | NH—CH$_2$ | Oxazolyl | $Z_1$: F (3) |
| S | Pyrazinyl | NH—CH$_2$ | Oxazolyl | $Z_1$: F (2) <br> $Z_2$: F (3) |

TABLE 2-continued

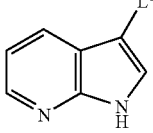

| L$^1$ | C$^1$ | L$^2$ | C$^2$ | Z |
|---|---|---|---|---|
| S | Pyrazinyl | NH—CH$_2$ | Oxazolyl | Z$_1$: Cl (2) |
| S | Pyrazinyl | NH—CH$_2$ | Oxazolyl | Z$_1$: Cl (3) |
| S | Pyrazinyl | NH—CH$_2$ | Oxazolyl | Z$_1$: Cl (2) |
|   |   |   |   | Z$_2$: Cl (3) |
| S | Pyrazinyl | NH—CH$_2$ | Oxazolyl | Z$_1$: F (2) |
|   |   |   |   | Z$_2$: Cl (3) |
| S | Pyrazinyl | NH—CH$_2$ | Oxazolyl | Z$_1$: Cl (2) |
|   |   |   |   | Z$_2$: F (3) |
| S | Pyrazinyl | NH—CH$_2$ | Oxazolyl | Z$_1$: CH$_3$ (2) |
| S | Pyrazinyl | NH—CH$_2$ | Oxazolyl | Z$_1$: CH$_3$ (3) |
| S | Pyrazinyl | NH—CH$_2$ | Oxazolyl | Z$_1$: CH$_2$—CH$_3$ (2) |
| S | Pyrazinyl | NH—CH$_2$ | Oxazolyl | Z$_1$: CH$_2$—CH$_3$ (3) |
| S | Pyrazinyl | NH—CH$_2$ | Oxazolyl | Z$_1$: CH$_2$—CH$_2$—CH$_3$ or iPr (2) |
| S | Pyrazinyl | NH—CH$_2$ | Oxazolyl | Z$_1$: CHF—CH$_2$—CH$_3$ or iPr (3) |
| S | Pyrazinyl | NH—CH$_2$ | Oxazolyl | Z$_1$: CH$_2$F (2) |
| S | Pyrazinyl | NH—CH$_2$ | Oxazolyl | Z$_1$: CH$_2$F (3) |
| S | Pyrazinyl | NH—CH$_2$ | Oxazolyl | Z$_1$: CHF$_2$ (2) |
| S | Pyrazinyl | NH—CH$_2$ | Oxazolyl | Z$_1$: CHF$_2$ (3) |
| S | Pyrazinyl | NH—CH$_2$ | Oxazolyl | Z$_1$: CF$_3$ (2) |
| S | Pyrazinyl | NH—CH$_2$ | Oxazolyl | Z$_1$: CF$_3$ (3) |
| S | Pyrazinyl | NH—CH$_2$ | Oxazolyl | Z$_1$: CH$_2$—CH$_2$F (2) |
| S | Pyrazinyl | NH—CH$_2$ | Oxazolyl | Z$_1$: CH$_2$—CH$_2$F (3) |
| S | Pyrazinyl | NH—CH$_2$ | Oxazolyl | Z$_1$: CH$_2$—CHF$_2$ (2) |
| S | Pyrazinyl | NH—CH$_2$ | Oxazolyl | Z$_1$: CH$_2$—CHF$_2$ (3) |
| S | Pyrazinyl | NH—CH$_2$ | Oxazolyl | Z$_1$: CH$_2$—CF$_3$ (2) |
| S | Pyrazinyl | NH—CH$_2$ | Oxazolyl | Z$_1$: CH$_2$—CF$_3$ (3) |
| S | Pyrazinyl | NH—CH$_2$ | Thiophenyl | None |
| S | Pyrazinyl | NH—CH$_2$ | Thiophenyl | Z$_1$: F (2) |
| S | Pyrazinyl | NH—CH$_2$ | Thiophenyl | Z$_1$: F (3) |
| S | Pyrazinyl | NH—CH$_2$ | Thiophenyl | Z$_1$: F (2) |
|   |   |   |   | Z$_2$: F (3) |
| S | Pyrazinyl | NH—CH$_2$ | Thiophenyl | Z$_1$: Cl (2) |
| S | Pyrazinyl | NH—CH$_2$ | Thiophenyl | Z$_1$: Cl (3) |
| S | Pyrazinyl | NH—CH$_2$ | Thiophenyl | Z$_1$: Cl (2) |
|   |   |   |   | Z$_2$: Cl (3) |
| S | Pyrazinyl | NH—CH$_2$ | Thiophenyl | Z$_1$: F (2) |
|   |   |   |   | Z$_2$: Cl (3) |
| S | Pyrazinyl | NH—CH$_2$ | Thiophenyl | Z$_1$: Cl (2) |
|   |   |   |   | Z$_2$: F (3) |
| S | Pyrazinyl | NH—CH$_2$ | Thiophenyl | Z$_1$: CH$_3$ (2) |
| S | Pyrazinyl | NH—CH$_2$ | Thiophenyl | Z$_1$: CH$_3$ (3) |
| S | Pyrazinyl | NH—CH$_2$ | Thiophenyl | Z$_1$: CH$_2$—CH$_3$ (2) |
| S | Pyrazinyl | NH—CH$_2$ | Thiophenyl | Z$_1$: CH$_2$—CH$_3$ (3) |
| S | Pyrazinyl | NH—CH$_2$ | Thiophenyl | Z$_1$: CH$_2$—CH$_2$—CH$_3$ or iPr (2) |
| S | Pyrazinyl | NH—CH$_2$ | Thiophenyl | Z$_1$: CH$_2$—CH$_2$—CH$_3$ or iPr (3) |
| S | Pyrazinyl | NH—CH$_2$ | Thiophenyl | Z$_1$: CH$_2$F (2) |
| S | Pyrazinyl | NH—CH$_2$ | Thiophenyl | Z$_1$: CH$_2$F (3) |
| S | Pyrazinyl | NH—CH$_2$ | Thiophenyl | Z$_1$: CHF$_2$ (2) |
| S | Pyrazinyl | NH—CH$_2$ | Thiophenyl | Z$_1$: CHF$_2$ (3) |
| S | Pyrazinyl | NH—CH$_2$ | Thiophenyl | Z$_1$: CF$_3$ (2) |
| S | Pyrazinyl | NH—CH$_2$ | Thiophenyl | Z$_1$: CF$_3$ (3) |
| S | Pyrazinyl | NH—CH$_2$ | Thiophenyl | Z$_1$: CH$_2$—CH$_2$F (2) |
| S | Pyrazinyl | NH—CH$_2$ | Thiophenyl | Z$_1$: CH$_2$—CH$_2$F (3) |
| S | Pyrazinyl | NH—CH$_2$ | Thiophenyl | Z$_1$: CH$_2$—CHF$_2$ (2) |
| S | Pyrazinyl | NH—CH$_2$ | Thiophenyl | Z$_1$: CH$_2$—CHF$_2$ (3) |
| S | Pyrazinyl | NH—CH$_2$ | Thiophenyl | Z$_1$: CH$_2$—CF$_3$ (2) |
| S | Pyrazinyl | NH—CH$_2$ | Thiophenyl | Z$_1$: CH$_2$—CF$_3$ (3) |
| S | Pyrazinyl | NH—CH$_2$ | Thiazolyl | None |
| S | Pyrazinyl | NH—CH$_2$ | Thiazolyl | Z$_1$: F (2) |
| S | Pyrazinyl | NH—CH$_2$ | Thiazolyl | Z$_1$: F (3) |
| S | Pyrazinyl | NH—CH$_2$ | Thiazolyl | Z$_1$: F (2) |
|   |   |   |   | Z$_2$: F (3) |
| S | Pyrazinyl | NH—CH$_2$ | Thiazolyl | Z$_1$: Cl (2) |
| S | Pyrazinyl | NH—CH$_2$ | Thiazolyl | Z$_1$: Cl (3) |
| S | Pyrazinyl | NH—CH$_2$ | Thiazolyl | Z$_1$: Cl (2) |
|   |   |   |   | Z$_2$: Cl (3) |
| S | Pyrazinyl | NH—CH$_2$ | Thiazolyl | Z$_1$: F (2) |
|   |   |   |   | Z$_2$: Cl (3) |

TABLE 2-continued

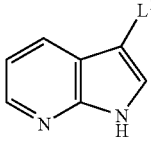

| L¹ | C¹ | L² | C² | Z |
|---|---|---|---|---|
| S | Pyrazinyl | NH—CH₂ | Thiazolyl | $Z_1$: Cl (2)<br>$Z_2$: F (3) |
| S | Pyrazinyl | NH—CH₂ | Thiazolyl | $Z_1$: CH₃ (2) |
| S | Pyrazinyl | NH—CH₂ | Thiazolyl | $Z_1$: CH₃ (3) |
| S | Pyrazinyl | NH—CH₂ | Thiazolyl | $Z_1$: CH₂—CH₃ (2) |
| S | Pyrazinyl | NH—CH₂ | Thiazolyl | $Z_1$: CH₂—CH₃ (3) |
| S | Pyrazinyl | NH—CH₂ | Thiazolyl | $Z_1$: CH₂—CH₂—CH₃ or iPr (2) |
| S | Pyrazinyl | NH—CH₂ | Thiazolyl | $Z_1$: CH₂—CH₂—CH₃ or iPr (3) |
| S | Pyrazinyl | NH—CH₂ | Thiazolyl | $Z_1$: CH₂F (2) |
| S | Pyrazinyl | NH—CH₂ | Thiazolyl | $Z_1$: CH₂F (3) |
| S | Pyrazinyl | NH—CH₂ | Thiazolyl | $Z_1$: CHF₂ (2) |
| S | Pyrazinyl | NH—CH₂ | Thiazolyl | $Z_1$: CHF₂ (3) |
| S | Pyrazinyl | NH—CH₂ | Thiazolyl | $Z_1$: CF₃ (2) |
| S | Pyrazinyl | NH—CH₂ | Thiazolyl | $Z_1$: CF₃ (3) |
| S | Pyrazinyl | NH—CH₂ | Thiazolyl | $Z_1$: CH₂—CH₂F (2) |
| S | Pyrazinyl | NH—CH₂ | Thiazolyl | $Z_1$: CH₂—CH₂F (3) |
| S | Pyrazinyl | NH—CH₂ | Thiazolyl | $Z_1$: CH₂—CHF₂ (2) |
| S | Pyrazinyl | NH—CH₂ | Thiazolyl | $Z_1$: CH₂—CHF₂ (3) |
| S | Pyrazinyl | NH—CH₂ | Thiazolyl | $Z_1$: CH₂—CF₃ (2) |
| S | Pyrazinyl | NH—CH₂ | Thiazolyl | $Z_1$: CH₂—CF₃ (3) |
| S | Pyrazinyl | NH—C(O) | Phenyl | None |
| S | Pyrazinyl | NH—C(O) | Phenyl | $Z_1$: F (para) |
| S | Pyrazinyl | NH—C(O) | phenyl | $Z_1$: F (meta) |
| S | Pyrazinyl | NH—C(O) | phenyl | $Z_1$: F (ortho) |
| S | Pyrazinyl | NH—C(O) | phenyl | $Z_1$: F (para)<br>$Z_2$: F (meta) |
| S | Pyrazinyl | NH—C(O) | Phenyl | $Z_1$: Cl (meta) |
| S | Pyrazinyl | NH—C(O) | Phenyl | $Z_1$: Cl (para) |
| S | Pyrazinyl | NH—C(O) | Phenyl | $Z_1$: Cl (para)<br>$Z_2$: Cl (meta) |
| S | Pyrazinyl | NH—C(O) | Phenyl | $Z_1$: F (para)<br>$Z_2$: Cl (meta) |
| S | Pyrazinyl | NH—C(O) | Phenyl | $Z_1$: Cl (para)<br>$Z_2$: F (meta) |
| S | Pyrazinyl | NH—C(O) | Phenyl | $Z_1$: CH₃ (para) |
| S | Pyrazinyl | NH—C(O) | Phenyl | $Z_1$: CH₃ (meta) |
| S | Pyrazinyl | NH—C(O) | Phenyl | $Z_1$: CH₃ (ortho) |
| S | Pyrazinyl | NH—C(O) | Phenyl | $Z_1$: CH₂—CH₃ (para) |
| S | Pyrazinyl | NH—C(O) | Phenyl | $Z_1$: CH₂—CH₃ (meta) |
| S | Pyrazinyl | NH—C(O) | Phenyl | $Z_1$: CH₂—CH₃ (ortho) |
| S | Pyrazinyl | NH—C(O) | Phenyl | $Z_1$: CH₂—CH₂—CH₃ or iPr (para) |
| S | Pyrazinyl | NH—C(O) | Phenyl | $Z_1$: CH₂—CH₂—CH₃ or iPr (meta) |
| S | Pyrazinyl | NH—C(O) | Phenyl | $Z_1$: CH₂—CH₂—CH₃ or iPr (ortho) |
| S | Pyrazinyl | NH—C(O) | Phenyl | $Z_1$: CH₂F (para) |
| S | Pyrazinyl | NH—C(O) | Phenyl | $Z_1$: CH₂F (meta) |
| S | Pyrazinyl | NH—C(O) | Phenyl | $Z_1$: CH₂F (ortho) |
| S | Pyrazinyl | NH—C(O) | Phenyl | $Z_1$: CHF₂ (para) |
| S | Pyrazinyl | NH—C(O) | Phenyl | $Z_1$: CHF₂ (meta) |
| S | Pyrazinyl | NH—C(O) | Phenyl | $Z_1$: CHF₂ (ortho) |
| S | Pyrazinyl | NH—C(O) | Phenyl | $Z_1$: CF₃ (para) |
| S | Pyrazinyl | NH—C(O) | Phenyl | $Z_1$: CF₃ (meta) |
| S | Pyrazinyl | NH—C(O) | Phenyl | $Z_1$: CF₃ (ortho) |
| S | Pyrazinyl | NH—C(O) | Phenyl | $Z_1$: CH₂—CH₂F (para) |
| S | Pyrazinyl | NH—C(O) | Phenyl | $Z_1$: CH₂—CH₂F (meta) |
| S | Pyrazinyl | NH—C(O) | Phenyl | $Z_1$: CH₂—CH₂F (ortho) |
| S | Pyrazinyl | NH—C(O) | Phenyl | $Z_1$: CH₂—CHF₂ (para) |
| S | Pyrazinyl | NH—C(O) | Phenyl | $Z_1$: CH₂—CHF₂ (meta) |
| S | Pyrazinyl | NH—C(O) | Phenyl | $Z_1$: CH₂—CHF₂ (ortho) |
| S | Pyrazinyl | NH—C(O) | Phenyl | $Z_1$: CH₂—CF₃ (para) |
| S | Pyrazinyl | NH—C(O) | Phenyl | $Z_1$: CH₂—CF₃ (meta) |
| S | Pyrazinyl | NH—C(O) | Phenyl | $Z_1$: CH₂—CF₃ (ortho) |
| S | Pyrazinyl | NH—C(O) | Pyridinyl | None |
| S | Pyrazinyl | NH—C(O) | Pyridinyl | $Z_1$: F (para) |
| S | Pyrazinyl | NH—C(O) | Pyridinyl | $Z_1$: F (meta) |
| S | Pyrazinyl | NH—C(O) | Pyridinyl | $Z_1$: F (ortho) |

TABLE 2-continued

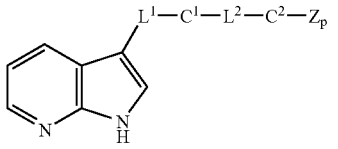

| L¹ | C¹ | L² | C² | Z |
|---|---|---|---|---|
| S | Pyrazinyl | NH—C(O) | Pyridinyl | $Z_1$: F (para) |
| | | | | $Z_2$: F (meta) |
| S | Pyrazinyl | NH—C(O) | Pyridinyl | $Z_1$: Cl (meta) |
| S | Pyrazinyl | NH—C(O) | Pyridinyl | $Z_1$: Cl (para) |
| S | Pyrazinyl | NH—C(O) | Pyridinyl | $Z_1$: Cl (para) |
| | | | | $Z_2$: Cl (meta) |
| S | Pyrazinyl | NH—C(O) | Pyridinyl | $Z_1$: F (para) |
| | | | | $Z_2$: Cl (meta) |
| S | Pyrazinyl | NH—C(O) | Pyridinyl | $Z_1$: Cl (para) |
| | | | | $Z_2$: F (meta) |
| S | Pyrazinyl | NH—C(O) | Pyridinyl | $Z_1$: CH₃ (para) |
| S | Pyrazinyl | NH—C(O) | Pyridinyl | $Z_1$: CH₃ (meta) |
| S | Pyrazinyl | NH—C(O) | Pyridinyl | $Z_1$: CH₃ (ortho) |
| S | Pyrazinyl | NH—C(O) | Pyridinyl | $Z_1$: CH₂—CH₃ (para) |
| S | Pyrazinyl | NH—C(O) | Pyridinyl | $Z_1$: CH₂—CH₃ (meta) |
| S | Pyrazinyl | NH—C(O) | Pyridinyl | $Z_1$: CH₂—CH₃ (ortho) |
| S | Pyrazinyl | NH—C(O) | Pyridinyl | $Z_1$: CH₂—CH₂—CH₃ or iPr (para) |
| S | Pyrazinyl | NH—C(O) | Pyridinyl | $Z_1$: CH₂—CH₂—CH₃ or iPr (meta) |
| S | Pyrazinyl | NH—C(O) | Pyridinyl | $Z_1$: CH₂—CH₂—CH₃ or iPr (ortho) |
| S | Pyrazinyl | NH—C(O) | Pyridinyl | $Z_1$: CH₂F (para) |
| S | Pyrazinyl | NH—C(O) | Pyridinyl | $Z_1$: CH₂F (meta) |
| S | Pyrazinyl | NH—C(O) | Pyridinyl | $Z_1$: CH₂F (ortho) |
| S | Pyrazinyl | NH—C(O) | Pyridinyl | $Z_1$: CHF₂ (para) |
| S | Pyrazinyl | NH—C(O) | Pyridinyl | $Z_1$: CHF₂ (meta) |
| S | Pyrazinyl | NH—C(O) | Pyridinyl | $Z_1$: CHF₂ (ortho) |
| S | Pyrazinyl | NH—C(O) | Pyridinyl | $Z_1$: CF₃ (para) |
| S | Pyrazinyl | NH—C(O) | Pyridinyl | $Z_1$: CF₃ (meta) |
| S | Pyrazinyl | NH—C(O) | Pyridinyl | $Z_1$: CF₃ (ortho) |
| S | Pyrazinyl | NH—C(O) | Pyridinyl | $Z_1$: CH₂—CH₂F (para) |
| S | Pyrazinyl | NH—C(O) | Pyridinyl | $Z_1$: CH₂—CH₂F (meta) |
| S | Pyrazinyl | NH—C(O) | Pyridinyl | $Z_1$: CH₂—CH₂F (ortho) |
| S | Pyrazinyl | NH—C(O) | Pyridinyl | $Z_1$: CH₂—CHF₂ (para) |
| S | Pyrazinyl | NH—C(O) | Pyridinyl | $Z_1$: CH₂—CHF₂ (meta) |
| S | Pyrazinyl | NH—C(O) | Pyridinyl | $Z_3$: CH₂—CHF₂ (ortho) |
| S | Pyrazinyl | NH—C(O) | Pyridinyl | $Z_1$: CH₂—CF₃ (para) |
| S | Pyrazinyl | NH—C(O) | Pyridinyl | $Z_1$: CH₂—CF₃ (meta) |
| S | Pyrazinyl | NH—C(O) | Pyridinyl | $Z_1$: CH₂—CF₃ (ortho) |
| S | Pyrazinyl | NH—C(O) | Pyrimidinyl | None |
| S | Pyrazinyl | NH—C(O) | Pyrimidinyl | $Z_1$: F (para) |
| S | Pyrazinyl | NH—C(O) | Pyrimidinyl | $Z_1$: F (meta) |
| S | Pyrazinyl | NH—C(O) | Pyrimidinyl | $Z_1$: F (ortho) |
| S | Pyrazinyl | NH—C(O) | Pyrimidinyl | $Z_1$: F (para) |
| | | | | $Z_2$: F (meta) |
| S | Pyrazinyl | NH—C(O) | Pyrimidinyl | $Z_1$: Cl (meta) |
| S | Pyrazinyl | NH—C(O) | Pyrimidinyl | $Z_1$: Cl (para) |
| S | Pyrazinyl | NH—C(O) | Pyrimidinyl | $Z_1$: Cl (para) |
| | | | | $Z_2$: Cl (meta) |
| S | Pyrazinyl | NH—C(O) | Pyrimidinyl | $Z_1$: F (para) |
| | | | | $Z_2$: Cl (meta) |
| S | Pyrazinyl | NH—C(O) | Pyrimidinyl | $Z_1$: Cl (para) |
| | | | | $Z_2$: F (meta) |
| S | Pyrazinyl | NH—C(O) | Pyrimidinyl | $Z_1$: CH₃ (para) |
| S | Pyrazinyl | NH—C(O) | Pyrimidinyl | $Z_1$: CH₃ (meta) |
| S | Pyrazinyl | NH—C(O) | Pyrimidinyl | $Z_1$: CH₃ (ortho) |
| S | Pyrazinyl | NH—C(O) | Pyrimidinyl | $Z_1$: CH₂—CH₃ (para) |
| S | Pyrazinyl | NH—C(O) | Pyrimidinyl | $Z_1$: CH₂—CH₃ (meta) |
| S | Pyrazinyl | NH—C(O) | Pyrimidinyl | $Z_1$: CH₂—CH₃ (ortho) |
| S | Pyrazinyl | NH—C(O) | Pyrimidinyl | $Z_1$: CH₂—CH₂—CH₃ or iPr (para) |
| S | Pyrazinyl | NH—C(O) | Pyrimidinyl | $Z_1$: CH₂—CH₂—CH₃ or iPr (meta) |
| S | Pyrazinyl | NH—C(O) | Pyrimidinyl | $Z_1$: CH₂—CH₂—CH₃ or iPr (ortho) |
| S | Pyrazinyl | NH—C(O) | Pyrimidinyl | $Z_1$: CH₂F (para) |
| S | Pyrazinyl | NH—C(O) | Pyrimidinyl | $Z_1$: CH₂F (meta) |
| S | Pyrazinyl | NH—C(O) | Pyrimidinyl | $Z_1$: CH₂F (ortho) |

TABLE 2-continued

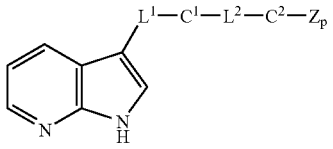

| L¹ | C¹ | L² | C² | Z |
|---|---|---|---|---|
| S | Pyrazinyl | NH—C(O) | Pyrimidinyl | $Z_1$: $CHF_2$ (para) |
| S | Pyrazinyl | NH—C(O) | Pyrimidinyl | $Z_1$: $CHF_2$ (meta) |
| S | Pyrazinyl | NH—C(O) | Pyrimidinyl | $Z_1$: $CHF_2$ (ortho) |
| S | Pyrazinyl | NH—C(O) | Pyrimidinyl | $Z_1$: $CF_3$ (para) |
| S | Pyrazinyl | NH—C(O) | Pyrimidinyl | $Z_1$: $CF_3$ (meta) |
| S | Pyrazinyl | NH—C(O) | Pyrimidinyl | $Z_1$: $CF_3$ (ortho) |
| S | Pyrazinyl | NH—C(O) | Pyrimidinyl | $Z_1$: $CH_2$—$CH_2F$ (para) |
| S | Pyrazinyl | NH—C(O) | Pyrimidinyl | $Z_1$: $CH_2$—$CH_2F$ (meta) |
| S | Pyrazinyl | NH—C(O) | Pyrimidinyl | $Z_1$: $CH_2$—$CH_2F$ (ortho) |
| S | Pyrazinyl | NH—C(O) | Pyrimidinyl | $Z_1$: $CH_2$—$CHF_2$ (para) |
| S | Pyrazinyl | NH—C(O) | Pyrimidinyl | $Z_1$: $CH_2$—$CHF_2$ (meta) |
| S | Pyrazinyl | NH—C(O) | Pyrimidinyl | $Z_1$: $CH_2$—$CHF_2$ (ortho) |
| S | Pyrazinyl | NH—C(O) | Pyrimidinyl | $Z_1$: $CH_2$—$CF_3$ (para) |
| S | Pyrazinyl | NH—C(O) | Pyrimidinyl | $Z_1$: $CH_2$—$CF_3$ (meta) |
| S | Pyrazinyl | NH—C(O) | Pyrimidinyl | $Z_1$: $CH_2$—$CF_3$ (ortho) |
| S | Pyrazinyl | NH—C(O) | Pyrazinyl | None |
| S | Pyrazinyl | NH—C(O) | Pyrazinyl | $Z_1$: F (para) |
| S | Pyrazinyl | NH—C(O) | Pyrazinyl | $Z_1$: F (meta) |
| S | Pyrazinyl | NH—C(O) | Pyrazinyl | $Z_1$: F (ortho) |
| S | Pyrazinyl | NH—C(O) | Pyrazinyl | $Z_1$: F (para)<br>$Z_2$: F (meta) |
| S | Pyrazinyl | NH—C(O) | Pyrazinyl | $Z_1$: Cl (meta) |
| S | Pyrazinyl | NH—C(O) | Pyrazinyl | $Z_1$: Cl (para) |
| S | Pyrazinyl | NH—C(O) | Pyrazinyl | $Z_1$: Cl (para)<br>$Z_2$: Cl (meta) |
| S | Pyrazinyl | NH—C(O) | Pyrazinyl | $Z_1$: F (para)<br>$Z_2$: Cl (meta) |
| S | Pyrazinyl | NH—C(O) | Pyrazinyl | $Z_1$: Cl (para)<br>$Z_2$: F (meta) |
| S | Pyrazinyl | NH—C(O) | Pyrazinyl | $Z_1$: $CH_3$ (para) |
| S | Pyrazinyl | NH—C(O) | Pyrazinyl | $Z_1$: $CH_3$ (meta) |
| S | Pyrazinyl | NH—C(O) | Pyrazinyl | $Z_1$: $CH_3$ (ortho) |
| S | Pyrazinyl | NH—C(O) | Pyrazinyl | $Z_1$: $CH_2$—$CH_3$ (para) |
| S | Pyrazinyl | NH—C(O) | Pyrazinyl | $Z_1$: $CH_2$—$CH_3$ (meta) |
| S | Pyrazinyl | NH—C(O) | Pyrazinyl | $Z_1$: $CH_2$—$CH_3$ (ortho) |
| S | Pyrazinyl | NH—C(O) | Pyrazinyl | $Z_1$: $CH_2$—$CH_2$—$CH_3$ or iPr (para) |
| S | Pyrazinyl | NH—C(O) | Pyrazinyl | $Z_1$: $CH_2$—$CH_2$—$CH_3$ or iPr (meta) |
| S | Pyrazinyl | NH—C(O) | Pyrazinyl | $Z_1$: $CH_2$—$CH_2$—$CH_3$ or iPr (ortho) |
| S | Pyrazinyl | NH—C(O) | Pyrazinyl | $Z_1$: $CH_2F$ (para) |
| S | Pyrazinyl | NH—C(O) | Pyrazinyl | $Z_1$: $CH_2F$ (meta) |
| S | Pyrazinyl | NH—C(O) | Pyrazinyl | $Z_1$: $CH_2F$ (ortho) |
| S | Pyrazinyl | NH—C(O) | Pyrazinyl | $Z_1$: $CHF_2$ (para) |
| S | Pyrazinyl | NH—C(O) | Pyrazinyl | $Z_1$: $CHF_2$ (meta) |
| S | Pyrazinyl | NH—C(O) | Pyrazinyl | $Z_1$: $CHF_2$ (ortho) |
| S | Pyrazinyl | NH—C(O) | Pyrazinyl | $Z_1$: $CF_3$ (para) |
| S | Pyrazinyl | NH—C(O) | Pyrazinyl | $Z_1$: $CF_3$ (meta) |
| S | Pyrazinyl | NH—C(O) | Pyrazinyl | $Z_1$: $CF_3$ (ortho) |
| S | Pyrazinyl | NH—C(O) | Pyrazinyl | $Z_1$: $CH_2$—$CH_2F$ (para) |
| S | Pyrazinyl | NH—C(O) | Pyrazinyl | $Z_1$: $CH_2$—$CH_2F$ (meta) |
| S | Pyrazinyl | NH—C(O) | Pyrazinyl | $Z_1$: $CH_2$—$CH_2F$ (ortho) |
| S | Pyrazinyl | NH—C(O) | Pyrazinyl | $Z_1$: $CH_2$—$CHF_2$ (para) |
| S | Pyrazinyl | NH—C(O) | Pyrazinyl | $Z_1$: $CH_2$—$CHF_2$ (meta) |
| S | Pyrazinyl | NH—C(O) | Pyrazinyl | $Z_1$: $CH_2$—$CHF_2$ (ortho) |
| S | Pyrazinyl | NH—C(O) | Pyrazinyl | $Z_1$: $CH_2$—$CF_3$ (para) |
| S | Pyrazinyl | NH—C(O) | Pyrazinyl | $Z_1$: $CH_2$—$CF_3$ (meta) |
| S | Pyrazinyl | NH—C(O) | Pyrazinyl | $Z_1$: $CH_2$—$CF_3$ (ortho) |
| S | Pyrazinyl | NH—C(O) | Pyrrolyl | None |
| S | Pyrazinyl | NH—C(O) | Pyrrolyl | $Z_1$: F (2) |
| S | Pyrazinyl | NH—C(O) | Pyrrolyl | $Z_1$: F (3) |
| S | Pyrazinyl | NH—C(O) | Pyrrolyl | $Z_1$: F (2)<br>$Z_2$: F (3) |
| S | Pyrazinyl | NH—C(O) | Pyrrolyl | $Z_1$: Cl (2) |
| S | Pyrazinyl | NH—C(O) | Pyrrolyl | $Z_1$: Cl (3) |
| S | Pyrazinyl | NH—C(O) | Pyrrolyl | $Z_1$: Cl (2)<br>$Z_2$: Cl (3) |

TABLE 2-continued

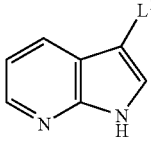

| L¹ | C¹ | L² | C² | Z |
|---|---|---|---|---|
| S | Pyrazinyl | NH—C(O) | Pyrrolyl | $Z_1$: F (2) |
| | | | | $Z_2$: Cl (3) |
| S | Pyrazinyl | NH—C(O) | Pyrrolyl | $Z_1$: Cl (2) |
| | | | | $Z_2$: F (3) |
| S | Pyrazinyl | NH—C(O) | Pyrrolyl | $Z_1$: $CH_3$ (2) |
| S | Pyrazinyl | NH—C(O) | Pyrrolyl | $Z_1$: $CH_3$ (3) |
| S | Pyrazinyl | NH—C(O) | Pyrrolyl | $Z_1$: $CH_2$—$CH_3$ (2) |
| S | Pyrazinyl | NH—C(O) | Pyrrolyl | $Z_1$: $CH_2$—$CH_3$ (3) |
| S | Pyrazinyl | NH—C(O) | Pyrrolyl | $Z_1$: $CH_2$—$CH_2$—$CH_3$ or iPr (2) |
| S | Pyrazinyl | NH—C(O) | Pyrrolyl | $Z_1$: $CH_2$—$CH_2$—$CH_3$ or iPr (3) |
| S | Pyrazinyl | NH—C(O) | Pyrrolyl | $Z_1$: $CH_2F$ (2) |
| S | Pyrazinyl | NH—C(O) | Pyrrolyl | $Z_1$: $CH_2F$ (3) |
| S | Pyrazinyl | NH—C(O) | Pyrrolyl | $Z_1$: $CHF_2$ (2) |
| S | Pyrazinyl | NH—C(O) | Pyrrolyl | $Z_1$: $CHF_2$ (3) |
| S | Pyrazinyl | NH—C(O) | Pyrrolyl | $Z_1$: $CF_3$ (2) |
| S | Pyrazinyl | NH—C(O) | Pyrrolyl | $Z_1$: $CF_3$ (3) |
| S | Pyrazinyl | NH—C(O) | Pyrrolyl | $Z_1$: $CH_2$—$CH_2F$ (2) |
| S | Pyrazinyl | NH—C(O) | Pyrrolyl | $Z_1$: $CH_2$—$CH_2F$ (3) |
| S | Pyrazinyl | NH—C(O) | Pyrrolyl | $Z_1$: $CH_2$—$CHF_2$ (2) |
| S | Pyrazinyl | NH—C(O) | Pyrrolyl | $Z_1$: $CH_2$—$CHF_2$ (3) |
| S | Pyrazinyl | NH—C(O) | Pyrrolyl | $Z_1$: $CH_2$—$CF_3$ (2) |
| S | Pyrazinyl | NH—C(O) | Pyrrolyl | $Z_1$: $CH_2$—$CF_3$ (3) |
| S | Pyrazinyl | NH—C(O) | Imidazolyl | None |
| S | Pyrazinyl | NH—C(O) | Imidazolyl | $Z_1$: F (2) |
| S | Pyrazinyl | NH—C(O) | Imidazolyl | $Z_1$: F (3) |
| S | Pyrazinyl | NH—C(O) | Imidazolyl | $Z_1$: F (2) |
| | | | | $Z_2$: F (3) |
| S | Pyrazinyl | NH—C(O) | Imidazolyl | $Z_1$: Cl (2) |
| S | Pyrazinyl | NH—C(O) | Imidazolyl | $Z_1$: Cl (3) |
| S | Pyrazinyl | NH—C(O) | Imidazolyl | $Z_1$: Cl (2) |
| | | | | $Z_2$: Cl (3) |
| S | Pyrazinyl | NH—C(O) | Imidazolyl | $Z_1$: F (2) |
| | | | | $Z_2$: Cl (3) |
| S | Pyrazinyl | NH—C(O) | Imidazolyl | $Z_1$: Cl (2) |
| | | | | $Z_2$: F (3) |
| S | Pyrazinyl | NH—C(O) | Imidazolyl | $Z_1$: $CH_3$ (2) |
| S | Pyrazinyl | NH—C(O) | Imidazolyl | $Z_1$: $CH_3$ (3) |
| S | Pyrazinyl | NH—C(O) | Imidazolyl | $Z_1$: $CH_2$—$CH_3$ (2) |
| S | Pyrazinyl | NH—C(O) | Imidazolyl | $Z_1$: $CH_2$—$CH_3$ (3) |
| S | Pyrazinyl | NH—C(O) | Imidazolyl | $Z_1$: $CH_2$—$CH_2$—$CH_3$ or iPr (2) |
| S | Pyrazinyl | NH—C(O) | Imidazolyl | $Z_1$: $CH_2$—$CH_2$—$CH_3$ or iPr (3) |
| S | Pyrazinyl | NH—C(O) | Imidazolyl | $Z_1$: $CH_2F$ (2) |
| S | Pyrazinyl | NH—C(O) | Imidazolyl | $Z_1$: $CH_2F$ (3) |
| S | Pyrazinyl | NH—C(O) | Imidazolyl | $Z_1$: $CHF_2$ (2) |
| S | Pyrazinyl | NH—C(O) | Imidazolyl | $Z_1$: $CHF_2$ (3) |
| S | Pyrazinyl | NH—C(O) | Imidazolyl | $Z_1$: $CF_3$ (2) |
| S | Pyrazinyl | NH—C(O) | Imidazolyl | $Z_1$: $CF_3$ (3) |
| S | Pyrazinyl | NH—C(O) | Imidazolyl | $Z_1$: $CH_2$—$CH_2F$ (2) |
| S | Pyrazinyl | NH—C(O) | Imidazolyl | $Z_1$: $CH_2$—$CH_2F$ (3) |
| S | Pyrazinyl | NH—C(O) | Imidazolyl | $Z_1$: $CH_2$—$CHF_2$ (2) |
| S | Pyrazinyl | NH—C(O) | Imidazolyl | $Z_1$: $CH_2$—$CHF_2$ (3) |
| S | Pyrazinyl | NH—C(O) | Imidazolyl | $Z_1$: $CH_2$—$CF_3$ (2) |
| S | Pyrazinyl | NH—C(O) | Imidazolyl | $Z_1$: $CH_2$—$CF_3$ (3) |
| S | Pyrazinyl | NH—C(O) | Furanyl | None |
| S | Pyrazinyl | NH—C(O) | Furanyl | $Z_1$: F (2) |
| S | Pyrazinyl | NH—C(O) | Furanyl | $Z_1$: F (3) |
| S | Pyrazinyl | NH—C(O) | Furanyl | $Z_1$: F (2) |
| | | | | $Z_2$: F (3) |
| S | Pyrazinyl | NH—C(O) | Furanyl | $Z_1$: Cl (2) |
| S | Pyrazinyl | NH—C(O) | Furanyl | $Z_1$: Cl (3) |
| S | Pyrazinyl | NH—C(O) | Furanyl | $Z_1$: Cl (2) |
| | | | | $Z_2$: Cl (3) |
| S | Pyrazinyl | NH—C(O) | Furanyl | $Z_1$: F (2) |
| | | | | $Z_2$: Cl (3) |
| S | Pyrazinyl | NH—C(O) | Furanyl | $Z_1$: Cl (2) |
| | | | | $Z_2$: F (3) |
| S | Pyrazinyl | NH—C(O) | Furanyl | $Z_1$: $CH_3$ (2) |
| S | Pyrazinyl | NH—C(O) | Furanyl | $Z_1$: $CH_3$ (3) |
| S | Pyrazinyl | NH—C(O) | Furanyl | $Z_1$: $CH_2$—$CH_3$ (2) |

TABLE 2-continued

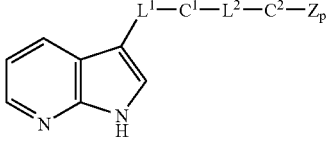

| L¹ | C¹ | L² | C² | Z |
|---|---|---|---|---|
| S | Pyrazinyl | NH—C(O) | Furanyl | $Z_1$: $CH_2$—$CH_3$ (3) |
| S | Pyrazinyl | NH—C(O) | Furanyl | $Z_1$: $CH_2$—$CH_2$—$CH_3$ or iPr (2) |
| S | Pyrazinyl | NH—C(O) | Furanyl | $Z_1$: $CH_2$—$CH_2$—$CH_3$ or iPr (3) |
| S | Pyrazinyl | NH—C(O) | Furanyl | $Z_1$: $CH_2F$ (2) |
| S | Pyrazinyl | NH—C(O) | Furanyl | $Z_1$: $CH_2F$ (3) |
| S | Pyrazinyl | NH—C(O) | Furanyl | $Z_1$: $CHF_2$ (2) |
| S | Pyrazinyl | NH—C(O) | Furanyl | $Z_1$: $CHF_2$ (3) |
| S | Pyrazinyl | NH—C(O) | Furanyl | $Z_1$: $CF_3$ (2) |
| S | Pyrazinyl | NH—C(O) | Furanyl | $Z_1$: $CF_3$ (3) |
| S | Pyrazinyl | NH—C(O) | Furanyl | $Z_1$: $CH_2$—$CH_2F$ (2) |
| S | Pyrazinyl | NH—C(O) | Furanyl | $Z_1$: $CH_2$—$CH_2F$ (3) |
| S | Pyrazinyl | NH—C(O) | Furanyl | $Z_1$: $CH_2$—$CHF_2$ (2) |
| S | Pyrazinyl | NH—C(O) | Furanyl | $Z_1$: $CH_2$—$CHF_2$ (3) |
| S | Pyrazinyl | NH—C(O) | Furanyl | $Z_1$: $CH_2$—$CF_3$ (2) |
| S | Pyrazinyl | NH—C(O) | Furanyl | $Z_1$: $CH_2$—$CF_3$ (3) |
| S | Pyrazinyl | NH—C(O) | Oxazolyl | None |
| S | Pyrazinyl | NH—C(O) | Oxazolyl | $Z_1$: F (2) |
| S | Pyrazinyl | NH—C(O) | Oxazolyl | $Z_1$: F (3) |
| S | Pyrazinyl | NH—C(O) | Oxazolyl | $Z_1$: F (2) $Z_2$: F (3) |
| S | Pyrazinyl | NH—C(O) | Oxazolyl | $Z_1$: Cl (2) |
| S | Pyrazinyl | NH—C(O) | Oxazolyl | $Z_1$: Cl (3) |
| S | Pyrazinyl | NH—C(O) | Oxazolyl | $Z_1$: Cl (2) $Z_2$: Cl (3) |
| S | Pyrazinyl | NH—C(O) | Oxazolyl | $Z_1$: F (2) $Z_2$: Cl (3) |
| S | Pyrazinyl | NH—C(O) | Oxazolyl | $Z_1$: Cl (2) $Z_2$: F (3) |
| S | Pyrazinyl | NH—C(O) | Oxazolyl | $Z_1$: $CH_3$ (2) |
| S | Pyrazinyl | NH—C(O) | Oxazolyl | $Z_1$: $CH_3$ (3) |
| S | Pyrazinyl | NH—C(O) | Oxazolyl | $Z_1$: $CH_2$—$CH_3$ (2) |
| S | Pyrazinyl | NH—C(O) | Oxazolyl | $Z_1$: $CH_2$—$CH_3$ (3) |
| S | Pyrazinyl | NH—C(O) | Oxazolyl | $Z_1$: $CH_2$—$CH_2$—$CH_3$ or iPr (2) |
| S | Pyrazinyl | NH—C(O) | Oxazolyl | $Z_1$: $CH_2$—$CH_2$—$CH_3$ or iPr (3) |
| S | Pyrazinyl | NH—C(O) | Oxazolyl | $Z_1$: $CH_2F$ (2) |
| S | Pyrazinyl | NH—C(O) | Oxazolyl | $Z_1$: $CH_2F$ (3) |
| S | Pyrazinyl | NH—C(O) | Oxazolyl | $Z_1$: $CHF_2$ (2) |
| S | Pyrazinyl | NH—C(O) | Oxazolyl | $Z_1$: $CHF_2$ (3) |
| S | Pyrazinyl | NH—C(O) | Oxazolyl | $Z_1$: $CF_3$ (2) |
| S | Pyrazinyl | NH—C(O) | Oxazolyl | $Z_1$: $CF_3$ (3) |
| S | Pyrazinyl | NH—C(O) | Oxazolyl | $Z_1$: $CH_2$—$CH_2F$ (2) |
| S | Pyrazinyl | NH—C(O) | Oxazolyl | $Z_1$: $CH_2$—$CH_2F$ (3) |
| S | Pyrazinyl | NH—C(O) | Oxazolyl | $Z_1$: $CH_2$—$CHF_2$ (2) |
| S | Pyrazinyl | NH—C(O) | Oxazolyl | $Z_1$: $CH_2$—$CHF_2$ (3) |
| S | Pyrazinyl | NH—C(O) | Oxazolyl | $Z_1$: $CH_2$—$CF_3$ (2) |
| S | Pyrazinyl | NH—C(O) | Oxazolyl | $Z_1$: $CH_2$—$CF_3$ (3) |
| S | Pyrazinyl | NH—C(O) | Thiophenyl | None |
| S | Pyrazinyl | NH—C(O) | Thiophenyl | $Z_1$: F (2) |
| S | Pyrazinyl | NH—C(O) | Thiophenyl | $Z_1$: F (3) |
| S | Pyrazinyl | NH—C(O) | Thiophenyl | $Z_1$: F (2) $Z_2$: F (3) |
| S | Pyrazinyl | NH—C(O) | Thiophenyl | $Z_1$: Cl (2) |
| S | Pyrazinyl | NH—C(O) | Thiophenyl | $Z_1$: Cl (3) |
| S | Pyrazinyl | NH—C(O) | Thiophenyl | $Z_1$: Cl (2) $Z_2$: Cl (3) |
| S | Pyrazinyl | NH—C(O) | Thiophenyl | $Z_1$: F (2) $Z_2$: Cl (3) |
| S | Pyrazinyl | NH—C(O) | Thiophenyl | $Z_1$: Cl (2) $Z_2$: F (3) |
| S | Pyrazinyl | NH—C(O) | Thiophenyl | $Z_1$: $CH_3$ (2) |
| S | Pyrazinyl | NH—C(O) | Thiophenyl | $Z_1$: $CH_3$ (3) |
| S | Pyrazinyl | NH—C(O) | Thiophenyl | $Z_1$: $CH_2$—$CH_3$ (2) |
| S | Pyrazinyl | NH—C(O) | Thiophenyl | $Z_1$: $CH_2$—$CH_3$ (3) |
| S | Pyrazinyl | NH—C(O) | Thiophenyl | $Z_1$: $CH_2$—$CH_2$—$CH_3$ or iPr (2) |
| S | Pyrazinyl | NH—C(O) | Thiophenyl | $Z_1$: $CH_2$—$CH_2$—$CH_3$ or iPr (3) |
| S | Pyrazinyl | NH—C(O) | Thiophenyl | $Z_1$: $CH_2F$ (2) |
| S | Pyrazinyl | NH—C(O) | Thiophenyl | $Z_1$: $CH_2F$ (3) |
| S | Pyrazinyl | NH—C(O) | Thiophenyl | $Z_1$: $CHF_2$ (2) |
| S | Pyrazinyl | NH—C(O) | Thiophenyl | $Z_1$: $CHF_2$ (3) |

TABLE 2-continued

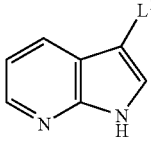

L¹—C¹—L²—C²—Z$_p$

| L¹ | C¹ | L² | C² | Z |
|---|---|---|---|---|
| S | Pyrazinyl | NH—C(O) | Thiophenyl | $Z_1$: CF$_3$ (2) |
| S | Pyrazinyl | NH—C(O) | Thiophenyl | $Z_1$: CF$_3$ (3) |
| S | Pyrazinyl | NH—C(O) | Thiophenyl | $Z_1$: CH$_2$—CH$_2$F (2) |
| S | Pyrazinyl | NH—C(O) | Thiophenyl | $Z_1$: CH$_2$—CH$_2$F (3) |
| S | Pyrazinyl | NH—C(O) | Thiophenyl | $Z_1$: CH$_2$—CHF$_2$ (2) |
| S | Pyrazinyl | NH—C(O) | Thiophenyl | $Z_1$: CH$_2$—CHF$_2$ (3) |
| S | Pyrazinyl | NH—C(O) | Thiophenyl | $Z_1$: CH$_2$—CF$_3$ (2) |
| S | Pyrazinyl | NH—C(O) | Thiophenyl | $Z_1$: CH$_2$—CF$_3$ (3) |
| S | Pyrazinyl | NH—C(O) | Thiazolyl | None |
| S | Pyrazinyl | NH—C(O) | Thiazolyl | $Z_1$: F (2) |
| S | Pyrazinyl | NH—C(O) | Thiazolyl | $Z_1$: F (3) |
| S | Pyrazinyl | NH—C(O) | Thiazolyl | $Z_1$: F (2)<br>$Z_2$: F (3) |
| S | Pyrazinyl | NH—C(O) | Thiazolyl | $Z_1$: Cl (2) |
| S | Pyrazinyl | NH—C(O) | Thiazolyl | $Z_1$: Cl (3) |
| S | Pyrazinyl | NH—C(O) | Thiazolyl | $Z_1$: Cl (2)<br>$Z_2$: Cl (3) |
| S | Pyrazinyl | NH—C(O) | Thiazolyl | $Z_1$: F (2)<br>$Z_2$: Cl (3) |
| S | Pyrazinyl | NH—C(O) | Thiazolyl | $Z_1$: Cl (2)<br>$Z_2$: F (3) |
| S | Pyrazinyl | NH—C(O) | Thiazolyl | $Z_1$: CH$_3$ (2) |
| S | Pyrazinyl | NH—C(O) | Thiazolyl | $Z_1$: CH$_3$ (3) |
| S | Pyrazinyl | NH—C(O) | Thiazolyl | $Z_1$: CH$_2$—CH$_3$ (2) |
| S | Pyrazinyl | NH—C(O) | Thiazolyl | $Z_1$: CH$_2$—CH$_3$ (3) |
| S | Pyrazinyl | NH—C(O) | Thiazolyl | $Z_1$: CH$_2$—CH$_2$—CH$_3$ or iPr (2) |
| S | Pyrazinyl | NH—C(O) | Thiazolyl | $Z_1$: CH$_2$—CH$_2$—CH$_3$ or iPr (3) |
| S | Pyrazinyl | NH—C(O) | Thiazolyl | $Z_1$: CH$_2$F (2) |
| S | Pyrazinyl | NH—C(O) | Thiazolyl | $Z_1$: CH$_2$F (3) |
| S | Pyrazinyl | NH—C(O) | Thiazolyl | $Z_1$: CHF$_2$ (2) |
| S | Pyrazinyl | NH—C(O) | Thiazolyl | $Z_1$: CHF$_2$ (3) |
| S | Pyrazinyl | NH—C(O) | Thiazolyl | $Z_1$: CF$_3$ (2) |
| S | Pyrazinyl | NH—C(O) | Thiazolyl | $Z_1$: CF$_3$ (3) |
| S | Pyrazinyl | NH—C(O) | Thiazolyl | $Z_1$: CH$_2$—CH$_2$F (2) |
| S | Pyrazinyl | NH—C(O) | Thiazolyl | $Z_1$: CH$_2$—CH$_2$F (3) |
| S | Pyrazinyl | NH—C(O) | Thiazolyl | $Z_1$: CH$_2$—CHF$_2$ (2) |
| S | Pyrazinyl | NH—C(O) | Thiazolyl | $Z_1$: CH$_2$—CHF$_2$ (3) |
| S | Pyrazinyl | NH—C(O) | Thiazolyl | $Z_1$: CH$_2$—CF$_3$ (2) |
| S | Pyrazinyl | NH—C(O) | Thiazolyl | $Z_1$: CH$_2$—CF$_3$ (3) |
| S | Pyrazinyl | NH—SO$_2$ | Phenyl | None |
| S | Pyrazinyl | NH—SO$_2$ | Phenyl | $Z_1$: F (para) |
| S | Pyrazinyl | NH—SO$_2$ | phenyl | $Z_1$: F (meta) |
| S | Pyrazinyl | NH—SO$_2$ | phenyl | $Z_1$: F (ortho) |
| S | Pyrazinyl | NH—SO$_2$ | phenyl | $Z_1$: F (para)<br>$Z_2$: F (meta) |
| S | Pyrazinyl | NH—SO$_2$ | Phenyl | $Z_1$: Cl (meta) |
| S | Pyrazinyl | NH—SO$_2$ | Phenyl | $Z_1$: Cl (para) |
| S | Pyrazinyl | NH—SO$_2$ | Phenyl | $Z_1$: Cl (para)<br>$Z_2$: Cl (meta) |
| S | Pyrazinyl | NH—SO$_2$ | Phenyl | $Z_1$: F (para)<br>$Z_2$: Cl (meta) |
| S | Pyrazinyl | NH—SO$_2$ | Phenyl | $Z_1$: Cl (para)<br>$Z_2$: F (meta) |
| S | Pyrazinyl | NH—SO$_2$ | Phenyl | $Z_1$: CH$_3$ (para) |
| S | Pyrazinyl | NH—SO$_2$ | Phenyl | $Z_1$: CH$_3$ (meta) |
| S | Pyrazinyl | NH—SO$_2$ | Phenyl | $Z_1$: CH$_3$ (ortho) |
| S | Pyrazinyl | NH—SO$_2$ | Phenyl | $Z_1$: CH$_2$—CH$_3$ (para) |
| S | Pyrazinyl | NH—SO$_2$ | Phenyl | $Z_1$: CH$_2$—CH$_3$ (meta) |
| S | Pyrazinyl | NH—SO$_2$ | Phenyl | $Z_1$: CH$_2$—CH$_3$ (ortho) |
| S | Pyrazinyl | NH—SO$_2$ | Phenyl | $Z_1$: CH$_2$—CH$_2$—CH$_3$ or iPr (para) |
| S | Pyrazinyl | NH—SO$_2$ | Phenyl | $Z_1$: CH$_2$—CH$_2$—CH$_3$ or iPr (meta) |
| S | Pyrazinyl | NH—SO$_2$ | Phenyl | $Z_1$: CH$_2$—CH$_2$—CH$_3$ or iPr (ortho) |
| S | Pyrazinyl | NH—SO$_2$ | Phenyl | $Z_1$: CH$_2$F (para) |
| S | Pyrazinyl | NH—SO$_2$ | Phenyl | $Z_1$: CH$_2$F (meta) |
| S | Pyrazinyl | NH—SO$_2$ | Phenyl | $Z_1$: CH$_2$F (ortho) |
| S | Pyrazinyl | NH—SO$_2$ | Phenyl | $Z_1$: CHF$_2$ (para) |

TABLE 2-continued

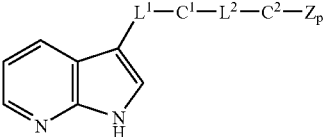

| L$^1$ | C$^1$ | L$^2$ | C$^2$ | Z |
|---|---|---|---|---|
| S | Pyrazinyl | NH—SO$_2$ | Phenyl | Z$_1$: CHF$_2$ (meta) |
| S | Pyrazinyl | NH—SO$_2$ | Phenyl | Z$_1$: CHF$_2$ (ortho) |
| S | Pyrazinyl | NH—SO$_2$ | Phenyl | Z$_1$: CF$_3$ (para) |
| S | Pyrazinyl | NH—SO$_2$ | Phenyl | Z$_1$: CF$_3$ (meta) |
| S | Pyrazinyl | NH—SO$_2$ | Phenyl | Z$_1$: CF$_3$ (ortho) |
| S | Pyrazinyl | NH—SO$_2$ | Phenyl | Z$_1$: CH$_2$—CH$_2$F (para) |
| S | Pyrazinyl | NH—SO$_2$ | Phenyl | Z$_1$: CH$_2$—CH$_2$F (meta) |
| S | Pyrazinyl | NH—SO$_2$ | Phenyl | Z$_1$: CH$_2$—CH$_2$F (ortho) |
| S | Pyrazinyl | NH—SO$_2$ | Phenyl | Z$_1$: CH$_2$—CHF$_2$ (para) |
| S | Pyrazinyl | NH—SO$_2$ | Phenyl | Z$_1$: CH$_2$—CHF$_2$ (meta) |
| S | Pyrazinyl | NH—SO$_2$ | Phenyl | Z$_1$: CH$_2$—CHF$_2$ (ortho) |
| S | Pyrazinyl | NH—SO$_2$ | Phenyl | Z$_1$: CH$_2$—CF$_3$ (para) |
| S | Pyrazinyl | NH—SO$_2$ | Phenyl | Z$_1$: CH$_2$—CF$_3$ (meta) |
| S | Pyrazinyl | NH—SO$_2$ | Phenyl | Z$_1$: CH$_2$—CF$_3$ (ortho) |
| S | Pyrazinyl | NH—SO$_2$ | Pyridinyl | None |
| S | Pyrazinyl | NH—SO$_2$ | Pyridinyl | Z$_1$: F (para) |
| S | Pyrazinyl | NH—SO$_2$ | Pyridinyl | Z$_1$: F (meta) |
| S | Pyrazinyl | NH—SO$_2$ | Pyridinyl | Z$_1$: F (ortho) |
| S | Pyrazinyl | NH—SO$_2$ | Pyridinyl | Z$_1$: F (para)<br>Z$_2$: F (meta) |
| S | Pyrazinyl | NH—SO$_2$ | Pyridinyl | Z$_1$: Cl (meta) |
| S | Pyrazinyl | NH—SO$_2$ | Pyridinyl | Z$_1$: Cl (para) |
| S | Pyrazinyl | NH—SO$_2$ | Pyridinyl | Z$_1$: Cl (para)<br>Z$_2$: Cl (meta) |
| S | Pyrazinyl | NH—SO$_2$ | Pyridinyl | Z$_1$: F (para)<br>Z$_2$: Cl (meta) |
| S | Pyrazinyl | NH—SO$_2$ | Pyridinyl | Z$_1$: Cl (para)<br>Z$_2$: F (meta) |
| S | Pyrazinyl | NH—SO$_2$ | Pyridinyl | Z$_1$: CH$_3$ (para) |
| S | Pyrazinyl | NH—SO$_2$ | Pyridinyl | Z$_1$: CH$_3$ (meta) |
| S | Pyrazinyl | NH—SO$_2$ | Pyridinyl | Z$_1$: CH$_3$ (ortho) |
| S | Pyrazinyl | NH—SO$_2$ | Pyridinyl | Z$_1$: CH$_2$—CH$_3$ (para) |
| S | Pyrazinyl | NH—SO$_2$ | Pyridinyl | Z$_1$: CH$_2$—CH$_3$ (meta) |
| S | Pyrazinyl | NH—SO$_2$ | Pyridinyl | Z$_1$: CH$_2$—CH$_3$ (ortho) |
| S | Pyrazinyl | NH—SO$_2$ | Pyridinyl | Z$_1$: CH$_2$—CH$_2$—CH$_3$ or iPr (para) |
| S | Pyrazinyl | NH—SO$_2$ | Pyridinyl | Z$_1$: CH$_2$—CH$_2$—CH$_3$ or iPr (meta) |
| S | Pyrazinyl | NH—SO$_2$ | Pyridinyl | Z$_1$: CH$_2$—CH$_2$—CH$_3$ or iPr (ortho) |
| S | Pyrazinyl | NH—SO$_2$ | Pyridinyl | Z$_1$: CH$_2$F (para) |
| S | Pyrazinyl | NH—SO$_2$ | Pyridinyl | Z$_1$: CH$_2$F (meta) |
| S | Pyrazinyl | NH—SO$_2$ | Pyridinyl | Z$_1$: CH$_2$F (ortho) |
| S | Pyrazinyl | NH—SO$_2$ | Pyridinyl | Z$_1$: CHF$_2$ (para) |
| S | Pyrazinyl | NH—SO$_2$ | Pyridinyl | Z$_1$: CHF$_2$ (meta) |
| S | Pyrazinyl | NH—SO$_2$ | Pyridinyl | Z$_1$: CHF$_2$ (ortho) |
| S | Pyrazinyl | NH—SO$_2$ | Pyridinyl | Z$_1$: CF$_3$ (para) |
| S | Pyrazinyl | NH—SO$_2$ | Pyridinyl | Z$_1$: CF$_3$ (meta) |
| S | Pyrazinyl | NH—SO$_2$ | Pyridinyl | Z$_1$: CF$_3$ (ortho) |
| S | Pyrazinyl | NH—SO$_2$ | Pyridinyl | Z$_1$: CH$_2$—CH$_2$F (para) |
| S | Pyrazinyl | NH—SO$_2$ | Pyridinyl | Z$_1$: CH$_2$—CH$_2$F (meta) |
| S | Pyrazinyl | NH—SO$_2$ | Pyridinyl | Z$_1$: CH$_2$—CH$_2$F (ortho) |
| S | Pyrazinyl | NH—SO$_2$ | Pyridinyl | Z$_1$: CH$_2$—CHF$_2$ (para) |
| S | Pyrazinyl | NH—SO$_2$ | Pyridinyl | Z$_1$: CH$_2$—CHF$_2$ (meta) |
| S | Pyrazinyl | NH—SO$_2$ | Pyridinyl | Z$_1$: CH$_2$—CHF$_2$ (ortho) |
| S | Pyrazinyl | NH—SO$_2$ | Pyridinyl | Z$_1$: CH$_2$—CF$_3$ (para) |
| S | Pyrazinyl | NH—SO$_2$ | Pyridinyl | Z$_1$: CH$_2$—CF$_3$ (meta) |
| S | Pyrazinyl | NH—SO$_2$ | Pyridinyl | Z$_1$: CH$_2$—CF3 (ortho) |
| S | Pyrazinyl | NH—SO$_2$ | Pyrimidinyl | None |
| S | Pyrazinyl | NH—SO$_2$ | Pyrimidinyl | Z$_1$: F (para) |
| S | Pyrazinyl | NH—SO$_2$ | Pyrimidinyl | Z$_1$: F (meta) |
| S | Pyrazinyl | NH—SO$_2$ | Pyrimidinyl | Z$_1$: F (ortho) |
| S | Pyrazinyl | NH—SO$_2$ | Pyrimidinyl | Z$_1$: F (para)<br>Z$_2$: F (meta) |
| S | Pyrazinyl | NH—SO$_2$ | Pyrimidinyl | Z$_1$: Cl (meta) |
| S | Pyrazinyl | NH—SO$_2$ | Pyrimidinyl | Z$_1$: Cl (para) |
| S | Pyrazinyl | NH—SO$_2$ | Pyrimidinyl | Z$_1$: Cl (para)<br>Z$_2$: Cl (meta) |

TABLE 2-continued

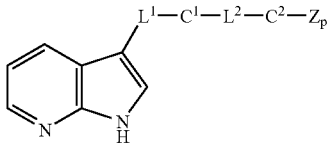

| L¹ | C¹ | L² | C² | Z |
|---|---|---|---|---|
| S | Pyrazinyl | NH—SO₂ | Pyrimidinyl | $Z_1$: F (para)<br>$Z_2$: Cl (meta) |
| S | Pyrazinyl | NH—SO₂ | Pyrimidinyl | $Z_1$: Cl (para)<br>$Z_2$: F (meta) |
| S | Pyrazinyl | NH—SO₂ | Pyrimidinyl | $Z_1$: $CH_3$ (para) |
| S | Pyrazinyl | NH—SO₂ | Pyrimidinyl | $Z_1$: $CH_3$ (meta) |
| S | Pyrazinyl | NH—SO₂ | Pyrimidinyl | $Z_1$: $CH_3$ (ortho) |
| S | Pyrazinyl | NH—SO₂ | Pyrimidinyl | $Z_1$: $CH_2$—$CH_3$ (para) |
| S | Pyrazinyl | NH—SO₂ | Pyrimidinyl | $Z_1$: $CH_2$—$CH_3$ (meta) |
| S | Pyrazinyl | NH—SO₂ | Pyrimidinyl | $Z_1$: $CH_2$—$CH_3$ (ortho) |
| S | Pyrazinyl | NH—SO₂ | Pyrimidinyl | $Z_1$: $CH_2$—$CH_2$—$CH_3$ or iPr (para) |
| S | Pyrazinyl | NH—SO₂ | Pyrimidinyl | $Z_1$: $CH_2$—$CH_2$—$CH_3$ or iPr (meta) |
| S | Pyrazinyl | NH—SO₂ | Pyrimidinyl | $Z_1$: $CH_2$—$CH_2$—$CH_3$ or iPr (ortho) |
| S | Pyrazinyl | NH—SO₂ | Pyrimidinyl | $Z_1$: $CH_2F$ (para) |
| S | Pyrazinyl | NH—SO₂ | Pyrimidinyl | $Z_1$: $CH_2F$ (meta) |
| S | Pyrazinyl | NH—SO₂ | Pyrimidinyl | $Z_1$: $CH_2F$ (ortho) |
| S | Pyrazinyl | NH—SO₂ | Pyrimidinyl | $Z_1$: $CHF_2$ (para) |
| S | Pyrazinyl | NH—SO₂ | Pyrimidinyl | $Z_1$: $CHF_2$ (meta) |
| S | Pyrazinyl | NH—SO₂ | Pyrimidinyl | $Z_1$: $CHF_2$ (ortho) |
| S | Pyrazinyl | NH—SO₂ | Pyrimidinyl | $Z_1$: $CF_3$ (para) |
| S | Pyrazinyl | NH—SO₂ | Pyrimidinyl | $Z_1$: $CF_3$ (meta) |
| S | Pyrazinyl | NH—SO₂ | Pyrimidinyl | $Z_1$: $CF_3$ (ortho) |
| S | Pyrazinyl | NH—SO₂ | Pyrimidinyl | $Z_1$: $CH_2$—$CH_2F$ (para) |
| S | Pyrazinyl | NH—SO₂ | Pyrimidinyl | $Z_1$: $CH_2$—$CH_2F$ (meta) |
| S | Pyrazinyl | NH—SO₂ | Pyrimidinyl | $Z_1$: $CH_2$—$CH_2F$ (ortho) |
| S | Pyrazinyl | NH—SO₂ | Pyrimidinyl | $Z_1$: $CH_2$—$CHF_2$ (para) |
| S | Pyrazinyl | NH—SO₂ | Pyrimidinyl | $Z_1$: $CH_2$—$CHF_2$ (meta) |
| S | Pyrazinyl | NH—SO₂ | Pyrimidinyl | $Z_1$: $CH_2$—$CHF_2$ (ortho) |
| S | Pyrazinyl | NH—SO₂ | Pyrimidinyl | $Z_1$: $CH_2$—$CF_3$ (para) |
| S | Pyrazinyl | NH—SO₂ | Pyrimidinyl | $Z_1$: $CH_2$—$CF_3$ (meta) |
| S | Pyrazinyl | NH—SO₂ | Pyrimidinyl | $Z_1$: $CH_2$—$CF_3$ (ortho) |
| S | Pyrazinyl | NH—SO₂ | Pyrazinyl | None |
| S | Pyrazinyl | NH—SO₂ | Pyrazinyl | $Z_1$: F (para) |
| S | Pyrazinyl | NH—SO₂ | Pyrazinyl | $Z_1$: F (meta) |
| S | Pyrazinyl | NH—SO₂ | Pyrazinyl | $Z_1$: F (ortho) |
| S | Pyrazinyl | NH—SO₂ | Pyrazinyl | $Z_1$: F (para)<br>$Z_2$: F (meta) |
| S | Pyrazinyl | NH—SO₂ | Pyrazinyl | $Z_1$: Cl (meta) |
| S | Pyrazinyl | NH—SO₂ | Pyrazinyl | $Z_1$: Cl (para) |
| S | Pyrazinyl | NH—SO₂ | Pyrazinyl | $Z_1$: Cl (para)<br>$Z_2$: Cl (meta) |
| S | Pyrazinyl | NH—SO₂ | Pyrazinyl | $Z_1$: F (para)<br>$Z_2$: Cl (meta) |
| S | Pyrazinyl | NH—SO₂ | Pyrazinyl | $Z_1$: Cl (para)<br>$Z_2$: F (meta) |
| S | Pyrazinyl | NH—SO₂ | Pyrazinyl | $Z_1$: $CH_3$ (para) |
| S | Pyrazinyl | NH—SO₂ | Pyrazinyl | $Z_1$: $CH_3$ (meta) |
| S | Pyrazinyl | NH—SO₂ | Pyrazinyl | $Z_1$: $CH_3$ (ortho) |
| S | Pyrazinyl | NH—SO₂ | Pyrazinyl | $Z_1$: $CH_2$—$CH_3$ (para) |
| S | Pyrazinyl | NH—SO₂ | Pyrazinyl | $Z_1$: $CH_2$—$CH_3$ (meta) |
| S | Pyrazinyl | NH—SO₂ | Pyrazinyl | $Z_1$: $CH_2$—$CH_3$ (ortho) |
| S | Pyrazinyl | NH—SO₂ | Pyrazinyl | $Z_1$: $CH_2$—$CH_2$—$CH_3$ or iPr (para) |
| S | Pyrazinyl | NH—SO₂ | Pyrazinyl | $Z_1$: $CH_2$—$CH_2$—$CH_3$ or iPr (meta) |
| S | Pyrazinyl | NH—SO₂ | Pyrazinyl | $Z_1$: $CH_2$—$CH_2$—$CH_3$ or iPr (ortho) |
| S | Pyrazinyl | NH—SO₂ | Pyrazinyl | $Z_1$: $CH_2F$ (para) |
| S | Pyrazinyl | NH—SO₂ | Pyrazinyl | $Z_1$: $CH_2F$ (meta) |
| S | Pyrazinyl | NH—SO₂ | Pyrazinyl | $Z_1$: $CH_2F$ (ortho) |
| S | Pyrazinyl | NH—SO₂ | Pyrazinyl | $Z_1$: $CHF_2$ (para) |
| S | Pyrazinyl | NH—SO₂ | Pyrazinyl | $Z_1$: $CHF_2$ (meta) |
| S | Pyrazinyl | NH—SO₂ | Pyrazinyl | $Z_1$: $CHF_2$ (ortho) |
| S | Pyrazinyl | NH—SO₂ | Pyrazinyl | $Z_1$: $CF_3$ (para) |
| S | Pyrazinyl | NH—SO₂ | Pyrazinyl | $Z_1$: $CF_3$ (meta) |
| S | Pyrazinyl | NH—SO₂ | Pyrazinyl | $Z_1$: $CF_3$ (ortho) |

TABLE 2-continued

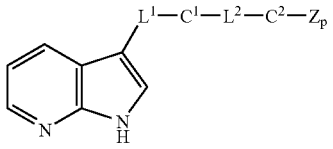

| L¹ | C¹ | L² | C² | Z |
|---|---|---|---|---|
| S | Pyrazinyl | NH—SO₂ | Pyrazinyl | $Z_1$: $CH_2$—$CH_2F$ (para) |
| S | Pyrazinyl | NH—SO₂ | Pyrazinyl | $Z_1$: $CH_2$—$CH_2F$ (meta) |
| S | Pyrazinyl | NH—SO₂ | Pyrazinyl | $Z_1$: $CH_2$—$CH_2F$ (ortho) |
| S | Pyrazinyl | NH—SO₂ | Pyrazinyl | $Z_1$: $CH_2$—$CHF_2$ (para) |
| S | Pyrazinyl | NH—SO₂ | Pyrazinyl | $Z_1$: $CH_2$—$CHF_2$ (meta) |
| S | Pyrazinyl | NH—SO₂ | Pyrazinyl | $Z_1$: $CH_2$—$CHF_2$ (ortho) |
| S | Pyrazinyl | NH—SO₂ | Pyrazinyl | $Z_1$: $CH_2$—$CF_3$ (para) |
| S | Pyrazinyl | NH—SO₂ | Pyrazinyl | $Z_1$: $CH_2$—$CF_3$ (meta) |
| S | Pyrazinyl | NH—SO₂ | Pyrazinyl | $Z_1$: $CH_2$—$CF_3$ (ortho) |
| S | Pyrazinyl | NH—SO₂ | Pyrrolyl | None |
| S | Pyrazinyl | NH—SO₂ | Pyrrolyl | $Z_1$: F (2) |
| S | Pyrazinyl | NH—SO₂ | Pyrrolyl | $Z_1$: F (3) |
| S | Pyrazinyl | NH—SO₂ | Pyrrolyl | $Z_1$: F (2) $Z_2$: F (3) |
| S | Pyrazinyl | NH—SO₂ | Pyrrolyl | $Z_1$: Cl (2) |
| S | Pyrazinyl | NH—SO₂ | Pyrrolyl | $Z_1$: Cl (3) |
| S | Pyrazinyl | NH—SO₂ | Pyrrolyl | $Z_1$: Cl (2) $Z_2$: Cl (3) |
| S | Pyrazinyl | NH—SO₂ | Pyrrolyl | $Z_1$: F (2) $Z_2$: Cl (3) |
| S | Pyrazinyl | NH—SO₂ | Pyrrolyl | $Z_1$: Cl (2) $Z_2$: F (3) |
| S | Pyrazinyl | NH—SO₂ | Pyrrolyl | $Z_1$: $CH_3$ (2) |
| S | Pyrazinyl | NH—SO₂ | Pyrrolyl | $Z_1$: $CH_3$ (3) |
| S | Pyrazinyl | NH—SO₂ | Pyrrolyl | $Z_1$: $CH_2$—$CH_3$ (2) |
| S | Pyrazinyl | NH—SO₂ | Pyrrolyl | $Z_1$: $CH_2$—$CH_3$ (3) |
| S | Pyrazinyl | NH—SO₂ | Pyrrolyl | $Z_1$: $CH_2$—$CH_2$—$CH_3$ or iPr (2) |
| S | Pyrazinyl | NH—SO₂ | Pyrrolyl | $Z_1$: $CH_2$—$CH_2$—$CH_3$ or iPr (3) |
| S | Pyrazinyl | NH—SO₂ | Pyrrolyl | $Z_1$: $CH_2F$ (2) |
| S | Pyrazinyl | NH—SO₂ | Pyrrolyl | $Z_1$: $CH_2F$ (3) |
| S | Pyrazinyl | NH—SO₂ | Pyrrolyl | $Z_1$: $CHF_2$ (2) |
| S | Pyrazinyl | NH—SO₂ | Pyrrolyl | $Z_1$: $CHF_2$ (3) |
| S | Pyrazinyl | NH—SO₂ | Pyrrolyl | $Z_1$: $CF_3$ (2) |
| S | Pyrazinyl | NH—SO₂ | Pyrrolyl | $Z_1$: $CF_3$ (3) |
| S | Pyrazinyl | NH—SO₂ | Pyrrolyl | $Z_1$: $CH_2$—$CH_2F$ (2) |
| S | Pyrazinyl | NH—SO₂ | Pyrrolyl | $Z_1$: $CH_2$—$CH_2F$ (3) |
| S | Pyrazinyl | NH—SO₂ | Pyrrolyl | $Z_1$: $CH_2$—$CHF_2$ (2) |
| S | Pyrazinyl | NH—SO₂ | Pyrrolyl | $Z_1$: $CH_2$—$CHF_2$ (3) |
| S | Pyrazinyl | NH—SO₂ | Pyrrolyl | $Z_1$: $CH_2$—$CF_3$ (2) |
| S | Pyrazinyl | NH—SO₂ | Pyrrolyl | $Z_1$: $CH_2$—$CF_3$ (3) |
| S | Pyrazinyl | NH—SO₂ | Imidazolyl | None |
| S | Pyrazinyl | NH—SO₂ | Imidazolyl | $Z_1$: F (2) |
| S | Pyrazinyl | NH—SO₂ | Imidazolyl | $Z_1$: F (3) |
| S | Pyrazinyl | NH—SO₂ | Imidazolyl | $Z_1$: F (2) $Z_2$: F (3) |
| S | Pyrazinyl | NH—SO₂ | Imidazolyl | $Z_1$: Cl (2) |
| S | Pyrazinyl | NH—SO₂ | Imidazolyl | $Z_1$: Cl (3) |
| S | Pyrazinyl | NH—SO₂ | Imidazolyl | $Z_1$: Cl (2) $Z_2$: Cl (3) |
| S | Pyrazinyl | NH—SO₂ | Imidazolyl | $Z_1$: F (2) $Z_2$: Cl (3) |
| S | Pyrazinyl | NH—SO₂ | Imidazolyl | $Z_1$: Cl (2) $Z_2$: F (3) |
| S | Pyrazinyl | NH—SO₂ | Imidazolyl | $Z_1$: $CH_3$ (2) |
| S | Pyrazinyl | NH—SO₂ | Imidazolyl | $Z_1$: $CH_3$ (3) |
| S | Pyrazinyl | NH—SO₂ | Imidazolyl | $Z_1$: $CH_2$—$CH_3$ (2) |
| S | Pyrazinyl | NH—SO₂ | Imidazolyl | $Z_1$: $CH_2$—$CH_3$ (3) |
| S | Pyrazinyl | NH—SO₂ | Imidazolyl | $Z_1$: $CH_2$—$CH_2$—$CH_3$ or iPr (2) |
| S | Pyrazinyl | NH—SO₂ | Imidazolyl | $Z_1$: $CH_2$—$CH_2$—$CH_3$ or iPr (3) |
| S | Pyrazinyl | NH—SO₂ | Imidazolyl | $Z_1$: $CH_2F$ (2) |
| S | Pyrazinyl | NH—SO₂ | Imidazolyl | $Z_1$: $CH_2F$ (3) |
| S | Pyrazinyl | NH—SO₂ | Imidazolyl | $Z_1$: $CHF_2$ (2) |
| S | Pyrazinyl | NH—SO₂ | Imidazolyl | $Z_1$: $CHF_2$ (3) |
| S | Pyrazinyl | NH—SO₂ | Imidazolyl | $Z_1$: $CF_3$ (2) |
| S | Pyrazinyl | NH—SO₂ | Imidazolyl | $Z_1$: $CF_3$ (3) |
| S | Pyrazinyl | NH—SO₂ | Imidazolyl | $Z_1$: $CH_2$—$CH_2F$ (2) |
| S | Pyrazinyl | NH—SO₂ | Imidazolyl | $Z_1$: $CH_2$—$CH_2F$ (3) |
| S | Pyrazinyl | NH—SO₂ | Imidazolyl | $Z_1$: $CH_2$—$CHF_2$ (2) |
| S | Pyrazinyl | NH—SO₂ | Imidazolyl | $Z_1$: $CH_2$—$CHF_2$ (3) |

TABLE 2-continued $$L^1-C^1-L^2-C^2-Z_p$$

(7-azaindole structure)

| L¹ | C¹ | L² | C² | Z |
|---|---|---|---|---|
| S | Pyrazinyl | NH—SO₂ | Imidazolyl | $Z_1$: CH₂—CF₃ (2) |
| S | Pyrazinyl | NH—SO₂ | Imidazolyl | $Z_1$: CH₂—CF₃ (3) |
| S | Pyrazinyl | NH—SO₂ | Furanyl | None |
| S | Pyrazinyl | NH—SO₂ | Furanyl | $Z_1$: F (2) |
| S | Pyrazinyl | NH—SO₂ | Furanyl | $Z_1$: F (3) |
| S | Pyrazinyl | NH—SO₂ | Furanyl | $Z_1$: F (2)<br>$Z_2$: F (3) |
| S | Pyrazinyl | NH—SO₂ | Furanyl | $Z_1$: Cl (2) |
| S | Pyrazinyl | NH—SO₂ | Furanyl | $Z_1$: Cl (3) |
| S | Pyrazinyl | NH—SO₂ | Furanyl | $Z_1$: Cl (2)<br>$Z_2$: Cl (3) |
| S | Pyrazinyl | NH—SO₂ | Furanyl | $Z_1$: F (2)<br>$Z_2$: Cl (3) |
| S | Pyrazinyl | NH—SO₂ | Furanyl | $Z_1$: Cl (2)<br>$Z_2$: F (3) |
| S | Pyrazinyl | NH—SO₂ | Furanyl | $Z_1$: CH₃ (2) |
| S | Pyrazinyl | NH—SO₂ | Furanyl | $Z_1$: CH₃ (3) |
| S | Pyrazinyl | NH—SO₂ | Furanyl | $Z_1$: CH₂—CH₃ (2) |
| S | Pyrazinyl | NH—SO₂ | Furanyl | $Z_1$: CH₂—CH₃ (3) |
| S | Pyrazinyl | NH—SO₂ | Furanyl | $Z_1$: CH₂—CH₂—CH₃ or iPr (2) |
| S | Pyrazinyl | NH—SO₂ | Furanyl | $Z_1$: CH₂—CH₂—CH₃ or iPr (3) |
| S | Pyrazinyl | NH—SO₂ | Furanyl | $Z_1$: CH₂F (2) |
| S | Pyrazinyl | NH—SO₂ | Furanyl | $Z_1$: CH₂F (3) |
| S | Pyrazinyl | NH—SO₂ | Furanyl | $Z_1$: CHF₂ (2) |
| S | Pyrazinyl | NH—SO₂ | Furanyl | $Z_1$: CHF₂ (3) |
| S | Pyrazinyl | NH—SO₂ | Furanyl | $Z_1$: CF₃ (2) |
| S | Pyrazinyl | NH—SO₂ | Furanyl | $Z_1$: CF₃ (3) |
| S | Pyrazinyl | NH—SO₂ | Furanyl | $Z_1$: CH₂—CH₂F (2) |
| S | Pyrazinyl | NH—SO₂ | Furanyl | $Z_1$: CH₂—CH₂F (3) |
| S | Pyrazinyl | NH—SO₂ | Furanyl | $Z_1$: CH₂—CHF₂ (2) |
| S | Pyrazinyl | NH—SO₂ | Furanyl | $Z_1$: CH₂—CHF₂ (3) |
| S | Pyrazinyl | NH—SO₂ | Furanyl | $Z_1$: CH₂—CF₃ (2) |
| S | Pyrazinyl | NH—SO₂ | Furanyl | $Z_1$: CH₂—CF₃ (3) |
| S | Pyrazinyl | NH—SO₂ | Oxazolyl | None |
| S | Pyrazinyl | NH—SO₂ | Oxazolyl | $Z_1$: F (2) |
| S | Pyrazinyl | NH—SO₂ | Oxazolyl | $Z_1$: F (3) |
| S | Pyrazinyl | NH—SO₂ | Oxazolyl | $Z_1$: F (2)<br>$Z_2$: F (3) |
| S | Pyrazinyl | NH—SO₂ | Oxazolyl | $Z_1$: Cl (2) |
| S | Pyrazinyl | NH—SO₂ | Oxazolyl | $Z_1$: Cl (3) |
| S | Pyrazinyl | NH—SO₂ | Oxazolyl | $Z_1$: Cl (2)<br>$Z_2$: Cl (3) |
| S | Pyrazinyl | NH—SO₂ | Oxazolyl | $Z_1$: F (2)<br>$Z_2$: Cl (3) |
| S | Pyrazinyl | NH—SO₂ | Oxazolyl | $Z_1$: Cl (2)<br>$Z_2$: F (3) |
| S | Pyrazinyl | NH—SO₂ | Oxazolyl | $Z_1$: CH₃ (2) |
| S | Pyrazinyl | NH—SO₂ | Oxazolyl | $Z_1$: CH₃ (3) |
| S | Pyrazinyl | NH—SO₂ | Oxazolyl | $Z_1$: CH₂—CH₃ (2) |
| S | Pyrazinyl | NH—SO₂ | Oxazolyl | $Z_1$: CH₂—CH₃ (3) |
| S | Pyrazinyl | NH—SO₂ | Oxazolyl | $Z_1$: CH₂—CH₂—CH₃ or iPr (2) |
| S | Pyrazinyl | NH—SO₂ | Oxazolyl | $Z_1$: CH₂—CH₂—CH₃ or iPr (3) |
| S | Pyrazinyl | NH—SO₂ | Oxazolyl | $Z_1$: CH₂F (2) |
| S | Pyrazinyl | NH—SO₂ | Oxazolyl | $Z_1$: CH₂F (3) |
| S | Pyrazinyl | NH—SO₂ | Oxazolyl | $Z_1$: CHF₂ (2) |
| S | Pyrazinyl | NH—SO₂ | Oxazolyl | $Z_1$: CHF₂ (3) |
| S | Pyrazinyl | NH—SO₂ | Oxazolyl | $Z_1$: CF₃ (2) |
| S | Pyrazinyl | NH—SO₂ | Oxazolyl | $Z_1$: CF₃ (3) |
| S | Pyrazinyl | NH—SO₂ | Oxazolyl | $Z_1$: CH₂—CH₂F (2) |
| S | Pyrazinyl | NH—SO₂ | Oxazolyl | $Z_1$: CH₂—CH₂F (3) |
| S | Pyrazinyl | NH—SO₂ | Oxazolyl | $Z_1$: CH₂—CHF₂ (2) |
| S | Pyrazinyl | NH—SO₂ | Oxazolyl | $Z_1$: CH₂—CHF₂ (3) |
| S | Pyrazinyl | NH—SO₂ | Oxazolyl | $Z_1$: CH₂—CF₃ (2) |
| S | Pyrazinyl | NH—SO₂ | Oxazolyl | $Z_1$: CH₂—CF₃ (3) |
| S | Pyrazinyl | NH—SO₂ | Thiophenyl | None |
| S | Pyrazinyl | NH—SO₂ | Thiophenyl | $Z_1$: F (2) |
| S | Pyrazinyl | NH—SO₂ | Thiophenyl | $Z_1$: F (3) |
| S | Pyrazinyl | NH—SO₂ | Thiophenyl | $Z_1$: F (2)<br>$Z_2$: F (3) |

TABLE 2-continued

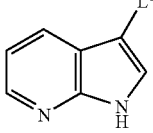

| $L^1$ | $C^1$ | $L^2$ | $C^2$ | Z |
|---|---|---|---|---|
| S | Pyrazinyl | NH—SO$_2$ | Thiophenyl | $Z_1$: Cl (2) |
| S | Pyrazinyl | NH—SO$_2$ | Thiophenyl | $Z_1$: Cl (3) |
| S | Pyrazinyl | NH—SO$_2$ | Thiophenyl | $Z_1$: Cl (2) |
| | | | | $Z_2$: Cl (3) |
| S | Pyrazinyl | NH—SO$_2$ | Thiophenyl | $Z_1$: F (2) |
| | | | | $Z_2$: Cl (3) |
| S | Pyrazinyl | NH—SO$_2$ | Thiophenyl | $Z_1$: Cl (2) |
| | | | | $Z_2$: F (3) |
| S | Pyrazinyl | NH—SO$_2$ | Thiophenyl | $Z_1$: CH$_3$ (2) |
| S | Pyrazinyl | NH—SO$_2$ | Thiophenyl | $Z_1$: CH$_3$ (3) |
| S | Pyrazinyl | NH—SO$_2$ | Thiophenyl | $Z_1$: CH$_2$—CH$_3$ (2) |
| S | Pyrazinyl | NH—SO$_2$ | Thiophenyl | $Z_1$: CH$_2$—CH$_3$ (3) |
| S | Pyrazinyl | NH—SO$_2$ | Thiophenyl | $Z_1$: CH$_2$—CH$_2$—CH$_3$ or iPr (2) |
| S | Pyrazinyl | NH—SO$_2$ | Thiophenyl | $Z_1$: CH$_2$—CH$_2$—CH$_3$ or iPr (3) |
| S | Pyrazinyl | NH—SO$_2$ | Thiophenyl | $Z_1$: CH$_2$F (2) |
| S | Pyrazinyl | NH—SO$_2$ | Thiophenyl | $Z_1$: CH$_2$F (3) |
| S | Pyrazinyl | NH—SO$_2$ | Thiophenyl | $Z_1$: CHF$_2$ (2) |
| S | Pyrazinyl | NH—SO$_2$ | Thiophenyl | $Z_1$: CHF$_2$ (3) |
| S | Pyrazinyl | NH—SO$_2$ | Thiophenyl | $Z_1$: CF$_3$ (2) |
| S | Pyrazinyl | NH—SO$_2$ | Thiophenyl | $Z_1$: CF$_3$ (3) |
| S | Pyrazinyl | NH—SO$_2$ | Thiophenyl | $Z_1$: CH$_2$—CH$_2$F (2) |
| S | Pyrazinyl | NH—SO$_2$ | Thiophenyl | $Z_1$: CH$_2$—CH$_2$F (3) |
| S | Pyrazinyl | NH—SO$_2$ | Thiophenyl | $Z_1$: CH$_2$—CHF$_2$ (2) |
| S | Pyrazinyl | NH—SO$_2$ | Thiophenyl | $Z_1$: CH$_2$—CHF$_2$ (3) |
| S | Pyrazinyl | NH—SO$_2$ | Thiophenyl | $Z_1$: CH$_2$—CF$_3$ (2) |
| S | Pyrazinyl | NH—SO$_2$ | Thiophenyl | $Z_1$: CH$_2$—CF$_3$ (3) |
| S | Pyrazinyl | NH—SO$_2$ | Thiazolyl | None |
| S | Pyrazinyl | NH—SO$_2$ | Thiazolyl | $Z_1$: F (2) |
| S | Pyrazinyl | NH—SO$_2$ | Thiazolyl | $Z_1$: F (3) |
| S | Pyrazinyl | NH—SO$_2$ | Thiazolyl | $Z_1$: F (2) |
| | | | | $Z_2$: F (3) |
| S | Pyrazinyl | NH—SO$_2$ | Thiazolyl | $Z_1$: Cl (2) |
| S | Pyrazinyl | NH—SO$_2$ | Thiazolyl | $Z_1$: Cl (3) |
| S | Pyrazinyl | NH—SO$_2$ | Thiazolyl | $Z_1$: Cl (2) |
| | | | | $Z_2$: Cl (3) |
| S | Pyrazinyl | NH—SO$_2$ | Thiazolyl | $Z_1$: F (2) |
| | | | | $Z_2$: Cl (3) |
| S | Pyrazinyl | NH—SO$_2$ | Thiazolyl | $Z_1$: Cl (2) |
| | | | | $Z_2$: F (3) |
| S | Pyrazinyl | NH—SO$_2$ | Thiazolyl | $Z_1$: CH$_3$ (2) |
| S | Pyrazinyl | NH—SO$_2$ | Thiazolyl | $Z_1$: CH$_3$ (3) |
| S | Pyrazinyl | NH—SO$_2$ | Thiazolyl | $Z_1$: CH$_2$—CH$_3$ (2) |
| S | Pyrazinyl | NH—SO$_2$ | Thiazolyl | $Z_1$: CH$_2$—CH$_3$ (3) |
| S | Pyrazinyl | NH—SO$_2$ | Thiazolyl | $Z_1$: CH$_2$—CH$_2$—CH$_3$ or iPr (2) |
| S | Pyrazinyl | NH—SO$_2$ | Thiazolyl | $Z_1$: CH$_2$—CH$_2$—CH$_3$ or iPr (3) |
| S | Pyrazinyl | NH—SO$_2$ | Thiazolyl | $Z_1$: CH$_2$F (2) |
| S | Pyrazinyl | NH—SO$_2$ | Thiazolyl | $Z_1$: CH$_2$F (3) |
| S | Pyrazinyl | NH—SO$_2$ | Thiazolyl | $Z_1$: CHF$_2$ (2) |
| S | Pyrazinyl | NH—SO$_2$ | Thiazolyl | $Z_1$: CHF$_2$ (3) |
| S | Pyrazinyl | NH—SO$_2$ | Thiazolyl | $Z_1$: CF$_3$ (2) |
| S | Pyrazinyl | NH—SO$_2$ | Thiazolyl | $Z_1$: CF$_3$ (3) |
| S | Pyrazinyl | NH—SO$_2$ | Thiazolyl | $Z_1$: CH$_2$—CH$_2$F (2) |
| S | Pyrazinyl | NH—SO$_2$ | Thiazolyl | $Z_1$: CH$_2$—CH$_2$F (3) |
| S | Pyrazinyl | NH—SO$_2$ | Thiazolyl | $Z_1$: CH$_2$—CHF$_2$ (2) |
| S | Pyrazinyl | NH—SO$_2$ | Thiazolyl | $Z_1$: CH$_2$—CHF$_2$ (3) |
| S | Pyrazinyl | NH—SO$_2$ | Thiazolyl | $Z_1$: CH$_2$—CF$_3$ (2) |
| S | Pyrazinyl | NH—SO$_2$ | Thiazolyl | $Z_1$: CH$_2$—CF$_3$ (3) |

In Table 2, where $C^2$ is a 5-membered ring, the number in parentheses following the specification of the Z substituent indicates the substituent ring position, wherein the atom attached to $L^2$ is numbered 1, and atoms are numbered consecutively around the ring, but excluding substitutions at those positions where linkage of the substituent to a heteroatom is not chemically reasonable.

In Table 2, where $C^2$ is a 6-membered ring, substituent position is indicated relative to the attachment to $L^2$ using para, meta, and ortho terms in similar manner as for phenyl groups, but excluding substitutions at those positions where linkage of the substitutent to a heteroatom is not chemically reasonable.

Additional embodiments are also described with reference to the compounds in Table 2. Each combination of $L^1$, $C^1$, $L^2$, and $C^2$ indicated in Table 2 also specifies a narrow generic description of a group of compounds that can include different substituents on $C^2$ and/or substitutents on one or more of the moieties, $L^1$, $C^1$, and $L^2$. Preferably such substituents each include no more than 7 non-hydrogen atoms.

Likewise, additional embodiments of narrow generic compound descriptions are provided in which for each combination of $L^1$, $C^1$, $L^2$, and $C^2$ the bi-cyclic core is also substituted at the 4-position, the 5-position, or both the 4- and 5-positions with substituents as specified for Formula I. In further embodiments, substitution at the 4- and/or 5-position is combined with substituents as described in the preceding paragraph.

Exemplary Diseases Associated with c-Kit.

The compounds described herein are useful for treating disorders related to c-Kit e.g., diseases related to improperly regulated kinase signal transduction, including cell proliferative disorders, fibrotic disorders and metabolic disorders, among others. As described in more detail below and in Lipson et al., U.S. 20040002534 (U.S. application Ser. No. 10/600,868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers, as described below. In addition, the association between abnormalities in c-kit and disease are not restricted to cancer. For example, as is also described in more detail below, c-kit has been associated with inflammatory diseases such as mastocytosis, asthmas, multiple sclerosis, inflammatory bowel syndrome and allergic rhinitis.

Exemplary Malignant Diseases Associated with c-Kit

Aberrant expression and/or activation of c-Kit has been implicated in a variety of cancers. Evidence for a contribution of c-Kit to neoplastic pathology includes its association with leukemias and mast cell tumors, small cell lung cancer, testicular cancer, and some cancers of the gastrointestinal tract and central nervous system. In addition, c-Kit has been implicated in playing a role in carcinogenesis of the female genital tract (Inoue, et al., 1994, *Cancer Res.* 54:3049-3053), sarcomas of neuroectodermal origin (Ricotti, et al., 1998, *Blood* 91:2397-2405), and Schwann cell neoplasia associated with neurofibromatosis (Ryan, et al., 1994, *J Neuro. Res.* 37:415-432). It was found that mast cells are involved in modifying the tumor microenvironment and enhancing tumor growth (Yang et al., 2003, *J Clin Invest.* 112:1851-1861; Viskochil, 2003, *J Clin Invest.* 112:1791-1793). Thus, c-Kit is a useful target in treating neurofibromatosis as well as malignant tumors.

Small cell lung carcinoma: c-Kit kinase receptor has been found to be aberrantly expressed in many cases of small cell lung carcinoma (SCLC) cells (Hibi, et al., 1991, *Oncogene* 6:2291-2296). Thus, as an example, inhibition of c-Kit kinase can be beneficial in treatment of SCLC, e.g., to improve the long term survival of patients with SCLC.

Leukemias: SCF binding to the c-Kit protects hematopoietic stem and progenitor cells from apoptosis (Lee, et al., 1997, *J. Immunol.* 159:3211-3219), thereby contributing to colony formation and hematopoiesis. Expression of c-Kit is frequently observed in acute myelocytic leukemia (AML), and in some cases of acute lymphocytic leukemia (ALL) (for reviews, see Sperling, et al., 1997, *Haemat* 82:617-621; Escribano, et al., 1998, *Leuk. Lymph.* 30:459-466). Although c-Kit is expressed in the majority of AML cells, its expression does not appear to be prognostic of disease progression (Sperling, et al, 1997, *Haemat* 82:617-621). However, SCF protected AML cells from apoptosis induced by chemotherapeutic agents (Hassan, et al., 1996, *Acta. Hem.* 95:257-262). Inhibition of c-Kit by the present invention will enhance the efficacy of these agents and can induce apoptosis of AML cells.

The clonal growth of cells from patients with myelodysplastic syndrome (Sawada, et al., *Blood* 1996, 88:319-327) or chronic myelogenous leukemia (CML) (Sawai, et al., *Exp. Hem.* 1996, 2:116-122) was found to be significantly enhanced by SCF in combination with other cytokines. CML is characterized by expansion of Philadelphia chromosome positive cells of the marrow (Verfaillie, et al., *Leuk.* 1998, 12:136-138), which appears to primarily result from inhibition of apoptotic death (Jones, *Curr. Opin. Onc.* 1997, 9:3-7). The product of the Philadelphia chromosome, $p210^{BCR-ABL}$, has been reported to mediate inhibition of apoptosis (Bedi, et al., *Blood* 1995, 86:1148-1158). Since $p210^{BCR-ABL}$ and the c-Kit RTK both inhibit apoptosis and $p62^{dok}$ has been suggested as a substrate (Carpino, et al., Cell 1997, 88:197-204), clonal expansion mediated by these kinases may occur through a common signaling pathway. However, c-Kit has also been reported to interact directly with $p210^{BCR-ABL}$ (Hallek, et al., *Brit. J. Haem.* 1996, 94:5-16), which suggests that c-Kit has a more causative role in CML pathology. Therefore, inhibition of c-Kit kinase will be useful in the treatment of the above disorders.

Gastrointestinal cancers: Normal colorectal mucosa does not express c-Kit (Bellone, et al., 1997, *J. Cell Physiol.* 172: 1-11). However, c-Kit is frequently expressed in colorectal carcinoma (Bellone, et al., 1997, *J. Cell Physiol.* 172: 1-11), and autocrine loops of SCF and c-Kit have been observed in several colon carcinoma cell lines (Toyota, et al., 1993, *Tum Biol* 14:295-302; Lahm, et al., 1995, *Cell Growth & Differ* 6:1111-1118; Bellone, et al., 1997, *J. Cell Physiol.* 172: 1-11). Furthermore, disruption of the autocrine loop by the use of neutralizing antibodies (Lahm, et al., 1995, *Cell Growth & Differ.* 6:1111-1118) and downregulation of c-Kit and/or SCF significantly inhibits cell proliferation (Lahm, et al., 1995, *Cell Growth & Differ* 6:1111-1118; Bellone, et al., 1997, *J. Cell Physiol.* 172: 1-11).

SCF/c-Kit autocrine loops have been observed in gastric carcinoma cell lines (Turner, et al., 1992, *Blood* 80:374-381; Hassan, et al., 1998, *Digest. Dis. Science* 43:8-14), and constitutive c-Kit activation also appears to be important for gastrointestinal stromal tumors (GISTs). GISTs are the most common mesenchymal tumor of the digestive system. More than 90% of GISTs express c-Kit, which is consistent with the putative origin of these tumor cells from interstitial cells of Cajal (ICCs) (Hirota, et al., 1998, *Science* 279:577-580). ICCs are thought to regulate contraction of the gastrointestinal tract, and patients lacking c-Kit in their ICCs exhibited a myopathic form of chronic idiopathic intestinal pseudo-obstruction (Isozaki, et al., 1997, *Amer. J of Gast.* 9:332-334). The c-Kit expressed in GISTs from several different patients was observed to have mutations in the intracellular juxtamembrane domain leading to constitutive activation of this RTK (Hirota, et al., 1998, *Science* 279:577-580). Hence, inhibition of c-Kit kinase will be an efficacious means for the treatment of these cancers.

Testicular cancers: Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, *Sem. Oncol.* 25:133-144). Both c-Kit and SCF have been reported to be essential for normal gonadal development during embryogenesis (Loveland, et al., 1997, *J. Endocrinol* 153:337-344). Loss of either the receptor or the ligand resulted in animals devoid of germ cells. In postnatal testes, c-Kit has been found to be expressed in Leydig cells and spermatogonia, while SCF was expressed in Sertoli cells (Loveland, et al., 1997, *J. Endocrinol* 153:337-344). Testicular tumors develop from Leydig cells with high frequency in transgenic mice expressing human papilloma virus 16 (HPV16) E6 and E7 oncogenes (Kondoh, et al., 1991, *J. Virol.* 65:3335-3339; Kondoh, et al., 1994, *J. Urol.* 152:2151-2154). These tumors express both c-Kit and SCF, and an autocrine loop may contribute to the tumorigenesis (Kondoh, et al., 1995, *Oncogene* 10:341-347) associated with cellular loss of functional p53 and the retinoblastoma gene product by association with E6 and E7 (Dyson, et al., 1989, *Science* 243:934-937; Werness, et al., 1990, *Science* 248:76-79; Scheffner, et al., 1990, *Cell* 63:1129-1136). Defective signaling mutants of SCF (Kondoh, et al., 1995, Oncogene 10:341-347) or c-Kit (Li, et al., 1996, Canc. Res. 56:4343-4346) inhibited formation of testicular tumors in mice expressing HPV16 E6 and E7. The c-Kit kinase activation is pivotal to tumorigenesis in these animals and thus modulation of the c-Kit kinase pathway by the present invention will prevent or treat such disorders.

Expression of c-Kit in germ cell tumors shows that the receptor is expressed by the majority of carcinomas in situ and seminomas, but c-Kit is expressed in only a minority of nonseminomas (Strohmeyer, et al., 1991, *Canc. Res.* 51:1811-1816; Rajpert-de Meyts, et al., 1994, *Int. J. Androl.* 17:85-92; Izquierdo, et al., 1995, *J. Pathol.* 177:253-258; Strohmeyer, et al., 1995, *J. Urol.* 153:511-515; Bokenmeyer, et al., 1996, *J. Cancer Res. Clin. Oncol.* 122:301-306; Sandlow, et al., 1996, *J. Androl.* 17:403-408). Therefore, inhibition of c-Kit kinase provides a means for treating these disorders.

CNS cancers: SCF and c-Kit are expressed throughout the CNS of developing rodents, and the pattern of expression indicates a role in growth, migration and differentiation of neuroectodermal cells. Expression of both receptor and ligand have also been reported in the adult brain (Hamel, et al., 1997, *J Neuro-Onc.* 35:327-333). Expression of c-Kit has also been observed in normal human brain tissue (Tada, et al. 1994, *J. Neuro* 80:1063-1073). Glioblastoma and astrocytoma, which define the majority of intracranial tumors, arise from neoplastic transformation of astrocytes (Levin, et al., 1997, *Principles & Practice of Oncology:* 2022-2082). Expression of c-Kit has been observed in glioblastoma cell lines and tissues (Berdel, et al., 1992, *Canc. Res.* 52:3498-3502; Tada, et al. 1994, *J. Neuro* 80:1063-1073; Stanulla, et al., 1995, *Act Neuropath* 89:158-165).

Cohen, et al., 1994, Blood 84:3465-3472 reported that all 14 neuroblastoma cell lines examined contained c-Kit/SCF autocrine loops, and expression of both the receptor and ligand were observed in 45% of tumor samples examined. In two cell lines, anti-c-Kit antibodies inhibited cell proliferation, suggesting that the SCF/c-Kit autocrine loop contributed to growth (Cohen, et al., 1994, *Blood* 84:3465-3472). Hence, c-Kit kinase inhibitors can be used to treat these cancers.

Exemplary Mast Cell Diseases Involving c-Kit

Excessive activation of c-Kit is also associated with diseases resulting from an over-abundance of mast cells. Mastocytosis is the term used to describe a heterogeneous group of disorders characterized by excessive mast cell proliferation (Metcalfe, 1991, *J. Invest. Derm* 93:2S-4S; Golkar, et al., 1997, *Lancet* 349:1379-1385). Elevated c-Kit expression was reported on mast cells from patients with aggressive mastocytosis (Nagata, et al., 1998, *Leukemia* 12:175-181).

Additionally, mast cells and eosinophils represent key cells involved in allergy, inflammation and asthma (Thomas, et al., 1996, *Gen. Pharmacol* 27:593-597; Metcalfe, et al., 1997, *Physiol Rev* 77:1033-1079; Naclerio, et al., 1997, *JAMA* 278:1842-1848; Costa, et al., 1997, *JAMA* 278:1815-1822). SCF, and hence c-Kit, directly and indirectly regulates activation of both mast cells and eosinophils, thereby influencing the primary cells involved in allergy and asthma through multiple mechanisms. Because of this mutual regulation of mast cell and eosinophil function, and the role that SCF can play in this regulation, inhibition of c-Kit can be used to treat allergy-associated chronic rhinitis, inflammation and asthma.

Mastocytosis: SCF (also known as mast cell growth factor) stimulation of c-Kit has been reported to be essential for the growth and development of mast cells (Hamel, et al., 1997, *J. Neuro-Onc.* 35:327-333; Kitamura, et al., 1995, *Int. Arch. Aller. Immunol.* 107:54-56). Mice with mutations of c-Kit that attenuate its signaling activity have exhibited significantly fewer mast cells in their skin (Tsujimura, 1996, *Pathol Int* 46:933-938). Excessive activation of c-Kit can be associated with diseases resulting from an over abundance of mast cells.

Mastocytosis is limited to the skin in the majority of patients, but can involve other organs in 15-20% of patients (Valent, 1996, *Wein/Klin Wochenschr* 108:385-397; Golkar, et al., 1997, *Lancet* 349:1379-1385). Even among patients with systemic mastocytosis, the disease can range from having a relatively benign prognosis to aggressive mastocytosis and mast cell leukemia. (Valent, 1996, *Wein/Klin Wochenschr* 108:385-397; Golkar, et al., 1997, *Lancet* 349:1379-1385). c-Kit has been observed on malignant mast cells from canine mast cell tumors (London, et al., 1996, *J. Compar. Pathol.* 115:399-414), as well as on mast cells from patients with aggressive systemic mastocytosis (Castells, et al., 1996, *J. Aller. Clin. Immunol.* 98:831-840).

SCF has been shown to be expressed on stromal cells as a membrane-bound protein, and its expression can be induced by fibrogenic growth factors such as PDGF. It has also been shown to be expressed on keratinocytes as a membrane-bound protein in normal skin. However, in the skin of patients with mastocytosis, an increased amount of soluble SCF has been observed (Longley, et al., 1993, *New Engl. J. Med.* 328:1302-1307).

Mast cell chymase has been reported to cleave membrane-associated SCF to a soluble and biologically active form. This mast cell-mediated process can generate a feedback loop to enhance mast cell proliferation and function (Longley, et al., 1997, *Proc. Natl. Acad. Sci.* 94:9017-9021), and may be important for the etiology of mastocytosis. Transgenic mice overexpressing a form of SCF that could not be proteolytically released from keratinocytes did not develop mastocytosis, while similar animals expressing normal SCF in keratinocytes exhibited a phenotype resembling human cutaneous mastocytosis (Kunisada, et al., 1998, *J. Exp. Med.* 187:1565-1573). Formation of large amounts of soluble SCF can contribute to the pathology associated with mastocytosis in some patients and the present invention can treat or prevent such disorders by modulating the interaction between SCF and c-Kit kinase. Several different mutations of the c-Kit RTK that resulted in constitutive kinase activity have been found in human and rodent mast cell tumor cell lines (Furitsu, et al., 1993, *J. Clin. Invest.* 92:1736-1744; Tsujimura, et al., 1994, *Blood* 9:2619-2626; Tsujimura, et al., 1995, *Int. Arch. Aller. Immunol* 106:377-385; Tsujimura, 1996, *Pathol Int* 46:933-

938). In addition, activating mutations of the c-Kit gene have been observed in peripheral mononuclear cells isolated from patients with mastocytosis and associated hematologic disorders (Nagata, et al., 1998, *Mastocytosis Leuk* 12:175-181), and in mast cells from a patient with urticaria pigmentosa and aggressive mastocytosis (Longley, et al., 1996, *Nat. Gen.* 12:312-314). Inhibition of c-Kit kinase will therefore prove to have an excellent therapeutic role in the treatment of these disorders.

In some patients, activating mutations of the c-Kit RTK may be responsible for the pathogenesis of the disease and these patients can be treated, or their diseases prevented, by modulation of the SCF interaction with c-Kit kinase. SCF activation of c-Kit as been shown to prevent mast cell apoptosis which may be critical for maintaining cutaneous mast cell homeostasis (Iemura, et al., 1994, *Amer. J. Pathol* 144:321-328; Yee, et al., 1994, *J. Exp. Med.* 179:1777-1787; Mekori, et al., 1994, *J. Immunol* 153:2194-2203; Mekori, et al., 1995, *Int. Arch. Allergy Immunol.* 107:137-138). Inhibition of mast cell apoptosis can lead to the mast cell accumulation associated with mastocytosis. Thus, observation of c-Kit activation resulting from overexpression of the receptor, excessive formation of soluble SCF, or mutations of the c-Kit gene that constitutively activate its kinase, provides a rationale that inhibition of the kinase activity of c-Kit will decrease the number of mast cells and provide benefit for patients with mastocytosis.

For cells with activating c-Kit mutations, it was found that inhibitors of c-Kit inhibit or even kill the cells (Ma et al., 2000, *J Invest Dermatol.* 114:392-394), particularly for mutations in the regulatory region (Ma et al., 2002, *Blood* 99:1741-1744). Ma et al., 2002, also showed that for mutations in the catalytic region, inhibitors ST1571 (Gleevec) and SU9529 did not inhibit the cells, such that additional types of c-Kit inhibitors are useful. Thus, c-Kit inhibitors can be used against both wild-type c-Kit as well as c-Kit having mutations, e.g., activating mutations in the regulatory region and/or catalytic region.

Asthma & Allergy: Mast cells and eosinophils represent key cells in parasitic infection, allergy, inflammation, and asthma (Thomas, et al., 1996, *Gen. Pharmacol* 27:593-597; Metcalfe, et al., 1997, *Physiol Rev* 77:1033-1079; Holgate, 1997, *CIBA Found. Symp.*; Naclerio, et al, 1997, *JAMA* 278:1842-1848; Costa, et al., 1997, *JAMA* 778:1815-1822). SCF has been shown to be essential for mast cell development, survival and growth (Kitamura, et al., 1995, *Int. Arch. Aller. Immunol.* 107:54-56; Metcalfe, et al., 1997, *Physiol Rev* 77:1033-1079). In addition, SCF cooperates with the eosinophil-specific regulator, IL-5, to increase the development of eosinophil progenitors (Metcalf, et al., 1998, *Proc. Natl. Acad. Sci., USA* 95:6408-6412). SCF has also been reported to induce mast cells to secrete factors (Okayama, et al., 1997, *Int. Arch. Aller. Immunol.* 114:75-77; Okayama, et al., 1998, *Eur. J. Immunol.* 28:708-715) that promote the survival of eosinophils (Kay, et al., 1997, *Int. Arch. Aller. Immunol.* 113:196-199), which may contribute to chronic, eosinophil-mediated inflammation (Okayama, et al., 1997, *Int. Arch. Aller. Immunol.* 114:75-77; Okayama, et al., 1998, *Eur. J. Immunol.* 28:708-715). In this regard, SCF directly and indirectly regulates activation of both mast cells and eosinophils.

SCF induces mediator release from mast cells, as well as priming these cells for IgE-induced degranulation (Columbo, et al., 1992, *J. Immunol* 149:599-602) and sensitizing their responsiveness to eosinophil-derived granule major basic protein (Furuta, et al., 1998, *Blood* 92:1055-1061). Among the factors released by activated mast cells are IL-5, GM-CSF and TNF-α, which influence eosinophil protein secretion (Okayama, et al., 1997, *Int. Arch. Aller. Immunol.* 114:75-77; Okayama, et al., 1998, *Eur. J. Immunol.* 28:708-715). In addition to inducing histamine release from mast cells (Luckacs, et al., 1996, *J. Immunol.* 156:3945-3951; Hogaboam, et al., 1998, *J. Immunol.* 160:6166-6171), SCF promotes the mast cell production of the eosinophil chemotactic factor, eotaxin (Hogaboam, et al., 1998, *J. Immunol.* 160:6166-6171), and eosinophil infiltration (Luckacs, et al., 1996, *J. Immunol.* 156:3945-3951).

SCF also directly influences the adhesion of both mast cells (Dastych, et al., 1994, *J. Immunol.* 152:213-219; Kinashi, et al., 1994, *Blood* 83:1033-1038) and eosinophils (Yuan, et al., 1997, *J. Exp. Med.* 186:313-323), which in turn, regulates tissue infiltration. Thus, SCF can influence the primary cells involved in allergy and asthma through multiple mechanisms. Currently, corticosteroids are the most effective treatment for chronic rhinitis and inflammation associated with allergy (Naclerio, et al., 1997, *JAMA* 278:1842-1848; Meltzer, 1997, *Aller.* 52:33-40). These agents work through multiple mechanisms including reduction of circulating and infiltrating mast cells and eosinophils, and diminished survival of eosinophils associated with inhibition of cytokine production (Meltzer, 1997, *Aller.* 52:33-40). Steroids have also been reported to inhibit the expression of SCF by fibroblasts and resident connective tissue cells, which leads to diminished mast cell survival (Finotto, et al., 1997, *J. Clin. Invest.* 99:1721-1728). Because of the mutual regulation of mast cell and eosinophil function, and the role that SCF can play in this regulation, inhibition of c-Kit kinase provides a means to treat allergy-associated chronic rhinitis, inflammation and asthma.

Inflammatory arthritis (e.g. rheumatoid arthritis): Due to the association of mast cells with the arthritic process (Lee et al., 2002, *Science* 297:1689-1692), c-Kit provides a useful target for prevention, delay, and/or treatment of inflammatory arthritis, such as rheumatoid arthritis.

Multiple sclerosis: Mast cells have been shown to play an extensive role in autoimmune diseases, as demonstrated in experimental allergic encephalomyelitis (EAE), the mouse model of multiple sclerosis (MS). Mast cells were indicated to be required for full manifestation of the disease. Secor et al., 2000, *J. Exp Med* 191:813-821. Thus, c-Kit also provides a useful target for the prevention, delay, and/or treatment of multiple sclerosis.

Modulators of c-Kit function thus can be used against diseases such as those indicated above.

II. c-Kit Structures

A crystal structure of c-Kit with binding compound STI-571 (Gleevec) has been reported, and atomic coordinates for that structure were deposited in the Protein Data Bank (PDB) as IPKG, and in the Molecular Modeling DataBase as 23938. Such a structure can be used for modeling the binding of different compounds by replacing STI-571 with another compound. For example, using convention molecular modeling software, coordinates for STI-571 can be removed, and replaced with coordinates for another compound. The structure is allowed to adjust to reflect binding of the replacement compound.

Similarly to the reported structure, co-crystals of c-Kit with a compound of Formula I can be formed and analyzed to provide co-crystal structures.

It is to be understood that the crystalline kinases and kinase domains of the invention are not limited to naturally occurring or native kinase. Indeed, the crystals of the invention include crystals of mutants of native kinases. Mutants of native kinases are obtained by replacing at least one amino acid residue in a native kinase with a different amino acid residue, or by adding or deleting amino acid residues within the native polypeptide or at the N- or C-terminus of the native polypeptide, and have substantially the same three-dimensional structure as the native kinase from which the mutant is derived.

By having substantially the same three-dimensional structure is meant having a set of atomic structure coordinates that have a root-mean-square deviation of less than or equal to about 2 Å when superimposed with the atomic structure coordinates of the native kinase from which the mutant is derived when at least about 50% to 100% of the Cα atoms of the native kinase domain are included in the superposition.

Amino acid substitutions, deletions and additions which do not significantly interfere with the three-dimensional structure of the kinase will depend, in part, on the region of the kinase where the substitution, addition or deletion occurs. In highly variable regions of the molecule, non-conservative substitutions as well as conservative substitutions may be tolerated without significantly disrupting the three-dimensional, structure of the molecule. In highly conserved regions, or regions containing significant secondary structure, conservative amino acid substitutions are preferred. Such conserved and variable regions can be identified by sequence alignment of c-Kit with other kinases.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

For c-Kit obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native kinase in order to provide convenient cloning sites in cDNA encoding the polypeptide, to aid in purification of the polypeptide, and for crystallization of the polypeptide. Such substitutions, deletions and/or additions which do not substantially alter the three dimensional structure of the native kinase domain will be apparent to those of ordinary skill in the art.

It should be noted that the mutants contemplated herein need not all exhibit kinase activity. Indeed, amino acid substitutions, additions or deletions that interfere with the kinase activity but which do not significantly alter the three-dimensional structure of the domain are specifically contemplated by the invention. Such crystalline polypeptides, or the atomic structure coordinates obtained therefrom, can be used to identify compounds that bind to the native domain. These compounds can affect the activity of the native domain.

The derivative crystals of the invention can comprise a crystalline kinase polypeptide in covalent association with one or more heavy metal atoms. The polypeptide may correspond to a native or a mutated kinase. Heavy metal atoms useful for providing derivative crystals include, by way of example and not limitation, gold, mercury, selenium, etc.

The co-crystals of the invention generally comprise a crystalline kinase domain polypeptide in association with one or more compounds. The association may be covalent or non-covalent. Such compounds include, but are not limited to, cofactors, substrates, substrate analogues, inhibitors, allosteric effectors, etc.

III. Three Dimensional Structure Determination Using X-ray Crystallography

X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated aqueous solution of that protein. The process of X-ray crystallography can include the following steps:

(a) synthesizing and isolating (or otherwise obtaining) a polypeptide;
(b) growing a crystal from an aqueous solution comprising the polypeptide with or without a modulator; and
(c) collecting X-ray diffraction patterns from the crystals, determining unit cell dimensions and symmetry, determining electron density, fitting the amino acid sequence of the polypeptide to the electron density, and refining the structure.

Production of Polypeptides

The native and mutated kinase polypeptides described herein may be chemically synthesized in whole or part using techniques that are well-known in the art (see, e.g., Creighton (1983) *Biopolymers* 22(1):49-58).

Alternatively, methods which are well known to those skilled in the art can be used to construct expression vectors containing the native or mutated kinase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the kinase coding sequence. These include but are not limited to microorganisms such as bacteria transformed with recombinant bacteriophage DNA, plasmid DNA or cosmid DNA expression vectors containing the kinase domain coding sequence; yeast transformed with recombinant yeast expression vectors containing the kinase domain coding sequence; insect cell systems infected with recombinant virus expression vectors (e.g., baculovirus) containing the kinase domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the kinase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the kinase domain DNA, SV40-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

Crystal Growth

Crystals are grown from an aqueous solution containing the purified and concentrated polypeptide by a variety of techniques. These techniques include batch, liquid, bridge, dialysis, vapor diffusion, and hanging drop methods. McPherson (1982) John Wiley, New York; McPherson (1990) *Eur. J. Biochem.* 189:1-23; Webber (1991) *Adv. Protein Chem.* 41:1-36, incorporated by reference herein in their entireties, including all figures, tables, and drawings.

The native crystals of the invention are, in general, grown by adding precipitants to the concentrated solution of the polypeptide. The precipitants are added at a concentration just below that necessary to precipitate the protein. Water is removed by controlled evaporation to produce precipitating conditions, which are maintained until crystal growth ceases.

For crystals of the invention, exemplary crystallization conditions are described in the Examples. Those of ordinary skill in the art will recognize that the exemplary crystallization conditions can be varied. Such variations may be used alone or in combination. In addition, other crystallization conditions may be found, e.g., by using crystallization screening plates to identify such other conditions. Those alternate conditions can then be optimized if needed to provide larger or better quality crystals.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or $KAu(CN)_2$ for about 2 hr to about 72 hr provides derivative crystals suitable for use as isomorphous replacements in determining the X-ray crystal structure.

Co-crystals of the invention can be obtained by soaking a native crystal in mother liquor containing compound that binds the kinase, or can be obtained by co-crystallizing the kinase polypeptide in the presence of a binding compound.

Generally, co-crystallization of kinase and binding compound can be accomplished using conditions identified for crystallizing the corresponding kinase without binding compound. It is advantageous if a plurality of different crystallization conditions have been identified for the kinase, and these can be tested to determine which condition gives the best co-crystals. It may also be benficial to optimize the conditions for co-crystallization. Alternatively, new crystallization conditions can be determined for obtaining co-crystals, e.g., by screening for crystallization and then optimizing those conditions. Exemplary co-crystallization conditions are provided in the Examples.

Determining Unit Cell Dimensions and the Three Dimensional Structure of a Polypeptide or Polypeptide Complex Once the crystal is grown, it can be placed in a glass capillary tube or other mounting device and mounted onto a holding device connected to an X-ray generator and an X-ray detection device. Collection of X-ray diffraction patterns are well documented by those in the art. See, e.g., Ducruix and Geige, (1992), IRL Press, Oxford, England, and references cited therein. A beam of X-rays enters the crystal and then diffracts from the crystal. An X-ray detection device can be utilized to record the diffraction patterns emanating from the crystal. Although the X-ray detection device on older models of these instruments is a piece of film, modem instruments digitally record X-ray diffraction scattering. X-ray sources can be of various types, but advantageously, a high intensity source is used, e.g., a synchrotron beam source.

Methods for obtaining the three dimensional structure of the crystalline form of a peptide molecule or molecule complex are well known in the art. See, e.g., Ducruix and Geige, (1992), IRL Press, Oxford, England, and references cited therein. The following are steps in the process of determining the three dimensional structure of a molecule or complex from X-ray diffraction data.

After the X-ray diffraction patterns are collected from the crystal, the unit cell dimensions and orientation in the crystal can be determined. They can be determined from the spacing between the diffraction emissions as well as the patterns made from these emissions. The unit cell dimensions are characterized in three dimensions in units of Angstroms (one $Å=10^{-10}$ meters) and by angles at each vertices. The symmetry of the unit cell in the crystals is also characterized at this stage. The symmetry of the unit cell in the crystal simplifies the complexity of the collected data by identifying repeating patterns. Application of the symmetry and dimensions of the unit cell is described below.

Each diffraction pattern emission is characterized as a vector and the data collected at this stage of the method determines the amplitude of each vector. The phases of the vectors can be determined using multiple techniques. In one method, heavy atoms can be soaked into a crystal, a method called isomorphous replacement, and the phases of the vectors can be determined by using these heavy atoms as reference points in the X-ray analysis. (Otwinowski, (1991), Daresbury, United Kingdom, 80-86). The isomorphous replacement method usually utilizes more than one heavy atom derivative.

In another method, the amplitudes and phases of vectors from a crystalline polypeptide with an already determined structure can be applied to the amplitudes of the vectors from a crystalline polypeptide of unknown structure and consequently determine the phases of these vectors. This second method is known as molecular replacement and the protein structure which is used as a reference must have a closely related structure to the protein of interest. (Naraza (1994) *Proteins* 11:281-296). Thus, the vector information from a kinase of known structure, such as those reported herein, are useful for the molecular replacement analysis of another kinase with unknown structure.

Once the phases of the vectors describing the unit cell of a crystal are determined, the vector amplitudes and phases, unit cell dimensions, and unit cell symmetry can be used as terms in a Fourier transform function. The Fourier transform function calculates the electron density in the unit cell from these measurements. The electron density that describes one of the molecules or one of the molecule complexes in the unit cell can be referred to as an electron density map. The amino acid structures of the sequence or the molecular structures of compounds complexed with the crystalline polypeptide may then be fitted to the electron density using a variety of computer programs. This step of the process is sometimes referred to as model building and can be accomplished by using computer programs such as Turbo/FRODO or "0". (Jones (1985) *Methods in Enzymology* 115:157-171).

A theoretical electron density map can then be calculated from the amino acid structures fit to the experimentally determined electron density. The theoretical and experimental electron density maps can be compared to one another and the agreement between these two maps can be described by a parameter called an R-factor. A low value for an R-factor describes a high degree of overlapping electron density between a theoretical and experimental electron density map.

The R-factor is then minimized by using computer programs that refine the theoretical electron density map. A computer program such as X-PLOR can be used for model refinement by those skilled in the art. (Brünger (1992) *Nature* 355:472-475.) Refinement may be achieved in an iterative process. A first step can entail altering the conformation of atoms defined in an electron density map. The conformations of the atoms can be altered by simulating a rise in temperature, which will increase the vibrational frequency of the bonds and modify positions of atoms in the structure. At a particular point in the atomic perturbation process, a force field, which typically defines interactions between atoms in terms of allowed bond angles and bond lengths, Van der Waals interactions, hydrogen bonds, ionic interactions, and hydrophobic interactions, can be applied to the system of atoms. Favorable interactions may be described in terms of free energy and the atoms can be moved over many iterations until a free energy minimum is achieved. The refinement process can be iterated until the R-factor reaches a minimum value.

The three dimensional structure of the molecule or molecule complex is described by atoms that fit the theoretical electron density characterized by a minimum R-value. A file can then be created for the three dimensional structure that defines each atom by coordinates in three dimensions.

IV. Structures of c-Kit Binding Site

High-resolution three-dimensional structures and atomic structure coordinates of crystalline c-Kit kinase domain with binding compound have been determined.

Those having skill in the art will recognize that atomic structure coordinates as determined by X-ray crystallography are not without error. Thus, it is to be understood that generally any set of structure coordinates obtained for crystals of a kinase, whether native crystals, kinase domain crystals, derivative crystals or co-crystals, that have a root mean square deviation ("r.m.s.d.") of less than or equal to about 1.5 Å when superimposed, using backbone atoms (N, $C_\alpha$, C and 0), on the structure coordinates listed in a coordinate table herein are considered to be identical with the structure coordinates listed in that table when at least about 50% to 100% of the backbone atoms of the crystallized protein are included in the superposition.

V. Uses of the Crystals and Atomic Structure Coordinates

The crystals of the invention, and particularly the atomic structure coordinates obtained therefrom, have a wide variety of uses. For example, the crystals described herein can be used as a starting point in any of the methods of use for kinases known in the art or later developed. Such methods of use include, for example, identifying molecules that bind to the native or mutated catalytic domain of kinases. The crystals and structure coordinates are particularly useful for identifying ligands that modulate kinase activity as an approach towards developing new therapeutic agents. In particular, the crystals and structural information are useful in methods for ligand development utilizing molecular scaffolds.

The structure coordinates described herein can be used as phasing models for determining the crystal structures of additional kinases, as well as the structures of co-crystals of such kinases with ligands such as inhibitors, agonists, antagonists, and other molecules. The structure coordinates, as well as models of the three-dimensional structures obtained therefrom, can also be used to aid the elucidation of solution-based structures of native or mutated kinases, such as those obtained via NMR.

VI. Electronic Representations of c-Kit Structures

Structural information of kinases or portions of kinases (e.g., kinase active sites) can be represented in many different ways. Particularly useful are electronic representations, as such representations allow rapid and convenient data manipulations and structural modifications. Electronic representations can be embedded in many different storage or memory media, frequently computer readable media. Examples include without limitations, computer random access memory (RAM), floppy disk, magnetic hard drive, magnetic tape (analog or digital), compact disk (CD), optical disk, CD-ROM, memory card, digital video disk (DVD), and others. The storage medium can be separate or part of a computer system. Such a computer system may be a dedicated, special purpose, or embedded system, such as a computer system that forms part of an X-ray crystallography system, or may be a general purpose computer (which may have data connection with other equipment such as a sensor device in an X-ray crystallographic system. In many cases, the information provided by such electronic representations can also be represented physically or visually in two or three dimensions, e.g., on paper, as a visual display (e.g., on a computer monitor as a two dimensional or pseudo-three dimensional image) or as a three dimensional physical model. Such physical representations can also be used, alone or in connection with electronic representations. Exemplary useful representations include, but are not limited to, the following:

Atomic Coordinate Representation

One type of representation is a list or table of atomic coordinates representing positions of particular atoms in a molecular structure, portions of a structure, or complex (e.g., a co-crystal). Such a representation may also include additional information, for example, information about occupancy of particular coordinates.

Energy Surface or Surface of Interaction Representation

Another representation is an energy surface representation, e.g., of an active site or other binding site, representing an energy surface for electronic and steric interactions. Such a representation may also include other features. An example is the inclusion of representation of a particular amino acid residue(s) or group(s) on a particular amino acid residue(s), e.g., a residue or group that can participate in H-bonding or ionic interaction. Such energy surface representations can be readily generated from atomic coordinate representations using any of a variety of available computer programs.

Structural Representation

Still another representation is a structural representation, i.e., a physical representation or an electronic representation of such a physical representation. Such a structural representation includes representations of relative positions of particular features of a molecule or complex, often with linkage between structural features. For example, a structure can be represented in which all atoms are linked; atoms other than hydrogen are linked; backbone atoms, with or without representation of sidechain atoms that could participate in significant electronic interaction, are linked; among others. However, not all features need to be linked. For example, for structural representations of portions of a molecule or complex, structural features significant for that feature may be represented (e.g., atoms of amino acid residues that can have significant binding interation with a ligand at a binding site. Those amino acid residues may not be linked with each other.

A structural representation can also be a schematic representation. For example, a schematic representation can represent secondary and/or tertiary structure in a schematic manner. Within such a schematic representation of a polypeptide, a particular amino acid residue(s) or group(s) on a residue(s) can be included, e.g., conserved residues in a binding site, and/or residue(s) or group(s) that may interact with binding compounds. Electronic structural representations can be generated, for example, from atomic coordinate information using computer programs designed for that function and/or by constructing an electronic representation with manual input based on interpretation of another form of structural information. Physical representations can be created, for example, by printing an image of a computer-generated image or by constructing a 3D model. An example of such a printed representation is the ribbon diagram presented in FIG. 2.

VII. Structure Determination for Kinases with Unknown Structure Using Structural Coordinates Structural coordinates, such as those available for c-Kit, can be used to determine the three dimensional structures of kinases with unknown structure. The methods described below can apply structural coordinates of a polypeptide with known structure to another data set, such as an amino acid sequence, X-ray crystallographic diffraction data, or nuclear magnetic resonance (NMR) data. Preferred embodiments of the invention relate to determining the three dimensional structures of modified kinases, other native kinases, and related polypeptides.

Structures Using Amino Acid Homology

Homology modeling is a method of applying structural coordinates of a polypeptide of known structure to the amino acid sequence of a polypeptide of unknown structure. This method is accomplished using a computer representation of the three dimensional structure of a polypeptide or polypeptide complex, the computer representation of amino acid sequences of the polypeptides with known and unknown structures, and standard computer representations of the structures of amino acids. Homology modeling generally involves (a) aligning the amino acid sequences of the polypeptides with and without known structure; (b) transferring the coordinates of the conserved amino acids in the known structure to the corresponding amino acids of the polypeptide of unknown structure; refining the subsequent three dimensional structure; and (d) constructing structures of the rest of the polypeptide. One skilled in the art recognizes that conserved amino acids between two proteins can be determined from the sequence alignment step in step (a).

The above method is well known to those skilled in the art. (Greer (1985) *Science* 228:1055; Blundell et al. A(1988) *Eur. J. Biochem.* 172:513. An exemplary computer program that can be utilized for homology modeling by those skilled in the art is the Homology module in the Insight II modeling package distributed by Accelerys Inc.

Alignment of the amino acid sequence is accomplished by first placing the computer representation of the amino acid sequence of a polypeptide with known structure above the amino acid sequence of the polypeptide of unknown structure. Amino acids in the sequences are then compared and groups of amino acids that are homologous (e.g., amino acid side chains that are similar in chemical nature—aliphatic, aromatic, polar, or charged) are grouped together. This method will detect conserved regions of the polypeptides and account for amino acid insertions or deletions. Such alignment and/or can also be performed fully electronically using sequence alignment and analyses software.

Once the amino acid sequences of the polypeptides with known and unknown structures are aligned, the structures of the conserved amino acids in the computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions are to be assigned manually by either using standard peptide geometries or molecular simulation techniques, such as molecular dynamics. The final step in the process is accomplished by refining the entire structure using molecular dynamics and/or energy minimization. The homology modeling method is well known to those skilled in the art and has been practiced using different protein molecules. For example, the three dimensional structure of the polypeptide corresponding to the catalytic domain of a serine/threonine protein kinase, myosin light chain protein kinase, was homology modeled from the cAMP-dependent protein kinase catalytic subunit. (Knighton et al. (1992) Science 258:130-135.)

Structures Using Molecular Replacement

Molecular replacement is a method of applying the X-ray diffraction data of a polypeptide of known structure to the X-ray diffraction data of a polypeptide of unknown sequence. This method can be utilized to define the phases describing the X-ray diffraction data of a polypeptide of unknown structure when only the amplitudes are known. X-PLOR is a commonly utilized computer software package used for molecular replacement. Brünger (1992) *Nature* 355:472-475. AMORE is another program used for molecular replacement. Navaza (1994) *Acta Crystallogr.* A50:157-163. Preferably, the resulting structure does not exhibit a root-mean-square deviation of more than 3 Å.

A goal of molecular replacement is to align the positions of atoms in the unit cell by matching electron diffraction data from two crystals. A program such as X-PLOR can involve four steps. A first step can be to determine the number of molecules in the unit cell and define the angles between them. A second step can involve rotating the diffraction data to define the orientation of the molecules in the unit cell. A third step can be to translate the electron density in three dimensions to correctly position the molecules in the unit cell. Once the amplitudes and phases of the X-ray diffraction data is determined, an R-factor can be calculated by comparing electron diffraction maps calculated experimentally from the reference data set and calculated from the new data set. An R-factor between 30-50% indicates that the orientations of the atoms in the unit cell are reasonably determined by this method. A fourth step in the process can be to decrease the R-factor to roughly 20% by refining the new electron density map using iterative refinement techniques described herein and known to those or ordinary skill in the art.

Structures Using NMR Data

Structural coordinates of a polypeptide or polypeptide complex derived from X-ray crystallographic techniques can be applied towards the elucidation of three dimensional structures of polypeptides from nuclear magnetic resonance (NMR) data. This method is used by those skilled in the art. (Wuthrich, (1986), John Wiley and Sons, New York: 176-199; Pflugrath et al. (1986) *J. Mol. Biol.* 189:383-386; Kline et al. (1986) *J. Mol. Biol.* 189:377-382.) While the secondary structure of a polypeptide is often readily determined by utilizing two-dimensional NMR data, the spatial connections between individual pieces of secondary structure are not as readily determinable. The coordinates defining a three-dimensional structure of a polypeptide derived from X-ray crystallographic techniques can guide the NMR spectroscopist to an understanding of these spatial interactions between secondary structural elements in a polypeptide of related structure.

The knowledge of spatial interactions between secondary structural elements can greatly simplify Nuclear Overhauser Effect (NOE) data from two-dimensional NMR experiments. Additionally, applying the crystallographic coordinates after the determination of secondary structure by NMR techniques only simplifies the assignment of NOEs relating to particular amino acids in the polypeptide sequence and does not greatly bias the NMR analysis of polypeptide structure. Conversely, using the crystallographic coordinates to simplify NOE data while determining secondary structure of the polypeptide would bias the NMR analysis of protein structure.

VIII. Structure-Based Design of Modulators of c-Kit Function Utilizing Structural Coordinates Structure-based modulator design and identification methods are powerful techniques that can involve searches of computer databases containing a wide variety of potential modulators and chemical functional groups. The computerized design and identification of modulators is useful as the computer databases contain more compounds than the chemical libraries, often by an order of magnitude. For reviews of structure-based drug design and identification (see Kuntz et al. (1994), *Acc. Chem. Res.* 27:117; Guida (1994) *Current Opinion in Struc. Biol.* 4: 777; Colman (1994) *Current Opinion in Struc. Biol.* 4: 868).

The three dimensional structure of a polypeptide defined by structural coordinates can be utilized by these design methods. In addition, the three dimensional structures of kinases determined by the homology, molecular replacement, and NMR techniques described herein can also be applied to modulator design and identification methods.

For identifying modulators, structural information for a native kinase, in particular, structural information for the active site of the kinase, can be used. However, it may be advantageous to utilize structural information from one or more co-crystals of the kinase with one or more binding compounds. It can also be advantageous if the binding compound has a structural core in common with test compounds.

Design by Searching Molecular Data Bases

One method of rational design searches for modulators by docking the computer representations of compounds from a database of molecules. Publicly available databases include, for example:

a) ACD from Molecular Designs Limited
b) NCI from National Cancer Institute
c) CCDC from Cambridge Crystallographic Data Center
d) CAST from Chemical Abstract Service
e) Derwent from Derwent Information Limited
f) Maybridge from Maybridge Chemical Company LTD
g) Aldrich from Aldrich Chemical Company
h) Directory of Natural Products from Chapman & Hall One such data base (ACD distributed by Molecular Designs Limited Information Systems) contains compounds that are synthetically derived or are natural products. Methods available to those skilled in the art can convert a data set represented in two dimensions to one represented in three dimensions. These methods are enabled by such computer programs as CONCORD from Tripos Associates or DE-Converter from Molecular Simulations Limited.

Multiple methods of structure-based modulator design are known to those in the art. (Kuntz et al., (1982), *J. Mol. Biol.* 162: 269; Kuntz et al., (1994), *Acc. Chem. Res.* 27: 117; Meng et al., (1992), *J. Compt. Chem.* 13: 505; Bohm, (1994), *J. Comp. Aided Molec. Design* 8: 623.)

A computer program widely utilized by those skilled in the art of rational modulator design is DOCK from the University of California in San Francisco. The general methods utilized by this computer program and programs like it are described in three applications below. More detailed information regarding some of these techniques can be found in the Accelerys User Guide, 1995. A typical computer program used for this purpose can perform a processes comprising the following steps or functions:

(a) remove the existing compound from the protein;
(b) dock the structure of another compound into the active-site using the computer program (such as DOCK) or by interactively moving the compound into the active-site;
(c) characterize the space between the compound and the active-site atoms;
(d) search libraries for molecular fragments which (i) can fit into the empty space between the compound and the active-site, and (ii) can be linked to the compound; and
(e) link the fragments found above to the compound and evaluate the new modified compound.

Part (c) refers to characterizing the geometry and the complementary interactions formed between the atoms of the active site and the compounds. A favorable geometric fit is attained when a significant surface area is shared between the compound and active-site atoms without forming unfavorable steric interactions. One skilled in the art would note that the method can be performed by skipping parts (d) and (e) and screening a database of many compounds.

Structure-based design and identification of modulators of kinase function can be used in conjunction with assay screening. As large computer databases of compounds (around 10,000 compounds) can be searched in a matter of hours or even less, the computer-based method can narrow the compounds tested as potential modulators of kinase function in biochemical or cellular assays.

The above descriptions of structure-based modulator design are not all encompassing and other methods are reported in the literature and can be used, e.g.:

(1) CAVEAT: Bartlett et al., (1989), in *Chemical and Biological Problems in Molecular Recognition*, Roberts, S. M.; Ley, S. V.; Campbell, M. M. eds.; Royal Society of Chemistry: Cambridge, pp. 182-196.
(2) FLOG: Miller et al., (1994), *J. Comp. Aided Molec. Design* 8:153.
(3) PRO Modulator: Clark et al., (1995), *J. Comp. Aided Molec. Design* 9:13.
(4) MCSS: Miranker and Karplus, (1991), *Proteins: Structure, Function, and Genetics* 11:29.
(5) AUTODOCK: Goodsell and Olson, (1990), *Proteins: Structure, Function, and Genetics* 8:195.
(6) GRID: Goodford, (1985), *J. Med. Chem.* 28:849.

Design by Modifying Compounds in Complex with c-Kit

Another way of identifying compounds as potential modulators is to modify an existing modulator in the polypeptide active site. For example, the computer representation of modulators can be modified within the computer representation of a c-Kit active site. Detailed instructions for this technique can be found, for example, in the Accelerys User Manual, 1995 in LUDI. The computer representation of the modulator is typically modified by the deletion of a chemical group or groups or by the addition of a chemical group or groups.

Upon each modification to the compound, the atoms of the modified compound and active site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

Design by Modifying the Structure of Compounds that Bind c-Kit

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound that has been removed from the active site of the three dimensional structure of a compound-kinase complex. Operating the program on such a compound is preferable since it is in a biologically active conformation.

A modulator construction computer program is a computer program that may be used to replace computer representations of chemical groups in a compound complexed with a kinase or other biomolecule with groups from a computer database. A modulator searching computer program is a computer program that may be used to search computer representations of compounds from a computer data base that have similar three dimensional structures and similar chemical groups as compound bound to a particular biomolecule.

A typical program can operate by using the following general steps:
(a) map the compounds by chemical features such as by hydrogen bond donors or acceptors, hydrophobic/lipophilic sites, positively ionizable sites, or negatively ionizable sites;
(b) add geometric constraints to the mapped features; and
(c) search databases with the model generated in (b).

Those skilled in the art also recognize that not all of the possible chemical features of the compound need be present in the model of (b). One can use any subset of the model to generate different models for data base searches.

Modulator Design Using Molecular Scaffolds

The present invention can also advantageously utilize methods for designing compounds, designated as molecular scaffolds, that can act broadly across families of molecules and/or for using a molecular scaffold to design ligands that target individual or multiple members of those families. Such design using molecular scaffolds is described in Hirth and Milburn, U.S. patent application Ser. No. 10/377,268, which is incorporated herein by reference in its entirety. Such design and development using molecular scaffolds is described, in part, below.

In preferred embodiments, the molecules can be proteins and a set of chemical compounds can be assembled that have properties such that they are 1) chemically designed to act on certain protein families and/or 2) behave more like molecular scaffolds, meaning that they have chemical substructures that make them specific for binding to one or more proteins in a family of interest. Alternatively, molecular scaffolds can be designed that are preferentially active on an individual target molecule.

Useful chemical properties of molecular scaffolds can include one or more of the following characteristics, but are not limited thereto: an average molecular weight below about 350 daltons, or between from about 150 to about 350 daltons, or from about 150 to about 300 daltons; having a clogP below 3; a number of rotatable bonds of less than 4; a number of hydrogen bond donors and acceptors below 5 or below 4; a polar surface area of less than 50 $Å^2$; binding at protein binding sites in an orientation so that chemical substituents from a combinatorial library that are attached to the scaffold can be projected into pockets in the protein binding site; and possessing chemically tractable structures at its substituent attachment points that can be modified, thereby enabling rapid library construction.

By "clog P" is meant the calculated log P of a compound, "P" referring to the partition coefficient between octanol and water.

The term "Molecular Polar Surface Area (PSA)" refers to the sum of surface contributions of polar atoms (usually oxygens, nitrogens and attached hydrogens) in a molecule. The polar surface area has been shown to correlate well with drug transport properties, such as intestinal absorption, or blood-brain barrier penetration.

Additional useful chemical properties of distinct compounds for inclusion in a combinatorial library include the ability to attach chemical moieties to the compound that will not interfere with binding of the compound to at least one protein of interest, and that will impart desirable properties to the library members, for example, causing the library members to be actively transported to cells and/or organs of interest, or the ability to attach to a device such as a chromatography column (e.g., a streptavidin column through a molecule such as biotin) for uses such as tissue and proteomics profiling purposes.

A person of ordinary skill in the art will realize other properties that can be desirable for the scaffold or library members to have depending on the particular requirements of the use, and that compounds with these properties can also be sought and identified in like manner. Methods of selecting compounds for assay are known to those of ordinary skill in the art, for example, methods and compounds described in U.S. Pat. Nos. 6,288,234, 6,090,912, 5,840,485, each of which is hereby incorporated by reference in its entirety, including all charts and drawings.

In various embodiments, the present invention provides methods of designing ligands that bind to a plurality of members of a molecular family, where the ligands contain a common molecular scaffold. Thus, a compound set can be assayed for binding to a plurality of members of a molecular family, e.g., a protein family. One or more compounds that bind to a plurality of family members can be identified as molecular scaffolds. When the orientation of the scaffold at the binding site of the target molecules has been determined and chemically tractable structures have been identified, a set of ligands can be synthesized starting with one or a few molecular scaffolds to arrive at a plurality of ligands, wherein each ligand binds to a separate target molecule of the molecular family with altered or changed binding affinity or binding specificity relative to the scaffold. Thus, a plurality of drug lead molecules can be designed to preferentially target individual members of a molecular family based on the same molecular scaffold, and act on them in a specific manner.

IX. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. The assays of the present invention can also include assaying compounds for low affinity binding to the target molecule. A large variety of assays indicative of binding are known for different target types and can be used for this invention. Compounds that act broadly across protein families are not likely to have a high affinity against individual targets, due to the broad nature of their binding. Thus, assays described herein allow for the identification of compounds that bind with low affinity, very low affinity, and extremely low affinity. Therefore, potency (or binding affinity) is not the primary, nor even the most important, indicia of identification of a potentially useful binding compound. Rather, even those compounds that bind with low affinity, very low affinity, or extremely low affinity can be considered as molecular scaffolds that can continue to the next phase of the ligand design process.

By binding with "low affinity" is meant binding to the target molecule with a dissociation constant ($k_d$) of greater than 1 µM under standard conditions. By binding with "very low affinity" is meant binding with a $k_d$ of above about 100 µM under standard conditions. By binding with "extremely low affinity" is meant binding at a $k_d$ of above about 1 mM under standard conditions. By "moderate affinity" is meant binding with a $k_d$ of from about 200 nM to about 1 µM under standard conditions. By "moderately high affinity" is meant binding at a $k_d$ of from about 1 nM to about 200 nM. By binding at "high affinity" is meant binding at a $k_d$ of below about 1 nM under standard conditions. For example, low affinity binding can occur because of a poorer fit into the binding site of the target molecule or because of a smaller number of non-covalent bonds, or weaker covalent bonds present to cause binding of the scaffold or ligand to the binding site of the target molecule relative to instances where higher affinity binding occurs. The standard conditions for binding are at pH 7.2 at 37° C. for one hour. For example, 100 µl/well can be used in HEPES 50 mM buffer at pH 7.2, NaCl 15 mM, ATP 2 µM, and bovine serum albumin 1 µg/well, 37° C. for one hour.

Binding compounds can also be characterized by their effect on the activity of the target molecule. Thus, a "low activity" compound has an inhibitory concentration ($IC_{50}$) or excitation concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

To design or discover scaffolds that act broadly across protein families, proteins of interest can be assayed against a compound collection or set. The assays can preferably be enzymatic or binding assays. In some embodiments it may be desirable to enhance the solubility of the compounds being screened and then analyze all compounds that show activity in the assay, including those that bind with low affinity or produce a signal with greater than about three times the standard deviation of the background signal. The assays can be any suitable assay such as, for example, binding assays that measure the binding affinity between two binding partners. Various types of screening assays that can be useful in the practice of the present invention are known in the art, such as those described in U.S. Pat. Nos. 5,763,198, 5,747,276, 5,877,007, 6,243,980, 6,294,330, and 6,294,330, each of which is hereby incorporated by reference in its entirety, including all charts and drawings.

In various embodiments of the assays at least one compound, at least about 5%, at least about 10%, at least about 15%, at least about 20%, or at least about 25% of the compounds can bind with low affinity. In general, up to about 20% of the compounds can show activity in the screening assay and these compounds can then be analyzed directly with high-throughput co-crystallography, computational analysis to group the compounds into classes with common structural properties (e.g., structural core and/or shape and polarity characteristics), and the identification of common chemical structures between compounds that show activity.

The person of ordinary skill in the art will realize that decisions can be based on criteria that are appropriate for the needs of the particular situation, and that the decisions can be made by computer software programs. Classes can be created containing almost any number of scaffolds, and the criteria selected can be based on increasingly exacting criteria until an arbitrary number of scaffolds is arrived at for each class that is deemed to be advantageous.

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, *Methods in Molecular Biology.* 121: 313-21; Liparoto et al., (1999) Biosensor analysis of the interleukin-2 receptor complex, *Journal of Molecular Recog-* nition. 12:316-21; Lipschultz et al., (2000) Experimental design for analysis of complex kinetics using surface plasmon resonance, *Methods.* 20:310-8; Malmqvist., (1999) BIA-CORE: an affinity biosensor system for characterization of biomolecular interactions, *Biochemical Society Transactions* 27:335-40; Alfthan, (1998) Surface plasmon resonance biosensors as a tool in antibody engineering, *Biosensors & Bioelectronics.* 13:653-63; Fivash et al., (1998) BIAcore for macromolecular interaction, *Current Opinion in Biotechnology.* 9:97-101; Price et al.; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology.* 1:378-83; O'Shannessy et al., (1996) Interpretation of deviations from pseudo-first-order kinetic behavior in the characterization of ligand binding by biosensor technology, *Analytical Biochemistry.* 236:275-83; Malmborg et al., (1995) BIAcore as a tool in antibody engineering, *Journal of Immunological Methods.* 183:7-13; Van Regenmortel, (1994) Use of biosensors to characterize recombinant proteins, *Developments in Biological Standardization.* 83:143-51; and O'Shannessy, (1994) Determination of kinetic rate and equilibrium binding constants for macromolecular interactions: a critique of the surface plasmon resonance literature, *Current Opinions in Biotechnology.* 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owickiet al., (1997), Application of Fluorescence Polarization Assays in High-Throughput Screening, *Genetic Engineering News*, 17:27.

FP is particularly desirable since its readout is independent of the emission intensity (Checovich, W. J., et al., (1995) *Nature* 375:254-256; Dandliker, W. B., et al., (1981) *Methods in Enzymology* 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, *J Biomol Screen* 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY®O FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan A G, Hombrechtikon, Switzerland). General multi-well plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) *Curr. Biol.* 6:178-182; Mitra et al., (1996) *Gene* 173:13-17; and Selvin et al., (1995) *Meth. Enzymol.* 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) *J. Lipid Res.* 38:2365-2373; Kahl et al., (1996) *Anal. Biochem.* 243:282-283; Undenfriend et al., (1987) *Anal. Biochem.* 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) *Anal. Biochem.* 257:112-119).

Assay Compounds and Molecular Scaffolds

Preferred characteristics of a scaffold include being of low molecular weight (e.g., less than 350 Da, or from about 100 to about 350 daltons, or from about 150 to about 300 daltons). Preferably clog P of a scaffold is from −1 to 8, more preferably less than 6, 5, or 4, most preferably less than 3. In particular embodiments the clog P is in a range −1 to an upper limit of 2, 3, 4, 5, 6, or 8; or is in a range of 0 to an upper limit of 2, 3, 4, 5, 6, or 8. Preferably the number of rotatable bonds is less than 5, more preferably less than 4. Preferably the number of hydrogen bond donors and acceptors is below 6, more preferably below 5. An additional criterion that can be useful is a polar surface area of less than 5. Guidance that can be useful in identifying criteria for a particular application can be found in Lipinski et al., (1997) *Advanced Drug Delivery Reviews* 23 3-25, which is hereby incorporated by reference in its entirety.

A scaffold may preferably bind to a given protein binding site in a configuration that causes substituent moieties of the scaffold to be situated in pockets of the protein binding site. Also, possessing chemically tractable groups that can be chemically modified, particularly through synthetic reactions, to easily create a combinatorial library can be a preferred characteristic of the scaffold. Also preferred can be having positions on the scaffold to which other moieties can be attached, which do not interfere with binding of the scaffold to the protein(s) of interest but do cause the scaffold to achieve a desirable property, for example, active transport of the scaffold to cells and/or organs, enabling the scaffold to be attached to a chromatographic column to facilitate analysis, or another desirable property. A molecular scaffold can bind to a target molecule with any affinity, such as binding at high affinity, moderate affinity, low affinity, very low affinity, or extremely low affinity.

Thus, the above criteria can be utilized to select many compounds for testing that have the desired attributes. Many compounds having the criteria described are available in the commercial market, and may be selected for assaying depending on the specific needs to which the methods are to be applied.

A "compound library" or "library" is a collection of different compounds having different chemical structures. A compound library is screenable, that is, the compound library members therein may be subject to screening assays. In preferred embodiments, the library members can have a molecular weight of from about 100 to about 350 daltons, or from about 150 to about 350 daltons. Examples of libraries are provided aove.

Libraries of the present invention can contain at least one compound than binds to the target molecule at low affinity. Libraries of candidate compounds can be assayed by many different assays, such as those described above, e.g., a fluorescence polarization assay. Libraries may consist of chemically synthesized peptides, peptidomimetics, or arrays of combinatorial chemicals that are large or small, focused or nonfocused. By "focused" it is meant that the collection of compounds is prepared using the structure of previously characterized compounds and/or pharmacophores.

Compound libraries may contain molecules isolated from natural sources, artificially synthesized molecules, or molecules synthesized, isolated, or otherwise prepared in such a manner so as to have one or more moieties variable, e.g., moieties that are independently isolated or randomly synthesized. Types of molecules in compound libraries include but are not limited to organic compounds, polypeptides and nucleic acids as those terms are used herein, and derivatives, conjugates and mixtures thereof.

Compound libraries of the invention may be purchased on the commercial market or prepared or obtained by any means including, but not limited to, combinatorial chemistry techniques, fermentation methods, plant and cellular extraction procedures and the like (see, e.g., Cwirla et al., (1990) *Biochemistry*, 87, 6378-6382; Houghten et al., (1991) *Nature*, 354, 84-86; Lam et al., (1991) *Nature*, 354, 82-84; Brenner et al., (1992) *Proc. Natl. Acad. Sci. USA*, 89, 5381-5383; R. A. Houghten, (1993) *Trends Genet.*, 9, 235-239; E. R. Felder, (1994) *Chimia*, 48, 512-541; Gallop et al., (1994) *J. Med. Chem.*, 37, 1233-1251; Gordon et al., (1994) *J. Med. Chem.*, 37, 1385-1401; Carell et al., (1995) Chem. Biol., 3, 171-183; Madden et al., *Perspectives in Drug Discovery and Design* 2, 269-282; Lebl et al., (1995) *Biopolymers*, 37 177-198); small molecules assembled around a shared molecular structure; collections of chemicals that have been assembled by various commercial and noncommercial groups, natural products; extracts of marine organisms, fungi, bacteria, and plants.

Preferred libraries can be prepared in a homogenous reaction mixture, and separation of unreacted reagents from members of the library is not required prior to screening. Although many combinatorial chemistry approaches are based on solid state chemistry, liquid phase combinatorial chemistry is capable of generating libraries (Sun C M., (1999) Recent advances in liquid-phase combinatorial chemistry, *Combinatorial Chemistry & High Throughput Screening.* 2:299-318).

Libraries of a variety of types of molecules are prepared in order to obtain members therefrom having one or more preselected attributes that can be prepared by a variety of techniques, including but not limited to parallel array synthesis (Houghton, (2000) *Annu Rev Pharmacol Toxicol* 40:273-82, Parallel array and mixture-based synthetic combinatorial chemistry; solution-phase combinatorial chemistry (Merritt, (1998) *Comb Chem High Throughput Screen* 1:57-72, Solution phase combinatorial chemistry, Coe et al., (1998-99) *Mol Divers.* 4:31-8, Solution-phase combinatorial chemistry, Sun, (1999) *Comb Chem High Throughput Screen* 2:299-318, Recent advances in liquid-phase combinatorial chemistry); synthesis on soluble polymer (Gravert et al., (1997) *Curr Opin Chem Biol* 1:107-13, Synthesis on soluble polymers: new reactions and the construction of small molecules); and the like. See, e.g., Dolle et al., (1999) *J Comb Chem* 1:235-82, Comprehensive survey of cominatorial library synthesis: 1998. Freidinger R M., (1999) Nonpeptidic ligands for peptide and protein receptors, *Current Opinion in Chemical Biology*; and Kundu et al., *Prog Drug Res;* 53:89-156, Combinatorial chemistry: polymer supported synthesis of peptide and non-peptide libraries). Compounds may be clinically tagged for ease of identification (Chabala, (1995) *Curr Opin Biotechnol* 6:633-9, Solid-phase combinatorial chemistry and novel tagging methods for identifying leads).

The combinatorial synthesis of carbohydrates and libraries containing oligosaccharides have been described (Schweizer et al., (1999) *Curr Opin Chem Biol.* 3:291-8, Combinatorial synthesis of carbohydrates). The synthesis of natural-product based compound libraries has been described (Wessjohann, (2000) *Curr Opin Chem Biol* 4:303-9, Synthesis of natural-product based compound libraries).

Libraries of nucleic acids are prepared by various techniques, including by way of non-limiting example the ones described herein, for the isolation of aptamers. Libraries that include oligonucleotides and polyaminooligonucleotides (Markiewicz et al., (2000) Synthetic oligonucleotide combinatorial libraries and their applications, *Farmaco.* 55:174-7) displayed on streptavidin magnetic beads are known. Nucleic acid libraries are known that can be coupled to parallel sampling and be deconvoluted without complex procedures such as automated mass spectrometry (Enjalbal C. Martinez J. Aubagnac J L, (2000) Mass spectrometry in combinatorial chemistry, *Mass Spectrometry Reviews.* 19:139-61) and parallel tagging. (Perrin D M., Nucleic acids for recognition and catalysis: landmarks, limitations, and looking to the future, *Combinatorial Chemistry & High Throughput Screening* 3:243-69).

Peptidomimetics are identified using combinatorial chemistry and solid phase synthesis (Kim H O. Kahn M., (2000) A merger of rational drug design and combinatorial chemistry: development and application of peptide secondary structure mimetics, *Combinatorial Chemistry & High Throughput Screening* 3:167-83; al-Obeidi, (1998) *Mol Biotechnol* 9:205-23, Peptide and peptidomimetric libraries. Molecular diversity and drug design). The synthesis may be entirely random or based in part on a known polypeptide.

Polypeptide libraries can be prepared according to various techniques. In brief, phage display techniques can be used to produce polypeptide ligands (Gram H., (1999) Phage display in proteolysis and signal transduction, *Combinatorial Chemistry & High Throughput Screening.* 2:19-28) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Large libraries of individual variants of human single chain Fv antibodies have been produced. See, e.g., Siegel R W. Allen B. Pavlik P. Marks J D. Bradbury A., (2000) Mass spectral analysis of a protein complex using single-chain antibodies selected on a peptide target: applications to functional genomics, *Journal of Molecular Biology* 302:285-93; Poul M A. Becerril B. Nielsen U B. Morisson P. Marks J D., (2000) Selection of tumor-specific internalizing human antibodies from phage libraries. Source *Journal of Molecular Biology*. 301:1149-61; Amersdorfer P. Marks J D., (2001) Phage libraries for generation of anti-botulinum scFv antibodies, *Methods in Molecular Biology*. 145:219-40; Hughes-Jones N C. Bye J M. Gorick B D. Marks J D. Ouwehand W H., (1999) Synthesis of Rh Fv phage-antibodies using VH and VL germline genes, *British Journal of Haematology*. 105: 811-6; McCall A M. Amoroso A R. Sautes C. Marks J D. Weiner L M., (1998) Characterization of anti-mouse Fc gamma $R^{11}$ single-chain Fv fragments derived from human phage display libraries, *Immunotechnology*. 4:71-87; Sheets M D. Amersdorfer P. Finnern R. Sargent P. Lindquist E. Schier R. Hemingsen G. Wong C. Gerhart J C. Marks J D. Lindquist E., (1998) Efficient construction of a large nonimmune phage antibody library: the production of high-affinity human single-chain antibodies to protein antigens (published erratum appears in *Proc Natl Acad Sci USA* 96:795), Proc Natl Acad Sci USA 95:6157-62).

Focused or smart chemical and pharmacophore libraries can be designed with the help of sophisticated strategies involving computational chemistry (e.g., Kundu B. Khare S K. Rastogi S K., (1999) Combinatorial chemistry: polymer supported synthesis of peptide and non-peptide libraries, *Progress in Drug Research* 53:89-156) and the use of structure-based ligands using database searching and docking, de novo drug design and estimation of ligand binding affinities (Joseph-McCarthy D., (1999) Computational approaches to structure-based ligand design, *Pharmacology & Therapeutics* 84:179-91; Kirkpatrick D L. Watson S. Ulhaq S., (1999) Structure-based drug design: combinatorial chemistry and molecular modeling, *Combinatorial Chemistry & High Throughput Screening*. 2:211-21; Eliseev A V. Lehn J M., (1999) Dynamic combinatorial chemistry: evolutionary formation and screening of molecular libraries, *Current Topics in Microbiology & Immunology* 243:159-72; Bolger et al., (1991) *Methods Enz.* 203:21-45; Martin, (1991) *Methods Enz.* 203:587-613; Neidle et al., (1991) Methods Enz. 203: 433-458; U.S. Pat. No. 6,178,384).

X. Crystallography

After binding compounds have been determined, the orientation of compound bound to target is determined. Preferably this determination involves crystallography on co-crystals of molecular scaffold compounds with target. Most protein crystallographic platforms can preferably be designed to analyze up to about 500 co-complexes of compounds, ligands, or molecular scaffolds bound to protein targets due to the physical parameters of the instruments and convenience of operation. If the number of scaffolds that have binding activity exceeds a number convenient for the application of crystallography methods, the scaffolds can be placed into groups based on having at least one common chemical structure or other desirable characteristics, and representative compounds can be selected from one or more of the classes. Classes can be made with increasingly exacting criteria until a desired number of classes (e.g., 500) is obtained. The classes can be based on chemical structure similarities between molecular scaffolds in the class, e.g., all possess a pyrrole ring, benzene ring, or other chemical feature. Likewise, classes can be based on shape characteristics, e.g., space-filling characteristics.

The co-crystallography analysis can be performed by co-complexing each scaffold with its target at concentrations of the scaffold that showed activity in the screening assay. This co-complexing can be accomplished with the use of low percentage organic solvents with the target molecule and then concentrating the target with each of the scaffolds. In preferred embodiments these solvents are less than 5% organic solvent such as dimethyl sulfoxide (DMSO), ethanol, methanol, or ethylene glycol in water or another aqueous solvent. Each scaffold complexed to the target molecule can then be screened with a suitable number of crystallization screening conditions at both 4 and 20 degrees. In preferred embodiments, about 96 crystallization screening conditions can be performed in order to obtain sufficient information about the co-complexation and crystallization conditions, and the orientation of the scaffold at the binding site of the target molecule. Crystal structures can then be analyzed to determine how the bound scaffold is oriented physically within the binding site or within one or more binding pockets of the molecular family member.

It is desirable to determine the atomic coordinates of the compounds bound to the target proteins in order to determine which is a most suitable scaffold for the protein family. X-ray crystallographic analysis is therefore most preferable for determining the atomic coordinates. Those compounds selected can be further tested with the application of medicinal chemistry. Compounds can be selected for medicinal chemistry testing based on their binding position in the target molecule. For example, when the compound binds at a binding site, the compound's binding position in the binding site of the target molecule can be considered with respect to the chemistry that can be performed on chemically tractable structures or sub-structures of the compound, and how such modifications on the compound might interact with structures or sub-structures on the binding site of the target. Thus, one can explore the binding site of the target and the chemistry of the scaffold in order to make decisions on how to modify the scaffold to arrive at a ligand with higher potency and/or selectivity. This process allows for more direct design of ligands, by utilizing structural and chemical information obtained directly from the co-complex, thereby enabling one to more efficiently and quickly design lead compounds that are likely to lead to beneficial drug products. In various embodiments it may be desirable to perform co-crystallography on all scaffolds that bind, or only those that bind with a particular affinity, for example, only those that bind with high affinity, moderate affinity, low affinity, very low affinity, or extremely low affinity. It may also be advantageous to perform co-crystallography on a selection of scaffolds that bind with any combination of affinities.

Standard X-ray protein diffraction studies such as by using a Rigaku RU-200® (Rigaku, Tokyo, Japan) with an X-ray imaging plate detector or a synchrotron beam-line can be performed on co-crystals and the diffraction data measured on a standard X-ray detector, such as a CCD detector or an X-ray imaging plate detector.

Performing X-ray crystallography on about 200 co-crystals should generally lead to about 50 co-crystals structures, which should provide about 10 scaffolds for validation in chemistry, which should finally result in about 5 selective leads for target molecules.

Virtual Assays

Commercially available software that generates three-dimensional graphical representations of the complexed target and compound from a set of coordinates provided can be used to illustrate and study how a compound is oriented when bound to a target. (e.g., QUANTA®, Accelerys, San Diego, Calif.). Thus, the existence of binding pockets at the binding site of the targets can be particularly useful in the present invention. These binding pockets are revealed by the crystallographic structure determination and show the precise chemical interactions involved in binding the compound to the binding site of the target. The person of ordinary skill will realize that the illustrations can also be used to decide where chemical groups might be added, substituted, modified, or deleted from the scaffold to enhance binding or another desirable effect, by considering where unoccupied space is located in the complex and which chemical substructures might have suitable size and/or charge characteristics to fill it. The person of ordinary skill will also realize that regions within the binding site can be flexible and its properties can change as a result of scaffold binding, and that chemical groups can be specifically targeted to those regions to achieve a desired effect. Specific locations on the molecular scaffold can be considered with reference to where a suitable chemical substructure can be attached and in which conformation, and which site has the most advantageous chemistry available.

An understanding of the forces that bind the compounds to the target proteins reveals which compounds can most advantageously be used as scaffolds, and which properties can most effectively be manipulated in the design of ligands. The person of ordinary skill will realize that steric, ionic, hydrogen bond, and other forces can be considered for their contribution to the maintenance or enhancement of the target-compound complex. Additional data can be obtained with automated computational methods, such as docking and/or Free Energy Perturbations (FEP), to account for other energetic effects such as desolvation penalties. The compounds selected can be used to generate information about the chemical interactions with the target or for elucidating chemical modifications that can enhance selectivity of binding of the compound.

Computer models, such as homology models (i.e., based on a known, experimentally derived structure) can be constructed using data from the co-crystal structures. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

Additives that promote co-crystallization can of course be included in the target molecule formulation in order to enhance the formation of co-crystals. In the case of proteins or enzymes, the scaffold to be tested can be added to the protein formulation, which is preferably present at a concentration of approximately 1 mg/ml. The formulation can also contain between 0%-10% (v/v) organic solvent, e.g. DMSO, methanol, ethanol, propane diol, or 1,3 dimethyl propane diol (MPD) or some combination of those organic solvents. Compounds are preferably solubilized in the organic solvent at a concentration of about 10 mM and added to the protein sample at a concentration of about 100 mM. The protein-compound complex is then concentrated to a final concentration of protein of from about 5 to about 20 mg/ml. The complexation and concentration steps can conveniently be performed using a 96-well formatted concentration apparatus (e.g., Amicon Inc., Piscataway, N.J.). Buffers and other reagents present in the formulation being crystallized can contain other components that promote crystallization or are compatible with crystallization conditions, such as DTT, propane diol, glycerol.

The crystallization experiment can be set-up by placing small aliquots of the concentrated protein-compound complex (1 µl) in a 96 well format and sampling under 96 crystallization conditions. (Other screening formats can also be used, e.g., plates with greater than 96 wells.) Crystals can typically be obtained using standard crystallization protocols that can involve the 96 well crystallization plate being placed at different temperatures. Co-crystallization varying factors other than temperature can also be considered for each protein-compound complex if desirable. For example, atmospheric pressure, the presence or absence of light or oxygen, a change in gravity, and many other variables can all be tested. The person of ordinary skill in the art will realize other variables that can advantageously be varied and considered.

Ligand Design and Preparation

The design and preparation of ligands can be performed with or without structural and/or co-crystallization data by considering the chemical structures in common between the active scaffolds of a set. In this process structure-activity hypotheses can be formed and those chemical structures found to be present in a substantial number of the scaffolds, including those that bind with low affinity, can be presumed to have some effect on the binding of the scaffold. This binding can be presumed to induce a desired biochemical effect when it occurs in a biological system (e.g., a treated mammal). New or modified scaffolds or combinatorial libraries derived from scaffolds can be tested to disprove the maximum number of binding and/or structure-activity hypotheses. The remaining hypotheses can then be used to design ligands that achieve a desired binding and biochemical effect.

But in many cases it will be preferred to have co-crystallography data for consideration of how to modify the scaffold to achieve the desired binding effect (e.g., binding at higher affinity or with higher selectivity). Using the case of proteins and enzymes, co-crystallography data shows the binding pocket of the protein with the molecular scaffold bound to the binding site, and it will be apparent that a modification can be made to a chemically tractable group on the scaffold. For example, a small volume of space at a protein binding site or pocket might be filled by modifying the scaffold to include a small chemical group that fills the volume. Filling the void volume can be expected to result in a greater binding affinity, or the loss of undesirable binding to another member of the protein family. Similarly, the co-crystallography data may show that deletion of a chemical group on the scaffold may decrease a hindrance to binding and result in greater binding affinity or specificity.

It can be desirable to take advantage of the presence of a charged chemical group located at the binding site or pocket of the protein. For example, a positively charged group can be complemented with a negatively charged group introduced on the molecular scaffold. This can be expected to increase binding affinity or binding specificity, thereby resulting in a more desirable ligand. In many cases, regions of protein binding sites or pockets are known to vary from one family member to another based on the amino acid differences in those regions. Chemical additions in such regions can result in the creation or elimination of certain interactions (e.g., hydrophobic, electrostatic, or entropic) that allow a compound to be more specific for one protein target over another or to bind with greater affinity, thereby enabling one to synthesize a compound with greater selectivity or affinity for a particular family member. Additionally, certain regions can contain amino acids that are known to be more flexible than others. This often occurs in amino acids contained in loops connecting elements of the secondary structure of the protein, such as alpha helices or beta strands. Additions of chemical moieties can also be directed to these flexible regions in order to increase the likelihood of a specific interaction occurring between the protein target of interest and the compound. Virtual screening methods can also be conducted in silico to assess the effect of chemical additions, subtractions, modifications, and/or substitutions on compounds with respect to members of a protein family or class.

The addition, subtraction, or modification of a chemical structure or sub-structure to a scaffold can be performed with any suitable chemical moiety. For example the following moieties, which are provided by way of example and are not intended to be limiting, can be utilized: hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbbamylthio, cyclohexyl, pyridyl, piperidinyl, alkylamino, amino, nitro, mercapto, cyano, hydroxyl, a halogen atom, halomethyl, an oxygen atom (e.g., forming a ketone or N-oxide) or a sulphur atom (e.g., forming a thiol, thione, di-alkylsulfoxide or sulfone) are all examples of moieties that can be utilized.

Additional examples of structures or sub-structures that may be utilized are an aryl optionally substituted with one, two, or three substituents independently selected from the group consisting of alkyl, alkoxy, halogen, trihalomethyl, carboxylate, carboxamide, nitro, and ester moieties; an amine of formula —$NX_2X_3$, where $X_2$ and $X_3$ are independently selected from the group consisting of hydrogen, saturated or unsaturated alkyl, and homocyclic or heterocyclic ring moieties; halogen or trihalomethyl; a ketone of formula —$COX_4$, where $X_4$ is selected from the group consisting of alkyl and homocyclic or heterocyclic ring moieties; a carboxylic acid of formula —$(X_5)_n COOH$ or ester of formula $(X_6)_n COOX_7$, where $X_5$, $X_6$, and $X_7$ and are independently selected from the group consisting of alkyl and homocyclic or heterocyclic ring moieties and where n is 0 or 1; an alcohol of formula $(X_8)_n OH$ or an alkoxy moiety of formula —$(X_8)_n OX_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; an amide of formula $NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; $SO_2$, $NX_{11}X_{12}$, where $X_{11}$ and $X_{12}$ are selected from the group consisting of hydrogen, alkyl, and homocyclic or heterocyclic ring moieties; a homocyclic or heterocyclic ring moiety optionally substituted with one, two, or three substituents independently selected from the group consisting of alkyl, alkoxy, halogen, trihalomethyl, carboxylate, carboxamide, nitro, and ester moieties; an aldehyde of formula —CHO; a sulfone of formula —$SO_2X_{13}$, where $X_{13}$ is selected from the group consisting of saturated or unsaturated alkyl and homocyclic or heterocyclic ring moieties; and a nitro of formula —$NO_2$.

Identification of Attachment Sites on Molecular Scaffolds and Ligands

In addition to the identification and development of ligands for kinases and other enzymes, determination of the orientation of a molecular scaffold or other binding compound in a binding site allows identification of energetically allowed sites for attachment of the binding molecule to another component. For such sites, any free energy change associated with the presence of the attached component should not destabilize the binding of the compound to the kinase to an extent that will disrupt the binding. Preferably, the binding energy with the attachment should be at least 4 kcal/mol., more preferably at least 6, 8, 10, 12, 15, or 20 kcal/mol. Preferably, the presence of the attachment at the particular site reduces binding energy by no more than 3, 4, 5, 8, 10, 12, or 15 kcal/mol.

In many cases, suitable attachment sites will be those that are exposed to solvent when the binding compound is bound in the binding site. In some cases, attachment sites can be used that will result in small displacements of a portion of the enzyme without an excessive energetic cost. Exposed sites can be identified in various ways. For example, exposed sites can be identified using a graphic display or 3-dimensional model. In a grahic display, such as a computer display, an image of a compound bound in a binding site can be visually inspected to reveal atoms or groups on the compound that are exposed to solvent and oriented such that attachment at such atom or group would not preclude binding of the enzyme and binding compound. Energetic costs of attachment can be calculated based on changes or distortions that would be caused by the attachment as well as entropic changes.

Many different types of components can be attached. Persons with skill are familiar with the chemistries used for various attachments. Examples of components that can be attached include, without limitation: solid phase components such as beads, plates, chips, and wells; a direct or indirect label; a linker, which may be a traceless linker; among others. Such linkers can themselves be attached to other components, e.g., to solid phase media, labels, and/or binding moieties.

The binding energy of a compound and the effects on binding energy for attaching the molecule to another component can be calculated approximately using any of a variety of available software or by manual calculation. An example is the following:

Calculations were performed to estimate binding energies of different organic molecules to c-kit. The organic molecules considered included Gleevec, identified compounds that bind to c-kit, and several linkers.

Calculated binding energies between protein-ligand complexes were obtained using the FlexX score (an implementation of the Bohm scoring function) within the Tripos software suite. The form for that equation is shown in the equation below:

$$\Delta Gbind = \Delta Gtr + \Delta Ghb + \Delta Gion + \Delta Glipo + \Delta Garom + \Delta Grot$$

where: $\Delta Gtr$ is a constant term that accounts for the overall loss of rotational and translational entropy of the ligand, $\Delta Ghb$ accounts for hydrogen bonds formed between the ligand and protein, $\Delta Gion$ accounts for the ionic interactions between the ligand and protein, ΔGlipo accounts for the lipophilic interaction that corresponds to the protein-ligand contact surface, ΔGarom accounts for interactions between aromatic rings in the protein and ligand, and ΔGrot accounts for the entropic penalty of restricting rotatable bonds in the ligand upon binding.

This method estimates the free energy that a lead compound should have to a target protein for which there is a crystal structure, and it accounts for the entropic penalty of flexible linkers. It can therefore be used to estimate the free energy penalty incurred by attaching linkers to molecules being screened and the binding energy that a lead compound should have in order to overcome the free energy penalty of the linker. The method does not account for solvation and the entropic penalty is likely overestimated for cases where the linker is bound to a solid phase through another binding complex, such as a biotin:streptavidin complex.

Co-crystals were aligned by superimposing residues of c-Kit with corresponding residues in FLT-3. Hydrogen atoms were added to the proteins and atomic charges were assigned using the AMBER95 parameters within Sybyl. Modifications to the compounds described were made within the Sybyl modeling suite from Tripos.

These calcualtions indicate that the calculated binding energy for compounds that bind strongly to a given target can be lower than −25 kcal/mol, while the calculated binding affinity for a good scaffold or an unoptimized binding compound can be in the range of −15 to −20. The free energy penalty for attachment to a linker such as the ethylene glycol or hexatriene is estimated as typically being in the range of +5 to +15 kcal/mol.

Linkers

Linkers suitable for use in the invention can be of many different types. Linkers can be selected for particular applications based on factors such as linker chemistry compatible for attachment to a binding compound and to another component utilized in the particular application. Additional factors can include, without limitation, linker length, linker stability, and ability to remove the linker at an appropriate time. Exemplary linkers include, but are not limited to, hexyl, hexatrienyl, ethylene glycol, and peptide linkers. Traceless linkers can also be used, e.g., as described in Plunkett, M. J., and Elhman, J. A., (1995), *J. Org. Chem.*, 60:6006.

Typical functional groups, that are utilized to link binding compound(s), include, but not limited to, carboxylic acid, amine, hydroxyl, and thiol. (Examples can be found in Solid-supported combinatorial and parallel synthesis of small molecular weight compound libraries; (1998) Tetrahedron organic chemistry series Vol. 17; Pergamon; p 85).

Labels

As indicated above, labels can also be attached to a binding compound or to a linker attached to a binding compound. Such attachment may be direct (attached directly to the binding compound) or indirect (attached to a component that is directly or indirectly attached to the binding compound). Such labels allow detection of the compound either directly or indirectly. Attachement of labels can be performed using conventional chemistries. Labels can include, for example, fluorescent labels, radiolabels, light scattering particles, light absorbent particles, magnetic particles, enzymes, and specific binding agents (e.g., biotin or an antibody target moiety).

Solid Phase Media

Additional examples of components that can be attached directly or indirectly to a binding compound include various solid phase media. Similar to attachment of linkers and labels, attachment to solid phase media can be performed using conventional chemistries. Such solid phase media can include, for example, small components such as beads, nanoparticles, and fibers (e.g., in suspension or in a gel or chromatographic matrix). Likewise, solid phase media can include larger objects such as plates, chips, slides, and tubes. In many cases, the binding compound will be attached in only a portion of such an objects, e.g., in a spot or other local element on a generally flat surface or in a well or portion of a well.

Identification of Biological Agents

The posession of structural information about a protein also provides for the identification of useful biological agents, such as epitopes for development of antibodies, identification of mutation sites expected to affect activity, and identification of attachment sites allowing attachment of the protein to materials such as labels, linkers, peptides, and solid phase media.

Antibodies (Abs) finds multiple applications in a variety of areas including biotechnology, medicine and diagnosis, and indeed they are one of the most powerful tools for life science research. Abs directed against protein antigens can recognize either linear or native three-dimensional (3D) epitopes. The obtention of Abs that recognize 3D epitopes require the use of whole native protein (or of a portion that assumes a native conformation) as immunogens. Unfortunately, this not always a choice due to various technical reasons: for example the native protein is just not available, the protein is toxic, or its is desirable to utilize a high density antigen presentation. In such cases, immunization with peptides is the alternative. Of course, Abs generated in this manner will recognize linear epitopes, and they might or might not recognize the source native protein, but yet they will be useful for standard laboratory applications such as western blots. The selection of peptides to use as immunogens can be accomplished by following particular selection rules and/or use of epitope prediction software.

Though methods to predict antigenic peptides are not infallible, there are several rules that can be followed to determine what peptide fragments from a protein are likely to be antigenic. These rules are also dictated to increase the likelihood that an Ab to a particular peptide will recognize the native protein.

1. Antigenic peptides should be located in solvent accessible regions and contain both hydrophobic and hydrophilic residues.

For proteins of known 3D structure, solvent accessibility can be determined using a variety of programs such as DSSP, NACESS, or WHATIF, among others.

If the 3D structure is not known, use any of the following web servers to predict accessibilities: PHD, JPRED, PredAcc (c) ACCpro 2. Preferably select peptides lying in long loops connecting Secondary Structure (SS) motifs, avoiding peptides located in helical regions. This will increase the odds that the Ab recognizes the native protein. Such peptides can, for example, be identified from a crystal structure or crystal structure-based homology model.

For protein with known 3D coordinates, SS can be obtained from the sequence link of the relevant entry at the Brookhaven data bank. The PDBsum server also offer SS analysis of pdb records.

When no structure is available secondary structure predictions can be obtained from any of the following servers: PHD, JPRED, PSI-PRED, NNSP, etc 3. When possible, choose peptides that are in the N- and C-terminal region of the protein. Because the N- and C-terminal regions of proteins are usually solvent accessible and unstructured, Abs against those regions are also likely to recognize the native protein.

4. For cell surface glycoproteins, eliminate from initial peptides those containing consesus sites for N-glycosilation.

N-glycosilation sites can be detected using Scanprosite, or NetNGlyc

In addition, several methods based on various physio-chemical properties of experimental determined epitopes (flexibility, hydrophibility, accessibility) have been published for the prediction of antigenic determinants and can be used. The antigenic index and Preditop are example.

Perhaps the simplest method for the prediction of antigenic determinants is that of Kolaskar and Tongaonkar, which is based on the occurrence of amino acid residues in experimentally determined epitopes. (Kolaskar and Tongaonkar (1990) A semi-empirical method for prediction of antigenic determinants on protein antigens. *FEBBS Lett.* 276:172-174.) The prediction algorithm works as follows:

1. Calculate the average propensity for each overlapping 7-mer and assign the result to the central residue (i+3) of the 7-mer.
2. Calculate the average for the whole protein.
3. (a) If the average for the whole protein is above 1.0 then all residues having average propensity above 1.0 are potentially antigenic.
3. (b) If the average for the whole protein is below 1.0 then all residues having above the average for the whole protein are potentially antigenic.
4. Find 8-mers where all residues are selected by step 3 above (6-mers in the original paper)

The Kolaskar and Tongaonkar method is also available from the GCG package, and it runs using the command egcg.

Crystal structures also allow identification of residues at which mutation is likely to alter the activity of the protein. Such residues include, for example, residues that interact with susbtrate, conserved active site residues, and residues that are in a region of ordered secondary structure of involved in tertiary interactions. The mutations that are likely to affect activity will vary for different molecular contexts. Mutations in an active site that will affect activity are typically substitutions or deletions that eliminate a charge-charge or hydrogen bonding interaction, or introduce a steric interference. Mutations in secondary structure regions or molecular interaction regions that are likely to affect activity include, for example, substitutions that alter the hydrophobicity/hydrophilicity of a region, or that introduce a sufficient strain in a region near or including the active site so that critical residue(s) in the active site are displaced. Such substitutions and/or deletions and/or insertions are recognized, and the predicted structural and/or energetic effects of mutations can be calculated using conventional software.

XI. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

An assay for kinase activity that can be used for c-Kit, can be performed according to the following procedure using purified c-Kit using the procedure described in the Examples.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

XII. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of kinase function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry; Reactions, Mechanisms and Structure*, New York, McGraw Hill. Thus, the techniques useful to synthesize a potential modulator of kinase function identified by computer-based methods are readily available to those skilled in the art of organic chemical synthesis.

XIII. Administration

The methods and compounds will typically be used in therapy for human patients. However, they may also be used to treat similar or identical diseases in other vertebrates such as other primates, sports animals, and pets such as horses, dogs and cats.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in *Remington's Pharmaceutical Sciences*, 18$^{th}$ ed., Mack Publishing Co., Easton, Pa., 1990 (hereby incorporated by reference herein).

Compounds can be formulated as prodrugs. The term "prodrug," as used herein, refers to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

Compounds can be formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, furmarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Carriers or excipients can be used to produce pharmaceutical compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, inhalant or transdermal. Oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, inhalant, or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

For inhalants, compounds of the invention may be formulated as dry powder or a suitable solution, suspension, or aerosol. Powders and solutions may be formulated with suitable additives known in the art. For example, powders may include a suitable powder base such as lacatose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

It is understood that use in combination includes delivery of compounds of the invention and one or more other inhaled therapeutics together in any formulation, including formulations where the two compounds are chemically linked such that they maintain their therapeutic activity when administered. Combination use includes administration of co-formulations or formulations of chemically joined compounds, or co-administration of the compounds in separate formulations. Separate formulations may be co-administered by delivery from the same inhalant device, or can be co-administered from separate inhalant devices, where co-administration in this case means administered within a short time of each other. Co-formulations of a compound of the invention and one or more additional inhaled therapies includes preparation of the materials together such that they can be administered by one inhalant device, including the separate compounds combined in one formulation, or compounds that are modified such that they are chemically joined, yet still maintain their biological activity.

The amounts of various compound to be administered can be determined by standard procedures taking into account factors such as the compound $IC_{50}$, the biological half-life of the compound, the age, size, and weight of the patient, and the disorder associated with the patient. The importance of these and other factors are well known to those of ordinary skill in the art. Generally, a dose will be between about 0.01 and 50 mg/kg, preferably 0.1 and 20 mg/kg of the patient being treated. Multiple doses may be used.

XIV. Manipulation of c-Kit

As the full-length coding sequence and amino acid sequence of c-Kit from various mammals including human is known, cloning, construction of recombinant c-Kit, production and purification of recombinant protein, introduction of c-Kit into other organisms, and other molecular biological manipulations of c-Kit are readily performed.

Techniques for the manipulation of nucleic acids, such as, e.g., subcloning, labeling probes (e.g., random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in *PCR Protocols*, Innis et al., Eds., Academic Press, San Diego, Calif. 1990, pp 13-20; Wharam et al., *Nucleic Acids Res.* 2001 29:E54-E54; Hafner et al., *Biotechniques* 2001 30:852-6, 858, 860; Zhong et al., *Biotechniques* 2001 30:852-6, 858, 860).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids of the invention can also be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picomoviridiae, herpesveridiae, poxyiridae, adenoviridiae, or picornnaviridiae. Chimeric vectors may also be employed which exploit advantageous merits of each of the parent vector properties (See e.g., Feng (1997) *Nature Biotechnology* 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) *J. Virol.* 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to fusion proteins, and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif* 12:404-414). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) *DNA Cell. Biol.* 12:441-53.

The nucleic acids and polypeptides of the invention can be bound to a solid support, e.g., for use in screening and diagnostic methods. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g., utilizing single reactive thiol groups of cysteine residues (see, e.g., Colliuod (1993) *Bioconjugate Chem.* 4:528-536) or non-covalently but specifically (e.g., via immobilized antibodies (see, e.g., Schuhmann (1991) *Adv. Mater.* 3:388-391; Lu (1995) *Anal. Chem.* 67:83-87; the biotin/strepavidin system (see, e.g., Iwane (1997) *Biophys. Biochem. Res. Comm.* 230:76-80); metal chelating, e.g., Langmuir-Blodgett films (see, e.g., Ng (1995) *Langmuir* 11:4048-55); metal-chelating self-assembled monolayers (see, e.g., Sigal (1996) *Anal. Chem.* 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) *Nature* 377:525-531 (1989).

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) *Curr. Biol.* 8:R171-R174; Schummer (1997) *Biotechniques* 23:1087-1092; Kern (1997) *Biotechniques* 23:120-124; Solinas-Toldo (1997) *Genes, Chromosomes & Cancer* 20:399-407; Bowtell (1999) *Nature Genetics Supp.* 21:25-32. See also published U.S. patent applications Nos. 20010018642; 20010019827; 20010016322; 20010014449; 20010014448; 20010012537; 20010008765.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus.* Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, *Molecular Cloning: A Laboratory Manual*, 1989, Cold Spring Harbor Laboratory Press, Cold Spring Harbor N.Y, pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 μM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples involved in the present invention are described below. In most cases, alternative techniques could also be used. The examples are intended to be illustrative and are not limiting or restrictive to the scope of the invention.

Example 1

Synthesis of Compound of Formula Ia, where $R^1$, $R^3$, $R^4$, and $R^5$ are Hydrogen

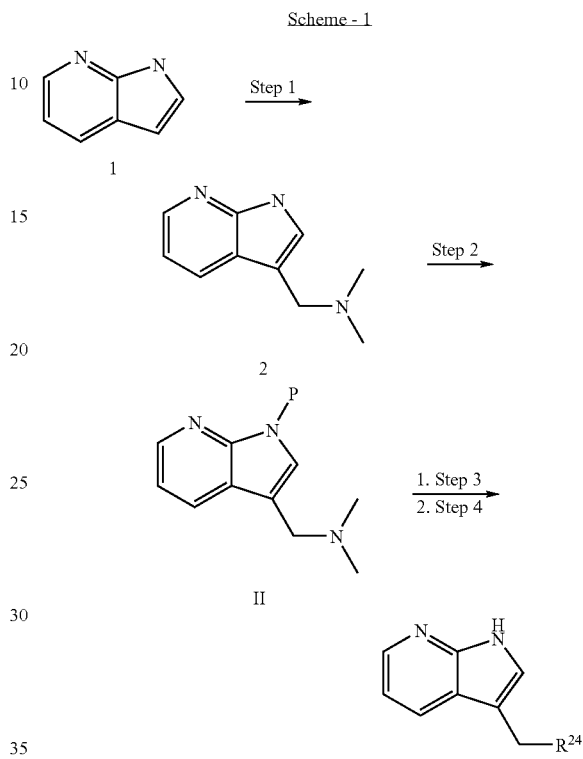

Formula Ia
where $R^2$ is aralkyl or heteroaralkyl
and $R^{24}$ is aryl or heteroaryl Step-1—Synthesis of Compound 2.

Compound 2 was synthesized from commercially available 7-azaindole following the literature procedure (Robinson, J. Am. Chem. Soc., 1955, 77, p. 457).

Step-2—Synthesis of Compound of Formula II.

Compound of formula II was synthesized by deprotonation using base (e.g. BuLi, NaH) in aprotic solvent like THF or ether and reacting the anion with a silyl chloride (e.g. TIPS) or an anhydride (e.g. Boc anhydride). The product was isolated by following standard procedure (quenching with ice-cold brine, work up, and purification by flash silica gel chromatography).

Step-3—Synthesis of Compound of Formula Ia.

Compounds of Formula Ia was synthesized through the reaction of compounds of formula II with isopropyl chloroformate (or ethyl chloroformate) at room temperature in toluene to give a 3-chloromethyl intermediate. This intermediate cooled to −78° C. and was immediately reacted with an organocopper reagent, which was generated from the reaction between a Grignard reagent (or organolithium reagent) and a solution of copper cyanide and LiCl. The mixture was stirred at −78° C. for one hour then allowed to warm to room temperature. The reaction was quenched with a solution of 4:1 ammonium chloride: ammonium Hydroxide. The reaction was worked up in the usual manner and purified by flash silica gel chromatography to give the nitrogen-protected product. The final product can be realized through the deprotection of the protecting group (Boc, TIPS) using standard conditions (TFA or NH₄F) at room temperature.

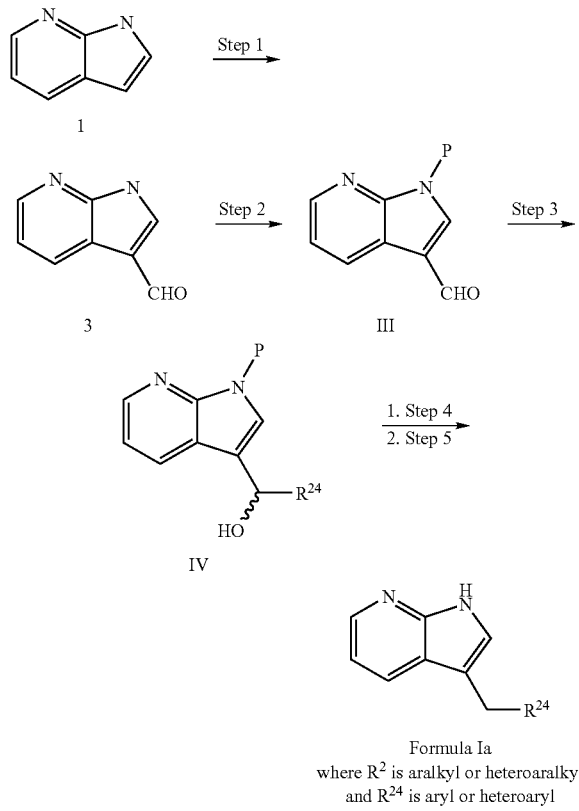

Step-1—Synthesis of Compound 3

Compound 3 was synthesized by reacting commercially available 7-azaindole, compound 1, with hexamethyltetramine and acetic acid in water with heating to reflux for two hours. After cooling, the desired product precipitated and was collected by filtration.

Step-2—Synthesis of Compound of Formula III

Compound of formula III, where P is a protecting group, was synthesized by reacting compound 3 with an appropriate reagent to introduce a protecting group (e.g. tert-butyloxycarbonyl di anhydride) and a base (e.g. sodium hydride) in a solvent (e.g. THF) typically at room temperature for 12-18 hours. The product can be isolated by conventional means (e.g. extraction).

Step-3—Synthesis of Compound of Formula IV

Compound of formula IV was synthesized by reacting compound of formula III in a solvent (e.g. 1,2-dimethoxyethane) with a Grignard reagent of the formula $R^{24}MgCl$ (e.g. phenyl magnesium bromide) or an equivalent nucleophile in a solvent (e.g. THF) under inert atmosphere cooled typically to −10° C. The reaction was typically allowed to warm to room temperature and stirred for 12-18 hours. The desired product was purified by reverse phase high pressure liquid chromatography.

Step-4—Synthesis of an Intermediate of Compound of Formula Ia where $R^2$ is Aralkyl or Heteroaralkyl and $R^{24}$ is Aryl or Heteroaryl An intermediate of compound of Formula Ia was synthesized by reacting compound of Formula IV with a reducing agent (e.g. sodium borohydride) in a solvent (e.g. ethanol) typically with heating to 80° C. for 1-4 hours. The reaction was quenched with the addition of methanol and concentrated and purified by reverse phase high performance liquid chromatography.

Step-5—Synthesis of Compound of Formula Ia Where $R^2$ is Aralkyl or Heteroaralkyl and $R^{24}$ is Aryl or Heteroaryl Compound of Formula Ia where $R^2$ is aralkyl or heteroaralkyl and $R^{24}$ is aryl or heteroaryl was synthesized by reacting the intermediate from Step 4 with an appropriate reagent to remove the protecting group, P, (e.g. hydrochloric acid) in an appropriate solvent (e.g. dioxane). The final product was isolated by standard procedures (e.g. reverse phase preparative high pressure liquid chromatography).

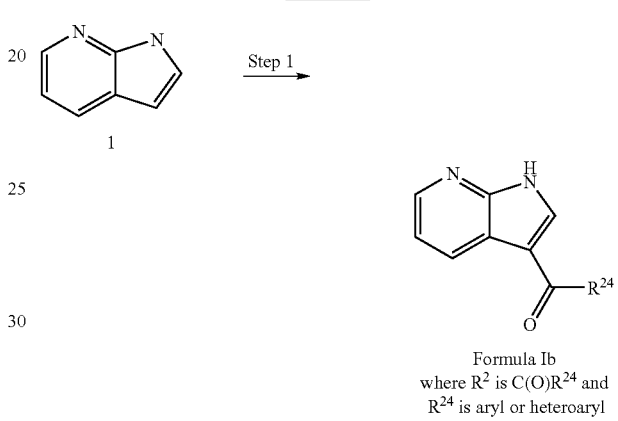

Step-1—Synthesis of compound of Formula Ib, where $R^2$ is Aralkyl or Heteroaralkyl and $R^{24}$ is Aryl or Heteroaryl Compound of Formula Ib, where $R^2$ is aralkyl or heteroaralkyl and $R^{24}$ is aryl or heteroaryl, was synthesized by reacting compound 1 with an activating agent (e.g. methyl magnesium bromide and zinc dichloride or anhydrous aluminum chloride) and an aryl acid chlorides (e.g benzoyl chloride) or heteroaryl acid chlorides (nicotinic acid chloride) in an inert solvent (e.g. methylene chloride), under inert atmosphere (e.g. argon), at room temperature or with heating up to reflux for 18-24 hours. The product was isolated by standard procedures (e.g. extraction and silica-gel chromatography).

Example 2

Synthesis of key intermediate Dimethyl-(1-triisopropylsilanyl-1H-pyrrolo[2,3-b]pyridin-3-ylmethyl)-amine (6)

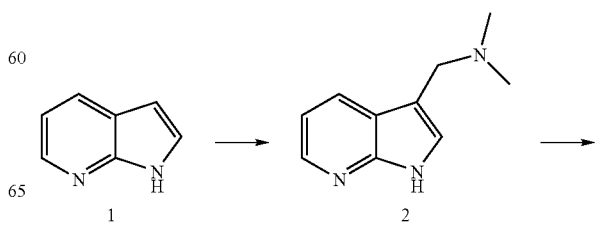

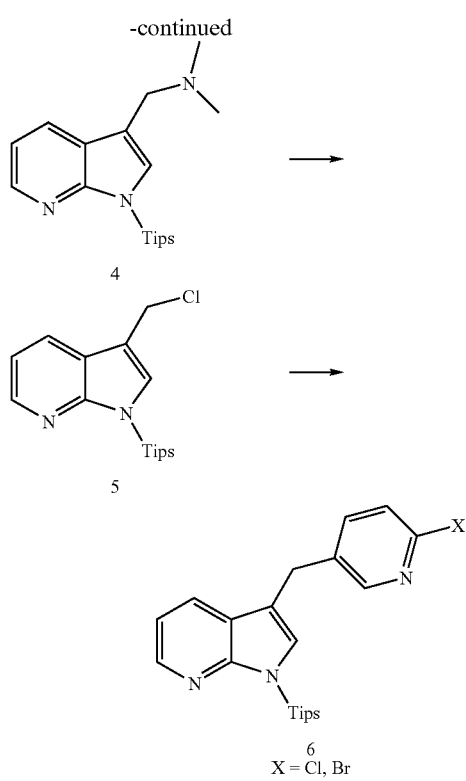

Step-1—Synthesis of dimethyl-(1H-pyrrolo[2,3-b]pyridin-3-ylmethyl)-amine (2).

Into a 3-neck round bottom flask was added Isopropyl alcohol (320.0 mL) followed by the addition of 1H-pyrrolo[2,3-b]pyridine 1 (7.10 g, 60.1 mmol), dimethylamine hydrochloride (5.4 g, 0.066 mol), and formaldehyde (2.0 g, 0.066 mol). The reaction mixture was stirred at room temperature for 12 hours, and then refluxed for 30 minutes. The suspension solution was evaporated to dryness in vacuo. To the residue was added water (60.0 mL, 3.33 mol) and concentratred hydrochloric acid (6.0 mL, 0.20 mol). The water layer was extracted with ether and the aqueous layer was neutralized with potassium carbonate. The aqueous layer was extracted with methylene chloride, dried over sodium sulfate and concentrated to give product, which was then further washed with ether and dried to afford the product 2 (7.1 g, yield=67.4%), as a white solid.

Step-2—Synthesis of dimethyl-(1-triisopropylsilanyl-1H-pyrrolo[2,3-b]pyridin-3-ylmethyl)-amine (4).

Into a round bottom flask 7-Azagramine 2 (5.38 g, 30.7 mmol), and N,N-dimethylformamide (25.0 mL), and sodium hydride (1.35 g, 33.8 mol). Into the reaction was added tri-isopropylsilyl chloride (6.8 mL, 0.032 mol). The reaction was stirred at 20 Celsius for 12 hours. The reaction mixture was poured into water, extracted with ethyl acetate. The organic layer was washed with brine, dried over sodium sulfate, concentrated and purified with biotage to give product 3 (6.0 g, yield=58.8%) as a colorless oil.

Step-3—Synthesis of 3-chloromethyl-1-triisopropylsilanyl-1H-pyrrolo[2,3-b]pyridine (5).

Into a round bottom flask was added compound 3 (500.0 mg, 1.51 mmol) and toluene (5.0 mL, 0.047 mol) under an atmosphere of nitrogen. Into the reaction mixture, was added 1.0 M of isopropyl chloroformate in toluene (1.6 mL) slowly at room temperature. The reaction mixture was stirred for another 2 hours to give desired product 5 using for next step without purification.

Step-4—Synthesis of 3-(6-Chloro-pyridin-3-ylmethyl)-1-triisopropylsilanyl-1H-pyrrolo[2,3-b]pyridine (6, where X=Cl).

Into a round bottom flask was added 5-iodo-2-chloro-pyridine (315.0 mg, 1.32 mmol) or 5-iodo-2-bromo-pyridine and tetrahydrofuran (12.0 mL, 0.15 mol) at –40 Celsius under an atmosphere of nitrogen. Into the reaction was added 2.0 M of isopropylmagnesium chloride in tetrahydrofuran (0.72 mL, 1.44 mmol). The reaction mixture was stirred for 40 minutes at –40 Celsius. TLC (hexane/ethyl acetate 2: 1) indicated no starting material. Into the reaction mixture was added 0.6 M of CuCN.2LiCl in tetrahydrofuran (2.4 mL, 1.44 mmol). The reaction mixture was allowed to room temperature for 5 min and trimethyl phosphite (0.29 mL, 2.4 mmol) was added. After 10 minutes, this solution was added into a round bottom flask, which contains compound 5 (315.0 mg, prepared in situ from the corresponding gramine 4 (323 mg, 0.98 mmol)) and toluene (8.0 mL). The reaction was stirred at 20 Celsius for 40 hours. The reaction mixture was poured into water and the product extracted with ethyl acetate. The organic layer was washed with brine, dried over sodium sulfate, concentrated and purified with biotage (methylene chloride/methanol 1:10) to give product 6, where X=Cl, (230 mg, yield=59.0%) as a white solid. The reaction conditions, work up procedure, and purifications for compound 6 where X=Br is same as that for the synthesis of compound 6 where X=Cl.

Example 3

Synthesis of key intermediate (6-Chloro-pyridin-3-yl)-(1H-pyrrolo[2,3-b]pyridin-3-yl)-methanone (7)

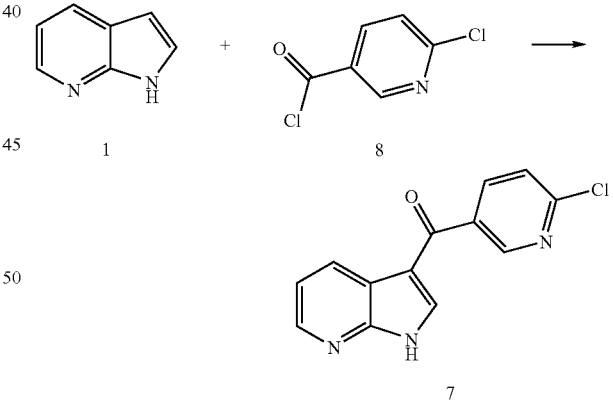

Into a round bottom flask was added aluminum trichloride (16.0 g, 0.12 mol) and methylene chloride (100.0 mL) under an atmosphere of nitrogen. Into the reaction mixture, was added 1H-Pyrrolo[2,3-b]pyridine 1 (3.2 g, 0.027 mol) in methylene dichloride (20.0 mL). The reaction was stirred at room temperature for 70.0 minutes, and then 6-Chloropyridine-3-carbonyl chloride 8 (5.4 g, 0.031 mol) in methylene chloride (10.0 mL) was added. The reaction mixture was stirred at room temperature for 3 hours. Methanol (10 mL) was added to the reaction mixture and the solvent was evaporated in vacuo. The residue was poured into water, and the precipitated product was removed by filtration. The aqueous layer was extracted with ethyl acetate, and then the organic layer was dried and concentrated and combined with the solid isolated by filtration to give 7 (6.2 g, yield=88.6%) as a white solid (M+1=258).

Example 4

Synthesis of benzyl-[5-(1H-pyrrolo[2,3-b]pyridin-3-ylmethyl)-pyridin-2-yl]-amine (9) (Compound 1-1, Table 1)

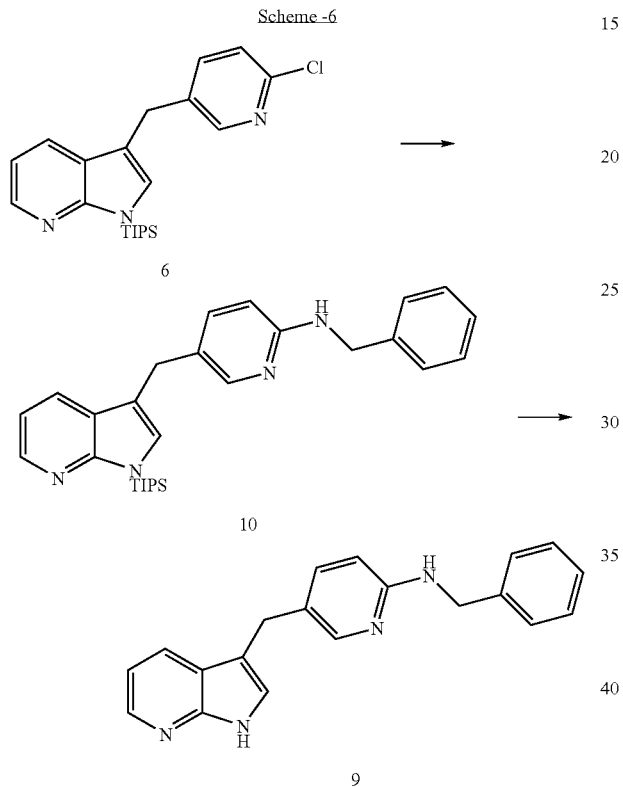

Step-1—Synthesis of benzyl-[5-(1-triisopropylsilanyl-1H-pyrrolo[2,3-b]pyridin-3-ylmethyl)-pyridin-2-yl]-amine (10)

Into a round bottom flask was added compound 6 (160.0 mg, 0.40 mmol), benzylamine (0.1 mL, 0.90 mmol), palladium acetate (17.0 mg, 0.076 mmol), toluene (10.0 mL), potassium tert-butoxide (80.0 mg, 0.71 mmol) and 2-(di-t-butylphosphino)biphenyl (31.4 mg, 0.11 mmol) under an atmosphere of nitrogen. The reaction was stirred under reflux for 3 hours. TLC and MS indicated no starting material. The reaction mixture was poured into water, extracted with ethyl acetate. The organic layer was washed with brine, dried over sodium sulfate, concentrated and purified with biotage (methylene chloride/methanol 1:20) to give product 10 (110 mg, yield=58.5%) as a white solid (M+1=471).

Step-2—Synthesis of benzyl-[5-(1H-pyrrolo[2,3-b]pyridin-3-ylmethyl)-pyridin-2-yl]-amine (9)

Into a round bottom flask was added compound 10 (400.0 mg, 0.85 mmol), tetrahydrofuran (20.0 mL) and tetra-n-butylammonium fluoride (240 mg, 0.93 mmol). The reaction mixture was stirred at 20 Celsius for 30 min. TLC indicated no starting material. The reaction mixture was poured into water, extracted with ethyl acetate. The organic layer was washed with brine, dried over sodium sulfate, concentrated and purified with biotage (methylene chloride/methanol 1:10) to give product 9 (Table 1 Cmpd 1-1) (220 mg, Yield=82.4%) as a white solid (M+1=315).

Example 5

Synthesis of (6-Benzylamino-pyridin-3-yl)-(1H-pyrrolo[2,3-b]pyridin-3-yl)-methanone (11) (Compound 1-2, Table 1)

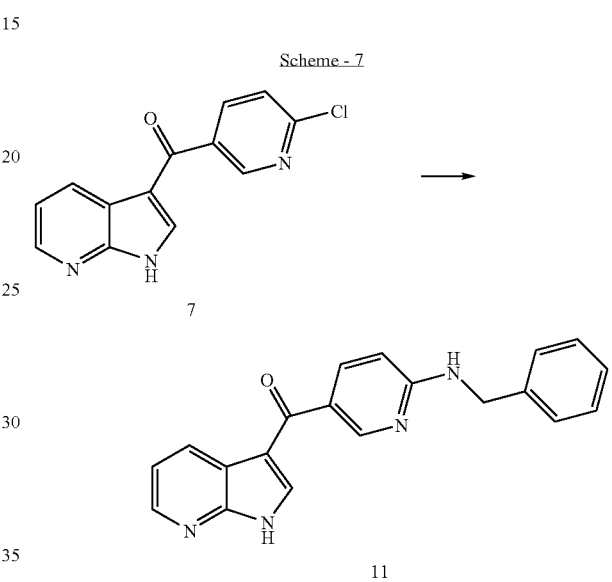

Into a pressure tube was added compound 7 (270.0 mg, 1.05 mmol), benzylamine (0.7 mL, 0.006 mol) and tetrahydrofuran (25.0 mL) under an atmosphere of nitrogen. The reaction mixture was heated to 185 Celsius for 60 hours. The reaction mixture was concentrated to remove most of the solvent and then the residue was poured into water and extracted with ethyl acetate. The organic layer was dried over sodium sulfate, concentrated and purified with biotage (methylene chloride/methanol 1:20) to give product 11 (Table 1 Cmpd 1-2) (30 mg, yield=8.7%) as a white solid (M+1=329).

Additional compounds made by this route, replacing benzylamine with 4-fluorobenzylamine, 3-fluorobenzylamine, 4-trifluoromethylbenzylamine and thiophen-2-yl methylamine to provide, respectively:

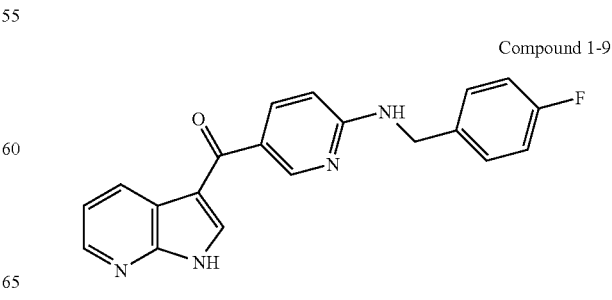

Compound 1-9

[6-(4-Fluoro-benzylamino)-pyridin-3-yl]-(1H-pyrrolo[2,3-b]pyridin-3-yl)-methanone (M+1=347.0)

Compound 1-10

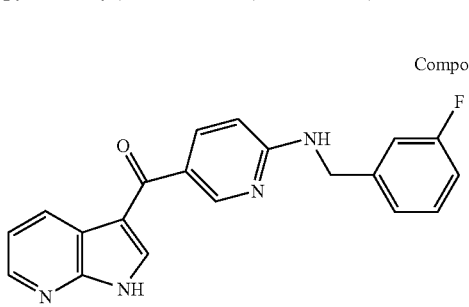

[6-(3-Fluoro-benzylamino)-pyridin-3-yl]-(1H-pyrrolo[2,3-b]pyridin-3-yl)-methanone (M+1=347.1)

Compound 1-11

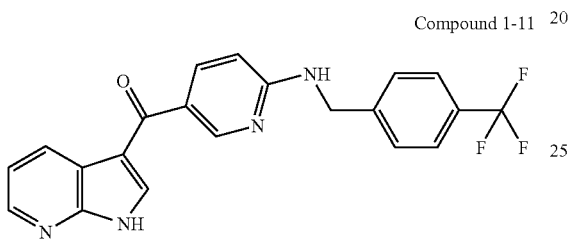

(1H-Pyrrolo[2,3-b]pyridin-3-yl)-[6-(4-trifluoromethyl-benzylamino)-pyridin-3-yl]-methanone (M+1=396.9)

Compound 1-12

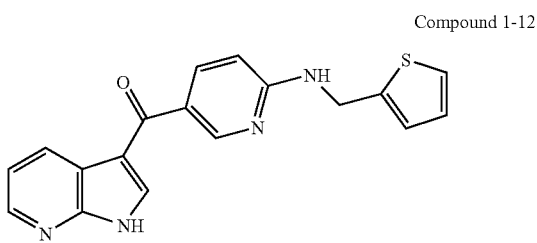

(1H-Pyrrolo[2,3-b]pyridin-3-yl)-{6-[(thiophen-2-ylmethyl)-amino]-pyridin-3-yl}-methanone (M+1=335.0)

Example 6

Synthesis of [5-(1H-Pyrrolo[2,3-b]pyridin-3-ylmethyl)-pyridin-2-yl]-(4-trifluoromethyl-benzyl)-amine (12) (Compound 1-3, Table 1)

Scheme - 8

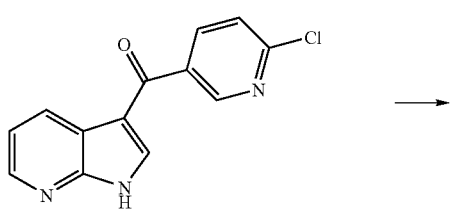

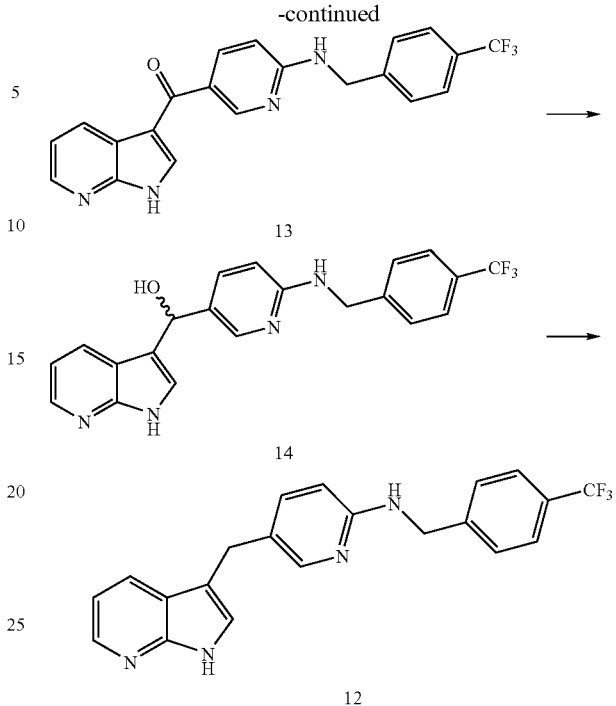

Step-1—Synthesis of (1H-Pyrrolo[2,3-b]pyridin-3-yl)-[6-(4-trifluoromethyl-benzylamino)-pyridin-3-yl]-methanone (13)

Into a pressure flask was added compound 7 (3.5 g, 0.014 mol) and 4-(trifluoromethyl)benzylamine (9.0 g, 0.051 mol) and tetrahydrofuran (30.0 mL, 0.37 mol) and palladium acetate (200.0 mg, 0.890 mmol) and 2-(di-t-butylphosphino)biphenyl (200.0 mg, 0.67 mmol). The reaction mixture was stirred at 180 Celsius overnight, poured into water, and extracted with ethyl acetate. The organic layer was washed with brine, dried over sodium sulfate, concentrated. To the residue was added acetic acid (15.0 mL) and $H_2O$ (5.0 mL). The reaction mixture was stirred at 100 Celsius for 5 hours and concentrated to remove acetic acid. The residue was then treated with aqueous $Na_2HCO_3$ and extracted with ethyl acetate. The organic layer was washed, dried, concentrated and purified to give product 13 (1.0 g, yield=18.5%) as a light yellow solid (M+1=397).

Step-2—Synthesis of (1H-Pyrrolo[2,3-b]pyridin-3-yl)-[6-(4-trifluoromethyl-benzylamino)-pyridin-3-yl]-methanol (14)

Into a round bottom flask was added compound 13 (210.0 mg, 0.53 mmol) and sodium tetrahydroborate (80.0 mg, 2.11 mmol) and dissolved in N,N-dimethylformamide (5.0 mL) and ethanol (20.0 mL). The reaction was stirred at room temperature overnight, poured into water, and the product was extracted with ethyl acetate. The organic layer was washed with brine, dried over sodium sulfate, concentrated and purified with biotage (methylene chloride/methanol 1:20) to give product 14 (63 mg, yield=30%) as a white solid (M+1=399)

Step-3—Synthesis of [5-(1H-Pyrrolo[2,3-b]pyridin-3-ylmethyl)-pyridin-2-yl]-(4-trifluoromethyl-benzyl)-amine (12)

Into a round bottom flask was added compound 14 (200.0 mg, 0.50 mmol) and trifluoroacetic acid (5.0 mL, 0.065 mol) and triethylsilane (3.0 mL, 0.019 mol). The reaction was stirred at room temperature for 30 min, poured into aqueous sodium bicarbonate, and the product was extracted with ethyl acetate. The organic layer was washed with brine, dried over sodium sulfate, concentrated and purified to give pure product 12 (Table 1 Cmpd 1-3) (120.0 mg, yield=62.8%) as a white solid (M+1=383).

Example 7

Synthesis of (4-methoxy-benzyl)-[5-(1H-pyrrolo[2,3-b]pyridin-3-ylmethyl)-pyridin-2-yl]-amine (15) (Compound 1-4, Table 1)

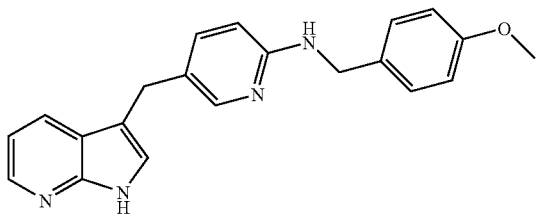

Compound 15 (Table 1 Cmpd 1-4) was synthesized as shown in Scheme-6 using compound 6, where X=Br, as a starting material and substituting 4-methoxy benzyl amine for benzyl amine (M=344.4)

Example 8

Synthesis of (4-chloro-benzyl)-[5-(1H-pyrrolo[2,3-b]pyridin-3-ylmethyl)-pyridin-2-yl]-amine (16) (Compound 1-5, Table 1)

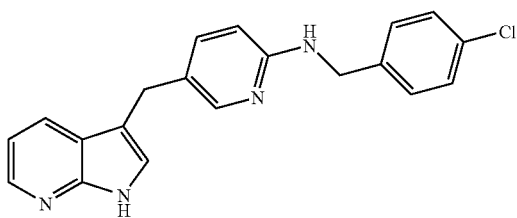

Compound 16 (Table 1 Cmpd 1-5) was synthesized as shown in Scheme-6 using compound 6, where X=Br, as a starting material and substituting 4-chloro benzyl amine for benzyl amine (M=348.8)

Example 9

Synthesis of (4-fluoro-benzyl)-[5-(1H-pyrrolo[2,3-b]pyridin-3-ylmethyl)-pyridin-2-yl]-amine (17) (Compound 1-6, Table 1)

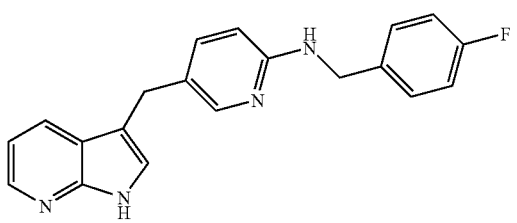

Compound 17 (Table 1 Cmpd 1-6) was synthesized as shown in Scheme-6 using compound 6, where X=Br, as a starting material and substituting 4-fluoro benzyl amine for benzyl amine (M=332.4)

Example 10

Synthesis of (4-methyl-benzyl)-[5-(1H-pyrrolo[2,3-b]pyridin-3-ylmethyl)-pyridin-2-yl]-amine (18) (Compound 1-7, Table 1)

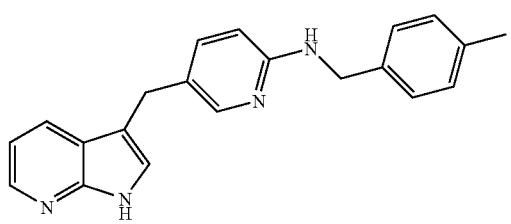

Compound 18 (Table 1 Cmpd 1-7) was synthesized as shown in Scheme-6 using compound 6, where X=Br, as a starting material and substituting 4-methyl benzyl amine for benzyl amine (M=328.4)

Example 11

Synthesis of [5-(1H-pyrrolo[2,3-b]pyridin-3-ylmethyl)-pyridin-2-yl]-thiophen-2-ylmethyl-amine (19) (Compound 1-8, Table 1)

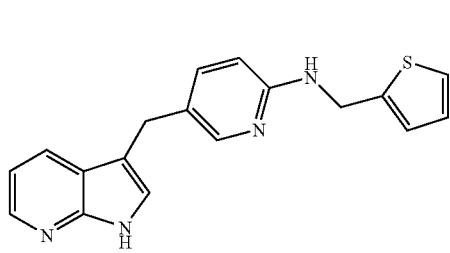

Compound 19 (Table 1 Cmpd 1-8) was synthesized as shown in Scheme-6 using compound 6, where X=Br, as a starting material and substituting 2-thienyl-methyl amine for benzyl amine (M=330.4)

Example 12 cKit Kinase Domain and Construction of c-Kit Sequences c-Kit cDNA sequence is available from NCBI, e.g., as GenBank accession number NM_000222 (SEQ ID NO:2). Using this sequence, c-Kit DNA sequences can be cloned from commercially available libraries (e.g., cDNA libraries) or can be synthesized by conventional cloning methods.

Using conventional cloning methods, constructs encoding three c-Kit polypeptides were prepared, and used to express c-Kit kinase domain polypeptides. One such active c-Kit kinase domain sequence included residues P551-S948, with the deletion of residues Q694-T753.

Example 13

Expression and Purification of c-Kit Kinase Domain

Purified c-Kit kinase domain can be obtained using conventional expression and purification methods. Exemplary methods are described, for example, in Lipson et al., U.S. 20040002534 (U.S. application Ser. No. 10/600,868, filed Jun. 23, 2003), which is incorporated herein by reference in its entirety.

Example 14

Binding Assays

Binding assays can be performed in a variety of ways, including a variety of ways known in the art. For example, as indicated above, binding assays can be performed using fluorescence resonance energy transfer (FRET) format, or using an AlphaScreen Alternatively, any method which can measure binding of a ligand to the ATP-binding site can be used. For example, a fluorescent ligand can be used. When bound to c-Kit, the emitted fluorescence is polarized. Once displaced by inhibitor binding, the polarization decreases.

Determination of $IC_{50}$ for compounds by competitive binding assays. (Note that $K_I$ is the dissociation constant for inhibitor binding; $K_D$ is the dissociation constant for substrate binding.) For this system, the $IC_{50}$, inhibitor binding constant and substrate binding constant can be interrelated according to the following formula:
When using radiolabeled substrate $$K_I = \frac{IC_{50}}{1 + [L^*]/K_D},$$

the $IC_{50} \sim K_I$ when there is a small amount of labeled substrate.

Example 15 c-Kit Activity Assays

The effect of potential modulators of kinase activity of c-Kit and other kinases can be measured in a variety of different assays known in the art, e.g., biochemical assays, cell-based assays, and in vivo testing (e.g., model system testing). Such in vitro and/or in vivo assays and tests can be used in the present invention.

In an exemplary biochemical assay, c-Kit kinase activity can be determined in the following assay format:

Exemplary Biochemical Assay $IC_{50}$ values were determined with respect to inhibition of c-Kit kinase activity, where inhibition of phosphorylation of a peptide substrate is measured as a function of compound concentration. Compounds 1-3, 1-5, 1-6, and 1-7 (Table 1) and 1-9 and 1-12 (Example 5) were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. The plate was mixed vigorously for 10 seconds after each dilution. The diluted samples were then distributed in 1 µl aliquots to an assay plate. 8 µl of substrate (Biotin-$(E_4Y)_3$, Open Source Biotech, Inc., 0.2 mg/ml in DMSO), PE alpha PY20 (acceptor) and Streptavidin (donor) beads (PY20 AlphaScreening kit, Perkin Elmer Life Science Inc. catalog #676601M) were mixed in 5.5 ml of kinase buffer (50 mM HEPES, pH 7.2, 5 mM $MgCl_2$, 5 mM $MnCl_2$, 0.1% NP-40, 50 µg/ml BSA). C-Kit kinase domain (starting amino acid M551, ending amino acid K949) was prepared by expression of plasmid P1332 (pET-N6 BI-PTP, N-terminal non-cleavable His tag and bicistronic PTP) in E. coli, added to the solution and mixed well. This was distributed into a polypropylene plate at 50 µl per well, then transferred 10 µl to each well of the assay plate, shaking the plate for 20 seconds to mix (final c-Kit of 50 ng/well). ATP (100 mM stock) was diluted 1 µl into 5 ml of kinase buffer and the solution mixed well, 50 µl per well was transferred to a polypropylene plate, then 10 µl per well transferred to the assay plate (final ATP 10 µM). The plate was shaken for 30 seconds, then incubated for 30 minutes at 30° C. Added 5 µl per well of stop buffer (50 mM EDTA in kinase buffer) and incubated for 30 minutes at room temperature, then read the signal per well on AlphaQuest reader. Phosphorylated substrate results in binding of the PY20 antibody and association of the donor and acceptor beads such that signal correlates with kinase activity. The signal vs. compound concentration was used to determine the $IC_{50}$. Compounds 1-3, 1-5, 1-6 and 1-7 (Table 1) were similarly assayed, using in a final reaction volume of 25 µl: c-Kit (h) (5-10 mU) in 8 mM MOPS pH 7.0, 0.2 mM EDTA, 10 mM MnCl2, 0.1 mg/ml poly (Glu, Tyr) 4:1, 10 mM MgAcetate and $\gamma$-$^{33}$P-ATP (approximately 500 cpm/pmol), with appropriate concentrations of compound. Incubated for 40 minutes at room temperature and stopped by addition of 5 µl of 3% phosphoric acid. Spotted 10 µl of each sample onto Filtermat A and washed 3× with 75 mM phosphoric acid, once with methanol, dried and measured on scintillation counter (performed at Upstate USA, Charlottesville, Va.). All compounds had $IC_{50}$ of less than 1 µM as measured by at least one of these assays.

Additional Biochemical and Cell-based Assays

In general, any protein kinase assay can be adapted for use with c-Kit. For example, assays (e.g., biochemical and cell-based assays) as described in Lipson et al., U.S. Patent Publ. 20040002534 (incorporated herein by reference in its entirety) can be used in the present invention.

As one example, M-07e cell line (DSMZ catalog #ACC 104) proliferation is stimulated by SCF (Stem Cell Factor), which binds and activates c-Kit tyrosine kinase receptor. Inhibitors of c-Kit kinase reduce or eliminate the SCF mediated kinase activation, resulting in reduced cell proliferation of SCF stimulated cells. This inhibition is measured by the effect of compound concentration on cell growth to assess $IC_{50}$ values. M-07e cells were seeded at $5\times10^4$ cells per well of a 96 well cell culture plate in 50 µl of cell culture medium of Iscove's Medium 1× (MOD, CellGro Mediatech catalog #15-016-CV) supplemented with 10% FBS (HyClone catalog #SH30071.03). Compounds 1-3 and 1-5 (Table 1) were dissolved in DMSO at a concentration of 0.1 mM and were serially diluted 1:3 for a total of eight points and added to the cells to final concentrations of 1, 0.33, 0.11, 0.037, 0.012, 0.0041, 0.0014 and 0.00046 µM in 100 µl cell culture medium (final concentration 0.8% DMSO). Cells were also treated with staurosporine as a positive control. Cells were stimulated by adding 20 µl of 600 ng/ml SCF to a final concentration of 100 ng/ml (Biosource International SCF kit ligand catalog #PHC2115) in cell culture medium. The cells were incubated at 37° C, 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1s per well. The luminescence reading assesses the ATP content, which correlates directly with cell number such that the reading as a function of compound concentration is used to determine the $IC_{50}$ value. Both compounds had $IC_{50}$ of less than 1 µM.

This cell based assay was also used to assess phosphorylation. Samples were prepared as described for the growth inhibition assay only M-07e cells were seeded at $2 \times 10^5$ cells per well in a 96 well filter plate. Cells were incubated for 1 hour at 37° C. with the compounds as described above, and then stimulated by adding SCF to a final concentration of 50 ng/ml and incubated for 10 minutes at 37° C. The culture medium was removed by centrifugation and the cells were lysed by addition of 30 µl lysis buffer (25 mM Tris HCl pH 7.5, 150 mM NaCl, 5 mM EDTA, 1% Triton X100, 5 mM NaF, 1 mM Na Vanadate, 10 mM Beta-glycerophosphate, no EDTA (Boehringer-Roche catatalog #1873580) and placed on ice for 30 minutes. A 15 µl aliquot of the lysate was taken and assayed according to Biosource Immunoassay Kit: Human c-Kit [pY823] (Catalog # KHO0401) by diluting the aliquot with 85 µl dilution buffer in the assay plate, incubating for 2 hours at room temperature and washing the plate 4 times with wash buffer. Detection antibody (100 µl) was added to the plate and samples incubated for 1 hour at room temperature, then washed 4 times with wash buffer. HRP anti-rabbit antibody (100 µl) was added and samples incubated for 30 minutes at room temperature, then washed 4 times with wash buffer. Stabilized chromogen (100 µl) was added and samples incubated for 15-25 minutes at room temperature, then washed 4 times with wash buffer. Stop solution (100 µl) was added and the samples read on a Wallac Victor reader at 450 nm. The absorbance was plotted against the compound concentration and the $IC_{50}$ concentration was determined. Both compounds had $IC_{50}$ of less than 1 µM.

In Vivo Model System Testing

For in vivo testing, a suitable animal model system can be selected for use. For example, for multiple scerosis, the rodent experimental allergic encephalomyelitis (EAE) is commently used. This system is well-known, and is described, for example, in Steinman, 1996, *Cell* 85:299-302 and Secor et al., 2000, *J Exp. Med* 5:813-821, which are incorporated herein by reference in their entireties.

Similarly, other model systems can be selected and used in the present invention.

Example 16

Site-Directed Mutagenesis of c-Kit and Other Kinases

Mutagenesis of c-Kit and other kinases (as well as other sequences of interest) can be carried out according to the following procedure as described in Molecular Biology: Current Innovations and Future Trends. Eds. A. M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps: (i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of *E. coli* is Dam-methylated at the sequence 5-GATC-3); (iv) using Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl2; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94 C, 2 min at 50 C and 2 min at 72° C.; followed by 5-10 cycles of 1 min at 94° C., 2 min at 54 C and 1 min at 72° C. (step 1).

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent *E. coli* (step 4).

In addition to the PCR-based site-directed mutagenesis described above, other methods are available. Examples include those described in Kunkel (1985) Proc. Natl. Acad.

Sci. 82:488-492; Eckstein et al. (1985) Nucl. Acids Res. 13:8764-8785; and using the GeneEditor™ Site-Directed Mutageneis Sytem from Promega.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formula I and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

---

What is claimed is:

1. A compound having the structure

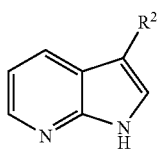

or a salt or isomer thereof,
wherein:
R² is

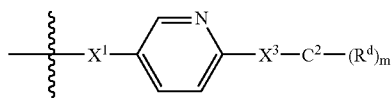

X¹ is selected from the group consisting of lower alkylene, substituted lower alkylene, —C(O)—, —CH₂—C(O)—, —C(O)CH₂—, —C(S)—, —CH₂—C(S)—, —C(S)CH₂—, —O—, —S—, —S(O₂)— and —NR$^a$,
wherein R$^a$ is selected from the group consisting of hydrogen, lower alkyl and lower alkyl substituted with fluoro, hydroxyl, alkoxy, thiol, thioalkoxy, or amino, provided, however, that hydroxyl, alkoxy, thiol, thioalkyoxy or amino are not substituted at the carbon bound to the nitrogen of —NR$^a$;

X³ is selected from the group consisting of

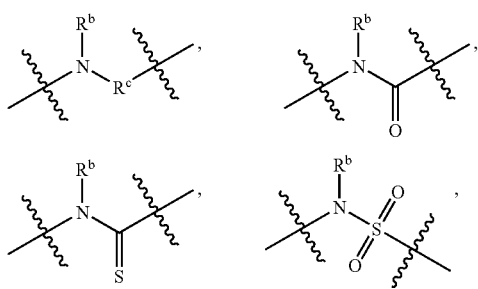

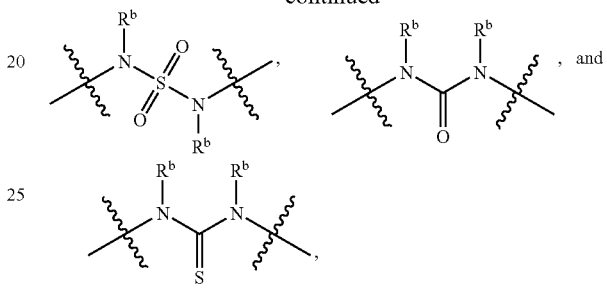

wherein
R$^b$ at each occurrence is independently selected from the group consisting of hydrogen, lower alkyl and lower alkyl substituted with fluoro, hydroxyl, alkoxy, thiol, thioalkoxy, or amino, provided, however, that hydroxyl, alkoxy, thiol, thioalkyoxy or amino are not substituted at the carbon bound to the nitrogen of NR$^b$; and
R$^c$ is selected from the group consisting of alkylene and substituted alkylene;
C² is selected group consisting of aryl and heteroaryl;
R$^d$ is selected from the group consisting of halogen, lower alkyl, substituted lower alkyl, optionally substituted lower alkoxy, optionally substituted alkylthio, optionally substituted alkenyl, optionally substituted alkyknyl, optionally substituted amine, optionally substituted amido, carboxyl, hydroxyl, optionally substituted aryl, aryloxy, optionally substituted heterocycle, optionally substituted heteroaryl, nitro, cyano, thiol, and sulfonylamino; and
m is in the range 0-2.

2. The compound of claim 1, wherein X¹ is selected from the group consisting of methylene and substituted methylene.

3. The compound of claim 2, wherein X¹ is difluoromethylene.

4. The compound of claim 1, wherein X¹ is —C(O)—.

5. The compound of claim 1,
wherein:
X³ is

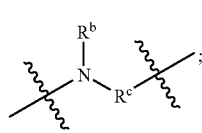

$R^b$ is selected from the group of hydrogen and lower alkyl;

$R^c$ is selected from the group consisting of methylene and substituted methylene.

6. The compound of claim 5, wherein $X^3$ is —NHCH$_2$—.

7. The compound of claim 1, wherein $X^3$ is —NHC(O)—.

8. The compound of claim 1, wherein:

$X^3$ is

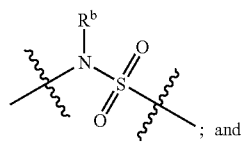

; and $R^b$ is selected from the group consisting of hydrogen and lower alkyl.

9. The compound of claim 1, wherein:

$C^2$ is phenyl;

$R^d$ at each occurrence is independently selected from the group consisting of halogen, lower alkyl, substituted lower alkyl, optionally substituted lower alkoxy, optionally substituted alkylthio, optionally substituted alkenyl, optionally substituted alkyknyl, optionally substituted amine, optionally substituted amido, carboxyl, hydroxyl, optionally substituted aryl, aryloxy, optionally substituted heterocycle, heteroaryl, substituted heteroaryl. nitro, cyano, thiol, and sulfonylamino; and m is in the range 0-2.

10. The compound of claim 1, wherein:

$C^2$ is selected from the group consisting of thienyl, pyridinyl, pyrimidinyl, pymzinyl, pyridazinyl, pyrrolyl, imidazolyl, and furanyl.

11. A composition comprising a compound according to claim 1

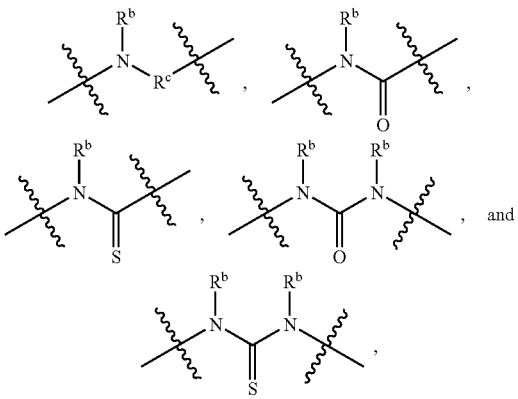

a pharmaceutially acceptable carrier.

* * * * *

UNITED STATES PATENT AND TRADEMARK OFFICE
CERTIFICATE OF CORRECTION

PATENT NO. : 7,498,342 B2
APPLICATION NO. : 11/154988
DATED : March 3, 2009
INVENTOR(S) : Prabha N. Ibrahim et al.

It is certified that error appears in the above-identified patent and that said Letters Patent is hereby corrected as shown below:

IN THE CLAIMS

Column 384, line 15, please amend Claim 11 as follows:

11. A composition comprising a compound according to claim 1, and a pharmaceutically acceptable carrier.

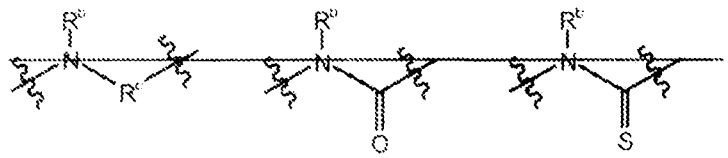

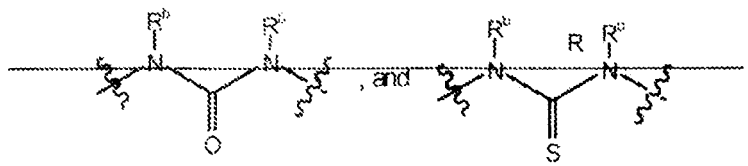

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,498,342 B2 | Page 1 of 1 |
| APPLICATION NO. | : 11/154988 | |
| DATED | : March 3, 2009 | |
| INVENTOR(S) | : Prabha Ibrahim et al. | |

It is certified that error appears in the above-identified patent and that said Letters Patent is hereby corrected as shown below:

TITLE PAGE, ITEM (73):

"(73) Assignee: Plexxikon, Inc., Berkeley, CA (US)" should read

--(73) Assignee: Plexxikon Inc., Berkeley, CA (US)--

Signed and Sealed this
Fourth Day of September, 2012

David J. Kappos
*Director of the United States Patent and Trademark Office*

SEQUENCE LISTING

<160> NUMBER OF SEQ ID NOS: 2

<210> SEQ ID NO 1
<211> LENGTH: 976
<212> TYPE: PRT
<213> ORGANISM: Homo sapiens

<400> SEQUENCE: 1

```
Met Arg Gly Ala Arg Gly Ala Trp Asp Phe Leu Cys Val Leu Leu Leu
 1               5                  10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
```

-continued

```
                165                 170                 175
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
        195                 200                 205
Lys Ala Val Pro Val Val Ser Val Ser Lys Ala Ser Tyr Leu Leu Arg
    210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
        515                 520                 525
Phe Val Ile Val Ala Gly Met Met Cys Ile Ile Val Met Ile Leu Thr
    530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
```

```
Lys Thr Leu Gly Ala Gly Ala Phe Gly Lys Val Glu Ala Thr Ala
            595                 600                 605

Tyr Gly Leu Ile Lys Ser Asp Ala Ala Met Thr Val Ala Val Lys Met
610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
        690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
            725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
            805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
            885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
        930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
            965                 970                 975

<210> SEQ ID NO 2
<211> LENGTH: 5084
<212> TYPE: DNA
<213> ORGANISM: Homo sapiens
```

```
<400> SEQUENCE: 2
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga agaagacaa cgacacgctg      420
gtccgctgtc ctctcacaga cccagaagtg accaattatt ccctcaaggg gtgccagggg     480
aagcctcttc ccaaggactt gaggtttatt cctgacccca aggcgggcat catgatcaaa     540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga cgtcaggca     840
acgttgacta tcagttcagc gagagttaat gattctggag tgttcatgtg ttatgccaat     900
aatacttttg gatcagcaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga atgaaagtaa tatcagatac    1140
gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca aatagattg gtattttgt ccaggaactg agcagagatg ctctgcttct     1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caaatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttggagcctg caccattgga gggcccaccc tggtcattac agaatattgt    2040
tgctatggtg atctttgaa ttttttgaga agaaacgtg attcatttat ttgttcaaag    2100
caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
```

```
taccaggtgg caaagggcat ggctttcctc gcctccaaga attgtattca cagagacttg   2400
gcagccagaa atatcctcct tactcatggt cggatcacaa agatttgtga ttttggtcta   2460
gccagagaca tcaagaatga ttctaattat gtggttaaag gaaacgctcg actacctgtg   2520
aagtggatgg cacctgaaag catttttcaac tgtgtataca cgtttgaaag tgacgtctgg   2580
tcctatggga ttttctcttg ggagctgttc tctttaggaa gcagcccta tcctggaatg   2640 ccggtcgatt ctaagttcta caagatgatc aaggaaggct tccggatgct cagccctgaa   2700
cacgcacctg ctgaaatgta tgacataatg aagacttgct gggatgcaga tccctaaaa   2760 agaccaacat tcaagcaaat tgttcagcta attgagaagc agatttcaga gagcaccaat   2820
catatttact ccaacttagc aaactgcagc cccaaccgac agaagcccgt ggtagaccat   2880
tctgtgcgga tcaattctgt cggcagcacc gcttcctcct cccagcctct gcttgtgcac   2940
gacgatgtct gagcagaatc agtgtttggg tcacccctcc aggaatgatc tcttcttttg   3000
gcttccatga tggttatttt ctttctcttc aacttgcatc caactccagg atagtgggca   3060
ccccactgca atcctgtctt tctgagcaca ctttagtggc cgatgatttt tgtcatcagc   3120
caccatccta ttgcaaaggt tccaactgta tatattccca atagcaacgt agcttctacc   3180
atgaacagaa acattctga tttggaaaaa gagagggagg tatggactgg gggccagagt   3240
cctttccaag gcttctccaa ttctgcccaa aaatatggtt gatagtttac ctgaataaat   3300
ggtagtaatc acagttggcc ttcagaacca tccatagtag tatgatgata caagattaga   3360
agctgaaaac ctaagtcctt tatgtggaaa acagaacatc attagaacaa aggacagagt   3420
atgaacacct gggcttaaga aatctagtat ttcatgctgg gaatgagaca taggccatga   3480
aaaaaatgat ccccaagtgt gaacaaaaga tgctcttctg tggaccactg catgagcttt   3540
tatactaccg acctggtttt taaatagagt ttgctattag agcattgaat tggagagaag   3600
gcctccctag ccagcacttg tatatacgca tctataaatt gtccgtgttc atacatttga   3660
gggaaaaaca ccataaggtt tcgtttctgt atacaaccct ggcattatgt ccactgtgta   3720
tagaagtaga ttaagagcca tataagtttg aaggaaacag ttaataccat tttttaagga   3780
aacaatataa ccacaaagca cagtttgaac aaaatctcct cttttagctg atgaacttat   3840
tctgtagatt ctgtggaaca agccatcag cttcagaatg gcattgtact caatggattt   3900
gatgctgttt gacaaagtta ctgattcact gcatggctcc cacaggagtg ggaaaacact   3960
gccatcttag tttggattct tatgtagcag gaaataaagt ataggtttag cctccttcgc   4020
aggcatgtcc tggacaccgg gccagtatct atatatgtgt atgtacgttt gtatgtgtgt   4080
agacaaatat ttggaggggt attttttgccc tgagtccaag agggtccttt agtacctgaa   4140
aagtaacttg gctttcatta ttagtactgc tcttgtttct tttcacatag ctgtctagag   4200
tagcttacca gaagcttcca tagtggtgca gaggaagtgg aaggcatcag tcccctatgta   4260 tttgcagttc acctgcactt aaggcactct gttatttaga ctcatcttac tgtacctgtt   4320
ccttagacct tccataatgc tactgtctca ctgaaacatt taaattttac cctttagact   4380
gtagcctgga tattattctt gtagtttacc tcttttaaaaa caaaacaaaa caaaacaaaa   4440
aactcccctt cctcactgcc aatataaaa ggcaaatgtg tacatggcag agttgtgtg   4500 ttgtcttgaa agattcaggt atgttgcctt tatggtttcc cccttctaca tttcttagac   4560
tacatttaga gaactgtggc cgttatctgg aagtaaccat ttgcactgga gttctatgct   4620
ctcgcacctt tccaaagtta acagattttg gggttgtgtt gtcacccaag agattgttgt   4680
```

-continued

```
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtctttt gaatattccc aagcccatga gtccttgaaa atattttta tatatacagt     4980
aactttatgt gtaaatacat aagcggcgta agtttaaagg atgttggtgt tccacgtgtt    5040
ttattcctgt atgttgtcca attgttgaca gttctgaaga attc                     5084
```